United States Patent
Broadhurst et al.

(10) Patent No.: US 6,867,299 B2
(45) Date of Patent: Mar. 15, 2005

(54) OXAMIDE IMPDH INHIBITORS

(75) Inventors: Michael John Broadhurst, Royston (GB); Christopher Huw Hill, Baldock (GB); David Nigel Hurst, Welwyn (GB); Philip Stephen Jones, Welwyn Garden City (GB); Paul Brittain Kay, Baldock (GB); Ian Reginald Kilford, Welwyn Garden City (GB); Robert Murray McKinnell, London (GB)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 09/779,116

(22) Filed: Feb. 8, 2001

(65) Prior Publication Data

US 2002/0052513 A1 May 2, 2002

(30) Foreign Application Priority Data

Feb. 24, 2000 (GB) ............................................. 0004392
Jun. 28, 2000 (GB) ............................................. 0015877
Aug. 17, 2000 (GB) ............................................. 0020322

(51) Int. Cl.$^7$ ...................... C07D 413/14; C07D 263/32
(52) U.S. Cl. .................. 544/137; 514/374; 514/254.02; 514/314; 514/340; 514/382; 544/369; 546/170; 546/271.4; 548/235; 548/236
(58) Field of Search ................................ 548/235, 236; 514/374, 254.02, 314, 340, 382; 544/369, 137; 546/170, 271.4

(56) References Cited

U.S. PATENT DOCUMENTS

| | | |
|---|---|---|
| 4,497,817 A | 2/1985 | Murase et al. |
| 5,807,876 A | 9/1998 | Armistead et al. |
| 5,932,600 A | 8/1999 | Saunders et al. |
| 6,624,184 B1 * | 9/2003 | Gu et al. ..................... 514/374 |

FOREIGN PATENT DOCUMENTS

| | | |
|---|---|---|
| EP | 0 122 627 | 10/1984 |
| EP | 0 613 893 | 9/1994 |
| WO | WO 97/24343 | 7/1997 |
| WO | WO 99/46237 | 9/1997 |
| WO | 97/40028 | 10/1997 |
| WO | 98/40381 | 9/1998 |
| WO | WO 98/48804 | 11/1998 |
| WO | WO 99/46236 | 9/1999 |
| WO | 99/55663 | 11/1999 |
| WO | WO 00/01666 | 1/2000 |
| WO | WO 00/26197 | 5/2000 |
| WO | 00/26197 | 5/2000 |

* cited by examiner

Primary Examiner—Laura L. Stockton
(74) Attorney, Agent, or Firm—George W. Johnston; Dennis P. Tramaloni

(57) ABSTRACT

Disclosed are compounds of the general formula

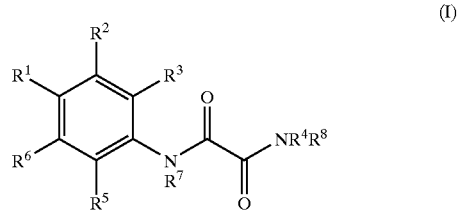

(I)

which are oxamide derivatives and inhibitors of the enzyme inosine monophosphate dehydrogenase (IMPDH).

17 Claims, No Drawings

OXAMIDE IMPDH INHIBITORS

BACKGROUND OF THE INVENTION

The present invention relates to novel oxamide derivatives, a process for their manufacture, pharmaceutical preparations containing these derivatives, and the use of these derivatives as medicaments. In particular, the present invention relates to novel oxamide derivatives which are inhibitors of inosine monophosphate dehydrogenase (IMPDH).

Inosine monophosphate dehydrogenase (IMPDH) is an enzyme involved in the de novo synthesis of guanine nucleotides. The enzyme catalyses the NAD-dependent oxidation of inosine-5'-monophosphate (IMP) to xanthosine-5'-monophosphate which is the rate limiting step in the synthesis of guanine nucleotides. As a result of the key role of the enzyme in guanine nucleotide biosynthesis, the enzyme represents an important target for the development of inhibitors which would have utility as therapeutic agents in the treatment of IMPDH related processes.

The de novo synthesis of guanine nucleotides is particularly important in B- and T-lymphocytes to provide sufficient levels of nucleotides to support a proliferative response to mitogen or antigen [Wu, J. C., Persp. in Drug Discovery and Design., 2, 185–204, (1994)]. IMPDH inhibition is thus an attractive target for selectively inhibiting the immune system. Inhibitors of IMPDH are known [Pankiewicz, K. W., Exp. Opin. Ther. Patents., 9, 55–65, (1999)], and the uncompetitive inhibitor mycophenolic acid (MPA) has been demonstrated to inhibit the response of B- and T-cells to mitogen or antigen [Allison, A. C. and Eugui, E. M., Transplant. Proc., 25, 8–18, (1993)]. MPA has therefore been utilised as an immunosuppressant.

It is also recognised that IMPDH plays a role in other rapidly proliferating cells such as tumour cell lines, indicating that IMPDH inhibition is a target for anti-cancer chemotherapy [Nagai, M. et al., 51, 3886–3890, (1990)].

IMPDH inhibition has also been shown to play a role in viral replication in some cell lines which support virus replication [Pankiewicz, K. W., Exp. Opin. Ther. Patents., 9, 55–65, (1999)]. Ribavirin, for example, is a broad spectrum antiviral agent which has been approved by the U.S. Flood and Drug Administration for use as an aerosol for infants with serious respiratory infections due to respiratory syncytial virus and is also in use as an agent for the treatment of patients infected with Hepatitis C virus when used in combination with interferon [Patterson, J. L. and Fernandez-Larsson, R., Rev. Infect. Dis., 12, 1139–1146, (1990); McHutchison, J. G. et al., New. Engl. J.Med., 339, 1549–1550, (1998)]. Ribavirin is converted in cells to ribavirin 5' monophosphate which is an inhibitor of IMPDH.

Additionally, the IMPDH inhibitors ribavirin and MPA have been shown to inhibit the replication of yellow fever virus (a RNA virus) whilst MPA has been demonstrated to inhibit Hepatitis B virus replication (a DNA virus) in vitro supporting the broad range antiviral activity of these inhibitors [Neyts, J. et al., Antiviral Res., 30, 125–132, (1996); Gong, Z. J. et al., J. Viral Hepatitis., 6, 229–236, (1999)]. Furthermore, MPA has also been shown to potentiate the antiviral effects of nucleoside analogues both in vitro and in animal models [Neyts, J. and De Clercq, E., Inter. Antiviral News., 7, 134–136, (1999)]. Together these observations indicate that IMPDH inhibitors have utility as broad spectrum antiviral agents.

IMPDH inhibitors would therefore have therapeutic potential as immunosuppressants, anti-cancer agents and anti-viral agents. Specifically, such compounds may be used in the treatment of transplant rejection, the treatment of cancer and as antiviral agents in the treatment of viral diseases such as retroviral infections and hepatitis C virus infections (either alone or in combination with other antiviral agents such as interferon or derivatives thereof, such as conjugates with polyethylene glycol).

SUMMARY OF THE INVENTION

The novel oxamide derivatives provided by the present invention are compounds of the general formula (I):

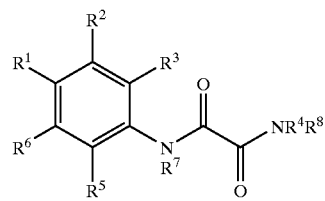

wherein
$R^1$ represents heterocyclyl;
$R^2$ represents hydrogen, unsubstituted lower alkyl, lower alkoxy, halo, hydroxy or cyano;
$R^3$ represents hydrogen, unsubstituted lower alkyl, lower alkoxy, halo, or cyano;
$R^4$ represents hydrogen, or unsubstituted lower alkyl;
$R^5$ represents hydrogen, unsubstituted lower alkyl, lower alkoxy, halo, or cyano;
$R^6$ represents hydrogen, unsubstituted lower alkyl, lower alkoxy, halo, or cyano;
$R^7$ represents hydrogen, or unsubstituted lower alkyl;
$R^8$ represents hydrogen, lower alkyl, lower cycloalkyl, aryl, or heterocyclyl;
or $R^4$ and $R^8$ together with the nitrogen atom to which they are attached represent heterocyclyl;
and pharmaceutically acceptable salts thereof.

The oxamide derivatives provided by the present invention are inhibitors of the enzyme inosine monophosphate dehydrogenase (IMPDH). They can be used as medicaments, especially for treating immune mediated conditions or diseases, viral diseases, bacterial diseases, parasitic diseases, inflammation, inflammatory diseases, hyperproliferative vascular diseases, tumours, and cancer. They can be used alone, or in combination with other therapeutically active agents, for example, an immunosuppressant, a chemotherapeutic agent, an anti-viral agent, an antibiotic, an anti-parasitic agent, an anti-inflammatory agent, an anti-fungal agent and/or an anti-vascular hyperproliferation agent.

In particular, compounds of the present invention and compositions containing the same are useful as chemotherapeutic agents, inhibitors of viral replication and modulators of the immune system, and can be used for the treatment of viral diseases such as retroviral infections and hepatitis C virus infections (either alone or in combination with other antiviral agents such as interferon or derivatives thereof, such as conjugates with polyethylene glycol), inflammatory diseases such as osteoarthritis, acute pancreatitis, chronic pancreatitis, asthma, and adult respiratory distress syndrome, hyperproliferative vascular diseases such as restenosis, stenosis and artherosclerosis, cancer, for example lymphoma and leukaemia, and as immunosupressants in the treatment of autoimmune diseases, graft versus host diseases and transplant rejection Compounds of the present invention which have antiviral effects and/or immuno-supressive properties are particularly useful for treating HCV infection.

DETAILED DESCRIPTION OF THE INVENTION

If not otherwise specified, an unmodified term includes both substituted and unsubstited forms if that term has been defined as substituted or unsubstituted. For example "lower alkyl" includes substituted and unsubstituted lower alkyl. Similarly, "optionally substituted" includes substituted or unsubstituted. The term "saturated" applied to ring structures includes fully and partially saturated rings.

As used herein, the term "lower alkyl", means a straight-chain or branched-chain alkyl group containing up to 10 carbon atoms, preferably from 1 to 8 carbon atoms, more preferably from 1 to 6 carbon atoms, e.g. methyl, ethyl, n-propyl, isopropyl, n-butyl, sec.butyl, tert-butyl, n-pentyl, n-hexyl and 1,1-dimethylethyl; and which is unsubstituted or substituted by e.g. one or more of cyano, halo, carboxyl, hydroxyl, lower alkoxy, lower cyclo alkoxy, aryloxy, heterocyclyloxy, heterocyclyl-(lower alkoxy)-aryl-amino-oxalyl-oxy, lower alkoxy-carbonyl, aryl, aryl-carbonyl-amino-aryl, lower alkyl-carbonyl-amino-aryl, heterocyclyl, lower alkyl-heterocyclyl, lower cycloalkyl, lower alkenyl, lower alkynyl, amino, mono- or di-(lower alkyl) amino, lower cycloalkyl amino, aryl amino, heterocyclyl-amino, lower alkyl-aryl-lower alkyl-amino, lower alkoxy-carbonyl-amino, lower alkenyl-carbonyl-amino, lower alkyl-carbonyl-amino, di-(aryl)-lower alkyl-carbonyl-amino, lower alkyl-sulphonyl-lower alkyl-carbonyl-amino, lower cycloalkyl-lower alkyl-carbonyl-amino, heterocyclyl-lower alkyl-carbonyl-amino, lower alkoxy-lower alkyl-carhonyl-amino), di-aryl-lower alkyl-carbonyl-amino, aryl-carbonyl-amino, lower alkyl-aryl-carbonyl-amino, tri-(lower alkyl)-aryl-carbonyl-amino, mono- or di-(lower alkoxy)-aryl-carbonyl-amino, di-(lower alkyl)-amino-aryl-carbonyl-amino, lower alkyl-carbonyl-amino-aryl-carbonyl-amino, heterocyclyl-aryl-carbonyl-amino, lower cycloalkyl-carbonyl-amino, mono- or tetra-(lower alkyl)-lower cycloalkyl-carbonyl-amino, heterocyclyl-carbonyl-amine, mono- or di-(lower alkyl)-heterocyclyl-carbonyl-amino, tri-(lower alkyl)-aryl-oxalyl-amino, lower alkyl-carbamoyl, or aryl-carbamoyl, thio, lower alkyl thio, lower cycloalkyl thio, aryl thio, heterocyclyl thio, lower alkyl sulphonyl, lower cycloalkyl sulphonyl, aryl sulphonyl, heterocyclyl sulphonyl.

Where there is more than one substituent, each substituent may be the same or different, for example tri-fluoromethyl, triphenylmethyl, 1-[1-methyl-1-[methylformyl]-2-phenyl] ethyl, or 2-[1-hydroxyl-3-cyclohexyl].

The term "unsubstituted lower alkyl" means an alkyl group as defined above where no substituents are present.

The term "lower alkenyl" means an alkenyl group containing from 2 to 7 carbon atoms, e.g. allyl, vinyl and butenyl.

The term "lower alkynyl" means an alkynyl group containing from 2 to 7 carbon atoms, e.g. propargyl or butynyl.

The term "lower cycloalkyl", alone or in combination as in "lower cycloalkyl-lower alkyl", means a cycloalkyl group containing 3 to 10 carbon atoms, preferably 3 to 7 carbon atoms, e.g. cyclopropyl, cyclobutyl, cyclopentyl, cyclohexyl, cycloheptyl and adamantyl, and which may be unsubstituted or substituted by e.g. one or more of lower alkyl, carboxyl, hydroxyl or aryl or optionally be benz-fused e.g. to aryl. Where there is more than one substituent, each substituent may be the same or different. Cyclopropylmethyl, 2-cyclobutyl-ethyl and 3-cyclohexyl-propyl are examples of lower cycloalkyl-lower alkyl groups.

The term "halo" denotes fluorine, chlorine, bromine or iodine.

The term "lower alkoxy" denotes an unsubstituted or substituted lower alkyl group as defined hereinbefore, which is bonded via an oxygen atom, e.g. methoxy, ethoxy, n-propoxy, isopropoxy, n-butoxy, isobutoxy, tert.-butoxy and the like. Suitable substituents are those applicable for "lower alkyl".

The term "aryl", alone or in combination as in "aryl-lower alkyl", means phenyl or naphthyl, optionally benz-fused, for example benz-fused to a lower cycloalkyl ring. "Aryl" denotes unsubstituted or substituted by e.g. one or more of halo, cyano, carboxyl, lower alkyl-thio, nitro, oxo, hydroxyl, lower alkoxy, lower cycloalkyloxy, aryloxy, heterocyclyl oxy lower alkyl-heterocyclyl, heterocyclyl, lower alkoxy-carbonyl, lower alkyl-carbonyl, heterocyclyl-carbonyl, lower alkyl-heterocyclyl-carbonyl, sulphamoyl, lower alkyl-sulphamoyl, thio, lower alkyl thio, lower cycloalkyl thio, aryl thio, heterocyclyl thio, lower alkyl-sulphonyl, lower cycloalkyl sulphonyl, aryl sulphonyl, heterocyclyl-sulphonyl, amino, mono- or di-(lower alkyl)amino, lower alkyl-sulphonyl-amino, di-(lower alkyl)-heterocyclyl-amino, lower alkyl-carbonyl-amino, (lower alkyl-carbonyl) (lower alkyl)-amino, alkoxy-carbonyl-amino, aryl-carbonyl-amino, mono- or di-(lower alkyl)-carbamoyl, aryl-carbamoyl, lower alkyl, aryl-lower alkyl, amino-lower alkyl, heterocyclyl-lower alkyl, lower alkoxy-carbonyl-lower alkyl, lower alkyl-sulphamoyl-lower alkyl, aryl-sulphonyl-amino-lower alkyl, lower alkyl-sulphonyl-amino-lower alkyl, lower alkoxy-carbonyl-amino-lower alkyl, heterocyclyl-oxy-carbonyl-amino-lower alkyl, aryloxy-carbonyl-amino-lower alkyl, lower alkyl-carbonyl-amino-lower alkyl, lower alkoxy-carbonyl-(lower alkyl)-amino-lower alkyl, lower alkyl-carbamoyl-lower alkyl, lower alkyl-aryl-carbonyl-amino-lower alkyl, aryl-carbamoyl-lower alkyl, lower cycloalkyl-carbonyl-amino-lower alkyl, heterocyclyl-carbonyl-amino-lower alkyl, or aryl-carbonyl-amino-lower alkyl. Where there is more than one substituent, each substituent may be the same or different, for example 1-(3-methoxy-4-oxazolyl)phenyl, 1-(3-chloro-4-methoxy)phenyl, 1-(3-chloro-4-methyl)phenyl and 1-(3-fluoro-4-methyl)phenyl.

The same substituents as listed above apply for all terms containing the phrase "phenyl" i.e. substituted or unsubstituted) phenyl.

The term "aryloxy" denotes an aryl group as defined hereinbefore, which is bonded via an oxygen atom, e.g. phenoxy, and the like.

As used herein, the term "heterocyclyl", alone or in combination as in "heterocyclyl-lower alkyl", means a saturated, unsaturated or partially saturated monocyclic or bicyclic ring system which contains one or more hetero atoms selected from nitrogen, sulphur and oxygen; and which is attached to the rest of the molecule via a carbon atom (C-linked), or a nitrogen atom (N-linked) in the ring system, and which is unsubstituted or substituted in the same manner as the aryl group defined hereinbefore and/or by oxido. Where there is more than one substituent, each substituent may be the same or different.

Examples of heterocyclyl groups are oxazolyl, isoxazolyl, furyl, tetrahydrofuryl, 1,3-dioxolanyl, dihydropyranyl, thienyl, pyrazinyl, isothiazolyl, isoquinolinyl, indolyl, indazolyl, quinolinyl, dihydrooxazolyl, pyrimidinyl, benzofuranyl, tetrazolyl, pyrrolidinonyl, (N-oxide)-pyridinyl, pyrrolyl, triazolyl e.g. 1,2,4-triazolyl, pyrazolyl, benzotriazolyl, piperidinyl, morpholinyl, thiazolyl, pyridinyl, dihydrothiazolyl, imidazolidinyl, pyrazolinyl, benzothienyl, piperazinyl, imidazolyl, thiadiazolyl e.g. 1,2,3-thiadiazolyl, and benzothiazolyl.

Any functional (i.e. reactive) group present in a side-chain may be protected, with the protecting group being a group which is known per se, for example, as described in "Protective Groups in Organic Synthesis", 2nd Ed., T. W. Greene and P. G. M. Wuts, John Wiley & Sons, New York, N.Y., 1991. For example, an amino group can be protected by a tert.-butoxycarbonyl, formyl, trityl, benzyloxycarbonyl, 9-fluorenylmethyloxycarbonyl (Fmoc), trifluoroacetyl, 2-(biphenylyl)isopropoxy-carbonyl or isobornyloxycarbonyl group or in the form of a phthalimido group; or a hydroxyl group can be protected by a tert.-butyldimethylsilyl, tetrahydropyranyl, 4-methoxybenzyl, or benzyl; or a carboxyl group can be protected in the form of an ester, for example as a methyl or tert.butyl ester. The protecting group may be retained in the final compound or optionally removed by techniques known in the art.

The compounds of this invention may contain one or more asymmetric carbon atoms and may therefore occur as racemates and racemic mixtures, single enantiomers, diastereomeric mixtures and individual diastereomers. Furthermore, where a compound of the invention contains an olefinic double bond, this can have the (E) or (Z) configuration. Also, each chiral centre may be of the R or S configuration. All such isomeric forms of these compounds are embraced by the present invention.

Examples of compounds of formula (I) are shown below in Table 1a and 1b:

TABLE 1a

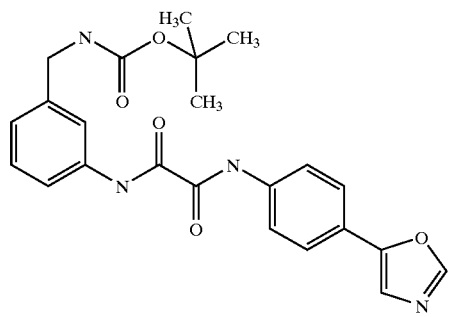

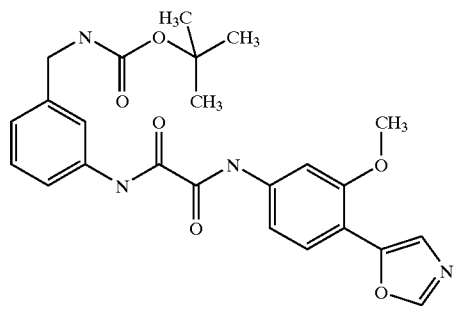

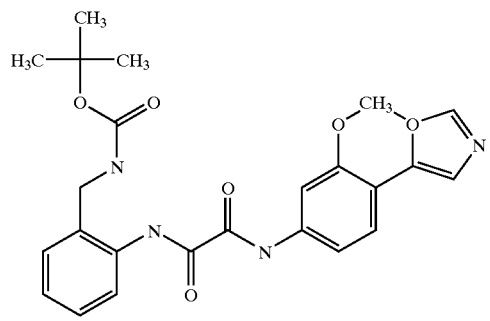

TABLE 1a-continued
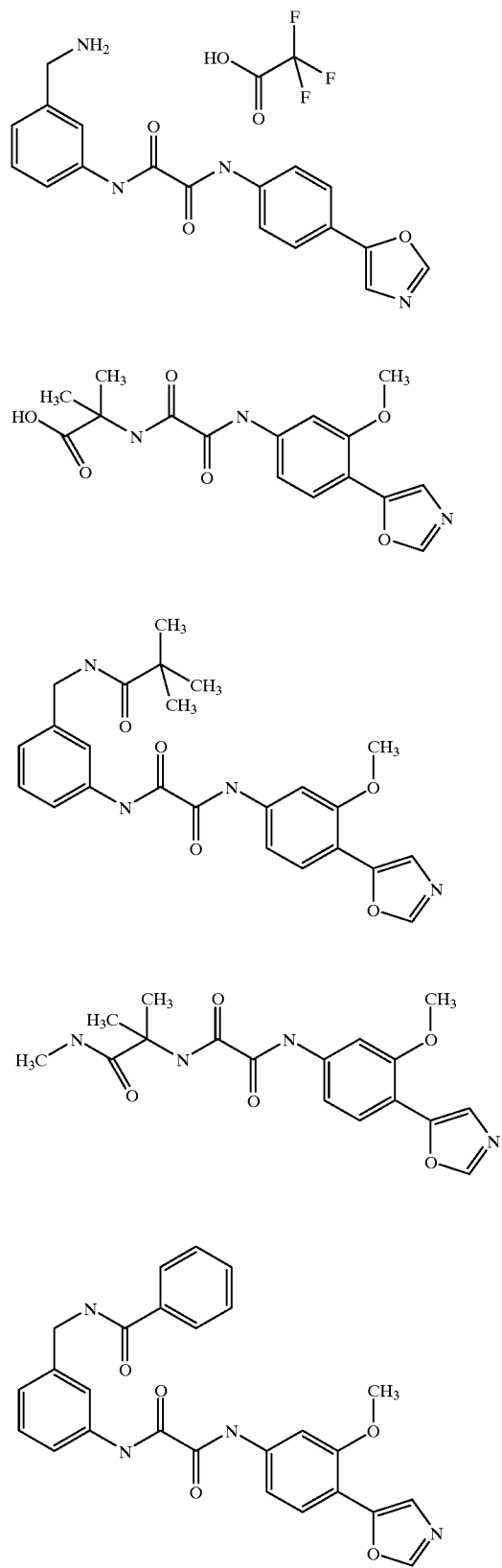

TABLE 1a-continued
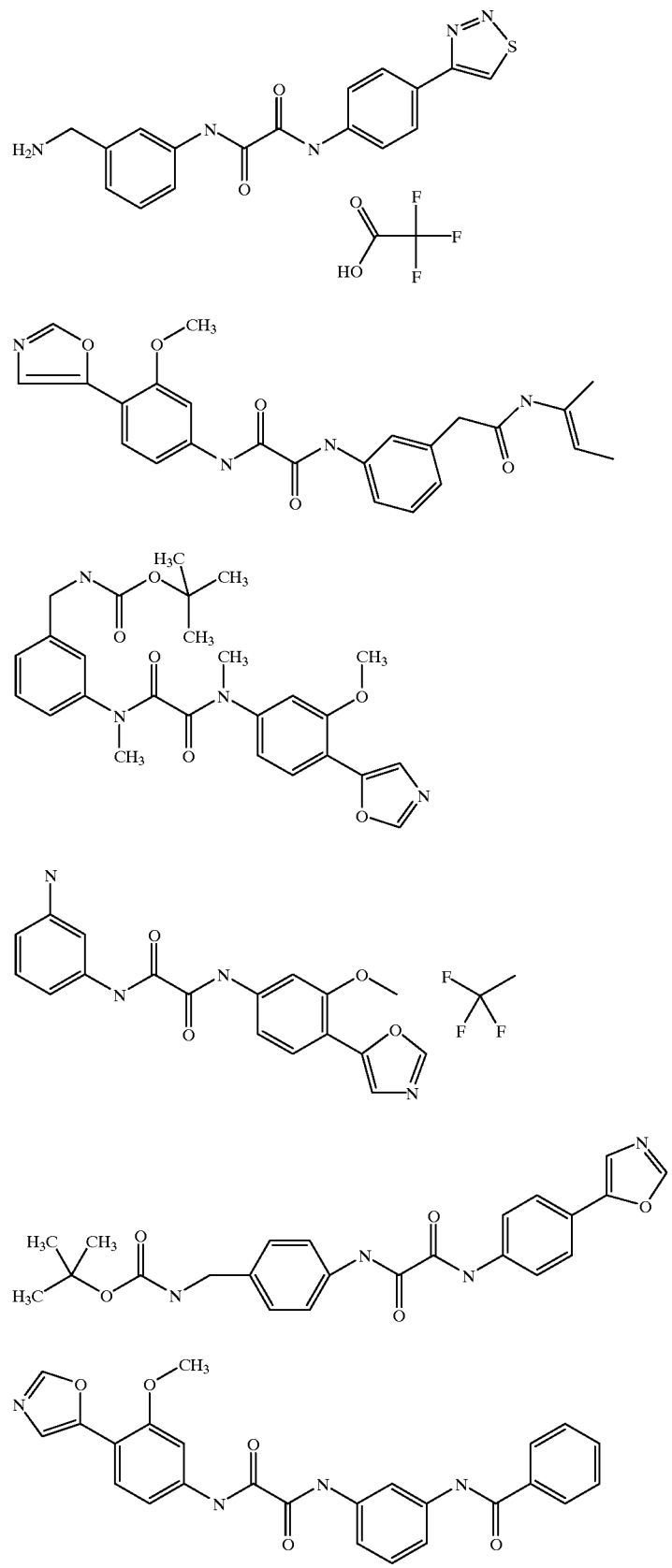

TABLE 1a-continued
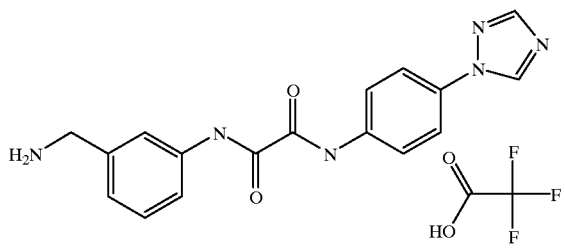
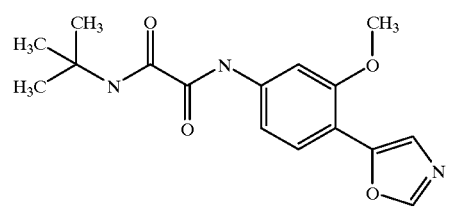
Chiral
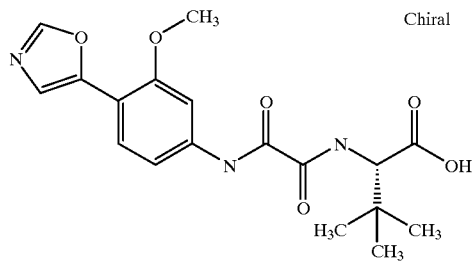
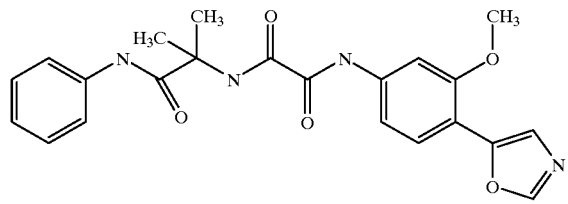
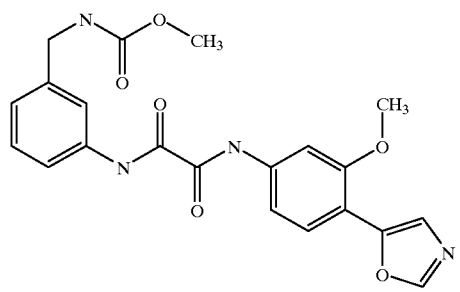
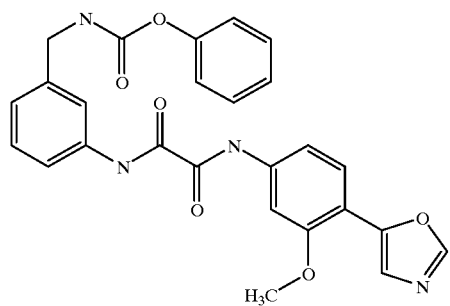

TABLE 1a-continued
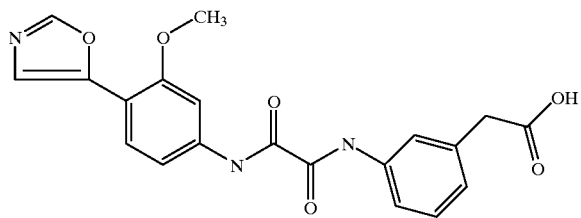
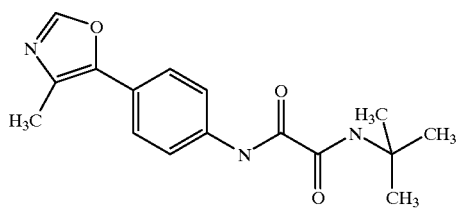
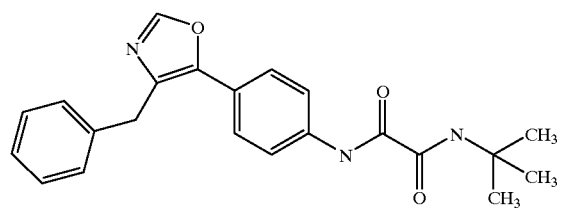
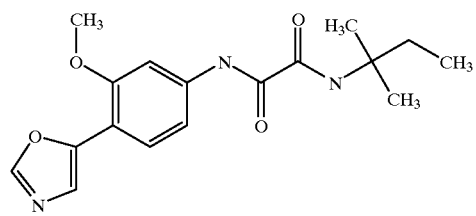
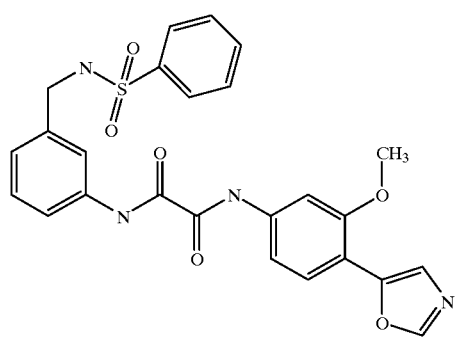
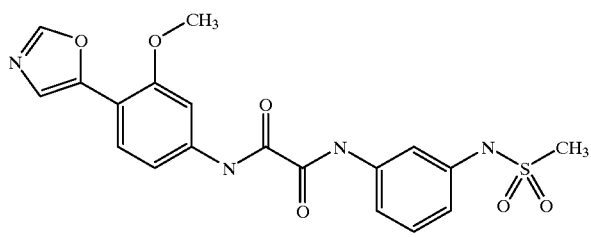

TABLE 1a-continued
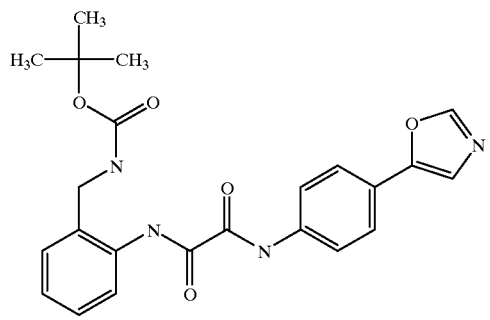
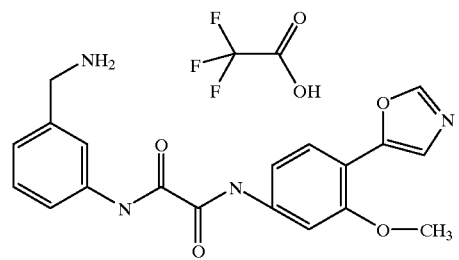
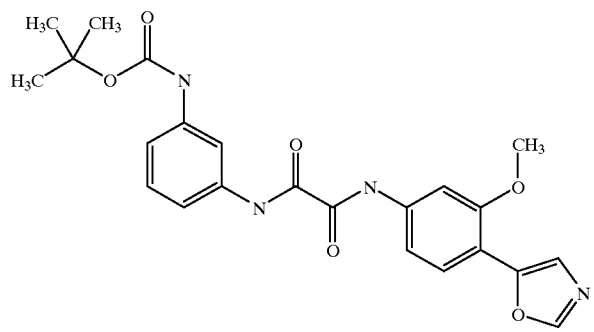
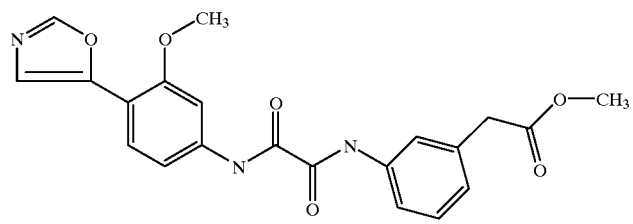
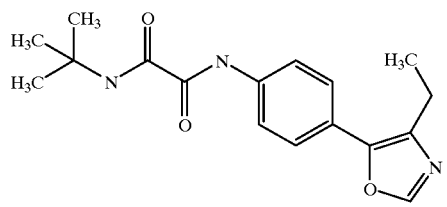

TABLE 1a-continued
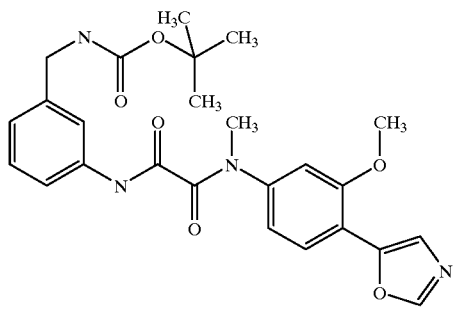
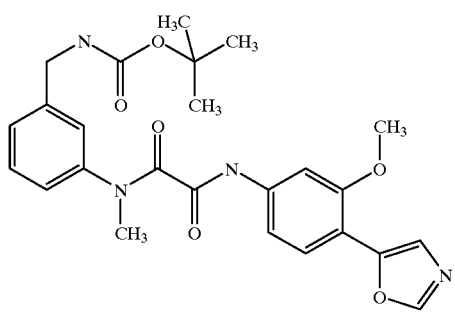
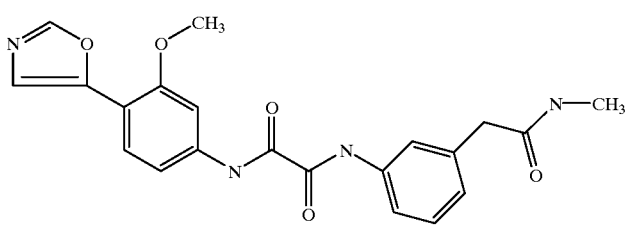
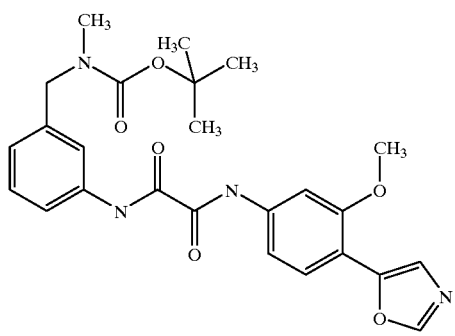
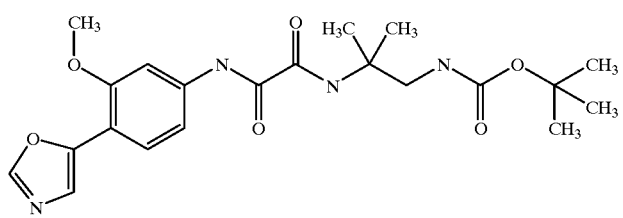

TABLE 1a-continued
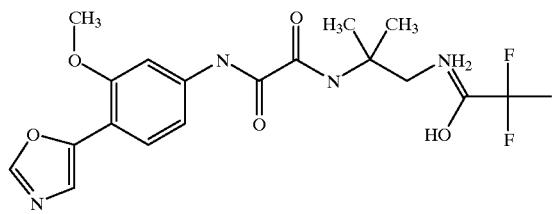
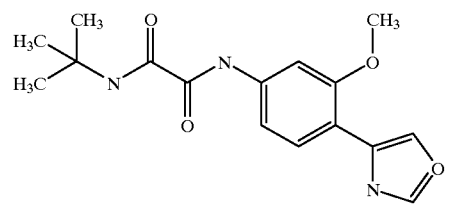
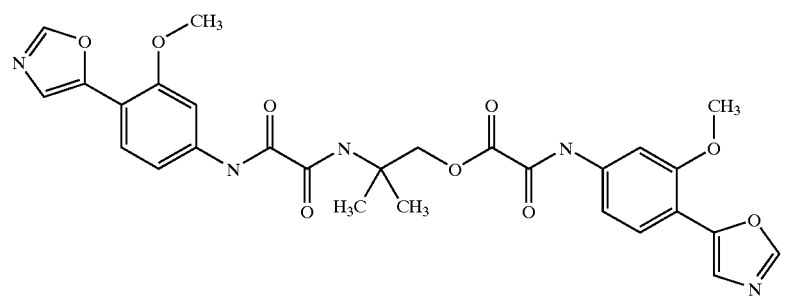
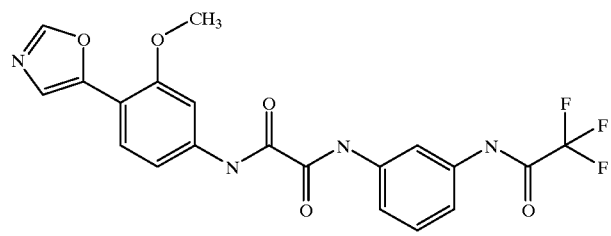
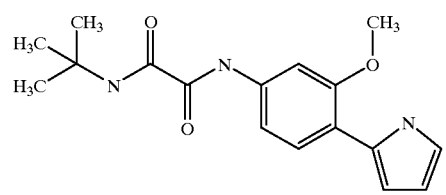
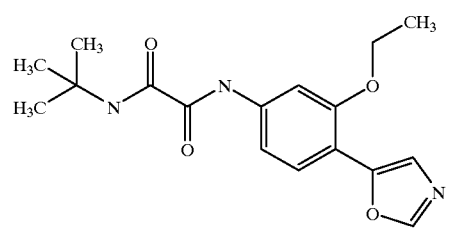

TABLE 1a-continued
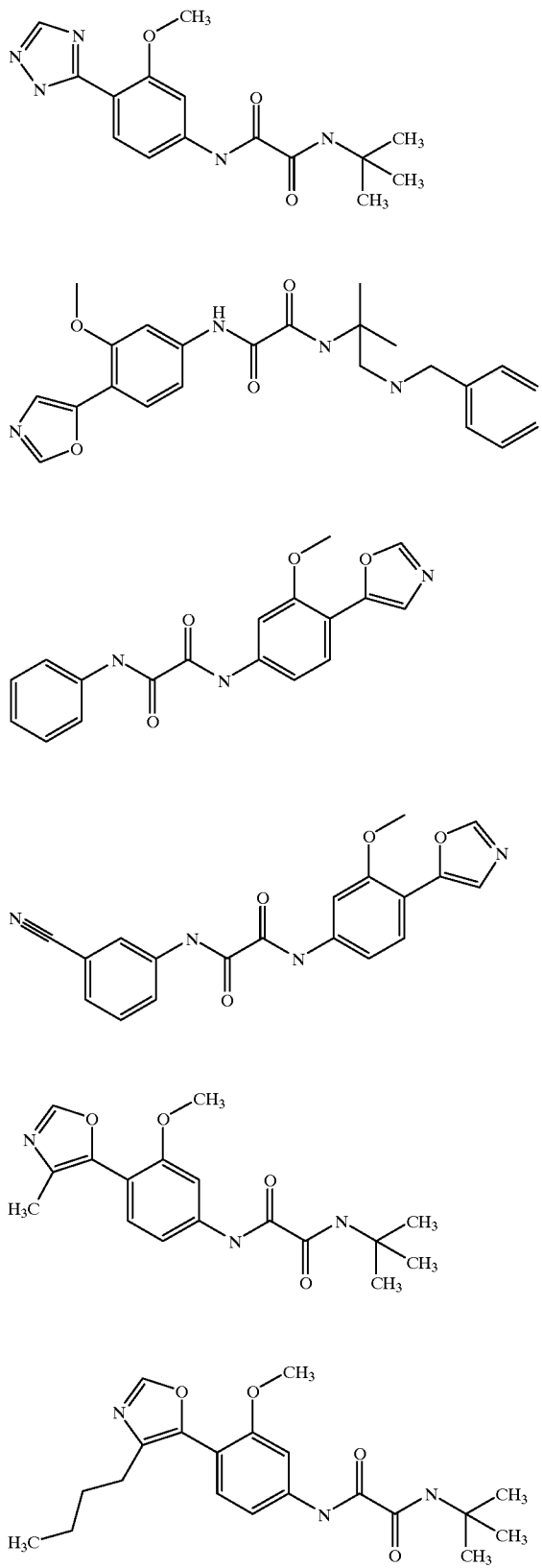

TABLE 1a-continued
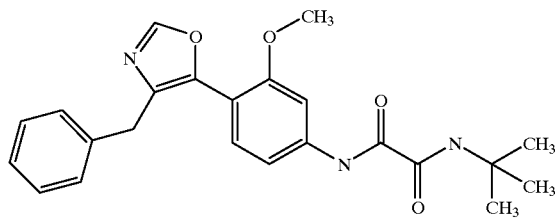
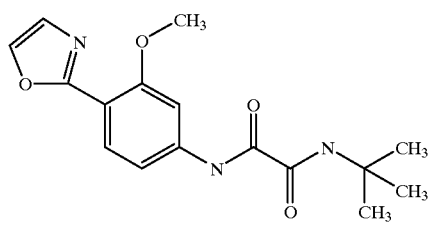
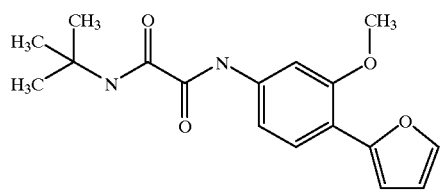
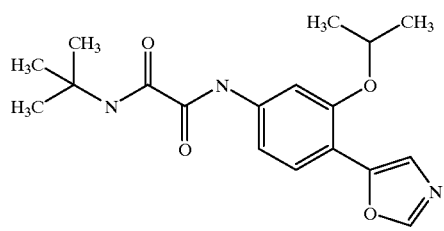
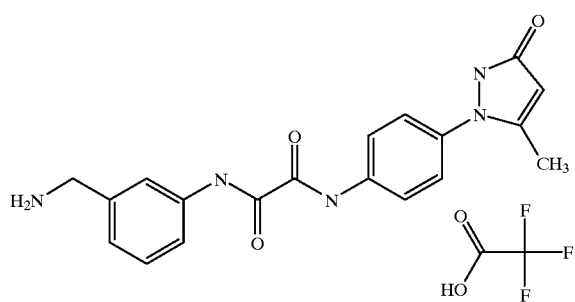
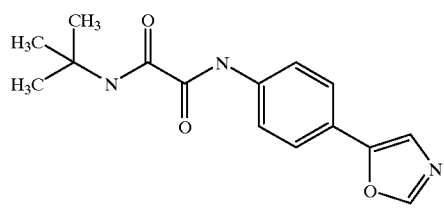

TABLE 1a-continued
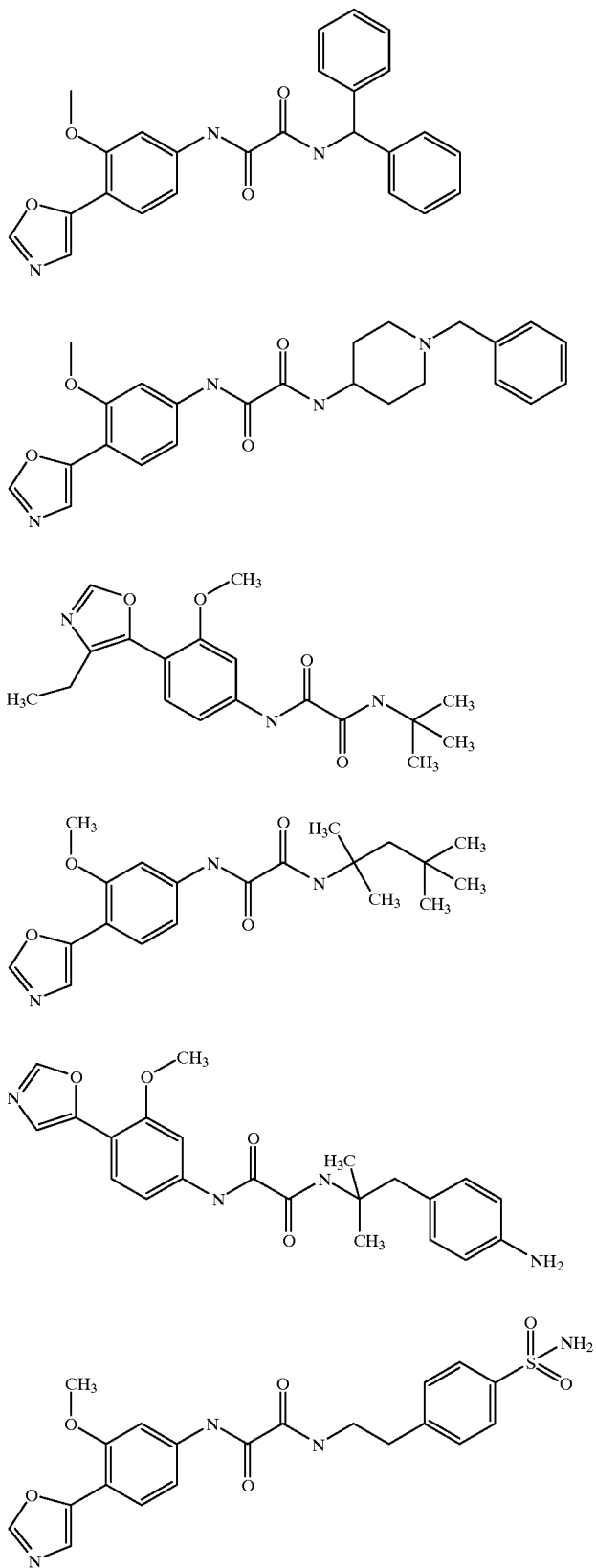

TABLE 1a-continued
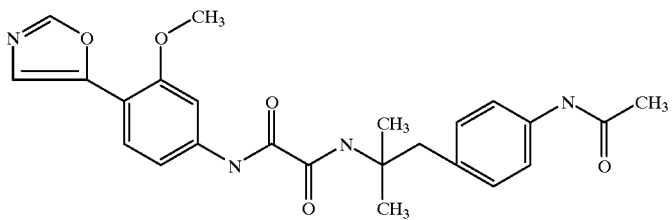
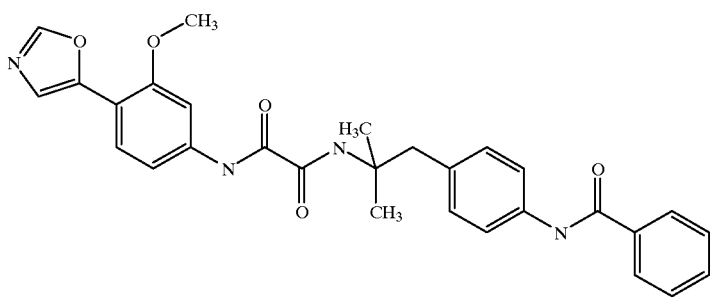
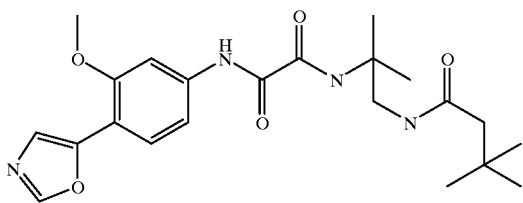
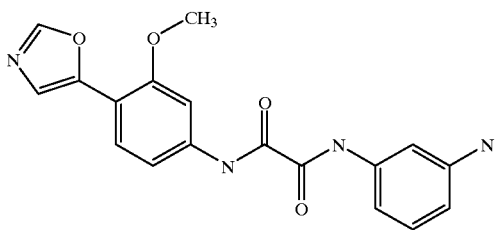
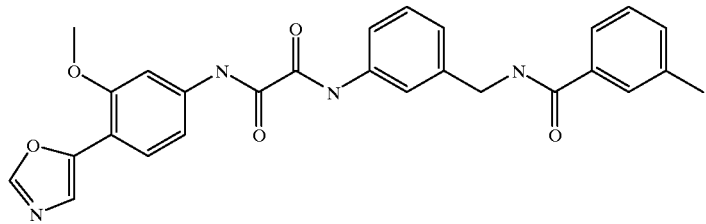
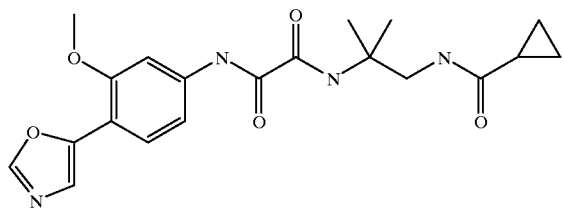

TABLE 1a-continued
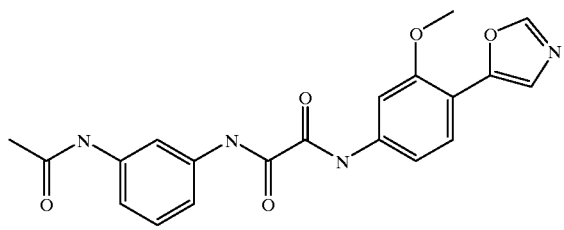
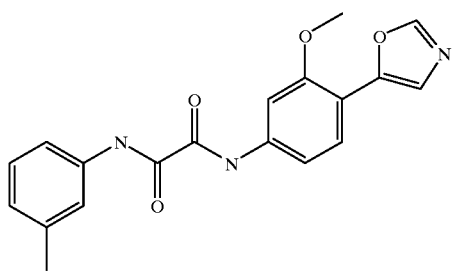
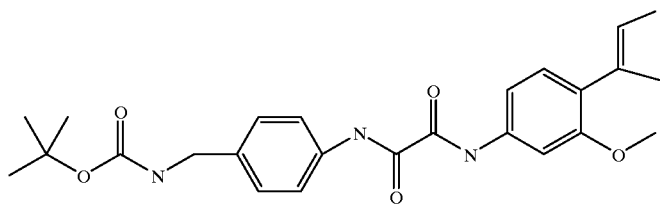
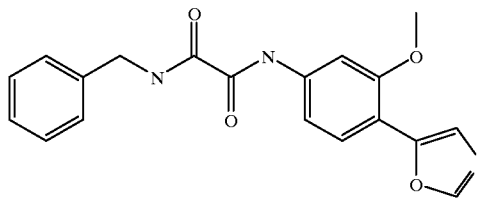
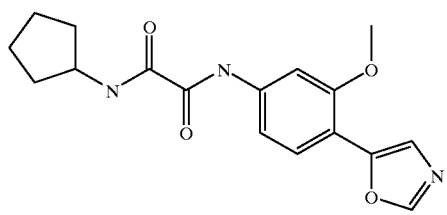
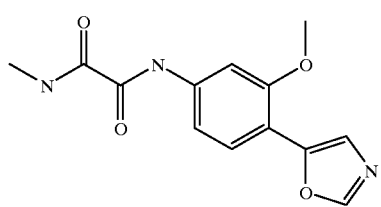

TABLE 1a-continued
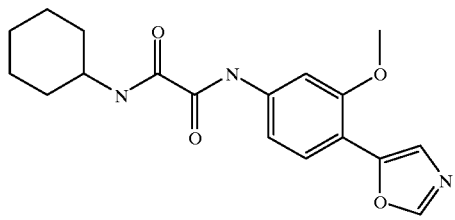
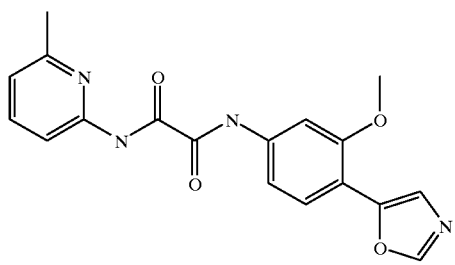
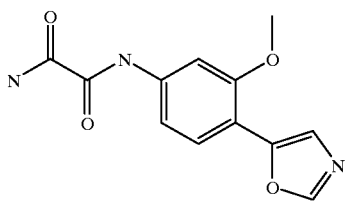
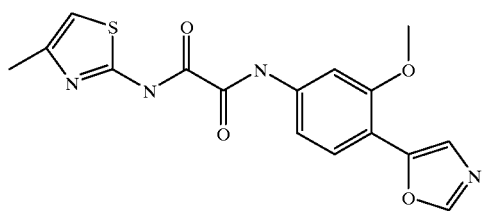
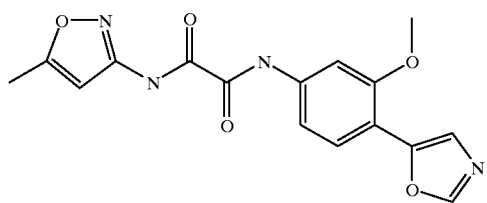
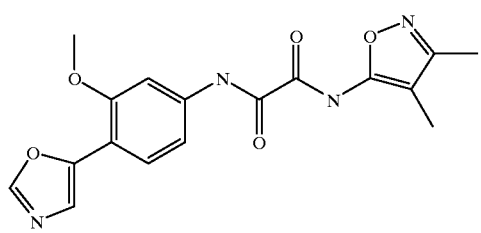

TABLE 1a-continued
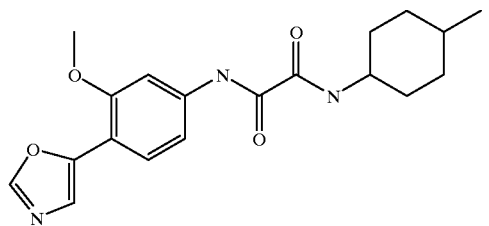
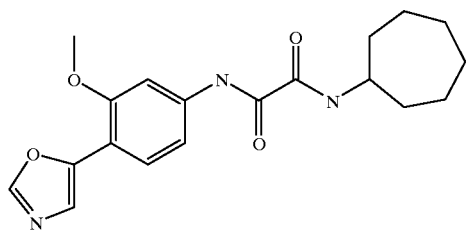
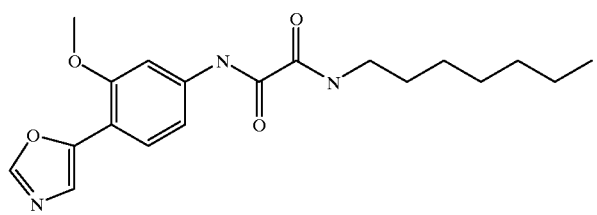
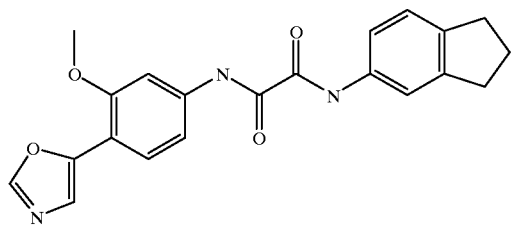
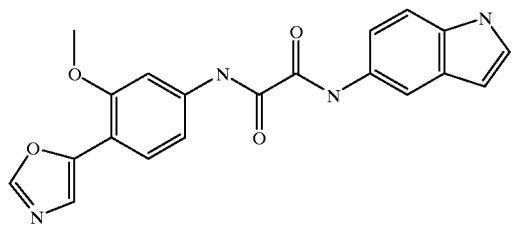
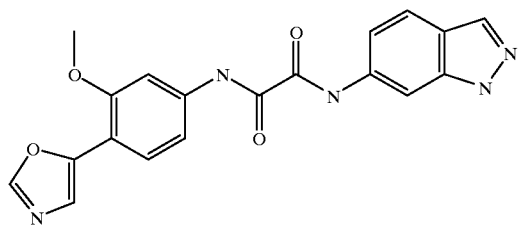

TABLE 1a-continued
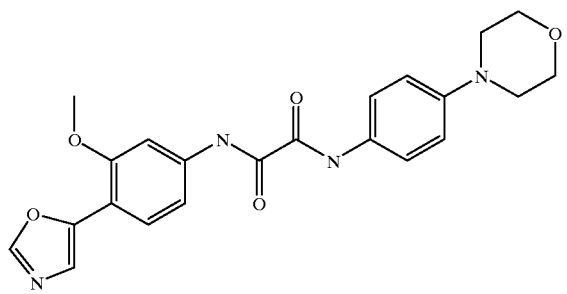
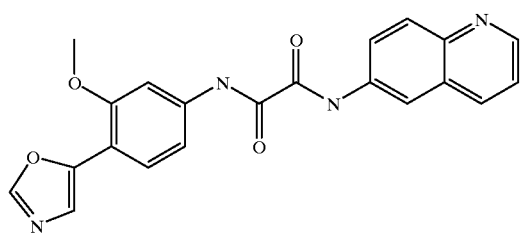
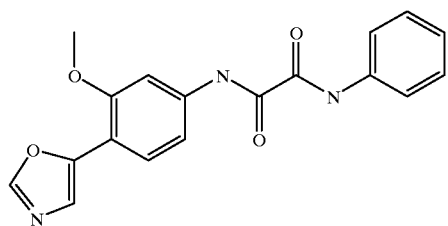
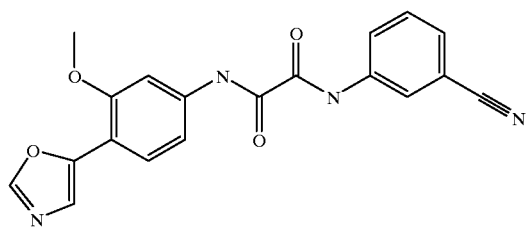
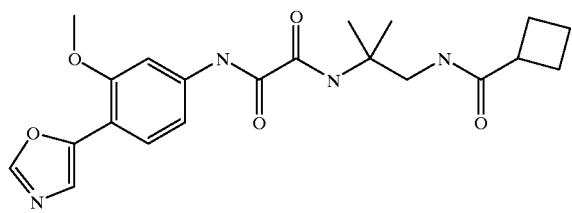
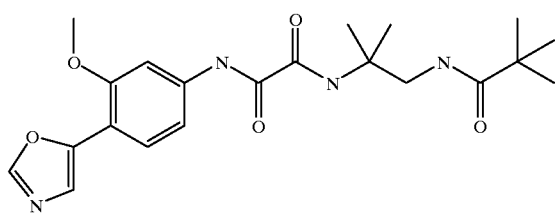

TABLE 1a-continued
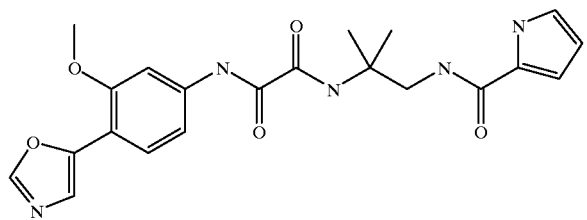
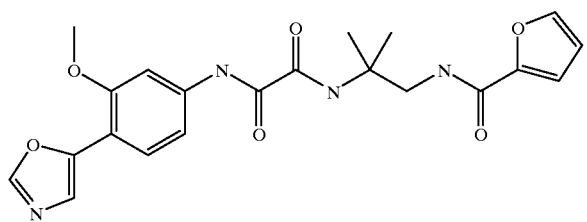
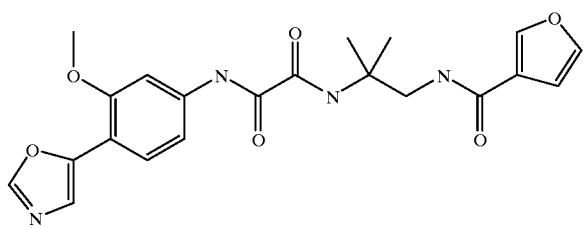
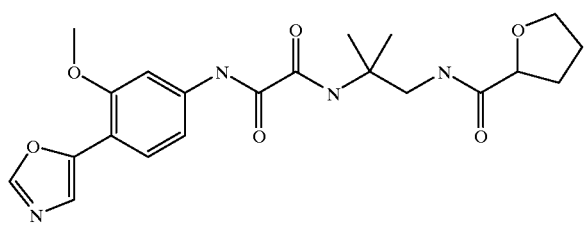
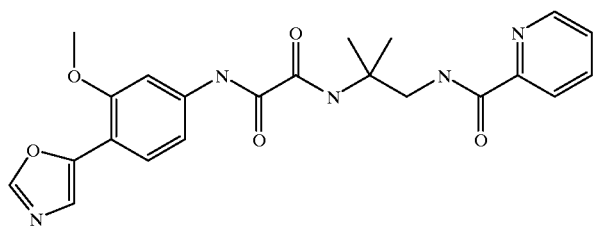
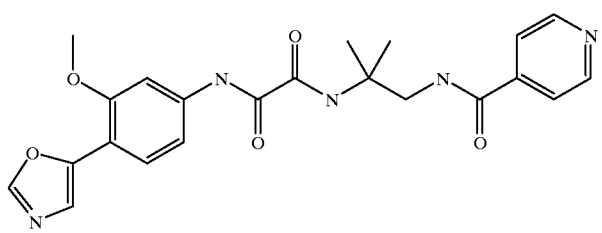

TABLE 1a-continued
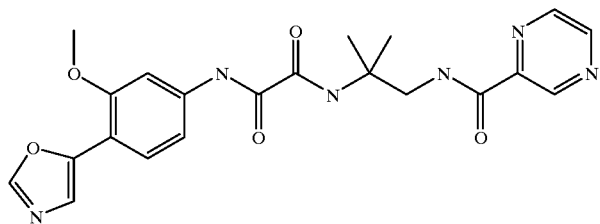
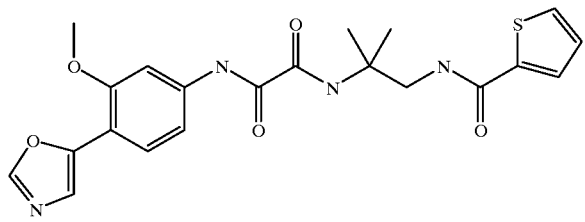
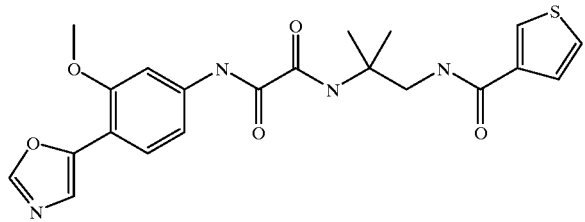
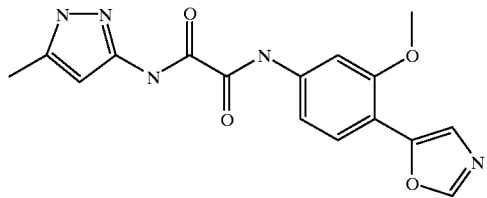
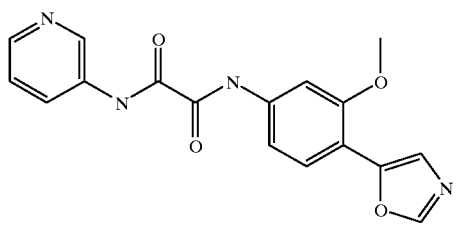
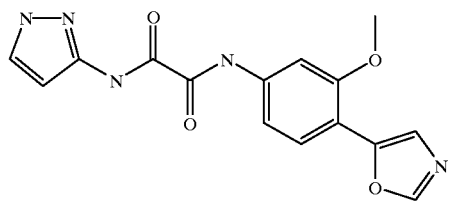
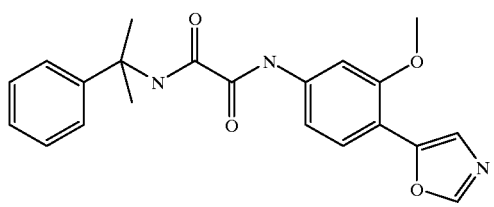

TABLE 1a-continued
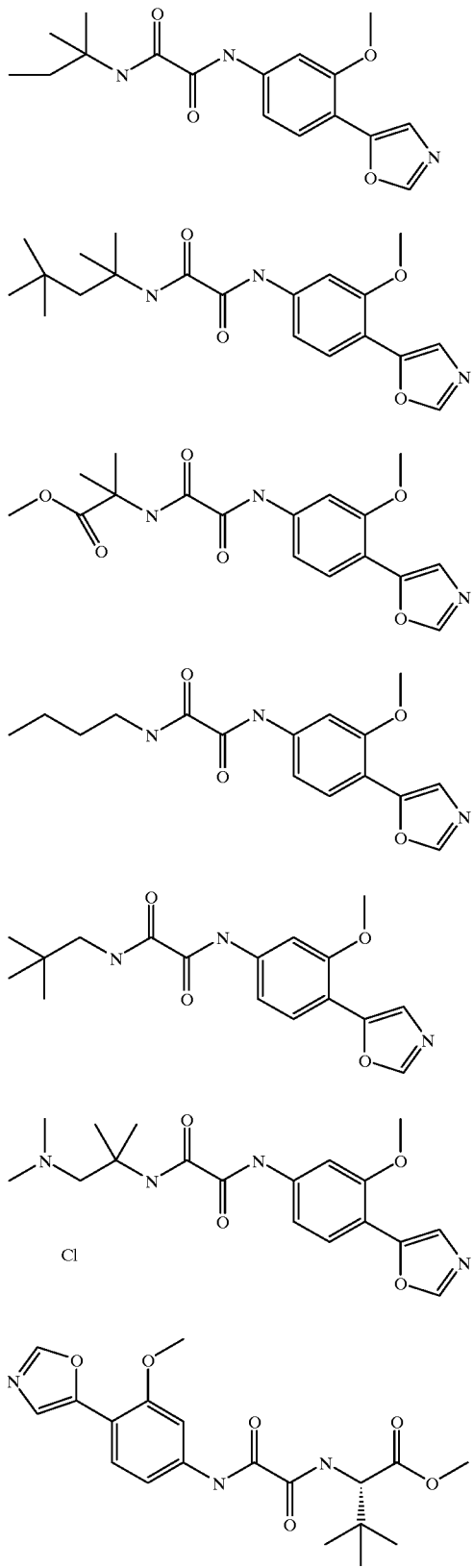

TABLE 1a-continued
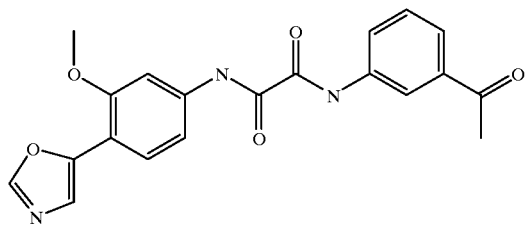
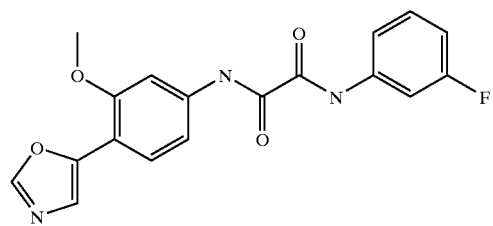
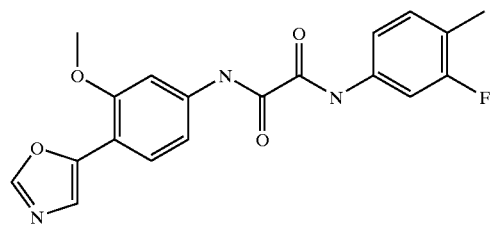
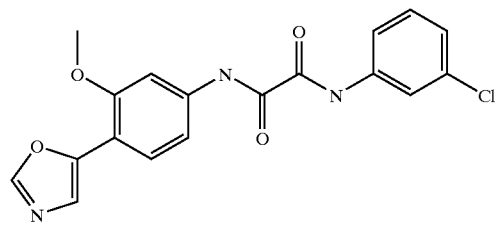
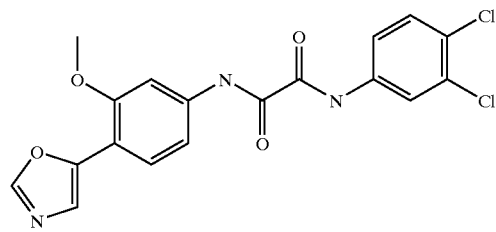
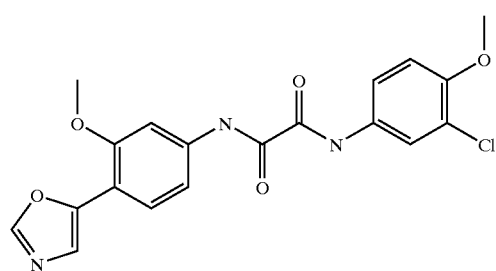

TABLE 1a-continued
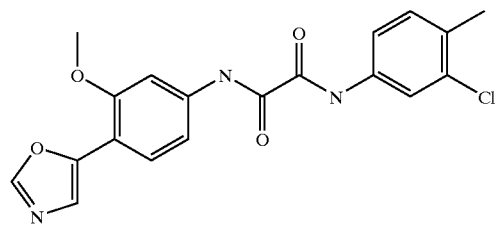
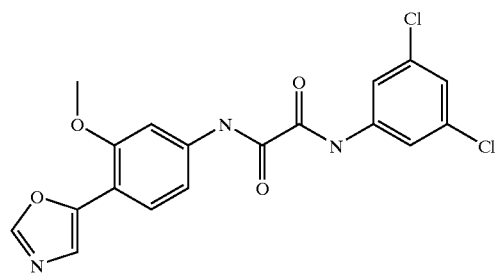
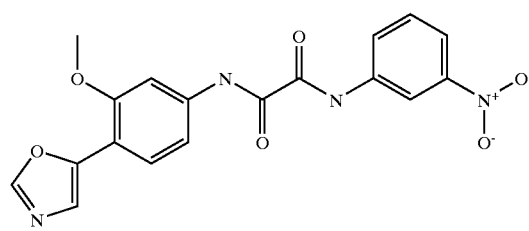
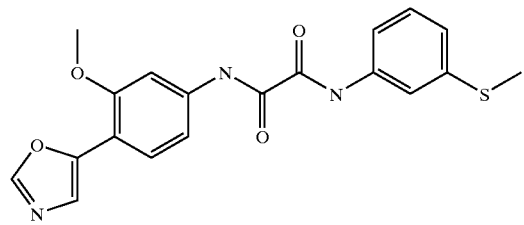
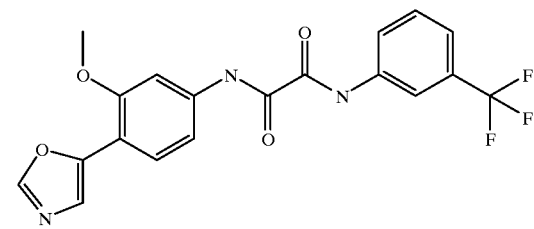
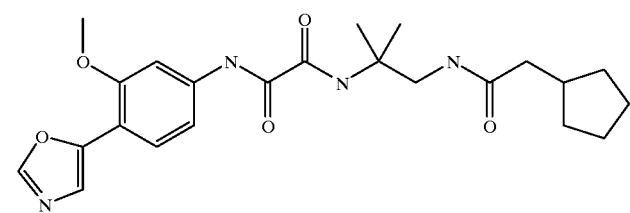

TABLE 1a-continued
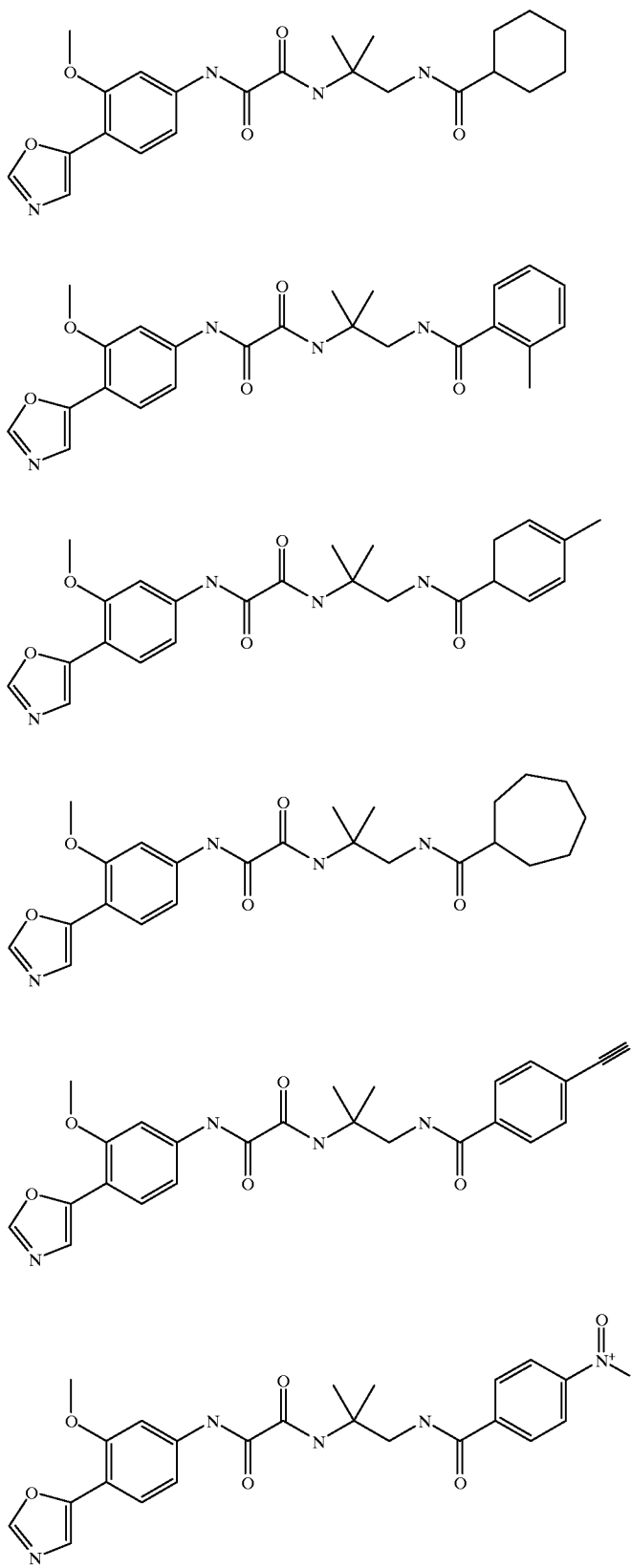

TABLE 1a-continued
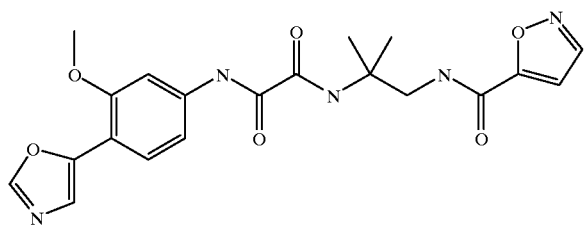
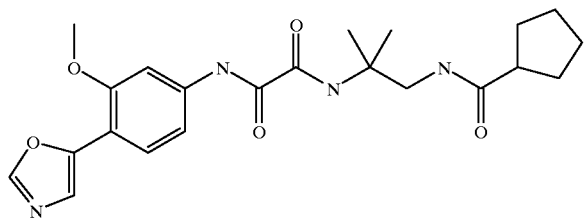
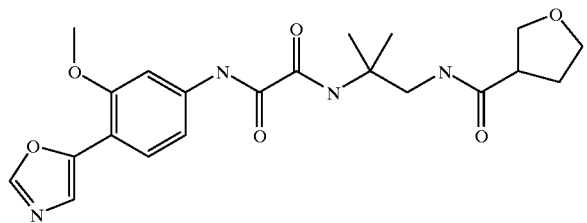
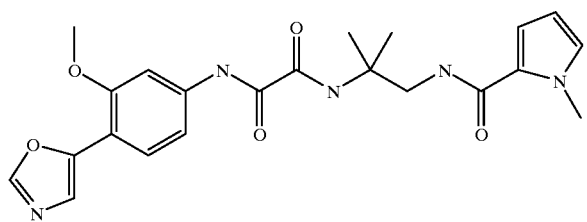
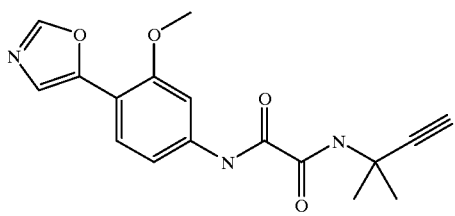
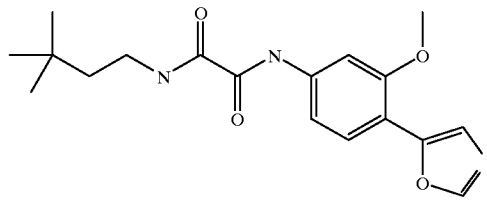
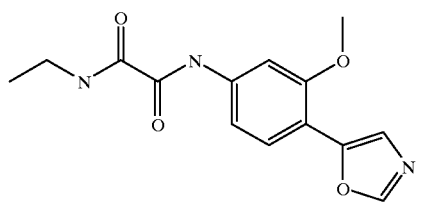

TABLE 1a-continued
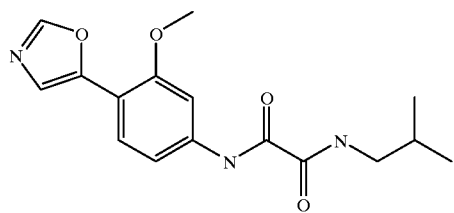
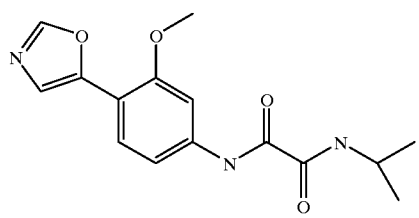
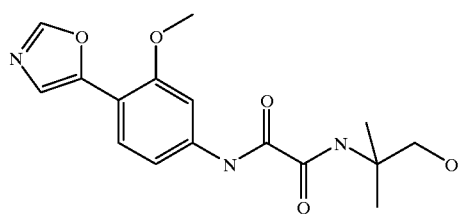
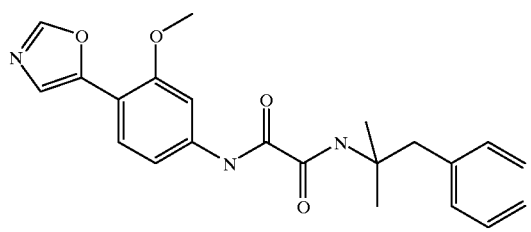
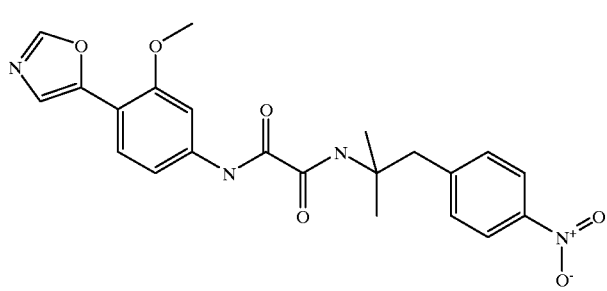
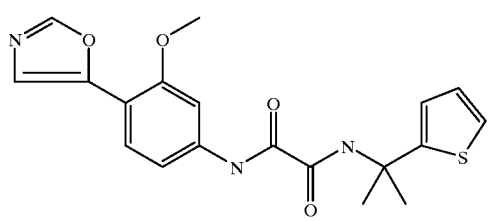

TABLE 1a-continued
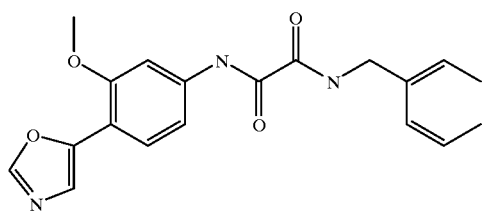
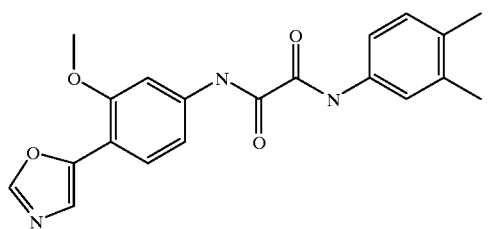
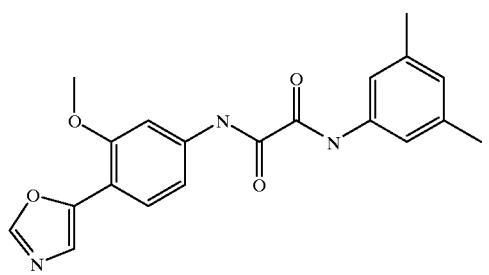
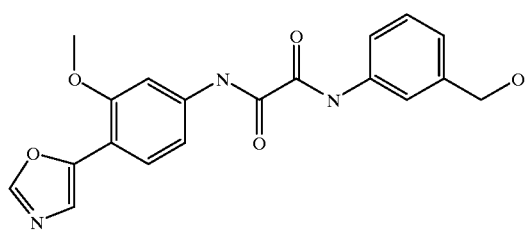
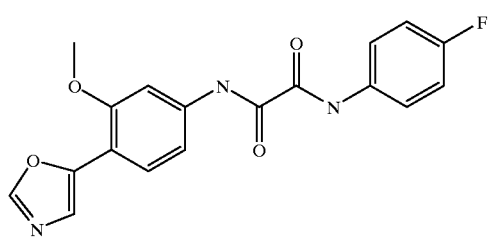

TABLE 1a-continued
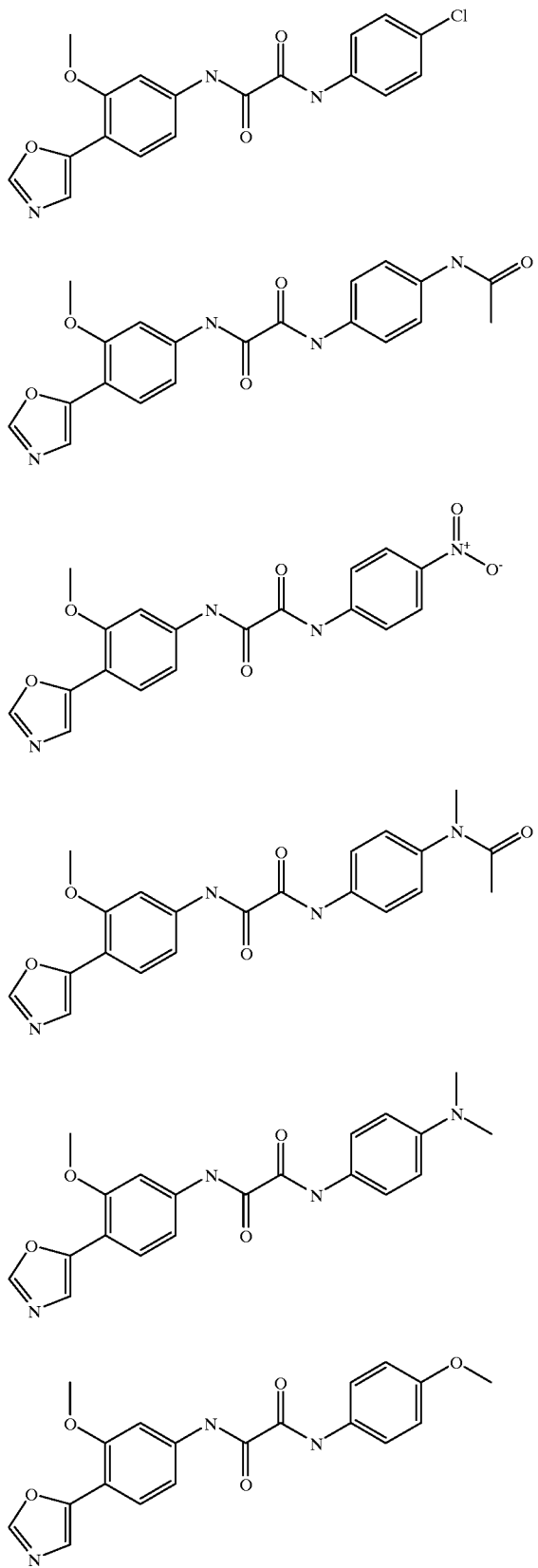

TABLE 1a-continued
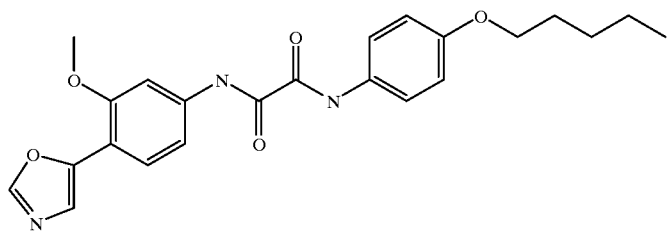
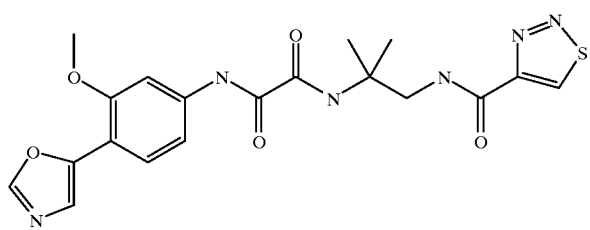
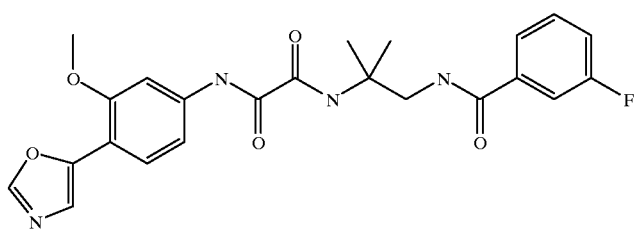
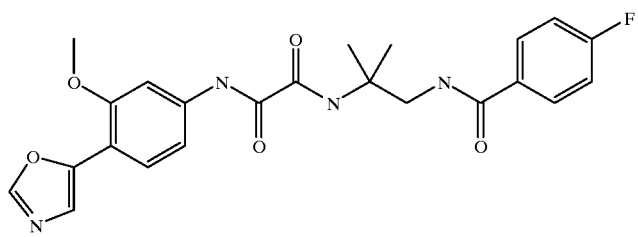
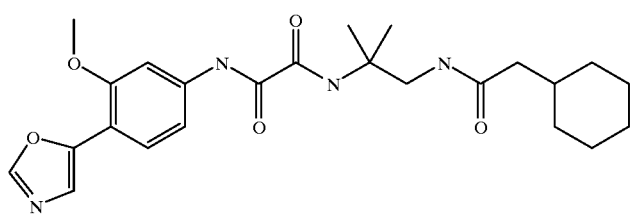
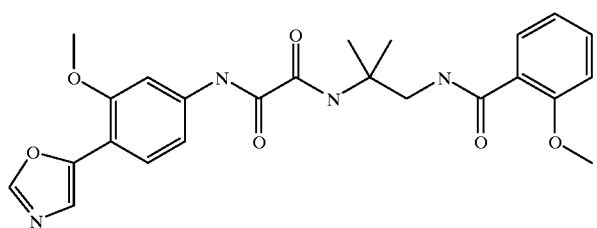

TABLE 1a-continued
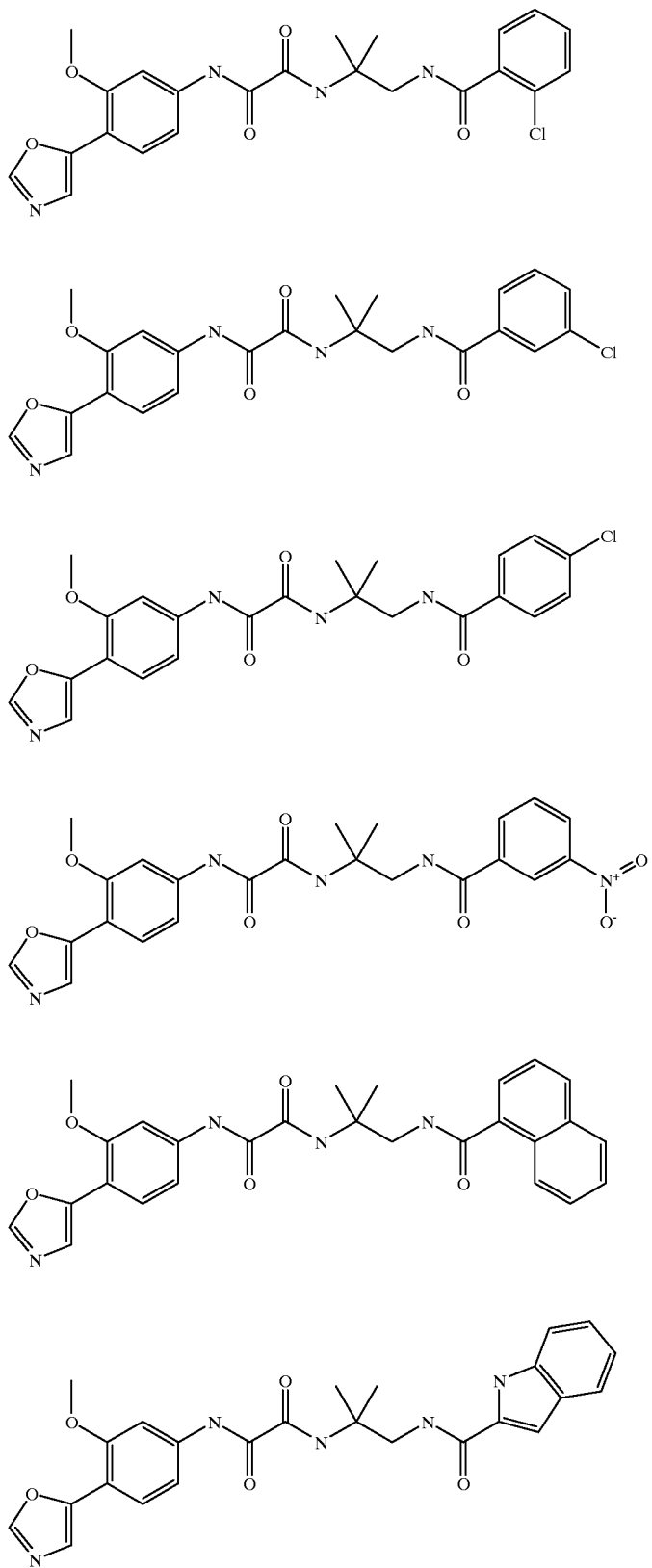

TABLE 1a-continued
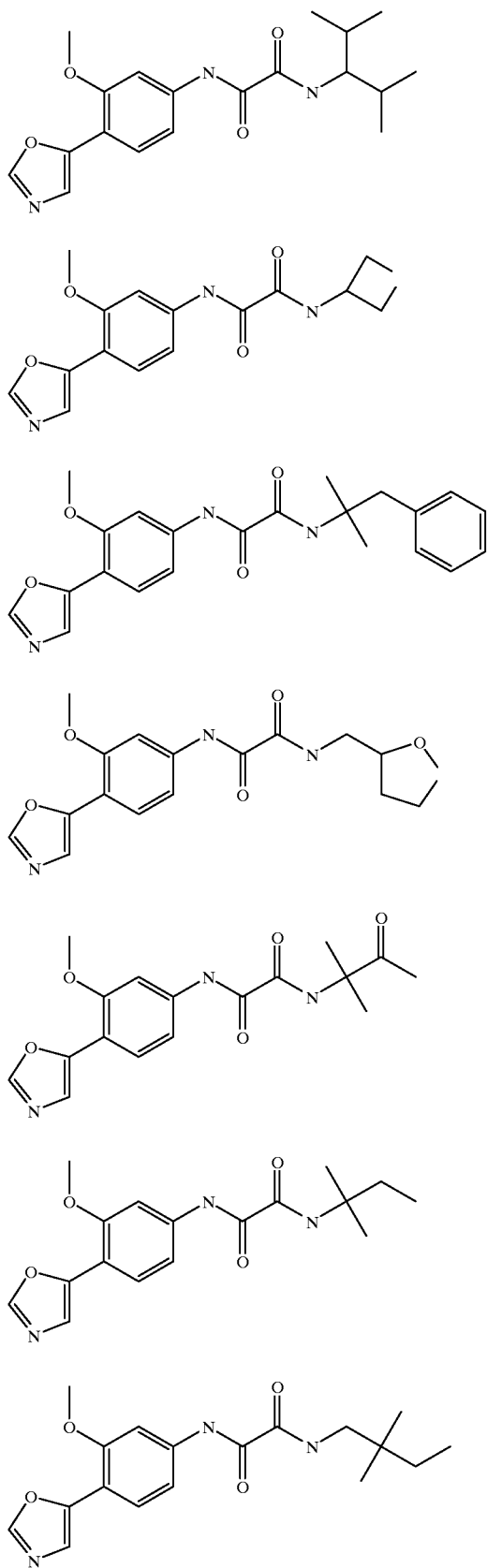

TABLE 1a-continued
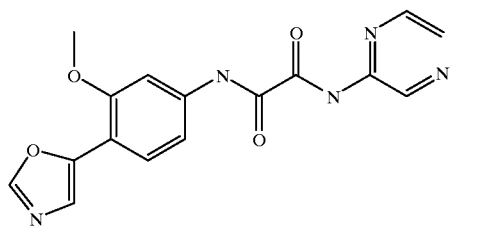
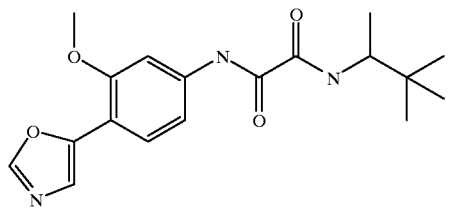
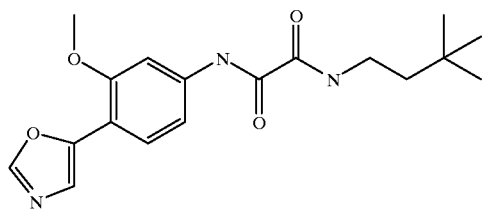
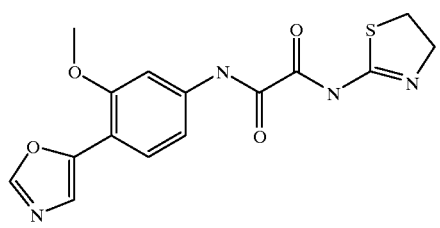
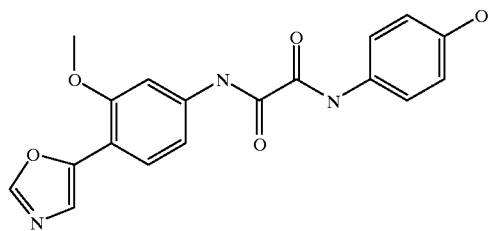
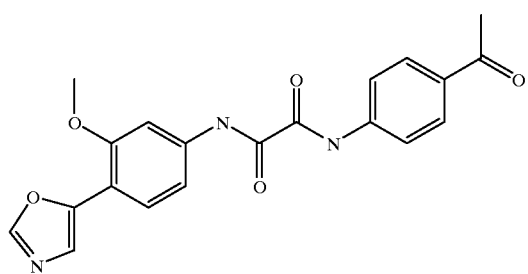

TABLE 1a-continued
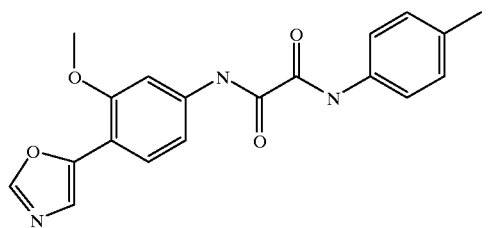
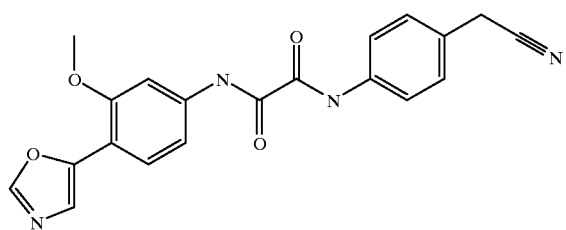
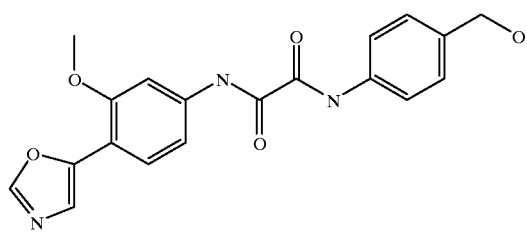
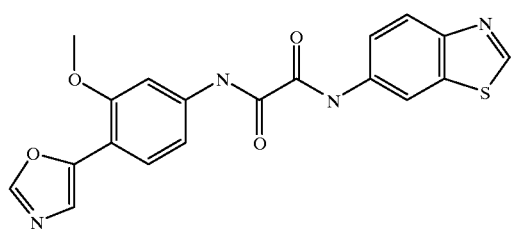
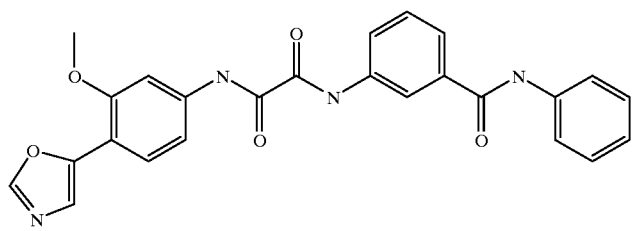
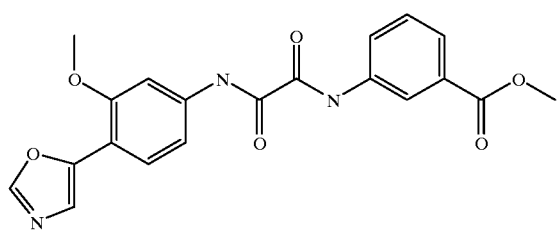

TABLE 1a-continued
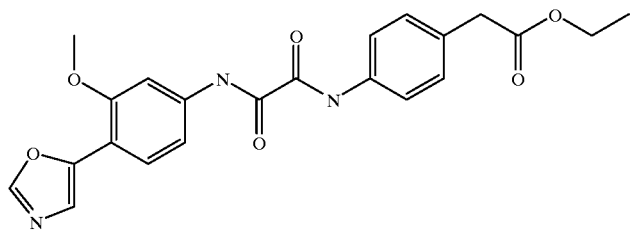
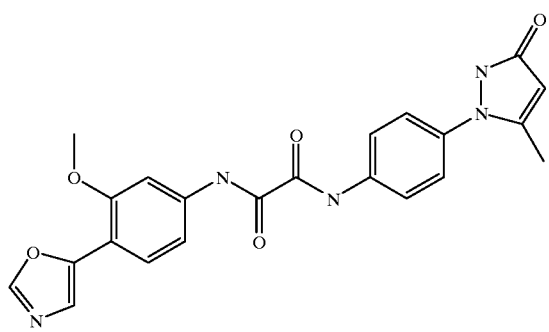
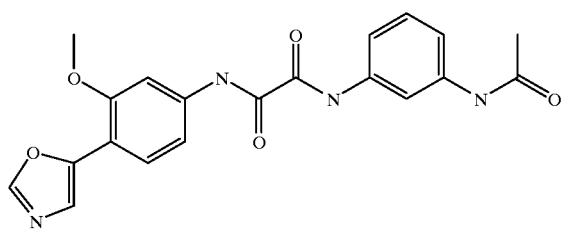
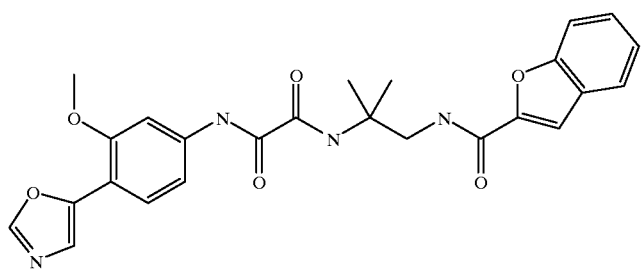
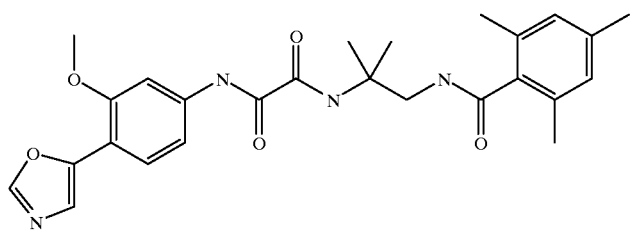

TABLE 1a-continued
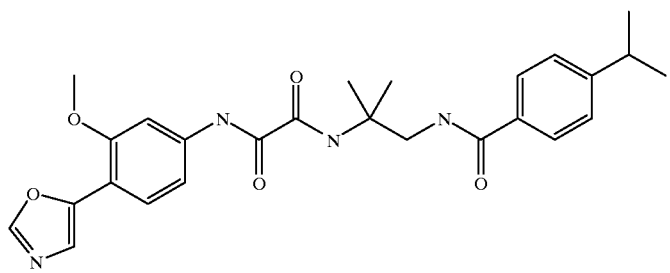
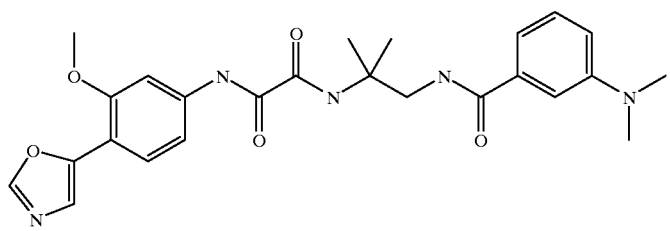
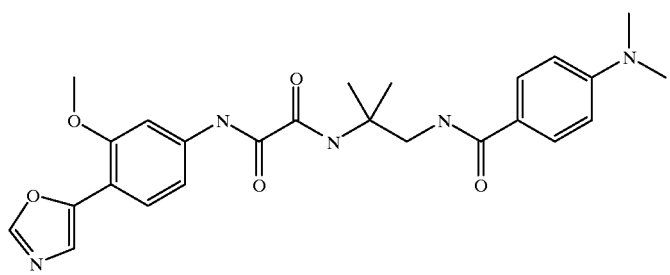
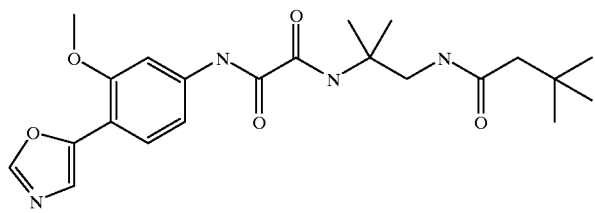
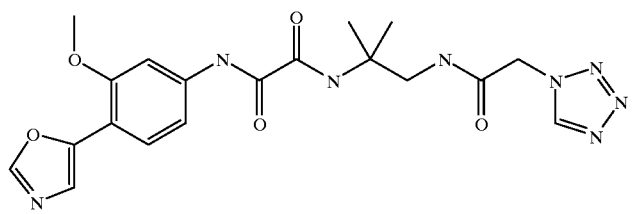
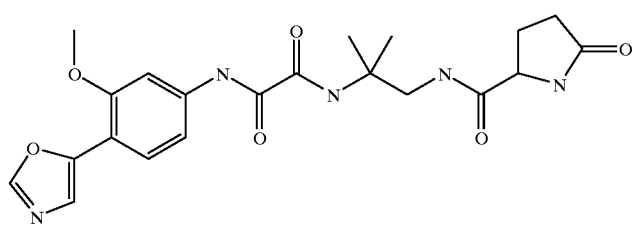

TABLE 1a-continued
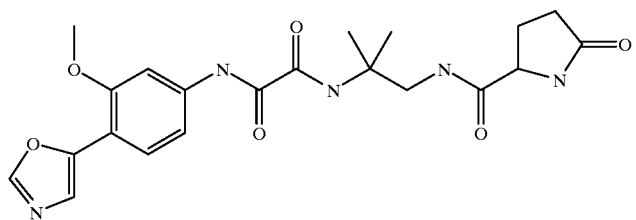
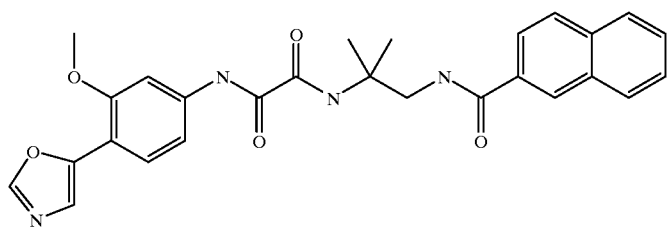
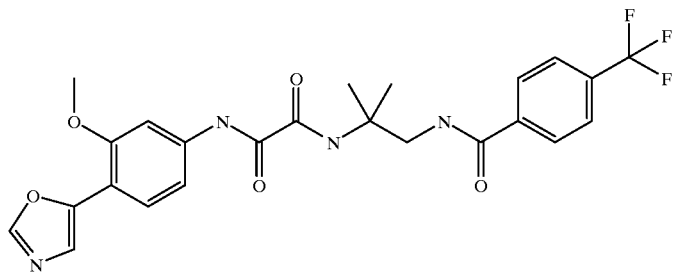
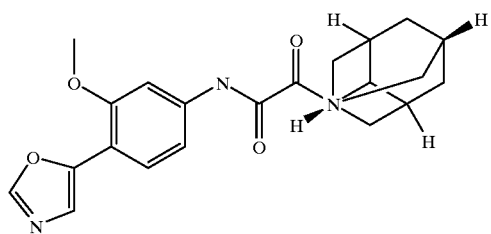
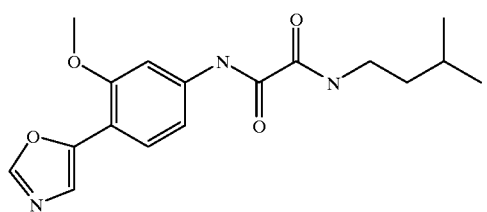
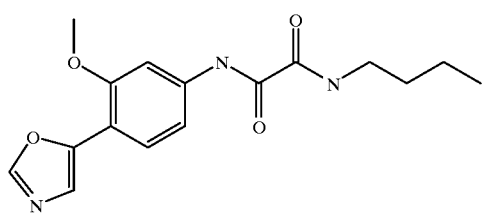

TABLE 1a-continued
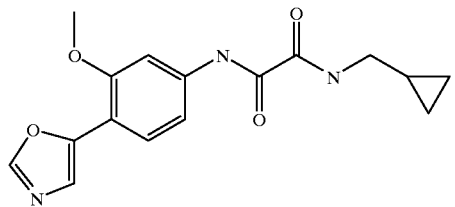
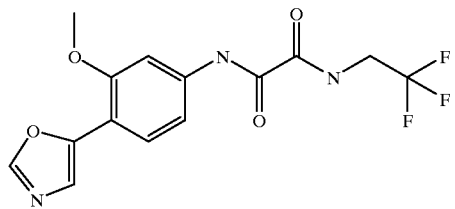
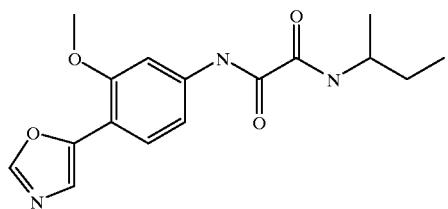
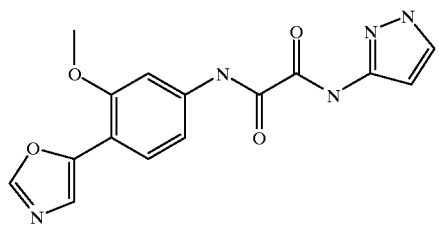
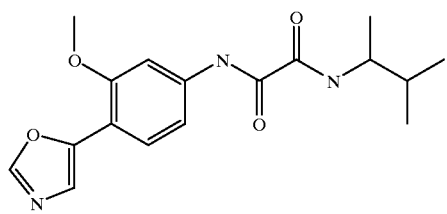
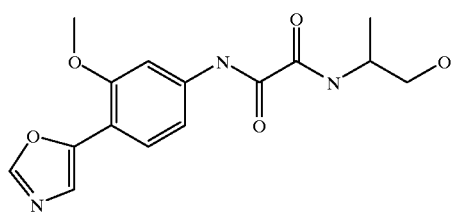
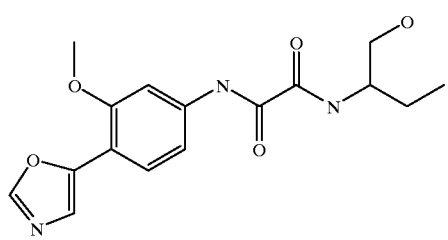

TABLE 1a-continued
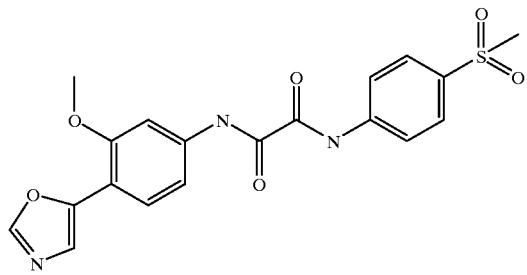
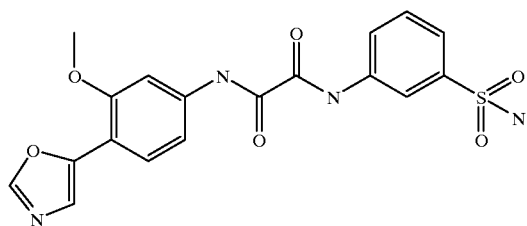
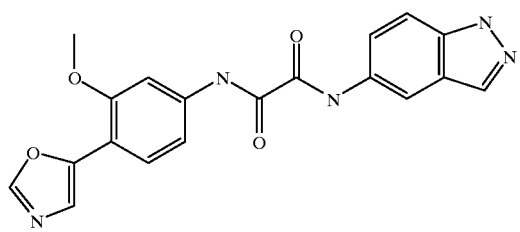
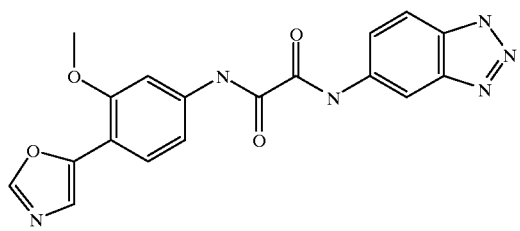
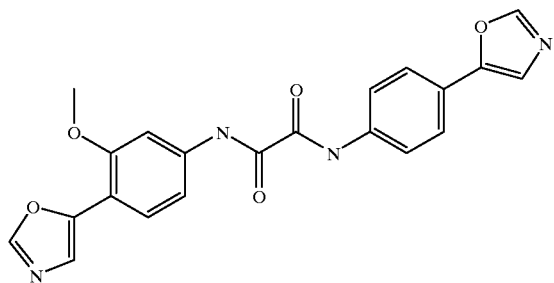
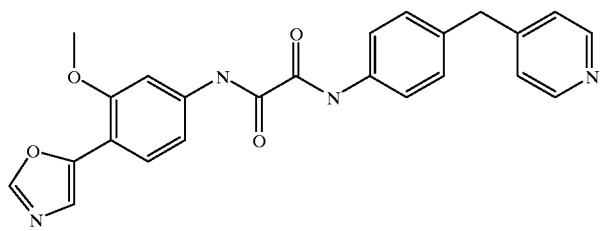

TABLE 1a-continued
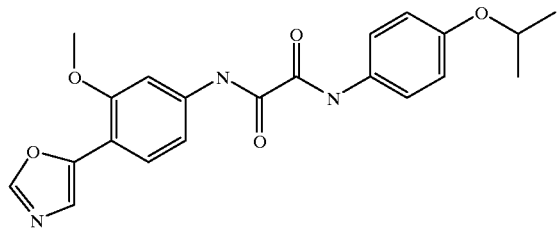
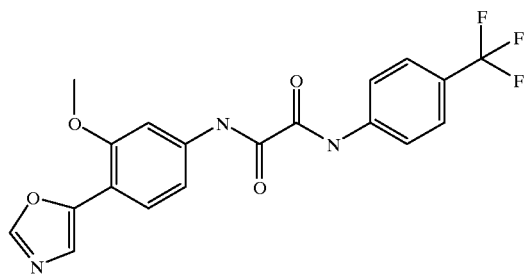
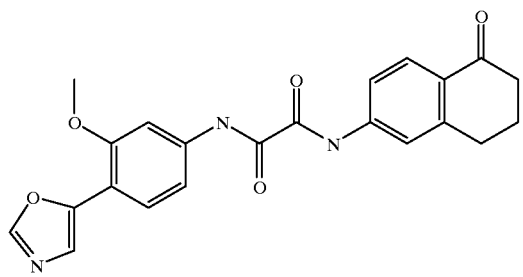
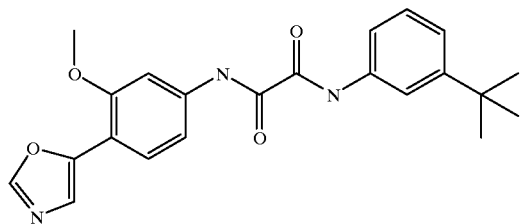
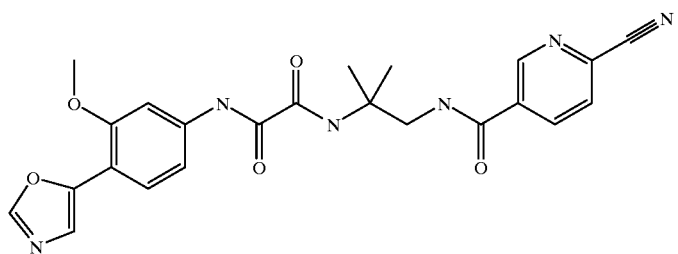
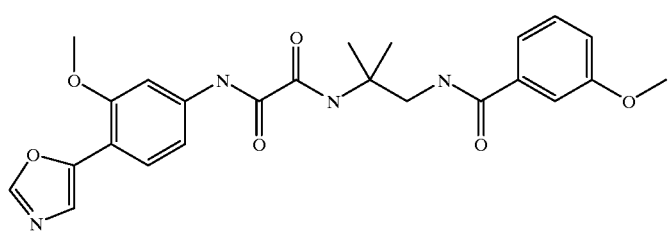

US 6,867,299 B2
TABLE 1a-continued
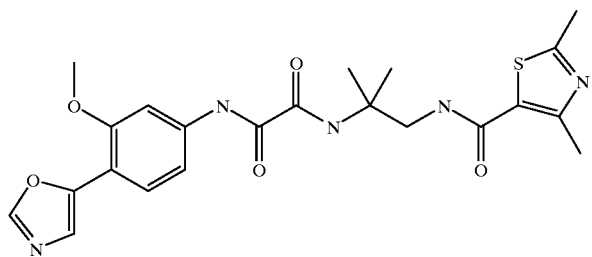
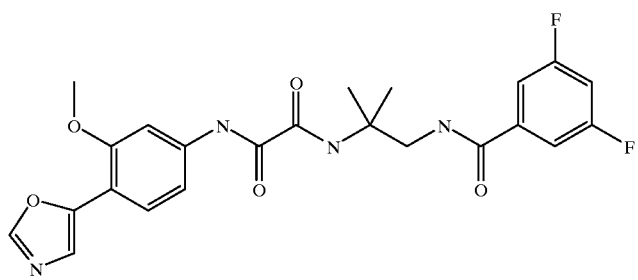
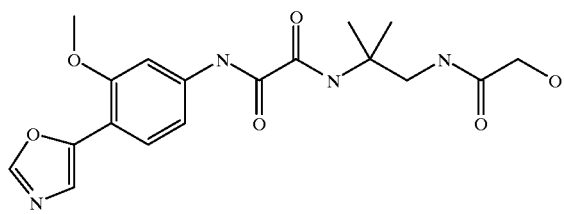
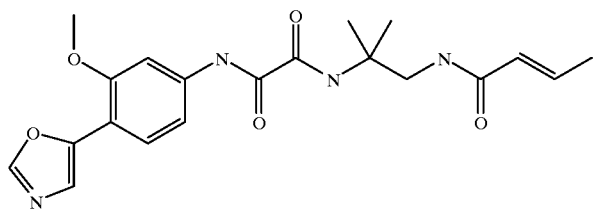
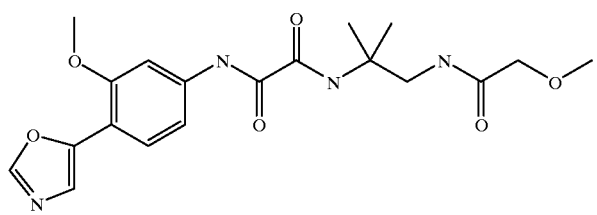
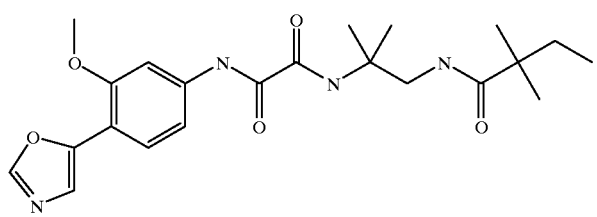

TABLE 1a-continued
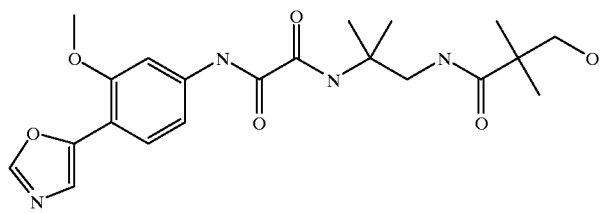
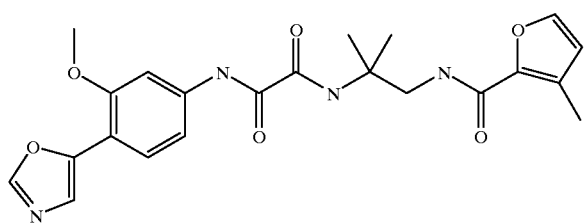
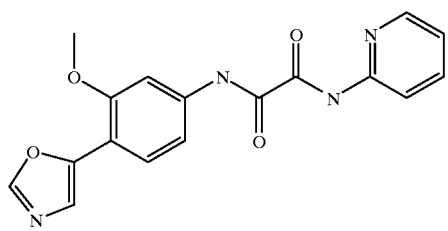
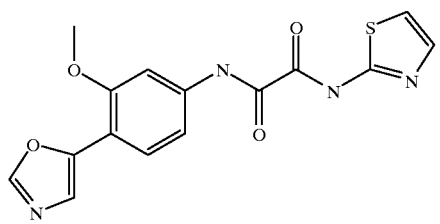
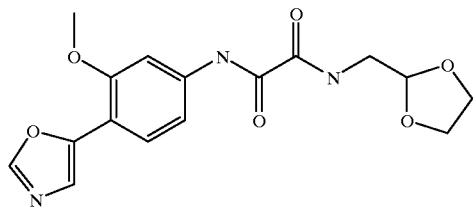
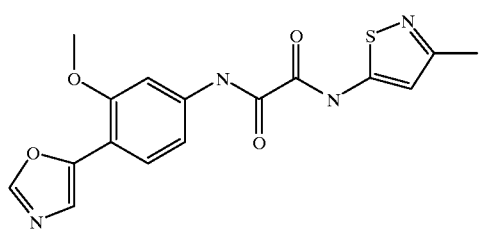

TABLE 1a-continued
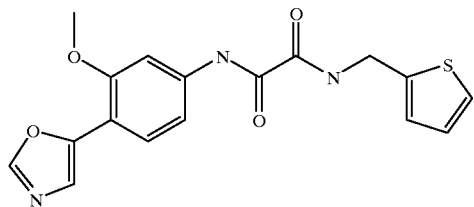
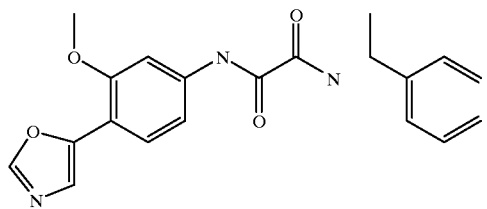
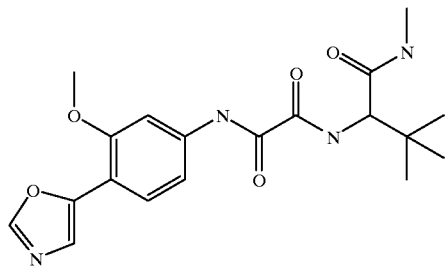
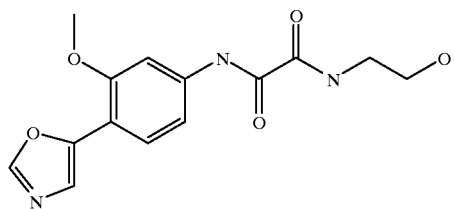
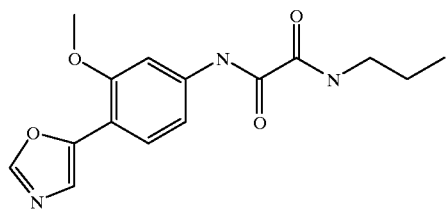
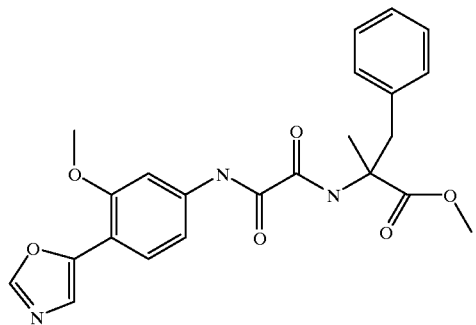

TABLE 1a-continued
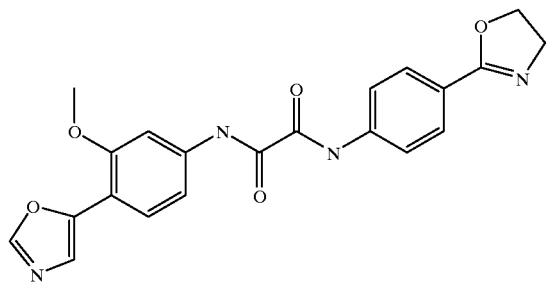
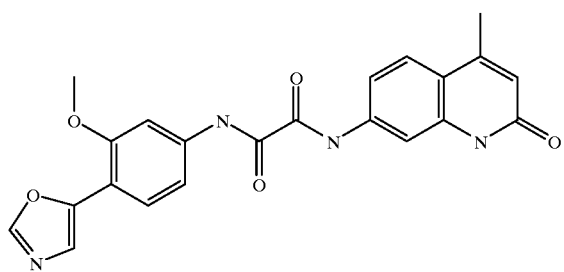
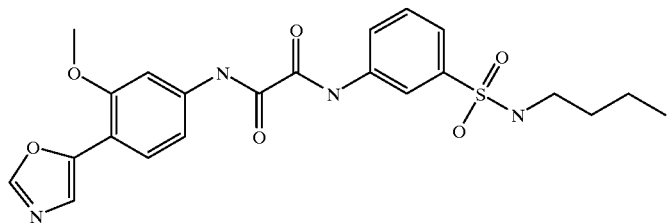
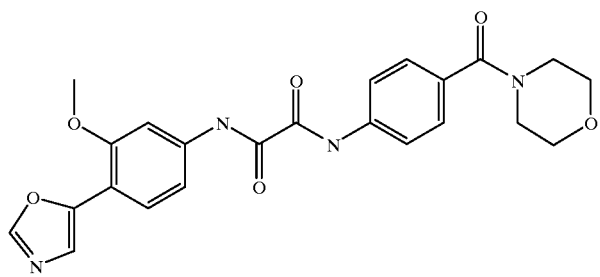
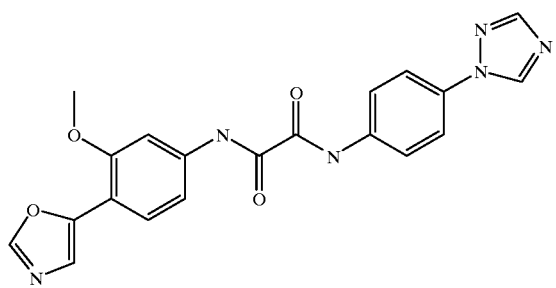

TABLE 1a-continued
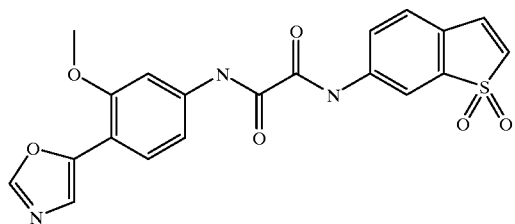
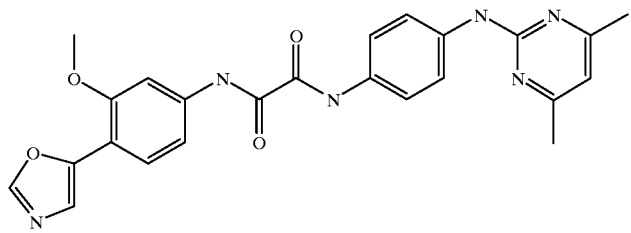
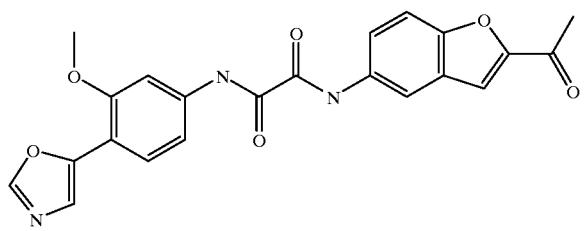
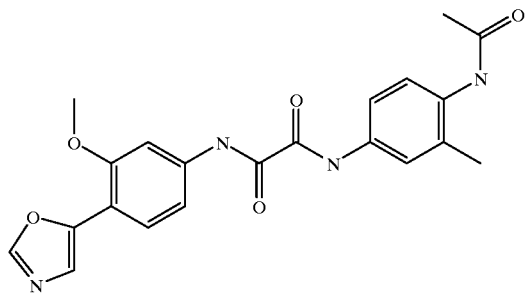
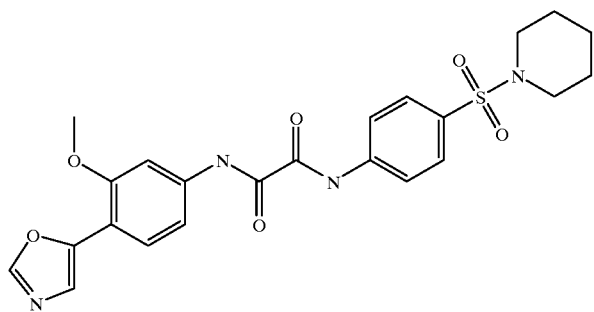
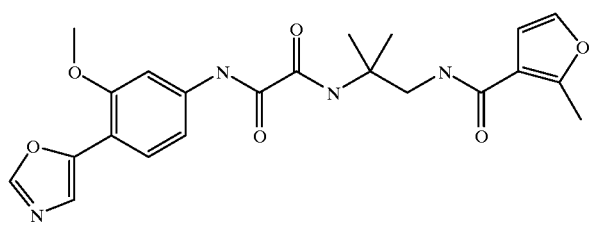

TABLE 1a-continued
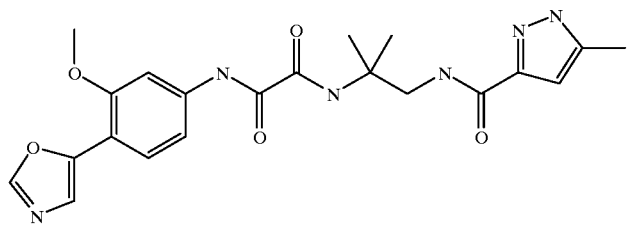
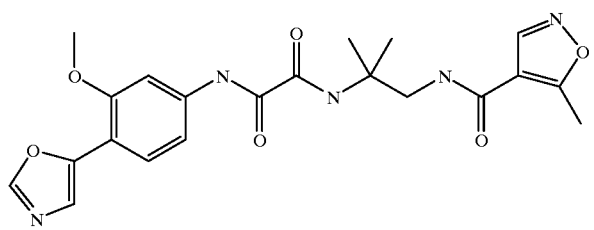
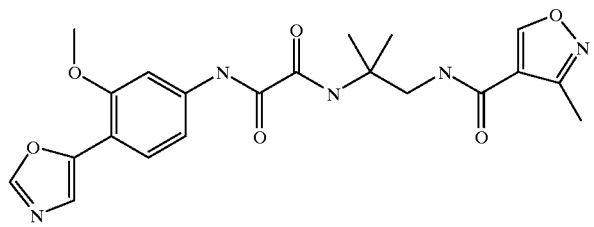
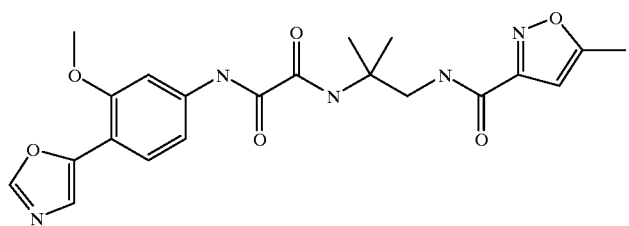
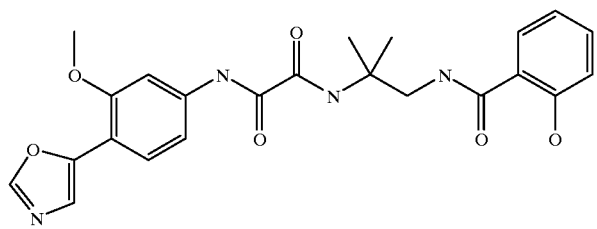
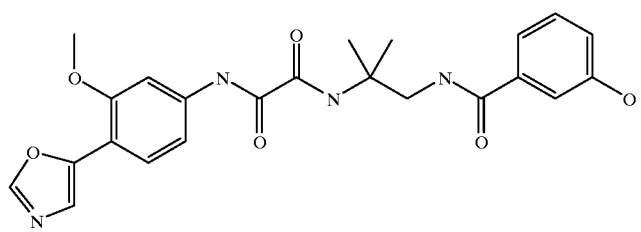

TABLE 1a-continued
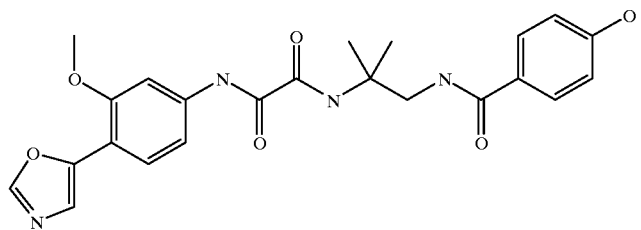
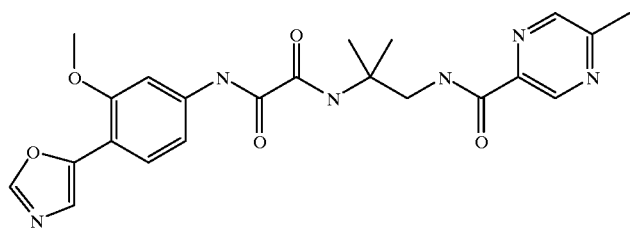
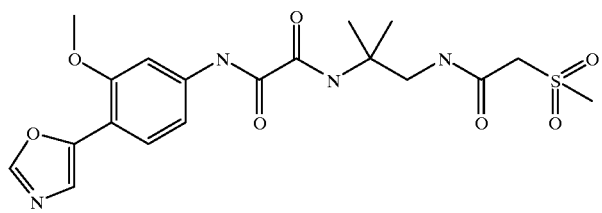
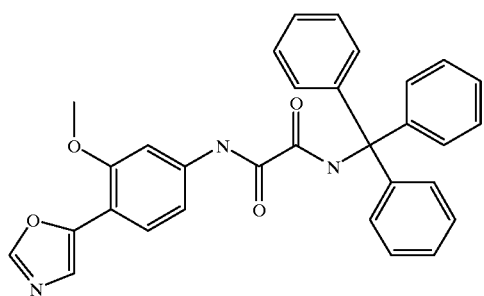
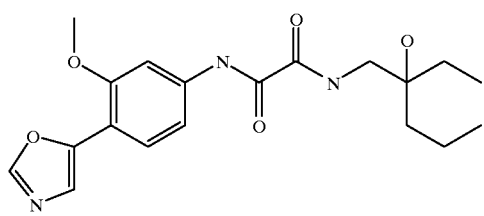
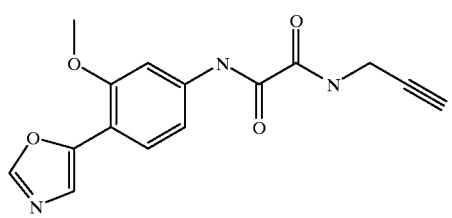

TABLE 1a-continued
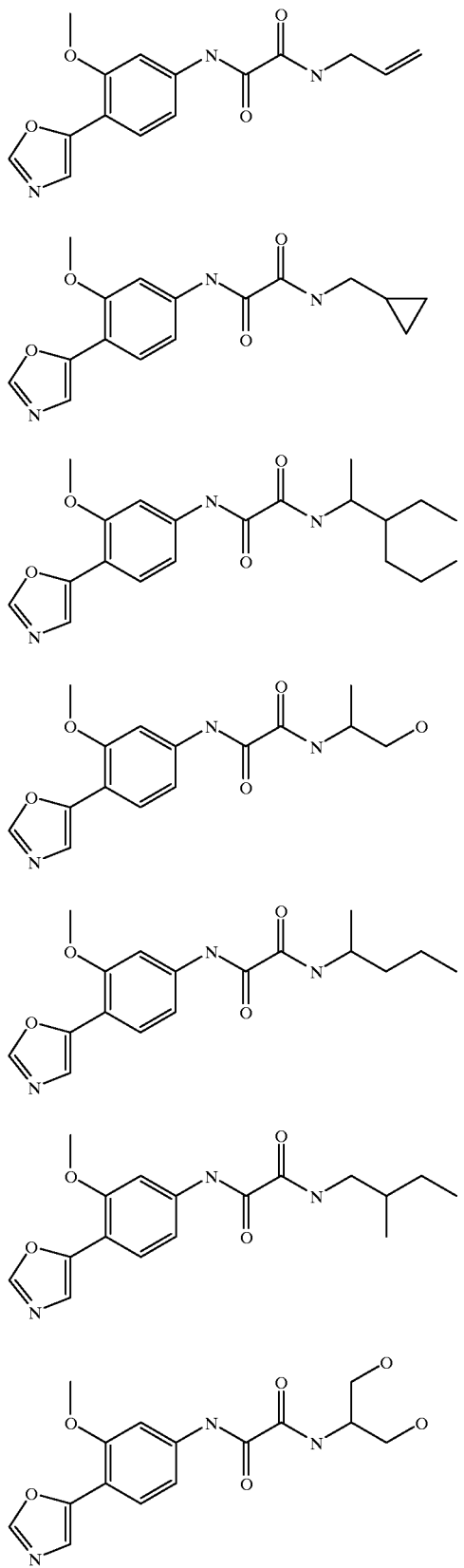

TABLE 1a-continued
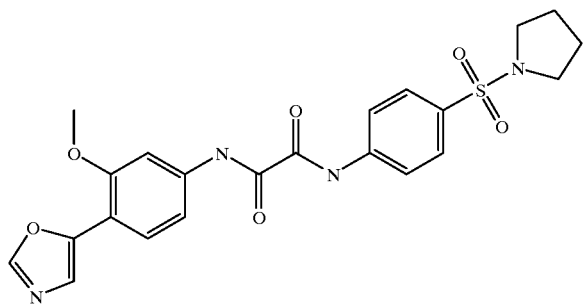
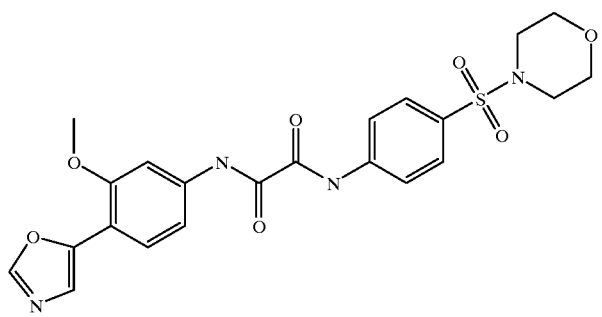
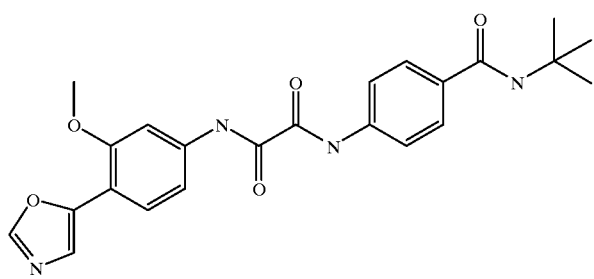
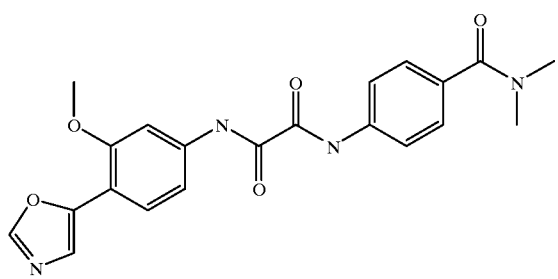
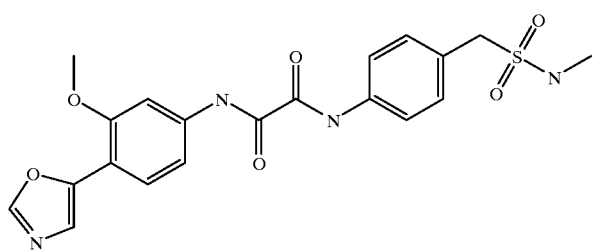

TABLE 1a-continued
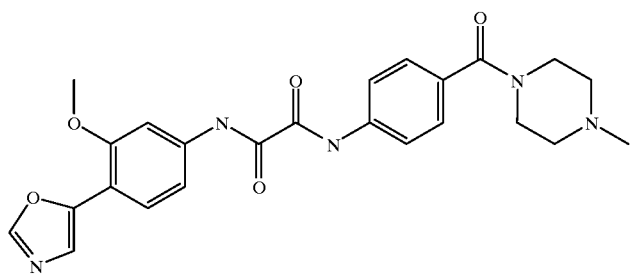
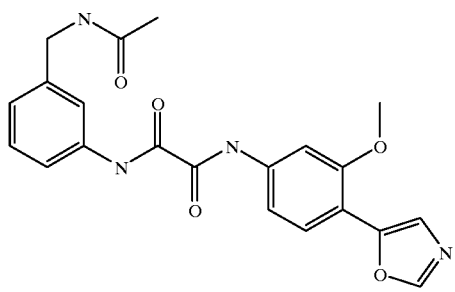
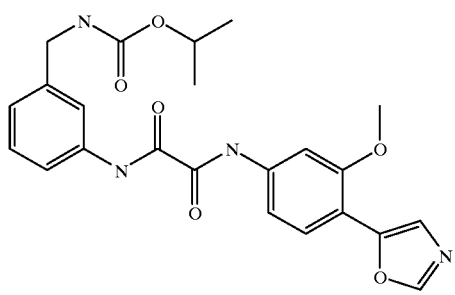
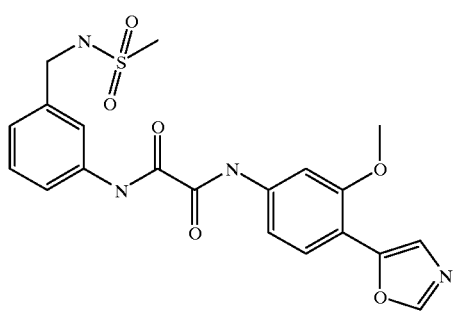
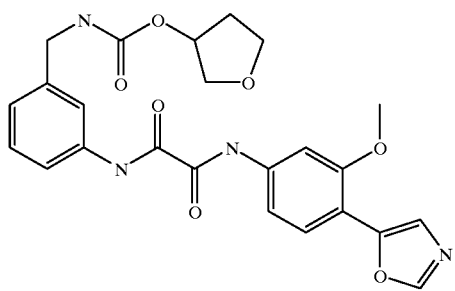

TABLE 1a-continued
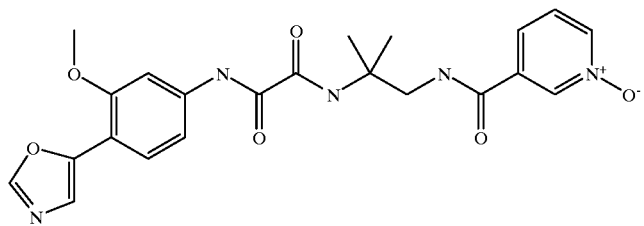
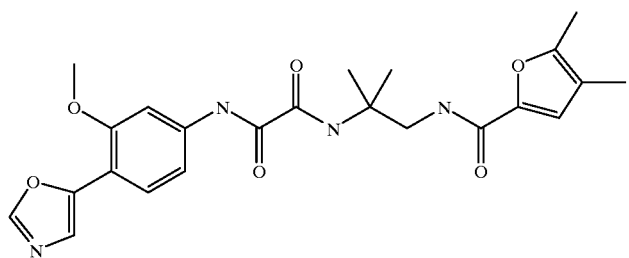
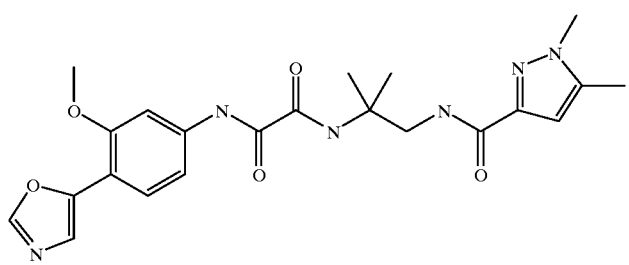
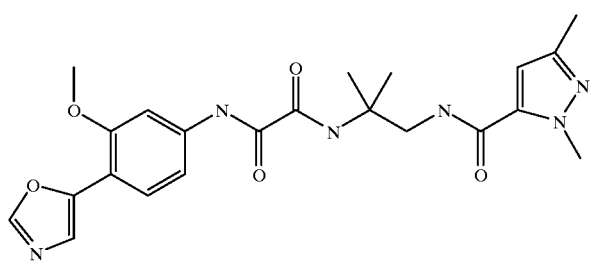
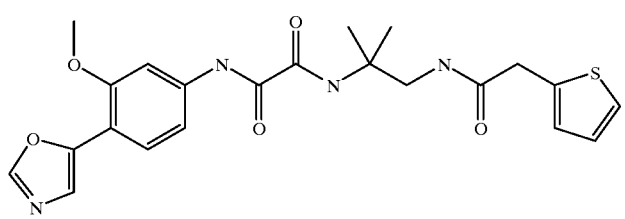
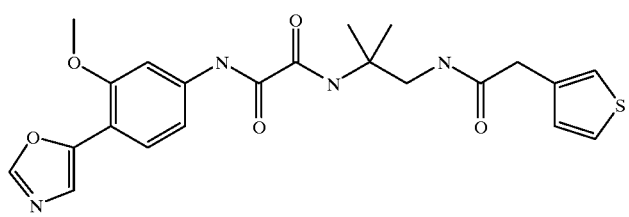

TABLE 1a-continued
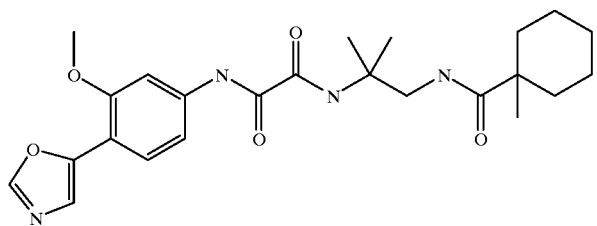
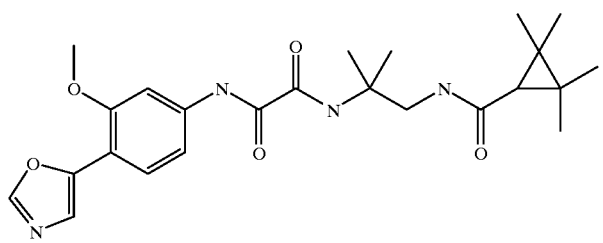
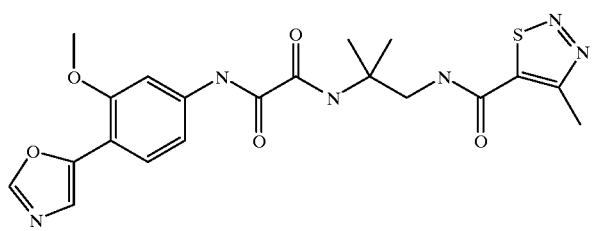
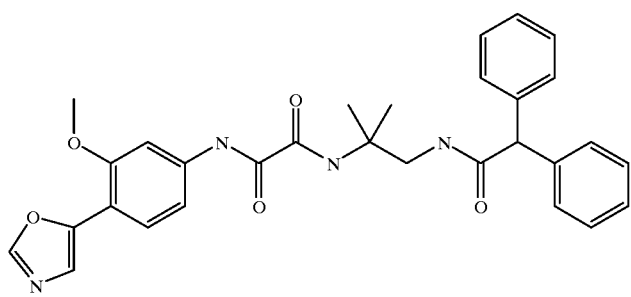
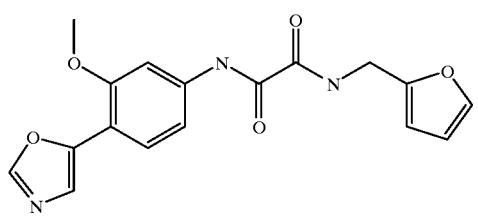
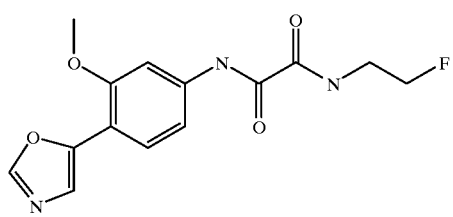

TABLE 1a-continued
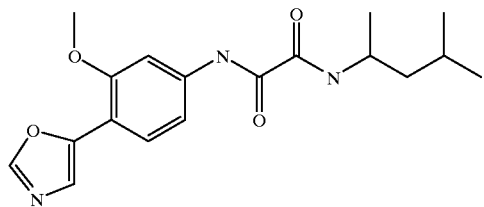
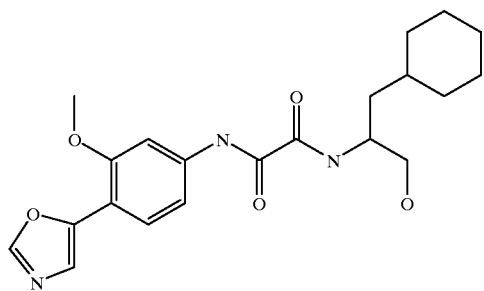
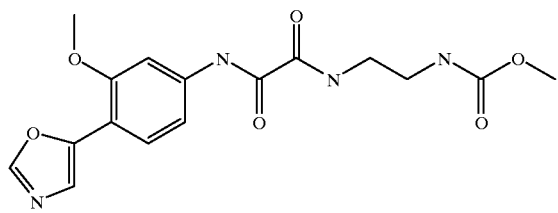
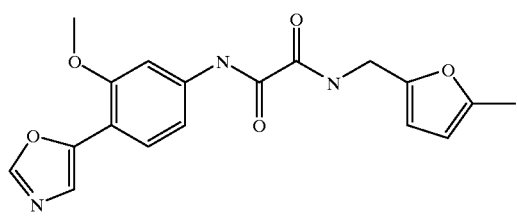
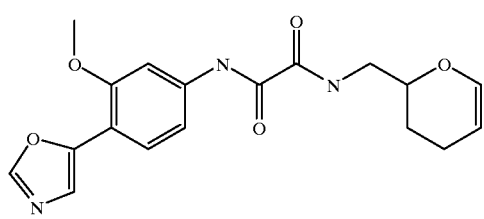
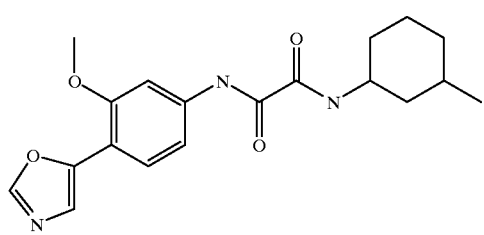

TABLE 1a-continued
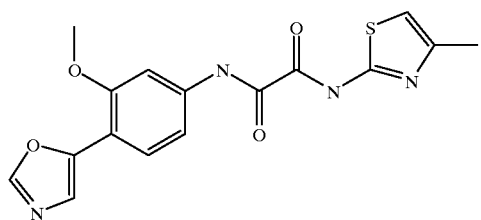
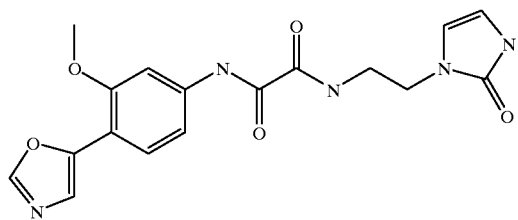
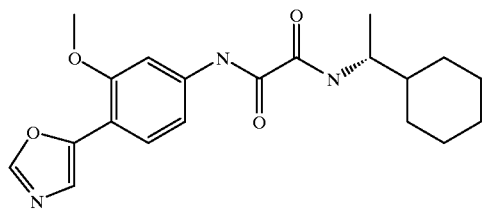
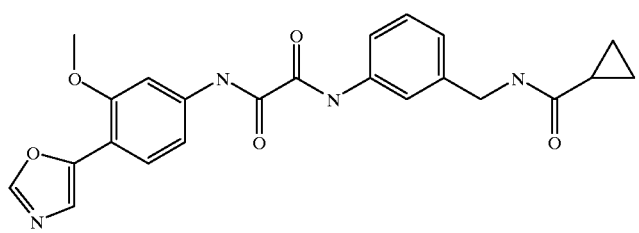
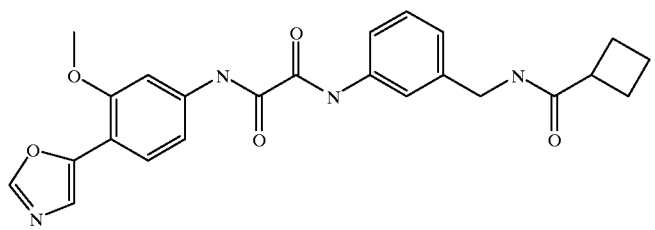
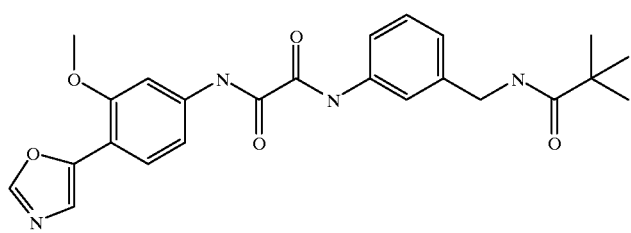

TABLE 1a-continued
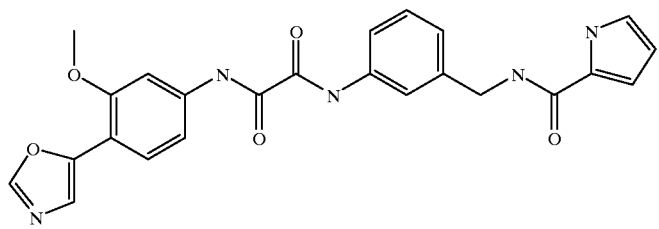
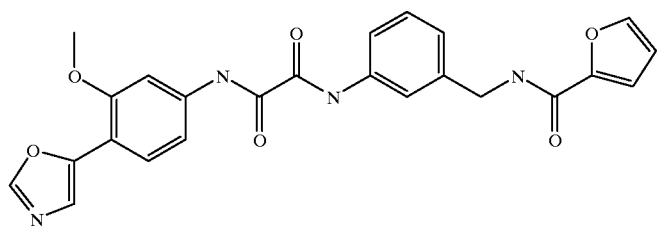
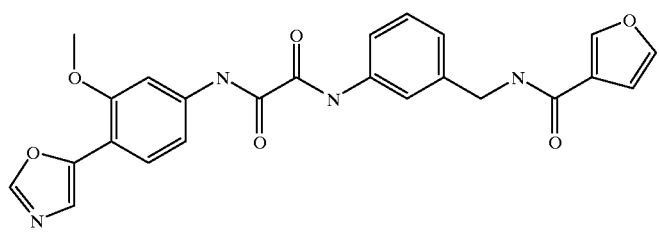
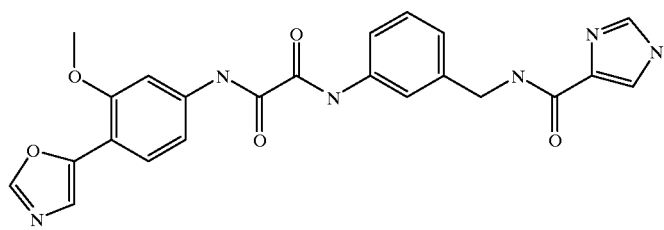
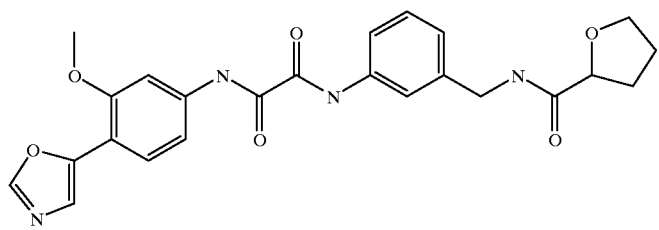
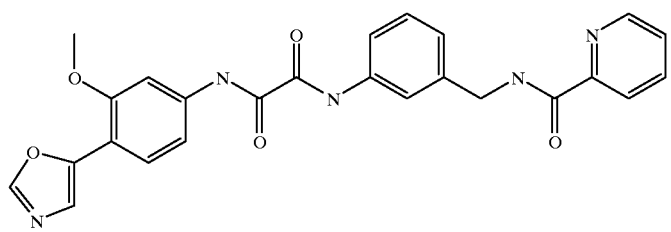

TABLE 1a-continued
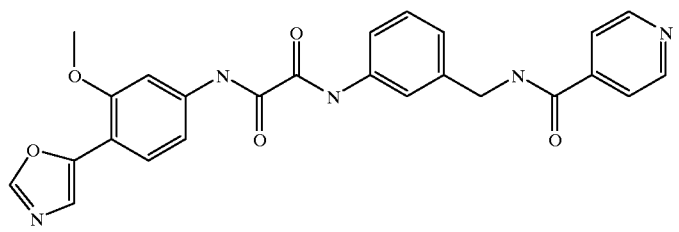
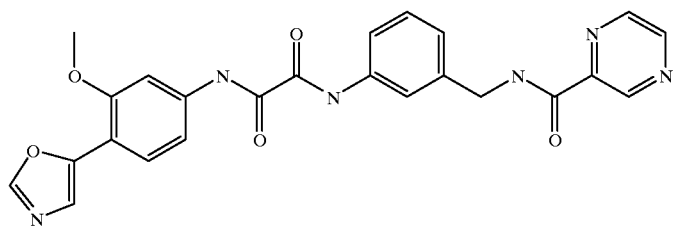
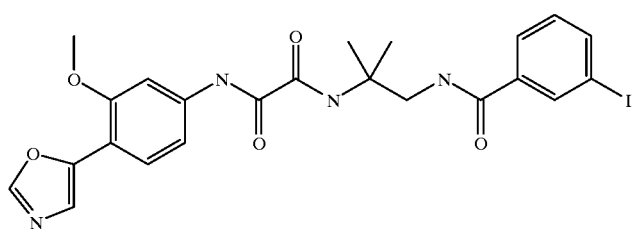
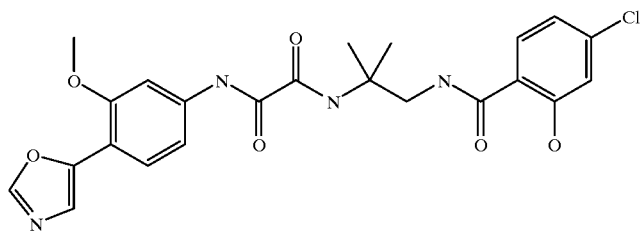
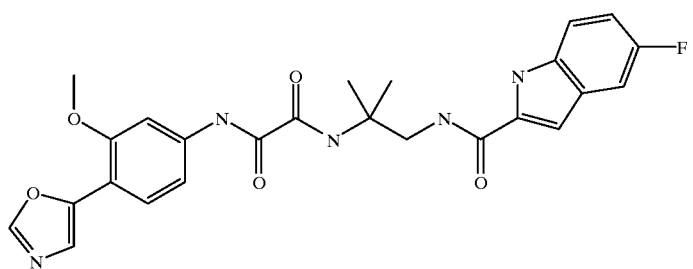
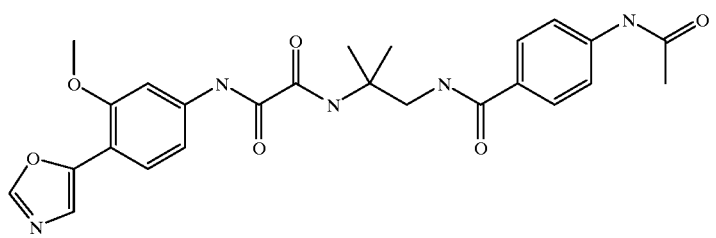

TABLE 1a-continued
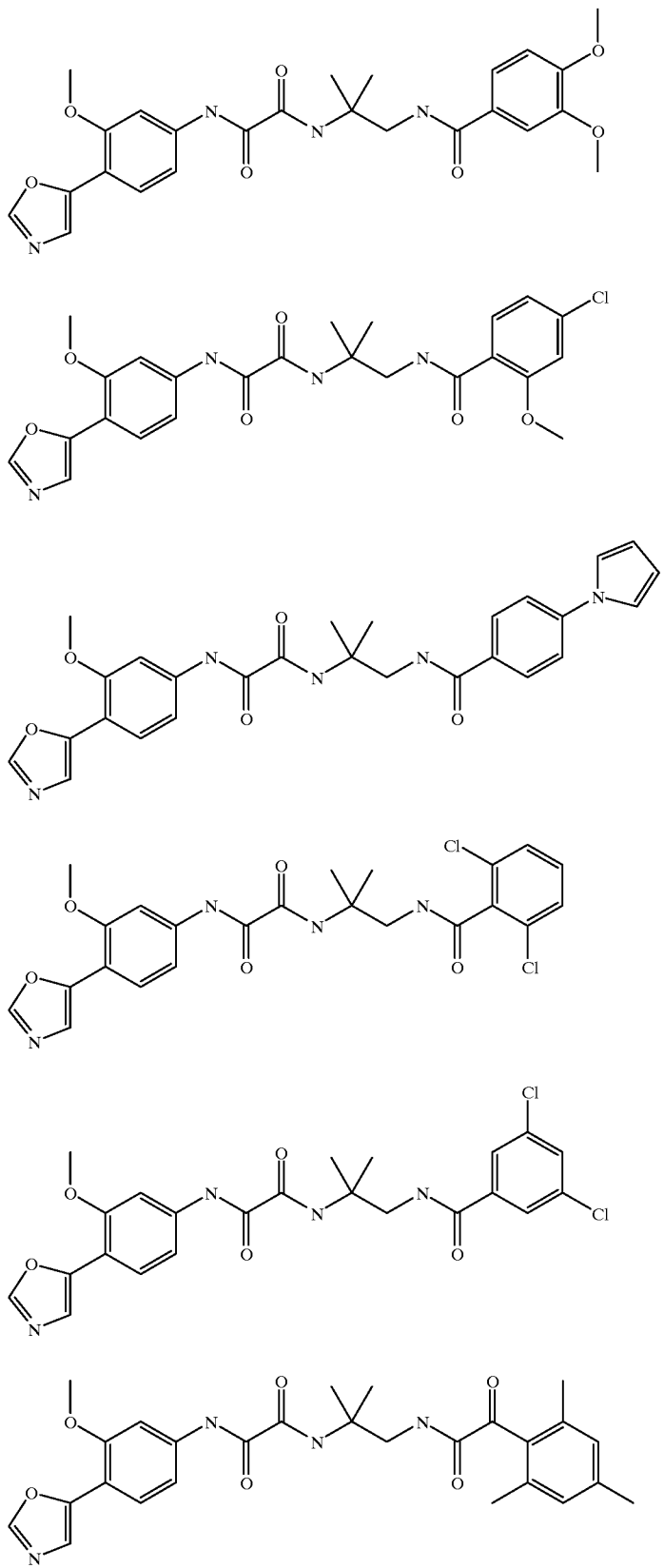

TABLE 1a-continued
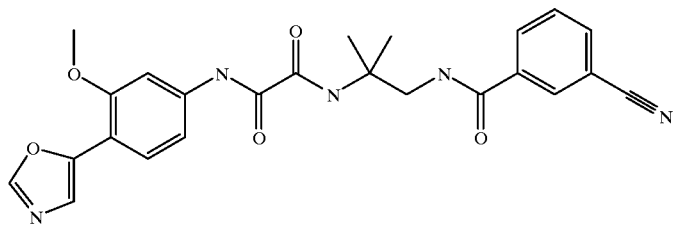
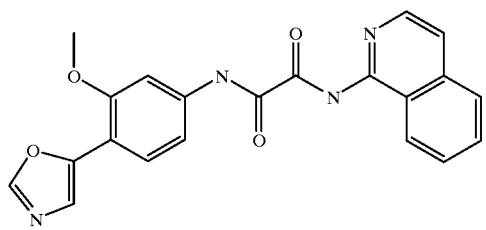
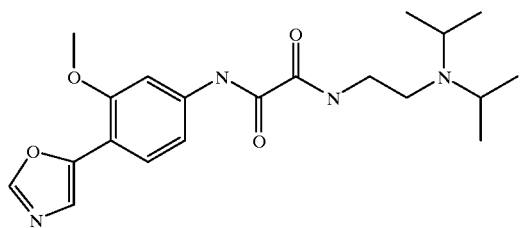
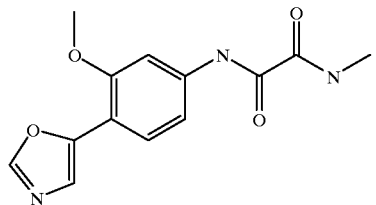
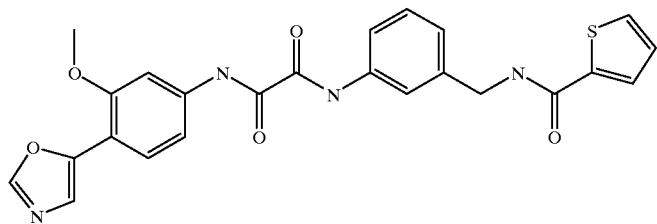
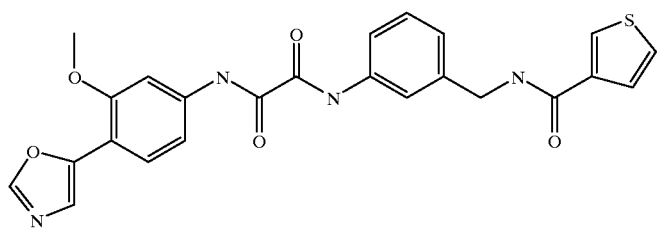

TABLE 1a-continued
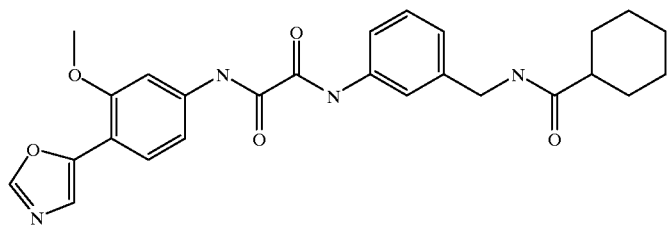
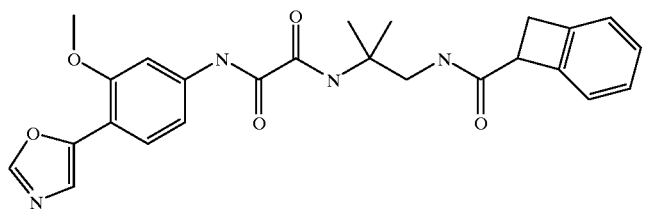
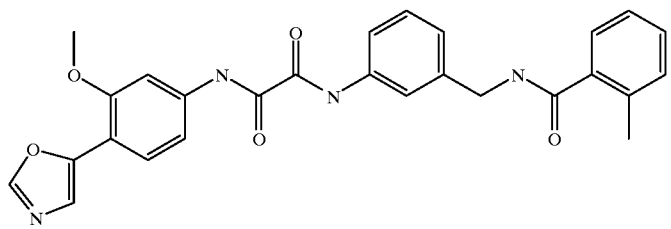
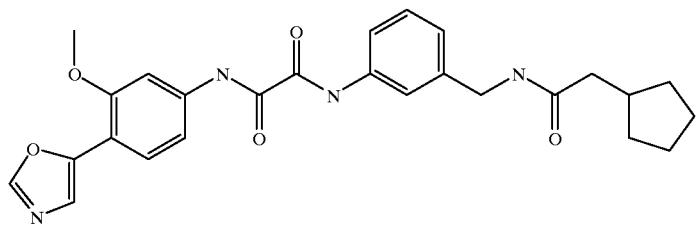
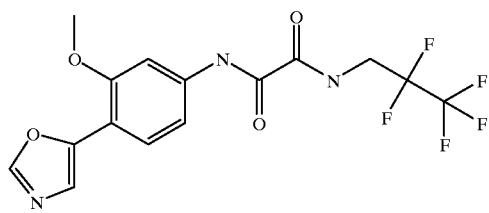
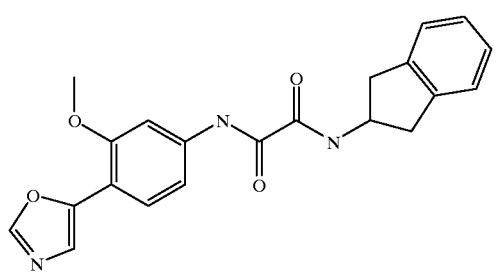
Compounds of formula (I), and formula (IX) below where $R^2$ is methoxy, $R^4$, $R^7$ and $R^8$ are as in formula (I) or formula (IX), and $R^3$, $R^5$, $R^6$, $R^9$, and $R^{10}$ are hydrogen are shown in table 1b below.

TABLE 1b

| Name | Structure | MS(ES) (M + H)+ | Ex No |
|---|---|---|---|
| Benzyl 4-{2-[[[3-methoxy-4-(5-oxazolyl)phenylamino]oxalyl]amino]-2-methylpropyl}-1-piperidinecarboxylate | 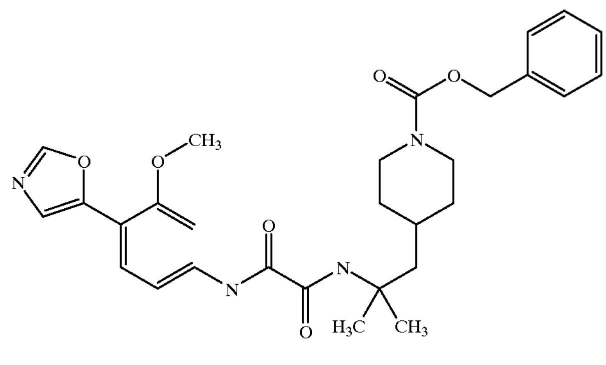 | 535 | 421 |
| N-[3-Methoxy-4-(5-oxazolyl)phenyl]-N'-[1,1-dimethyl-2-(phenylthio)ethyl]oxalamide | 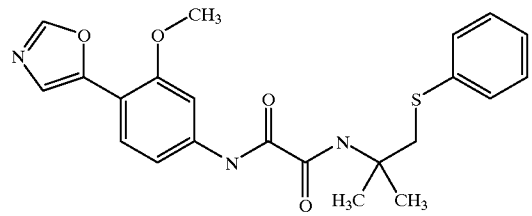 | 426 | 422 |
| N-[2-(1-Acetyl-4-piperidinyl)-1,1-dimethylethyl]-N'-[3-methoxy-4-(5-oxazolyl)phenyl]oxalamide | 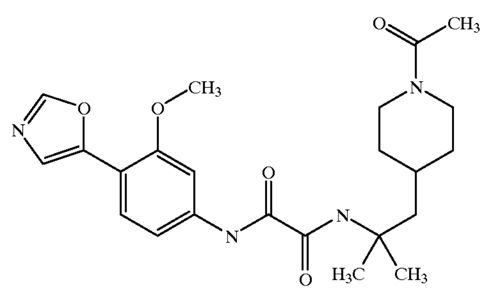 | 443 | 423 |
| N-(2-Cyclohexyl-1,1-dimethylethyl)-N'-[3-methoxy-4-(5-oxazolyl)phenyl]oxalamide | 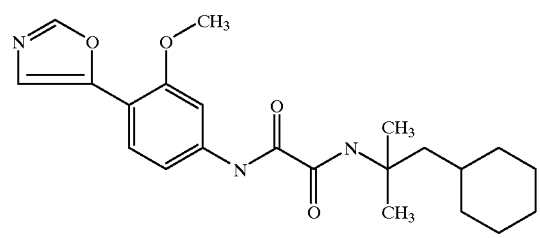 | 400 | 424 |
| N-[3-Methoxy-4-(5-oxazolyl)phenyl]-N'-[1,1-dimethyl-2-(N-methylanilino)ethyl]oxalamide | 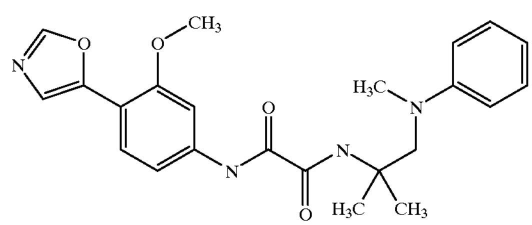 | 423 | 425 |

TABLE 1b-continued

| Name | Structure | MS(ES) (M + H)+ | Ex No |
|---|---|---|---|
| N-[2-(1,2,3,4-Tetrahydro-1-quinolyl)-1,1-dimethylethyl]-N'-[3-methoxy-4-(5-oxazolyl)phenyl]oxalamide | 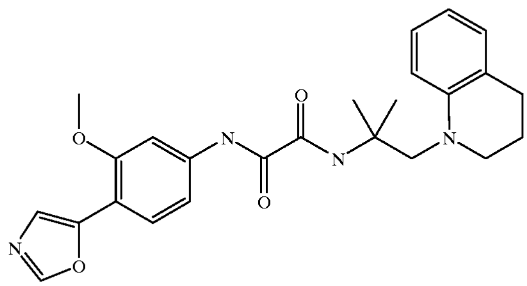 | 449 | 426 |
| N-[2-(4-Hydroxyphenylthio)-1,1-dimethylethyl]-N'-[3-methoxy-4-(5-oxazolyl)phenyl]oxalamide | 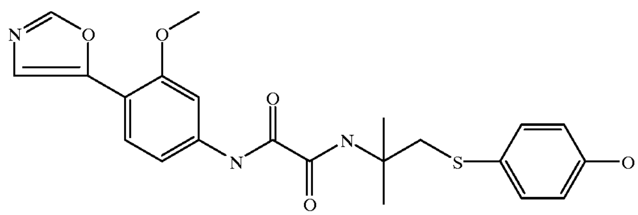 | 442 | 427 |
| N-[3-(4-Hydroxyphenyl)-1,1-dimethylpropyl]-N'-[3-methoxy-4-(5-oxazolyl)phenyl]oxalamide | 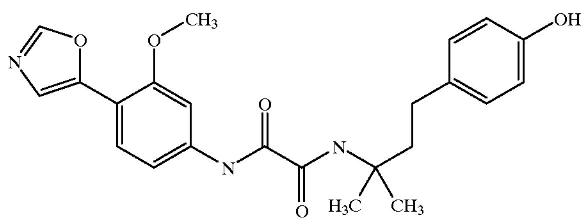 | 424 | 598 |
| N-[3-Methoxy-4-(5-oxazolyl)phenyl]-N'-[1,1-dimethyl-2-[(1-oxido-4-pyridyl)carboxamido]ethyl]oxalamide | 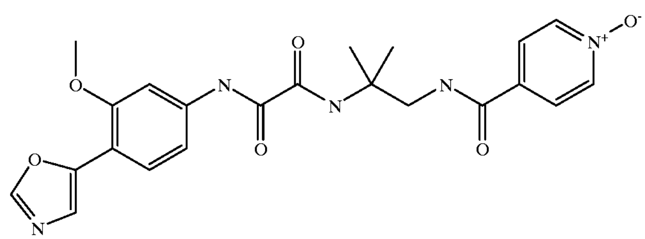 | 454 | 599 |
| N-[2-(4-Acetylbenzamido)-1,1-dimethylethyl]-N'-[3-methoxy-4-(5-oxazolyl)phenyl]oxalamide | 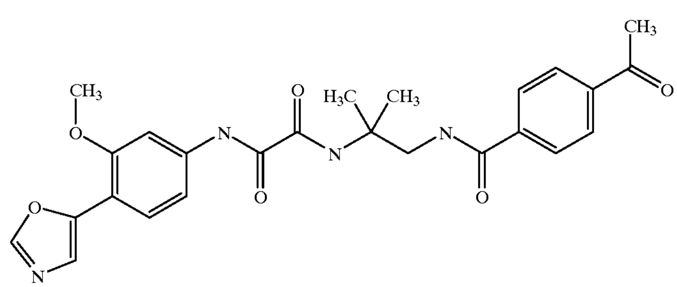 | 479.1 | 600 |
| N-[3-Methoxy-4-(5-oxazolyl)phenyl]-N'-[3-[(4-methylbenzamido)methyl]phenyl]oxalamide | 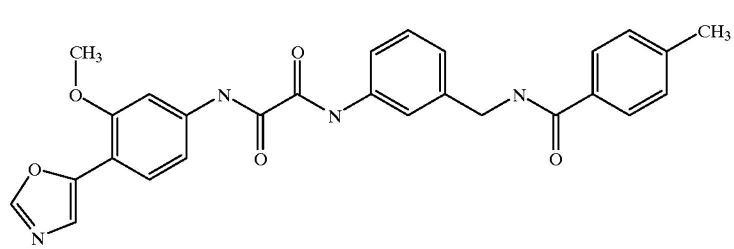 | 485.1 | 601 |

TABLE 1b-continued

| Name | Structure | MS(ES) (M + H)+ | Ex No |
|---|---|---|---|
| N-[3-[(2-Methoxybenzamido)methyl]phenyl]-N'-[3-methoxy-4-(5-oxazolyl)phenyl]oxalamide | 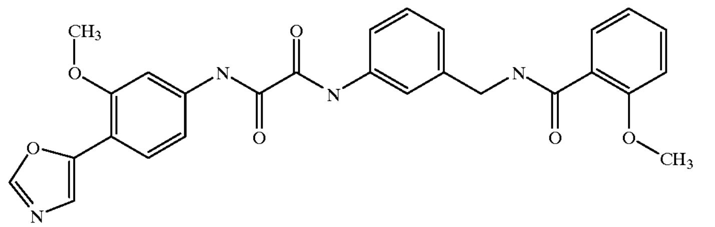 | 501.1 | 602 |
| N-[3-[(4-Chlorobenzmido)methyl]phenyl]-N'-[3-methoxy-4-(5-oxazolyl)phenyl]oxalamide | 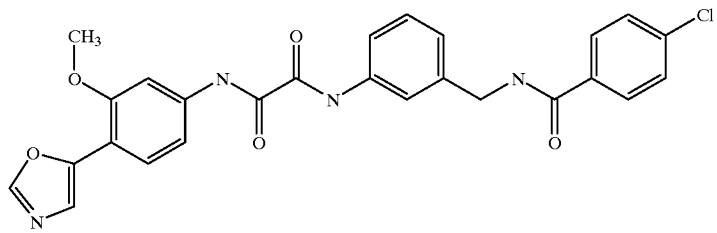 | 505.1 | 603 |
| N-[3-[[(1,3-Benzodioxol-5-yl)carboxamido]methyl]phenyl]-N'-[3-methoxy-4-(5-oxazolyl)phenyl]oxalamide | 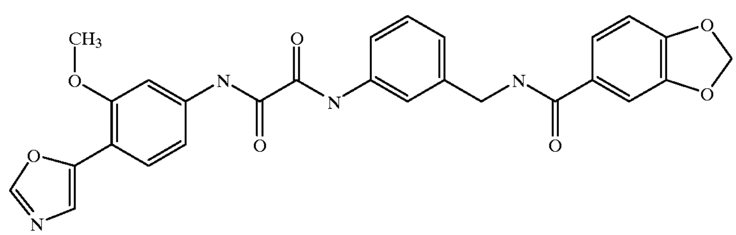 | 515.2 | 604 |
| N-[2-(2,3-Dihydro-1-indolyl)-1,1-dimethylethyl]-N'-[3-methoxy-4-(5-oxazolyl)phenyl]oxalamide | 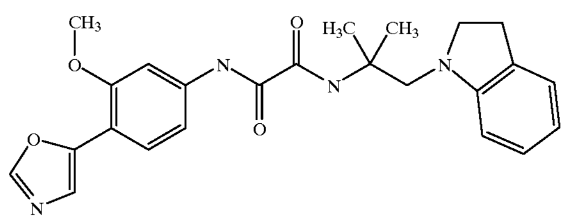 | 435 | 605 |
| N-[2-(3,4-Dihydro-6-methyl-2H-quinol-1-yl)-1,1-dimethylethyl]-N'-[3-methoxy-4-(5-oxazolyl)phenyl]oxalamide | 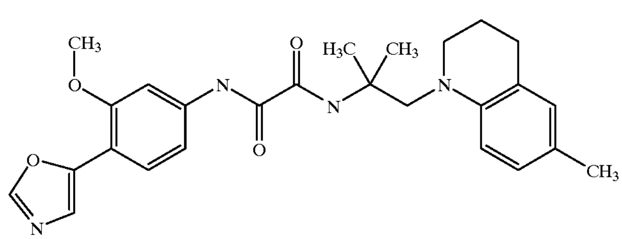 | 463 | 606 |
| N-[1-(3-Benzofuranyl)-1-methylethyl]-N'-[3-methoxy-4-(5-oxazolyl)phenyl]oxalamide | 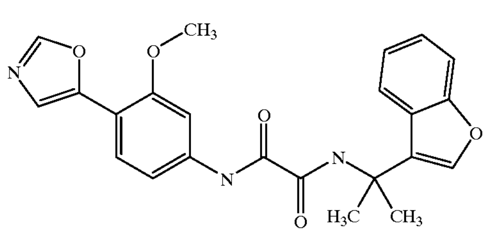 | 420 | 607 |

TABLE 1b-continued

| Name | Structure | MS(ES) (M + H)+ | Ex No |
|---|---|---|---|
| N-[3-Methoxy-4-(5-oxazolyl)phenyl]-N'-[1,1-dimethyl-3-(4-phenoxypiperidino)propyl]oxalamide | 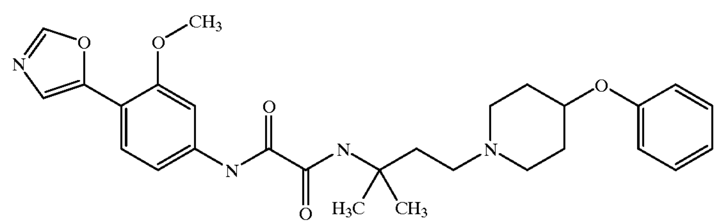 | 507 | 608 |
| N-[2-(1-Butyryl-4-piperidinyl)-1,1-dimethylethyl]-N'-[3-methoxy-4-(5-oxazolyl)phenyl]oxalamide | 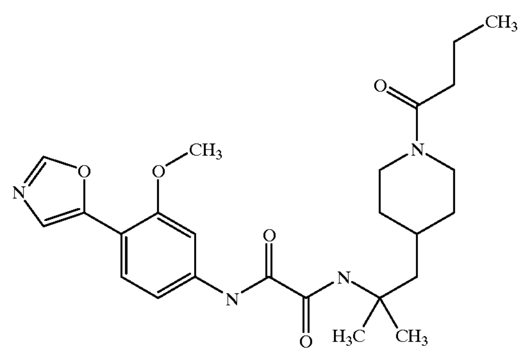 | 471 | 609 |
| N-[2-[1-(Methanesulfonyl)-4-piperidinyl]-1,1-dimethylethyl]-N'-[3-methoxy-4-(5-oxazolyl)phenyl]oxalamide | 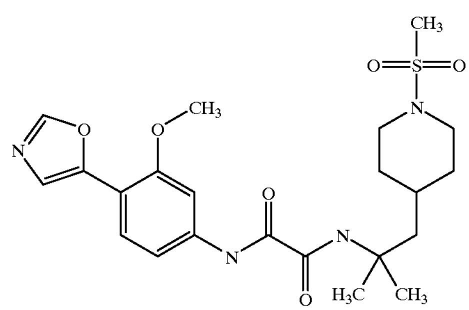 | 479 | 610 |
| N-[2-[1-(Benzenesulfonyl)-4-piperidinyl]-1,1-dimethylethyl]-N'-[3-methoxy-4-(5-oxazolyl)phenyl]oxalamide | 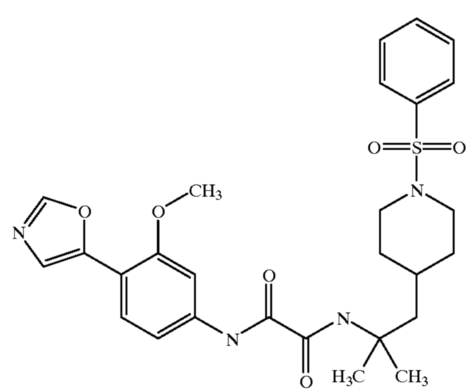 | 541 | 611 |

TABLE 1b-continued

| Name | Structure | MS(ES) (M + H)+ | Ex No |
|---|---|---|---|
| N-[2-(1-Isobutyryl-4-piperidinyl)-1,1-dimethylethyl]-N'-[3-methoxy-4-(5-oxazolyl)phenyl]oxalamide | 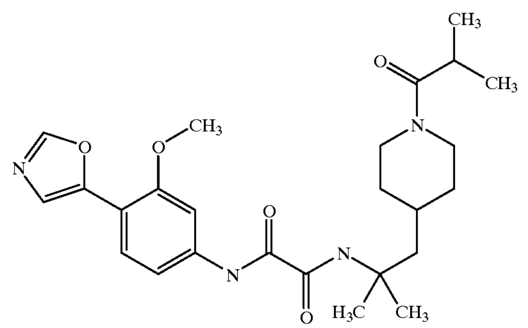 | 471 | 612 |
| tert-Butyl 4-[3-[[[3-methoxy-4-(5-oxazolyl)anilino] oxalyl] amino]-3-methylbutyl]-1-piperidinecarboxylate | 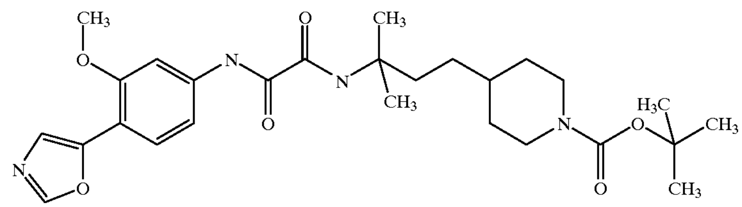 | 515 | 613 |
| N-[3-Methoxy-4-(5-oxazolyl) phenyl]-N'-[1,1-dimethyl-3-(4-piperidinyl)propyl]oxalamide | 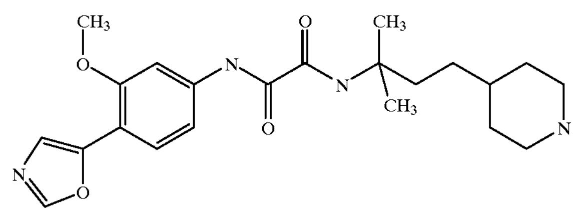 | 415 | 614 |

Preferred compounds of formula (I) and any of the compounds of formula (I) described below are those where at least one of $R^2$, $R^3$, $R^5$ and $R^6$ is not hydrogen especially where $R^2$ represents lower alkoxy, preferably methoxy.

In preferred compounds of formula (I) and any of the compounds of formula (I) described below, $R^1$ represents a five-membered heterocycle with one to three heteroatoms selected from nitrogen, oxygen, and sulfur. Furthermore, preferred compounds of formula (I) are those where $R^1$ represents an unsubstituted or substituted oxazole ring or triazole ring. When substituted, the preferred substituents are methyl, ethyl, or benzyl.

Also preferred are compounds of formula (I) and any of the compounds of formula (I) described below as follows: where $R^4$ represents hydrogen or branched lower alkyl, and where $R^3$, $R^6$, and $R^7$ represent hydrogen. Most preferably, $R^1$ represents oxazolyl (especially unsubstituted), $R^2$ represents lower alkoxy (especially methoxy) and $R^3$, $R^4$, $R^6$ and $R^7$ represent hydrogen.

Also preferred are compounds of formula (I) and any of the compounds of formula (I) described below where $R^8$ represents branched lower alkyl, aryl, a 3 to 7 membered cycloalkyl ring, or a 5 or 6 membered monocyclic or 9 or 10 membered bicyclic saturated or unsaturated heterocyclic ring with 1 to 4 heteroatoms selected from nitrogen, oxygen, and sulfur. These compounds may be substituted or unsubstituted as defined above. It is additionally preferred for these compounds that $R^1$ represents oxazolyl (especially unsubstituted), $R^2$ represents lower alkoxy (especially methoxy) and $R^3$, $R^4$, $R^6$ and $R^7$ represent hydrogen.

In formula (I) and any of the compounds of formula (I) described below, $R^8$ may be branched lower alkyl, aryl, and/or cycloalkyl, and/or a heterocyclic ring as defined immediately above.

In particular, preferred compounds of formula (I) are those of the general formula:

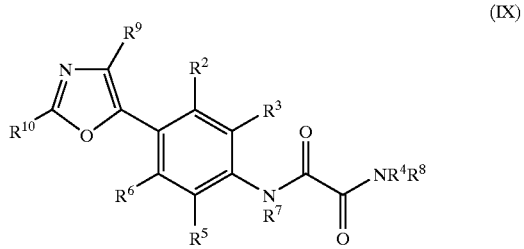

(IX)

wherein $R^2$ to $R^8$ are defined as above; and, $R^9$ is hydrogen, lower alkyl, aryl-lower alkyl;

$R^{10}$ is hydrogen.

In some compounds of formula (IX), $R^9$ represents methyl, ethyl, or benzyl, and $R^{10}$ preferably is hydrogen. In others, $R^9$ and $R^{10}$ both represent hydrogen. It is preferred that $R^8$ represents branched lower alkyl, aryl, a 3 to 7 membered cycloalkyl ring, or a 5 or 6 membered monocyclic or 9 or 10 membered bicyclic saturated or unsaturated heterocyclic ring with 1 to 4 heteroatoms selected from nitrogen, oxygen, and sulfur, and in addition is preferred that $R^2$ represent lower alkoxy, $R^3$, $R^4$, $R^6$, and $R^7$ represent hydrogen.

More particularly, preferred compounds of formula (I) are those of the general formula (IX), wherein $R^2$ is methoxy or chloro; $R^3$, $R^4$, $R^5$, $R^6$, $R^7$ $R^9$, and $R^{10}$ are hydrogen, and $R^8$ is heterocyclyl, aryl, or branched chain lower alkyl;

Examples of such compounds are:

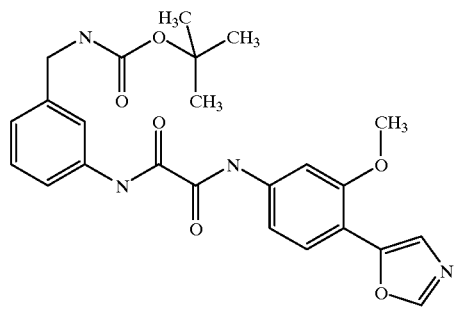

tert-Butyl[3-[[[3-methoxy-4-(5-oxazolyl)anilino]oxalyl]amino]benzyl]carbamate

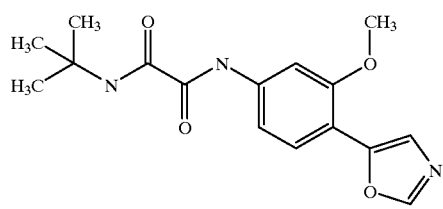

N-tert-Butyl-N'-[3-methoxy-4-(5-oxazolyl)phenyl]oxalamide

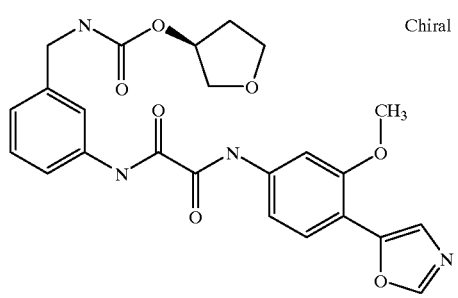

Chiral

[3-[[[3-Methoxy-4-(5-oxazolyl)anilino]oxalyl]amino]benzyl]carbamic acid tetrahydro-3(S)-furyl ester

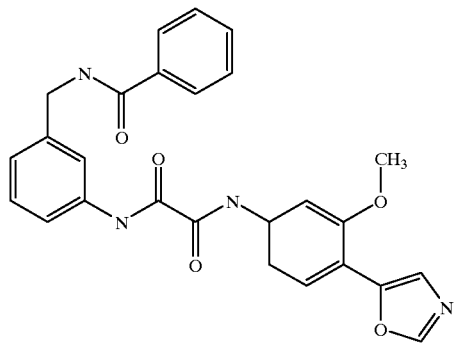

N-[3-(Benzamidomethyl)phenyl]-N'-[3-methoxy-4-(5-oxazolyl)phenyl]oxalamide

-continued

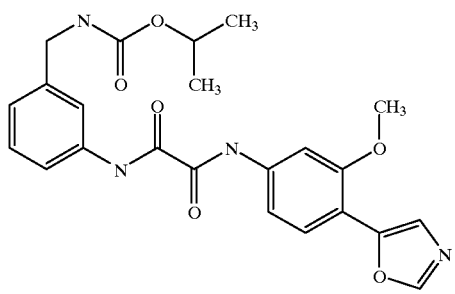

Isopropyl [3-[[[3-methoxy-4-(5-oxazolyl)anilino]oxalyl]amino]benzyl]carbamate

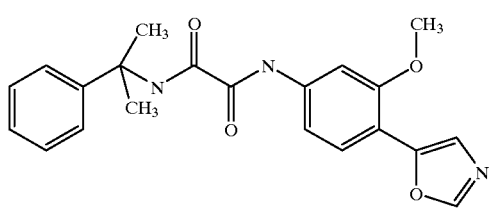

N-[3-Methoxy-4-(5-oxazolyl)phenyl]-N'-(1-methyl-1-phenylethyl)oxalamide

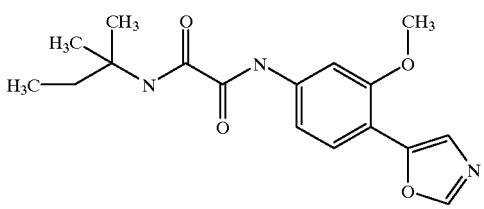

N-(1,1-Dimethylpropyl)-N'-[3-methoxy-4-(5-oxazolyl)phenyl]oxalamide

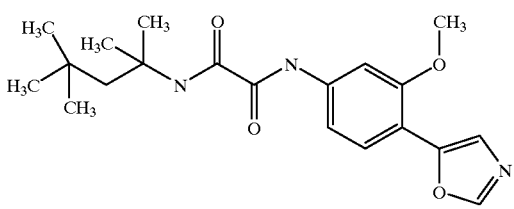

N-[3-Methoxy-4-(5-oxazolyl)phenyl]-N'-(1,1,3,3-tetramethyl-butyl)oxalamide

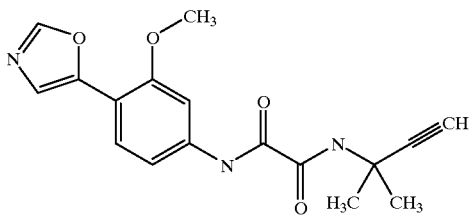

N-(1,1-Dimethylpropargyl)-N'-[3-methoxy-4-(5-oxazolyl)phenyl]oxalamide

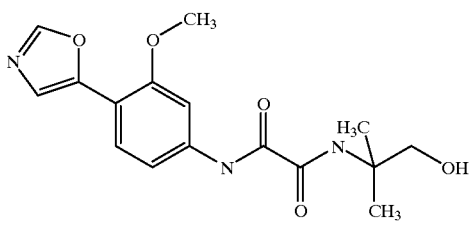

N-(2-Hydroxy-1,1-dimethylethyl)-N'-[3-methoxy-4-(5-oxazolyl)phenyl]oxalamide

-continued

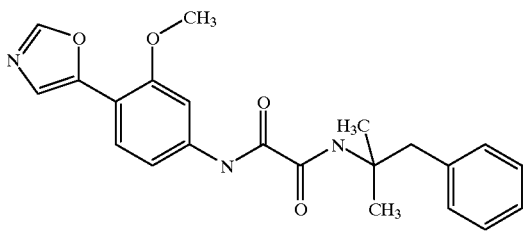
N-(1,1-Dimethyl-2-phenylethyl)-N'-[3-methoxy-4-(5-oxazolyl)phenyl]oxalamide

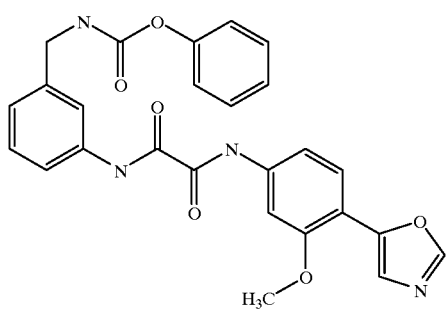
Phenyl [3-[[[4-(5-oxazolyl)anilino]oxalyl]amino]benzyl]carbamate

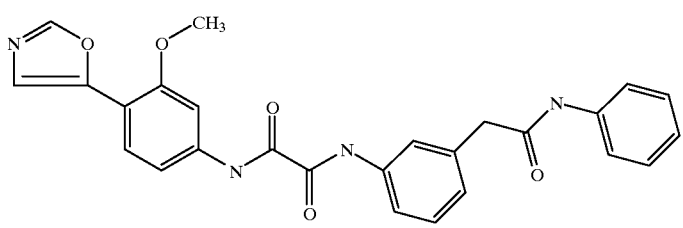
N-[3-Methoxy-4-(5-oxazolyl)phenyl]-N'-[3-[(phenylcarbamoyl)methyl]phenyl]oxalamide

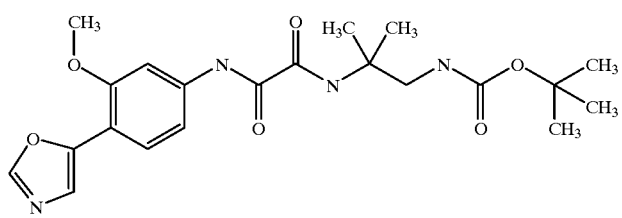
tert-Butyl [2-[[[3-methoxy-4-(5-oxazolyl)anilino]oxalyl]amino]-2-methylpropyl]carbamate

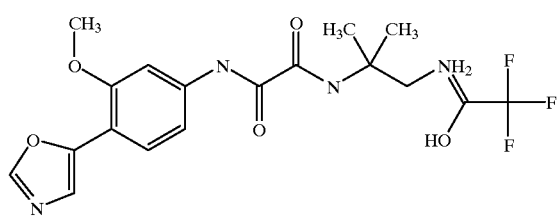
N-(2-Amino-1,1-dimethylethyl)-N'-[3-methoxy-4-(5-oxazolyl)phenyl]oxalamide trifluoroacetate (1:1)

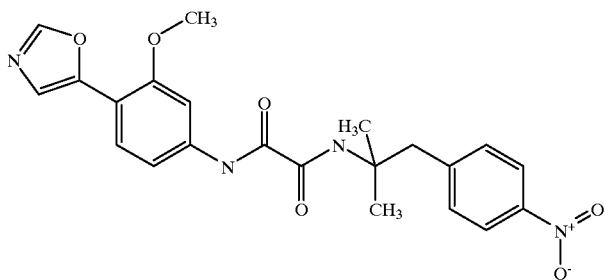
N-[3-Methoxy-4-(5-oxazolyl)phenyl]-N'-[1,1-dimethyl-2-(4-nitrophenyl)ethyl]oxalamide -continued

| Structure | Name |
|---|---|
| | N-[3-(Aminomethyl)phenyl]-N'-[3-methoxy-4-(5-oxazolyl)phenyl]oxalamide trifluoroacetate (1:1) |
| | Methyl [3-[[[3-methoxy-4-(5-oxazolyl)anilino]oxalyl]amino]benzyl]carbamate |
| | N-[3-Methoxy-4-(5-oxazolyl)phenyl]-N'-(3-pyridyl)oxalamide |
| | N-[3-[(Benzenesulfonamido)methyl]phenyl]-N'-[3-methoxy-4-(5-oxazolyl)phenyl]oxalamide |
| | N-(2-Dimethylamino-1,1-dimethylethyl)-N'-[3-methoxy-4-(5-oxazolyl)phenyl]oxalamide hydrochloride (1:1) |
| | N-[3-Methoxy-4-(5-oxazolyl)phenyl]-N'-[1-methyl-1-(methylcarbamoyl)ethyl]oxalamide |

-continued

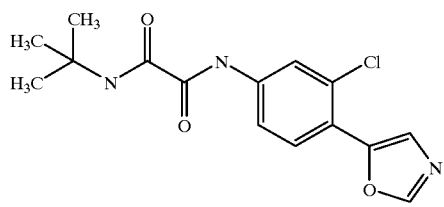

N-tert-Butyl-N'-[3-chloro-4-(5-oxazolyl)phenyl]oxalamide

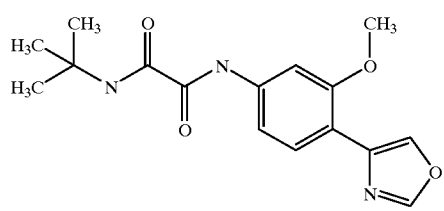

N-tert-Butyl-N'-[3-methoxy-4-(4-oxazolyl)phenyl]oxalamide or their pharmaceutically acceptable salts.

In particular, preferred compounds of formula (I) and (IX) are also those of the general formulas:

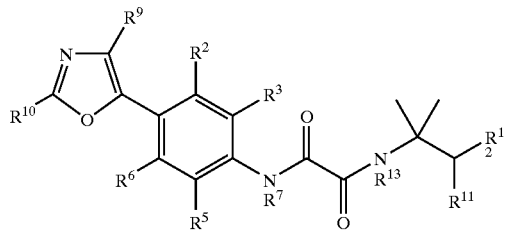 XIa

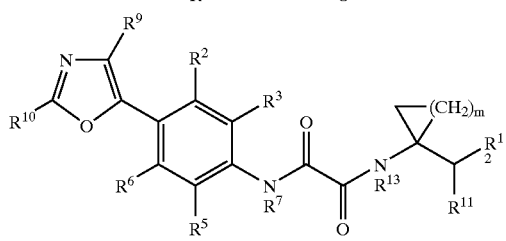 XIb wherein $R^2$, $R^3$, $R^5$, $R^6$, $R^7$, $R^9$ and $R^{10}$ are defined as above $R^{11}$ and $R^{13}$ is H or lower alkyl, m=1 to 5 and $R^{12}$ is heterocyclyl, or aryl (substituted or unsubstited) other than 4-fluorophenyl.

Particularly preferred compounds of formula (XIa or XIb) are those wherein $R^2$ is methoxy, $R^3$, $R^5$, $R^6$, $R^9$, $R^{10}$, $R^{11}$ and $R^{13}$ are hydrogen and wherein $R^{12}$ is (unsubstituted or substituted) phenyl other than 4-fluorophenyl and (unsubstituted or substituted heteroaryl). Also preferred are those compounds where $R^{12}$ represents a 5 or 6 membered monocyclic or a 9 or 10 membered bicyclic saturated or unsaturated heteroaromatic ring with 1 to 4 heteroatoms selected from nitrogen, oxygen, and sulfur.

Examples of such compounds are listed in table 1c

TABLE 1c

| Name | Structure | MS(ES) (M + H)+ | Ex No |
|---|---|---|---|
| N-[3-Methoxy-4-(5-oxazolyl)phenyl]-N'-[1,1-dimethyl-2-(4-methylphenyl)ethyl]oxalamide | 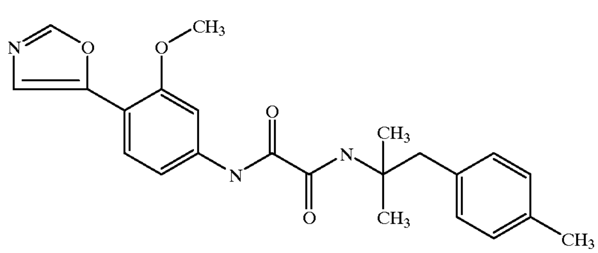 | 408 | 302 |

TABLE 1c-continued

| Name | Structure | MS(ES) (M + H)+ | Ex No |
|---|---|---|---|
| N-[1,1-Dimethyl-2-(2-methylphenyl)ethyl]-N'-[3-methoxy-4-(5-oxazolyl)phenyl] oxalamide | 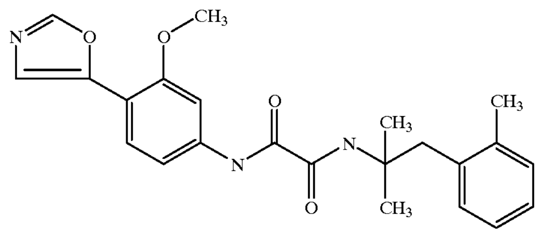 | 408 | 303 |
| N-[3-Methoxy-4-(5-oxazolyl)phenyl]-N'-[1,1-dimethyl-2-(3-pyridyl)ethyl] oxalamide | 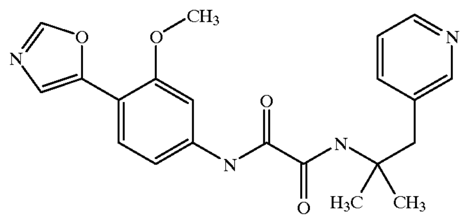 | 395 | 304 |
| N-[3-Methoxy-4-(5-oxazolyl)phenyl]-N'-[1,1-dimethyl-2-(3-methylphenyl)ethyl] oxalamide | 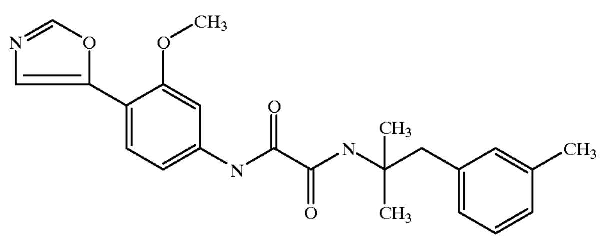 | 408 | 305 |
| N-[3-Methoxy-4-(5-oxazolyl)phenyl]-N'-[1,1-dimethyl-2-(2-thienyl)ethyl] oxalamide | 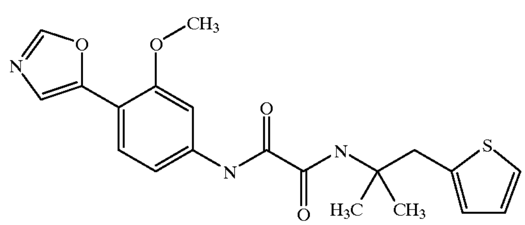 | 400 | 306 |
| N-[2-(4-Benzyloxy-phenyl)-1,1-dimethyl-ethyl]-N'-(3-methoxy-4-oxazol-5-yl-phenyl)-oxalamide | 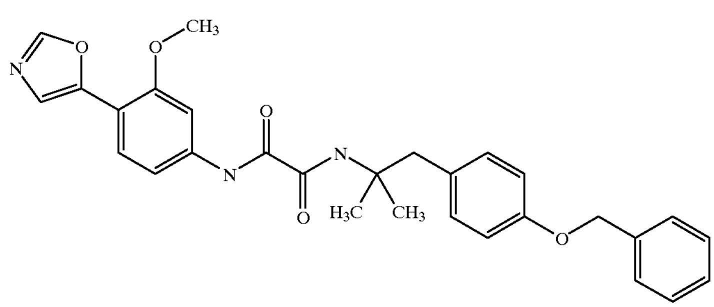 | 500 | 307 |
| N-[2-(4-Hydroxy-phenyl)-1,1-dimethyl-ethyl]-N'-(3-methoxy-4-oxazol-5-yl-phenyl)-oxalamide | 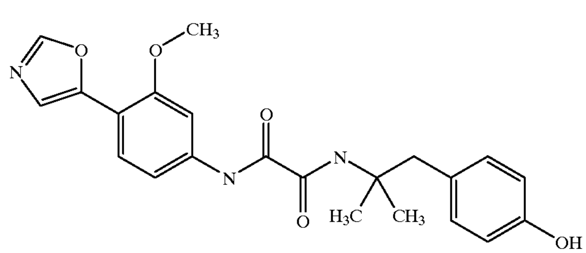 | 410 | 308 |

TABLE 1c-continued

| Name | Structure | MS(ES) (M + H)+ | Ex No |
|---|---|---|---|
| N-(3-Methoxy-4-oxazol-5-yl-phenyl)-N'-[2-(4-methoxy-phenyl)-1,1-dimethyl-ethyl]-oxalamide | 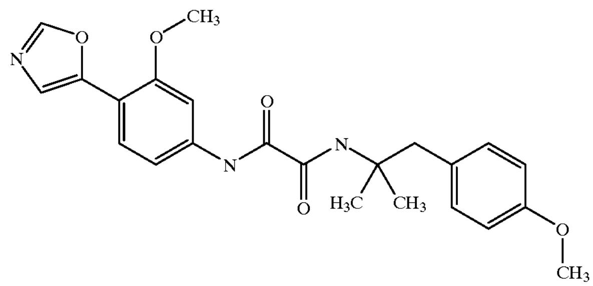 | 424 | 309 |
| N-[2-(2-Hydroxy-phenyl)-1,1-dimethyl-ethyl]-N'-(3-methoxy-4-oxazol-5-yl-phenyl)-oxalamide | 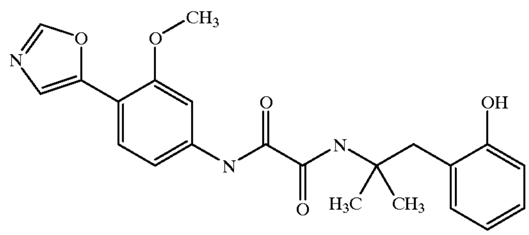 | 410 | 310 |
| N-(1,1-Dimethyl-2-phenyl-propyl)-N'-(3-methoxy-4-oxazol-5-yl-phenyl)-oxalamide | 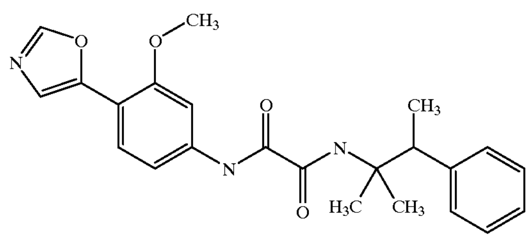 | 408 | 311 |
| N-[2-(3-Hydroxy-phenyl)-1,1-dimethyl-ethyl]-N'-(3-methoxy-4-oxazol-5-yl-phenyl)-oxalamide | 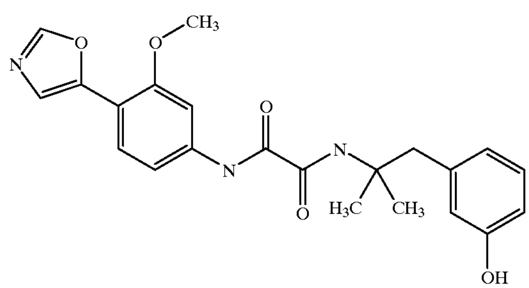 | 410 | 312 |
| N-(3-Methoxy-4-oxazol-5-yl-phenyl)-N'-[2-(3-methoxy-phenyl)-1,1-dimethyl-ethyl]-oxalamide | | 424 | 313 |

TABLE 1c-continued

| Name | Structure | MS(ES) (M + H)+ | Ex No |
|---|---|---|---|
| N-[2-[4-(Cyanomethoxy)phenyl]-1,1-dimethylethyl]-N'-[3-methoxy-4-(5-oxazolyl)phenyl] oxalamide | 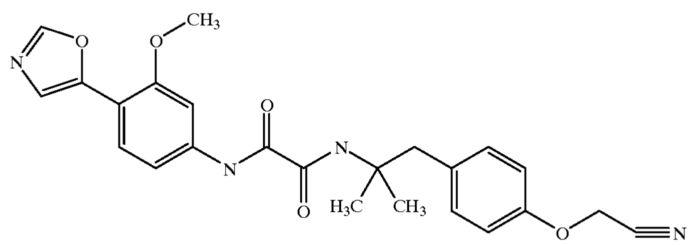 | 449 | 314 |
| 2-[4-[2-[[[3-Methoxy-4-(5-oxazolyl)anilino]oxalyl]amino]-2-methylpropyl]phenoxy]acetic acid | 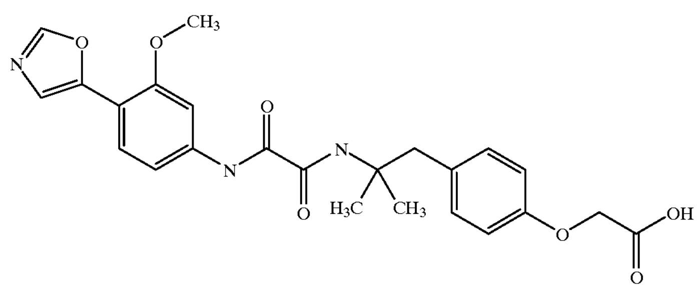 | 468 | 315 |
| 2-[2-[2-[[[3-Methoxy-4-(5-oxazolyl)anilino]oxalyl]amino]-2-methylpropyl]phenoxy]acetic acid | 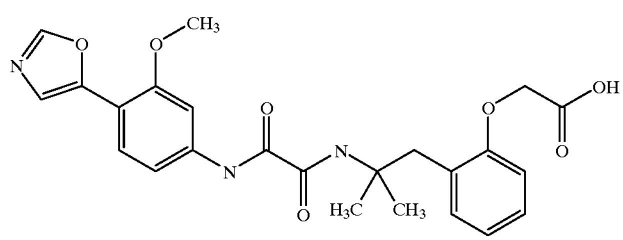 | 468 | 438 |
| 2-[3-[2-[[[3-Methoxy-4-(5-oxazolyl)anilino]oxalyl]amino]-2-methylpropyl]phenoxy]acetic acid | 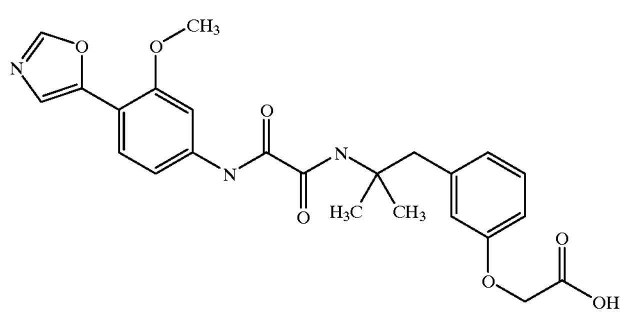 | 468 | 439 |
| N-[3-Methoxy-4-(5-oxazolyl)phenyl]-N'-[1,1-dimethyl-2-(1-oxido-4-pyridyl)ethyl] oxalamide | 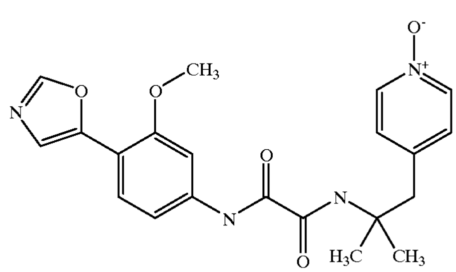 | 411 | 440 |

TABLE 1c-continued

| Name | Structure | MS(ES) (M + H)+ | Ex No |
|---|---|---|---|
| N-[3-Methoxy-4-(5-oxazolyl)phenyl]-N'-[1,1-dimethyl-2-(1-oxido-3-pyridyl)ethyl] oxalamide | 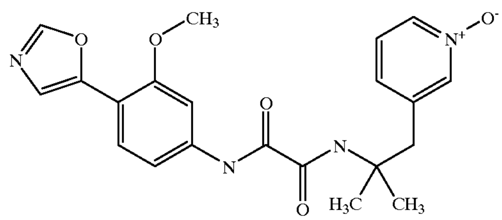 | 411 | 441 |
| N-[3-Methoxy-4-(5-oxazolyl)phenyl]-N'-[1,1-dimethyl-2-(1-oxido-2-pyridyl)ethyl] oxalamide | 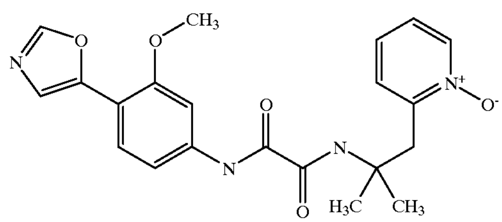 | 411 | 442 |
| 2-[3-[2-[[[3-Methoxy-4-(5-oxazolyl)anilino]oxalyl)]amino]-2-methylpropyl]phenoxy]acetic acid | 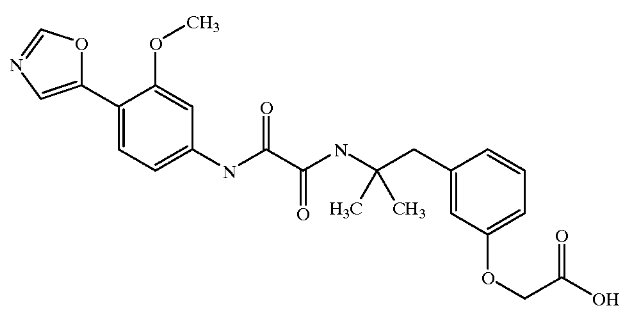 | 468 | 443 |
| N-[2-(2-Benzofuranyl)-1,1-dimethylethyl]-N'-[3-methoxy-4-(5-oxazolyl)phenyl] oxalamide | 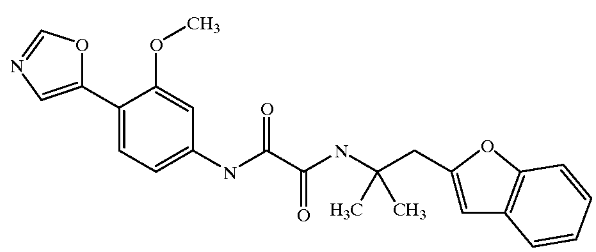 | 434 | 444 |
| N-[3-Methoxy-4-(5-oxazolyl)phenyl]-N'-[1,1-dimethyl-2-(3-methyl-2-benzofuranyl)ethyl] oxalamide | 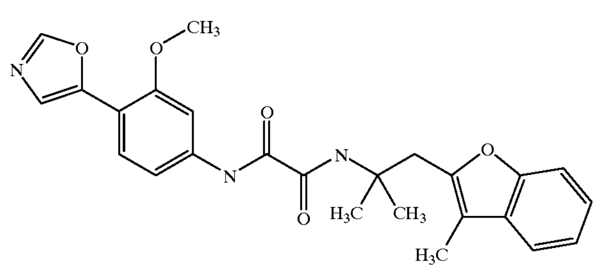 | 448 | 445 |
| N-[2-(7-Methoxy-2-benzofuranyl)-1,1-dimethylethyl]-N'-[3-methoxy-4-(5-oxazolyl)phenyl] oxalamide | 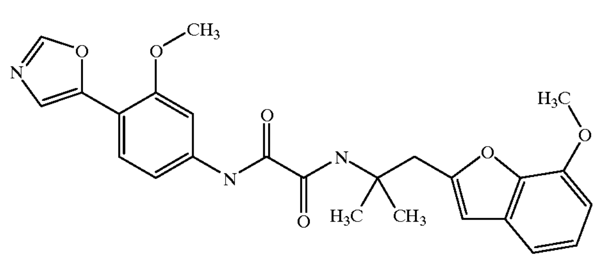 | 464 | 446 |

TABLE 1c-continued

| Name | Structure | MS(ES) (M + H)+ | Ex No |
|---|---|---|---|
| N-[2-(5-Methoxy-2-benzofuranyl)-1,1-dimethylethyl]-N'-[3-methoxy-4-(5-oxazolyl)phenyl]oxalamide | 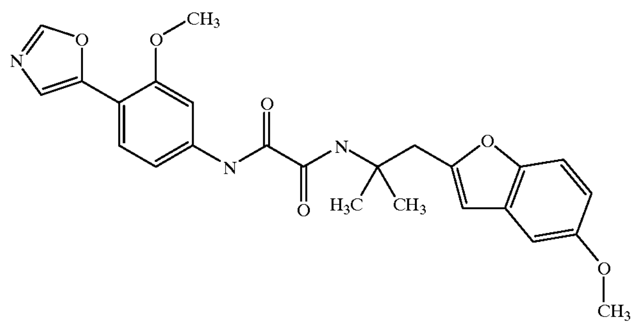 | 464 | 447 |
| N-[2-(6-Methoxy-2-benzofuranyl)-1,1-dimethylethyl]-N'-[3-methoxy-4-(5-oxazolyl)phenyl]oxalamide | 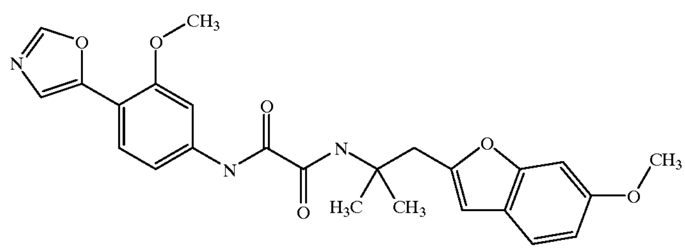 | 464 | 448 |
| Benzyl 4-[2-[[[3-methoxy-4-(5-oxazolyl)anilino]oxalyl]amino]-2-methylpropyl]benzoate | 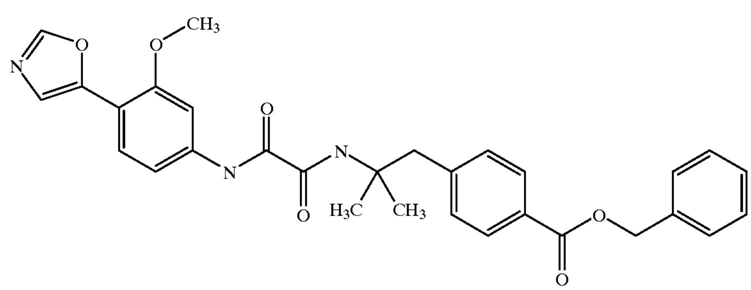 | 528 | 449 |
| 4-[2-[[[3-Methoxy-4-(5-oxazolyl)anilino]oxalyl]amino]-2-methylpropyl]benzoic acid | 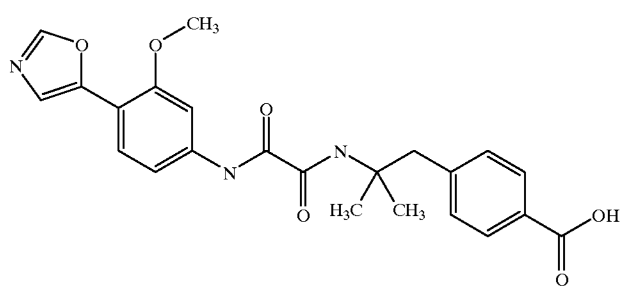 | 438 | 450 |
| Benzyl 3-[2-[[[3-methoxy-4-(5-oxazolyl)anilino]oxalyl]amino]-2-methylpropyl]benzoate | 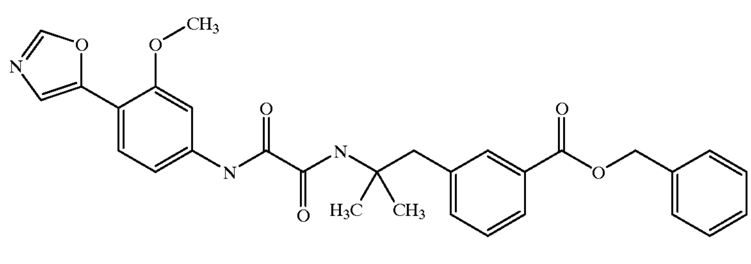 | 528 | 451 |

TABLE 1c-continued

| Name | Structure | MS(ES) (M + H)+ | Ex No |
|---|---|---|---|
| 3-[2-[[[3-Methoxy-4-(5-oxazolyl)anilino]oxalyl]amino]-2-methylpropyl]benzoic acid | 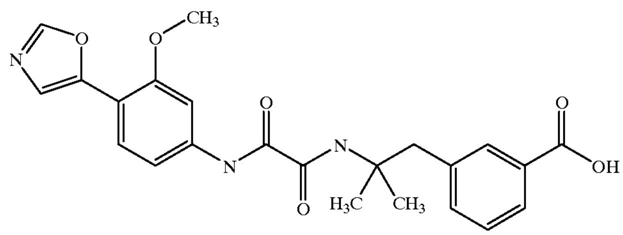 | 438 | 452 |
| N-[2-(3-Benzofuranyl)-1,1-dimethylethyl]-N'-[3-methoxy-4-(5-oxazolyl)phenyl]oxalamide | 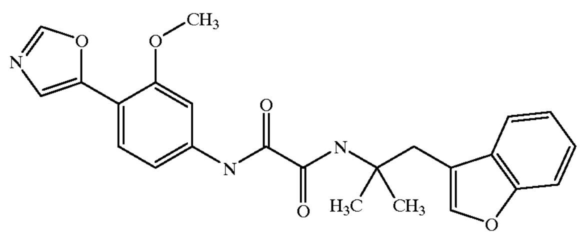 | 434 | 453 |
| Benzyl 2-[[[[3-methoxy-4-(5-oxazolyl)anilino]oxalyl]amino]-2-methylpropyl]-5-benzofurancarboxylate | 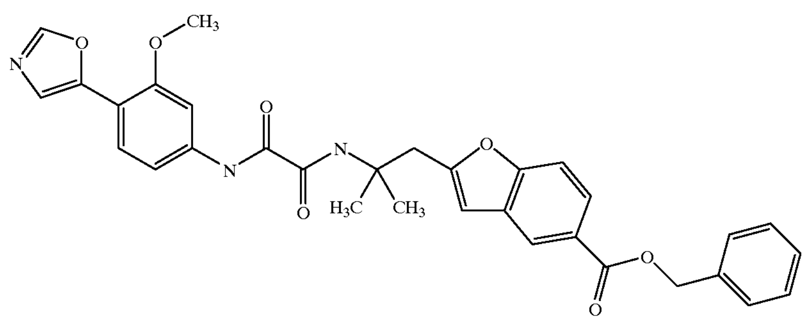 | 568 | 454 |
| 2-[2-[[[3-Methoxy-4-(5-oxazolyl)anilino]oxalyl]amino]-2-methylpropyl]-5-benzofurancarboxylic acid | 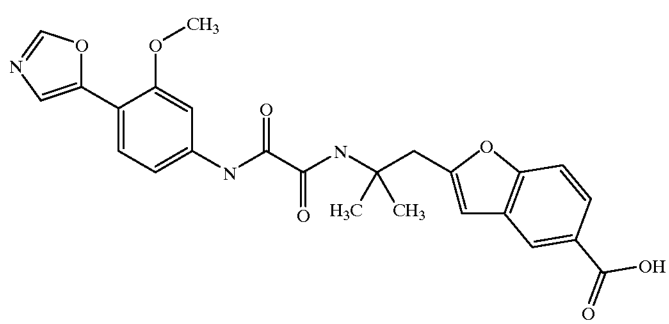 | 477.9 | 455 |
| N-[3-Methoxy-4-(5-oxazolylphenyl]-N'-[1-[(4-pyridyl)methyl]-1-cyclopentyl]oxalamide | 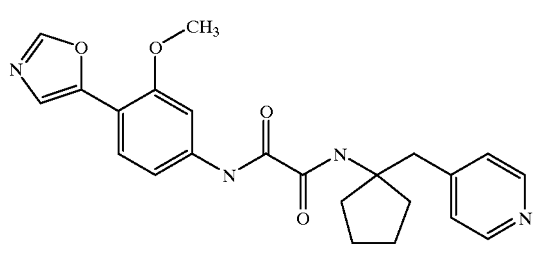 | 421 | 456 |

TABLE 1c-continued

| Name | Structure | MS(ES) (M + H)+ | Ex No |
|---|---|---|---|
| N-[3-Methoxy-4-(5-oxazolyl)phenyl]-N'-[1-[(1-oxido-4-pyridyl)methyl]-1-cyclopentyl]oxalamide | 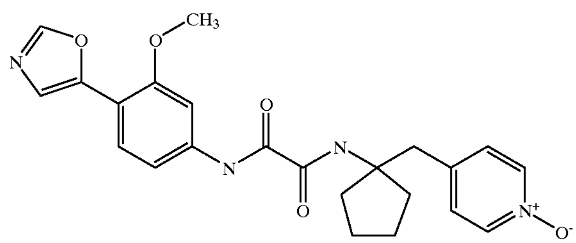 | 437 | 457 |
| N-[2-(4-Methoxy-2-benzofuranyl)-1,1-dimethylethyl]-N'-[3-methoxy-4-(5-oxazolyl)phenyl]oxalamide | 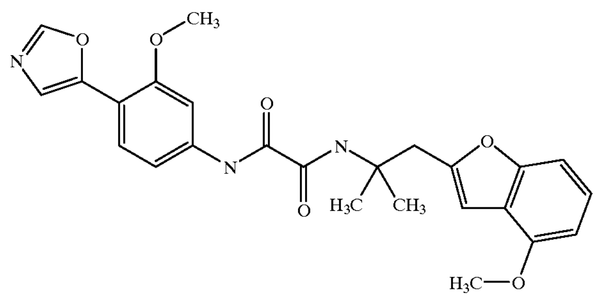 | 464 | 458 |
| N'-[3-Methoxy-4-(5-oxazolyl)phenyl]-N'-[2-(2,6-dimethyl-4-pyridyl)-1,1-dimethylethyl]oxalamide | 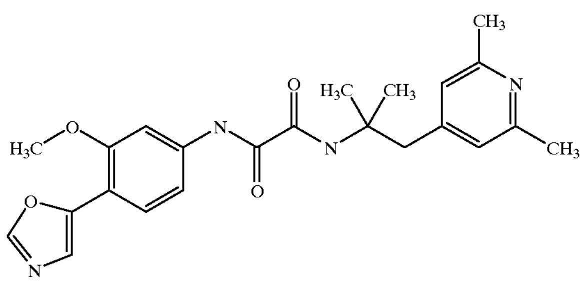 | 423.22 | 653 |
| N-[3-Methoxy-4-(5-oxazolyl)phenyl]-N'-[1,1-dimethyl-2-(2,6-dimethyl-1-oxido-4-pyridyl)ethyl]oxalamide | 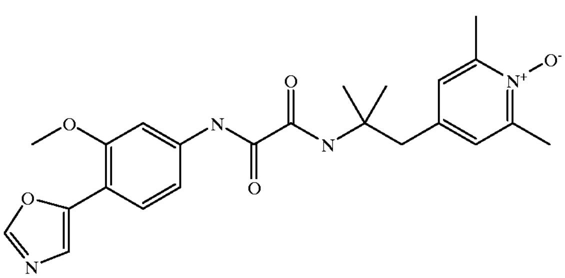 | 439.3 | 654 |
| N-[3-Methoxy-4-(5-oxazolyl)phenyl]-N'-[1-[(4-pyridyl)methyl]-1-cyclopropyl]oxalamide | 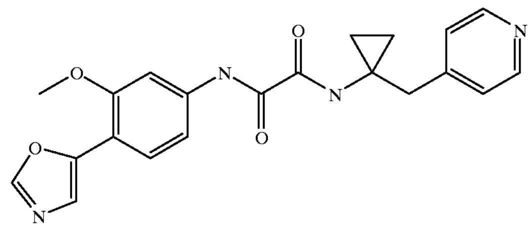 | 393 | 655 |

TABLE 1c-continued

| Name | Structure | MS(ES) (M + H)+ | Ex No |
|---|---|---|---|
| N-[3-Methoxy-4-(5-oxazolyl)phenyl]-N'-[1-[(1-oxido-4-pyridyl)methyl]-1-cyclopropyl]oxalamide | 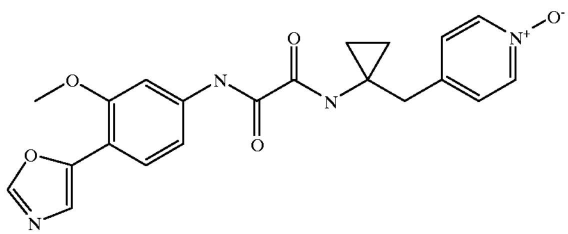 | 409 | 656 |
| N-[3-Methoxy-4-(5-oxazolyl)phenyl]-N'-[1-[4-pyridyl)methyl]-1-cyclobutyl]oxalamide | 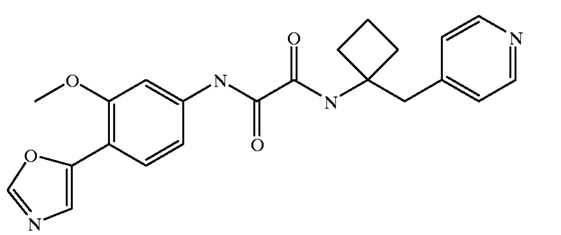 | 407 | 657 |
| N-[3-Methoxy-4-(5-oxazolyl)phenyl]-N'-[1-[(1-oxido-4-pyridyl)methyl]-1-cyclobutyl]oxalamide | 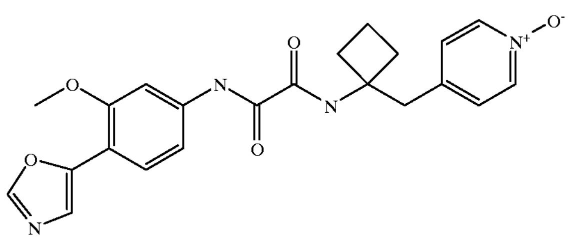 | 421 | 658 |
| N-[3-Methoxy-4-(5-oxazolyl)phenyl]-N'-[1-[(4-pyridyl)methyl]-1-cyclohexyl]oxalamide | 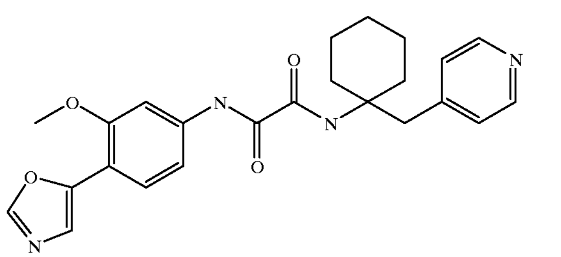 | 435 | 659 |
| N-[3-Methoxy-4-(5-oxazolyl)phenyl]-N'-[1-[(1-oxido-4-pyridyl)methyl]-1-cyclohexyl]oxalamide | 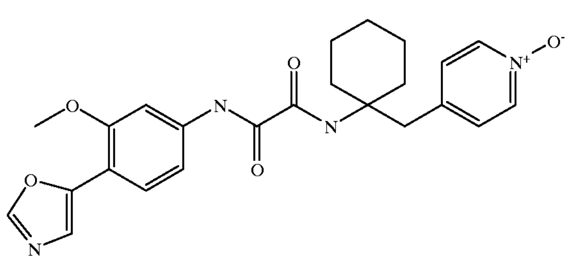 | 451 | 660 |
| N-[3-Methoxy-4-(5-oxazolyl)phenyl]-N'-[1,1-dimethyl-2-(2-methyl-4-pyridyl)ethyl]oxalamide | 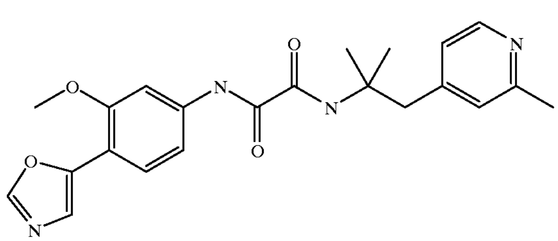 | 409 | 661 |

TABLE 1c-continued

| Name | Structure | MS(ES) (M + H)+ | Ex No |
|---|---|---|---|
| N-[3-Methoxy-4-(5-oxazolyl)phenyl]-N'-[1,1-dimethyl-2-(2-methyl-1-oxido-4-pyridyl)ethyl]oxalamide | 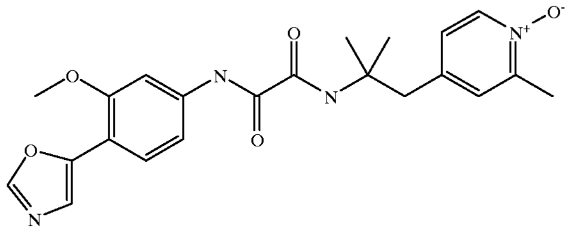 | 425 | 662 |
| 2-[2-[[[3-Methoxy-4-(5-oxazolyl)anilino]oxalyl]amino]-2-methylpropyl]-5-benzothiophene-carboxylic acid | 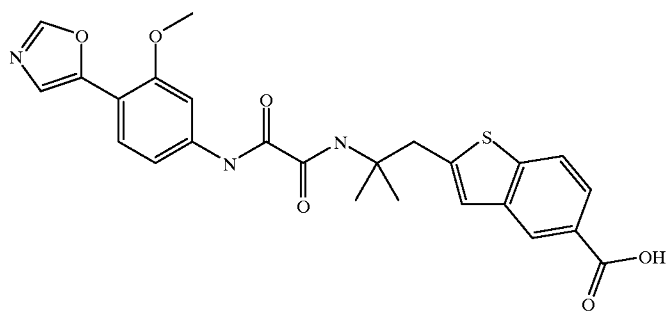 | 494 | 663 |

Particularly preferred compounds of formula (I) and (IX) are also those of the general formula

XII wherein $R^2$, $R^3$, $R^5$, $R^6$, $R^7$, $R^9$ and $R^{10}$ are defined as above, $R^{11}$, $R^{13}$, $R^{14}$, $R^{15}$, $R^{16}$, $R^{17}$ and $R^{18}$ are H or lower alkyl and $R^{19}$ is alkyl, cycloalkylalkyl, heterocyclyl alkyl or aryl alkyl.

Particularly preferred compounds of formula (XII) are those wherein $R^2$ is methoxy and $R^3$, $R^5$, $R^6$, $R^9$, $R^{10}$, $R^{11}$ and $R^{13}$ are hydrogen. Also preferred are compounds wherein $R^{19}$ represents arylalkyl, branched lower alkyl, a 3 to 7 membered cycloalkyl alkyl, or a 5 or 6 membered monocyclic or 9 or 10 membered bicyclic saturated or unsaturated heterocyclyl alkyl with 1 to 4 heteroatoms selected from nitrogen, oxygen, and sulfur.

Examples of such compounds are listed in table 1d below

| Name | Structure | MS(ES) (M + H)+ | Ex No |
|---|---|---|---|
| N-[3-Methoxy-4-(5-oxazolyl)phenyl]-N'-[1,1-dimethyl-2-[4-[(2-pyridinyl)methylamino]phenyl]ethyl]oxalamide | 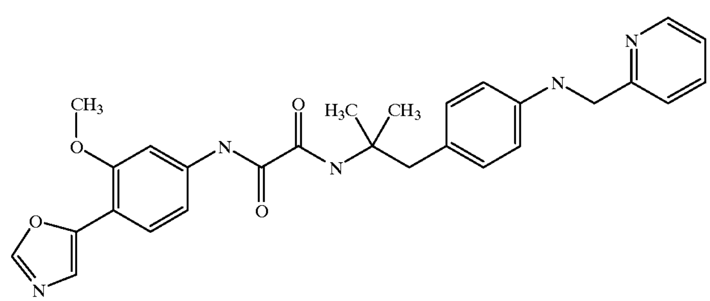 | 500.1 | 316 |

| Name | Structure | MS(ES) (M + H)+ | Ex No |
|---|---|---|---|
| N-[3-Methoxy-4-(5-oxazolyl)phenyl]-N'-[1,1-dimethyl-2-[4-[(3-pyridyl)methylamino]phenyl]ethyl]oxalamide | 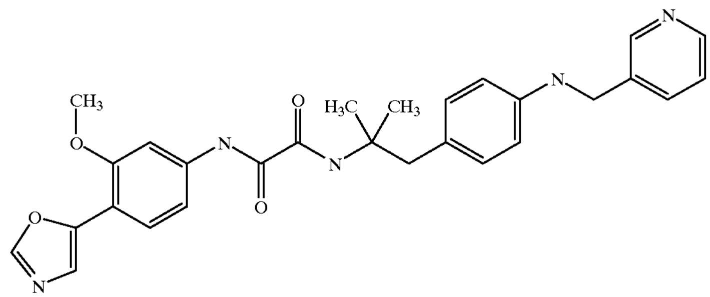 | 500.1 | 317 |
| N-[2-[4-(2-Furfurylamino)phenyl]-1,1-dimethylethyl]-N'-[3-methoxy-4-(5-oxazolyl)phenyl]oxalamide | 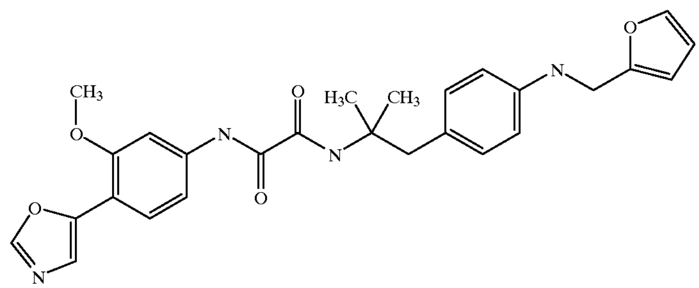 | 489.1 | 318 |
| N-[3-Methoxy-4-(5-oxazolyl)phenyl]-N'-[1,1-Dimethyl-2-[4-(2-thenylamino)phenyl]ethyl]oxalamide | 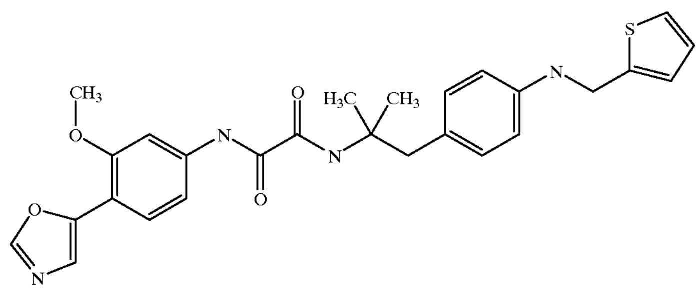 | 505.1 | 319 |
| N-[3-Methoxy-4-(5-oxazolyl)phenyl]-N'-[1,1-dimethyl-2-[4-(2,2-dimethylpropylamino)phenyl]ethyl]oxalamide | 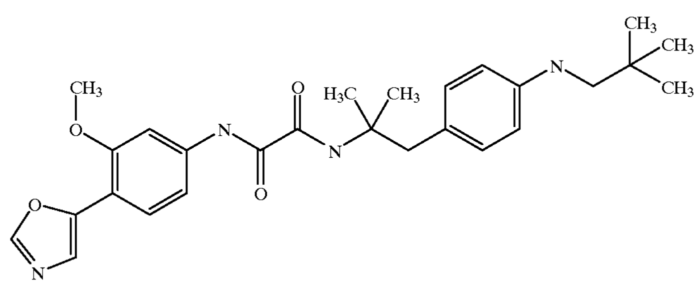 | 479.2 | 320 |
| N-[2-[4-[(1H-Imidazol-2-yl)methylamino]phenyl]-1,1-dimethylethyl]-N'-[3-methoxy-4-(5-oxazolyl)phenyl]oxalamide | 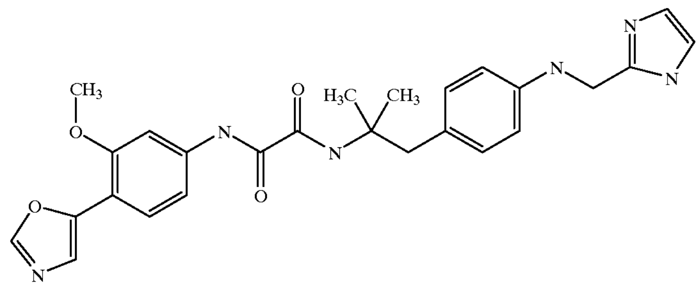 | 489.1 | 321 |

-continued

| Name | Structure | MS(ES) (M + H)+ | Ex No |
|---|---|---|---|
| N-[3-Methoxy-4-(5-oxazolyl)phenyl]-N'-[1,1-dimethyl-2-[4-[(4-pyridyl)methylamino]phenyl]ethyl]oxalamide | 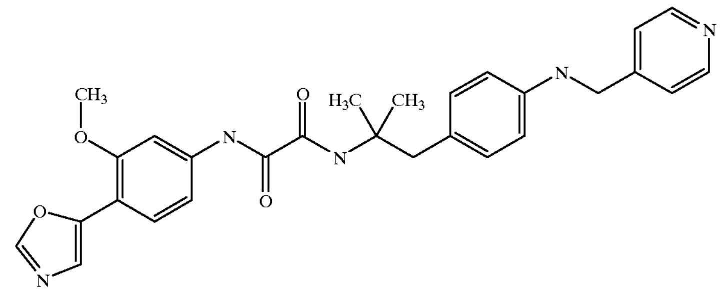 | 500.1 | 322 |
| N-[3-Methoxy-4-(5-oxazolyl)phenyl]-N'-[1,1-dimethyl2-2[4-[(2-thiazolyl)methylamino]phenyl]ethyl]oxalamide | 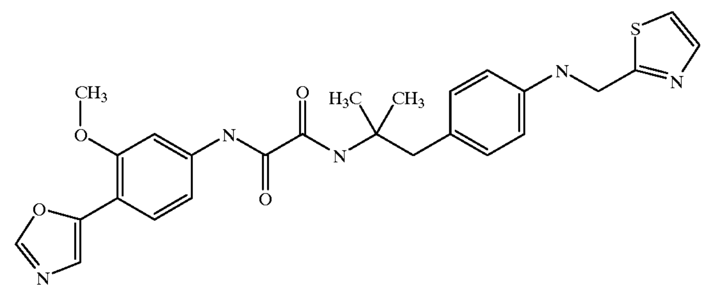 | 506.1 | 323 |
| N-[2-[4-(3-Furfurylamino)phenyl]-1,1-dimethylethyl]-N'-[3-methoxy-4-(5-oxazolyl)phenyl]oxalamide | 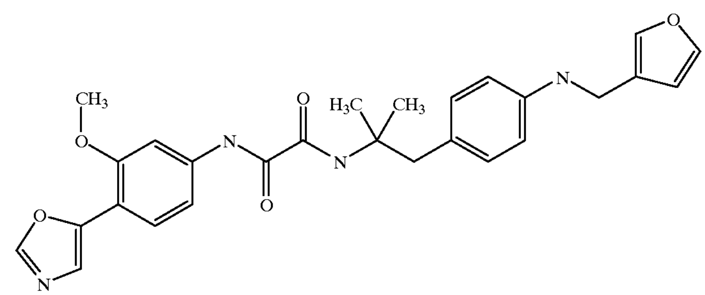 | 489.1 | 324 |
| N-[2-[4-[5-(Hydroxymethyl)-2-furfurylamino]phenyl]-1,1-dimethylethyl]-N'-[3-methoxy-4-(5-oxazolyl)phenyl]oxalamide | 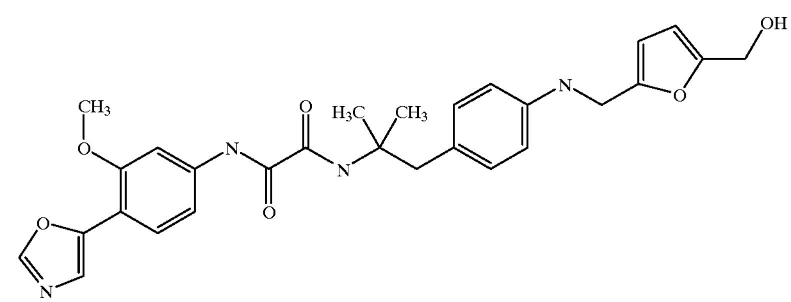 | 519.1 | 325 |
| N-[2-(4-Benzylaminophenyl)-1,1-dimethylethyl]-N'-[3-methoxy-4-(5-oxazolyl)phenyl]oxalamide | 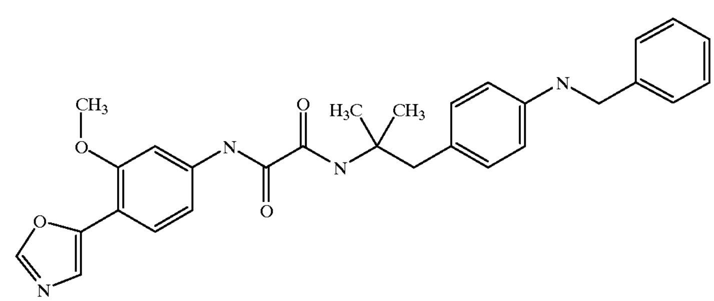 | 499.1 | 326 |

-continued

| Name | Structure | MS(ES) (M + H)+ | Ex No |
|---|---|---|---|
| N-[2-[4-(2-Hydroxybenzylamino)phenyl]-1,1-dimethylethyl]-N'-[3-methoxy-4-(5-oxazolyl)phenyl]oxalamide | 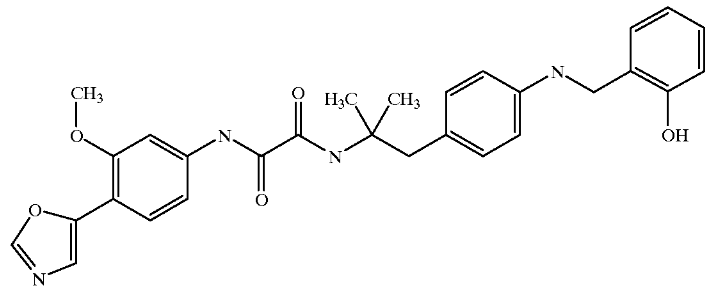 | 515.1 | 327 |
| N-[2-[4-(3-Cyanobenzylamino)phenyl]-1,1-dimethylethyl]-N'-[3-methoxy-4-(5-oxazolyl)phenyl]oxalamide | 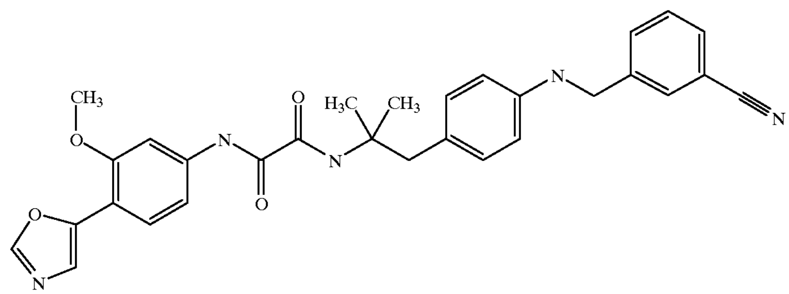 | 524.1 | 328 |
| N-[3-Methoxy-4-(5-oxazolyl)phenyl]-N'-[1,1-dimethyl-2-[4-[4-(3-pyridyl)benzylamino]phenyl]ethyl]oxalamide | 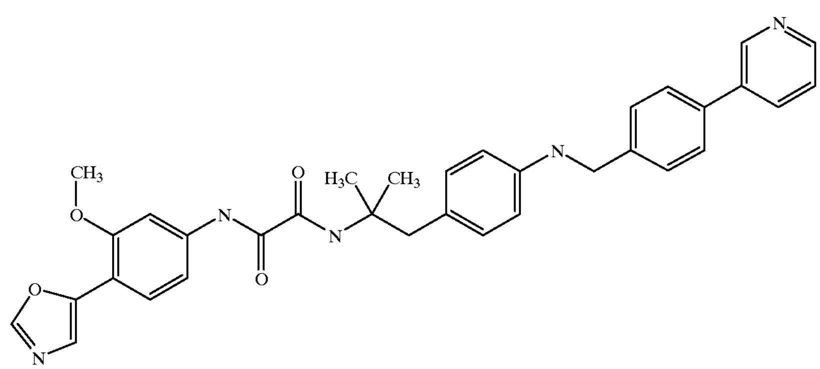 | 576.2 | 329 |
| N-[2-[4-(2-Fluorobenzylamino)phenyl]-1,1-dimethylethyl]-N'-[3-methoxy-4-(5-oxazolyl)phenyl]oxalamide | 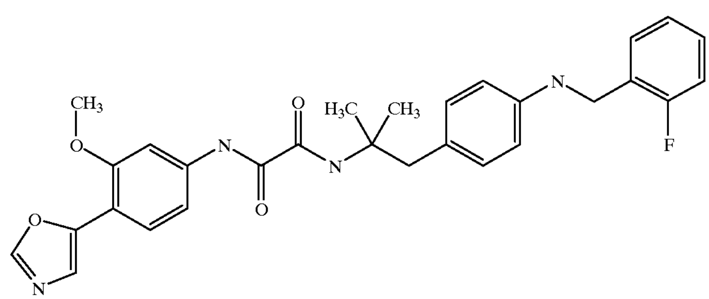 | 517.1 | 330 |

Particularly preferred compounds of formula (I) and (IX) are also those of general formula

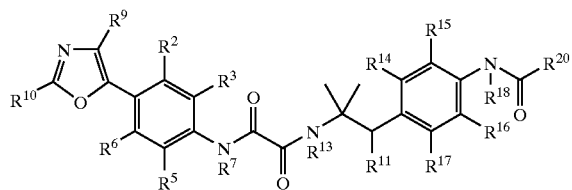

XIII wherein $R^2$, $R^3$, $R^5$, $R^6$, $R^7$, $R^9$ and $R^{10}$ are defined as above, $R^{11}$, $R^{13,}$ $R^{14}$, $R^{15}$, $R^{16}$, $R^{17}$ and $R^{18}$ are H or lower alkyl and $R^{20}$ is alkyl, cycloalkyl, aryl, heterocyclyl.

Particularly preferred compounds of formula (XIII) are those wherein $R^2$ is methoxy and $R^3$, $R^5$, $R^6$, $R^9$, $R^{10}$, $R^{11}$ and $R^{13}$ are hydrogen. Also preferred are compounds where $R^{20}$ represents aryl, branched lower alkyl, a 3 to 7 membered cycloalkyl ring, or a 5 or 6 membered or 9 or 10 membered bicyclic saturated or unsaturated heterocyclic ring with 1 to 4 heteroatoms selected from nitrogen, oxygen, and sulfur.

Examples of such compounds are listed in table 1e below

TABLE 1e

| Name | Structure | MS(ES) (M + H)+ | Ex No |
|---|---|---|---|
| N-[2-[4-(Cyclopropyl-carboxamido)phenyl]-1,1-dimethylethyl]-N'-[3-methoxy-4-(5-oxazolyl)phenyl] oxalamide | 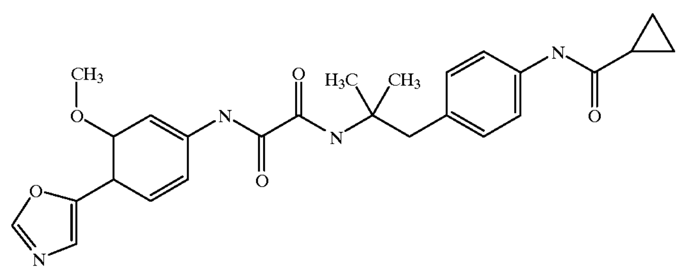 | 477.1 | 331 |
| N-[2-[4-(Cyclobutyl-carboxamido)phenyl]-1,1-dimethylethyl]-N'-[3-methoxy-4-(5-oxazolyl)phenyl oxalamide | 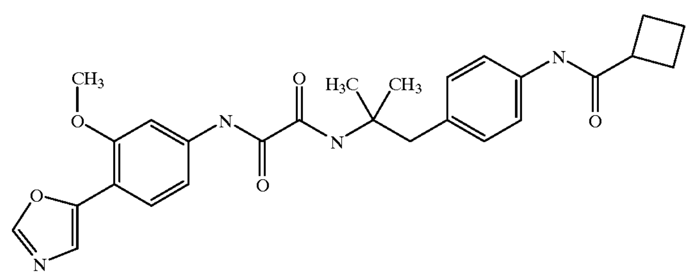 | 491.1 | 332 |
| N-{3-Methoxy-4-(5-oxazolyl)phenyl]-N'-[1,1-dimethyl-2-(4-pivalamidophenyl)-1,1-dimethylethyl] oxalamide | 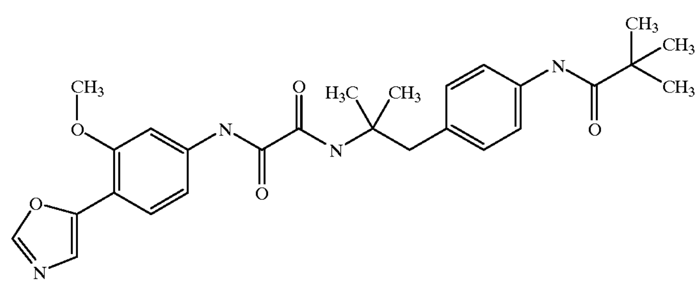 | 493.1 | 333 |
| N-[3-Methoxy-4-(5-oxazolyl)phenyl]-N'-[1,1-dimethyl-2-[4-[(1H-pyrrol-2-yl)carboxamido]phenyl]ethyl] oxalamide | 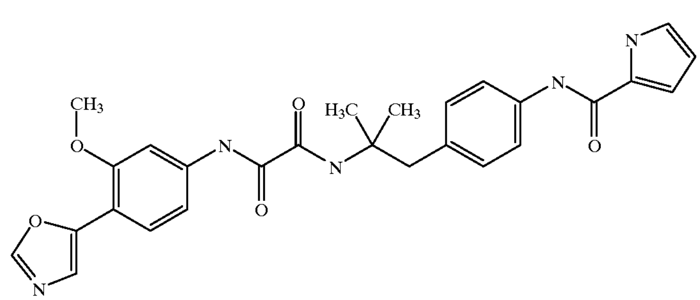 | 502.1 | 334 |

TABLE 1e-continued

| Name | Structure | MS(ES) (M + H)+ | Ex No |
|---|---|---|---|
| N-[2-[4-[(2-Furyl)carboxamido]phenyl]-1,1-dimethylethyl]-N'-[3-methoxy-4-(5-oxazolyl)phenyl]oxalamide | 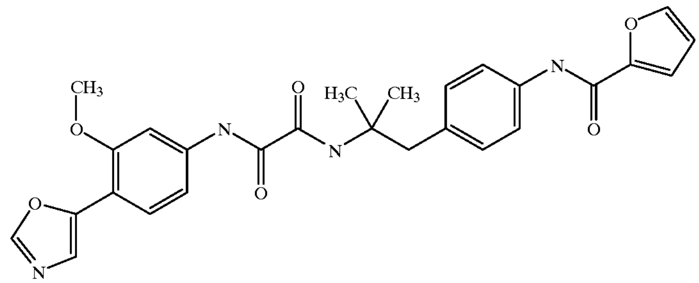 | 503.1 | 335 |
| N-[2-[4-[(3-Furyl)carboxamido]phenyl]-1,1-dimethylethyl]-N'-[3-methoxy-4-(5-oxazolyl)phenyl]oxalamide | 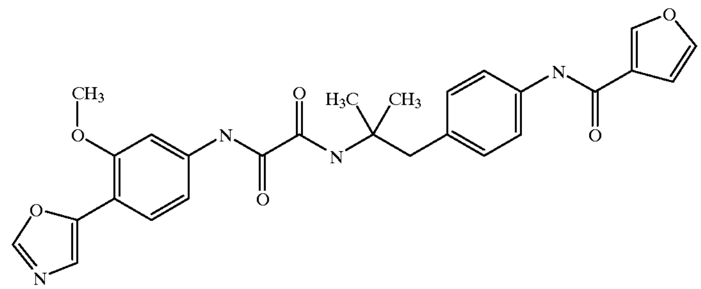 | 503.1 | 336 |
| N-[2-[4-[(1H-Imidazol-4-yl)carboxamido]phenyl]-1,1-dimethylethyl]-N'-[3-methoxy-4-(5-oxazolyl)phenyl]oxalamide | 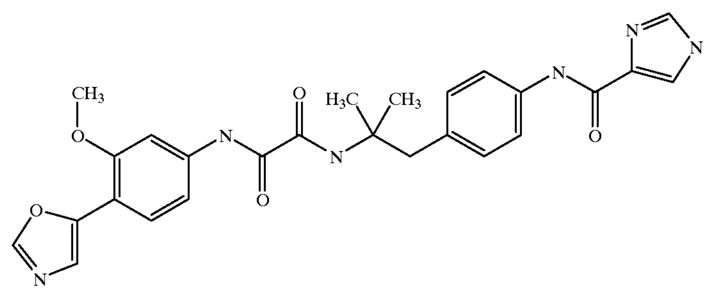 | 503.1 | 337 |
| N-[2-[4-[(Tetrahydro-2(RS)-furyl)carboxamido]phenyl]-1,1-dimethylethyl]-N'-[3-methoxy-4-(5-oxazolyl)phenyl]oxalamide | 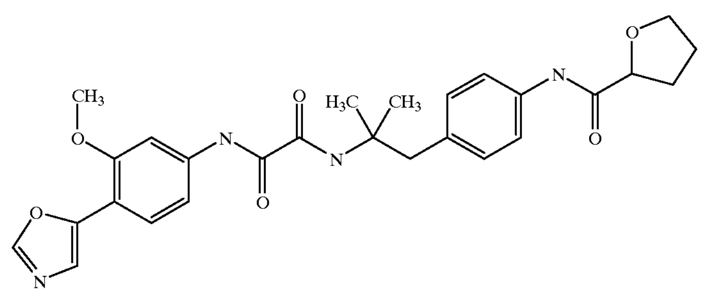 | 507.2 | 338 |
| N-[3-Methoxy-4-(5-oxazolyl)phenyl]-N'-[1,1-dimethyl-2-[4-[(2-pyridyl)carboxamido]phenyl]ethyl]oxalamide | 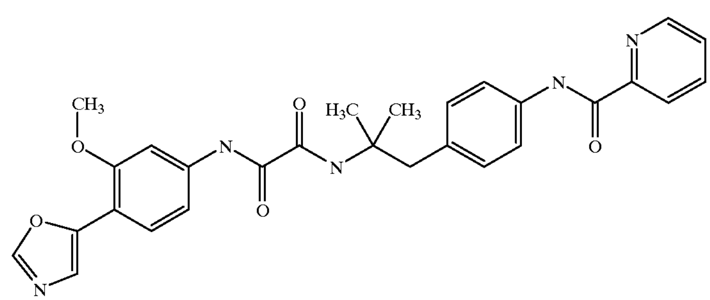 | 514.1 | 340 |

TABLE 1e-continued

| Name | Structure | MS(ES) (M + H)+ | Ex No |
|---|---|---|---|
| N-[3-Methoxy-4-(5-oxazolyl)phenyl]-N'-[1,1-dimethyl-2-[4-[(4-pyridyl)carboxamido]phenyl]ethyl] oxalamide | 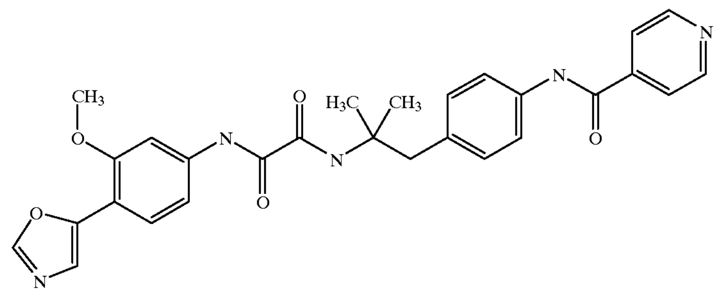 | 514.1 | 340 |
| N-[3-Methoxy-4-(5-oxazolyl)phenyl]-N'-[1,1-dimethyl-2-[4-[(2-thienyl)carboxamido]phenyl]ethyl] oxalamide | 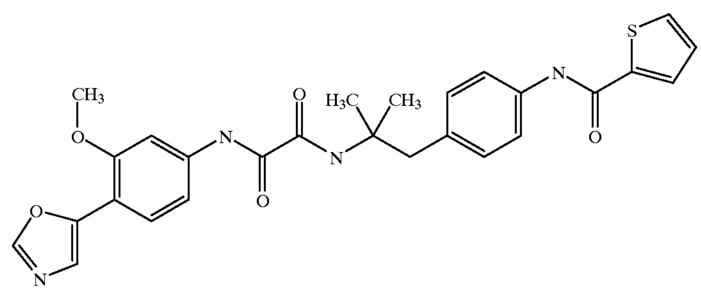 | 519.1 | 341 |
| N-[3-Methoxy-4-(5-oxazolyl)phenyl]-N'-[1,1-dimethyl-2-[4-[(3-thienyl)carboxamido]phenyl]ethyl] oxalamide | | 519.1 | 342 |
| N-[2-[4-(2-Cyclopentyl-acetamido)phenyl]-1,1-dimethylethyl]-N'-[3-methoxy-4-(5-oxazolyl)phenyl] oxalamide | 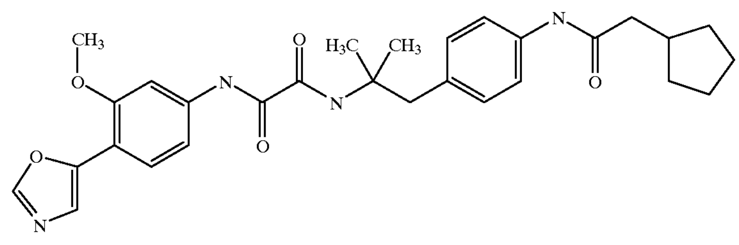 | 519.2 | 343 |
| N-[3-Methoxy-4-(5-oxazolyl) phenyl]-N'-[1,1-dimethyl-2-[4-(2-methylbenzamido)phenyl]ethyl] oxalamide | 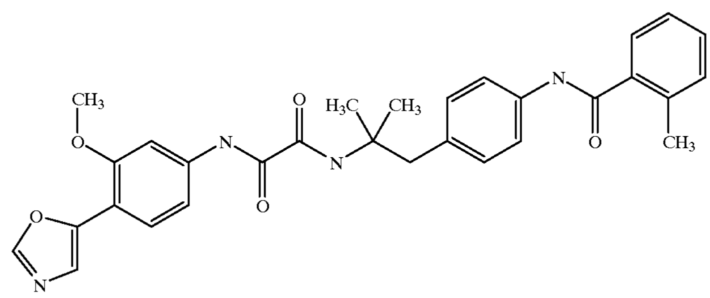 | 527.2 | 344 |

TABLE 1e-continued

| Name | Structure | MS(ES) (M + H)+ | Ex No |
|---|---|---|---|
| N-[3-Methoxy-4-(5-oxazolyl)phenyl]-N'-[1,1-dimethyl-2-[4-(4-methylbenzamido)phenyl]ethyl]oxalamide | 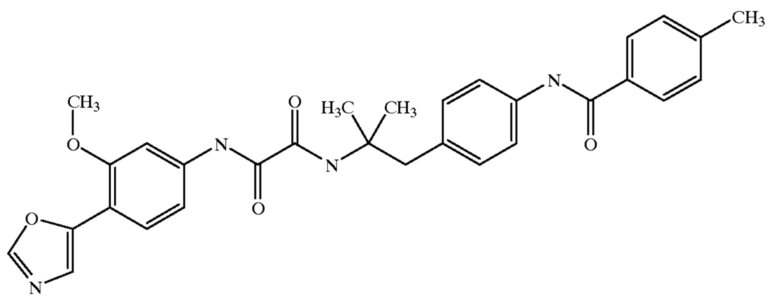 | 527.2 | 345 |
| N-[2-[4-(Cycloheptyl-carboxamido)phenyl]-1,1-dimethylethyl]-N'-[3-methoxy-4-(5-oxazolyl)phenyl]oxalamide | 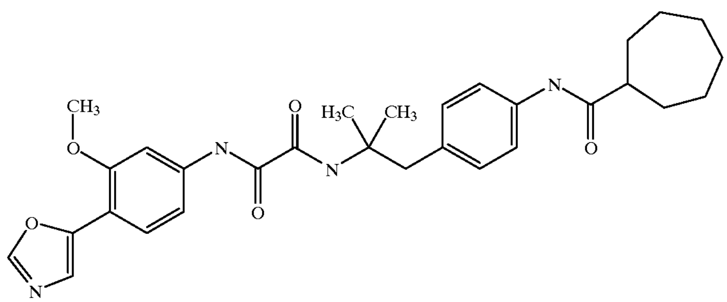 | 533.2 | 346 |
| N-[2-[4-[(5-Isoxazolyl)carboxamido]phenyl]-1,1-dimethylethyl]-N'-[3-methoxy-4-(5-oxazolyl)phenyl]oxalamide | 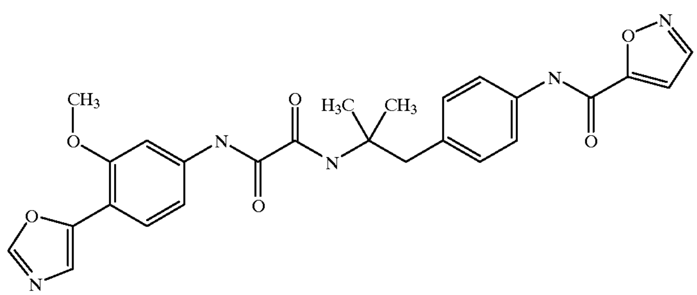 | 504.1 | 347 |
| N-[2-[4-(Cyclopentyl-carboxamido)phenyl]-1,1-dimethylethyl]-N'-[3-methoxy-4-(5-oxazolyl)phenyl]oxalamide | 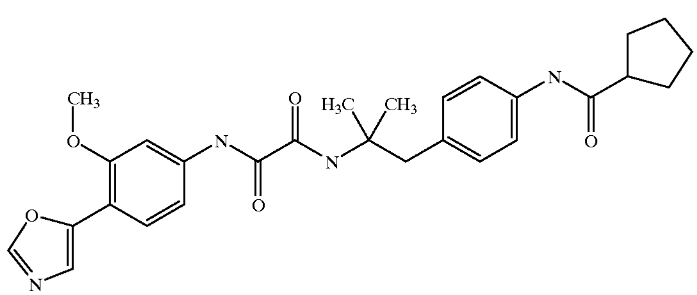 | 505.2 | 348 |
| N-[2-{4-[(Tetrahydro-3(RS)-furyl)carboxamido]phenyl]-1,1-dimethylethyl]-N'-[3-methoxy-4-(5-oxazolyl)phenyl]oxalamide | 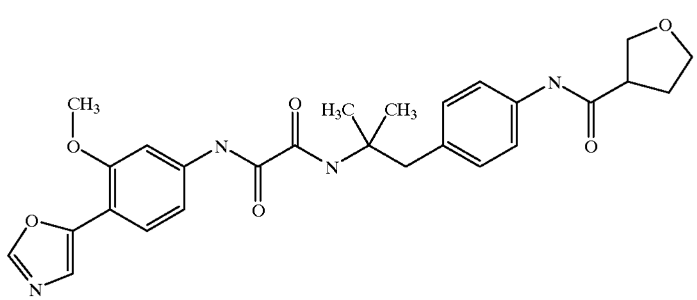 | 507.1 | 349 |

TABLE 1e-continued

| Name | Structure | MS(ES) (M + H)+ | Ex No |
|---|---|---|---|
| N-[3-Methoxy-4-(5-oxazolyl)phenyl]-N'-[1,1-dimethyl-2-[4-[(1-methyl-1H-pyrrol-2-yl)carboxamido]phenyl]ethyl]oxalamide | 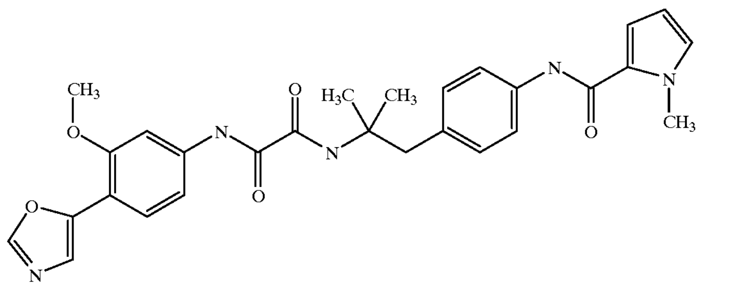 | 516.1 | 350 |
| N-[3-Methoxy-4-(5-oxazolyl)phenyl]-N'-(1,1-dimethyl-2-[4-[(1,2,3-thiadiazol-4-yl)carboxamido]phenyl]ethyl]oxalamide | 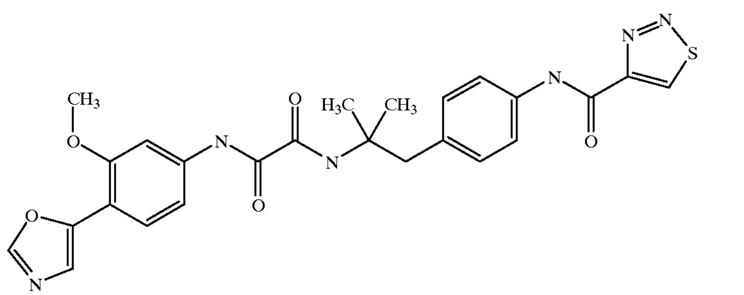 | 521.1 | 351 |
| N-[2-[4-(3-Fluorobenzamido)phenyl]-1,1-dimethylethyl]-N'-[3-methoxy-4-(5-oxazolyl)phenyl]oxalamide | 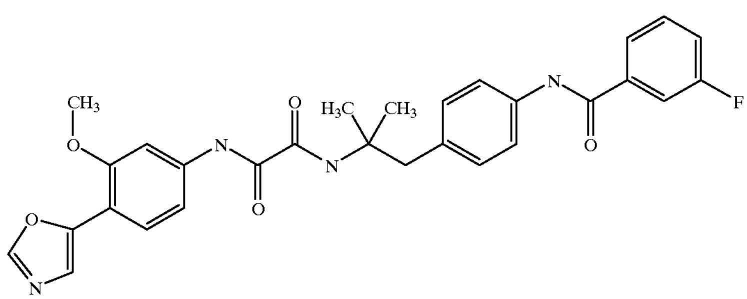 | 531.1 | 352 |
| N-[2-[4-(4-Fluorobenzamido)phenyl]-1,1-dimethylethyl]-N'-[3-methoxy-4-(5-oxazolyl)phenyl]oxalamide | 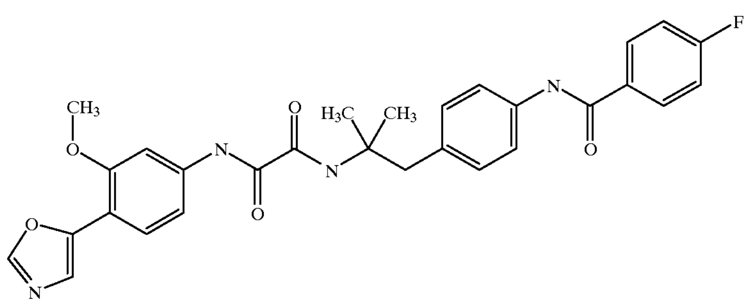 | 531.1 | 353 |
| N-[2-[4-(2-Methoxybenzamido)phenyl]-1,1-dimethylethyl]N'-[3-methoxy-4-(5-oxazolyl)phenyl]oxalamide | 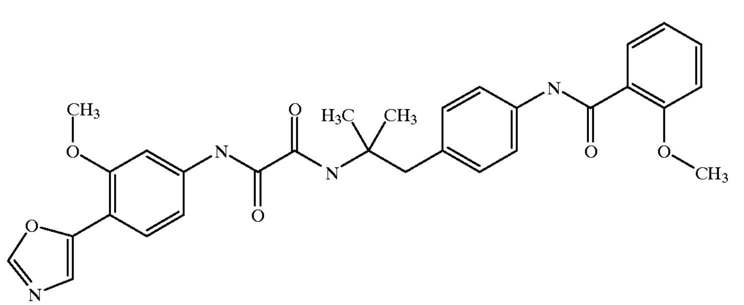 | 543.2 | 354 |

TABLE 1e-continued

| Name | Structure | MS(ES) (M + H)+ | Ex No |
|---|---|---|---|
| N-[2-[4-(2-Chlorobenzamido)phenyl]-1,1-dimethylethyl]-N'-[3-methoxy-4-(5-oxazolyl)phenyl]oxalamide | 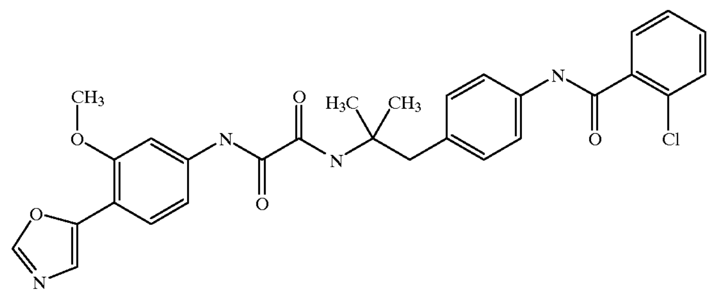 | 547.1 | 355 |
| N-[2-[4-(3-Chlorobenzamido)phenyl]-1,1-dimethylethyl]-N'-[3-methoxy-4-(5-oxazolyl)phenyl]oxalamide | 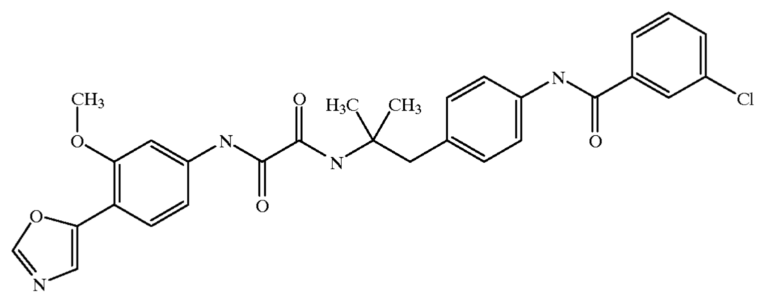 | 547.1 | 356 |
| N-[2-[4-(4-Chlorobenzamido)phenyl]-1,1-dimethylethyl]-N'-[3-methoxy-4-(5-oxazolyl)phenyl]oxalamide | 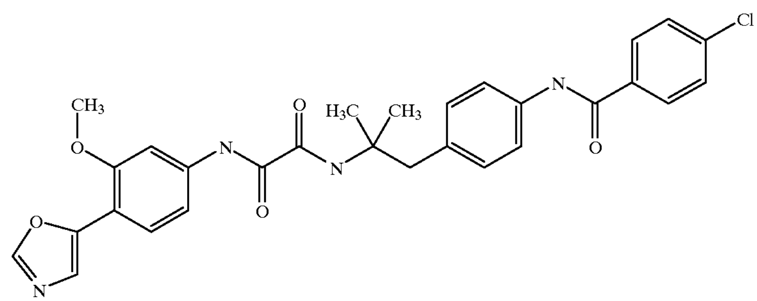 | 547.1 | 357 |
| N-[2-[4-[(1H-Indol-2-yl)carboxamido]phenyl]-1,1-dimethylethyl]-N'-[3-methoxy-4-(5-oxazolyl)phenyl]oxalamide | 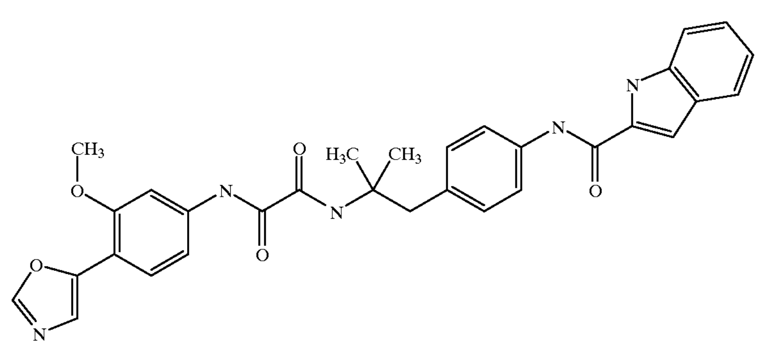 | 552.1 | 358 |

TABLE 1e-continued

| Name | Structure | MS(ES) (M + H)+ | Ex No |
|---|---|---|---|
| N-[3-Methoxy-4-(5-oxazolyl)phenyl]-N'-[1,1-dimethyl-2-[4-[4-(dimethylamino)benzamido]phenyl]ethyl]oxalamide | 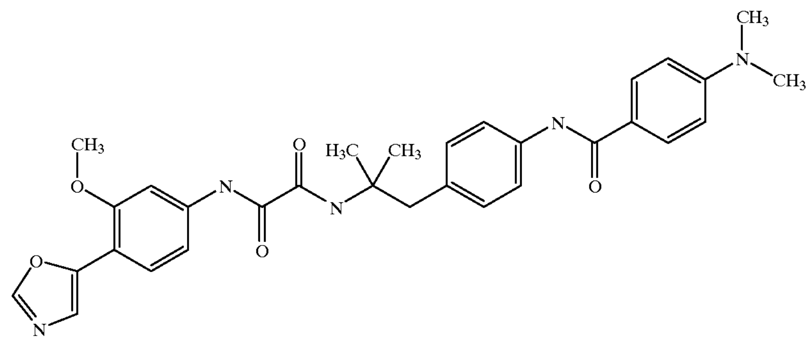 | 556.1 | 359 |
| N-[3-Methoxy-4-(5-oxazolyl)phenyl]-N'-[1,1-dimethyl-2-[4-(3,3-dimethyl-butyramido)]phenyl]ethyl]oxalamide | 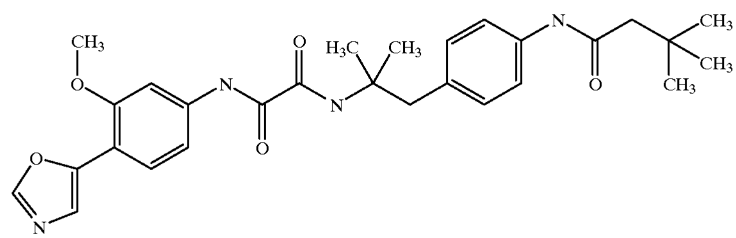 | 507.1 | 360 |
| N-[3-Methoxy-4-(5-oxazolyl)phenyl]-N'-[1,1-dimethyl-2-[4-[2-(1-tetrazolyl)acetamido]phenyl]ethyl]oxalamide | 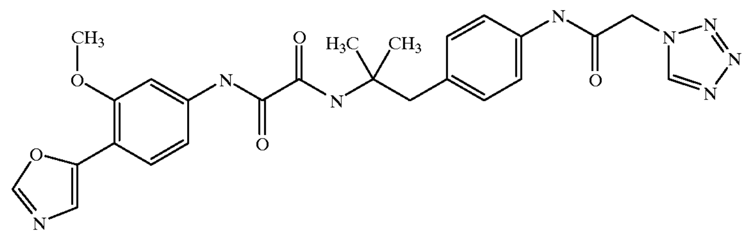 | 519.1 | 361 |
| N-[3-Methoxy-4-(5-oxazolyl)phenyl]-N'-[1,1-dimethyl-2-[4-[(5-oxo-2(S)-pyrrolidinyl)carboxamido]phenyl]ethyl]oxalamide | 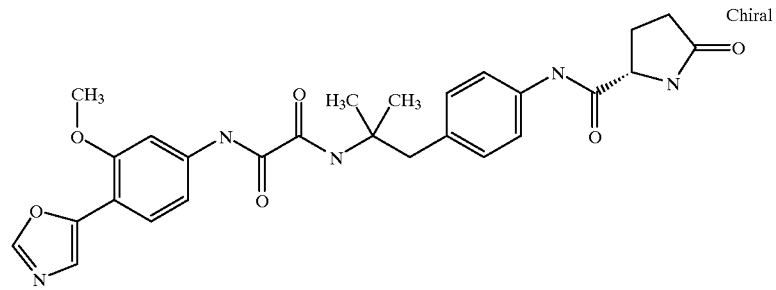 | 520.1 | 362 |
| N-[3-Methoxy-4-(5-oxazolyl)phenyl]-N'-(1,1-dimethyl-20{4-[(5-oxo-2(R)-pyrrolidinyl)carboxamido]phenyl]ethyl]oxalamide | 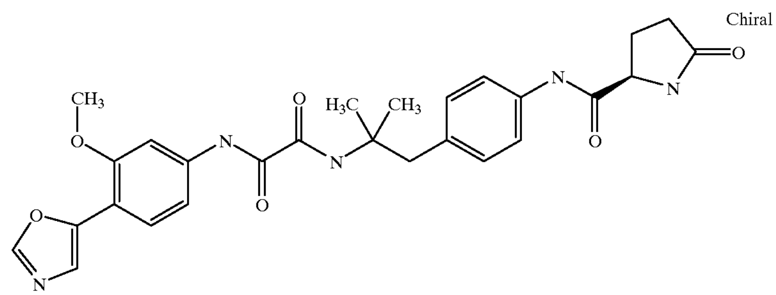 | 520.1 | 363 |

TABLE 1e-continued

| Name | Structure | MS(ES) (M + H)+ | Ex No |
|------|-----------|-----------------|-------|
| N-[3-Methoxy-4-(5-oxazolyl)phenyl]-N'-[1,1-dimethyl-2-[4-[2-naphthyl) carboxamido]phenyl]ethyl] oxalamide | 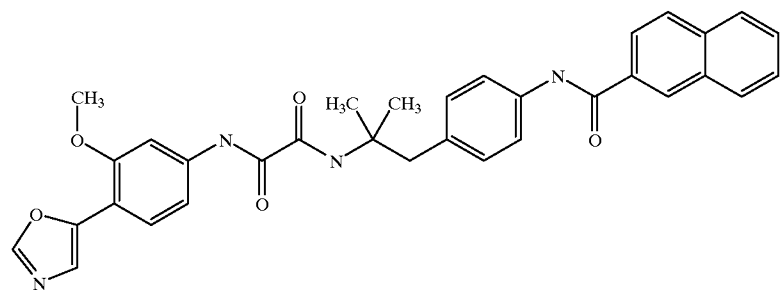 | 563.1 | 364 |
| N-[2-{4-[(6-Cyano-3-pyridyl)carboxamido]phenyl}-1,1-dimethylethyl]-N'-[3-methoxy-4-(5-oxazolyl)phenyl] oxalamide | 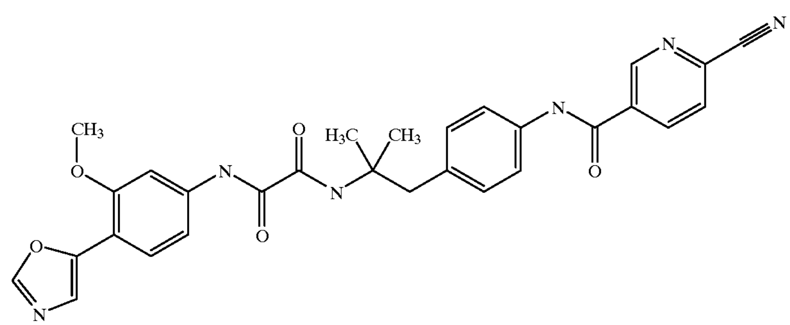 | 580.1 (M + H + ACN) | 365 |
| N-[2-[4-(3-Methoxybenzamido)phenyl]-1,1-dimethylethyl]-N'-[3-methoxy-4-(5-oxazolyl)pehnyl] oxalamide | 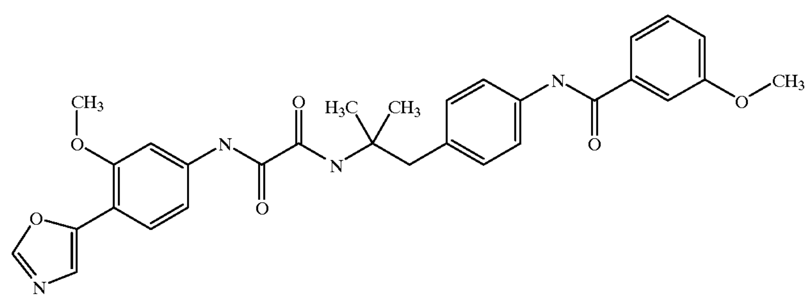 | 543.1 | 366 |
| N-[2-[4-(3,5-Difluorobenzamido)phenyl]-1,1-dimethylethyl]-N'-[3-methoxy-4-(5-oxazolyl)phenyl] oxalamide | 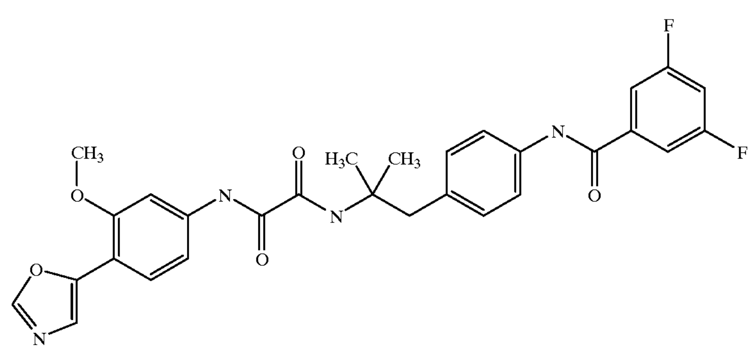 | 549.1 | 367 |

TABLE 1e-continued

| Name | Structure | MS(ES) (M + H)+ | Ex No |
|---|---|---|---|
| N-[2-[4-[1H-Indol-5-yl)carboxamido]phenyl]-1,1-dimethylethyl]-N'-[3-methoxy-4-(5-oxazolyl)phenyl]oxalamide | 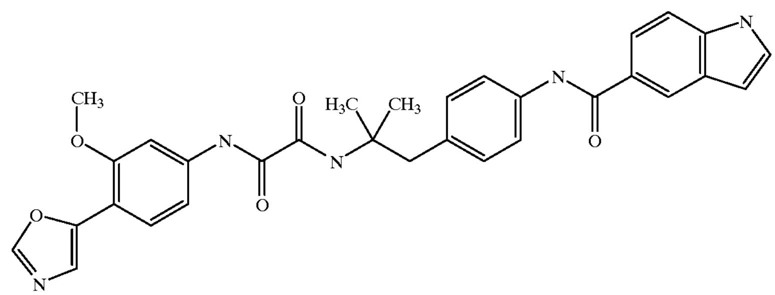 | 552.1 | 368 |
| (E)-N-[2-[4-(2-Butenamido)phenyl]-1,1-dimethylethyl]-N'-[3-methoxy-4-(5-oxazolyl)phenyl]oxalamide | 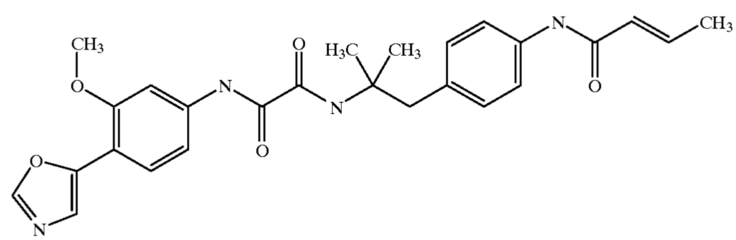 | 477.1 | 369 |
| N-[2-[4-(2-Methoxyacetamido)phenyl]-1,1-dimethylethyl]-N'-[3-methoxy-4-(5-oxazolyl)phenyl]oxalamide | 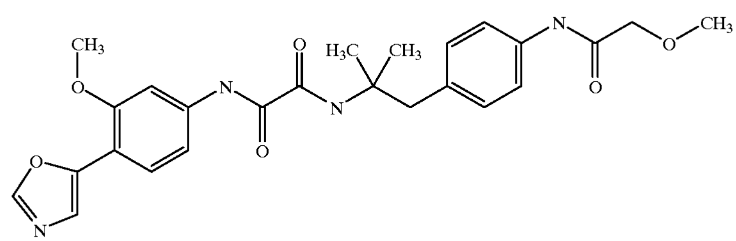 | 481.2 | 370 |
| N-[3-methoxy-4-(5-oxazolyl)phenyl]-N'-[1,1-dimethyl-2-[4-[(2-methyl-3-furyl)carboxamido]phenyl]ethyl]oxalamide | 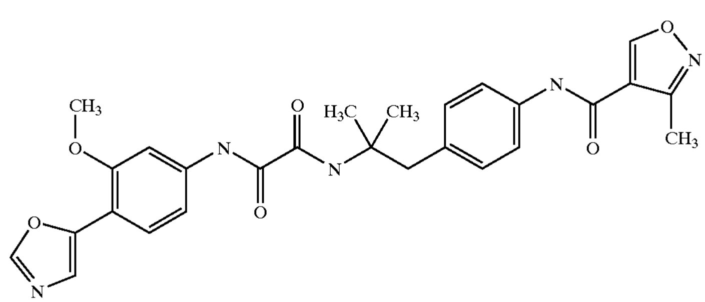 | 517.1 | 371 |
| N-[3-Methoxy-4-(5-oxazolyl)phenyl]-N'-[1,1-dimethyl-2-[4-[(5-methyl-4-isoxazolyl)carboxamido]phenyl]ethyl]oxalamide | 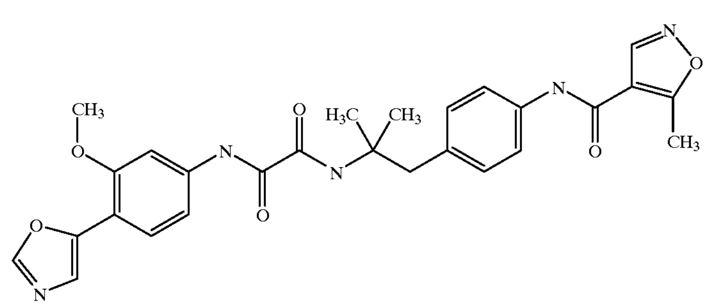 | 518.1 | 372 |

TABLE 1e-continued

| Name | Structure | MS(ES) (M + H)+ | Ex No |
|------|-----------|-----------------|-------|
| N-[3-Methoxy-4-(5-oxazolyl)phenyl]-N'-[1,1-dimethyl-2-[4-[(3-methyl-4-isoxazolyl)carboxamido]phenyl]ethyl]oxalamide | 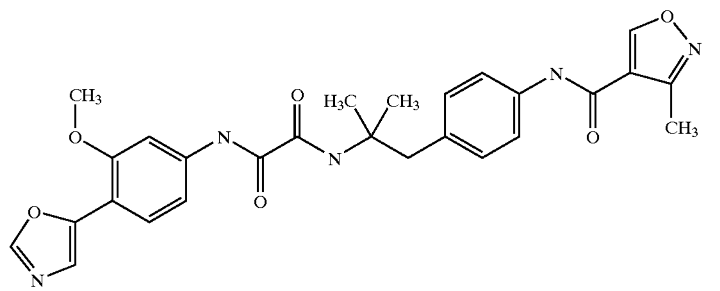 | 518.1 | 373 |
| N-[3-Methoxy-4-(5-oxazolyl)phenyl]-N'-[1,1-dimethyl-2-[4-[(5-methyl-3-isoxazolyl)carboxamido]phenyl]ethyl]oxalamide | 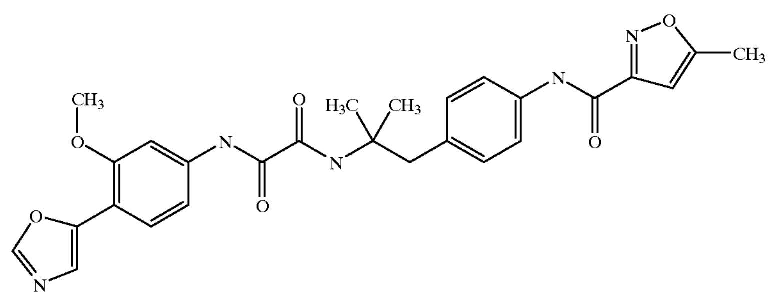 | 518.1 | 374 |
| N-[3-Methoxy-4-(5-oxazolyl)phenyl]-N-[1,1-dimethyl-2-[4-[(1-oxido-3-pyridyl)carboxamido]phenyl]ethyl]oxalamide | 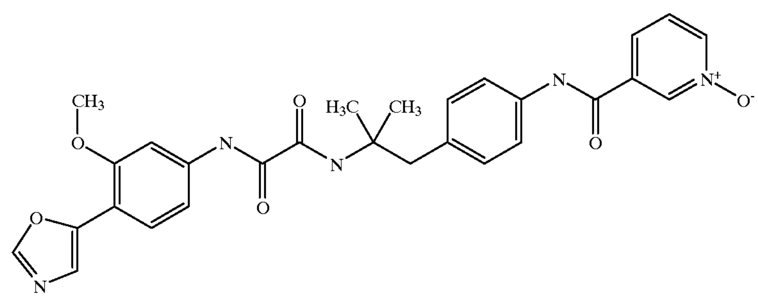 | 530.1 | 375 |
| N-[3-Methoxy-4-(5-oxazolyl)phenyl]-N'-[1,1-dimethyl-2-[4-[(1-oxido-4-pyridyl)carboxamido]phenyl]ethyl]oxalamide | 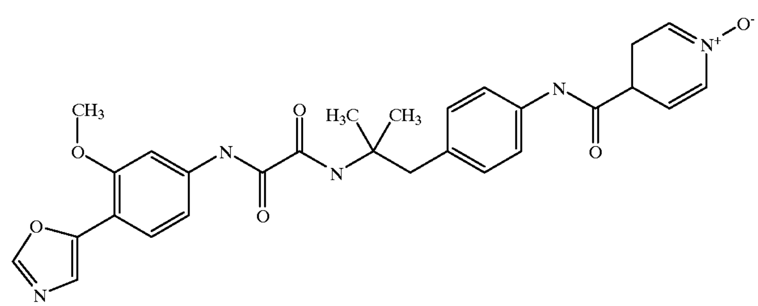 | 530.1 | 376 |
| N-[3-Methoxy-4-(5-oxazolyl)phenyl]-N'-[1,1-dimethyl-2-[4-[(4,5-dimethyl-2-furyl)carboxamido]phenyl]ethyl]oxalamide | 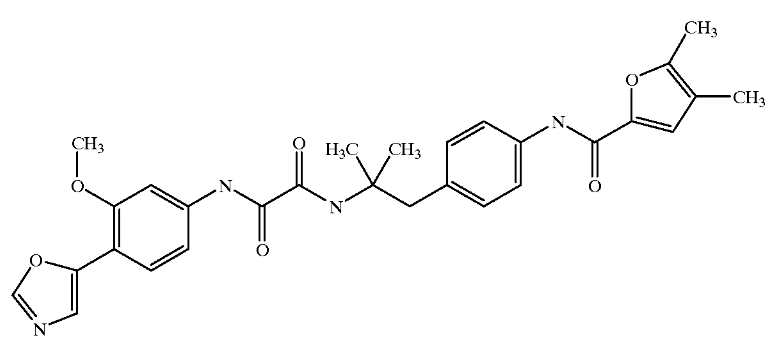 | 531.1 | 377 |

TABLE 1e-continued

| Name | Structure | MS(ES) (M + H)+ | Ex No |
|---|---|---|---|
| N-[3-Methoxy-4-(5-oxazolyl)phenyl]-N'-[1,1-dimethyl-2-[4-[(2,5-dimethyl-2H-pyrazol-3-yl)carboxamido]phenyl]-1,1-dimethylethyl]oxalamide | 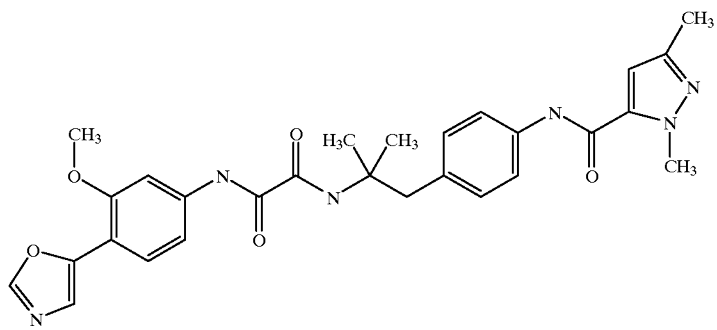 | 531.1 | 378 |
| N-[3-Methoxy-4-(5-oxazolyl)phenyl]-N'-[1,1-dimethyl-2-[4-[(3-methyl-2-thienyl)carboxamido]phenyl]ethyl]oxalamide | 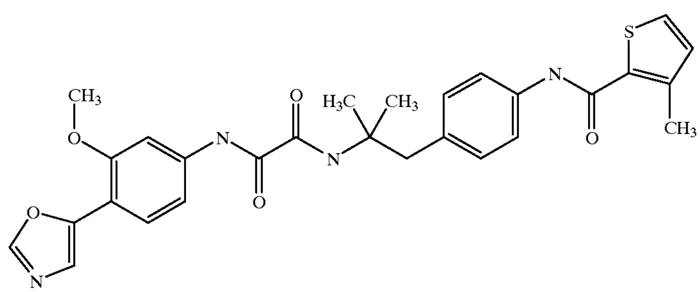 | 533.1 | 379 |
| N-[3-Methoxy-4-(5-oxazolyl)phenyl]-N'-[1,1-dimethyl-2-[4-[2-(3-thienyl)acetamido]phenyl]ethyl]oxalamide | 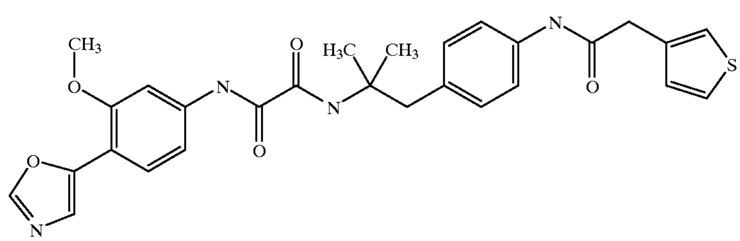 | 533.1 | 380 |
| N-[3-Methoxy-4-(5-oxazolyl)phenyl]-N'-[1,1-dimethyl-2-[4-[(4-methyl-2-thienyl)carboxamido]phenyl]ethyl]oxalamide | 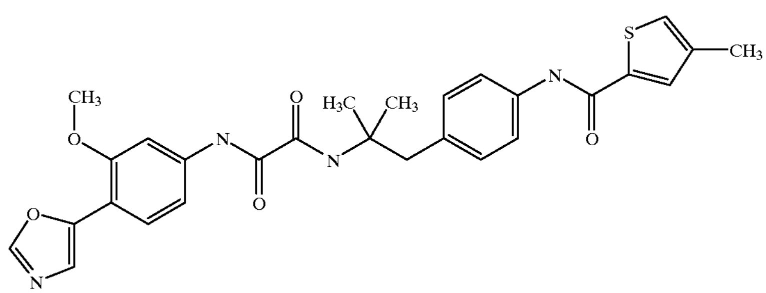 | 533.1 | 381 |
| N-[3-Methoxy-4-(5-oxazolyl)phenyl]-N'-[1,1-dimethyl-2-[4-[(4-methyl-1,2,3-thiadiazol-5-yl)carboxamido]phenyl]ethyl]oxalamide | 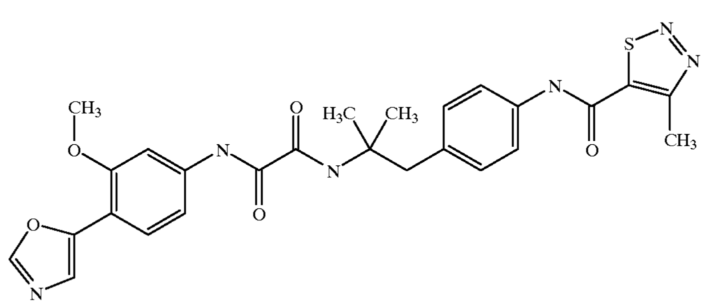 | 535 | 382 |

TABLE 1e-continued

| Name | Structure | MS(ES) (M + H)+ | Ex No |
|---|---|---|---|
| N-[2-[4-(4-Acetamido-benzamido)phenyl]-1,1-dimethylethyl]-N'-[3-methoxy-4-(5-oxazolyl)phenyl]oxalamide | 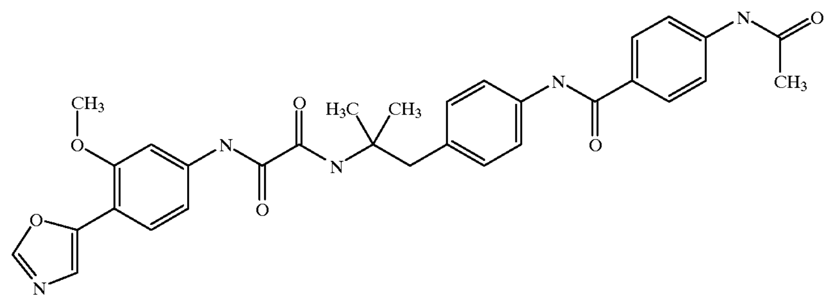 | 570.1 | 383 |
| N-[2-[4-(3,4-Dimethoxy-benzamido)phenyl]-1,1-dimethylethyl]-N'-[3-methoxy-4-(5-oxazolyl)phenyl]oxalamide | 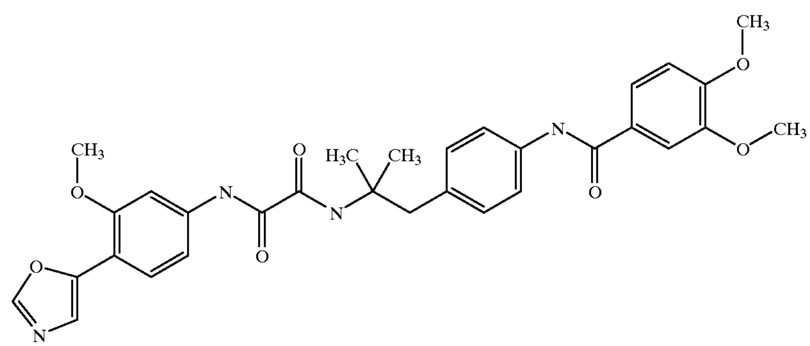 | 573.1 | 384 |
| N-[2-[4-(4-Chloro-2-methoxy-benzamido)phenyl]-1,1-dimethylethyl]-N'-[3-methoxy-4-(5-oxazolyl)phenyl]oxalamide | 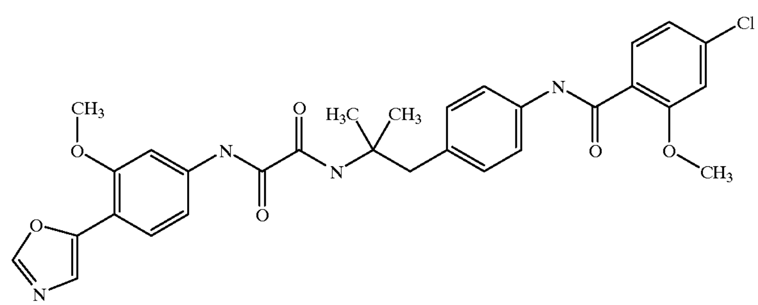 | 578.2 | 385 |
| N-[2-[4-(2,6-Dichlorobenzamido)phenyl]-1,1-dimethylethyl]-N'-[3-methoxy-4-(5-oxazolyl)phenyl]oxalamide | 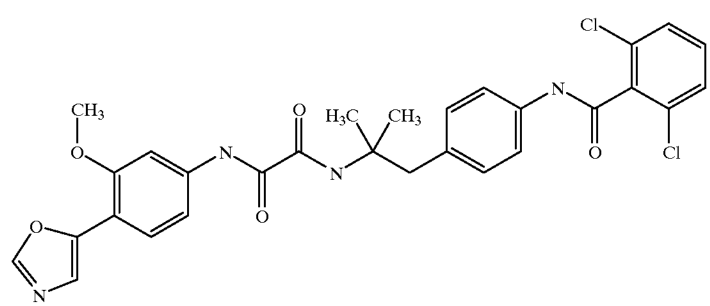 | 581 | 386 |
| N-[2-[4-[(Bicyclo[4.2.0]octa-1(6),2,4-triene-7(RS)-yl)carboxamido]phenyl]-1,1-dimethylethyl]-N'-[3-methoxy-4-(5-oxazolyl)phenyl]oxalamide | 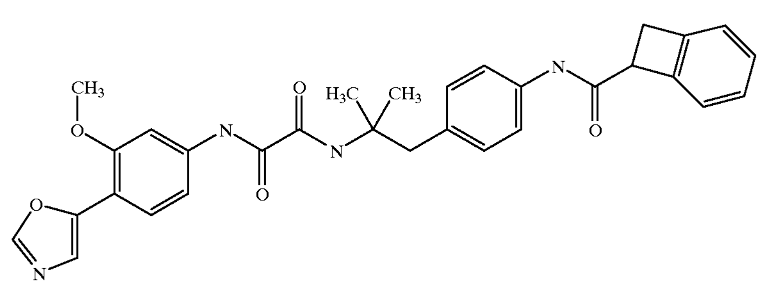 | 539.1 | 387 |

TABLE 1e-continued

| Name | Structure | MS(ES) (M + H)+ | Ex No |
|---|---|---|---|
| N-[3-Methoxy-4-(5-oxazolyl)phenyl]-N'-[1,1-dimethyl-2-[4-(2-oxo-2-phenylacetamido)phenyl]ethyl]oxalamide | 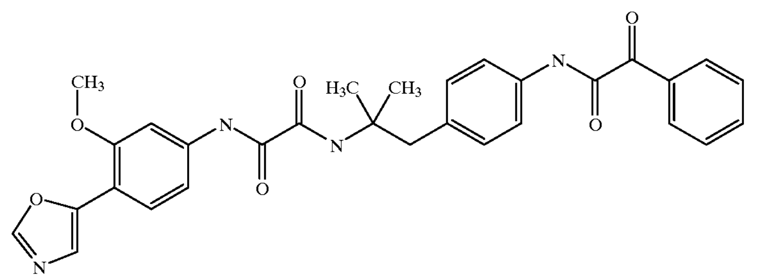 | 541.1 | 388 |
| N-[2-{4-[2-(2-Fluorophenyl)acetamido]phenyl}-1,1-dimethylethyl]-N'-[3-methoxy-4-(5-oxazolyl)phenyl]oxalamide | 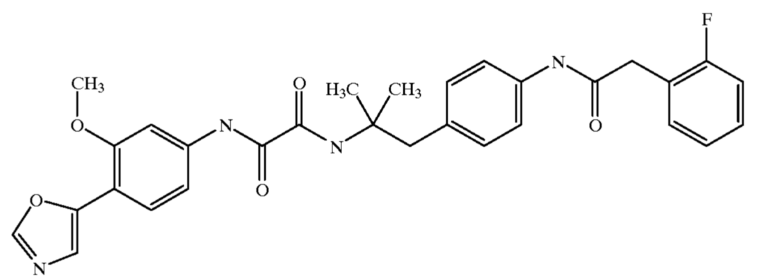 | 545 | 389 |
| N-[2-{4-[2-(4-Fluorophenyl)acetamido]phenyl}-1,1-dimethylethyl]-N'-[3-methoxy-4-(5-oxazolyl)phenyl]oxalamide | | 545 | 390 |
| N-[3-Methoxy-4-(5-oxazolyl)phenyl]-N'-[2-{4-[4-methoxy-3-thienyl)carboxamido]phenyl}-1,1-dimethylethyl]oxalamide | | 549 | 391 |
| N-[2-[4-(4-Acetylbenzamido)phenyl]-1,1-dimethylethyl]-N'-[3-methoxy-4-(5-oxazolyl)phenyl]oxalamide | 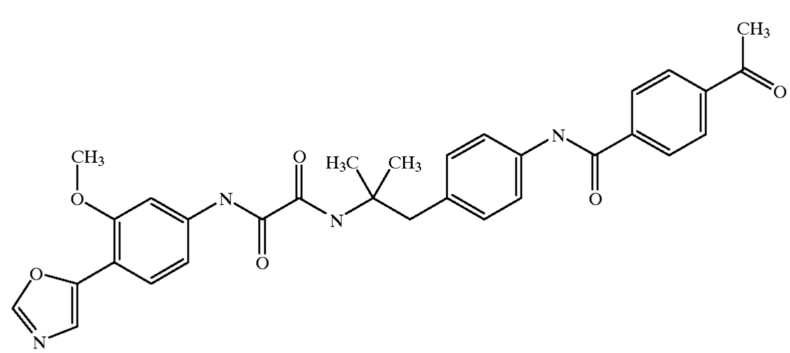 | 555.1 | 392 |

TABLE 1e-continued

| Name | Structure | MS(ES) (M + H)+ | Ex No |
|---|---|---|---|
| N-[2-[4-[(1,3-Benzodioxol-5-yl)carboxamido]phenyl]-1,1-dimethylethyl]-N'-[3-methoxy-4-(5-oxazolyl)phenyl]oxalamide | 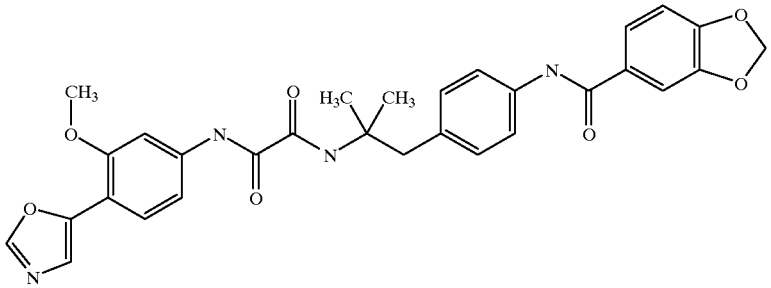 | 557.1 | 393 |
| N-[2-[4-[2-(2-Chlorophenyl)acetamido]phenyl]-1,1-dimethylethyl]-N'-[3-methoxy-4-(5-oxazolyl)phenyl]oxalamide | 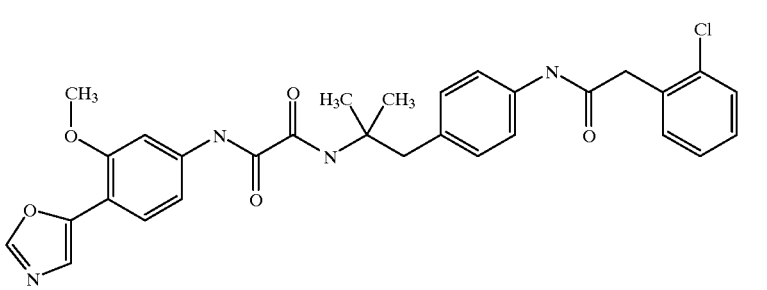 | 561.1 | 394 |
| N-[2-[4-[2-(4-Chlorophenyl)acetamido]phenyl]-1,1-dimethylethyl]-N'-[3-methoxy-4-(5-oxazolyl)phenyl]oxalamide | 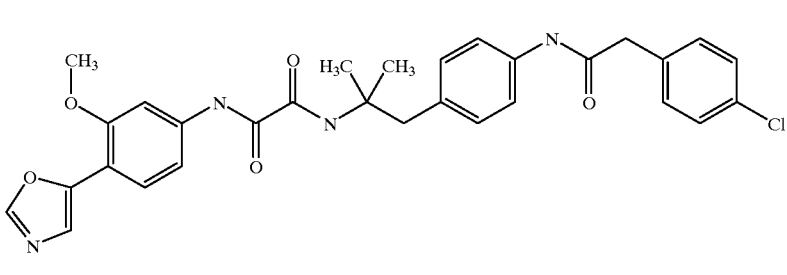 | 561.1 | 395 |
| tert-Butyl 4-[[4-[2-[[[3-methoxy-4-(5-oxazolyl)anilino]oxalyl]amino]-2-methylpropyl]phenyl]carbamoyl)benzoate | 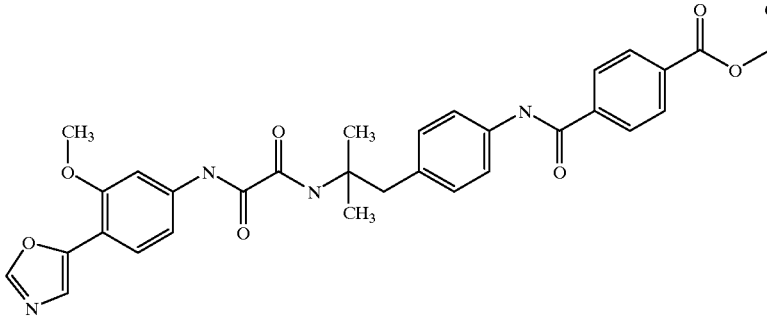 | 613 | 596 |
| 4-[[4-[2-[[[3-Methoxy-4-(5-oxazolyl)anilino]oxalyl]amino]-2-methylpropyl]phenyl]carbamoyl]benzoic acid | 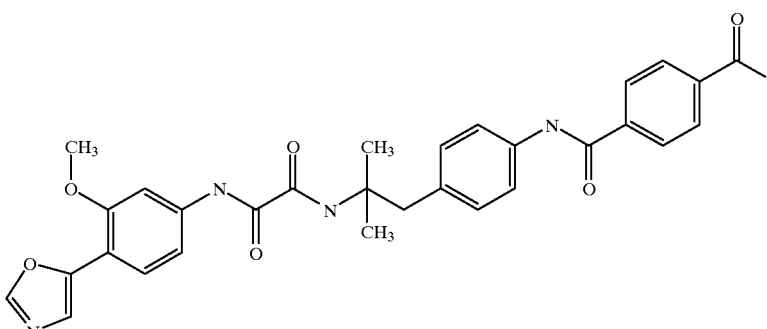 | 557 | 597 |

Particularly preferred compounds of formula (I) and formula (IX) are also those of general formula

XVIII

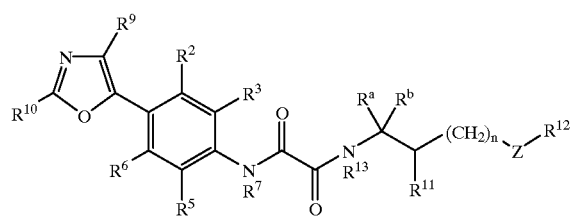

wherein $R^2$, $R^3$, $R^5$, $R^6$, $R^7$, $R^9$ and $R^{10}$ are defined as above, $R^{11}$ and $R^{13}$ are H or lower alkyl, n=0 or 1, $R^a$, $R^b$ are lower alkyl or $R^a$ and $R^b$ taken together with the carbon atom to which they are attached form a 3 to 7 member carbocycle, and $R^{12}$ is heterocyclyl, aryl or lower cycloalkyl and Z is O, S or $NR^{28}$, wherein $R^{28}$ is H or lower alkyl.

Further preferred compounds of formula XVIII are those of general formulas:

XIa

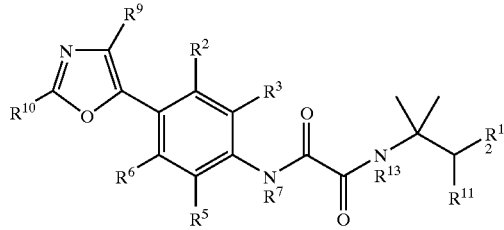

XIb wherein $R^2$, $R^3$, $R^5$, $R^6$, $R^7$, $R^9$ and $R^{10}$ are defined as above; $R^{11}$ and $R^{13}$ is H or lower alkyl, n=0 or 1, m=1 to 5 and, $R^{12}$ is heterocyclyl, aryl or lower cycloalkyl.

Particularly preferred compounds of formulae (XVIII), and (XIVa and XIVb) are those wherein $R^2$ is methoxy and $R^3$, $R^5$, $R^6$, $R^9$, $R^{10}$, $R^{11}$ and $R^{13}$ are hydrogen.

Also preferred are compounds of formulae (XVIII), and (XIVa and XIVb) where $R^{12}$ represents aryl, a 3 to 7 membered cycloalkyl ring, or a 5 or 6 membered monocyclic or 9 or 10 membered bicyclic saturated or unsaturated heterocyclic ring with 1 to 4 heteroatoms selected from nitrogen, oxygen, and sulfur.

Examples of such compounds are listed in table 1f¹ below

TABLE 1f¹

| Name | Structure | MS(ES) (M + H)⁺ | Ex No |
|---|---|---|---|
| N-[3-(4-Hydroxy-phenoxy)-1,1-dimethyl-propyl]-N'-(3-methoxy-4-oxazol-5-yl-phenyl)-oxalamide | 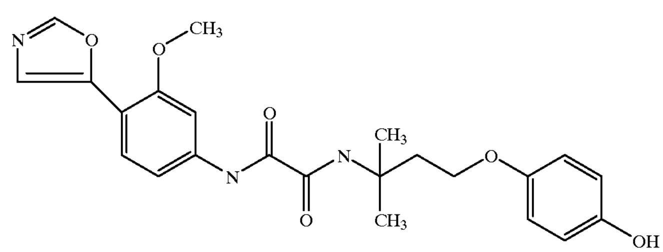 | 440 | 396 |
| N-[3-Methoxy-4-(5-oxazolyl)phenyl]-N'-[3-(4-methoxyphenoxy)-1,1-dimethylpropyl]oxalamide | 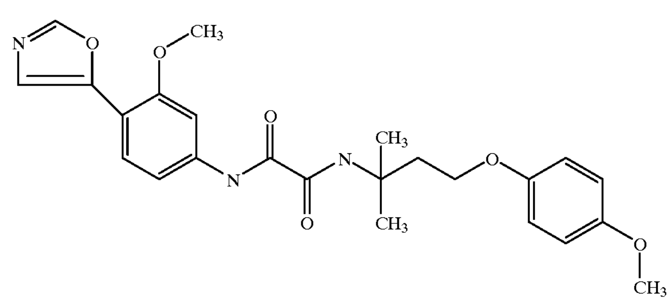 | 454 | 397 |

TABLE 1f¹-continued

| Name | Structure | MS(ES) (M + H)⁺ | Ex No |
|---|---|---|---|
| N-[3-Methoxy-4-(5-oxazolyl) phenyl]-N'-[1,1-dimethyl-3-(4-nitrophenoxy)propyl]oxalamide | 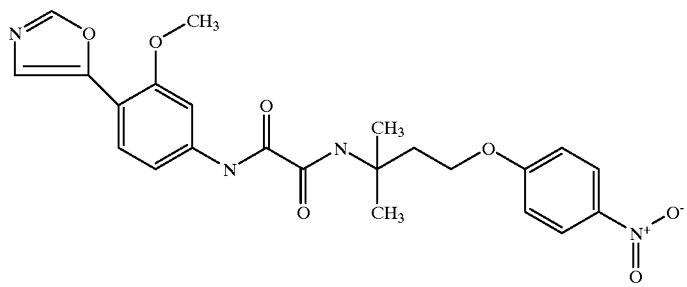 | 469 | 398 |
| N-[3-(2-Hydroxyphenoxy)-1,1-dimethylpropyl]-N'-[3-methoxy-4-(5-oxazolyl)phenyl]oxalamide | 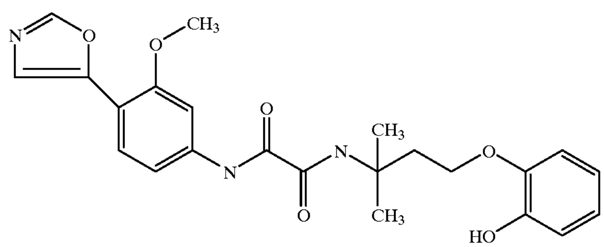 | 440 | 399 |
| N-[3-(4-Amino-phenoxy)-1,1-dimethyl-propyl]-N'-(3-methoxy-4-oxazol-5-yl-phenyl)-oxalamide | 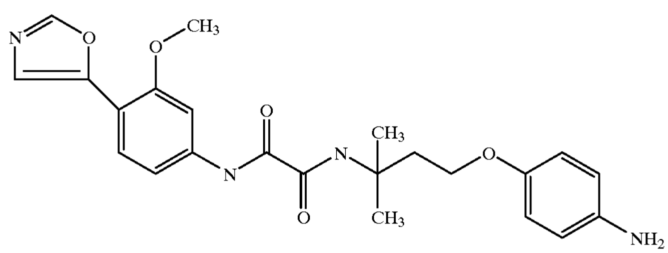 | 439 | 400 |
| N-[3-(4-Acetylamino-phenoxy)-1,1-dimethyl-propyl]-N'-(3-methoxy-4-oxazol-5-yl-phenyl)-oxalamide | 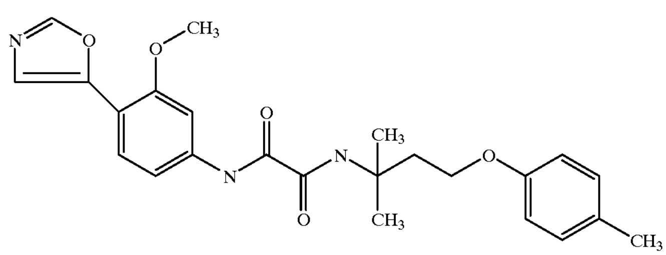 | 481 | 401 |
| N-[3-Methoxy-4-(5-oxazolyl) phenyl]-N'-[1,1-dimethyl-3-(3-pyridyloxy)propyl]oxalamide | 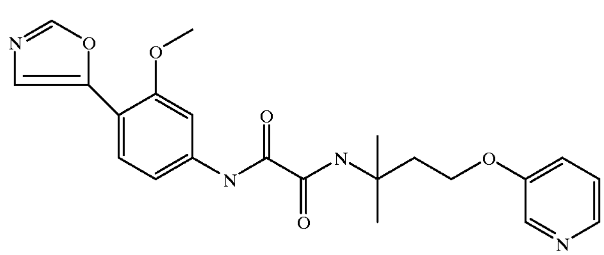 | 425 | 402 |

TABLE 1f¹-continued

| Name | Structure | MS(ES) (M + H)⁺ | Ex No |
|---|---|---|---|
| N-[3-(3-Hydroxyphenoxy)-1,1-dimethylpropyl]-N'-[3-methoxy-4-(5-oxazolyl)phenyl]oxalamide | 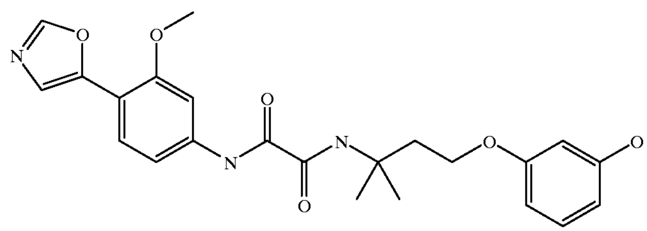 | 440 | 403 |
| N-[3-Methoxy-4-(5-oxazolyl)phenyl]-N'-[3-(3-methoxyphenoxy)-1,1-dimethylpropyl]oxalamide | 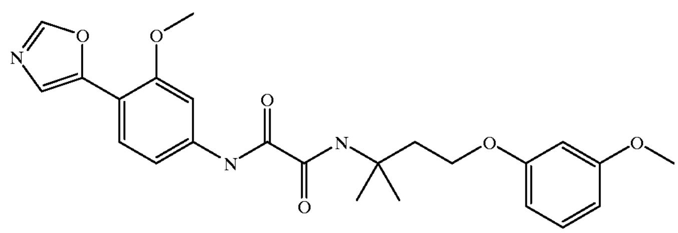 | 454 | 404 |
| N-[3-Methoxy-4-(5-oxazolyl)phenyl]-N'-[1,1-dimethyl-3-(3-nitrophenoxy)propyl]oxalamide | 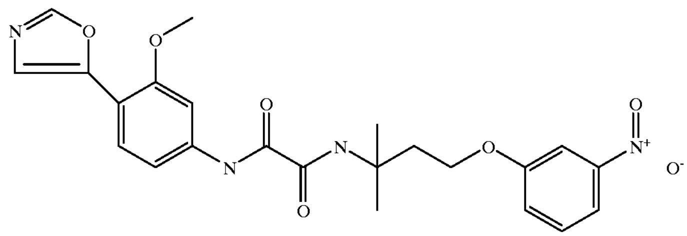 | 469 | 405 |
| N-[3-(3-Aminophenoxy)-1,1-dimethylpropyl]-N'-[3-methoxy-4-(5-oxazolyl)phenyl]oxalamide | 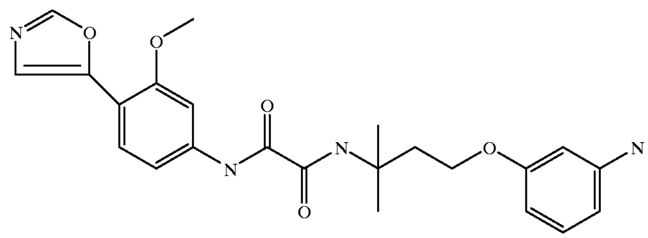 | 439 | 406 |
| 4-[3-[[[3-Methoxy-4-(5-oxazolyl)anilino]oxalyl]amino]-3-methylbutoxy]benzoic acid | 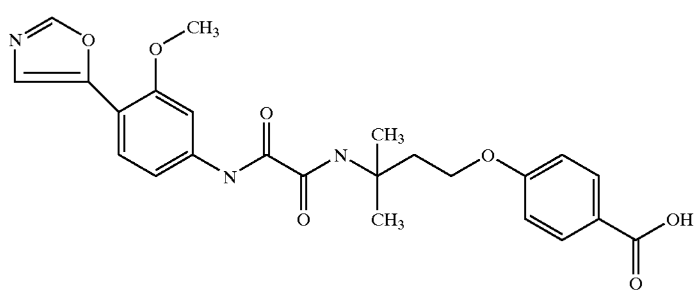 | 468 | 433 |
| 2-[3-[[[3-Methoxy-4-(5-oxazolyl)anilino]oxalyl]amino]-3-methylbutoxy]benzoic acid | 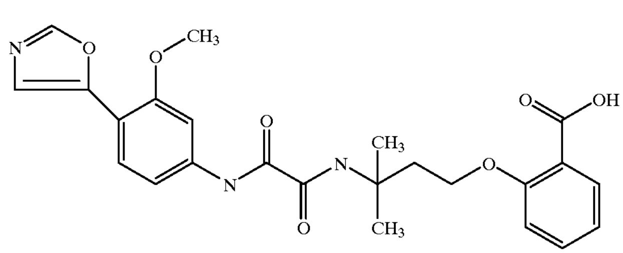 | 468 | 434 |

TABLE 1f¹-continued

| Name | Structure | MS(ES) (M + H)+ | Ex No |
|---|---|---|---|
| 3-[3-[[[3-Methoxy-4-(5-oxazolyl) anilino]oxalyl]amino]-3-methylbutoxy]benzoic acid | 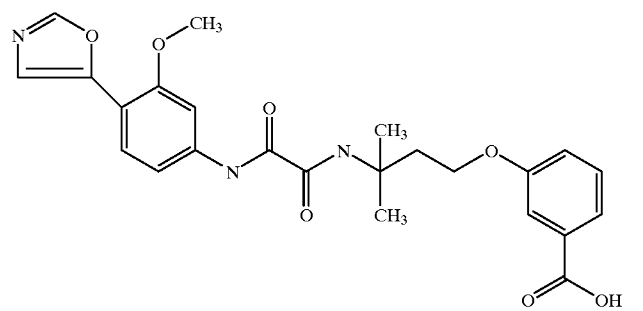 | 468 | 435 |
| 2-[4-[3-[[[3-Methoxy-4-(5-oxazolyl)anilino]oxalyl]amino]-3-methylbutoxy]phenoxy]acetic acid | 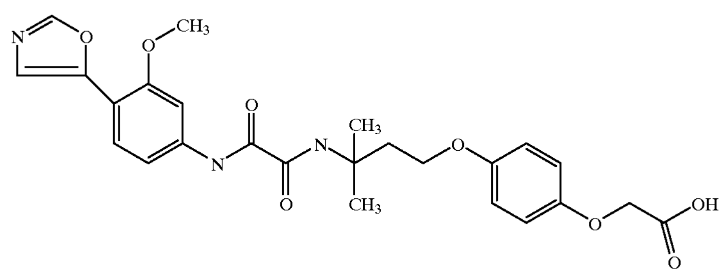 | 498 | 436 |
| 2-[2-[3-[[[3-Methoxy-4-(5-oxazolyl)anilino]oxalyl]amino]-3-methylbutoxy]phenoxy]acetic acid | 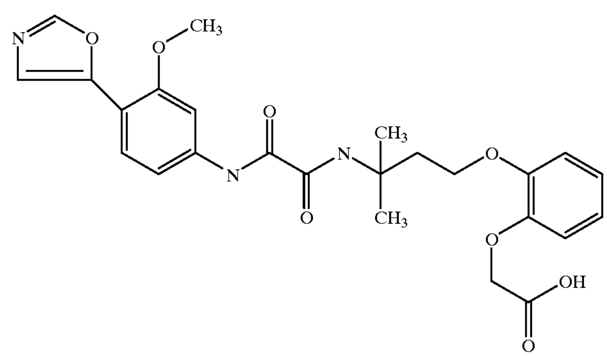 | 498 | 437 |
| N-[3-Methoxy-4-(5-oxazolyl)phenyl]-N'-(1,1-dimethyl-3-phenoxypropyl)oxalamide | 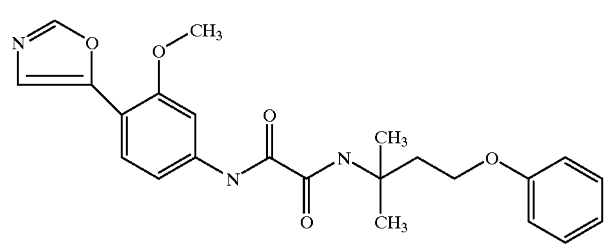 | 424 | 542 |
| N-[3-Methoxy-4-(5-oxazolyl)phenyl]-N'-[1,1-dimethyl-3-(1-oxido-3-pyridyloxy)propyl]oxalamide | 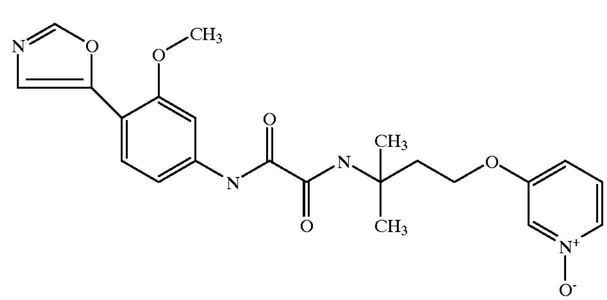 | 441 | 543 |

TABLE 1f¹-continued

| Name | Structure | MS(ES) (M + H)⁺ | Ex No |
|---|---|---|---|
| N-[3-(3,4-Dihydroxyphenoxy)-1,1-dimethylpropyl]-N'-[3-methoxy-4-(5-oxazolyl)phenyl]oxalamide | 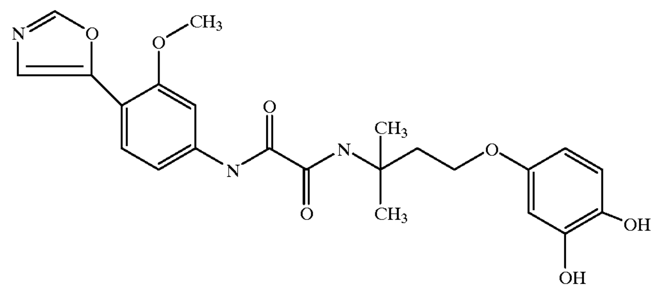 | 456 | 544 |
| N-[3-Methoxy-4-(5-oxazolyl)phenyl]-N'-[1,1-dimethyl-3-[4-(methylcarbamoyl)phenoxy]propyl]oxalamide | 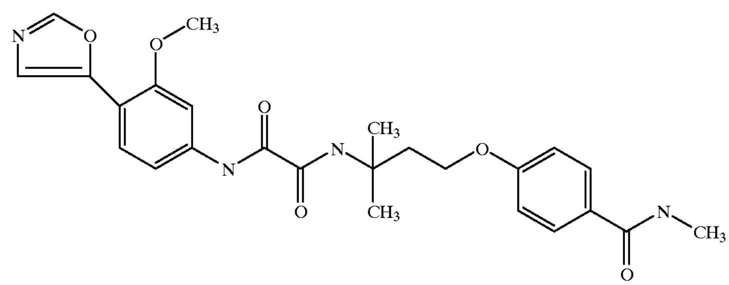 | 481 | 545 |
| N-[3-Methoxy-4-(5-oxazolyl)phenyl]-N'-[3-(3,4-dimethoxyphenoxy)-1,1-dimethylpropyl]oxalamide | 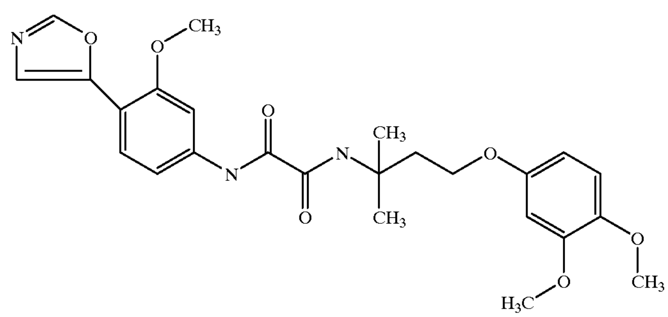 | 484 | 546 |
| N-[3-[4-[2-Hydroxyethyl)carbamoyl]phenoxy]-1,1-dimethylpropyl]-N'-[3-methoxy-4-(5-oxazolyl)phenyl]oxalamide | | 511 | 547 |
| N-[3-(3-Chlorophenoxy)-1,1-dimethylpropyl]-N'-[3-methoxy-4-(5-oxazolyl)phenyl]oxalamide | 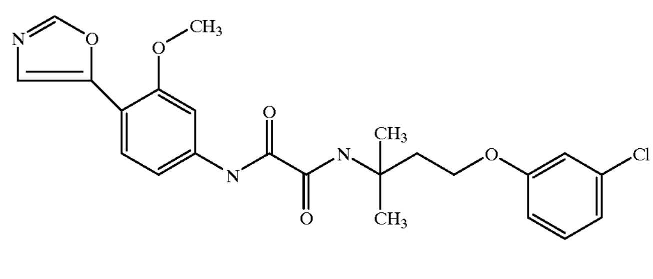 | 458 | 548 |

TABLE 1f¹-continued

| Name | Structure | MS(ES) (M + H)+ | Ex No |
|---|---|---|---|
| N-[3-Methoxy-4-(5-oxazolyl) phenyl]-N'-[1,1-dimethyl-3-(3-pyridyloxy)propyl]oxalamide | 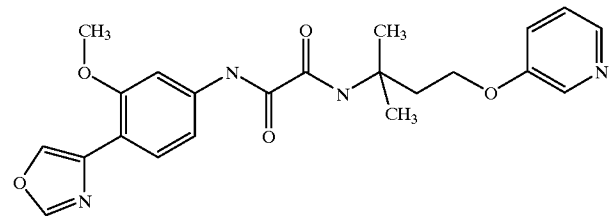 | 425 | 549 |
| N-[3-Methoxy-4-(5-oxazolyl) phenyl]-N'-[1,1-dimethyl-3-(2-pyridyloxy)propyl]oxalamide | 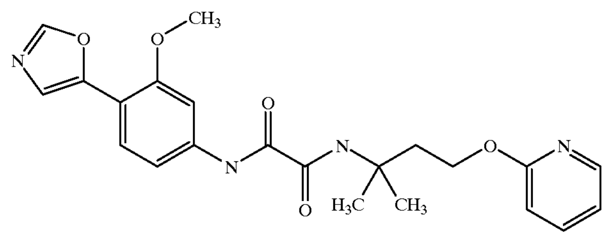 | 425 | 550 |
| 2-[4-[3-[[[3-Methoxy-4-(5-oxazolyl)anilino]oxalyl]amino]-3-methylbutoxy]phenyl]acetic acid | 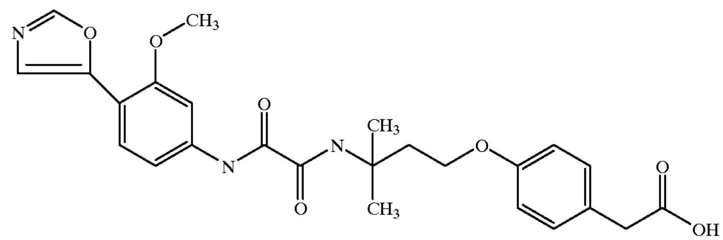 | 482 | 551 |
| 2-[3-[3-[[[3-Methoxy-4-(5-oxazolyl)anilino]oxalyl]amino]-3-methylbutoxy]phenyl]acetic acid | 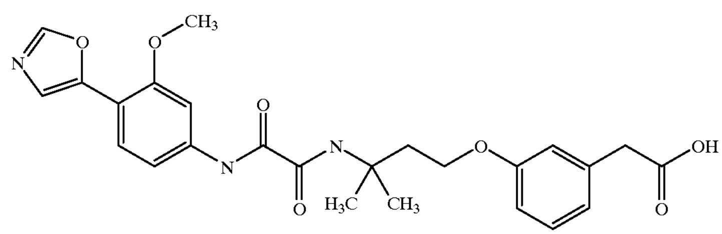 | 482 | 552 |
| 4-[2-[[[3-Methoxy-4-(5-oxazolyl)anilino]oxalyl]amino]-2-methylpropoxy]benzoic acid | 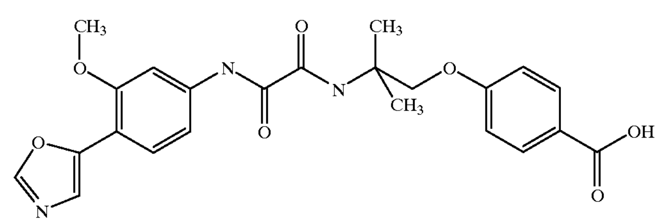 | 454 | 553 |
| 4-[3-[[[3-Methoxy-4-(5-oxazolyl)anilino]oxalyl]amino]-3-methylbutoxy]-2-methylbenzoic acid | 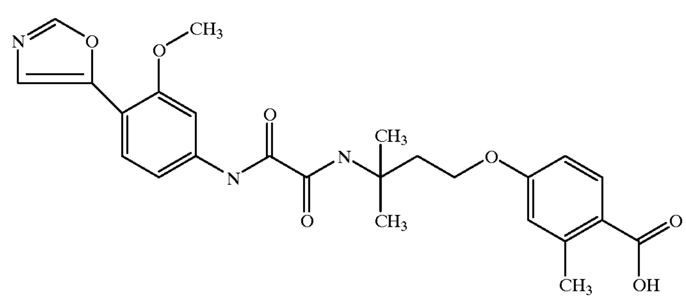 | 482 | 554 |

TABLE 1f¹-continued

| Name | Structure | MS(ES) (M + H)+ | Ex No |
|---|---|---|---|
| 3-[3-[3-[[[3-Methoxy-4-(5-oxazolyl)anilino]oxalyl]amino]-3-methylbutoxy]phenyl]propionic acid | 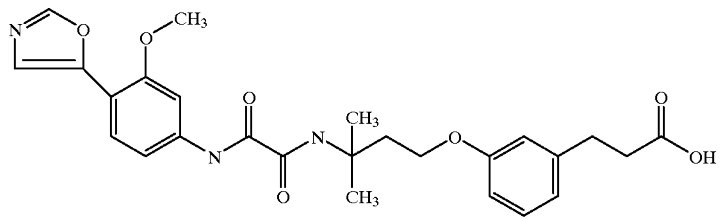 | 496 | 555 |
| 3-[4-[3-[[[3-Methoxy-4-(5oxazolyl)anilino]oxalyl]amino]-3-methylbutoxy]phenyl]propionic acid | 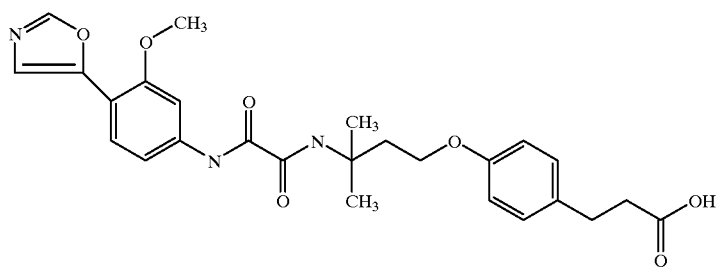 | 496 | 556 |
| 3-[2-[3-[[[3-Methoxy-4-(5-oxazolyl)anilino]oxalyl]amino]-3-methylbutoxy]phenyl]propionic acid | 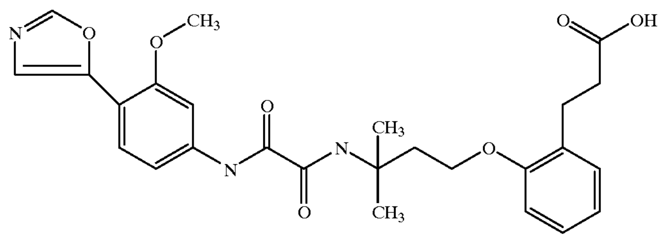 | 496 | 557 |
| 2-[3-[3-[[[3-Methoxy-4-(5-oxazolyl)anilino]oxalyl]amino]-3-methylbutoxy]phenoxy]acetic acid | 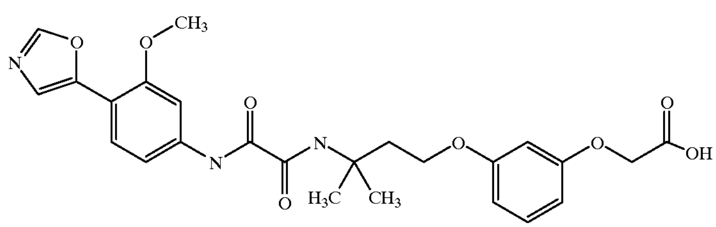 | 498 | 558 |
| 4-[3-[[[3-Methoxy-4-(5-oxazolyl anilino]oxalyl]amino]-3-methylbutoxy]-3-methylbenzoic acid | 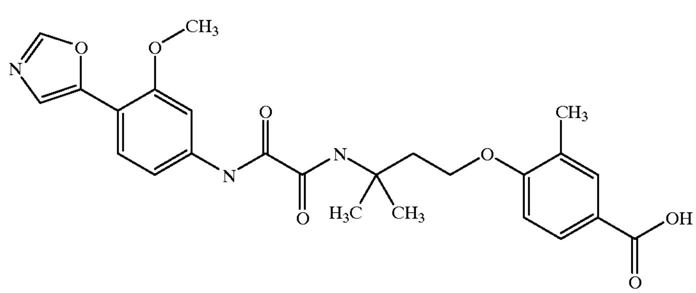 | 482 | 559 |
| N-[3-(4-Cyano-2-methoxyphenoxy)-1,1-dimethylpropyl]-N'-[3-methoxy-4-(5-oxazolyl)phenyl]oxalamide | 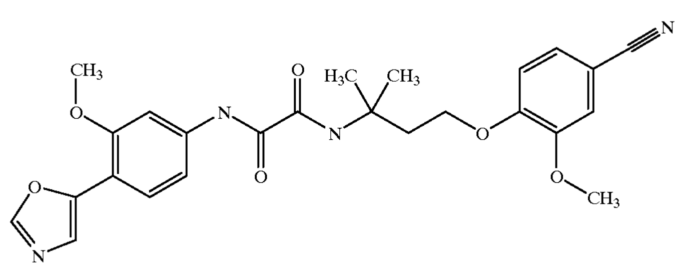 | 479 | 560 |

TABLE 1f¹-continued

| Name | Structure | MS(ES) (M + H)⁺ | Ex No |
|---|---|---|---|
| N-[3-(3-Cyanophenoxy)-1,1-dimethylpropyl]-N'-[3-methoxy-4-(5-oxazolyl)phenyl]oxalamide | 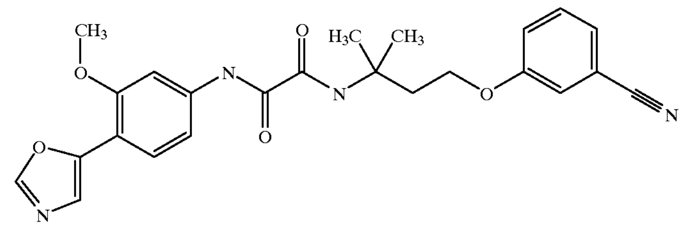 | 449.6 | 561 |
| N-[3-[4-(4-Acetyl-1-piperazinyl)phenoxy]-1,1-dimethylpropyl]-N'-[3-methoxy-4-(5-oxazolyl)phenyl]oxalamide | 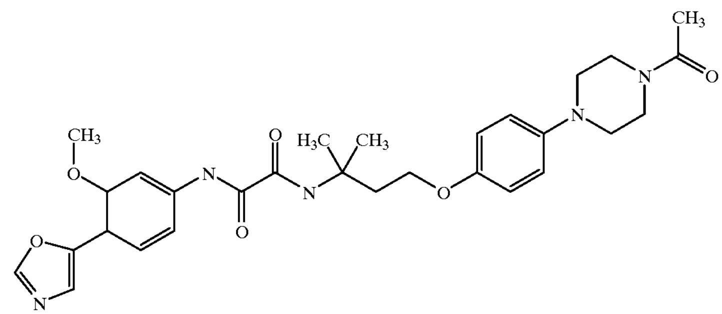 | 550.4 | 562 |
| N-[3-Methoxy-4-(5-oxazolyl)phenyl]-N'-[1,1-dimethyl-3-(2-morpholinophenoxy)propyl]oxalamide | 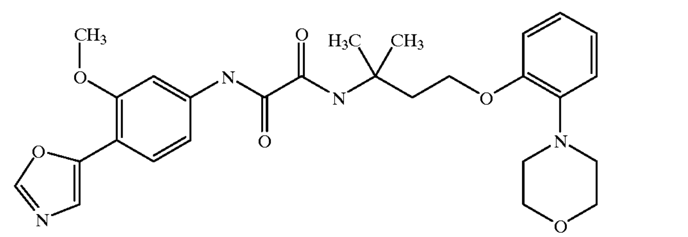 | 531.4 (M +Na)⁺ | 563 |
| N-[3-Methoxy-4-(5-oxazolyl)phenyl]-N'-[1,1-dimethyl-3-[3-(dimethylamino)phenoxy]propyl]oxalamide | 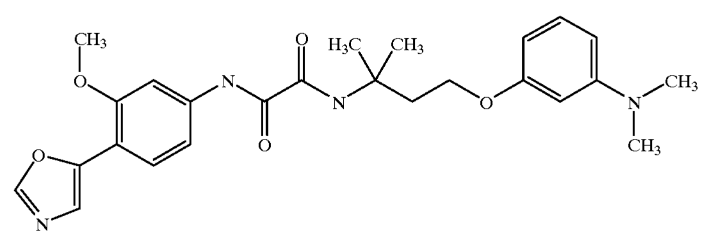 | 489.6 (M +Na)⁺ | 564 |
| N-[3-(1,3-Benzodioxol-5-yloxy)-1,1-dimethylpropyl]-N'-[3-methoxy-4-(5-oxazolyl)phenyl]oxalamide | 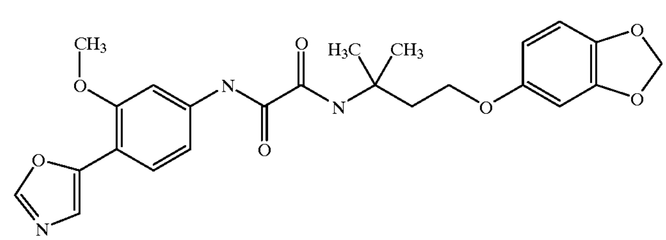 | 468.4 | 565 |

TABLE 1f¹-continued

| Name | Structure | MS(ES) (M + H)⁺ | Ex No |
|---|---|---|---|
| N-[3-Methoxy-4-(5-oxazolyl)phenyl]-N'-[3-(3,4,5-trimethoxyphenoxy)-1,1-dimethylpropyl]oxalamide | 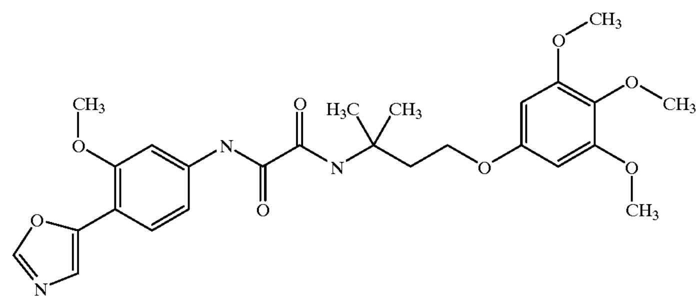 | 514.4 | 566 |
| N-[3-Methoxy-4-(5-oxazolyl)phenyl]-N'-[3-(3,5-dimethoxyphenoxy)-1,1-dimethylpropyl]oxalamide | 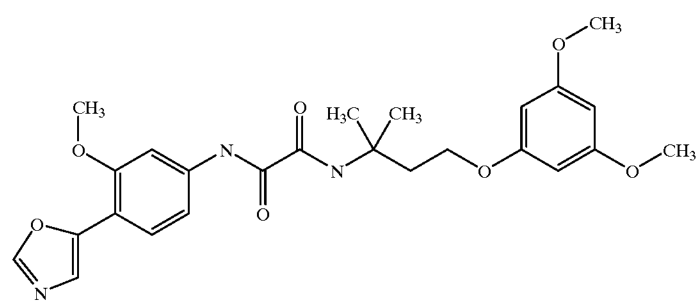 | 506 (M +Na)⁺ | 567 |
| N-[3-(5,6,7,8-Tetrahydro-5-oxo-2-naphthyloxy)-1,1-dimethylpropyl]-N'-[3-methoxy-4-(5-oxazolyl)phenyl]oxalamide | 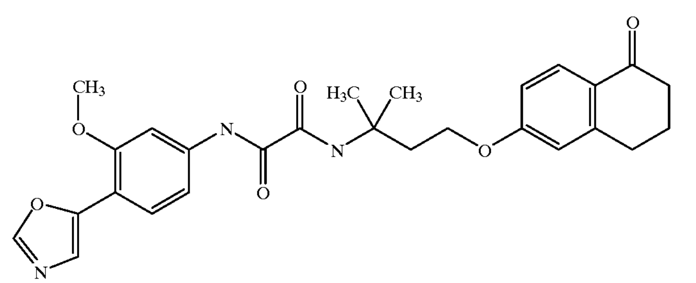 | 492.4 | 568 |
| N-[3-(2-Acetamido-5-methylphenoxy)-1,1-dimethylpropyl]-N'-[3-methoxy-4-(5-oxazolyl)phenyl]oxalamide | 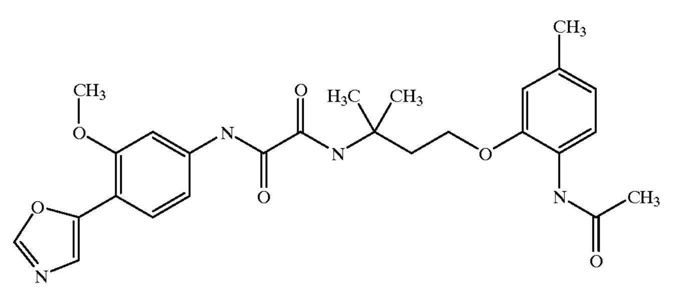 | 517.6 (M +Na)⁺ | 569 |
| N-[3-(3-Acetamidophenoxy)-1,1-dimethylpropyl]-N'-[3-methoxy-4-(5-oxazolyl)phenyl]oxalamide | 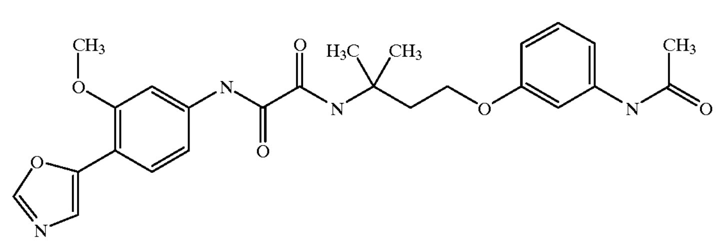 | 503.6 (M +Na)⁺ | 570 |

TABLE 1f¹-continued

| Name | Structure | MS(ES) (M + H)⁺ | Ex No |
|---|---|---|---|
| N-[3-(1H-Indol-4-yloxy)-1,1-dimethylpropyl]-N'-[3-methoxy-4-(5-oxazolyl)phenyl]oxalamide | 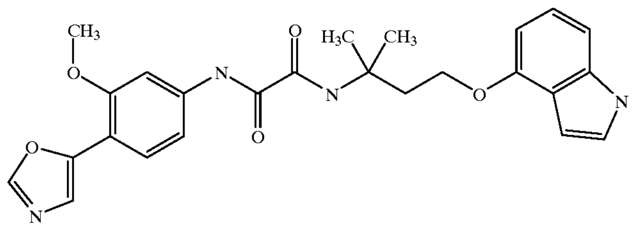 | 485.2 (M +Na)⁺ | 571 |
| N-[3-(2-Fluoro-6-methoxyphenoxy)-1,1-dimethylpropyl]-N'-[3-methoxy-4-(5-oxazolyl)phenyl]oxalamide | 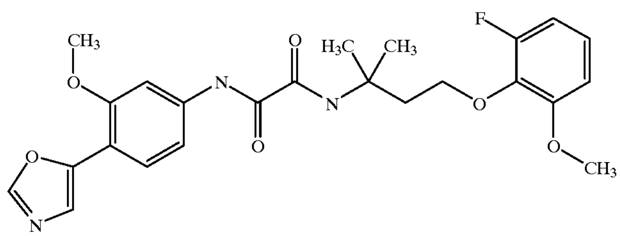 | 472.2 | 572 |
| N-[3-Methoxy-4-(5-oxazolyl)phenyl]-N'-[1,1-dimethyl-3-(2-oxo-2H-1-benzopyran-7-yloxy)propyl]oxalamide | 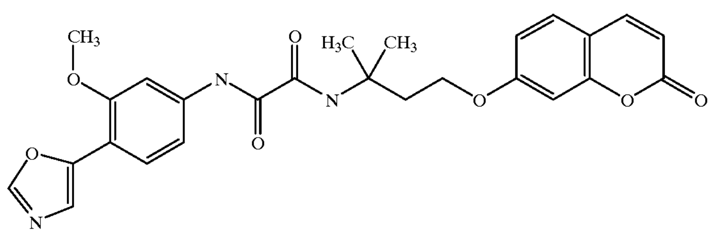 | 492.4 | 573 |
| N-[3-(4-Acetyl-3-methylphenoxy)-1,1-dimethylpropyl]-N'-[3-methoxy-4-(5-oxazolyl)phenyl]oxalamide | 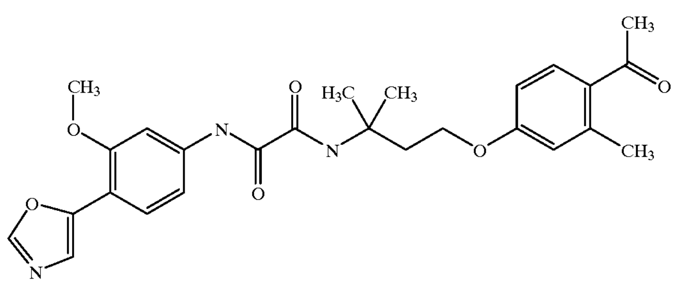 | 480.2 | 574 |
| (E)-N-[3-Methoxy-4-(5-oxazolyl)phenyl]-N'-[1,1-dimethyl-3-[4-(3-oxo-1-butenyl)phenoxy]propyl]oxalamide | 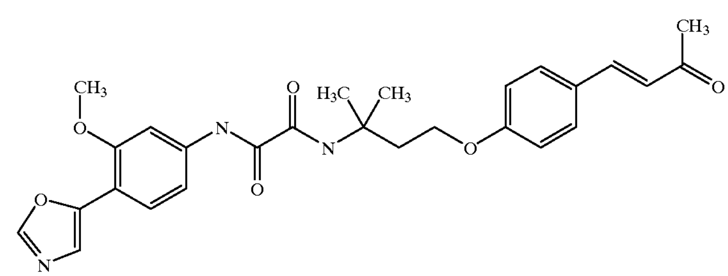 | 492.4 | 575 |
| N-[3-(3-Acetylphenoxy)-1,1-dimethylpropyl]-N'-[3-methoxy-4-(5-oxazolyl)phenyl]oxalamide | 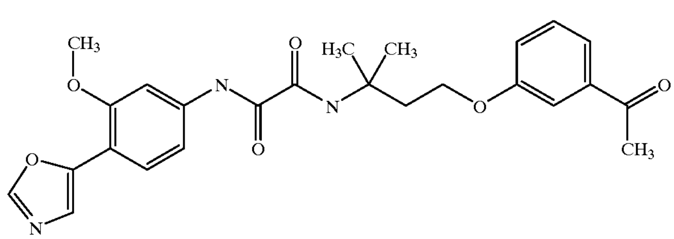 | 466.4 | 576 |

TABLE 1f¹-continued

| Name | Structure | MS(ES) (M + H)⁺ | Ex No |
|---|---|---|---|
| N-[3-(4-Acetyophenoxy)-1,1-dimethylpropyl]-N'-[3-methoxy-4-(5-oxazolyl)phenyl]oxalamide | 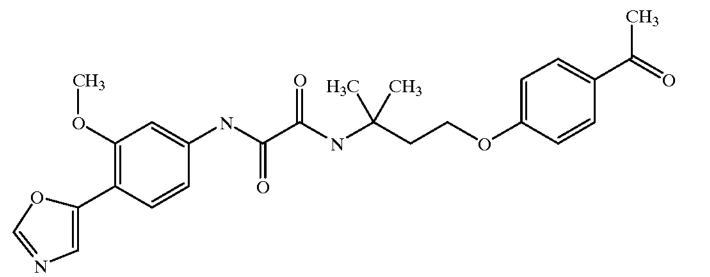 | 466.2 | 577 |
| N-[3-(4-Acetamido-2-chlorophenoxy)-1,1-dimethylpropyl]-N'-[3-methoxy-4-(5-oxazolyl)phenyl]oxalamide | 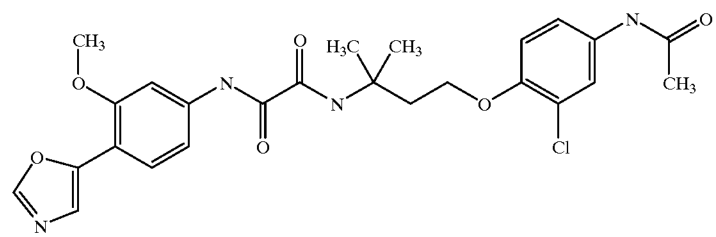 | 515.6 | 578 |
| N-[3-Methoxy-4-(5-oxazolyl)phenyl]-N'-[1,1-dimethyl-3-(4-pyridyloxy)propyl]oxalamide | 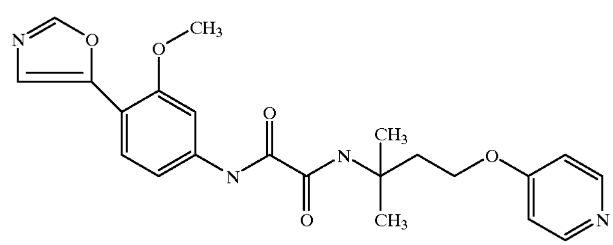 | 425 | 579 |
| N-[3-Methoxy-4-(5-oxazolyl)phenyl]-N'-[1,1-dimethyl-3-(1-oxido-4-pyridyloxy)propyl]oxalamide | 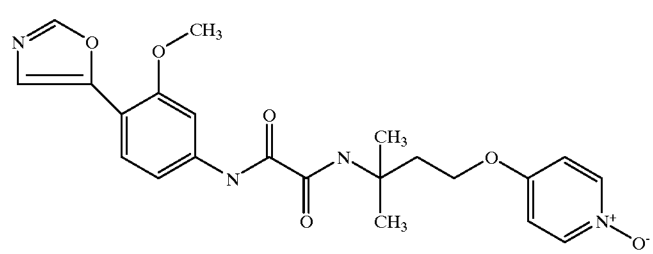 | 441 | 580 |
| N-[3-Methoxy-4-(5-oxazolyl)phenyl]-N'-[1,1-dimethyl-3-(2,6-dimethyl-4-pyridyloxy)propyl]oxalamide | 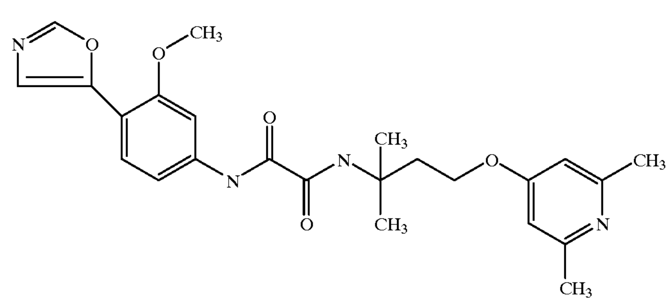 | 453 | 581 |

TABLE 1f¹-continued

| Name | Structure | MS(ES) (M + H)+ | Ex No |
|---|---|---|---|
| N-[3-Methoxy-4-(5-oxazolyl) phenyl]-N'-[1,1-dimethyl-3-(2,6-dimethyl-1-oxido-4-pyridyloxy) propyl]oxalamide | 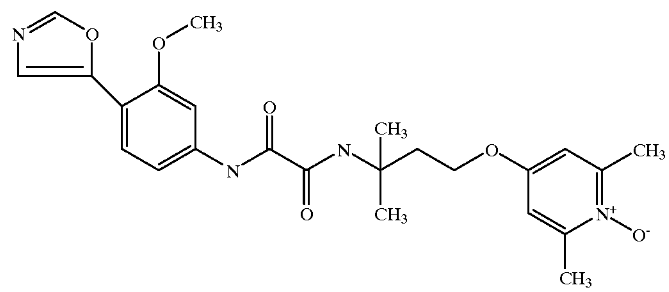 | 469 | 582 |
| N-[2-(4-Cyanophenoxy)-1,1-dimethylethyl]-N'-[3-methoxy-4-(5-oxazolyl)phenyl]oxalamide | 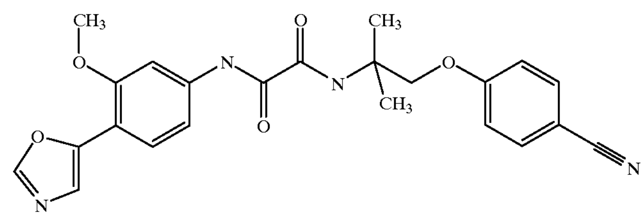 | 435 | 583 |
| N-[3-Methoxy-4-(5-oxazolyl) phenyl]-N'-[3-(2-methoxy-4-pyridyloxy)-1,1-dimethylpropyl] oxalamide | 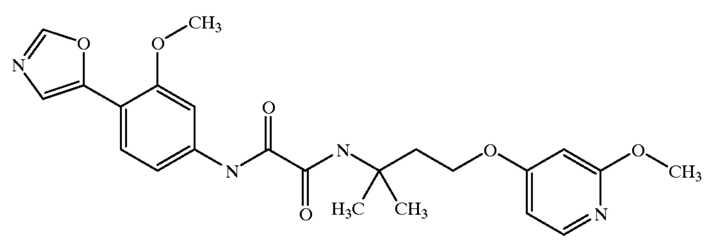 | 455 | 584 |
| N-[3-Methoxy-4-(5-oxazolyl) phenyl]-N'-[1,1-dimethyl-2-[4-(1H-tetrazol-5-yl)phenoxy]ethyl] oxalamide | 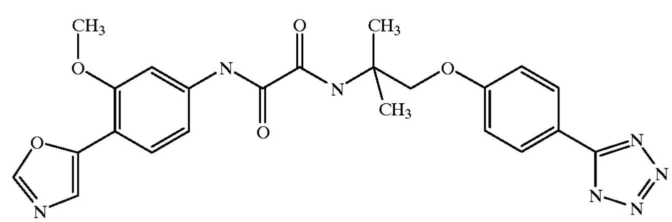 | 478 | 585 |
| N-[3-(4-Cyanophenoxy)-1,1-dimethylpropyl]-N'-[3-methoxy-4-(5-oxazolyl)phenyl]oxalamide | 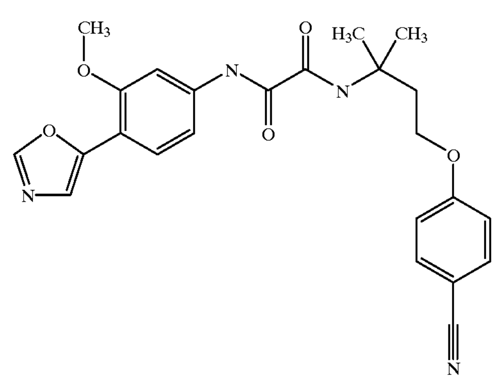 | 449 | 586 |

TABLE 1f¹-continued

| Name | Structure | MS(ES) (M + H)+ | Ex No |
|---|---|---|---|
| N-[2-(3-Cyanophenoxy)-1,1-dimethylethyl]-N'-[3-methoxy-4-(5-oxazolyl)phenyl]oxalamide | 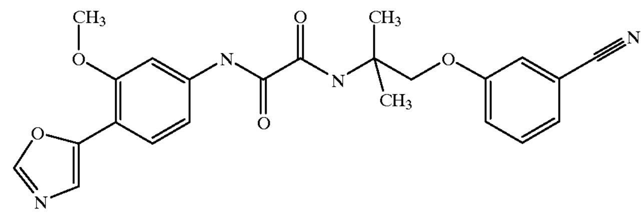 | 476 | 587 |
| N-[3-Methoxy-4-(5-oxazolyl)phenyl]-N'-[1,1-dimethyl-2-[3-(1H-tetrazol-5-yl)phenoxy]ethyl]oxalamide | 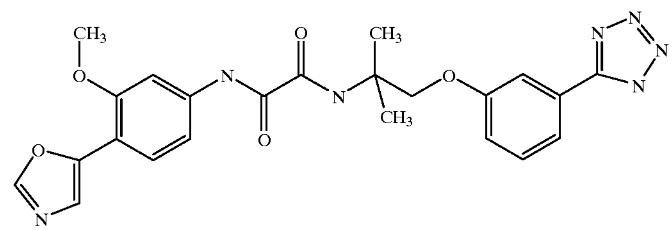 | 478 | 588 |
| N-[3-Methoxy-4-(5-oxazolyl)phenyl]-N'-[1,1-dimethyl-3-[4-(1H-tetrazol-5-yl)phenoxy]propyl]oxalamide | 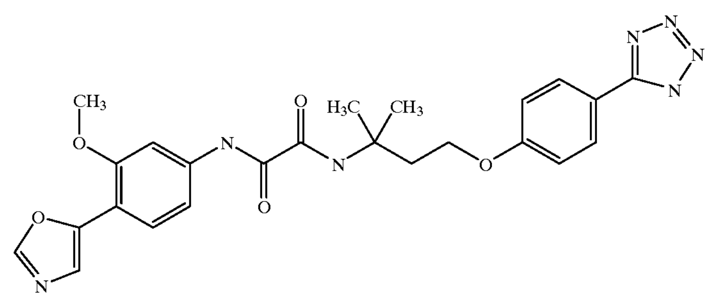 | 492 | 589 |
| Benzyl 4-[2-[1-[[[3-methoxy-4-(5-oxazolyl)anilino]amino]-1-cyclobutyl]ethoxy]benzoate | 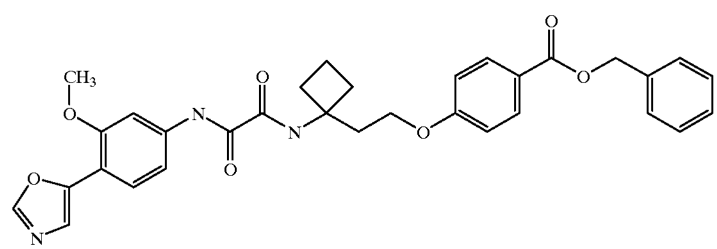 | 570.2 | 590 |
| Benzyl 4-[2-[1-[[[3-methoxy-4-(5-oxazolyl)anilino]oxalyl]amino]-1-cyclopentyl]ethoxy]benzoate | 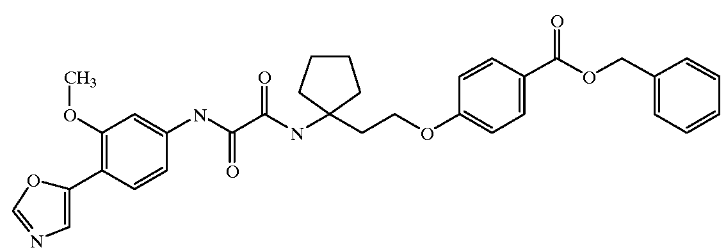 | 584.3 | 591 |
| Benzyl 4-[2-[1-[[[3-methoxy-4-(5-oxazolyl)anilino]oxalyl]amino]-1-cyclohexyl]ethoxy]benzoate | 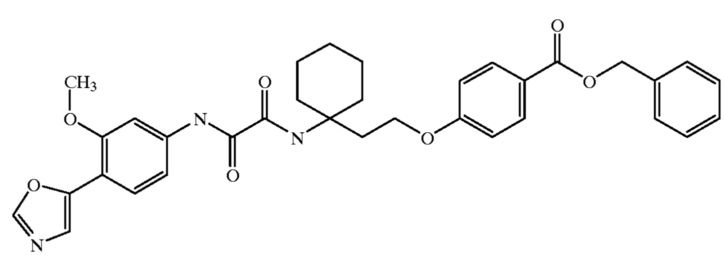 | 598.3 | 592 |

TABLE 1f¹-continued

| Name | Structure | MS(ES) (M + H)⁺ | Ex No |
|---|---|---|---|
| 4-[2-[1-[[[3-Methoxy-4-(5-oxazolyl)anilino]oxalyl]amino]-1-cyclopentyl]ethoxy]benzoic acid | 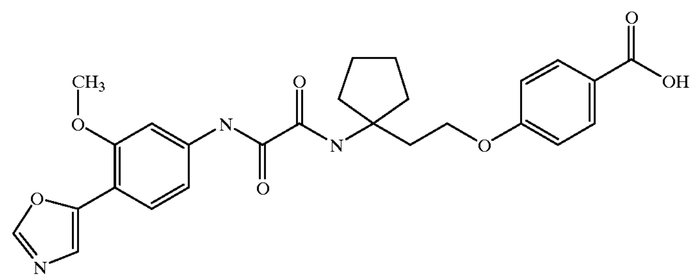 | 494.2 | 593 |
| 4-[2-[1-[[[3-Methoxy-4-(5-oxazolyl)anilino]oxalyl]amino]-1-cyclohexyl]ethoxy]benzoic acid | 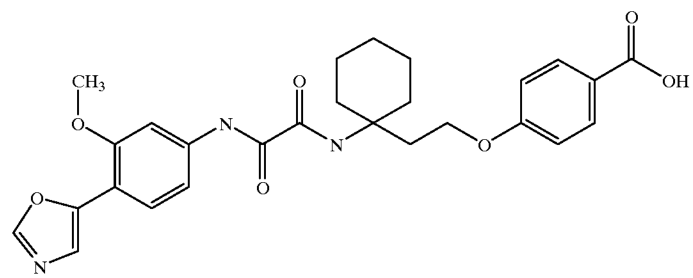 | 508.2 | 594 |
| 4-[2-[1-[[[3-Methoxy-4-(5-oxazolyl)anilino]oxalyl)amino]1-1 cyclobutyl]ethoxy]benzoic acid | 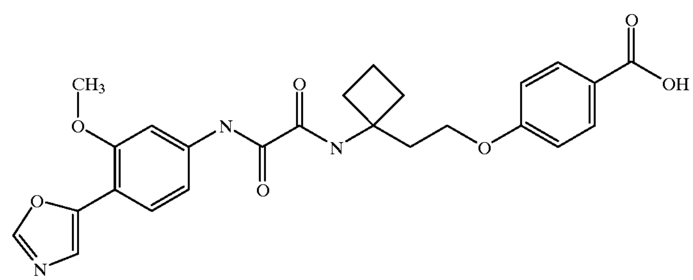 | 480.2 | 595 |
| Benzyl 2-methoxy-4-[3-[[[3-methoxy-4-(5-oxazolyl)anilino]oxalyl]amino]-3-methylbutoxy]benzoate | 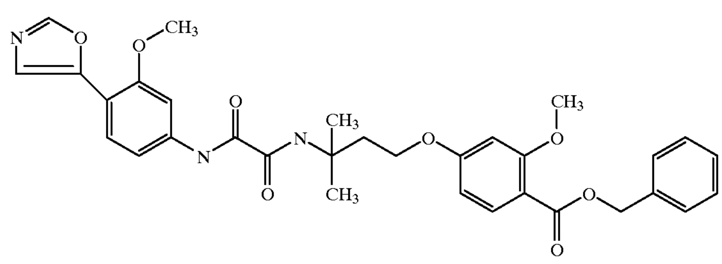 | 588 | 635 |
| 3-Chloro-4-[3-[[[3-methoxy-4-(5-oxazolyl)anilino]oxalyl]amino]-3-methylbutoxy]benzoic acid | 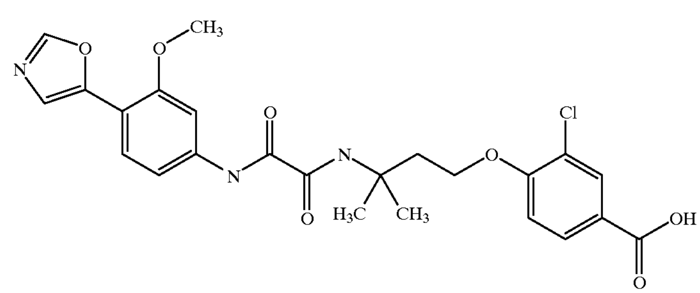 | 502 | 636 |

TABLE 1f¹-continued

| Name | Structure | MS(ES) (M + H)+ | Ex No |
|---|---|---|---|
| 2-Methoxy-4-[3-[[[3-methoxy-4-(5-oxazolyl)anilino]oxalyl]amino]-3-methylbutoxy]benzoic acid | 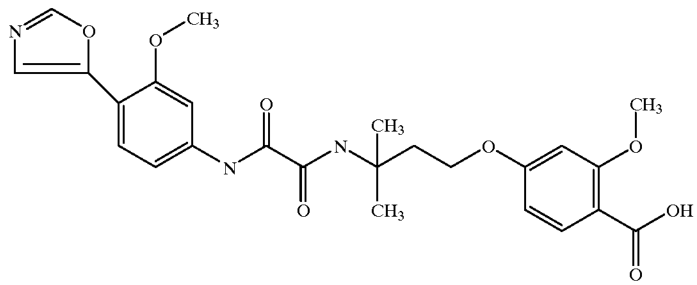 | 498 | 637 |
| 3-Methoxy-4-[3-[[[3-methoxy-4-(5-oxazolyl)anilino]oxalyl]amino]-3-methylbutoxy]benzoic acid | 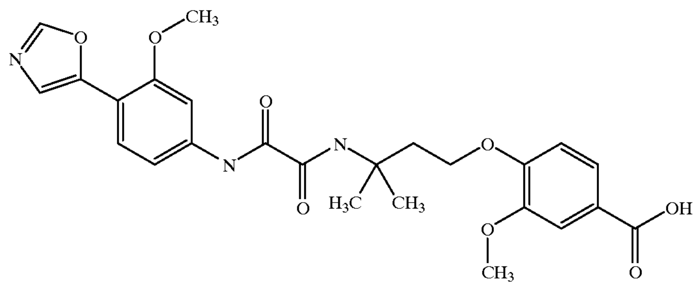 | 498 | 638 |
| 4-[2-[1-[[[3-Methoxy-4-(5-oxazolyl)anilino]oxalyl]amino]-1-cyclopropyl]ethoxy]benzoic acid | 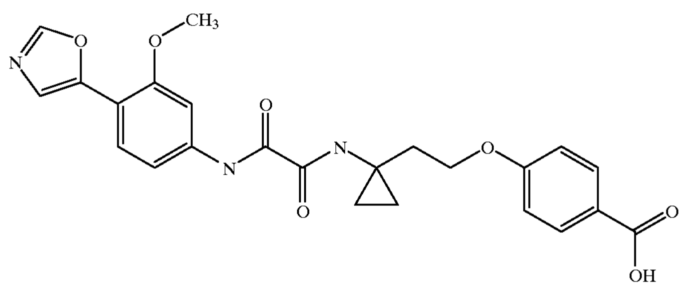 | 466 | 639 |
| 2-Chloro-4-[3-[[[3-methoxy-4-(5-oxazolyl)anilino]oxalyl]amino]-3-methylbutoxy]benzoic acid | 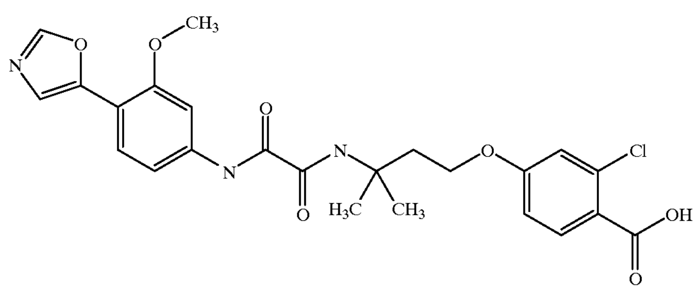 | 502 | 640 |
| 4-[3-[[[3-Methoxy-4-(5-oxazolyl)anilino]oxalyl]amino]-3-methylbutoxy]-2-quinolinecarboxylic acid | 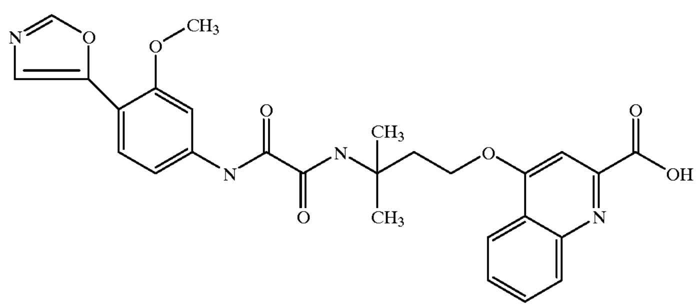 | 519 | 641 |

TABLE 1f¹-continued

| Name | Structure | MS(ES) (M + H)⁺ | Ex No |
|---|---|---|---|
| (cis/trans)-4-[3-[[[3-Methoxy-4-(5-oxazolyl)anilino]oxalyl]amino]-3-methylbutoxy]1-1 cyclohexanecarboxylic acid | 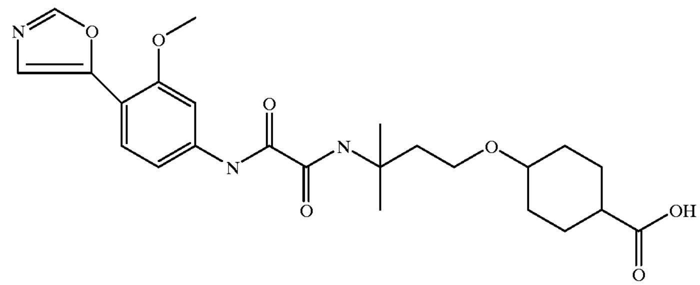 | 474 | 642 |
| (cis/trans)-4-[2-[[[3-Methoxy-4-(5-oxazolyl)anilino]oxalyl]amino]-2-1-2-methylpropoxy]-1-cyclohexanecarboxylic acid | 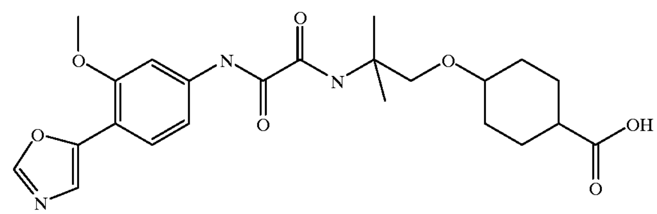 | 460 | 643 |
| 3-Fluoro-4-[3-[[[3-methoxy-4-(5-oxazolyl)anilino]oxalyl]amino]-3-methylbutoxy]benzoic acid | 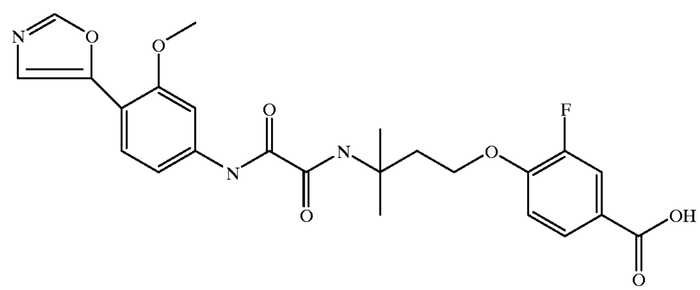 | 486 | 644 |
| 3-Acetamido-4-[3-[[[3-methoxy-4-(5-oxazolyl)anilino]oxalyl]amino]-3-methylbutoxy]benzoic acid | 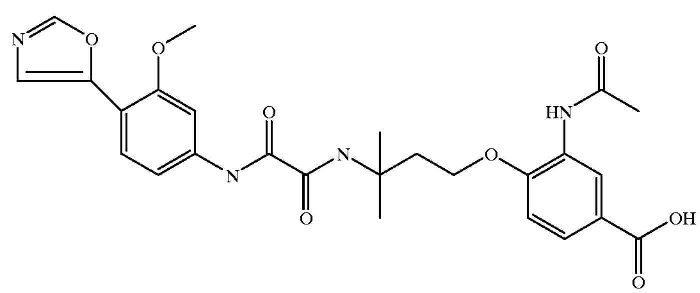 | 525 | 645 |
| 3-(Methanesulfonamido)-4-[3-[[[3-methoxy-4-(5-oxazolyl)anilino]oxalyl]amino]-3-methylbutoxy]benzoic acid | 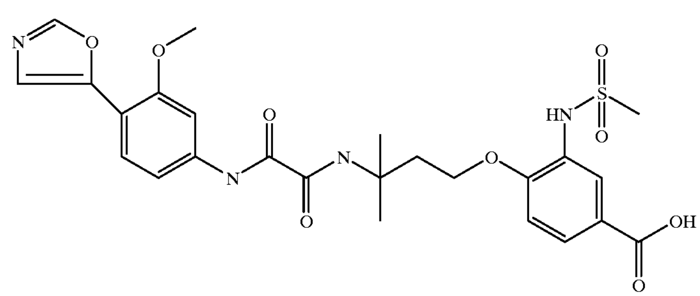 | 561 | 646 |

TABLE 1f¹-continued

| Name | Structure | MS(ES) (M + H)⁺ | Ex No |
|---|---|---|---|
| 4-[3-[[[3-Methoxy-4-(5-oxazolyl) anilino]oxalyl]amino]-3-methylbutoxy]-3,5-dimethylbenzoic acid | 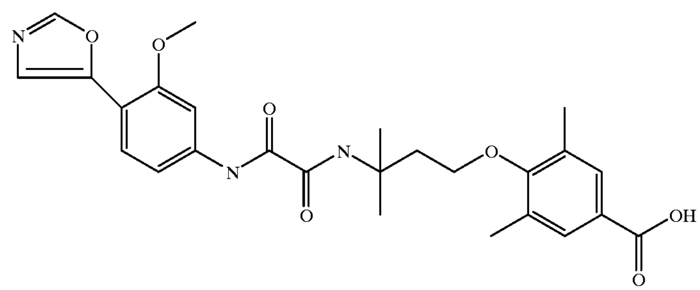 | 496 | 647 |
| 3-[3-[[[3-Methoxy-4-(5-oxazolyl) anilino]oxalyl]amino]-3-methylbutoxy]-2-pyridinecarboxylic acid | 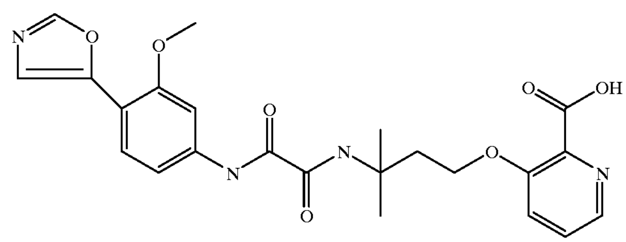 | 469 | 648 |
| 8-[3-[[[3-Methoxy-4-(5-oxazolyl) anilino]oxalyl]amino]-3-methylbutoxy]-2-quinolinecarboxylic acid | 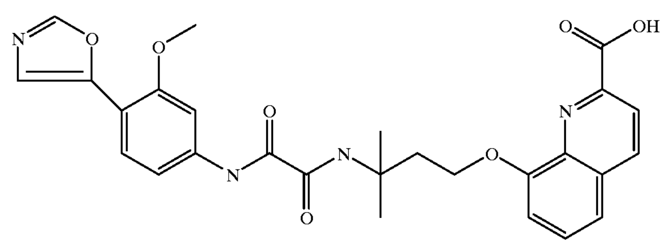 | 519 | 649 |
| 5-[3-[[[3-Methoxy-4-(5-oxazolyl) anilino]oxalyl]amino]-3-methylbutoxy]-2-indolecarboxylic acid | 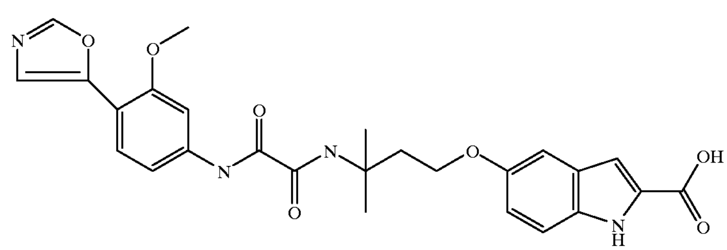 | 507 | 650 |

Further preferred compounds of formula XVIII are those of general formula

XIX

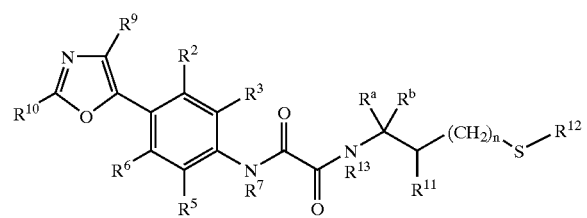

wherein $R^2$, $R^3$, $R^5$, $R^6$, $R^7$, $R^9$ and $R^{10}$ are defined as above, $R^{11}$ and $R^{13}$ are H or lower alkyl, n=0 or 1, $R^a$, $R^b$ are lower alkyl or $R^a$ and $R^b$ taken together with the carbon atom to which they are attached form a 3 to 7 member carbocycle, and $R^{12}$ is heterocyclyl, aryl or lower cycloalkyl, especially aryl, a 3 to 7 membered cycloalkyl ring, or a 5 to 6 membered monocyclic or 9 to 10 membered bicyclic saturated or unsaturated heterocyclic ring with 1 to 4 heteroatoms selected from nitrogen, oxygen, and sulfur.

Particularly preferred compounds of formula (XIX) are those wherein $R^2$ is methoxy and $R^3$, $R^5$, $R^6$, $R^9$, $R^{10}$, $R^{11}$ and $R^{13}$ are hydrogen.

Examples of such compounds are listed in table 1f² below:

| Name | Structure | MS(ES) (M + H)+ | Ex No |
|---|---|---|---|
| N-[3-Methoxy-4-(5-oxazolyl) phenyl]-N'-[1,1-dimethyl-2-(phenylthio)ethyl]oxalamide | | 426 | 615 |
| N-[2-(4-Hydroxyphenylthio)-1,1-dimethylethyl]-N'-[3-methoxy-4-(5-oxazolyl)phenyl]oxalamide | 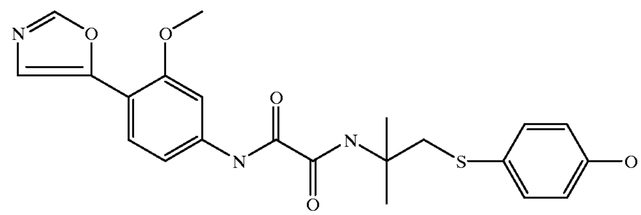 | 442 | 616 |
| N-[3-Methoxy-4-(5-oxazolyl) phenyl]-N'-[1,1-dimethyl-2-(phenylthio)ethyl]oxalamide | | 440 | 617 |
| N-[3-Methoxy-4-(5-oxazolyl) phenyl]-N'-[1,1-dimethyl-2-(2-pyridylthio)ethyl]oxalamide | 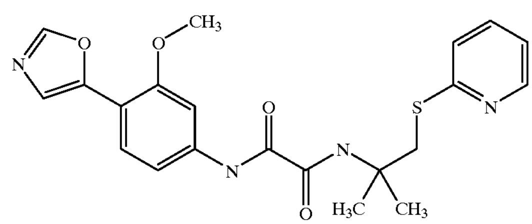 | 427 | 618 |
| N-[3-Methoxy-4-(5-oxazolyl) phenyl]-N'-[1,1-dimethyl-3-(2-pyridylthio)propyl]oxalamide | 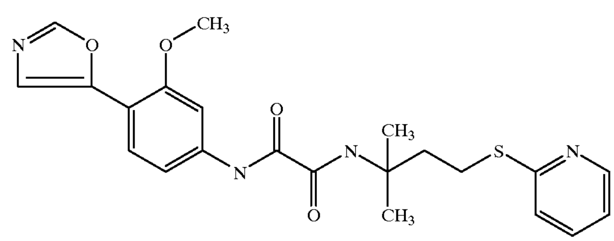 | 441 | 619 |
| N-[3-Methoxy-4-(5-oxazolyl) phenyl]-N'-[1,1-dimethyl-3-(2-thienylthio)propyl]oxalamide | 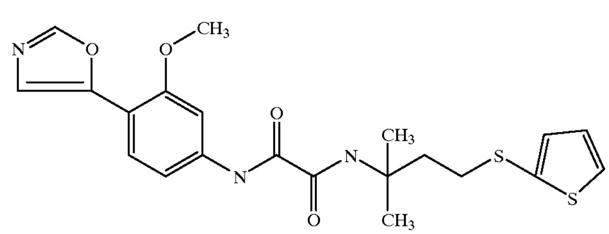 | 446 | 620 |

-continued

| Name | Structure | MS(ES) (M + H)+ | Ex No |
|---|---|---|---|
| N-[3-Methoxy-4-(5-oxazolyl) phenyl]-N'-[1,1-dimethyl-3-(2-pyrimidylthio)propyl]oxalamide | 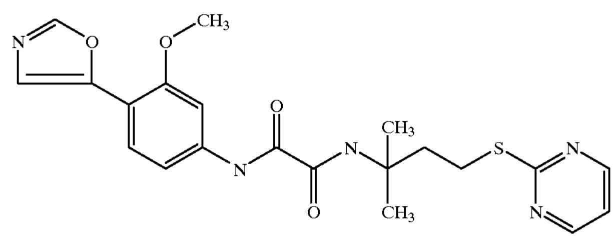 | 442 | 621 |
| N-[3-Methoxy-4-(5-oxazolyl) phenyl]-N'-[1,1-dimethyl-3-(4-pyridylthio)propyl]oxalamide | 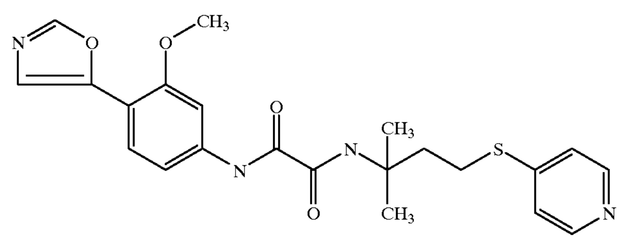 | 441 | 622 |
| N-[3-Methoxy-4-(5-oxazolyl) phenyl]-N'-[1,1-dimethyl-3-(2-thiazolylthio)propyl]oxalamide | 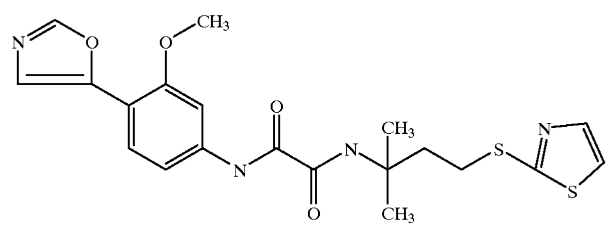 | 447 | 623 |
| N-[3-(4-Hydroxyphenylthio)-1,1-dimethylpropyl]-N'-[3-methoxy-4-(5-oxazolyl)phenyl]oxalamide | 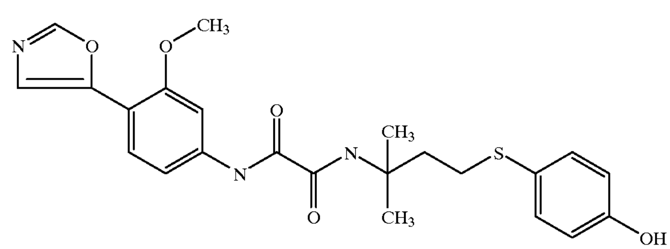 | 456 | 624 |
| N-[3-Methoxy-4-(5-oxazolyl) phenyl]-N'-[1,1-dimethyl-3-(5-methyl-1,3,4-thiadiazol-2-ylthio) propyl]oxalamide | 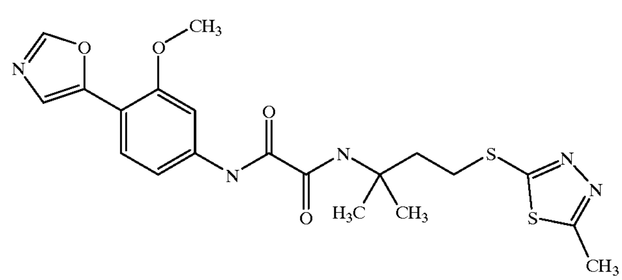 | 462 | 625 |
| N-[3-(2-Benzooxazolylthio)-1,1-dimethylpropyl]-N'-[3-methoxy-4-(5-oxazolyl)phenyl]oxalamide | 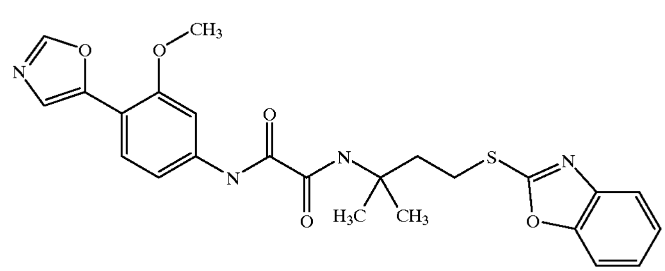 | 481 | 626 |

-continued

| Name | Structure | MS(ES) (M + H)+ | Ex No |
|---|---|---|---|
| N-[3-(2-Benzothiazolylthio)-1,1-dimethylpropyl]-N'-[3-methoxy-4-(5-oxazolyl)phenyl]oxalamide | 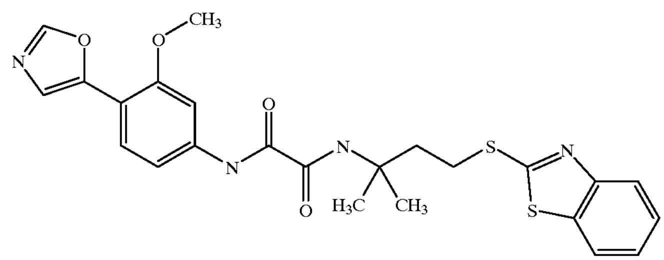 | 497 | 627 |
| Methyl 4-[2-[[[3-methoxy-4-(5-oxazolyl)anilino]oxalyl]amino]-2-methylpropylthio]benzoate | 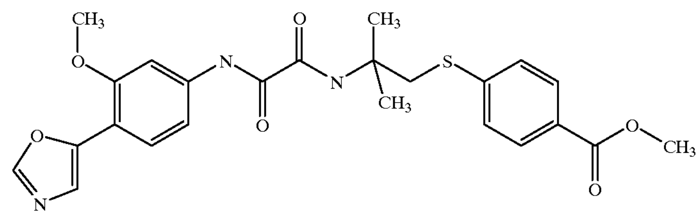 | 484 | 628 |
| tert-Butyl 6-[3-[[[3-methoxy-4-(5-oxazolyl)anilino]oxalyl]amino]-3-methylbutylthio]-3-pyridinecarboxylate | 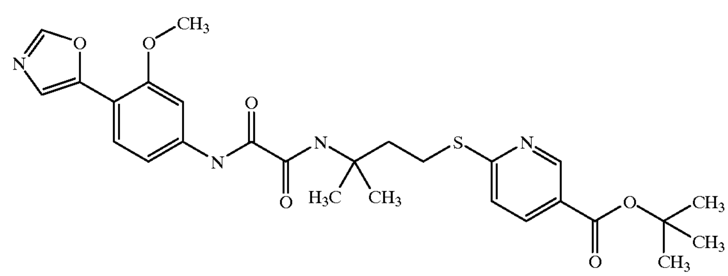 | 541 | 629 |
| 6-[3-[[[3-Methoxy-4-(5-oxazolyl)anilino]oxalyl]amino]-3-methylbutylthio]-3-pyridinecarboxylic acid trifluoroacetate (1:1) | 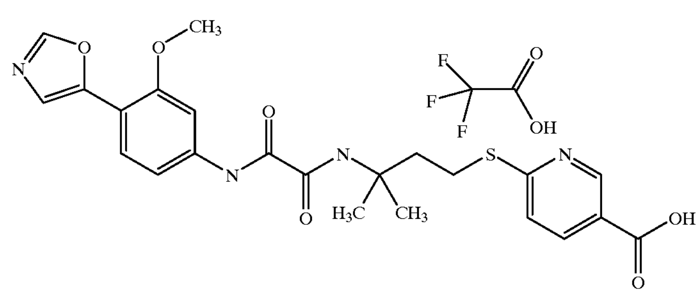 | 485 | 630 |
| 4-[3-[[[3-Methoxy-4-(5-oxazolyl)anilino]oxalyl]amino]-3-methylbutylthio]benzoic acid | 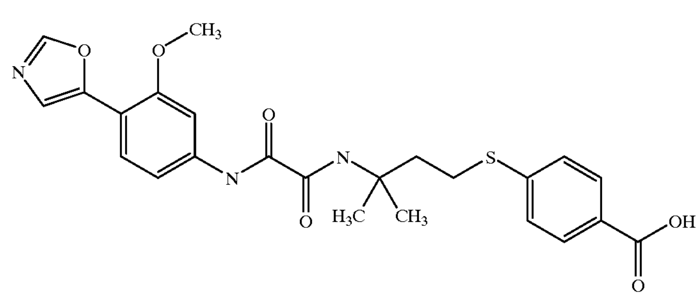 | 484 | 631 |

-continued

| Name | Structure | MS(ES) (M + H)+ | Ex No |
| --- | --- | --- | --- |
| N-[2-(4-Benzyloxyphenylthio)-1,1-dimethylethyl]-N'-[3-methoxy-4-(5-oxazolyl)phenyl]oxalamide | 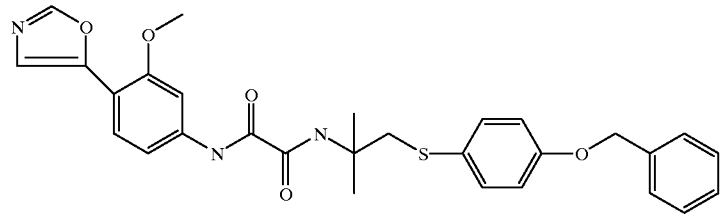 | 532 | 664 |
| N-[2-(4-Benzyloxyphenylthio)-1,1-dimethylpropyl]-N'-[3-methoxy-4-(5-oxazolyl)phenyl]oxalamide | 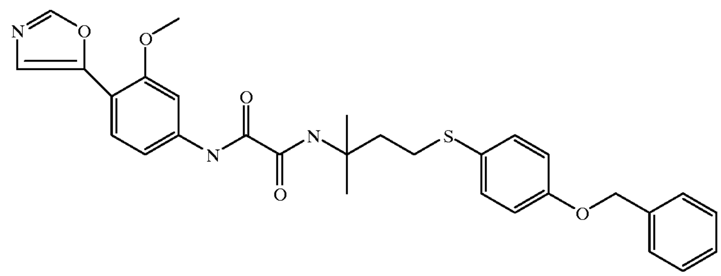 | 546 | 665 |
| 2-[3-[[[3-Methoxy-4-(5-oxazolyl)anilino]oxalyl]amino]-3-methylbutylthio]-5-benzoxazolecarboxylic acid | 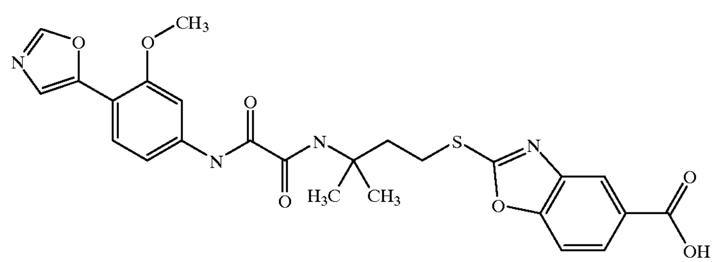 | 525 | 666 |
| N-[3-(1H-Imidazol-2-ylthio)-1,1-dimethylpropyl]-N'-[3-methoxy-4-(5-oxazolyl)phenyl]oxalamide | 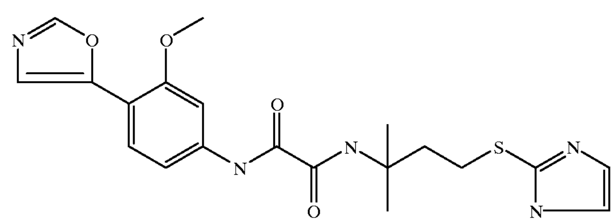 | 430 | 667 |
| 2-[3-[[[3-Methoxy-4-(5-oxazolyl)anilino]oxalyl]amino]-3-methylbutylthio]-3-pyridinecarboxylic acid trifluoroacetate (1:1) | 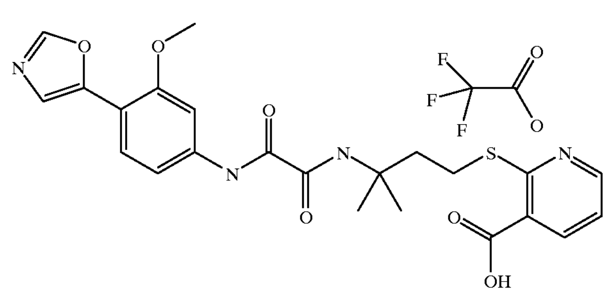 | 485 | 668 |

-continued

| Name | Structure | MS(ES) (M + H)+ | Ex No |
|---|---|---|---|
| 4-[2-[[[3-methoxy-4-(5-oxazolyl)anilino]oxalyl]amino]-2-methylpropylthio]benzoic acid | 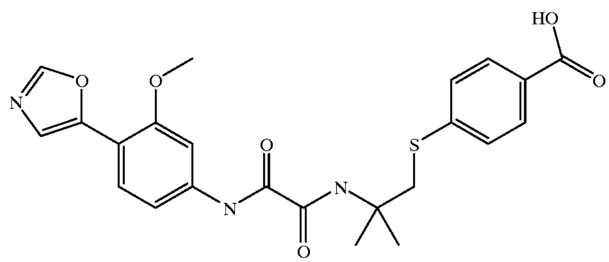 | 470 | 669 |
| 2-[3-[[[3-Methoxy-4-(5-oxazolyl)anilino]oxalyl]amino]-3-methylbutylthio]-6-benzoxazolecarboxylic acid | 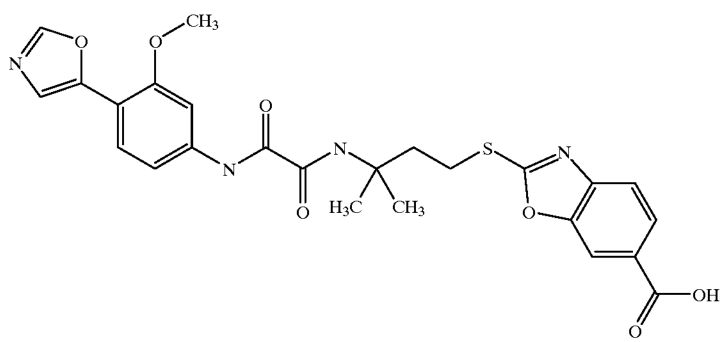 | 525 | 670 |

Further preferred compounds of formula (XVIII) are those of general formula

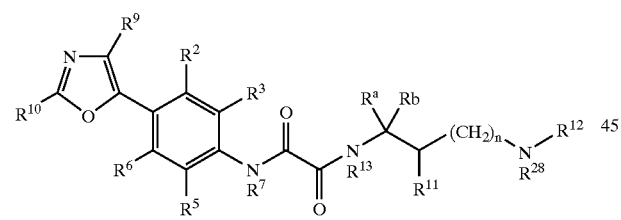

XX wherein $R^2$, $R^3$, $R^5$, $R^6$, $R^7$, $R^9$ and $R^{10}$ are defined as above, $R^{11}$, $R^{13}$ and $R^{28}$ are H or lower alkyl, n=0 or 1, $R^a$, $R^b$ are lower alkyl or $R^a$ and $R^b$ taken together with the carbon atom to which they are attached form a 3 to 7 number carbocycle, and $R^{12}$ is heterocyclyl, aryl or lower cycloalkyl preferably aryl such as phenyl.

Particularly preferred compounds of formula (XX) are those wherein $R^2$ is methoxy and $R^3$, $R^5$, $R^6$, $R^9$, $R^{10}$, $R^{11}$ and $R^{13}$ are hydrogen and $R^{28}$ is hydrogen or methyl.

Examples of such compounds are listed in table 1f³ below.

| Name | Structure | MS(ES) (M + H)+ | Ex No |
|---|---|---|---|
| N-[3-Methoxy-4-(5-oxazolyl)phenyl]-N'-[1,1-dimethyl-2-(N-methylanilino) ethyl] oxalamide | 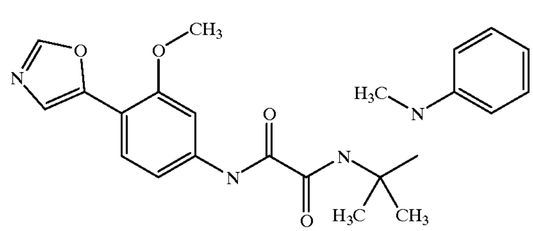 | 423 | 632 |

-continued

| Name | Structure | MS(ES) (M + H)+ | Ex No |
|---|---|---|---|
| N-(3-Anilino-1,1-dimethylpropyl)-N'-[3-methoxy-4-(5-oxazolyl)phenyl]oxalamide hydrochloride (1:1) | 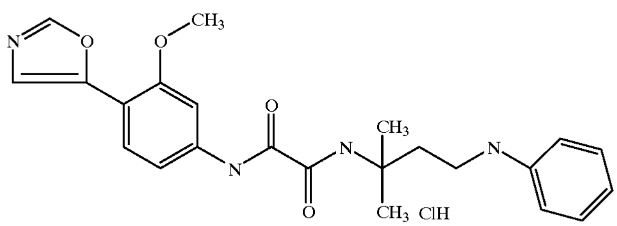 | 423 | 633 |
| 4-[3-[[[3-Methoxy-4-(5-oxazolyl)anilino]oxalyl]amino]-3-methylbutylamino]benzoic acid | 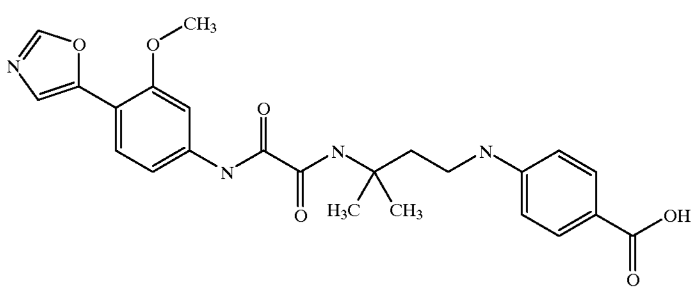 | 467 | 634 |

Particularly preferred compounds of formula (I) or formula (IX) are also those of general formula

XV wherein $R^2$, $R^3$, $R^5$, $R^6$, $R^7$, $R^9$ and $R^{10}$ are defined as above, $R^{11}$ and $R^{13}$ is H or lower alkyl, n=0 or 1; $R^{21}$ is alkyl, cycloalkyl, phenyl, heterocyclyl, cycloalkyl alkyl, phenyl alkyl or heterocyclyl alkyl, alkyl carhonyl, cycloalkyl carbonyl, phenyl carbonyl, heterocyclyl carbonyl, alkyl sulphonyl, cycloalkyl sulphonyl, phenyl sulphonyl, heterocyclyl sulphonyl. Preferably $R^{21}$ is phenyl, phenyl alkyl, phenyl carbonyl, or phenyl sulfonyl.

Particularly preferred compounds of formula (XV) are also those wherein $R^2$ is methoxy, $R^3$, $R^5$, $R^6$, $R^9$, $R^{10}$, $R^{11}$ and $R^{13}$ are hydrogen.

Examples of such compounds are listed in table 1g below

| Name | Structure | MS(ES) (M + H)+ | Ex No |
|---|---|---|---|
| N-[3-Methoxy-4-(5-oxazolyl)phenyl]-N'-[1,1-dimethyl-2-(4-phenyl-1-piperazinyl)ethyl]oxalamide | 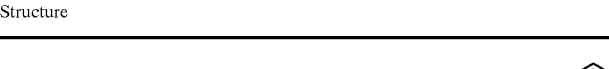 | 478 | 407 |

-continued

| Name | Structure | MS(ES) (M + H)+ | Ex No |
|---|---|---|---|
| N-[3-Methoxy-4-(5-oxazolyl)phenyl]-N'-[2-[4-(4-methoxyphenyl)-1-piperazinyl]-1,1-dimethylethyl]oxalamide | 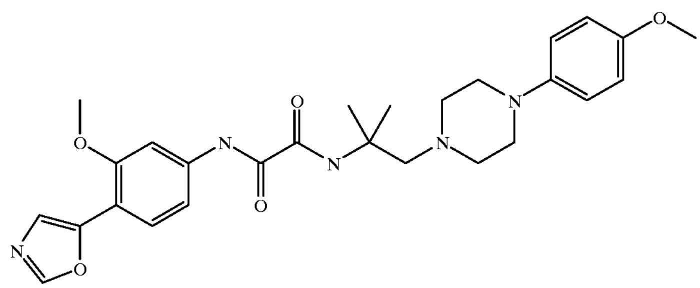 | 508 | 408 |
| N-[3-Methoxy-4-(5-oxazolyl)phenyl]-N'-[2-[4-(3-methoxyphenyl)-1-piperazinyl]-1,1-dimethylethyl]oxalamide | 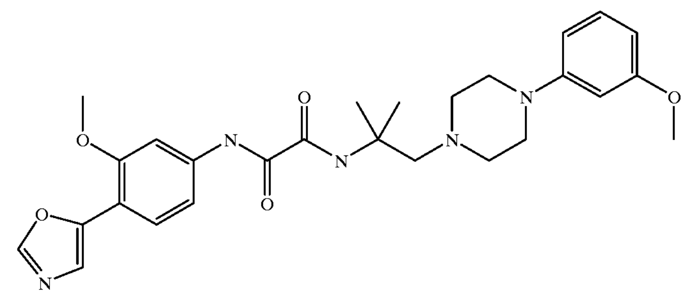 | 508 | 409 |
| N-[3-Methoxy-4-(5-oxazolyl)phenyl]-N'-[1,1-dimethyl-3-(4-phenyl-1-piperazinyl)propyl]oxalamide | 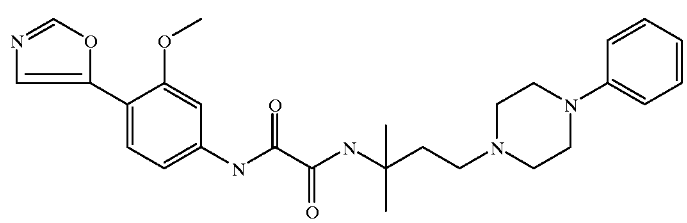 | 492 | 410 |
| N-[3-Methoxy-4-(5-oxazolyl)phenyl]-N'-[2-[4-(2-methoxy-phenyl)-1-piperazinyl]-1,1-dimethylethyl]oxalamide | 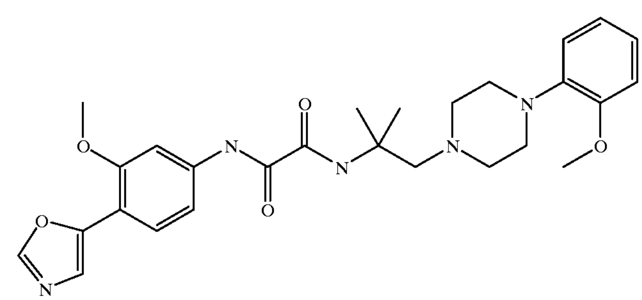 | 508 | 411 |
| N-[2-(4-Benzyl-1-piperazinyl)-1,1-dimethylethyl]-N'-[3-methoxy-4-(5-oxazolyl)phenyl]oxalamide | 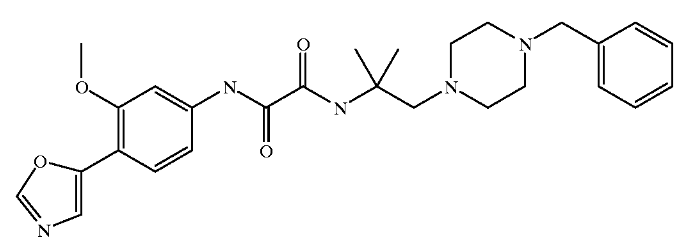 | 492 | 412 |

-continued

| Name | Structure | MS(ES) (M + H)+ | Ex No |
|---|---|---|---|
| N-[2-[4-(Benzenesulfonyl)-1-piperazinyl]-N'-[3-methoxy-4-(5-oxazolyl)phenyl]oxalamide | 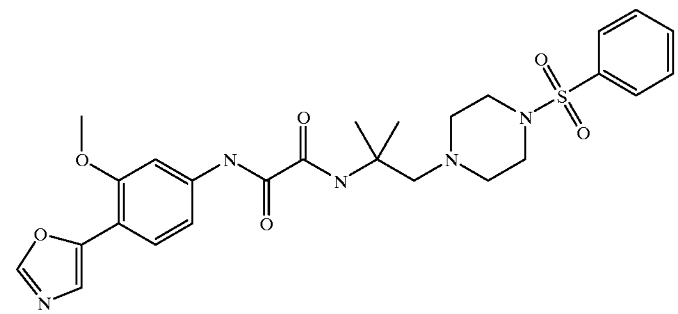 | 452 | 413 |
| N-[2-(4-Benzoyl-1-piperazinyl)-1,1-dimethylethyl]-N'-[3-methoxy-4-(5-oxazolyl)phenyl]oxalamide | 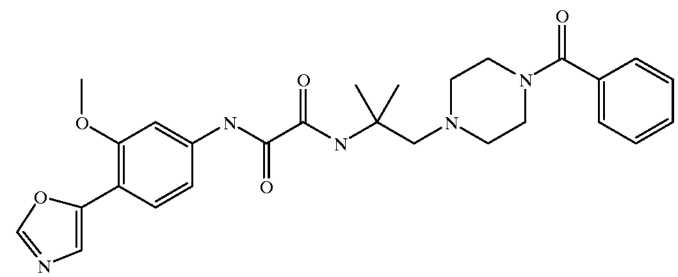 | 506 | 414 |
| N-[2-[4-[4-(Trifluoromethyl)phenyl]-1-piperazinyl]-1,1-dimethylethyl]-N'-[3-methoxy-4-(5-oxazolyl)phenyl]oxalamide | 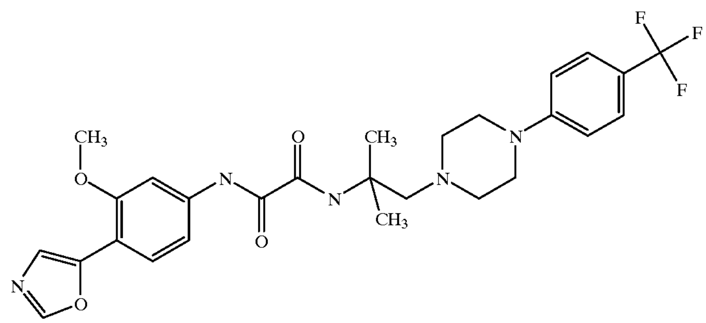 | 546 | 459 |
| N-[3-Methoxy-4-(5-oxazolyl)phenyl]-N'-[1,1-dimethyl-2-[4-(2-methylphenyl)1-1 piperazinyl]ethyl]oxalamide | 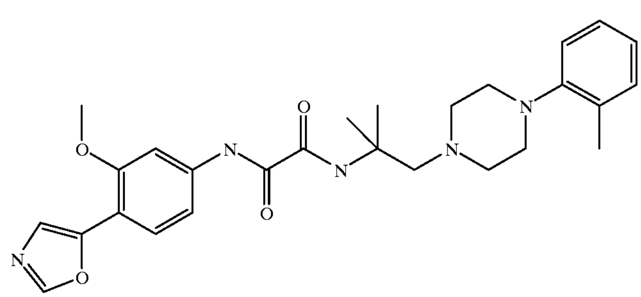 | 492 | 460 |
| N-[2-[4-(2-Fluorophenyl)-1-piperazinyl]-1,1-dimethylethyl]-N'-[3-methoxy-4-(5-oxazolyl)phenyl]oxalamide | 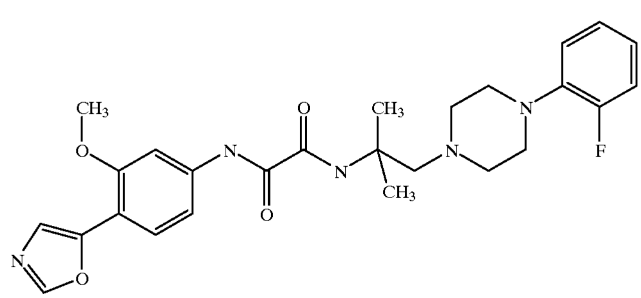 | 496 | 461 |

-continued

| Name | Structure | MS(ES) (M + H)+ | Ex No |
|---|---|---|---|
| N-[2-[4-(4-Fluorophenyl)-1-piperazinyl]-1,1-dimethylethyl]-N'-[3-methoxy-4-(5-oxazolyl)phenyl]oxalamide | 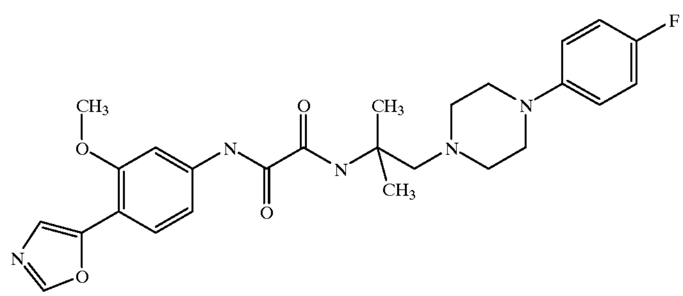 | 496 | 462 |
| N-[3-Methoxy-4-(5-oxazolyl)phenyl]-N'-[2-[4-(2-methoxyphenyl)-1-piperazinyl]-1,1-dimethylethyl]oxalamide | 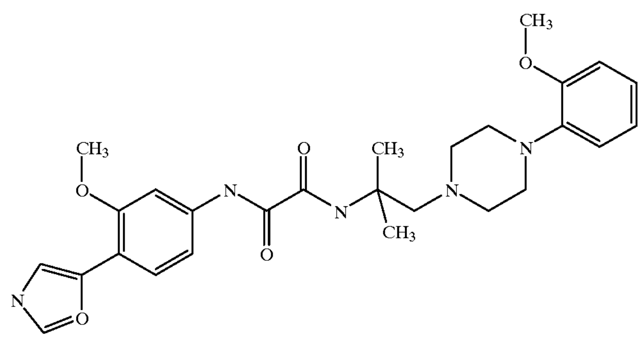 | 508 | 463 |
| N-[3-Methoxy-4-(5-oxazolyl)phenyl]-N'-[1,1-dimethyl-2-[4-(2-thiophenesulfonyl)-1-piperazinyl]ethyl]oxalamide | 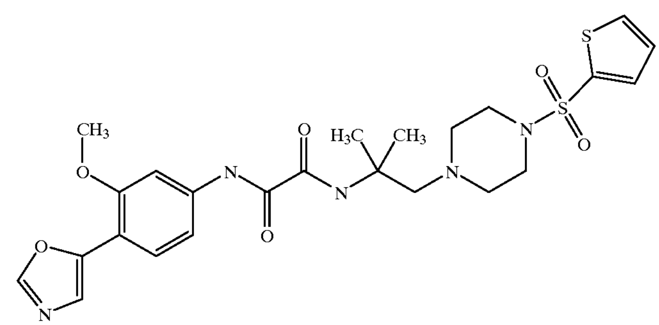 | 548 | 464 |
| N-[3-Methoxy-4-(5-oxazolyl)phenyl]-N'-[1,1-dimethyl-2-[4-(2,4,6-trimethylbenzenesulfonyl)-1-piperazinyl]ethyl]oxalamide | 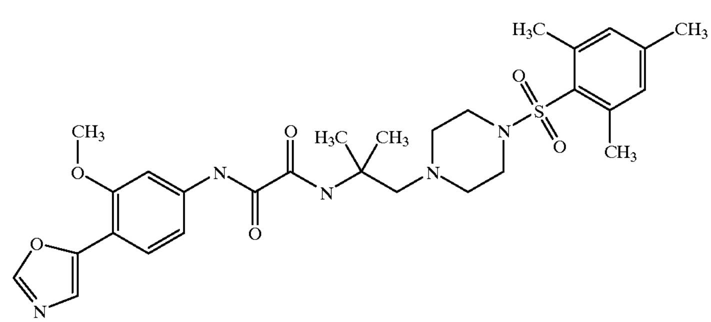 | 584.1 | 465 |

-continued

| Name | Structure | MS(ES) (M + H)+ | Ex No |
|---|---|---|---|
| N-[2-[4-(4-Fluorobenzenesulfonyl)-1-piperazinyl]-1,1-dimethylethyl]-N'-[3-methoxy-4-(5-oxazolyl)phenyl]oxalamide | 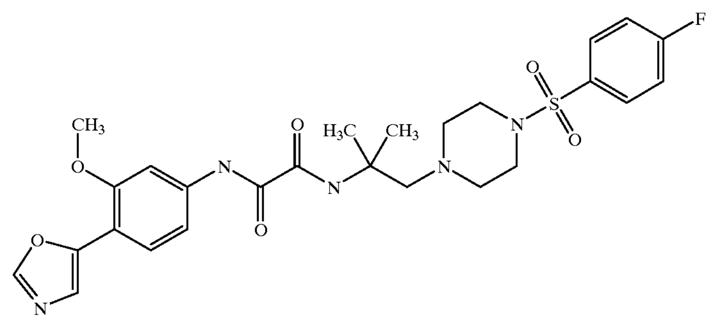 | 560.1 | 466 |
| N-[2-[4-(Trifluoromethanesulfonyl)-1-Piperazinyl]-1,1-dimethylethyl]-N'-[3-methoxy-4-(5-oxazolyl)phenyl)]oxalamide | 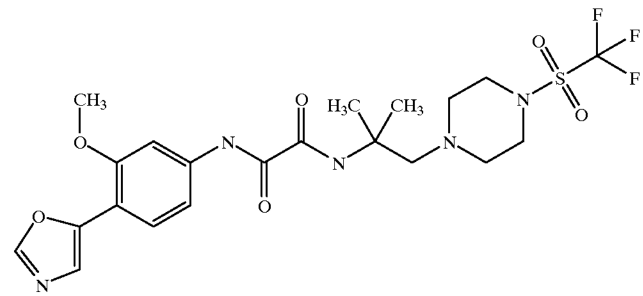 | 534 | 467 |
| N-[2-[4-(Isopropylsulfonyl)-1-piperazinyl]-1,1-dimethylethyl]-N'-[3-methoxy-4-(5-[oxazolyl)phenyl]oxalamide | 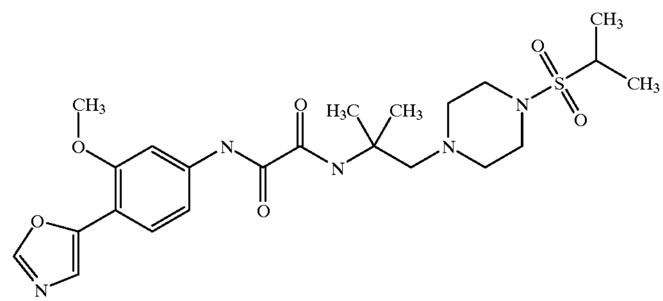 | 508.1 | 468 |
| (E)-N-[3-Methoxy-4-(5-oxazolyl)phenyl]-N'-[1,1-dimethyl-2-[4-(styrylsulfonyl)-1-piperazinyl]ethyl]oxalamide | 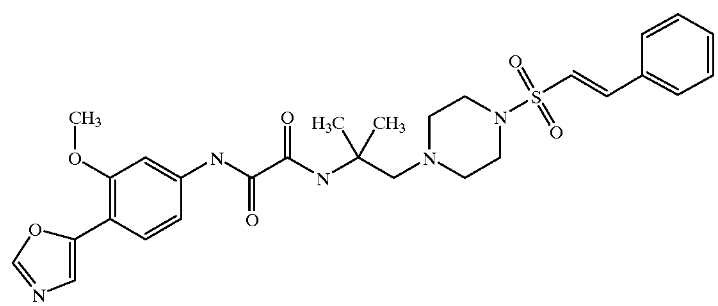 | 568.1 | 469 |
| N-[2-[4-(Ethanesulfonyl)-1-piperazinyl]-1,1-dimethylethyl]-N'-[3-methoxy-4-(5-oxazolyl)phenyl]oxalamide | 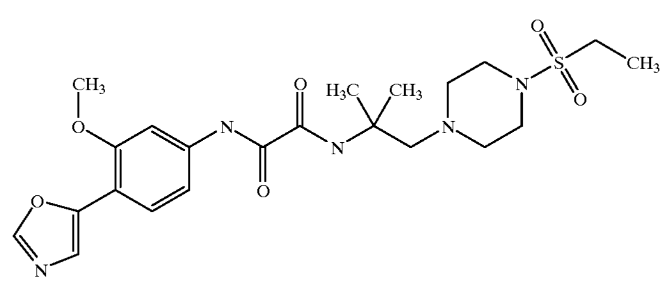 | 494.1 | 470 |

-continued

| Name | Structure | MS(ES) (M + H)+ | Ex No |
| --- | --- | --- | --- |
| N-[3-Methoxy-4-(5-oxazolyl)phenyl]-N'-[1,1-dimethyl-2-[4-(propanesulfonyl)-1-piperazinly]ethyl]oxalamide | 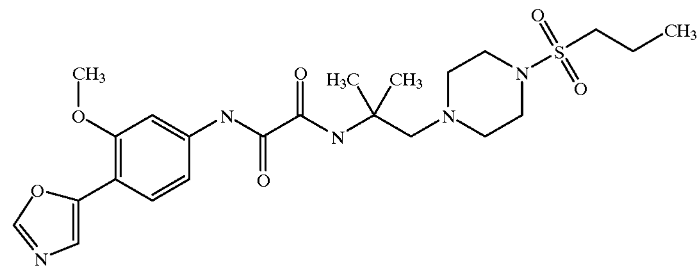 | 508.1 | 471 |
| N-[2-[4-(3-Chloropropanesulfonyl)-1-piperazinyl]-1,1-dimethylethyl]-N'-[3-methoxy-4-(5-oxazolyl)phenyl]oxalamide | 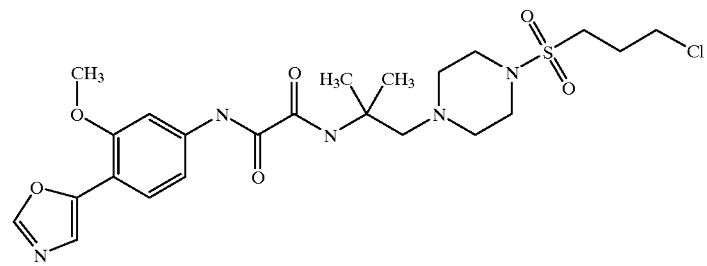 | 542.1 | 472 |
| N-[3-Methoxy-4-(5-oxazolyl)phenyl]-N'-[1,1-dimethyl-2-[4-(o-toluenesulfonyl)-1-piperazinyl]ethyl]oxalamide | 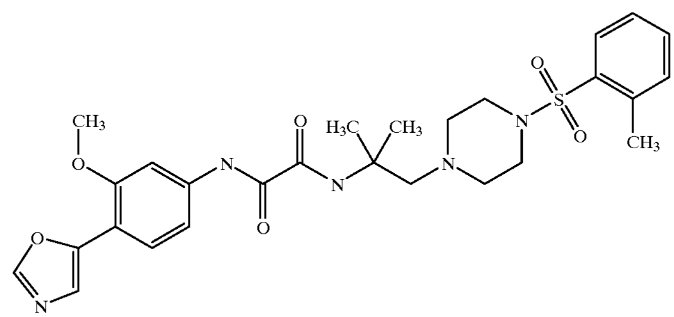 | 556.1 | 473 |
| N-[2-[4-(2-Fluorobenzenesulfonyl)-1-piperazinyl]-1,1-dimethylethyl]-N'-[3-methoxy-4-(5-oxazolyl)phenyl]oxalamide | 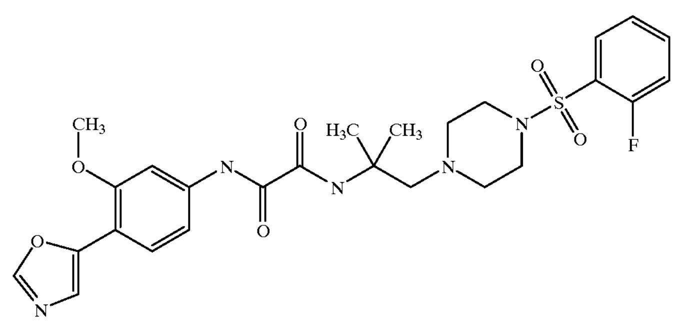 | 560.1 | 474 |
| N-[2-[4-(2-Cyanobenzenesulfonyl)-1-piperazinyl]-1,1-dimethylethyl]-N'-[3-methoxy-4-(5-oxazolyl)phenyl]oxalamide | 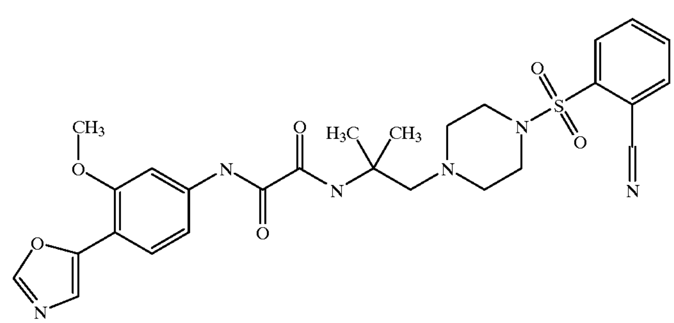 | 567.1 | 475 |

-continued

| Name | Structure | MS(ES) (M + H)+ | Ex No |
|---|---|---|---|
| N-[3-Methoxy-4-(5-oxazolyl)phenyl]-N'-[2-[4-(3,5-dimethyl-4-isoxazolylsulfonyl)-1-piperazinyl]-1,1-dimethylethyl]oxalamide | | 561.1 | 476 |
| N-[2-[4-(5-Fluoro-2-methylbenzenesulfonyl)-1-piperazinyl]-1,1-dimethylethyl]-N'-[3-methoxy-4-(5-oxazolyl)phenyl]oxalamide | 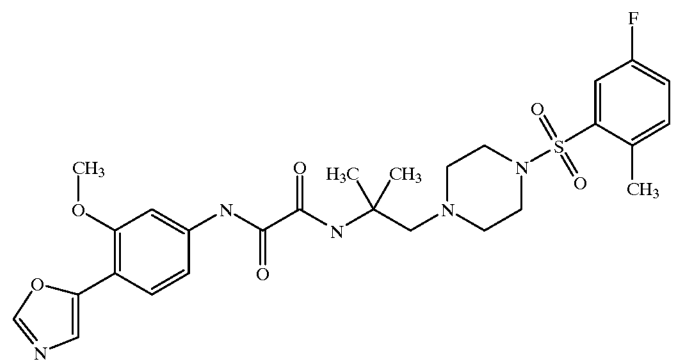 | 574.1 | 477 |
| N-[2-[4-(2,5-Difluorobenzenesulfonyl)-1-piperazinyl]-1,1-dimethylethyl]-N'-[3-methoxy-4-(5-oxazolyl)phenyl]oxalamide | 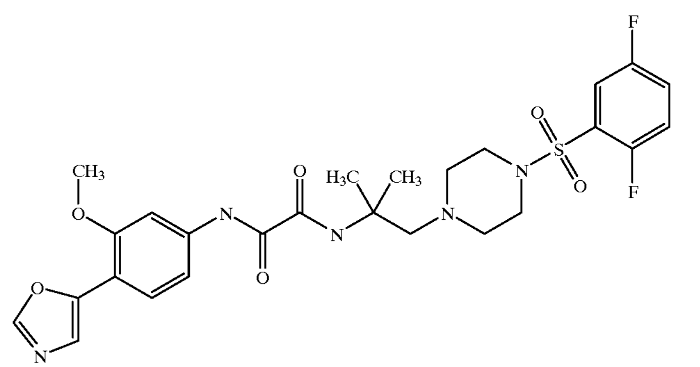 | 578.1 | 478 |
| N-[3-Methoxy-4-(5-oxazolyl)phenyl]-N'-[1,1-dimethyl-2-[4-(1-methyl-1H-imidazole-4-sulfonyl)-1-piperazinyl]ethyl]oxalamide | 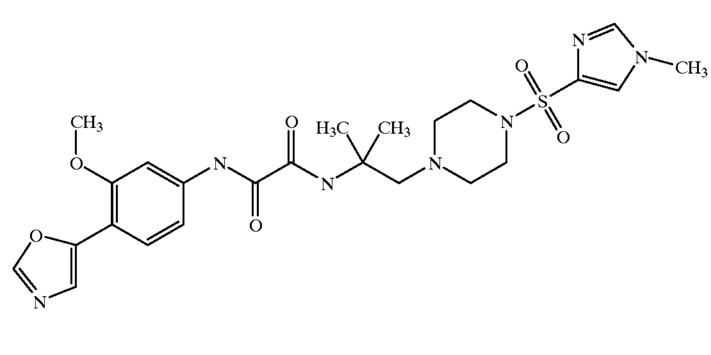 | 546.1 | 479 |

-continued

| Name | Structure | MS(ES) (M + H)+ | Ex No |
|---|---|---|---|
| N-[2-[4-(2,6-Difluorobenzenesulfonyl)-1-piperazinyl]-1,1-dimethylethyl]-N'-[3-methoxy-4-(5-oxazolyl)phenyl]oxalamide | 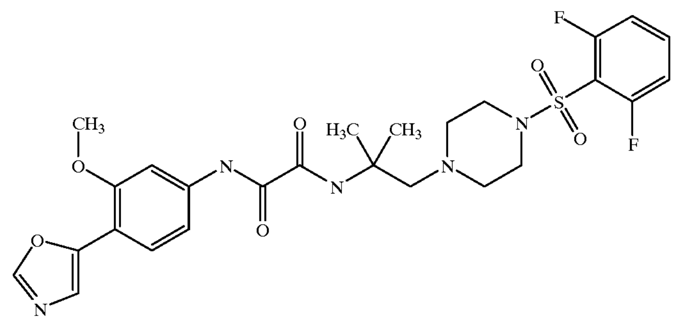 | 578.1 | 480 |
| N-[2-[4-(3,4-Difluorobenzenesulfonyl)-1-piperazinyl]-1,1-dimethylethyl]-N'-[3-methoxy-4-(5-oxazolyl)phenyl]oxalamide | 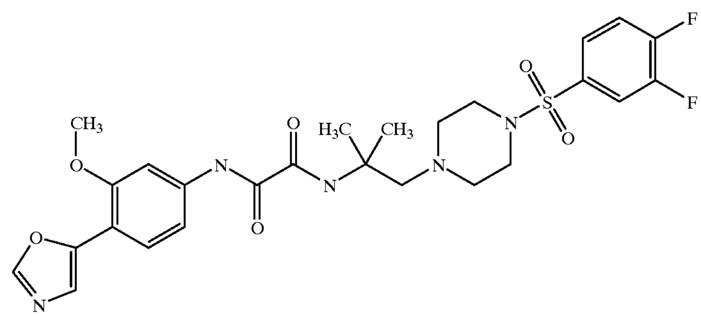 | 578.1 | 481 |
| N-[2-[4-(Cyclohexylmethanesulfonyl)-1-piperazinyl]-1,1-dimethylethyl]-N'-[3-methoxy-4-(5-oxazolyl)phenyl]oxalamide | 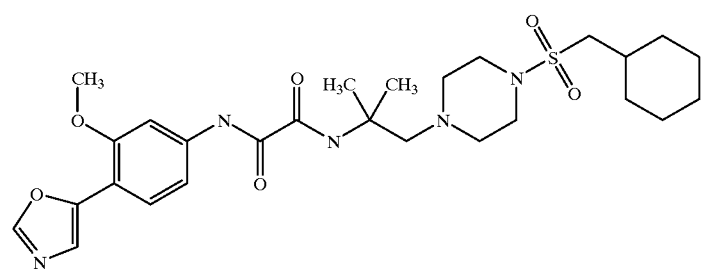 | 562.2 | 482 |
| N-[3-Methoxy-4-(5-oxazolyl)phenyl]-N'-[1,1-dimethyl-2-[4-(2-phenylethanesulfonyl)-1-piperazinyl]ethyl]oxalamide | 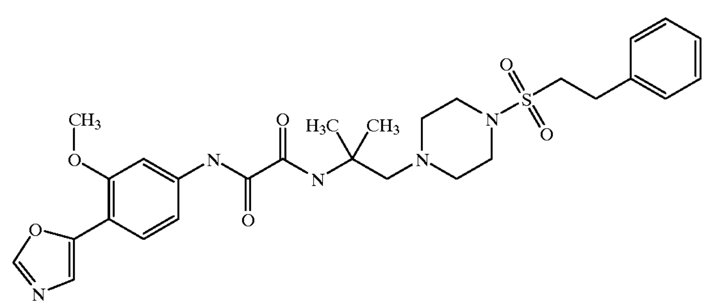 | 570.1 | 483 |

-continued

| Name | Structure | MS(ES) (M + H)+ | Ex No |
|---|---|---|---|
| N-[3-Methoxy-4-(5-oxazolyl)phenyl]-N'-[2-[4-(2,4-dimethoxyphenyl)-1-piperazinyl]-1,1-dimethylethyl]oxalamide | 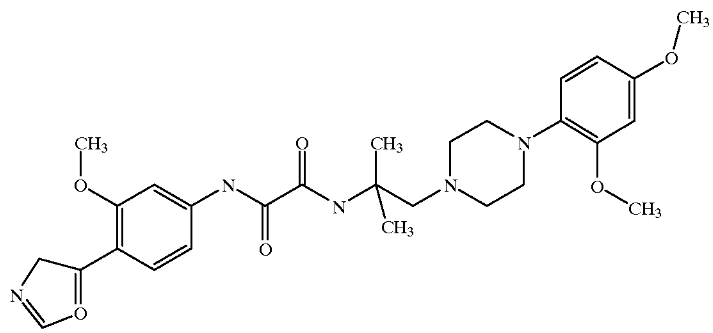 | 538 | 484 |
| N-[3-Methoxy-4-(5-oxazolyl)phenyl]-N'-[1,1-dimethyl-2-[4-(4-methylphenyl)-1-piperazinyl]ethyl]oxalamide | 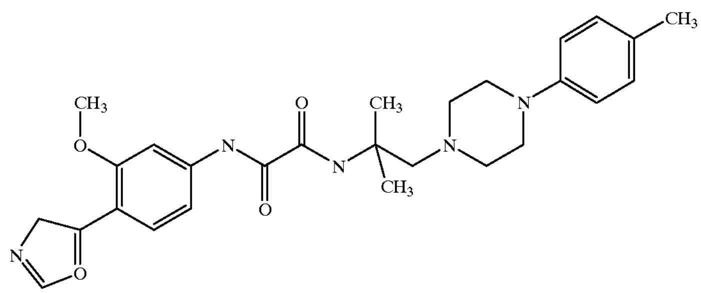 | 492 | 485 |
| N-[3-Methoxy-4-(5-oxazolyl)phenyl]-N'-[1,1-dimethyl-2-[4-(2,4-dimethylphenyl)1-1 piperazinyl]ethyl]oxalamide | 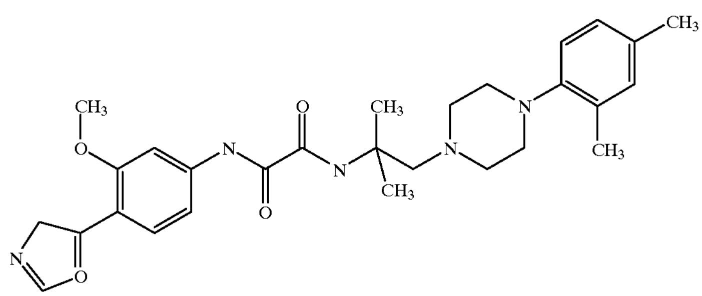 | 506 | 486 |
| N-[3-Methoxy-4-(5-oxazolyl)phenyl]-N'-[2-[4-(3,4-dimethoxyphenyl)-1-piperazinyl]-1,1-dimethylethyl]oxalamide | 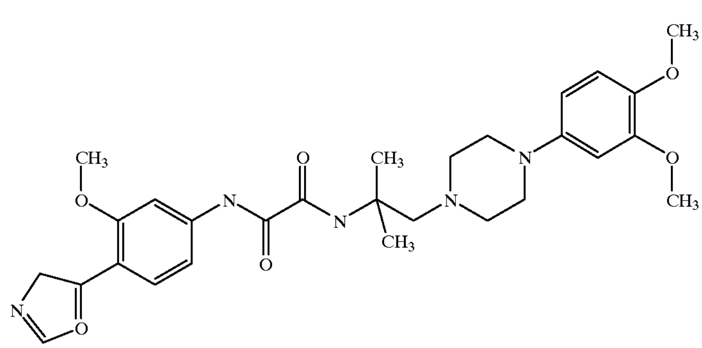 | 538 | 487 |

-continued

| Name | Structure | MS(ES) (M + H)+ | Ex No |
|---|---|---|---|
| N-[2-(4-Cyclohexyl-1-piperazinyl)-1,1-dimethylethyl]-N'-[3-methoxy-4-(5-oxazolyl)phenyl]oxalamide | 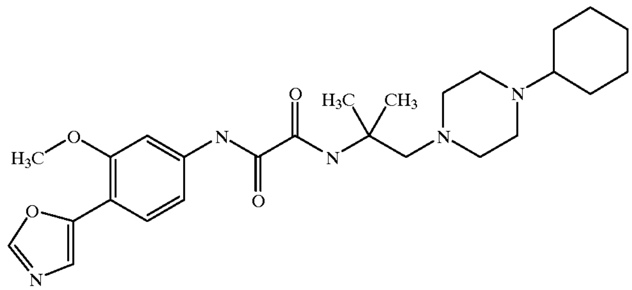 | 484.4 | 488 |
| N-[2-[4-(Cyclohexylmethyl)-1-piperazinyl]-1,1-dimethylethyl]-N'-[3-methoxy-4-(5-oxazolyl)phenyl]oxalamide | 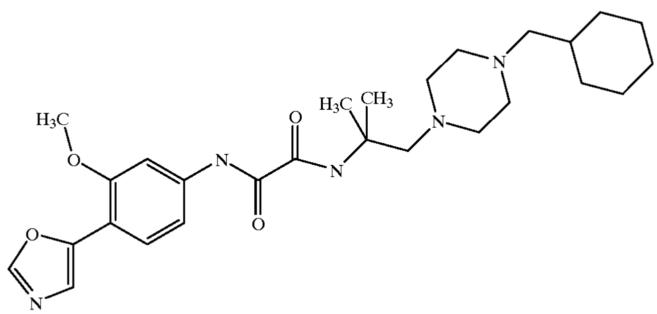 | 498.2 | 489 |
| N-[2-[4-(2-Methoxybenzyl)-1-piperazinyl]-1,1-dimethylethyl]-N'-[3-methoxy-4-(5-oxazolyl)phenyl]oxalamide | 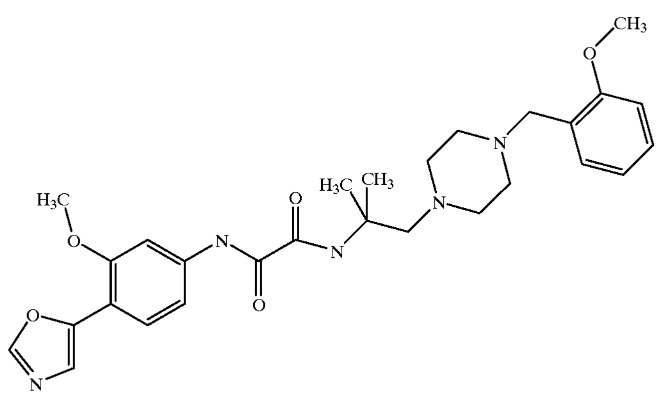 | 522.1 | 490 |
| N-[2-[4-(2-Hydroxybenzyl)1-1 piperazinyl]-1,1-dimethylethyl]-N'-[3-methoxy-4-(5-oxazolyl)phenyl]oxalamide | 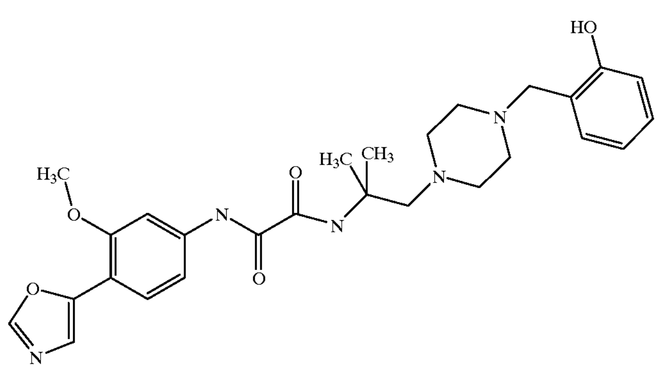 | 508.1 | 491 |

-continued

| Name | Structure | MS(ES) (M + H)+ | Ex No |
|---|---|---|---|
| N-[3-Methoxy-4-(5-oxazolyl)phenyl]-N'-[1,1-dimethyl-2-[4-(2-methylbenzyl)-1-piperazinyl]ethyl]oxalamide | 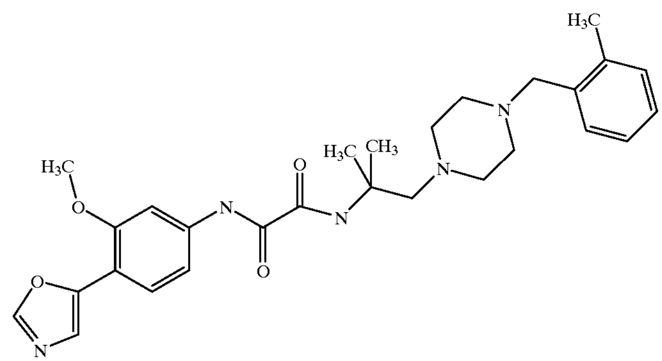 | 506.1 | 492 |
| N-[3-Methoxy-4-(5-oxazolyl)phenyl]-N'-[1,1-dimethyl-2-[4-(2-thenyl)-1-piperazinyl]ethyl]oxalamide | 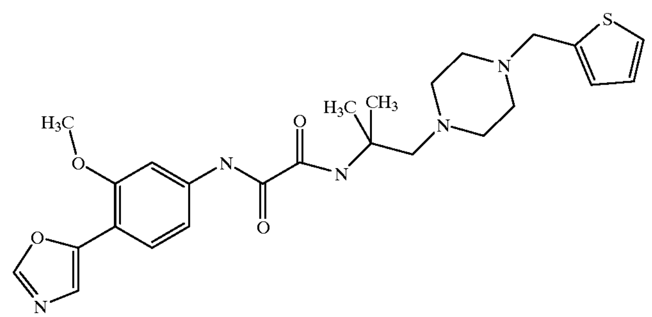 | 498.1 | 493 |
| N-[3-Methoxy-4-(5-oxazolyl)phenyl]-N'-[1,1-dimethyl-2-[4-(2(RS)-phenylpropyl)-1-piperazinyl]ethyl]oxalamide | 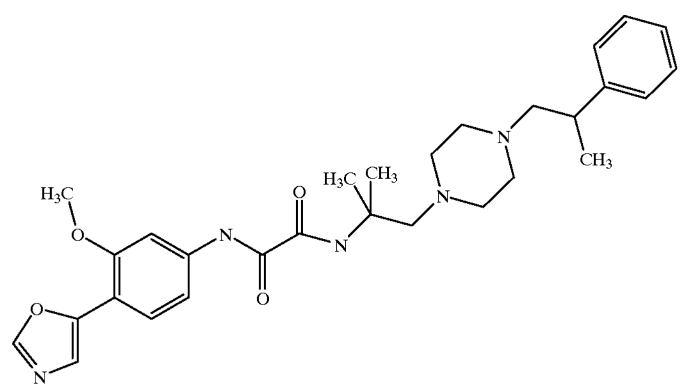 | 520.2 | 494 |
| N-[3-methoxy-4-(5-oxazolyl)phenyl]-N'-[1,1-dimethyl-2-(4-pivaloyl-1-piperazinyl)ethyl]oxalamide | 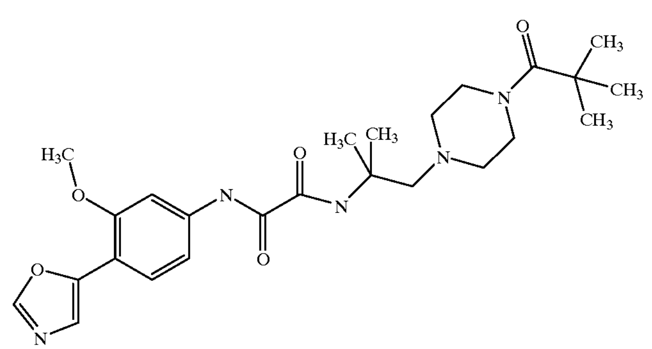 | 486.1 | 495 |

-continued

| Name | Structure | MS(ES) (M + H)+ | Ex No |
|---|---|---|---|
| N-[2-[4-(2-Furoyl)-1-piperazinyl]-1,1-dimethylethyl]-N'-[3-methoxy-4-(5-oxazolyl)phenyl]oxalamide | 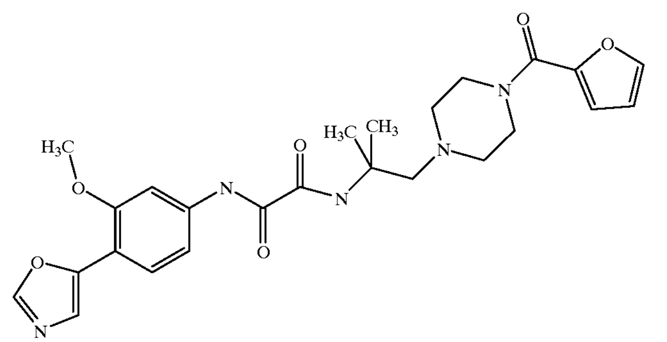 | 496.1 | 496 |
| N-[3-Methoxy-4-(5-oxazolyl)phenyl]-N'-[1,1-dimethyl-2-[4-(2-thenoyl)-1-piperazinyl]ethyl]oxalamide | 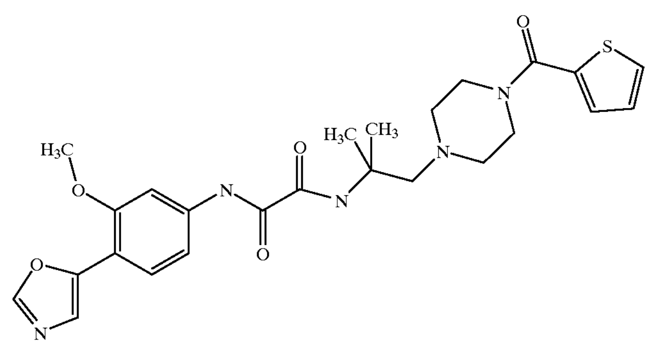 | 512.1 | 497 |
| N-[3-Methoxy-4-(5-oxazolyl)phenyl]-N'-[1,1-dimethyl-2-[4-(3-thenoyl)-1-piperazinyl]ethyl]oxalamide | 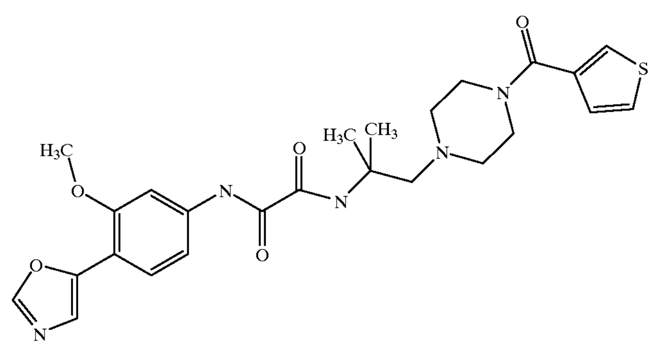 | 512 | 498 |
| N-[2-[4-(2-Cyclopentylacetyl)-1-piperazinyl]-1,1-dimethyl-ethyl]-N'-[3-methoxy-4-(5-oxazolyl)phenyl)]oxalamide | 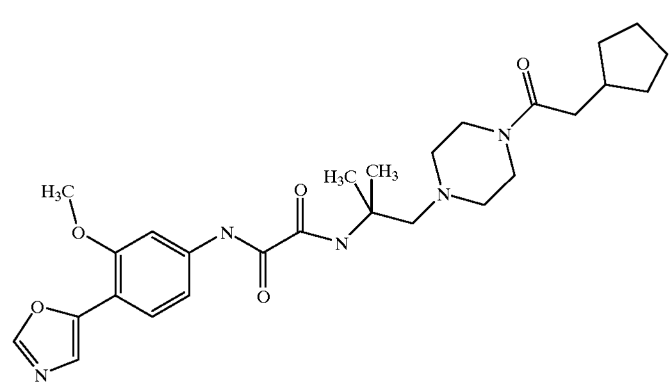 | 512.1 | 499 |

-continued

| Name | Structure | MS(ES) (M + H)+ | Ex No |
|---|---|---|---|
| N-[2-[4-(Cyclohexylcarbonyl)-1-piperazinyl]-1,1-dimethylethyl]-N'-[3-methoxy-4-(5-oxazolyl)phenyl]oxalamide | 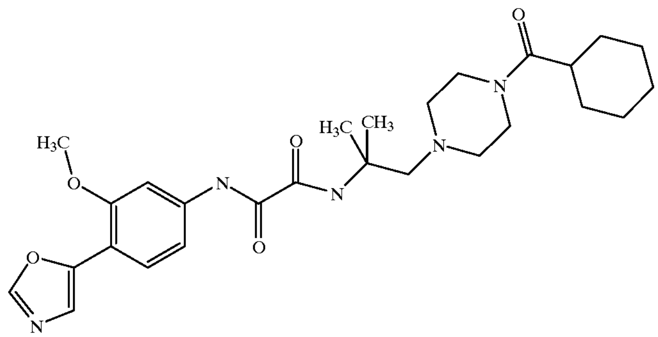 | 512.1 | 500 |
| N-[3-Methoxy-4-(5-oxazolyl)phenyl]-N'-[1,1-dimethyl-2-[4-(2-methylbenzoyl)-1-piperazinyl]ethyl]oxalamide | 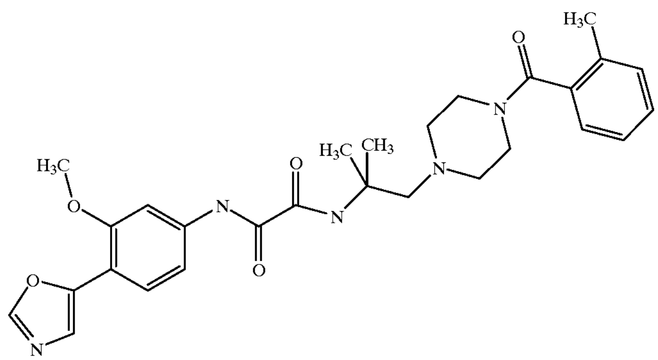 | 520.1 | 501 |
| N-[3-Methoxy-4-(5-oxazolyl)phenyl]-N'-[1,1-dimethyl-2-[4-(4-methylbenzoyl)-1-piperazinyl]ethyl]oxalamide | 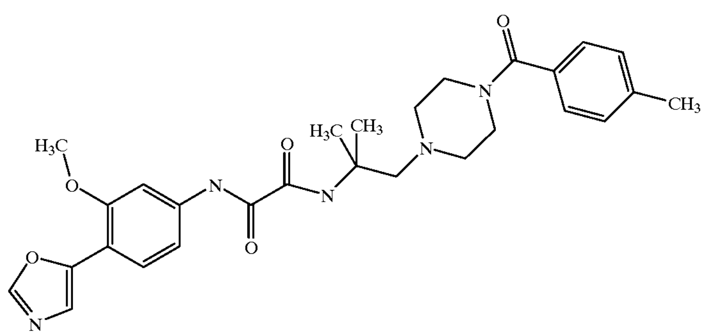 | 520.1 | 502 |
| N-[2-[4-(Cycloheptylcarbonyl)-1-piperazinyl]-1,1-dimethylethyl]-N'-[3-methoxy-4-(5-oxazolyl)phenyl]oxalamide | 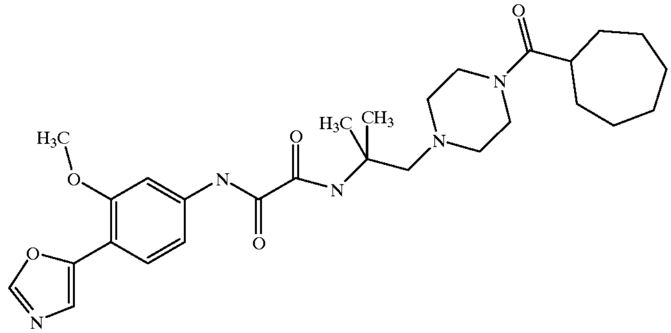 | 526.2 | 503 |

-continued

| Name | Structure | MS(ES) (M + H)+ | Ex No |
|------|-----------|-----------------|-------|
| N-[3-Methoxy-4-(5-oxazolyl)phenyl]-N'-]1,1-dimethyl-2-[4-[(1H-pyrazol-4-yl)carbonyl]-1-piperazinyl]ethyl]oxalamide | 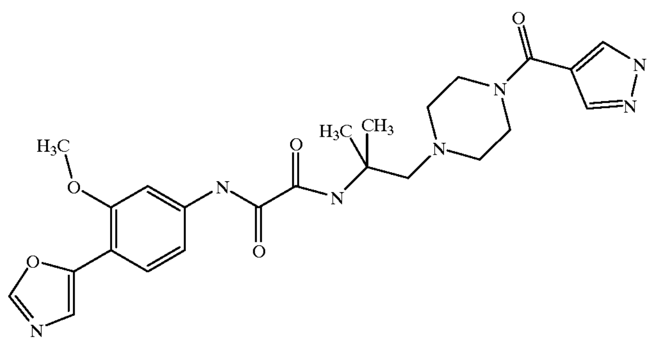 | 496.1 | 504 |
| N-[2-[4-(Cyclopentylcarbonyl)-1-piperazinyl]-1,1-dimethylethyl]-N'-[3-methoxy-4-(5-oxazolyl)phenyl]oxalamide | 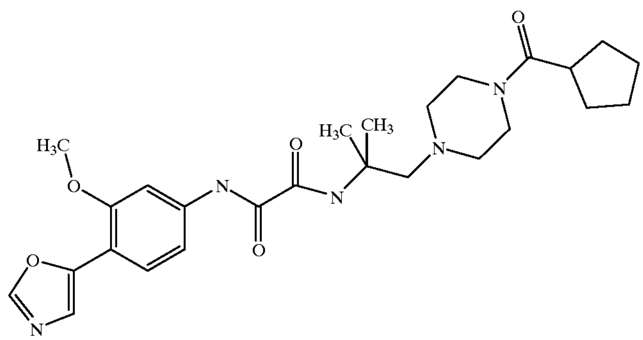 | 498.1 | 505 |
| N-[3-Methoxy-4-(5-oxazolyl)phenyl]-N'-[1,1-Dimethyl-2-[4-[(1-methyl-1H-pyrrol-2-yl)carbonyl]-1-piperazinyl]ethyl]oxalamide | 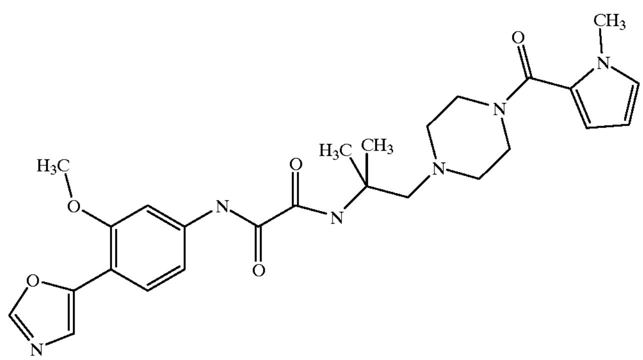 | 509.1 | 506 |
| N-[3-Methoxy-4-(5-oxazolyl)phenyl]-N'-[1,1-dimethyl-2-[4-[(1,2,3-thiadiazol-4-yl)carbonyl]-1-piperazinyl]-ethyl]oxalamide | 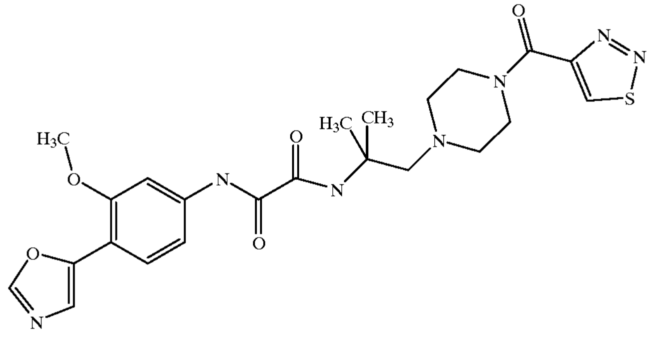 | 514.1 | 507 |

-continued

| Name | Structure | MS(ES) (M + H)+ | Ex No |
|---|---|---|---|
| N-[2-[4-(3-Fluorobenzoyl)-1-piperazinyl]-1,1-dimethylethyl]-N'-[3-methoxy-4-(5-oxazolyl)phenyl]oxalamide | 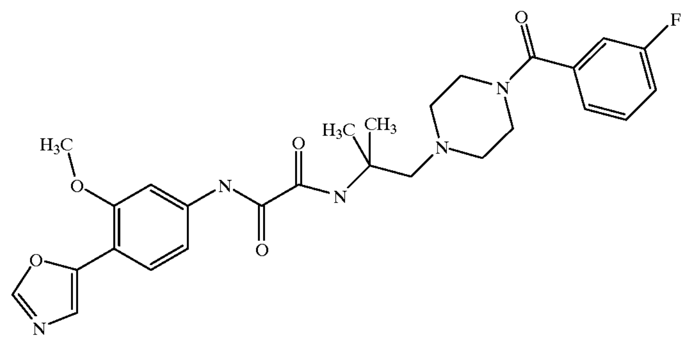 | 524.1 | 508 |
| N-[2-[4-(4-Fluorobenzoyl)-1-piperazinyl]-1,1-dimethylethyl]-N'-[3-methoxy-4-(5-oxazolyl)phenyl]oxalamide | 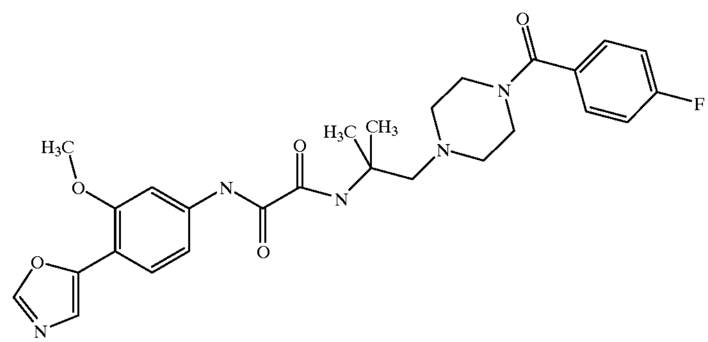 | 524.1 | 509 |
| N-[2-[4-(Cyclopropylcarbonyl)-1-piperazinyl]-1,1-dimethylethyl]-N'-[3-methoxy-4-(5-oxazolyl)phenyl]oxalamide | 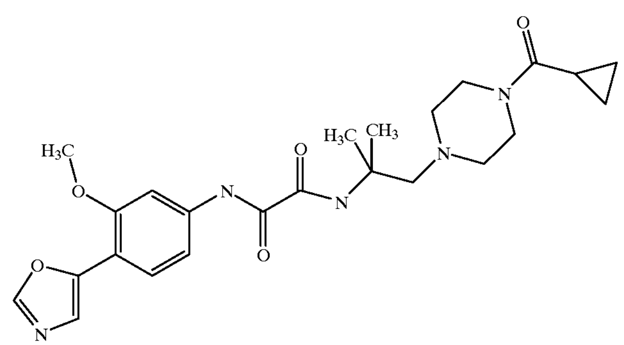 | 470.1 | 510 |
| N-[2-[4-(2-Cyclohexylacetyl)-1-piperazinyl]-1,1-dimethylethyl]-N'-[3-methoxy-4-(5-oxazolyl)phenyl]oxalamide | 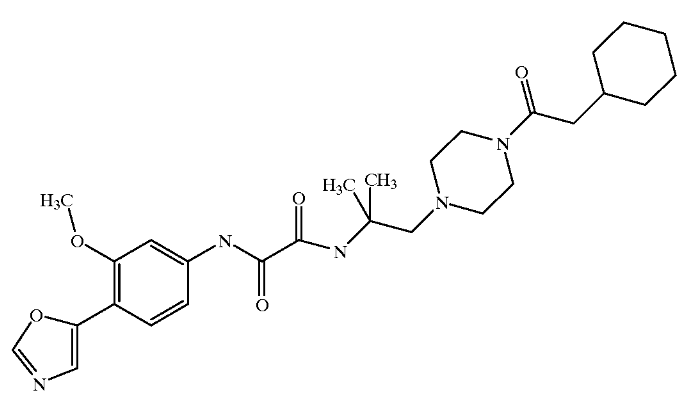 | 526.2 | 511 |

-continued

| Name | Structure | MS(ES) (M + H)+ | Ex No |
|---|---|---|---|
| N-[3-Methoxy-4-(5-oxazolyl)phenyl]-N'-[2-[4-(3,3-dimethylbutyryl)-1-piperazinyl]-1,1-dimethylethyl]oxalamide | 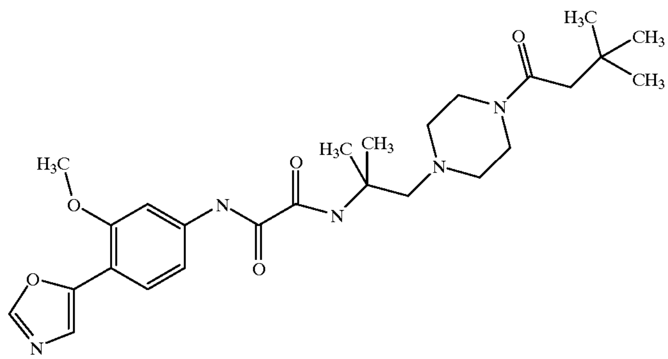 | 500.2 | 512 |
| N-[2-[4-(3-Hydroxy-2,2-dimethylpropionyl)-1-piperazinyl]-1,1-dimethylethyl]-N'-[3-methoxy-4-(5-oxazolyl)phenyl]oxalamide | 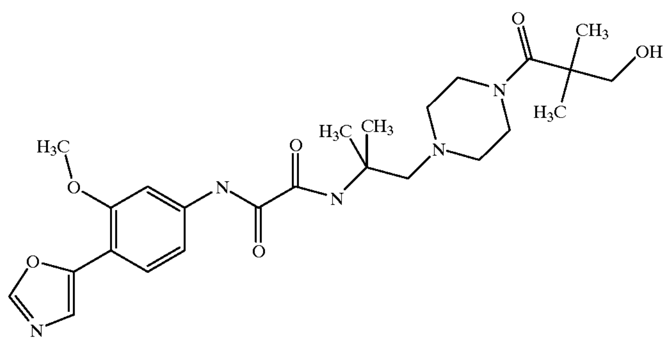 | 502.1 | 513 |
| N-[3-Methoxy-4-(5-oxazolyl)phenyl]-N'-[1,1-dimethyl-2-[4-(3-methyl-2-furoyl)-1-piperazinyl]ethyl]oxalamide | 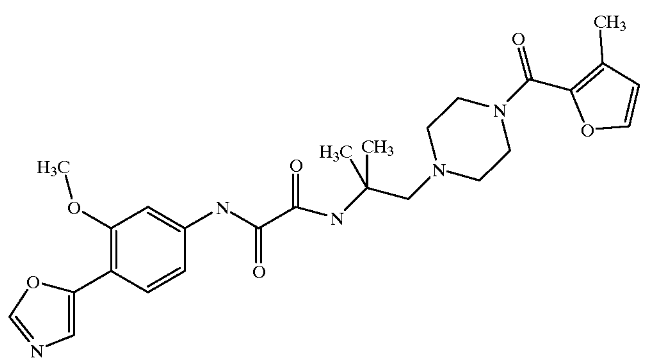 | 510.1 | 514 |
| N-[3-Methoxy-4-(5-oxazolyl)phenyl]-N'-[1,1-dimethyl-2-[4-(2-methyl-3-furoyl)-1-piperazinyl]ethyl]oxalamide | 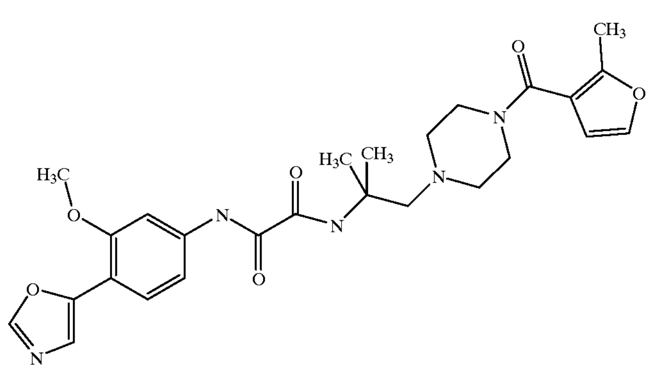 | 510.1 | 515 |

| Name | Structure | MS(ES) (M + H)+ | Ex No |
| --- | --- | --- | --- |
| N-[3-Methoxy-4-(5-oxazolyl)phenyl]-N'-[1,1-dimethyl-2-[4-[(5-methyl-1H-pyrazol-3-yl)carbonyl]-1-piperazinyl]ethyl]oxalamide | 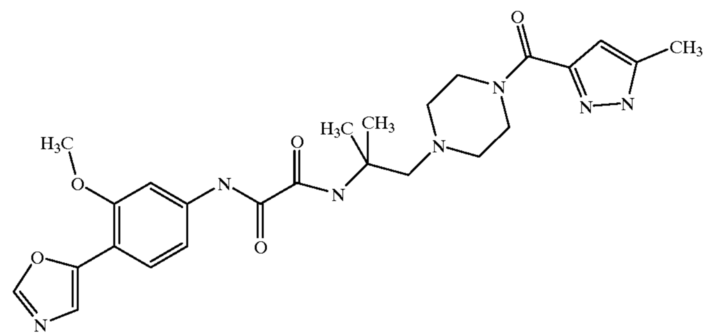 | 510.1 | 516 |
| N-[3-Methoxy-4-(5-oxazolyl)phenyl]-N'-[1,1-dimethyl-2-[4-[(5-methyl-4-isoxazolyl)carbonyl]-1-piperazinyl]ethyl]oxalamide | 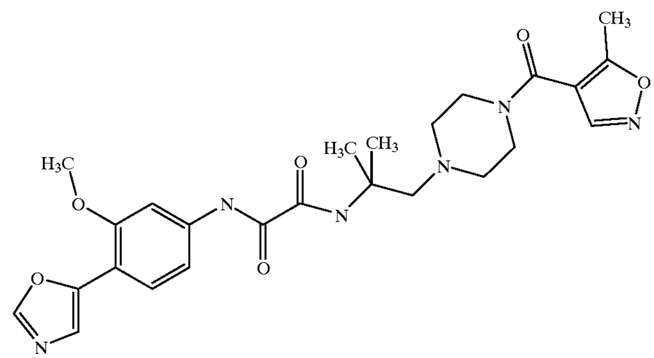 | 511.1 | 517 |
| N-[3-Methoxy-4-(5-oxazolyl)phenyl]-N'-[1,1-dimethyl-2-[4-[(5-methyl-3-isoxazolyl)carbonyl]-1-piperazinyl]ethyl]oxalamide | 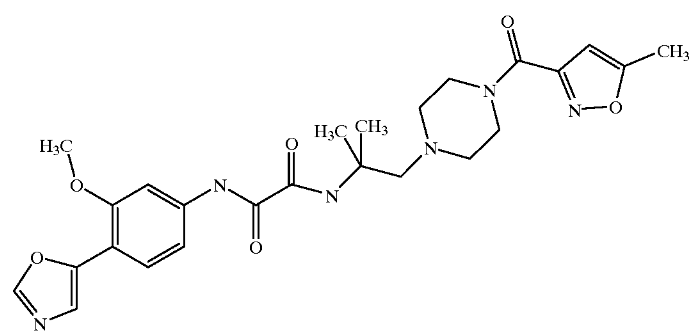 | 511.1 | 518 |
| N-[2-[4-(4-Aminobenzoyl)1-1 piperazinyl]-1,1-dimethylethyl]-N'-[3-methoxy-4-(5-oxazolyl)phenyl]oxalamide | 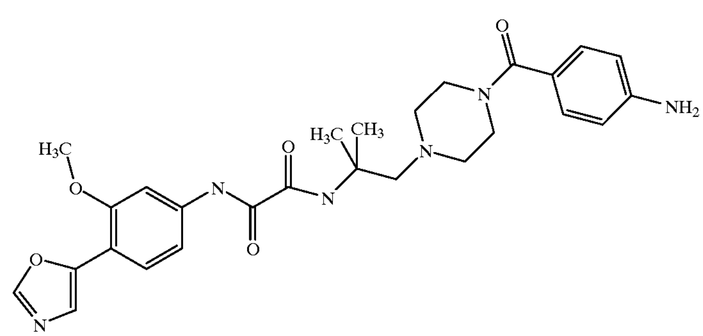 | 521.1 | 519 |

-continued

| Name | Structure | MS(ES) (M + H)+ | Ex No |
|---|---|---|---|
| N-[2-[4-(2-Hydroxybenzoyl)-1-piperazinyl]-1,1-dimethylethyl]-N'-[3-methoxy-4-(5-oxazolyl)phenyl]oxalamide | 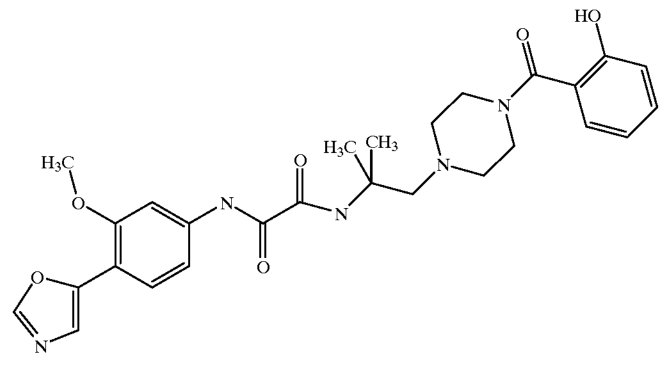 | 522.1 | 520 |
| N-[2-[4-(4-Hydroxybenzoyl)-1-piperazinyl]-1,1-dimethylethyl]-N'-[3-methoxy-4-(5-oxazolyl)phenyl]oxalamide | 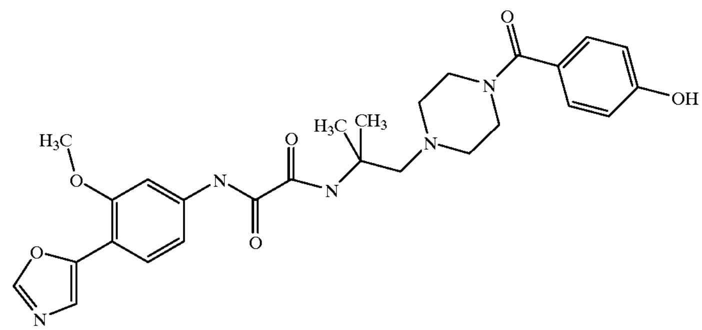 | 522.1 | 521 |
| N-[3-Methoxy-4-(5-oxazolyl)phenyl]-N'-[1,1-dimethyl-2-[4-[(2,5-dimethyl-2H-pyrazol-3-yl)carbonyl]-1-piperazinyl]ethyl]oxalamide | 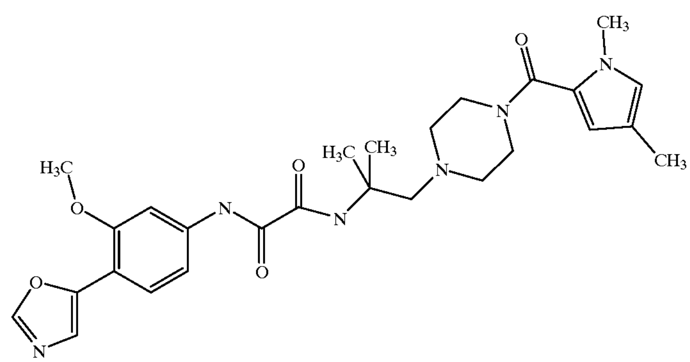 | 524.1 | 522 |
| N-[3-Methoxy-4-(5-oxazolyl)phenyl]-N'-[1,1-dimethyl-2-[4-(3-methyl-2-thenoyl)-1-piperazinyl]ethyl]oxalamide | 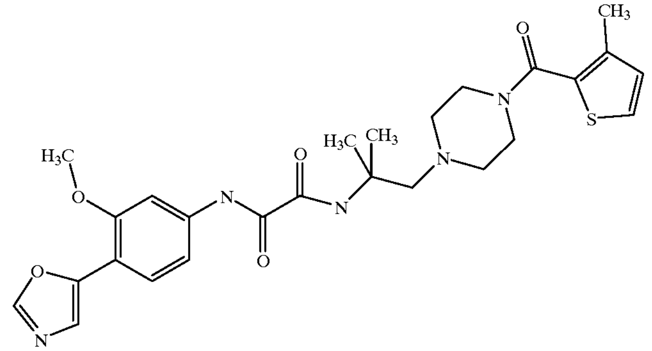 | 526.1 | 523 |

-continued

| Name | Structure | MS(ES) (M + H)+ | Ex No |
|---|---|---|---|
| N-[3-Methoxy-4-(5-oxazolyl)phenyl]-N'-[1,1-dimethyl-2-[4-(4-methyl-2-thenoyl)-1-piperazinyl]ethyl]oxalamide | 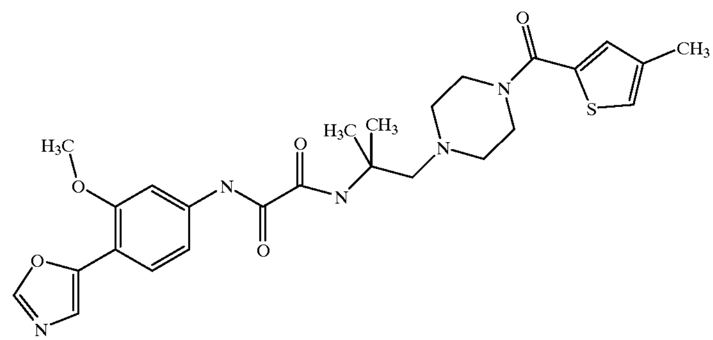 | 526.1 | 524 |
| N-[3-Methoxy-4-(5-oxazolyl)phenyl]-N'-[1,1-dimethyl-2-[4-[(2,2,3,3-tetramethyl-1-cyclopropyl)carbonyl]-1-piperazinyl]ethyl]oxalamide | 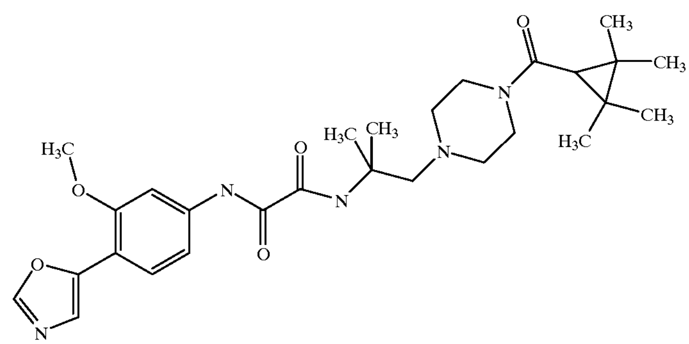 | 526.2 | 525 |
| N-[3-Methoxy-4-(5-oxazolyl)phenyl]-N'-[1,1-dimethyl-2-[4-[(4-methyl-1,2,3-thiadiazol-5-yl)carbonyl]-1-piperazinyl]ethyl]oxalamide | 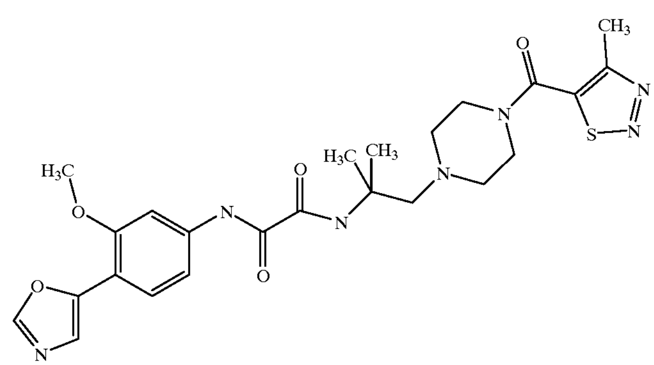 | 528.1 | 526 |
| N-[2-[4-(3-Cyanobenzoyl)-1-piperazinyl]-1,1-dimethylethyl]-N'-[3-methoxy-4-(5-oxazolyl)phenyl]oxalamide | 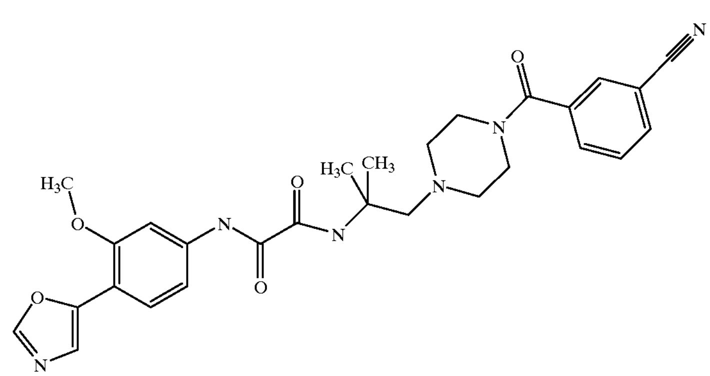 | 531.1 | 527 |

-continued

| Name | Structure | MS(ES) (M + H)+ | Ex No |
|---|---|---|---|
| N-[2-[4-[(Bicyclo[4.2.0]octa-1(6),2,4-trien-7-yl)carbonyl]-1-piperazinyl]-1,1-dimethylethyl]-N'-[3-methoxy-4-(5-oxazolyl)phenyl]oxalamide | 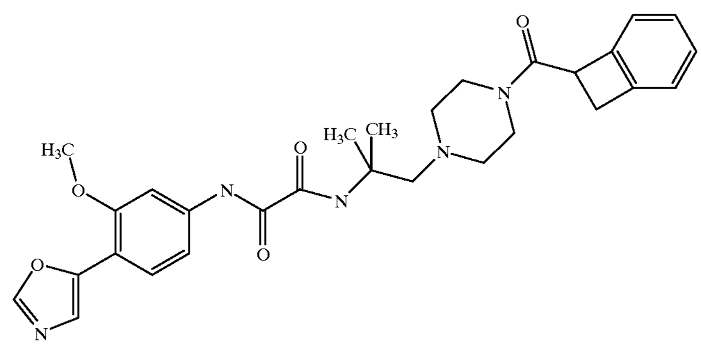 | 532.1 | 528 |
| N-[2-[4-(3-Hydroxybenzoyl)-1-piperazinyl]-1,1-dimethylethyl]-N'-[3-methoxy-4-(5-oxazolyl)phenyl]oxalamide | 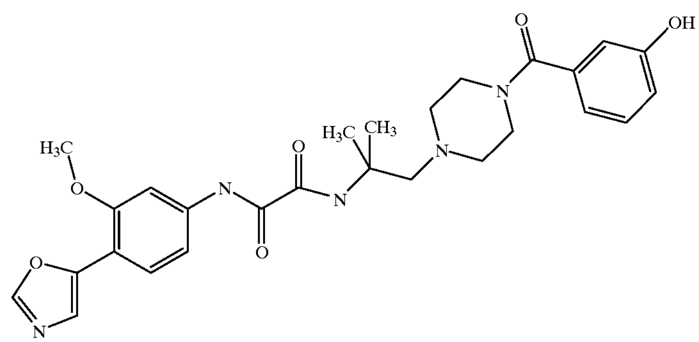 | 522.1 | 529 |
| N-[2-[4-(2-Ethylbutyl)-1-piperazinyl]-1,1-dimethylethyl]-N'-[3-methoxy-4-(5-oxazolyl)phenyl]oxalamide | 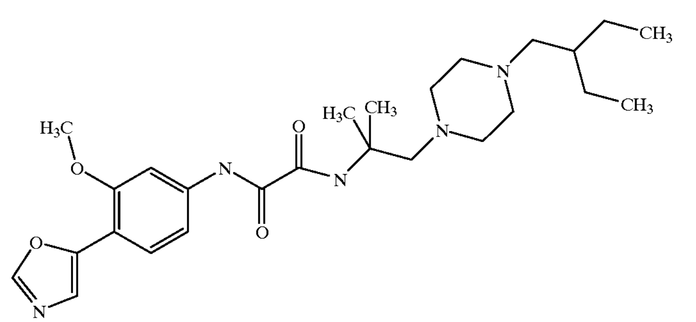 | 486.1 | 530 |
| N-[3-Methoxy-4-(5-oxazolyl)phenyl]-N'-[1,1-dimethyl-2-[4-(2-phenylethyl)-1-piperazinyl]ethyl]oxalamide | 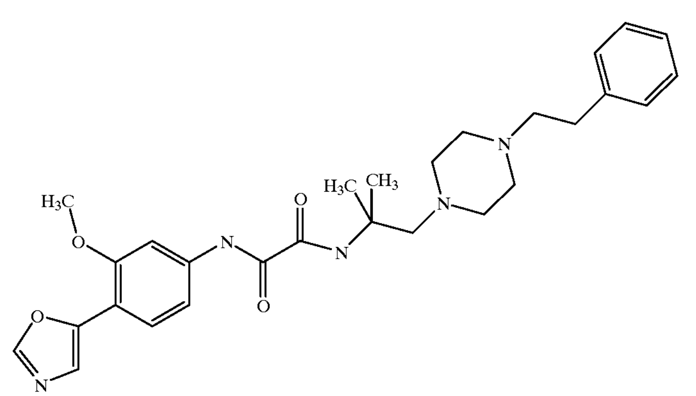 | 506.2 | 531 |

-continued

| Name | Structure | MS(ES) (M + H)+ | Ex No |
|---|---|---|---|
| N-[3-Methoxy-4-(5-oxazolyl)phenyl]-N'-[1,1-dimethyl-2-[4-[3-(methylthio)propyl]-1-piperazinyl]ethyl]oxalamide | 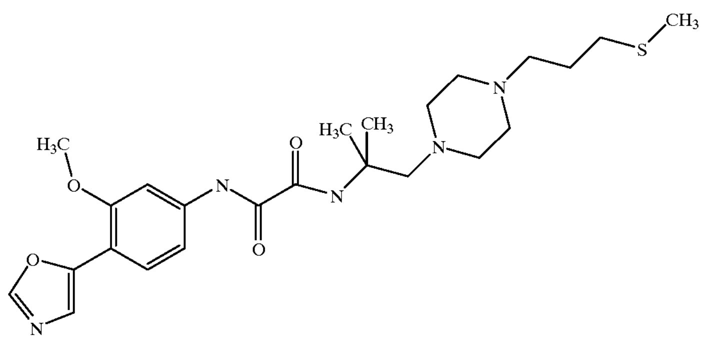 | 490.1 | 532 |
| N-[2-[4-(2,6-Difluorobenzyl)-1-piperazinyl]-1,1-dimethylethyl]-N'-[3-methoxy-4-(5-oxazolyl)phenyl]oxalamide | 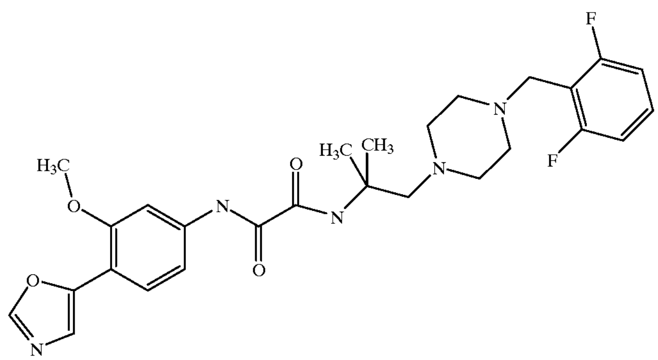 | 528.1 | 533 |
| N-[2-[4-(3-Furfuryl)-1-piperazinyl]-1,1-dimethylethyl]-N'-[3-methoxy-4-(5-oxazolyl)phenyl]oxalamide | 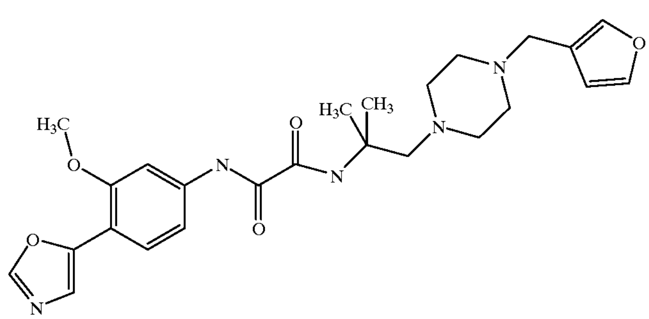 | 482.1 | 534 |
| N-[2-[4-[(2-Benzofuranyl)methyl]-1-piperazinyl]-1,1-dimethylethyl]-N'-[3-methoxy-4-(5-oxazolyl)phenyl)]oxalamide | 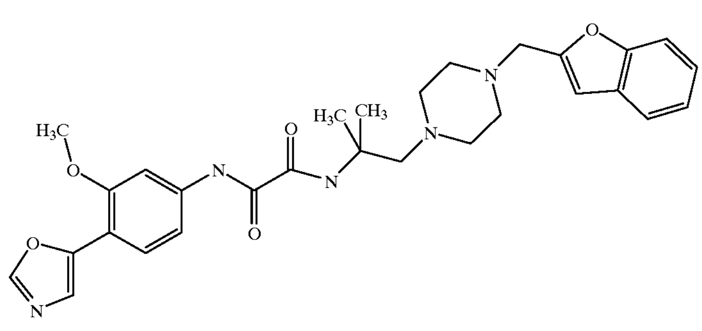 | 532.1 | 535 |

-continued

| Name | Structure | MS(ES) (M + H)+ | Ex No |
|---|---|---|---|
| N-[2-[4-(2-Cyanobenzyl)-1-piperazinyl]-1,1-dimethylethyl]-N'-[3-methoxy-4-(5-oxazolyl)phenyl]oxalamide | 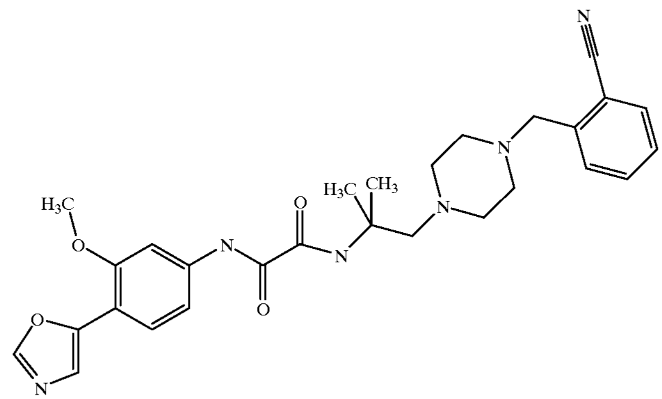 | 517.1 | 536 |
| N-[3-Methoxy-4-(5-oxazolyl)phenyl]-N'-[2-[4-(3,3-dimethylbutyl)-1-piperazinyl]-1,1-dimethylethyl]oxalamide | 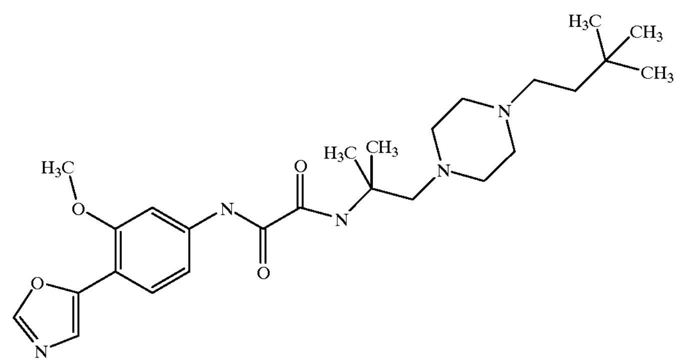 | 486.2 | 537 |
| N-[3-Methoxy-4-(5-oxazolyl)phenyl]-N'-[1,1-dimethyl-2-[4-[(2-quinolinyl)methyl]-1-piperazinyl]ethyl]oxalamide | 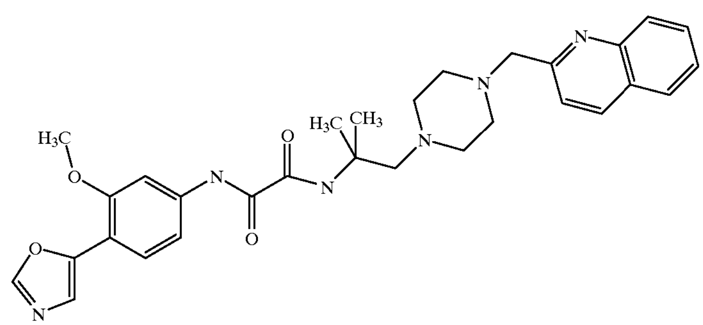 | 543.2 | 538 |
| tert-Butyl 4-[2-[[[3-methoxy-4-(5-oxazolyl)anilino]oxalyl]amino]-2-methylpropyl]-1-piperazineacetate | 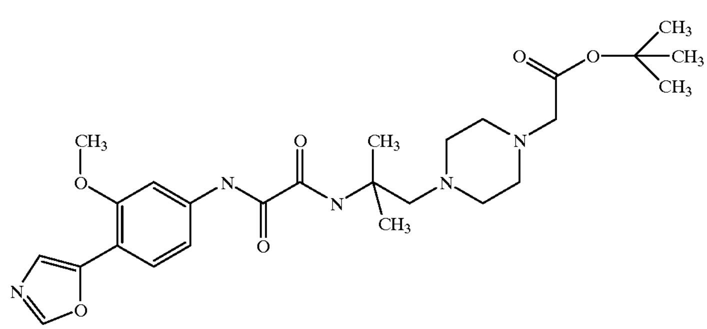 | 516 | 539 |

-continued

| Name | Structure | MS(ES) (M + H)+ | Ex No |
|---|---|---|---|
| 4-[2-[[[3-Methoxy-4-(5-oxazolyl)anilino]oxalyl]amino]-2-methylpropyl]-1-piperazineacetic acid trifluoroacetate (1:1) | 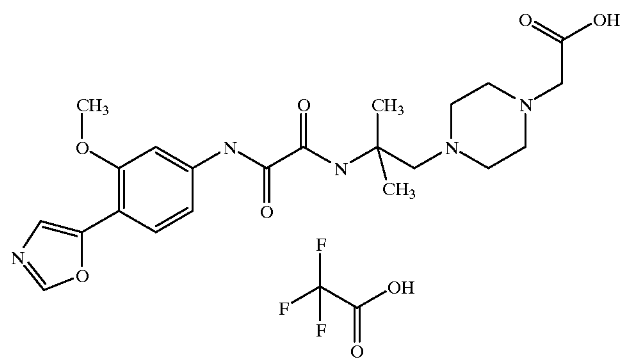 | 460 | 540 |
| N-[2-[4-(Cyclopropylmethyl)-1-piperazinyl]-1,1-dimethylethyl]-N'-[3-methoxy-4-(5-oxazolyl)phenyl]oxalamide | 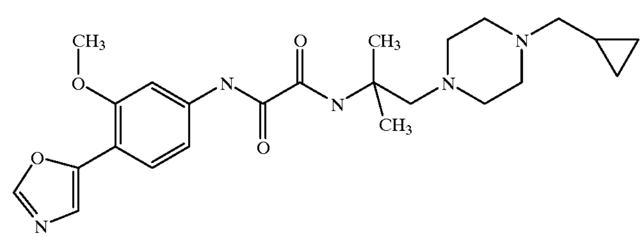 | 456 | 541 |
| tert-Butyl 4-[4-[2-[[[3-methoxy-4-(5-oxazolyl)anilino]oxalyl]amino]-2-methylpropyl]-1-piperazinyl] benzoate | 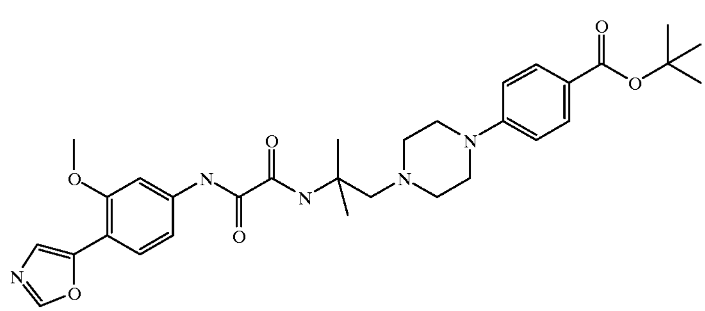 | 578 | 651 |
| 4-[4-[2-[[[3-Methoxy-4-(5-oxazolyl)anilino]oxalyl]amino]-2-methylpropyl]-1-piperazinyl]benzoic acid trifluoroacetate (1:1) | 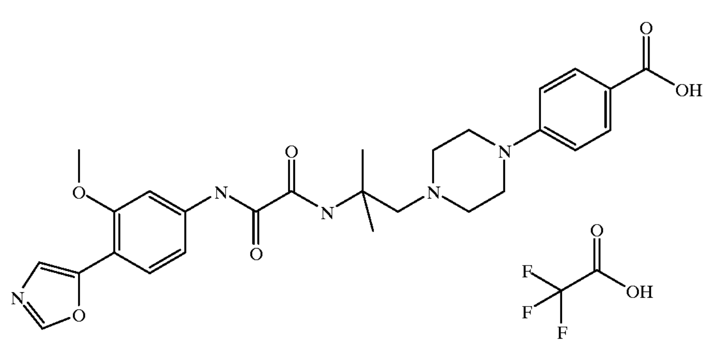 | 522 | 652 |

In particular preferred compounds of formula (I) and formula (IX) are also those of the general formula

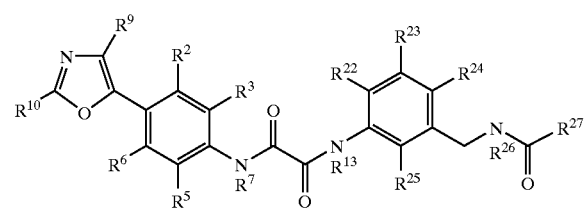

XVI wherein $R^2$, $R^3$, $R^5$, $R^6$, $R^7$, $R^9$, $R^{10}$ and $R^{13}$ are defined as above, $R^{22}$, $R^{23}$, $R^{24}$, $R^{25}$ and $R^{26}$ are H or lower alkyl, $R^{27}$ is alkyl, aryl or heterocyclyl, alkoxy, aryloxy, heterocyclyl oxy, especially aryl or aryloxy.

Particularly preferred compounds of formula (XVI) are those wherein $R^2$ is methoxy, $R^3$, $R^5$, $R^6$, $R^9$, $R^{10}$, $R^{13}$, $R^{22}$, $R^{23}$, $R^{24}$, $R^{25}$ and $R^{26}$ are hydrogen.

Examples of such compounds are listed in table 1h below:

| Name | Structure | ME(ES) (M + H)+ | Ex No |
|---|---|---|---|
| Phenyl [3-[[[4-(5-oxazolyl)anilino]oxalyl]amino]benzyl] carbamate | 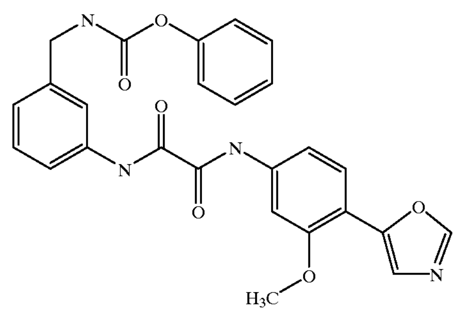 | 487 | 415 |
| N-[3-[(3-Fluorobenzamido)methyl]phenyl]-N'-[3-methoxy-4-(5-oxazolyl)phenyl]oxalamide | 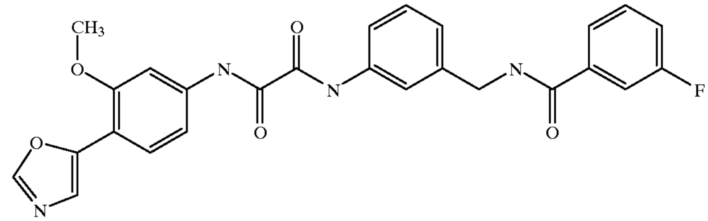 | 489 | 416 |
| N-[3-[(3-Chlorobenzamido)methyl]phenyl]-N'-[3-methoxy-4-(5-oxazolyl)phenyl]oxalamide | 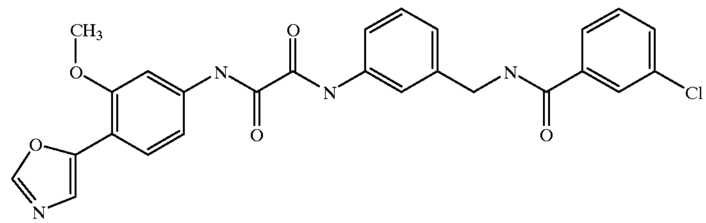 | 505 | 417 |
| N-[3-[(3-Methoxybenzamido)methyl]phenyl]-N'-[3-methoxy-4-(5-oxazolyl)phenyl]oxalamide | 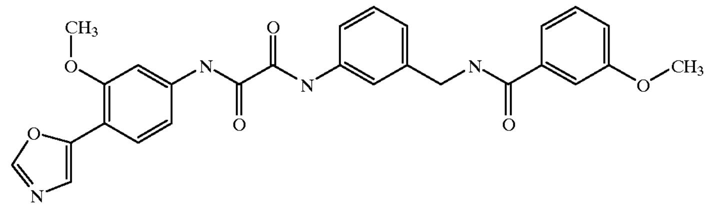 | 501.2 | 418 |

| Name | Structure | ME(ES) (M + H)+ | Ex No |
|---|---|---|---|
| N-[3-[(3,4-Dimethoxybenzamido)methyl]phenyl]-N'-[3-methoxy-4-(5-oxazolyl)phenyl]oxalamide | 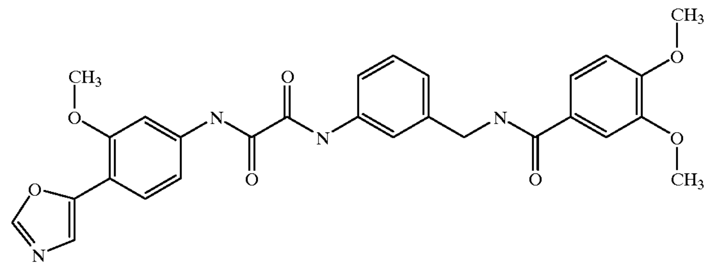 | 531.2 | 419 |
| N-[3-[(3-Cyanobenzamido)methyl]phenyl]-N'-[3-methoxy-4-(5-oxazolyl)phenyl]oxalamide | 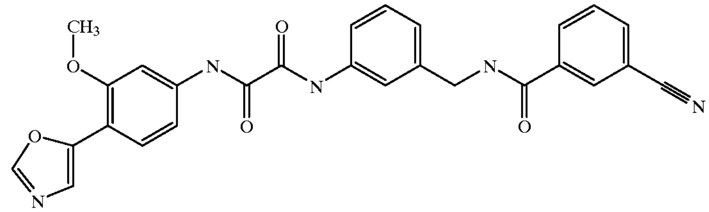 | 496.1 | 420 |

In particular preferred compounds of formula (I) or formula (IX) are also those of the general formula

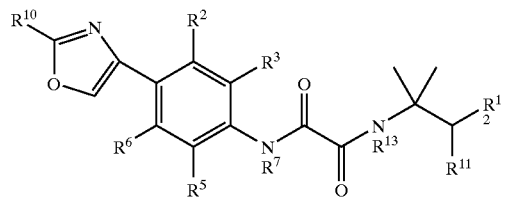

XVII wherein $R^2$, $R^3$, $R^5$, $R^6$, $R^7$ and $R^{10}$ are defined as above; $R^{11}$ and $R^{13}$ is H or lower alkyl and $R^{12}$ is heterocyclyl, aryl or lower cycloalkyl.

Particularly, preferred compounds of formula (XVII) are those wherein $R^2$ is methoxy, $R^3$, $R^5$, $R^6$, $R^9$, $R^{10}$, $R^{11}$ and $R^{13}$ are hydrogen and wherein $R^{12}$ is phenyl or

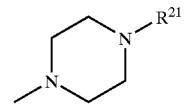

wherein $R^{21}$ is as above.

Examples of such compounds are listed in table 1i below:

| Name | Structure | MS(ES) (M + H)+ | Ex No |
|---|---|---|---|
| N-[3-Methoxy-4-(4-oxazolyl)phenyl]-N'-[1,1-dimethyl-2-(4-phenyl-1-piperazinyl)ethyl]oxalamide | 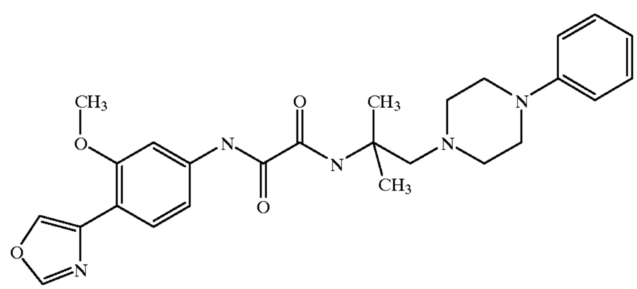 | 478 | 428 |
| N-[2-(4-Benzyloxyphenyl)-1,1-dimethylethyl]-N'-[3-methoxy-4-(4-oxazolyl)phenyl]oxalamide | 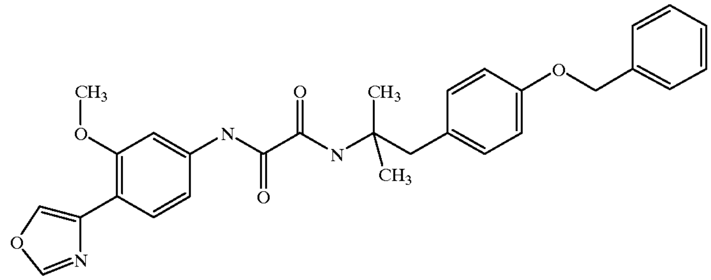 | 500 | 429 |

-continued

| Name | Structure | MS(ES) (M + H)+ | Ex No |
|---|---|---|---|
| N-[2-(4-Hydroxyphenyl)-1,1-dimethylethyl]-N'-[3-methoxy-4-(4-oxazolyl)phenyl]oxalamide | 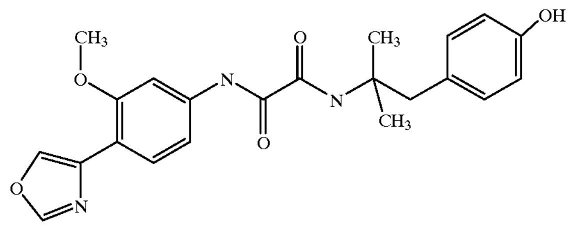 | 410 | 430 |
| N-[3-Methoxy-4-(4-oxazolyl)phenyl]-N'- [2-[4-(4-methoxyphenyl)-1-piperazinyl]-1,1-dimethylethyl]oxalamide | 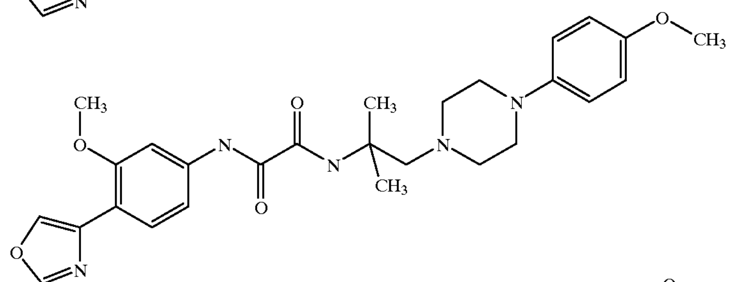 | 508 | 431 |
| N-[3-Methoxy-4-(2-methyl-4-oxazolyl)-phenyl]-N'-[2-[4-(4-methoxyphenyl)-1-piperazinyl]-1,1-dimethylethyl]oxalamide | 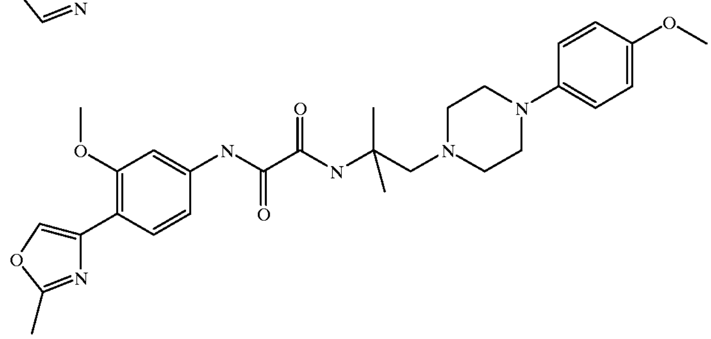 | 522.4 | 432 |

The compounds of formula (IV) and (VIII) which are intermediates in the foregoing processes are novel and are also provided by the present invention.

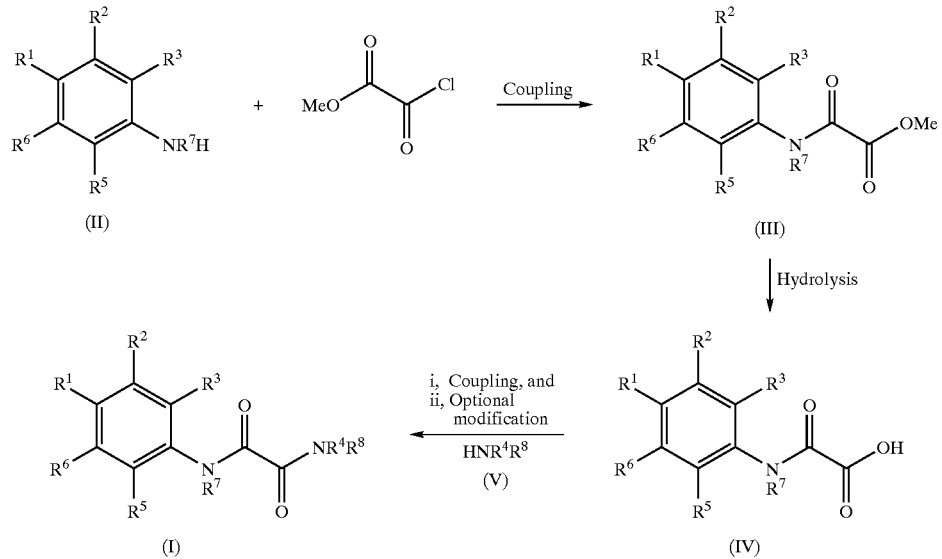

Reaction Scheme A

With reference to Reaction Scheme A, the first step comprises the coupling of a compound of formula (II) with an activated oxalyl derivative, such as methyl chlorooxoacetate, to give a compound of formula (III). The reaction may be carried out in a conventional manner, suitably in an organic solvent which is inert under the reaction conditions and in the presence of an organic base at about 0° C. to about room temperature. Suitable solvents include halogenated hydrocarbons, e.g. dichloromethane. Pyridine and tri(lower alkyl)amines, e.g. triethylamine, can be mentioned as examples of suitable organic bases which can be used.

Subsequent hydrolysis of the compound of formula (III) to give the acid compound of formula (IV) may be carried out by treatment with a solution of an alkali metal hydroxide, such as sodium hydroxide, in a suitable solvent system, such as aqueous methanol.

Alternatively, a compound of formula (II) may be coupled with tert.butyl chlorooxoacetate, followed by treatment with acid to remove the tert.butyl group, to give a compound of formula (IV).

The compound of formula (IV) is then coupled with an amine compound of formula (V) using standard peptide coupling reagents, such as hydroxybenzotriazole in the presence of 1-ethyl-3-(3-dimethylaminopropyl) carbodiimide hydrochloride, to give the oxamide compound of formula (I).

After this coupling step, the R groups of the resulting compound may be further modified by techniques known in the art, for example, functional groups may be altered, and/or connected to further groups ment with acid to remove the tert.butyl group, to give a compound of formula (VIII).

The compound of formula (VIII) is then coupled with an amine compound of formula (V) to give the oxamide compound of formula (IX), under the conditions described above for the coupling of a compound of formula (IV) with a compound of formula (V).

After this coupling step, the R groups of the resulting compound may be further modified by techniques known in the art, for example, functional groups may be altered, and/or connected to further groups Reaction Scheme C

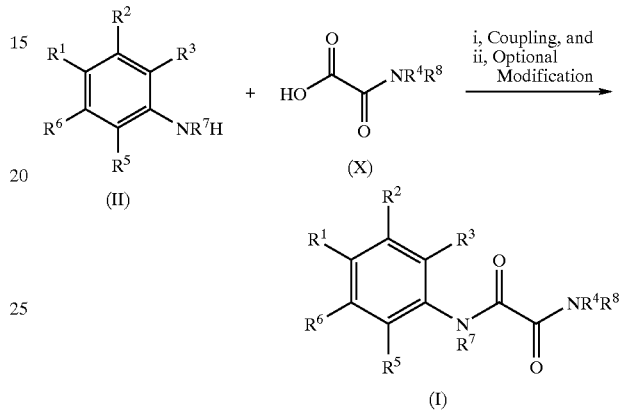

Alternatively, compounds of formula (I) are made by the coupling of a compound of formula (II) with an oxalamic Reaction Scheme B

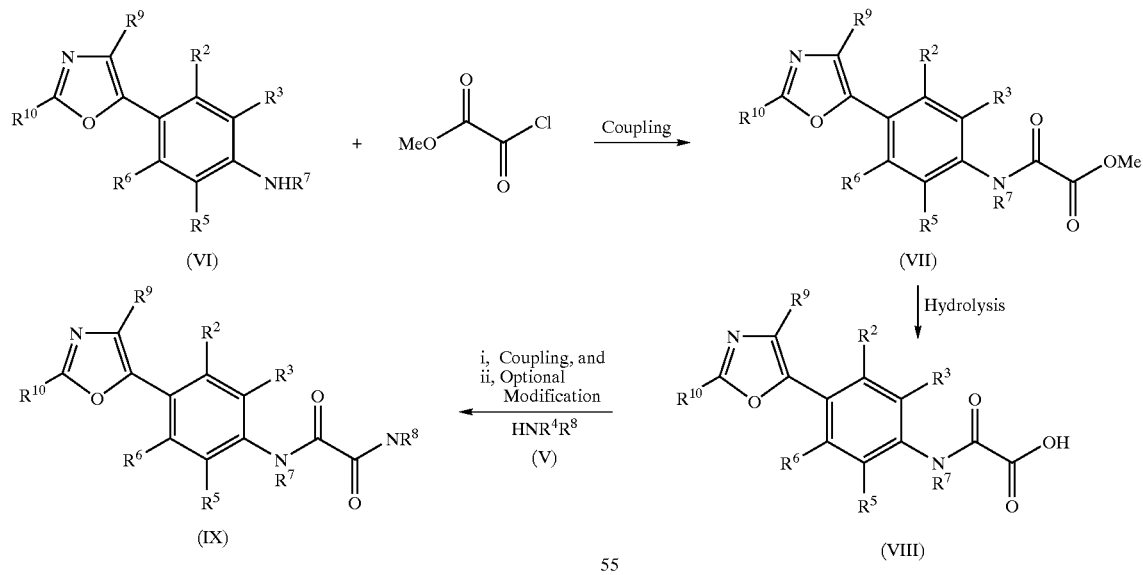

Referring to Reaction Scheme B, the first step comprises the coupling of a compound of formula (VI) with an activated oxalyl derivative, such as methyl chlorooxoacetate, to give a compound of formula (VII). The reaction is carried out in the manner described above for the formation of a compound of formula (III) from a compound of formula (II).

Subsequent hydrolysis of the compound of formula (VII) to give the acid compound of formula (VIII) is then carried out as described above for the hydrolysis of a compound of formula (III).

Alternatively, a compound of formula (VI) may be coupled with tert.butyl chlorooxoacetate, followed by treatacid compound of formula (X), using standard peptide coupling reagents, such as hydroxybenzotriazole in the presence of 1-ethyl-3-(3-dimethylaminopropyl) carbodiimide hydrochloride, to give the oxamide compound of formula (I).

After this coupling step, the R groups of the resulting compound may be further modified by techniques known in the art, for example, functional groups may be altered, and/or connected to further groups As mentioned above, the compounds of formula (I) and salts thereof are inhibitors of IMPDH enzyme both in vitro and in vivo, and can be used in the control or prevention of IMPDH mediated conditions or diseases.

IMPDH activity can be assayed using an adaptation of the method reported by Carr [S. Carr et al., J. Biol. Chem. 268, p.27286 (1993)], the disclosure of which is herein incorporated by reference. IMPDH activity was measured spectrophotometrically, by monitoring the increase in absorbance at 340 nm due to the formation of NADH ($\epsilon$340 is 6220 M−1 cm−1) from the reduction of NAD. The IMPDH reaction mixture contained 0.1M Tris pH8.0, 0.1M KCl, 1 mM DTT, 3 mM EDTA, 100 mM IMP and 100 mM NAD. The reaction was initiated by the addition of IMPDH (human type II) to a final concentration in the assay of between 1 nM and 5 nM with respect to the IMPDH tetramer. The initial rate is measured by following the linear increase in absorbance at 340 nm at 37° C. for 45 minutes.

The reading was conducted using a Spectromax 190 (Molecular Devices) spectrophotometer in a 96 well plate format with a final reaction volume of 200 $\mu$l.

For inhibitor assay analysis, the compound is dissolved in DMSO to a final concentration of 10 mM and added to the initial reaction mixture as 5 $\mu$l to give final DMSO concentration of 2.5%. The enzyme reaction is initiated by the addition of IMPDH and the initial rates measured as above. $IC_{50}$ determinations are made by measuring the initial rates in the presence of 10 concentrations of inhibitor and fitting the data using the 4 parameter curve fit from the Softmax pro software (Molecular Devices).

Preferred compounds of the invention tested in the above assay have an $IC_{50}$ value up to 500 nM i.e. 0.5 $\mu$M.

Specific examples of $IC_{50}$ values for preferred compounds of formula (I) are set out below in Table 2:

TABLE 2

| Compound of Formula (I) | | $IC_{50}$ ($\mu$M) |
|---|---|---|
| 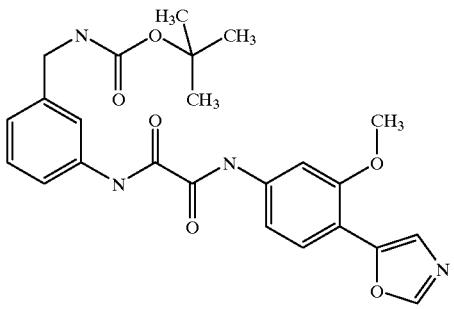 | tert-Butyl [3-[[[3-methoxy-4-(5-oxazolyl)anilino]oxalyl]amino]benzyl]carbamate | 0.036 |
| 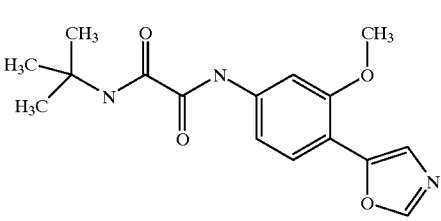 | N-tert-Butyl-N'-[3-methoxy-4-(5-oxazolyl)phenyl]oxalamide | 0.037 |
| 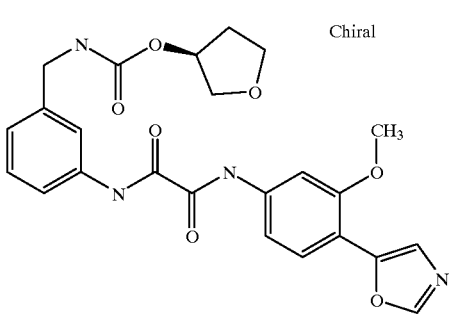 Chiral | [3-[[[3-Methoxy-4-(5-oxazolyl)anilino]oxalyl]amino]benzyl]carbamic acid tetrahydro-3(S)-furyl ester | 0.044 |

TABLE 2-continued

| Compound of Formula (I) | | IC$_{50}$ ($\mu$M) |
|---|---|---|
| | N-[3-(Benzamidomethyl)phenyl]-N'-[3-methoxy-4-(5-oxazolyl)phenyl]oxalamide | 0.013 |
| | Isopropyl [3-[[[3-methoxy-4-(5-oxazolyl)anilino]oxalyl]amino]benzyl]carbamate | 0.033 |
| | N-[3-Methoxy-4-(5-oxazolyl)phenyl]-N'-(1-methyl-1-phenylethyl)oxalamide | 0.03 |
| | N-(1,1-Dimethylpropyl)-N'-[3-methoxy-4-(5-oxazolyl)phenyl]oxalamide | 0.031 |
| | N-[3-Methoxy-4-(5-oxazolyl)phenyl]-N'-(1,1,3,3-tetramethyl-butyl)oxalamide | 0.034 |
| | N-(1,1-Dimethylpropargyl)-N'-[3-methoxy-4-(5-oxazolyl)phenyl]oxalamide | 0.048 |

TABLE 2-continued

| Compound of Formula (I) | IC$_{50}$ ($\mu$M) |
|---|---|
| N-(2-Hydroxy-1,1-dimethylethyl)-N'-[3-methoxy-4-(5-oxazolyl)phenyl]oxalamide | 0.072 |
| N-(1,1-Dimethyl-2-phenylethyl)-N'-[3-methoxy-4-(5-oxazolyl)phenyl]oxalamide | 0.015 |
| Phenyl [3-[[[4-(5-oxazolyl)anilino]oxalyl]amino]benzyl]carbamate | 0.011 |
| N-[3-Methoxy-4-(5-oxazolyl)phenyl]-N'-[3-[(phenylcarbamoyl)methyl]phenyl]oxalamide | 0.035 |
| tert-Butyl [2-[[[3-methoxy-4-(5-oxazolyl)anilino]oxalyl]amino]-2-methylpropyl]carbamate | 0.075 |
| N-(2-Amino-1,1-dimethylethyl)-N'-[3-methoxy-4-(5-oxazolyl)kphenyl]oxalamide trifluoroacetate (1:1) | 0.097 |

TABLE 2-continued

| Compound of Formula (I) | | IC$_{50}$ ($\mu$M) |
|---|---|---|
| | N-[3-Methoxy-4-(5-oxazolyl)phenyl]-N'-[1,1-dimethyl-2-(4-nitrophenyl)ethyl]oxalamide | 0.010 |
| | N-[3-(Aminomethyl)phenyl]-N'-[3-methoxy-4-(5-oxazolyl)phenyl]oxalamide trifluoroacetate (1:1) | 0.233 |
| | Methyl [3-[[[3-methoxy-4-(5-oxazolyl)anilino]oxalyl]amino]benzyl]carbamate | 0.121 |
| | N-[3-Methoxy-4-(5-oxazolyl)phenyl]-N'-(3-pyridyl)oxalamide | 0.277 |
| | N-[3-[(Benzenesulfonamido)methyl]phenyl]-N'-[3-methoxy-4-(5-oxazolyl)phenyl]oxalamide | 0.125 |

TABLE 2-continued

| Compound of Formula (I) | | IC$_{50}$ ($\mu$M) |
|---|---|---|
| [structure] | N-(2-Dimethylamino-1,1-dimethylethyl)-N'-[3-methoxy-4-(5-oxazolyl)phenyl]oxalamide hydrochloride (1:1) | 0.17 |
| [structure] | N-[3-Methoxy-4-(5-oxazolyl)phenyl]-N'-[1-methyl-1-(methylcarbamoyl)ethyl]oxalamide | 0.199 |
| [structure] | N-tert-Butyl-N'-[3-chloro-4-(5-oxazolyl)phenyl]oxalamide | 0.169 |
| [structure] | N-tert-Butyl-N'-[3-methoxy-4-(4-oxazolyl)phenyl]oxalamide | 0.46 |

Compounds of formula (I) which are acidic can form pharmaceutically acceptable salts with bases such as alkali metal hydroxides, e.g. sodium hydroxide and potassium hydroxide; alkaline earth metal hydroxides, e.g. calcium hydroxide, barium hydroxide and magnesium hydroxide, and the like; with organic bases e.g. N-ethyl piperidine, dibenzylamine, and the like. Those compounds of formula (I) which are basic can form pharmaceutically acceptable salts with inorganic acids, e.g. with hydrohalic acids such as hydrochloric acid and hydrobromic acid, sulphuric acid, nitric acid and phosphoric acid, and the like, and with organic acids, e.g. with acetic acid, tartaric acid, succinic acid, fumaric acid, maleic acid, malic acid, salicylic acid, citric acid, methanesulphonic acid and p-toluene sulphonic acid, and the like. The formation and isolation of such salts can be carried out according to methods known in the art.

The oxamide derivatives provided by the present invention (i.e. the compounds of formula (I) and their pharmaceutically acceptable salts, especially as depicted in all the formulae herein), can be used as medicaments, for example in the form of pharmaceutical preparations. The pharmaceutical preparations can be administered enterally, such as orally, in the form of tablets, coated tablets, dragées, hard and soft gelatine capsules, solutions, emulsions or suspensions, or nasally, e.g. in the form of nasal sprays. They can also be administered rectally, e.g. in the form of suppositories, or parenterally, (e.g. intramuscularly, intravenously, or subcutaneously), for example, in the form of injection solutions.

For the manufacture of pharmaceutical preparations the oxamide derivatives can be formulated with therapeutically inert, inorganic or organic carriers. Lactose, corn starch or derivatives thereof, talc, stearic acid or its salts can be used, for example, as such carriers for tablets, coated tablets, dragées and hard gelatine capsules. Suitable carriers for soft gelatine capsules are, for example, vegetable oils, waxes, fats, semi-solid and liquid polyols and the like. Depending on the nature of the active ingredient no carriers are, however, generally required in the case of soft gelatine capsules. Suitable carriers for the manufacture of solutions and syrups are, for example, water, polyols, sucrose, saccharose, invert sugar, glucose and the like. Suitable carriers for the manufacture of injection solutions are, for example, water, saline, alcohols, polyols, glycerine, vegetable oils and the like. Natural or hardened oils, waxes, fats, semi-liquid or liquid polyols and the like are suitable carriers for the manufacture of suppositories. The pharmaceutical preparations of the present invention may also be provided as sustained release formulations or other appropriate formulations.

The pharmaceutical preparations can also contain preservatives, solubilizers, stabilizers, wetting agents, emulsifiers, sweeteners, colourants, flavourants, salts for adjustment of the osmotic pressure, buffers, masking agents or antioxidants. They may also contain other therapeutically active substances, such as an immunosuppressant, a chemotherapeutic agent, an anti-viral agent, an antibiotic, an anti-parasitic agent, an anti-fungal agent, an anti-inflammatory agent and/or an anti-vascular hyperproliferation agent. A preferred agent that may be used with the compounds of the present invention is interferon or derivatives thereof, such as conjugates with polyethylene glycol.

Accordingly part of this invention is a pharmaceutical composition comprising a compound of formula (I) or its pharmaceutically acceptable salt and a pharmaceutically acceptable carrier, and, optionally, one or more additional therapeutically active substance(s). Such substances may be one or more immunosuppressants, chemotherapeutic agents, antivirals, antibiotic, antiparasitics, antifungals, antiinflammatories, or antivascular antiproliferation agents. Preferably the substance is interferon or an interferon derivative.

Medicaments containing compounds of formula (I) or salts thereof and a therapeutically acceptable carrier, as well as a process for the manufacture of such medicaments are also objects of the present invention. This process comprises bringing a compound of formula (I) or a pharmaceutically acceptable salt thereof into a galenical administration form together with a therapeutically inert carrier material and, if desired, one or more additional therapeutically active substances.

A further object of the invention comprises the use of the oxamide derivatives provided by the invention in the treatment of an immune mediated condition or disease, a viral disease, a bacterial disease, a parasitic disease, inflammation, an inflammatory disease, a hyperproliferative vascular disease, a tumour, or cancer. The dosage can vary within wide limits and will, of course, be adjusted to the individual requirements in each particular case. Dosage levels of between about 0.01 and about 100 mg/kg body weight per day (preferably 0.5–75 mg/kg/day) in monotherapy and/or in combination therapy are preferred, administered from about 1–5 times per day. The active ingredient may be combined with a carrier material. A typical preparation will contain from about 5%–95% active compound (w/w) (preferably from about 20%–80% active compound). The daily dosage can be administered as a single dosage or in divided dosages.

Accordingly this invention is also directed to a method for treating an immune mediated condition or disease, a viral, bacterial, parasitic, inflammatory ,hyperproliferative vascular disease, inflammation, a tumor, or cancer in a subject by administering to the subject a therapeutically effective amount of a compound of formula (I) or its pharmaceutically acceptable salts. In addition, this method includes concurrent or sequential administration of one or more therapeutically active substances taken from immunosuppressants, chemotherapeutics, antivirals, antibiotics, antiparasitics, antifungals, antiinflammatories, and anti-vascular hyperproliferation agents. Preferably the substance is interferon or an interferon derivative.

This invention is especially directed to a method for treating IMPDH mediated diseases.

The compounds and compositions of the present invention may be for use in monotherapy and/or combination therapy, i.e. the treatment may be in conjunction with the administration of one or more additional therapeutically active substance(s). When the treatment is combination therapy, such adminstration may be concurrent or sequential with respect to that of the oxamide derivatives of the present invention. Thus, concurrent administration, as used herein, includes administration of the agents in conjunction or combination, together, or before or after each other.

It will be understood that references herein to treatment extend to prophylaxis as well as to treatment of existing conditions. Treatment of a disease or condition, as used herein, also includes preventing, inhibiting, regressing, reversing, alleviating or relieving the disease or condition, or the clinical symptoms thereof. The term "subject" as used herein refers to animals, including humans and other mammals.

The following Examples illustrate the present invention.

With regard to the starting materials that are known compounds some of these may be purchased from commercial suppliers. Other starting materials that are known and their analogues can be prepared by methods well known in the art. Examples of compounds available from commercial suppliers, and citations to the synthesis of other compounds and their analogues are provided in the following:

Compounds of formula (II) and the compounds of formula (VI) are obtained from commercial suppliers (e.g. 4-(5-oxazolyl)aniline, Maybridge catalogue number DFP 00120), or prepared by adaptation of the methods disclosed in published patent application WO 974002, or prepared by adaptation of the methods provided in Palacz et al., FEBS Lett., 1984, 176(2), 365–370.

The compounds of formula (V) are obtained from commercial suppliers (e.g. tert-butylamine, Aldrich catalogue number B8,920-5; Cumylamine, TCI-US catalogue number C1293), or prepared by adaptation of the methods provided in Kazuo Achiwa et al., Chem.Pharm.Bull., 1998, 46(4), 697–670.

The compounds of formula (X) are prepared by adaptation of the methods provided in Minisci et al., J. Org. Chem., 1995, 60(17), 5430–5433.

Examples of commercially available reagents include those used in Examples 7, 10 and 11, (2-methoxy-4-nitrobenzoic acid, Aldrich catalogue number 42,291-6; tert-butylacetic acid, Aldrich catalogue number B8,840-3; and p-tolualdehyde, Aldrich catalogue number T3,560-2, respectively).

Where indicated, the NMR spectra were recorded on a Bruker DRX 400 MHz spectrometer with the probe temperature set at 300 K.

Where indicated by "(M+;EI)", mass spectra were recorded under electron impact conditions (EI), on a THERMOQUEST MAT95 S with a source temperature of 200° C. Other mass spectra were recorded under electrospray ionisation spectra (ESI) conditions, on one of the following machines:

a) THERMOQUEST SSQ 7000 [Solvent 0.085% TFA in 90% Acetonitrile/water; flow rate 100 microliters/minute; capillary 250° C.; spray voltage 5 KV; sheath gas 80 psi], or b) LC-MS system (liquid chromatograph coupled to mass spectrum) THERMOQUEST TSQ 7000 ELECTROSPRAY or MICROMASS PLATFORM ELECTROSPRAY [Solvent 0.1% TFA in water or 0.085% TFA in 90% acetonitrile/water or 0.085% TFA in acetonitrile].

Unless otherwise indicated, the mass spectroscopy values recorded in the MS(ES) column refer to $(M+H)^+$ values, apart from the ones shown as $(M^+;EI)$.

EXAMPLE 1

N-Tert-butyl-N'-[3-methoxy-4-(5-oxazolyl)phenyl]oxalamide

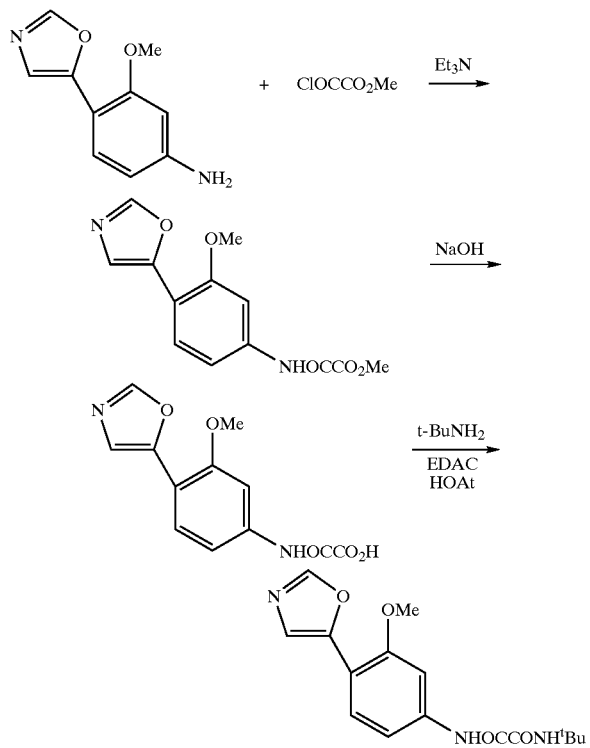

EXAMPLE 1, Alternative Synthesis

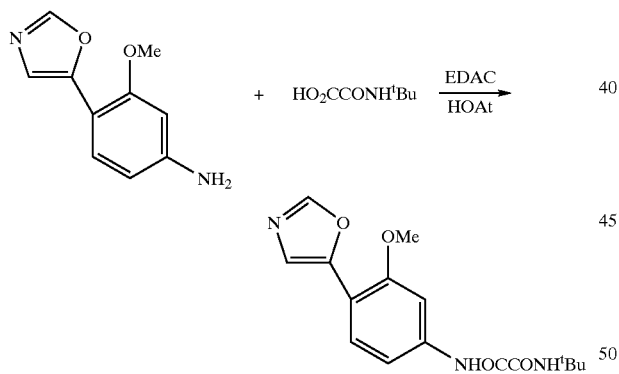

A solution of 26 mg (0.1 mmol) of N-[3-methoxy-4-(5-oxazolyl)phenyl]oxalamic acid, 15 mg (0.2 mmol) of tertiary butylamine, 28 mg (0.15 mmol) of 1-(3-dimethylaminopropyl)-3-ethylcarbodiimide hydrochloride and 15 mg (0.11 mmol) of 1-hydroxy-7-azabenzotriazole in 1 ml of dimethylformamide was stirred at room temperature for 4 hours then diluted with ethyl acetate and washed with 2M hydrochloric acid, saturated sodium bicarbonate and water. The resulting solution was dried over magnesium sulphate and evaporated to dryness. The residue was triturated with diethyl ether/petrol (1:1) and collected by filtration to give 11 mg of N-tert-butyl-N'-[3-methoxy-4-(5-oxazolyl)phenyl]oxalamide as a white solid. MS: m/e 318.0 [M+H]$^+$.

The starting material was prepared as follows:

i) 5.7 g (30 mmol) of 3-methoxy-4-(5-oxazolyl)aniline and 3.33 g (33 mmol) of triethylamine were dissolved in 50 ml of dichloromethane and the solution was cooled to 0° C. A solution of 3.86 g (31.5 mmol) of methyl oxalyl chloride in 10 ml of dichloromethane was added dropwise and the resulting mixture was stirred for 1 hour then washed with 2M hydrochloric acid. The precipitated solid was collected by filtration and washed with dichloromethane and water to give 6.2 of methyl N-[3-methoxy-4-(5-oxazolyl)phenyl]oxalamate as a yellow solid. $^1$H NMR (400 MHz, DMSO-d$_6$) δ: 3.88 (3H,s), 3.94 (3H,s), 7.48 (1H,s), 7.58 (1H,dd), 7.65 (1H,d), 7.68 (1H,d)), 8.39 (1H,s), 10.92 (1H,s).

ii) 6.2 g (22.46 mmol) of methyl N-[3-methoxy-4-(5-oxazolyl)phenyl]oxalamate and 1.2 g (30 mmol) of sodium hydroxide were refluxed in 240 ml of methanol/water (1:1) for 2 hours then cooled, filtered and acidified with 2M hydrochloric acid. The precipitated solid was collected by filtration and washed with water, acetone and diethyl ether to give 5.1 g of N-[3-methoxy-4-(5-oxazolyl)phenyl]oxalamic acid as a pale yellow solid. MS: m/e 262.9 [M+H]$^+$.

Alternatively N-tert-butyl-N'-[3-methoxy-4-(5-oxazolyl) phenyl]oxalamide can be prepared as follows:

A solution of 95 mg (0.5 mmol) of 3-methoxy-4-(5-oxazolyl)aniline, 73 mg (0.5 mmol) of N-tert-butyloxalamic acid, 134 mg (0.7 mmol) of 1-(3-dimethylaminopropyl)-3-ethylcarbodiimide hydrochloride and 75 mg (0.55 mmol) of 1-hydroxy-7-azabenzotriazole in 4 ml of dichloromethane was stirred a room temperature for 18 hours. The resulting mixture was washed with 2M hydrochloric acid and saturated sodium bicarbonate, dried over magnesium sulphate and evaporated to dryness. The residue was triturated with petrol and collected by filtration to give 128 mg of N-tert-butyl-N'-[3-methoxy-4-(5-oxazolyl)phenyl]oxalamide as a pale yellow solid. MS: 318 (M+H)$^+$.

EXAMPLE 2

Tert-butyl [3-[[[3-methoxy-4-(5-oxazoyl)anilino]oxalyl] amino]benzyl] carbamate

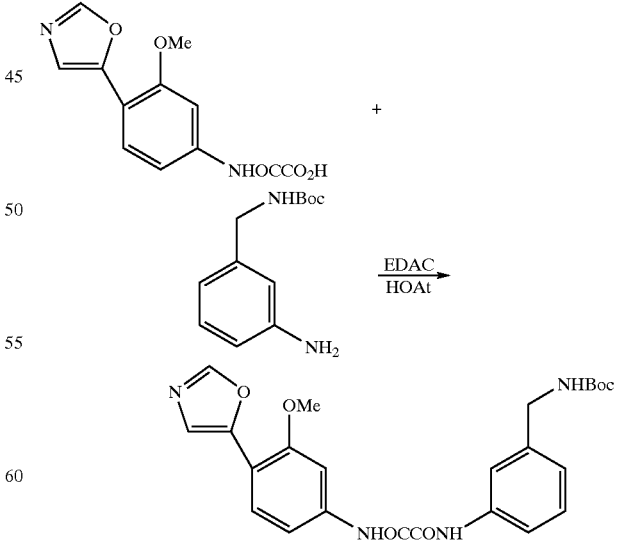

A mixture of 2.04 g (7.79 mmol) of N-(3-methoxy-4-(5-oxazolyl)phenyl]oxalamic acid, prepared as described above in Example 1 above, 1.9 g (8.56 mmol) of tert-butyl(3-aminobenzyl)carbamate, 1.8 g (9.4 mmol) of 1-(3- dimethylaminopropyl)-3-ethylcarbodiimide hydrochloride and 1.3 g (9.6 mmol) of 1-hydroxy-7-azabenzotriazole in 30 ml of dimethylformamide was stirred for 20 hours at room temperature. The resulting precipitate was collected by filtration and washed with dichloromethane to give 1.8 g of tert-butyl[3-[[[3-methoxy-4-(5-oxazolyl)anilino]oxalyl]amino]benzyl]carbamate as a white solid. MS: m/e 466 M$^+$.

EXAMPLE 3

N-[3-(Aminomethylphenyl]-N'-[3-methoxy-4-(5-oxazoyl)phenyl]oxalamide trifluoroacetate

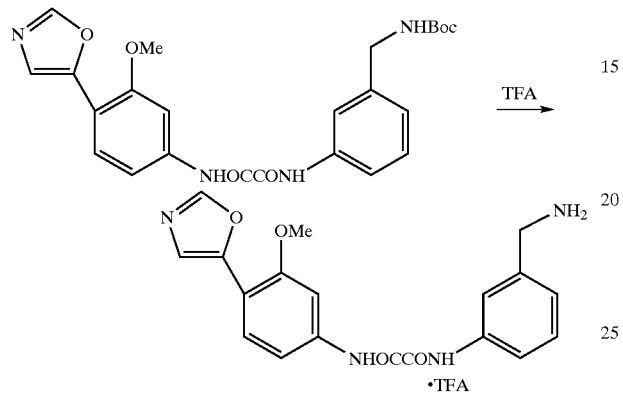

15 mg (0.032 mmol) of tert-butyl[3-[[[3-methoxy-4-(5-oxazolyl)anilino]oxalyl]amino]benzyl]carbamate, prepared as described in Example 2 above, were dissolved in 1 ml of dichloromethane and 1 ml of trifluoroacetic acid at room temperature for 5 minutes. The solution was evaporated to dryness, the residue triturated with diethyl ether and collected by filtration to give 11 mg of N-[3-(aminomethylphenyl]-N'-[3-methoxy-4-(5-oxazolyl)phenyl]oxalamide trifluoroacetate as a white solid. MS: m/e 408 [M+H+MeCN]$^+$.

EXAMPLE 4

N-[3-(Benzamidomethyl)phenyl]-N'-[3-methoxy-4-(5-oxazoyl)phenyl]oxalamide

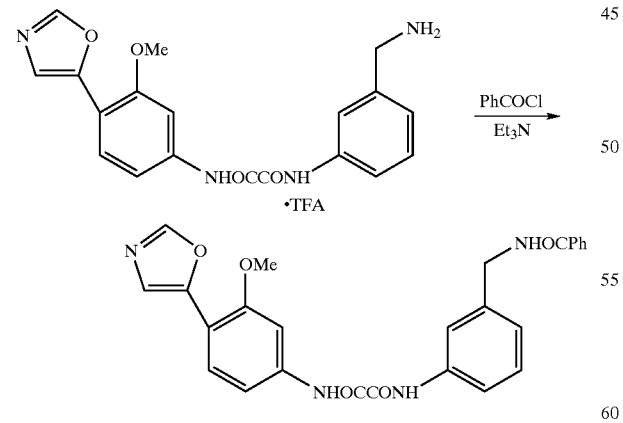

29 mg (0.21 mmol) of benzoyl chloride were added to a solution of 100 mg (0.21 mmol) of N-[3-(aminomethyl)phenyl]-N'-[3-methoxy-4-(5-oxazolyl)phenyl]oxalamide trifluoroacetate, prepared as described in Example 3 above, and 46 mg (0.46 mmol) of triethylamine in a mixture of 2 ml of dimethylformamide and 5 ml of dichloromethane, and stirred at room temperature for 18 hours. The solution was washed with 2M hydrochloric acid and saturated sodium bicarbonate then dried over magnesium sulphate and evaporated to dryness. The residue was chromatographed on silica gel using ethyl acetate/petrol (2:1) for the elution. After trituration with diethyl ether there was obtained 45 mg of N-[3-(benzamidomethyl)phenyl]-N'-[3-methoxy-4-(5-oxazolyl)phenyl]oxalamide as a white solid. MS: m/e 471.0 [M+H]$^+$.

EXAMPLE 5

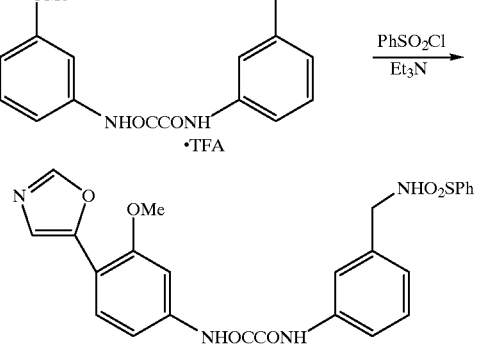

In an analogous manner to that described in Example 4 but replacing benzoyl chloride with phenylsulphonyl chloride there was obtained N-[3-[(benzenesulphonamido)methyl]phenyl]-N'-[3-methoxy-4-(5-oxazolyl)phenyl]oxalamide as a white solid. MS: m/e 507 [M+H]$^+$.

EXAMPLE 6

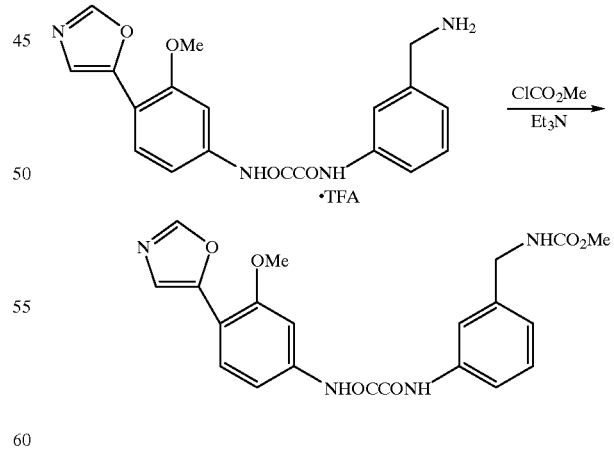

In an analogous manner to that described in Example 4 but replacing benzoyl chloride with methyl chloroformate there was obtained methyl[3-[[[3-methoxy-4-(5-oxazolyl)anilino]oxalyl]amino]benzyl]carbamate as a white solid. MS: m/e 425 [M+H]$^+$.

EXAMPLE 7

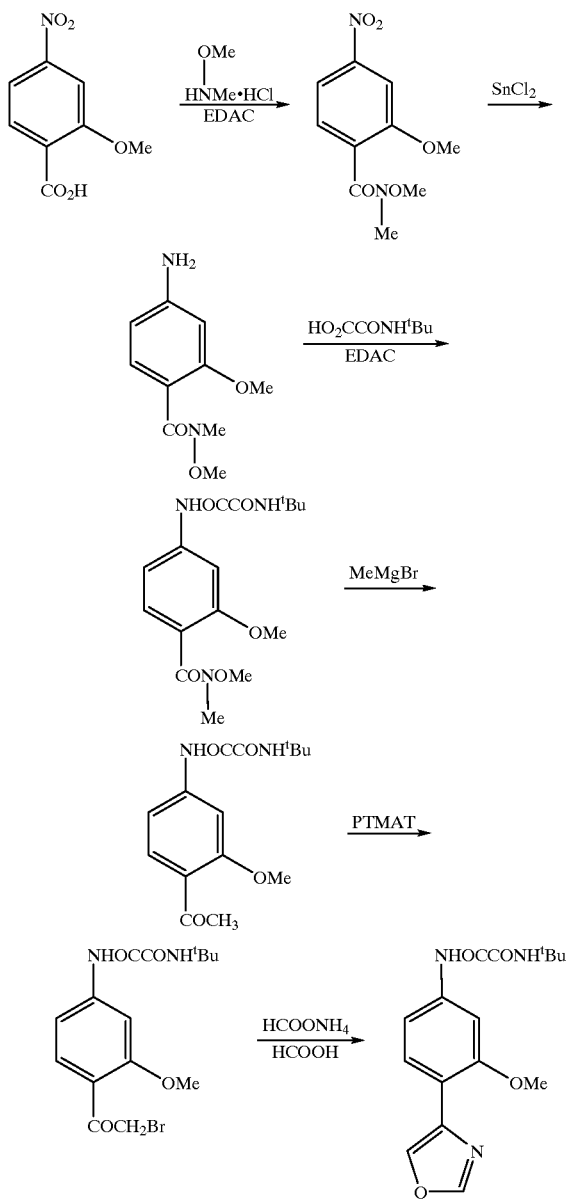

A mixture of 371 mg (1 mmol) of N-[4-(bromoacetyl)-3-methoxyphenyl]-N'-tert-butyloxalamide and 315 mg (5 mmol) of ammonium formate was refluxed in 10 ml of formic acid for 4 hours then cooled and evaporated to dryness. The residue was dissolved in ethyl acetate, washed with 2M sodium hydroxide and dried over magnesium sulphate. The solution was evaporated to dryness and the residue chromatographed on silica gel using ethyl acetate/petrol (7:18) for the elution. There was obtained after trituration with diethyl ether/petrol (1:1) 65 mg of N-tert-butyl-N'-[3-methoxy-4-(4-oxazolyl)phenyl]oxalamide as a white solid. MS: m/e 318 [M+H]⁺.

The starting material was prepared as follows:
i) A mixture of 3.94 g (20 mmol) of 2-methoxy-4-nitrobenzoic acid, 3.9 g (40 mmol) of N,O-dimethylhydroxylamine hydrochloride, 5.73 g (29.92 mmol) of 1-(3-dimethylaminopropyl)-3-ethylcarbodiimide hydrochloride, 3.37 g (22 mmol) of 1-hydroxybenzo)triazole hydrate and 5.06 g (44 mmol) of N-ethylmorpholine in 50 ml of dichloromethane was stirred at room temperature for 3 hours then washed with 2M hydrochloric acid and saturated bicarbonate. The resulting solution was dried over magnesium sulphate, evaporated to dryness and the residue triturated with diethyl ether and collected by filtration to give 3.95 g of N,O-dimethyl 2-methoxy-4-nitrobenzohydroxamate as a white solid. $^1$H NMR (400 MHz, CDCl$_3$) δ: 3.37 (3H,s), 3.48 (3H,s), 3.97 (3H,s), 7.45 (1H,d), 7.80 (1H,d), 7.91 (1H,dd).

ii) A mixture of 1.2 g (5 mmol) of N,O-dimethyl 2-methoxy-4-nitrobenzohydroxamate and 4.75 g (25 mmol) of tin(II) chloride in 40 ml of ethanol was heated at 80° C. for 30 minutes then cooled and evaporated to dryness. The residue was dissolved in dichloromethane, washed with 2M sodium hydroxide and the organic phase dried over magnesium sulphate and evaporated to dryness to give 960 mg of N,O-dimethyl 4-amino-2-methoxybenzohydroxamate as an off-white solid. $^1$H NMR (400 MHz, CDCl$_3$) δ: 3.25 (3H,s), 3.62 (3H,s), 3.79 (3H,s), 6.22 (1H,d), 6.28 (1H,dd), 7.09 (1H,d).

iii) A mixture of 700 mg (3.33 mmol) of N,O-dimethyl 4-amino)-2-methoxybenzohydroxamate, 483 mg (3.33 mmol) of N-tert-butyloxalamide acid, 600 mg (3.92 mmol) of 1-hydroxybenzotriazole hydrate and 960 mg (5.01 mmol) of 1-(3-dimethylaminopropyl)-3-ethylcarbodiimide hydrochloride in 15 ml of dichloromethane was stirred at room temperature for 3 hours then washed with 2M hydrochloric acid and saturated sodium bicarbonate. The organic phase was dried over magnesium sulphate, evaporated to dryness and the residue chromatographed on silica gel using ethyl acetate/petrol (3:1) for the elution to give 960 mg of N,O-dimethyl 4-[[(tert-butylamino)oxalyl]amino]-2-methoxybenzohydroxamate as a white solid. $^1$H NMR (400 MHz, CDCl$_3$) δ: 1.46 (9H,s), 3.25–3.4 (3H,br.s.), 3.45–3.65 (3H,br.s.), 3.89 (3H,s), 7.08 (1,dd), 7.29 (1H, d), 7.44 (1H,s), 7.53 (1H,d), 9.40 (1H,s).

iv) 3.1 ml (4.34 mmol) of 1.4M methylmagnesium bromide in tetrahydrofuran were added in portions over 1 hour to a solution of 337 mg (1 mmol) of N,O-dimethyl 4-[[(tert-butylamino)oxalyl]amino]-2-methoxybenzohydroxamate in 10 ml of anhydrous tetrahydrofuran. The resulting solution was diluted with diethyl ether and washed with 2M hydrochloric acid. The organic phase was dried over magnesium sulphate, evaporated to dryness and the residue chromatographed on silica gel using ethyl acetate/petrol (3:7) for the elution to give 255 mg of N-(4-acetyl-3-methoxyphenyl)-N'-tert-butyloxalamide as a white solid. $^1$H NMR (400 MHz, CDCl$_3$) δ: 1.45 (9H,s), 2.61 (3H,s), 3.96 (3H,s), 7.03 (1H,dd), 7.43 (1H,s), 7.64 (1H, d), 7.82 (1H,d), 9.47 (1H,s).

v) 320 mg (0.85 mmol) of phenyltrimethylammonium tribromide were added in portions over 10 minutes to a stirred solution of 247 mg (0.85 mmol) of N-(4-acetyl-3-methoxyphenyl)-N'-tert-butyloxalamide in 5 ml of anhydrous tetrahydrofuran. After 15 minutes a further 100 mg (0.26 mmol) of phenyltrimethylammonium tribromide were added. The resulting suspension was diluted with diethyl ether, washed with water and the organic phase was dried over magnesium sulphate. Evaporation gave a gum which was chromatographed on silica gel using firstly 0.5% methanol in dichloromethane then 1% methanol in dichloromethane for the elution. The product was dissolved in diethyl ether/petrol (2:1) and the resulting crystals were collected by filtration to give 135 mg of N-[4-(bromoacetyl)-3-methoxyphenyl]-N'-tert-butyloxalamide as a white solid. $^1$H NMR (400 MHz, CDCl$_3$) δ: 1.44 (9H,s), 3.99 (3H,s), 4.61 (2H,s), 7.06 (1H,dd), 7.42 (1H,s), 7.68 (1H,d), 7.93 (1H,d), 9.51 (1H,s).

EXAMPLES 8–11

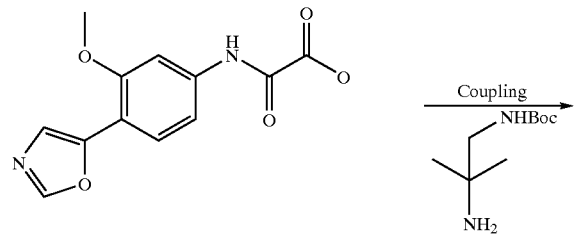

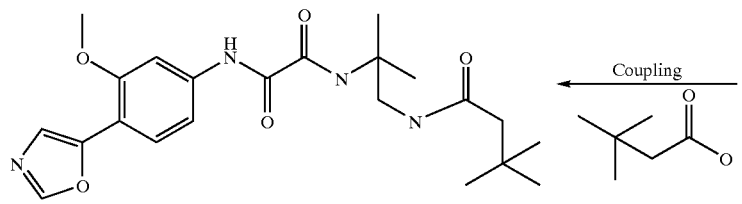

Example 10

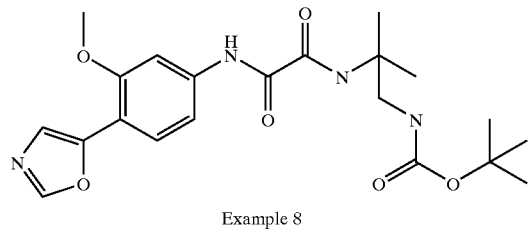

Example 8

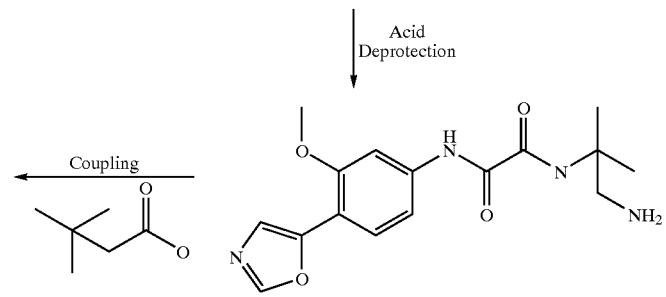

Example 9

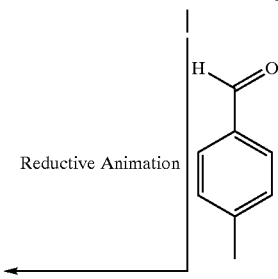

Example 11

EXAMPLE 8

Tert-butyl[2-[[[3-methoxy-4-(5-oxazolyl)anilino]oxalyl]amino]-2-methylpropyl]carbamate 77 mg (0.87 mmol) of tert-butyl (2-amino-2-methylpropyl)carbamate, 207 mg (1.05 mmol) of 1-(3-dimethylaminopropyl)-3-ethylcarbodiimide hydrochloride, 166 mg (1.08 mmol) of 1-hydroxy-7-azabenzotriazole and 200 mg (0.76 mmol) of N-[3-methoxy-4-(5-oxazolyl)phenyl]oxalamic acid were dissolved in 5 ml of dichloromethane and 5 ml of dimethylformamide and stirred for 16 hours at room temperature. The mixture was then diluted with 50 ml of dichloromethane and washed with a 10% solution of citric acid and brine. The organic layer was then dried with anhydrous magnesium sulphate, filtered and evaporated to dryness. The residue was chromatographed on silica gel using 30% ethyl acetate in hexane for the elution to give 165 mg of tert-butyl[2-[[[3-methoxy-4-(5-oxazolyl)anilino]oxalyl]amino]-2-methylpropyl]carbamate as a yellow solid, $^1$H NMR (400 MHz, d6 DMSO) δ: 1.35 (s, 6H), 1.45 (s, 9H), 3.25 (d, 2H), 3.95 (s, 3H), 7.25 (t, 1H), 7.55 (s,1H), 7.70 (m, 2H), 7.80 (s,1H), 8.25 (s, 1H), 8.50 (s, 1H), 10.8 (s, 1H).

EXAMPLE 9

N-(2-Amino-1,1-dimethylethyl)-N'-[3-methoxy-4-(5-oxazolyl)phenyl]oxalamide trifluoroacetate (1:1)

26 mg (0.29 mmol) of tert-butyl[2-[[[3-methoxy-4-(5-oxazolyl)anilino]oxalyl]amino]-2-methylpropyl]carbamate was dissolved and stirred in 10 ml of a 1:1 mixture of 1,1,1-trifluoroacetic acid and dichloromethane. After 1 hour the solvent mixture was co-evaporated with toluene three times and dichloromethane twice. The resulting gum was then triturated with 40–60 petroleum ether to give 124 mg of N-(2-amino-1,1-dimethylethyl)-N'-[3-methoxy-4-(5-oxazolyl)phenyl]oxalamide trifluoroacetate (1:1) as a yellow solid, $^1$H NMR (400 MHz, d6 DMSO) δ: 1.40 (s,6H), 3.20 (m,2H), 3.90 (s, 3H), 7.50 (s,1H), 7.60–7.74 (m, 2H), 7.80 (s, 1H), 7.90 (s(br), 3H), 8.30 (s,1H), 8.40 (s,1H), 10.80(s, 1H).

The previously described trifluoroacetic acid salt was partitioned between a saturated sodium hydrogencarbonate solution and ethyl acetate. The organic layer was then dried with magnesium sulphate, filtered and evaporated to give the free base used in Example 10.

EXAMPLE 10

N-(3-Methoxy-4-(5-oxazolyl)phenyl]-N'-[2-(3,3-dimethylbutyramido)-1,1-dimethylethyl]oxalamide 30 mg (0.09 mmol) of N-(2-amino-1,1-dimethyl-ethyl)-N'-(3-methoxy-4-oxazol-5-yl-phenyl)-oxalamide, 52 mg (0.45 mmol) of tert-butylacetic acid, 86 mg (0.45 mmol) of 1-(3-dimethylaminopropyl)-3-ethylcarbodiimide hydrochloride and 69 mg of HOAt were dissolved and stirred in 2 ml of dimethylformamide. After stirring for 16 hours the mixture was diluted with 10 ml of dichloromethane and washed with 10% citric acid solution in water, saturated sodium hydrogen carbonate solution and brine. The organic solution was then dried with solid magnesium sulphate, filtered and evaporated to give N-(3-methoxy-4-(5-oxazolyl)phenyl]-N'-[2-(3,3-dimethylbutyramido)-1,1-dimethylethyl]oxalamide as a pale yellow solid, MS: m/e 431.3 [M+H]+.

EXAMPLE 11

N-[3-Methoxy-4-(5-oxazolyl)phenyl]-N'-[2-(4-methylbenzylamino)-1,1-dimethylethyl]oxalamide 30 mg (0.09 mmol) of N-(2-amino-1,1-dimethyl-ethyl)-N'-(3-methoxy-4-oxazol-5-yl-phenyl)-oxalamide, 11.3 mg (0.095 mmol) of 4-methylbenzaldehyde and 30 mg (0.14 mmol) of sodium triacetoxyborohydride were dissolved in 2 ml of a 5% acetic acid dichloromethane mixture for 16 hours. The reaction mixture was then diluted with 8 ml of dichloromethane and washed with water, saturated sodium hydrogen carbonate and brine. The resulting organic solution was then dried with magnesium sulphate, filtered and evaporated to give N-[3-methoxy-4-(5-oxazolyl)phenyl-N'-[2-(4-methylbenzylamino)-1,1-dimethylethyl]oxalamide as a yellow solid MS: m/e 437.3 [M+H]+.

EXAMPLE 12

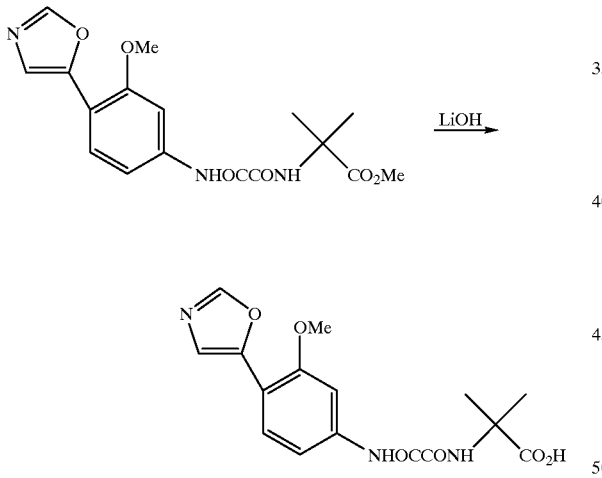

A mixture of 161 mg (0.446 mmol) of methyl 2-[[3-methoxy-4-(5-oxazolyl)anilinooxalyl]amino]-2-methylpropionate and 56 mg (1.33 mmol) of lithium hydroxide hydrate in 3 ml of methanol and 0.5 ml of water was heated at 50° C. for 2 hours then diluted with water and washed with diethyl ether. The aqueous phase was acidified to pH2 with 2M hydrochloric acid and extracted twice with ethyl acetate. The combined organic extracts were dried over magnesium sulphate and evaporated to dryness. The residue was chromatographed on silica gel using dichloromethane/methanol/acetic acid/water (120:15:3:2) for the elution. After trituration with ether there was obtained 70 mg of 2-[[[3-methoxy-4-(5-oxazolyl)anilino]oxalyl]amino]-2-methylpropionic acid as a white solid. MS: m/e 247.9 [M+H]$^+$.

EXAMPLE 13

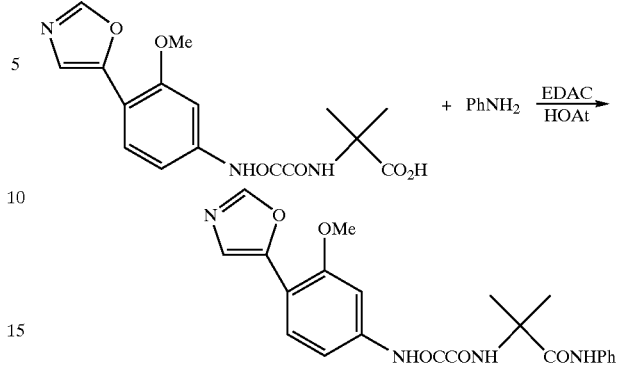

A solution of 30 mg (0.086 mmol) of 2-[[[3-methoxy-4-(5-oxazolyl)anilino]oxalyl]amino]-2-methylpropionic acid, 16 mg (0.172 mmol) of aniline, 18 mg (0.132 mmol) of 1-hydroxy-7-azabenzotriazole and 25 mg (0.131 mmol) of 1-(3-dimethylaminopropyl)-3-ethylcarbodiimide hydrochloride in 2 ml of dimethylformamide was stirred at room temperature for 18 hours then diluted with ethyl acetate and washed with 2M hydrochloric acid and saturated sodium bicarbonate. The organic phase was dried over magnesium sulphate and after evaporation the residue was triturated with diethyl ether and collected by filtration to give 20 mg of N-[3-methoxy-4-(5-oxazolyl)phenyl]-N'-[1-methyl-1-(phenylcarbamoyl)ethyl]oxalamide as a white solid. MS: m/e 423.0 [M+H]$^+$.

EXAMPLE 14

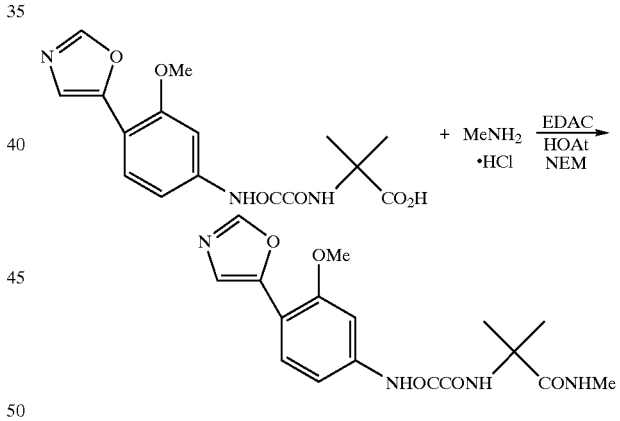

A mixture of 30 mg (0.086 mmol) of 2-[[[3-methoxy-4-(5-oxazolyl)anilino]oxalyl]amino]-2-methylpropionic acid, 12 mg (0.178 mmol) of methylamine hydrochloride, 18 mg (0.132 mmol) of 1-hydroxy-7-azabenzotriazole, 25 mg (0.131 mmol) of 1-(3-dimethylaminopropyl)-3-ethylcarbodiimide hydrochloride and 22 mg (0.218 mmol) of triethylamine in 2 ml of dimethylformamide was stirred at room temperature for 18 hours then diluted with ethyl acetate and washed with 2M hydrochloric acid and saturated sodium bicarbonate. The organic solution was dried over magnesium sulphate, evaporated to dryness and the residue chromatographed on silica gel using dichloromethane/methanol (24:1) for the elution. After trituration with ether there was obtained 17 mg of N-[3-methoxy-4-(5-oxazolyl)phenyl]-N'-[1-methyl-1-(methylcarbamoyl)ethyl]oxalamide as a white solid. MS: m/e 361.0 [M+H]$^+$.

EXAMPLE 15

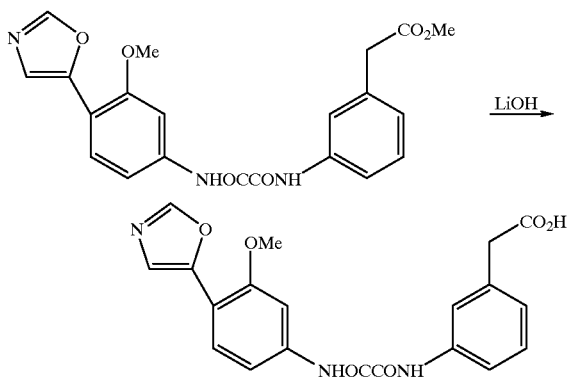

A solution of 740 mg (1.81 mmol) of methyl 2-[3-[[[3-methoxy-4-(5-oxazolyl)anilino]oxalyl]amino]phenyl]acetate and 152 mg (3.62 mmol) of lithium hydroxide hydrate in 10 ml of methanol, 10 ml of 1,4-dioxane and 5 ml of water was stirred at room temperature for 18 hours. The solvent was removed by evaporation and the residue dissolved in water. The aqueous solution was washed with diethyl ether and acidified with citric acid solution. The solid which precipitated was collected by filtration and washed with water, ethanol and diethyl ether to give 414 mg of 2-[3-[[[3-methoxy-4-(5-oxazolyl)anilino]oxalyl]amino]phenyl]acetic acid as a white solid. MS: m/e 396.0 [M+H]$^+$.

EXAMPLE 16

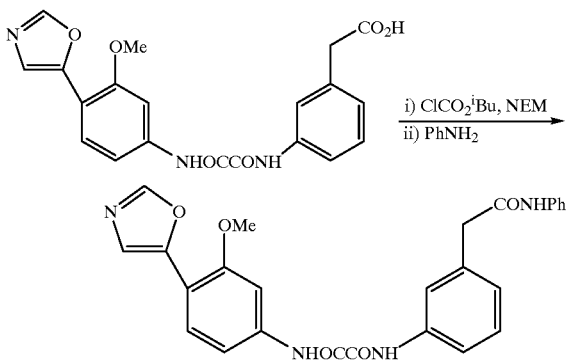

A solution of 30 mg (0.076 mmol) of 2-[3-[[[3-methoxy-4-(5-oxazolyl)anilino]oxalyl]amino]phenyl]acetic acid and 11 mg (0.096 mmol) of N-ethylmorpholine in 1 ml of dimethylformamide was cooled to 0° C. and a solution of 12 mg (0.088 mmol) of isobutyl chloroformate in 1 ml of dichloromethane was added. The resulting mixture was stirred for 30 minutes at 0° C. then a solution of 7 mg (0.075 mmol) of aniline in 1 ml of dichloromethane was added and stirring was continued for a further hour at 0° C. After 18 hours at room temperature the mixture was evaporated to dryness and the residue chromatographed on silica gel using dichloromethane/methanol (19:1) for the elution. There was obtained 3 mg of N-[3-methoxy-4-(5-oxazolyl)phenyl]-N'-[3-[(phenylcarbamoyl)methyl]phenyl]oxalamide as a white solid MS: m/e 471.0 [M+H]$^+$.

EXAMPLE 17

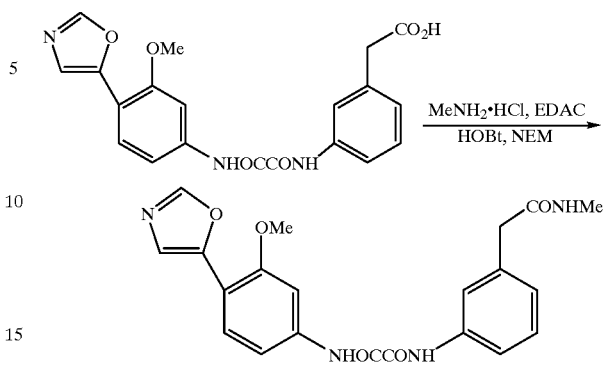

A mixture of 30 mg (0.076 mmol) of 2-[3-[[[3-methoxy-4-(5-oxazolyl)anilino]oxalyl]amino]phenyl]acetic acid, 22 mg (0.115 mmol) of 1-(3-dimethylaminopropyl)-3-ethylcarbodiimide hydrochloride, 14 mg (0.092 mmol) of 1-hydroxybenzotriazole hydrate, 26 mg (0.385 mmol) of methylamine hydrochloride and 52 mg (0.452 mmol) of N-ethylmorpholine in 1 ml of dimethylformamide was stirred at room temperature for 18 hours. The solvent was removed by evaporation and the residue chromatographed on silica gel using dichloromethane/methanol (1:19) for the elution. There was obtained 15 mg of N-[3-methoxy-4-(5-oxazolyl)phenyl]-N'-3-[(methylcarbamoyl)methyl]phenyl]oxalamide as a white solid. MS: m/e 409 [M+H]$^+$.

EXAMPLE 18

N-(3-Aminophenyl)-N'-[3-methoxy-4-(5-oxazolyl) phenyl]oxalamide trifluoroacetate

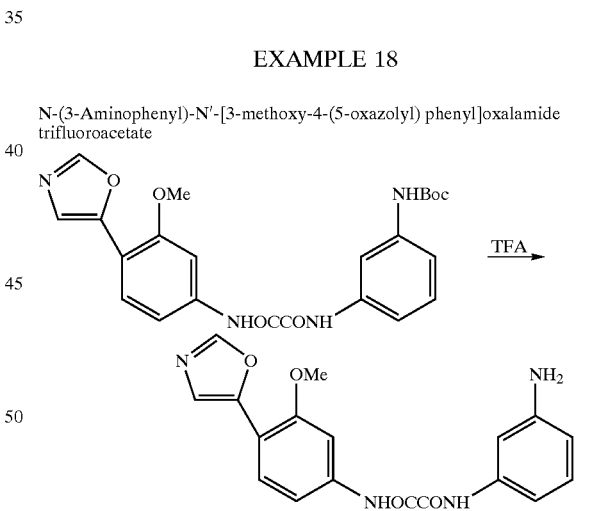

20 mg (0.043 mmol) of tert-butyl[3-[[[3-methoxy-4-(5-oxazolyl)anilino]oxalyl]amino]phenyl]carbamate were dissolved in a mixture of 1 ml of dichloromethane and 1 ml of trifluoroacetic acid at room temperature for 10 minutes. The solvent was removed by evaporation and the residue triturated with diethyl ether. The resulting solid was collected by filtration to give 18 mg of N-(3-aminophenyl)-N'-[3-methoxy-4-(5-oxazolyl)phenyl]oxalamide trifluoroacetate as a white solid. MS: m/e 394.0 [M+H+MeCN]$^+$.

EXAMPLE 19

N-[3-(Benzamido) phenyl]-N'[3-methoxy-4-(5-oxazolyl) phenyl] oxalamide

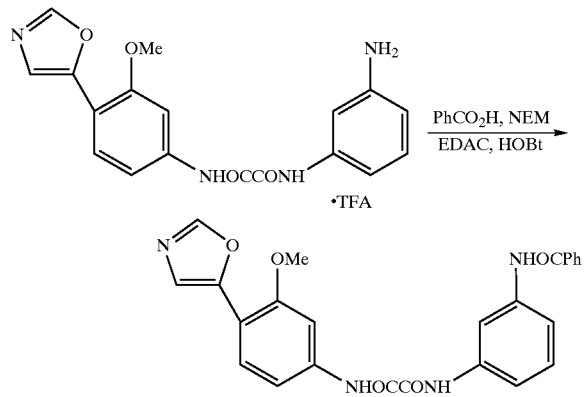

A mixture of 30 mg (0.064 mmol) of N-(3-aminophenyl)-N'-[3-methoxy-4-(5-oxazolyl)phenyl]oxalamide trifluoroacetate, 9 mg (0.074 mmol) of benzoic acid, 15 mg (0.078 mmol) of 1-(3-dimethylaminopropyl)-3-ethylcarbodiimide hydrochloride, 15 mg (0.096 mmol) of 1-hydroxybenzotriazole hydrate and 22 mg (0.19 mmol) of N-ethylmorpholine in 0.5 ml of dimethylformamide was stirred at room temperature for 18 hours then diluted with ethyl acetate and washed with 10% citric acid solution, saturated sodium bicarbonate and water. The organic phase was dried over magnesium sulphate, evaporated to dryness and the residue chromatographed on silica gel using dichloromethane/methanol (19:1) for the elution. There was obtained after trituration with diethyl ether/petrol (1:1). 12 mg of N-[3-(benzamidophenyl]-N'-[3-methoxy-4-(5-oxazolyl)phenyl]oxalamide as a white solid. MS: m/e 457.0 [M+H]⁺.

EXAMPLE 20

N-[3-(Methanesulphonamido) phenyl]-N'-[3-methoxy-4-(5-oxazolyl) phenyl] oxalamide

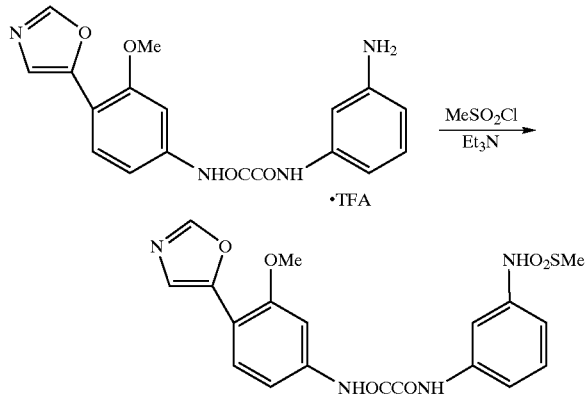

12 mg (0.011 mmol) of methanesulphonyl chloride were added to a solution of 50 mg (0.011 mmol) of N-(3-aminophenyl)-N'-[3-methoxy-4-(5-oxazolyl)phenyl] oxalamide trifluoroacetate and 32 mg (0.317 mmol) of triethylamine in 0.5 ml of dimethylformamide. The resulting solution was left at room temperature for 18 hours then diluted with ethyl acetate and washed with 10% citric acid solution, saturated sodium bicarbonate and water. The organic phase was dried over magnesium sulphate, evaporated to dryness and the residue chromatographed on silica gel using ethyl acetate/petrol (1:1) for the elution. There was obtained 5 mg of N-[3-(methanesulphonamido)phenyl]-N'-[3-methoxy-4-(5-oxazolyl)phenyl]oxalamide as a white solid. MS: m/e 431.0 [M+H]⁺.

EXAMPLE 21

N-[2-(4-Aminophenyl)-1,1-dimethylethyl]-N'-[3-methoxy-4-(5-oxazolyl) phenyl] oxalamide

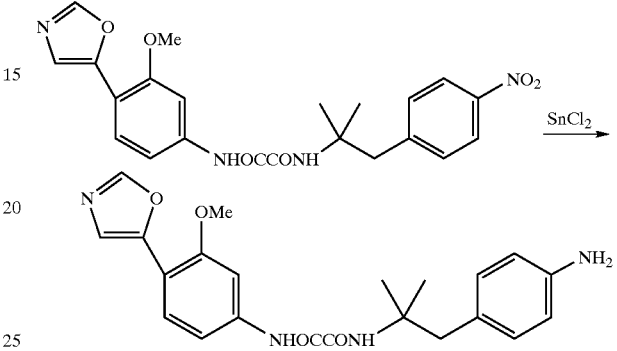

A mixture of 44 mg (0.1 mmol) of N-[3-methoxy-4-(5-oxazolyl)phenyl]-N'-[1,1-dimethyl-2-(4-nitrophenyl)ethyl] oxalamide and 90 mg (0.5 mmol) of tin(II) chloride were stirred and heated at 85° C. in 2 ml of ethanol and 1 ml of 1,4-dioxane for 5 hours. The resulting solution was cooled, diluted with ethyl acetate and washed with 2M sodium hydroxide. The organic phase was dried over magnesium sulphate, evaporated to dryness and the residue chromatographed on silica gel using ethyl acetate/petrol (2:1) for the elution. After trituration with petrol there was obtained 31 mg of N-[2-(4-aminophenyl)-1,1-dimethylethyl]-N'-[3-methoxy-4-(5-oxazolyl)phenyl]oxalamide as a white solid. MS: m/e 409 M+H]⁺.

EXAMPLE 22

N-[2-(4-Benzamidophenyl)-1,1-dimethylethyl]-N'-[3-methoxy-4-(5-oxazolyl) phenyl] oxalamide

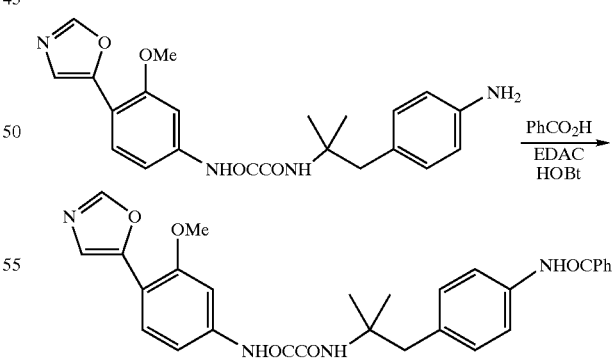

A mixture of 30 mg (0.074 mmol) of N-[2-(4-aminophenyl)-1,1-dimethylethyl]-N'-[3-methoxy-4-(5-oxazolyl)phenyl]oxalamide, 10 mg (0.082 mmol) of benzoic acid, 14 mg (0.092 mmol) of 1-hydroxybenzotriazole hydrate, 21 mg (0.11 mmol) of 1-(3-dimethylaminopropyl)-3-ethylcarbodiimide hydrochloride and 18 mg (0.16 mmol) of N-ethylmorpholine in 2 ml of dichloromethane was stirred at room temperature for 18 hours then diluted with dichloromethane and washed with 2M hydrochloric acid and saturated sodium bicarbonate. The organic phase was dried over magnesium sulphate, evaporated to dryness and the residue chromatographed on silica gel using ethyl acetate/ petrol (2:1) for the elution. There was obtained 9 mg of N-[2-(4-benzamidophenyl)-1,1-dimethylethyl]-N'-[3-methoxy-4-(5-oxazolyl)phenyl]oxalamide as a white solid. MS: m/e 513 [M+H]$^+$.

EXAMPLE 23

N-[2-(4-Acetamidophenyl)-1,1-dimethylethyl]-N'-[3-methoxy-4-(5-oxazolyl) phenyl] oxalamide

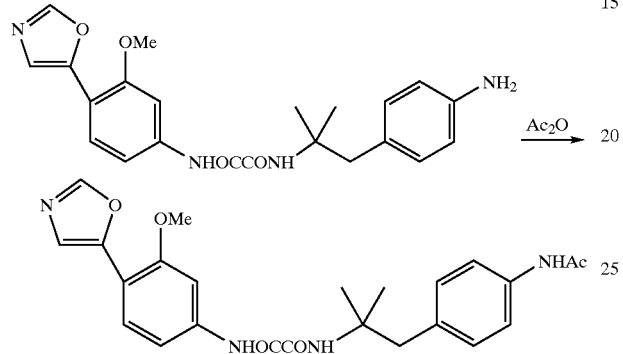

A mixture of 30 mg (0.074 mmol) of N-[2-(4-aminophenyl)-1,1-dimethylethyl]-N'-[3-methoxy-4-(5-oxazolyl)phenyl]oxalamide, 8 mg (0.078 mmol) of acetic anhydride and 17 mg (0.15 mmol) of N-ethylmorpholine in 1 ml of dichloromethane was stirred at room temperature for 2 hours. The solvent was removed by evaporation and the residue triturated with diethyl ether and collected by filtration to give 14 mg of N-[2-(4-acetamidophenyl)-1,1-dimethylethyl]-N'-[3-methoxy-4-(5-oxazolyl)phenyl] oxalamide as a white solid. MS: m/e 451 [M+H]$^+$.

EXAMPLE 24

N2-[[3-Methoxy-4-(5-oxazolyl) anilino] oxalyl]-N1,3-dimethyl-1,-valinamide

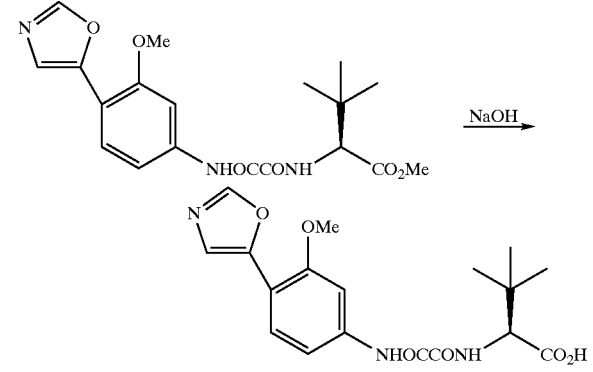

290 mg (0.75 mmol) of N-[[3-methoxy-4-(5-oxazolyl) anilino]oxalyl]-3-methyl-L-valine methyl ester in 3 ml of methanol and 1 ml of 1M aqueous sodium hydroxide were warmed gently and the resulting solution left at room temperature for 18 hours. The mixture was diluted with water, washed with diethyl ether and the aqueous phase acidified with 2M hydrochloric acid. The solution was extracted with ethyl acetate and the organic phase dried over magnesium sulphate, evaporated to dryness and the residue chromatographed on silica gel using ethyl acetate/acetic acid (99:1) for the elution. After trituration with diethyl ether there was obtained 110 mg of N2-[[3-methoxy-4-(5-oxazolyl)anilino]oxalyl]-N1,3-dimethyl-L-valinamide as a white solid. MS: m/e 376.0 [M+]$^+$.

EXAMPLE 25

Tert-butyl [3-[[[4-(5-oxazolyl) anilino] oxalyl] amino] benzyl] carbarnate

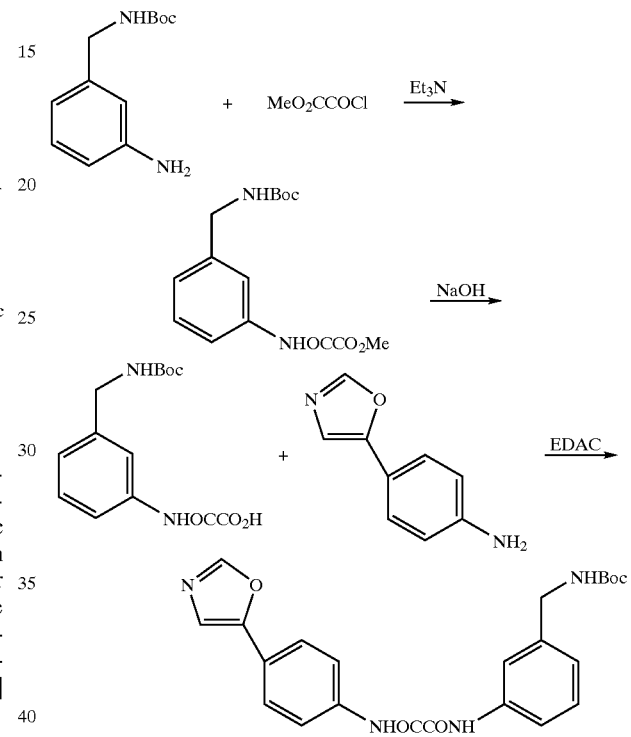

In an analogous manner to that described in Example 1 but replacing 3-methoxy-4-(5-oxazolyl)aniline with 4-(5-oxazolyl)aniline and N-tert-butyloxalamic acid with N-[3-[(tert-butoxyformamido)methyl]phenyl]oxamic acid there was obtained tert-butyl[3-[[[4-(5-oxazolyl)anilino]oxalyl] amino]benzyl]carbamate as a white solid. $^1$H NMR (400 MHz, DMSO) δ: 1.4 (9H,s), 4.1 (2H,d), 7.02 (1H,d), 7.32 (1H,t), 7.40 (1H,t), 7.63 (1H,s), 7.69 (1H,d), 7.70–7.79 (3H,m, 7.97 (2H,d), 8.43 (1H,s), 10.82 (1H,s), 10.99 (1H,s).

The starting material was prepared as follows:

i) 586 mg (4.78 mmol) of methyl oxalyl chloride were added to a solution of 1 g (4.5 mmol) of tert-butyl (3-aminobenzyl)carbamate and 508 mg (5.03 mmol) of triethylamine in 10 ml of dichloromethane. The resulting solution was stirred at room temperature for 30 minutes then washed with 5% citric acid solution and saturated sodium bicarbonate. The organic phase was dried over magnesium sulphate and the solvent removed by evaporation to give 1.5 g of methyl N-[3-[(tert-butoxyformamido)methyl]phenyl]oxamate as a viscous gum. $^1$H NMR (400 MHz, CDCl$_3$) δ: 1.43 (9H,s), 3.96 (3H,s), 4.31 (2H,d) 4.9–5.0 (br.s, 1H), 7.11 (1H,d), 7.33 (1H,t), 7.51 (1H,s), 7.52 (1H,d), 8.86 (br.s. 1H).

ii) A mixture of 1.232 g (4 mmol) of methyl N-[3-[(tert-butoxy formamido)methyl]phenyl]oxamate and 0.24 g (6 mmol) of sodium hydroxide in 15 ml of methanol/water (2:1) was stirred at room temperature for 2 hours. The solvent was removed by evaporation and the residue dissolved in water and diethyl ether. The aqueous layer was acidified with citric acid and washed twice with ethyl acetate. The combined organic solutions were dried over magnesium sulphate and the solvent removed by evaporation to give 670 mg of N-[3-[(tert-butoxyformamido)methyl]phenyl]oxamic acid as a white solid. $^1$H NMR (400 MHz, DMSO) δ: 1.48 (9H,s), 4.17 (2H,d), 7.09 (1H,d), 7.36 (1H,t), 7.49 (1H, t), 7.64 (1H,d), 7.74 (1H,s), 10.75 (1H,s).

EXAMPLE 26

Tert-butyl [2-[[[4-(5-oxazolyl) anilino] oxalyl] amino] benzyl] carbarnate

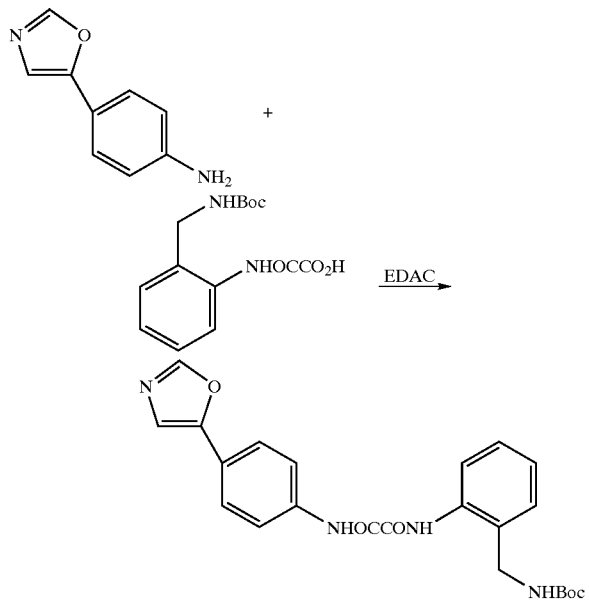

In an analogous manner to that described in Example 25 but replacing N-[3-[(tert-butoxyformamido)methyl]phenyl] oxamic acid with N-[2-[tert-butoxyformamido)methyl] phenyl]oxamic acid there was obtained tert-butyl[2-[[[4-(5-oxazolyl)anilino]oxalyl]amino]benzyl]carbamate as a white solid MS: m/e 437.0 [M+H]$^+$.

EXAMPLE 27

Tert-butyl [4-[[[4-(5-oxazolyl) anilino] oxalyl] amino] benzyl] carbarnate

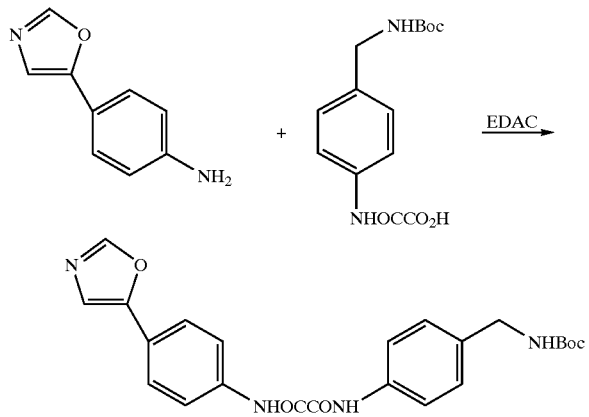

In an analogous manner to that described in Example 25 but replacing N-[3-[(tert-butoxyformamido)methyl]phenyl] oxamic acid with N-[4-[tert-butoxyformamido)methyl] phenyl]oxamic acid there was obtained tert-butyl[4-[[[4-(5-oxazolyl)anilino]oxalyl]amino]benzyl]carbamate as a white solid. MS: m/e 436.6 [M+H]$^+$.

EXAMPLE 28

N-Tert-butyl-N'-[4-(5-oxazoyl)phenyl]oxalamide

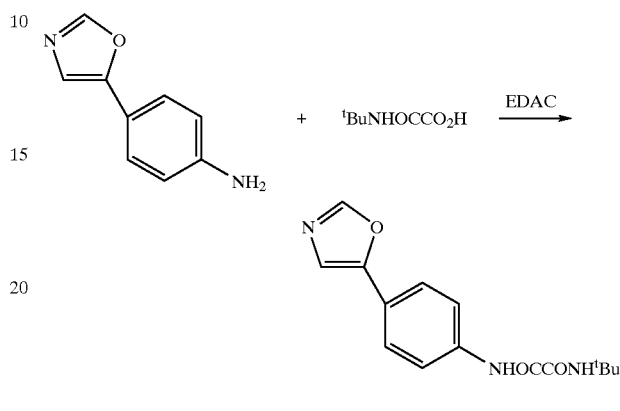

In an analogous manner to that described in Example 1 but replacing 3-methoxy-4-(5-oxazolyl)aniline with 4-(5-oxazolyl)aniline there was obtained N-tert-butyl-N'-[4-(5-oxazolyl)phenyl]oxalamide as a pale yellow solid. MS: m/e 329.0 [M+H+MeCN]$^+$.

EXAMPLE 29

N-[3-(Aminomethylphenyl]-N'-[4-(5-oxazoyl)phenyl]oxalamide trifluoroacetate

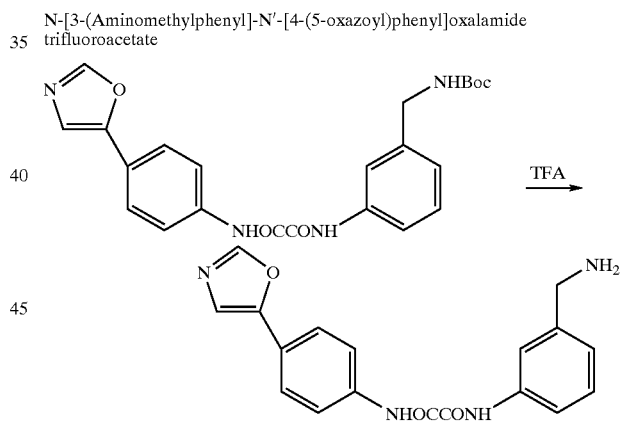

In an analogous manner to that described in Example 3 but replacing tert-butyl[3-[[[3-methoxy-4-(5-oxazolyl)anilino]oxalyl]amino]benzyl]carbamate with tert-butyl[3-[[[4-(5-oxazolyl)oxalyl]amino]benzyl]carbamate there was obtained N-[3-(aminomethylphenyl]-N'-[4-(5-oxazolyl)phenyl]oxalamide trifluoroacetate as a white solid. MS: m/e 336 [M]$^+$.

EXAMPLES 30–193

In a manner analogous to that described in Example 1, starting with N-[3-methoxy-4-(5-oxazoyl)phenyl oxalamic acid (prepared as described in Example 1, parts (i) and (ii)) and the appropriate amine the compounds shown in Table 3 were also prepared:

TABLE 3
| Example | Structure | MS (ES) |
|---------|-----------|---------|
| 30. | 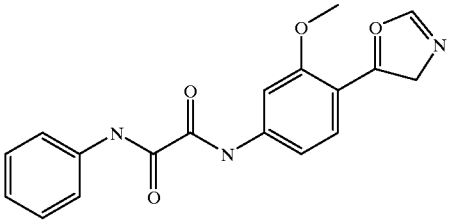 | 338.0 |
| 31. | 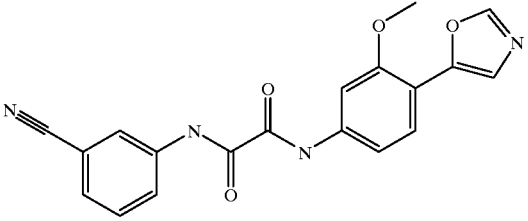 | 362.9 |
| 32. | 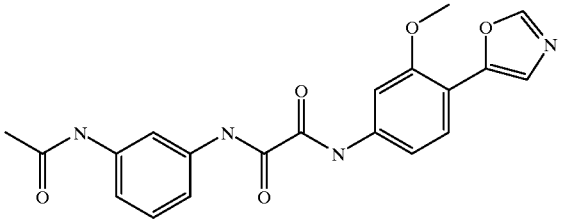 | 395.0 |
| 33. | 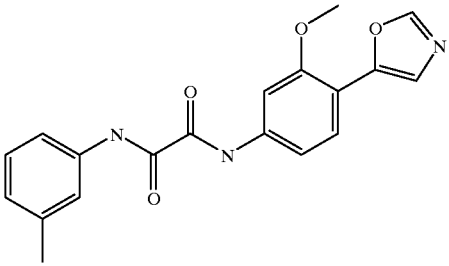 | 352.0 |
| 34. | 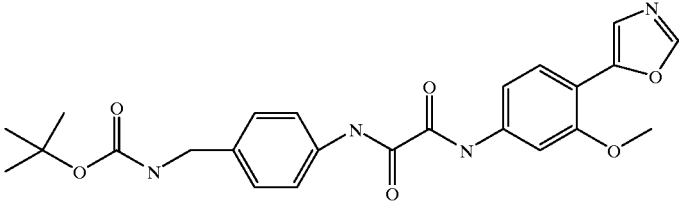 | 466 (M+; EI) |
| 35. | 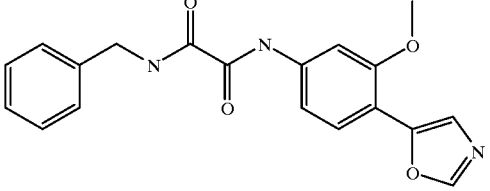 | 352.0 |

TABLE 3-continued

| Example | Structure | MS (ES) |
|---|---|---|
| 36. | 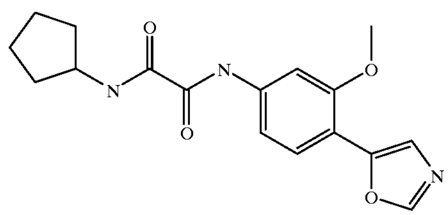 | 330.0 |
| 37. | 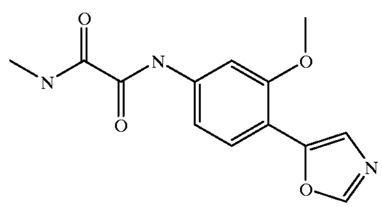 | 275.9 |
| 38. | 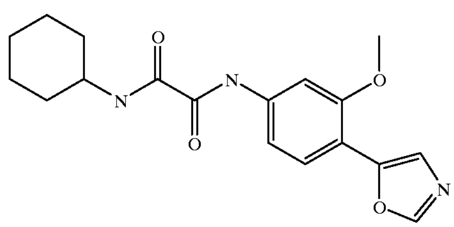 | 344.0 |
| 39. | 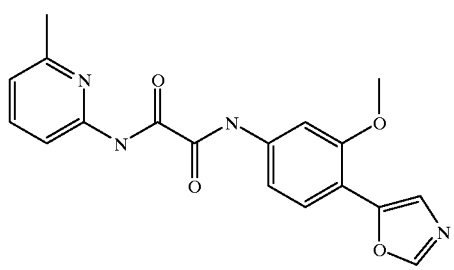 | 352.9 |
| 40. | 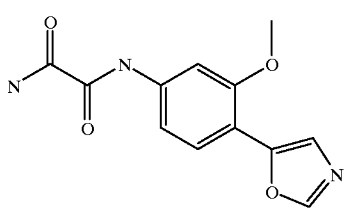 | 261.9 |
| 41. | 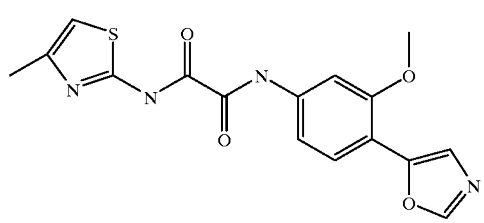 | 358.9 |

TABLE 3-continued

| Example | Structure | MS (ES) |
|---|---|---|
| 42. | 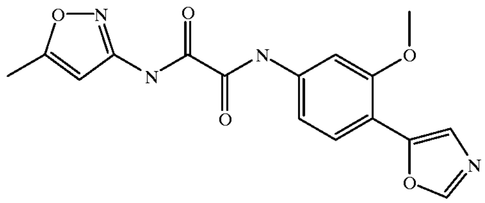 | 342.9 |
| 43. | 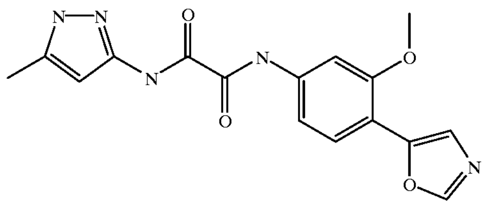 | 341.9 |
| 44. | 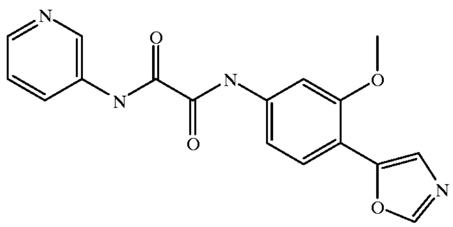 | 338.9 |
| 45. | 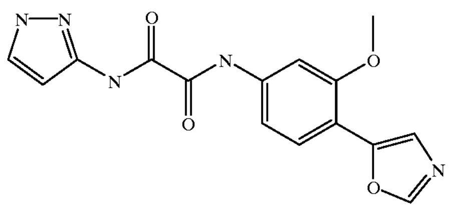 | 327.9 |
| 46. | 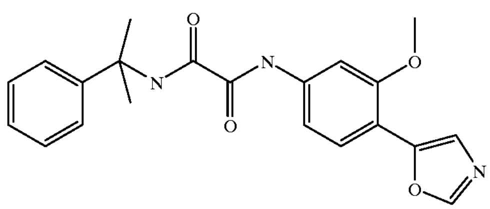 | 380.0 |
| 47. | 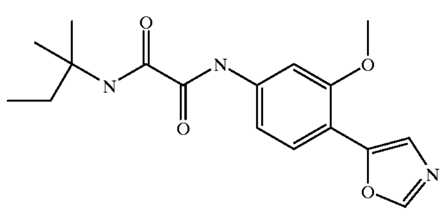 | 332.0 |
| 48. | 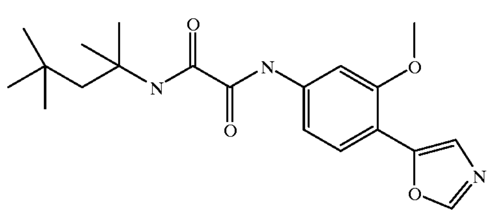 | 374.0 |

TABLE 3-continued

| Example | Structure | MS (ES) |
|---|---|---|
| 49. | 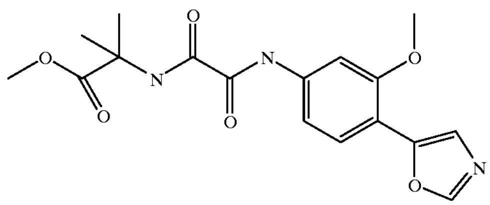 | 362.0 |
| 50. | 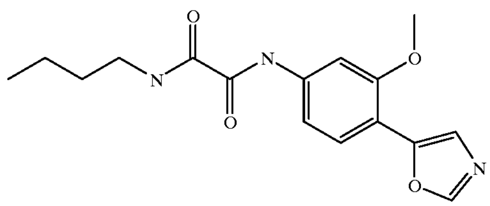 | 317.9 |
| 51. | 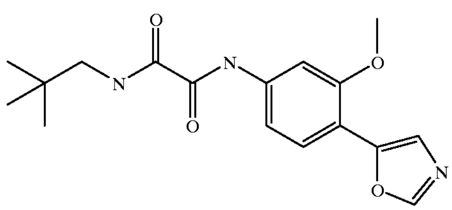 | 332.0 |
| 52. | 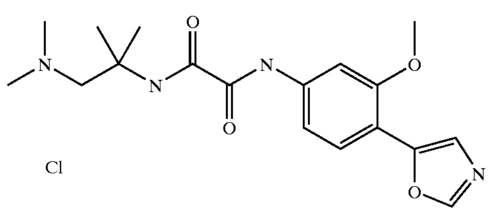 | 361.0 |
| 53. | 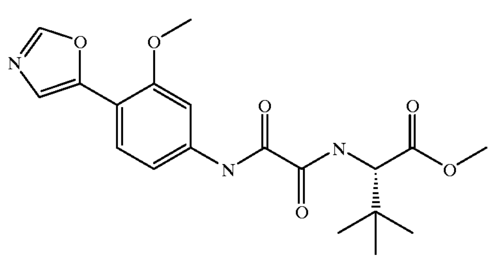 | 389.9 |
| 54. | 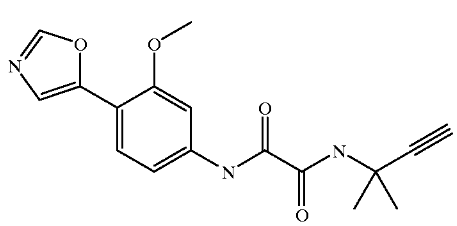 | 328.0 |

TABLE 3-continued

| Example | Structure | MS (ES) |
|---------|-----------|---------|
| 55. | 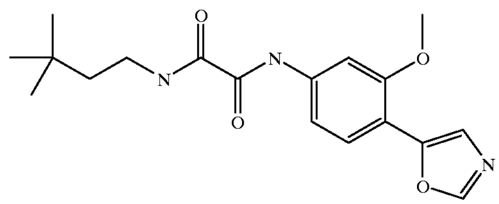 | 346.0 |
| 56. | 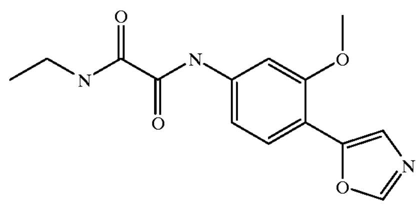 | 289.9 |
| 57. | 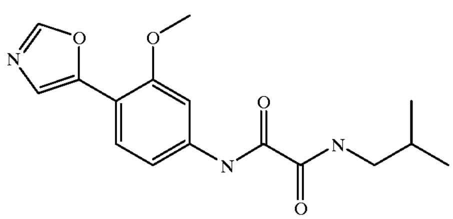 | 318.0 |
| 58. | 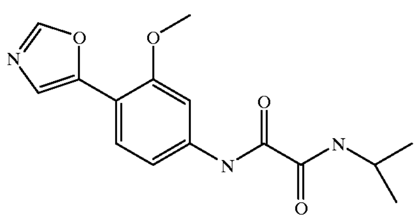 | 304.0 |
| 59. | 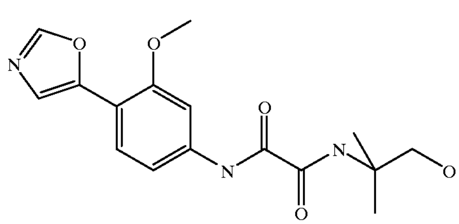 | 333.9 |
| 60. | 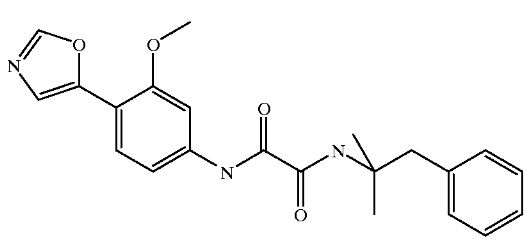 | 394.0 |

TABLE 3-continued

| Example | Structure | MS (ES) |
|---|---|---|
| 61. | 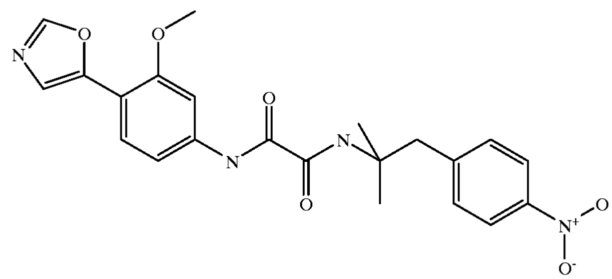 | 439 (M+; EI) |
| 62. | 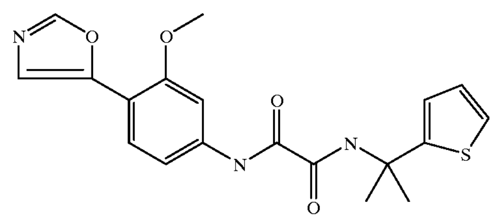 | 386 (M+; EI) |
| 63. | 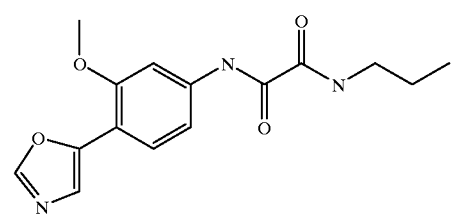 | 304.0 |
| 64. | 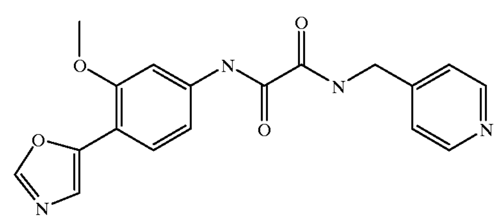 | 353.2 |
| 65. | 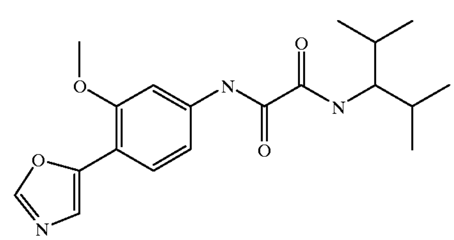 | 360.2 |
| 66. | 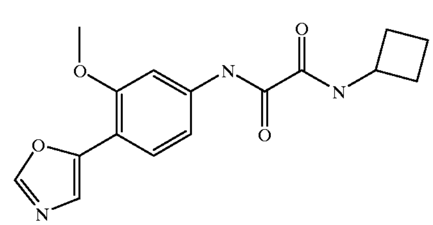 | 316.2 |

TABLE 3-continued
| Example | Structure | MS (ES) |
|---|---|---|
| 67. | 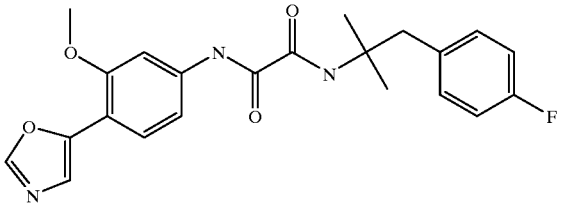 | 412.2 |
| 68. | 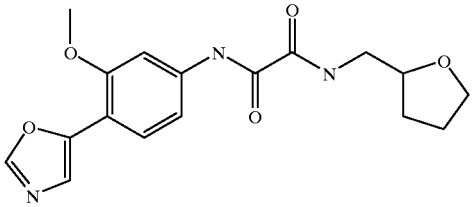 | 345.8 |
| 69. | 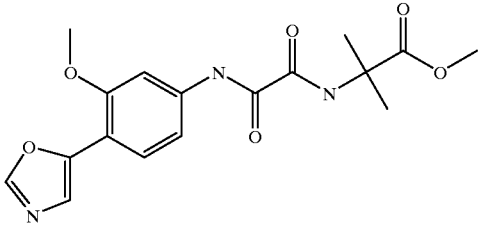 | 362.4 |
| 70. | 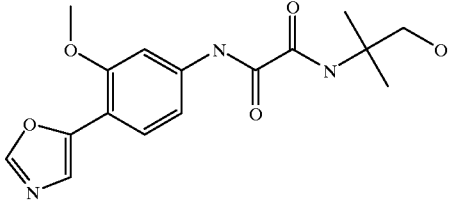 | 334.2 |
| 71. | 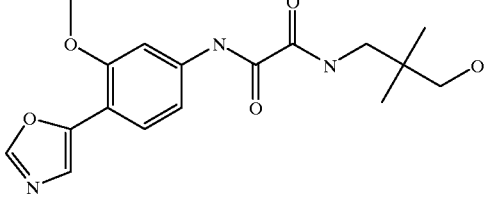 | 348.0 |
| 72. | 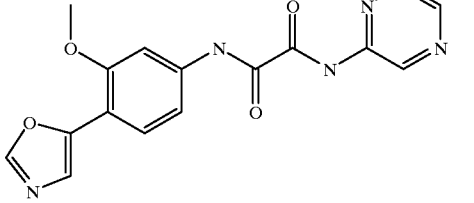 | 340.0 |

TABLE 3-continued

| Example | Structure | MS (ES) |
|---|---|---|
| 73. | 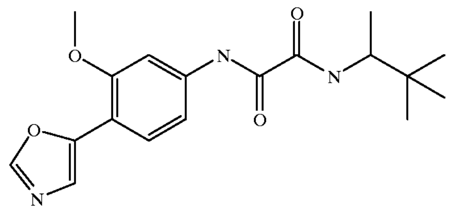 | 345.8 |
| 74. | 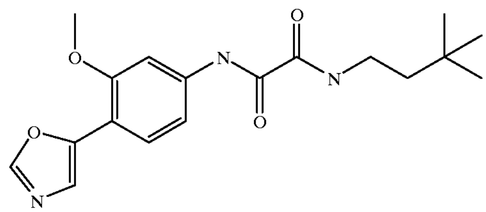 | 346.0 |
| 75. | 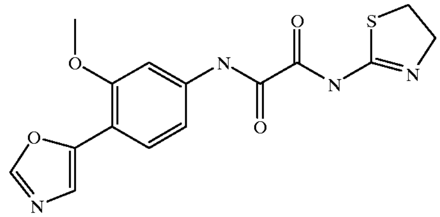 | 346.8 |
| 76. | 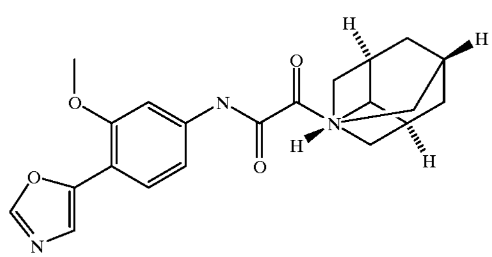 | 395.8 |
| 77. | 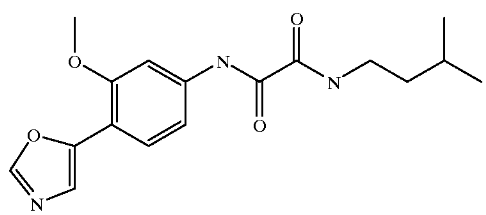 | 332.4 |
| 78. | 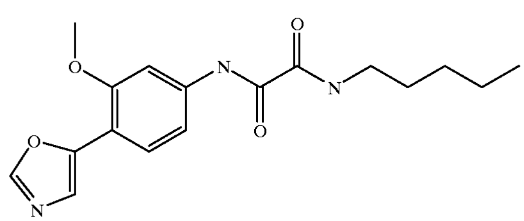 | 332.4 |

TABLE 3-continued

| Example | Structure | MS (ES) |
|---|---|---|
| 79. | 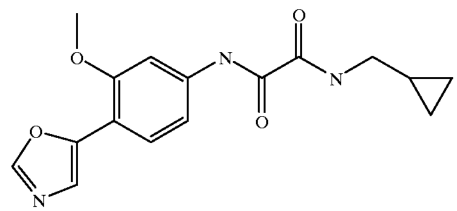 | 316.2 |
| 80. | 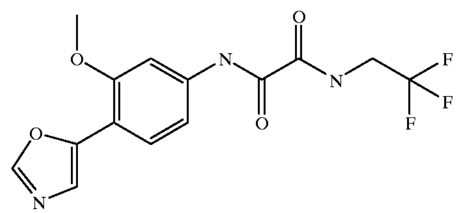 | 344.0 |
| 81. | 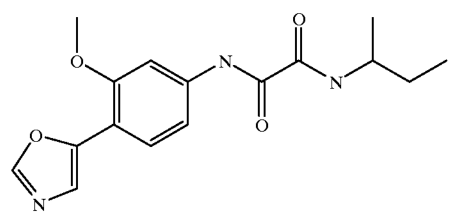 | 317.8 |
| 82. | 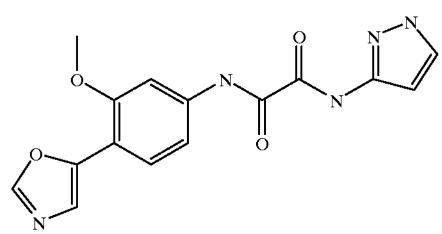 | 328.2 |
| 83. | 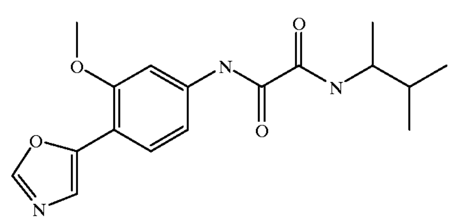 | 332.4 |
| 84. | 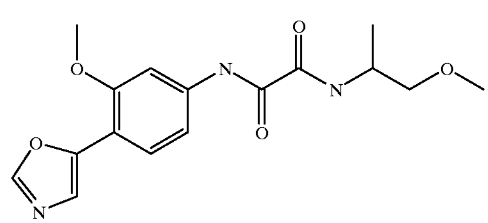 | 334.2 |

TABLE 3-continued

| Example | Structure | MS (ES) |
|---|---|---|
| 85. | 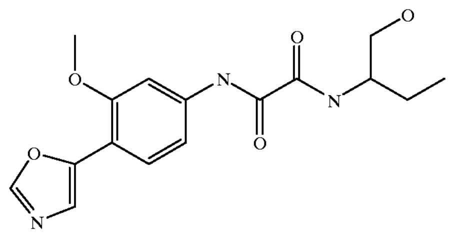 | 334.2 |
| 86. | 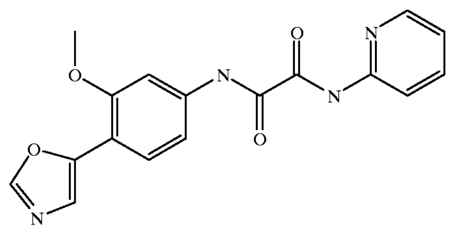 | 339.2 |
| 87. | 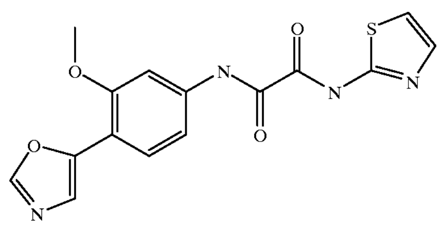 | 344.8 |
| 88. | 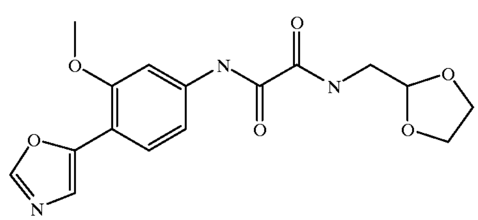 | 348.0 |
| 89. | 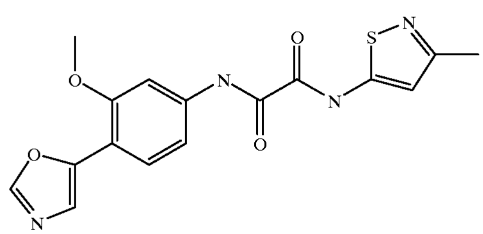 | 359.2 |
| 90. | 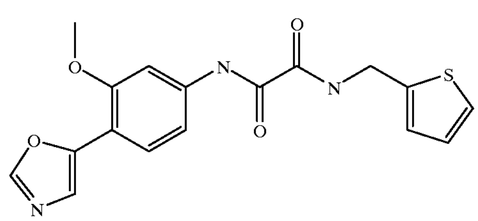 | 358.2 |

TABLE 3-continued
| Example | Structure | MS (ES) |
|---|---|---|
| 91. | 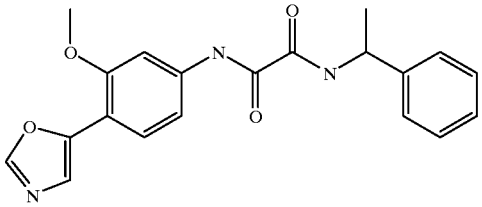 | 366.2 |
| 92. | 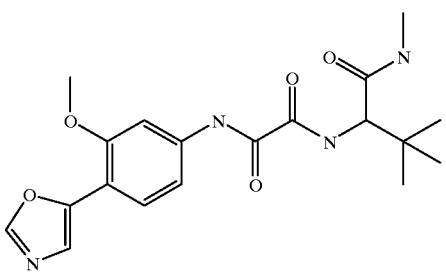 | 389.4 |
| 93. | 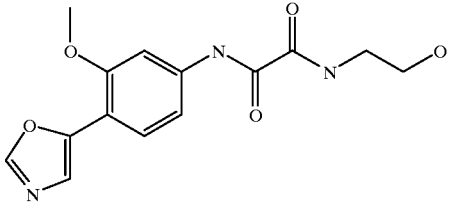 | 306.2 |
| 94. | 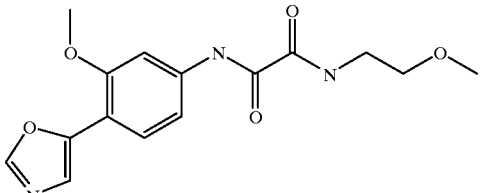 | 319.8 |
| 95. | 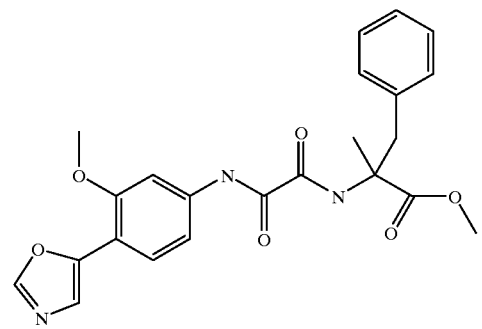 | 438.0 |
| 96. | 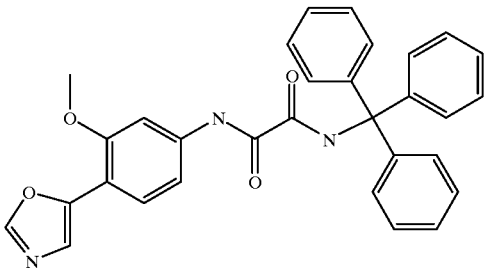 | 504.2 |

TABLE 3-continued

| Example | Structure | MS (ES) |
|---|---|---|
| 97. | 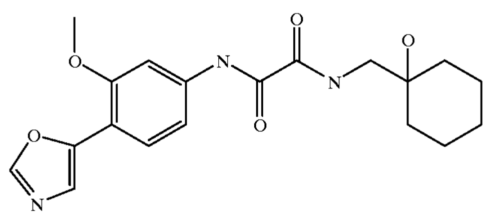 | 374.0 |
| 98. | 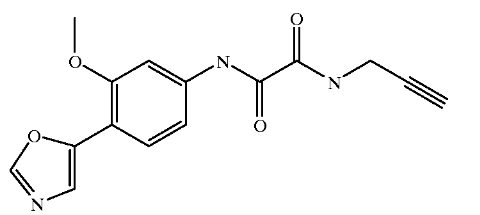 | 299.8 |
| 99. | 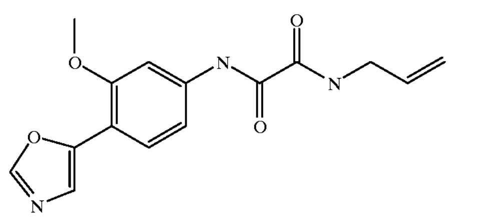 | 302.2 |
| 100. | 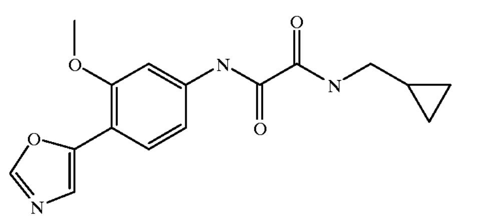 | 316.2 |
| 101. | 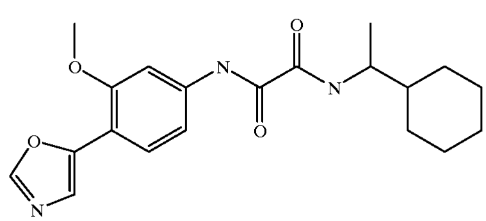 | 372.0 |
| 102. | 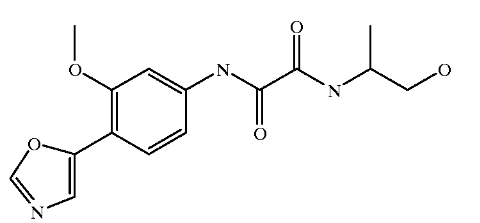 | 319.8 |

TABLE 3-continued
| Example | Structure | MS (ES) |
|---------|-----------|---------|
| 103. | 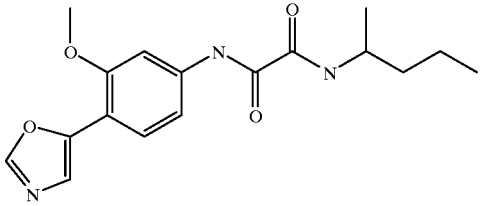 | 332.4 |
| 104. | 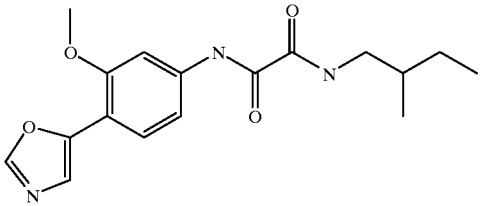 | 332.4 |
| 105. | 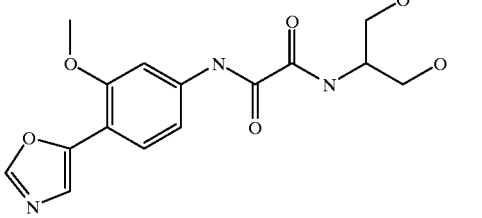 | 336.6 |
| 106. | 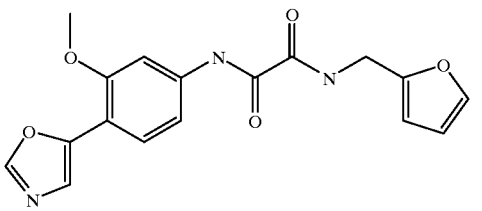 | 342.0 |
| 107. | 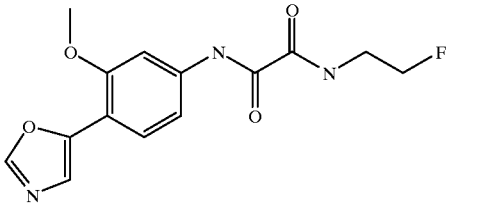 | 308.0 |
| 108. | 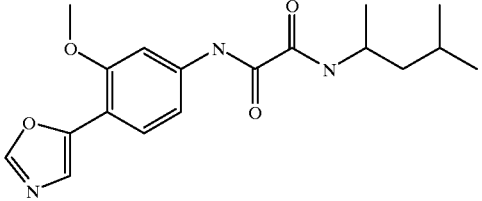 | 345.8 |

TABLE 3-continued

| Example | Structure | MS (ES) |
|---|---|---|
| 109. | 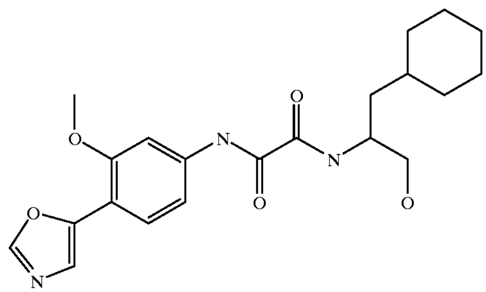 | 402.0 |
| 110. | 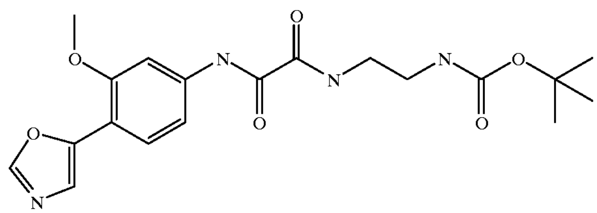 | 405.2 |
| 111. | 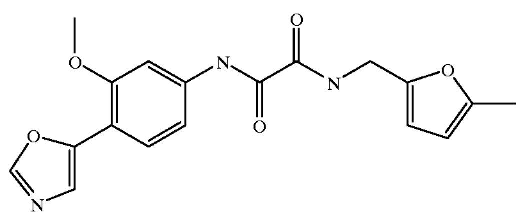 | 356.0 |
| 112. | 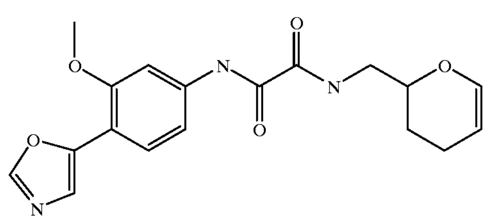 | 358.2 |
| 113. | 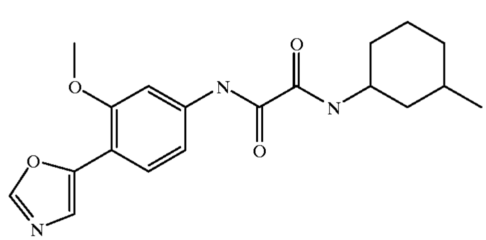 | 358.2 |
| 114. | 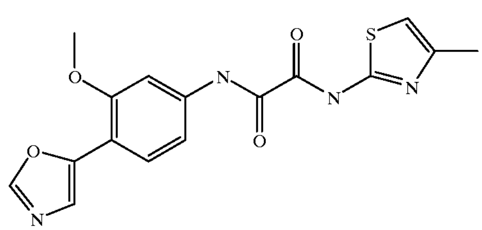 | 359.2 |

TABLE 3-continued

| Example | Structure | MS (ES) |
|---|---|---|
| 115. | 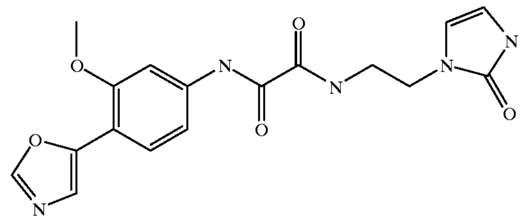 | 374.0 |
| 116. | 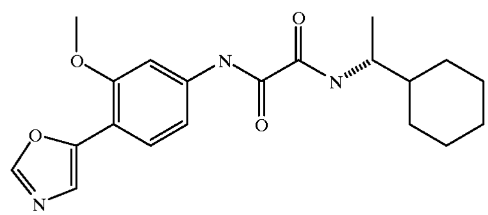 | 372.0 |
| 117. | 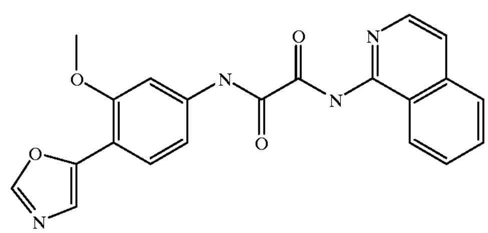 | 389.2 |
| 118. | 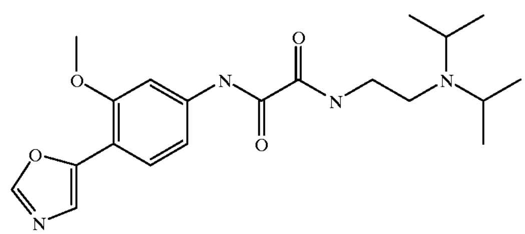 | 389.4 |
| 119. | 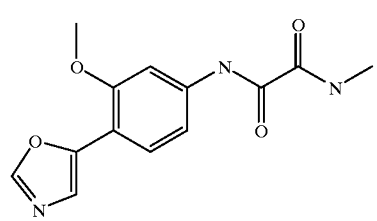 | 276.0 |
| 120. | 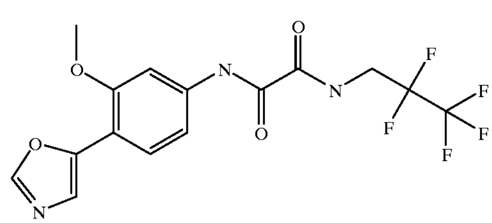 | 394 (M+; EI) |

TABLE 3-continued

| Example | Structure | MS (ES) |
|---|---|---|
| 121. | 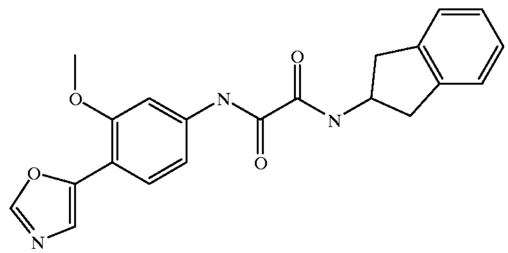 | 378.4 |
| 122. | 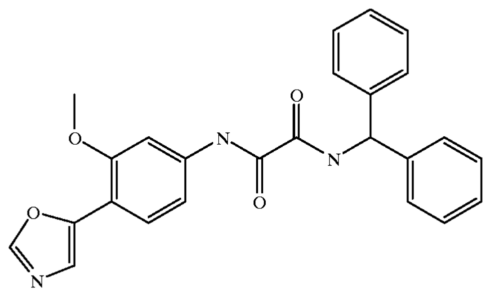 | 428 (M+; EI) |
| 123. | 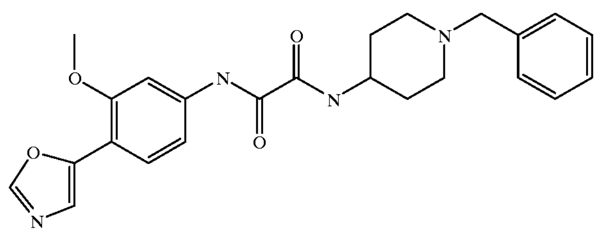 | 435.2 |
| 124. | 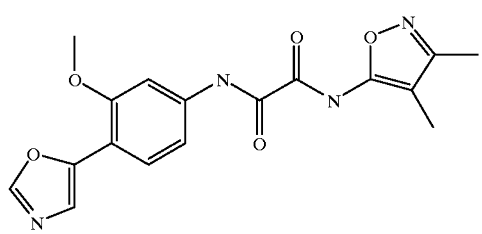 | 357.2 |
| 125. | 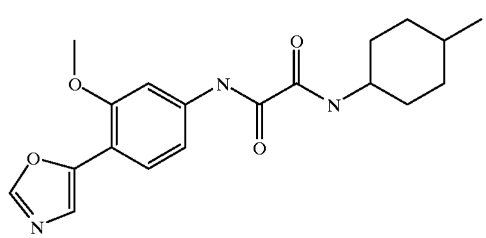 | 358.2 |
| 126. | 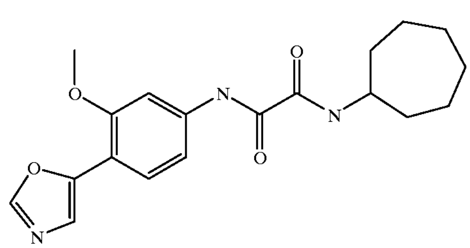 | 358.2 |

TABLE 3-continued

| Example | Structure | MS (ES) |
|---------|-----------|---------|
| 127. | 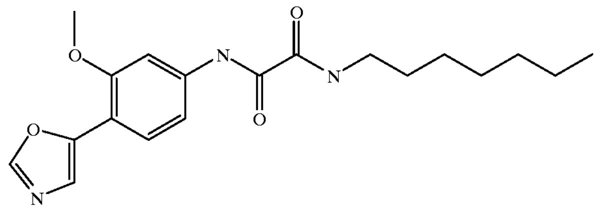 | 360.2 |
| 128. | 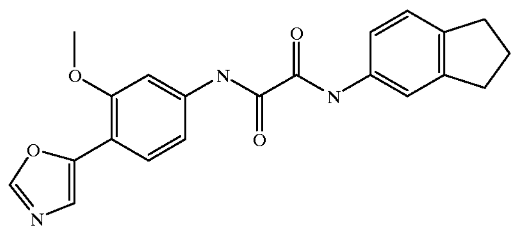 | 378.4 |
| 129. | 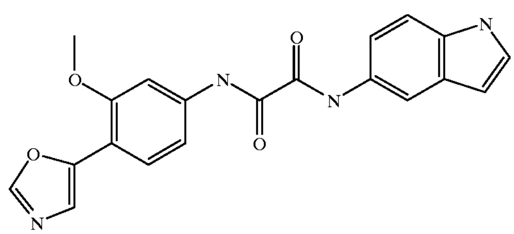 | 377.4 |
| 130. | 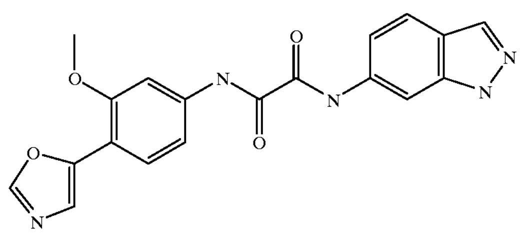 | 378.4 |
| 131. | 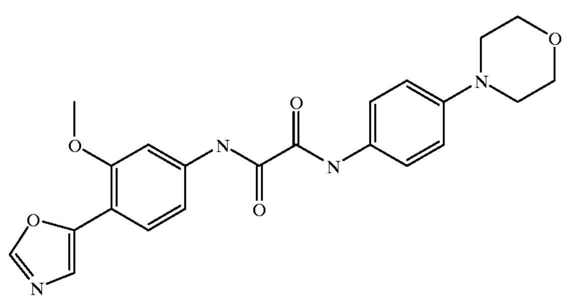 | 423 |
| 132. | 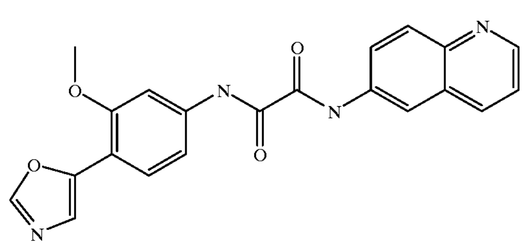 | 389.4 |

TABLE 3-continued

| Example | Structure | MS (ES) |
|---|---|---|
| 133. | 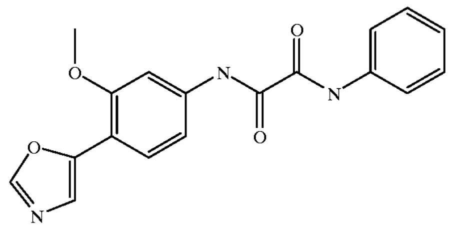 | 338.2 |
| 134. | 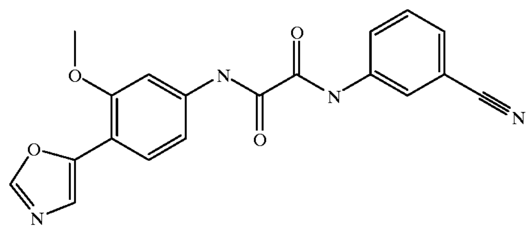 | 363.4 |
| 135. | 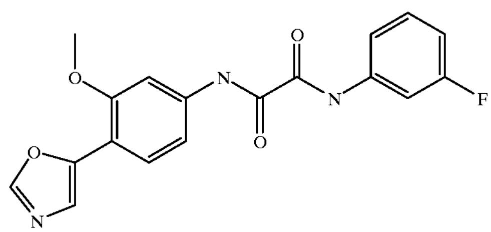 | 356 |
| 136. | 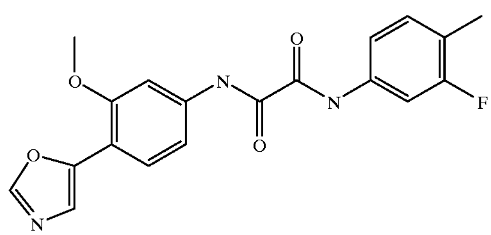 | 370 |
| 137. | 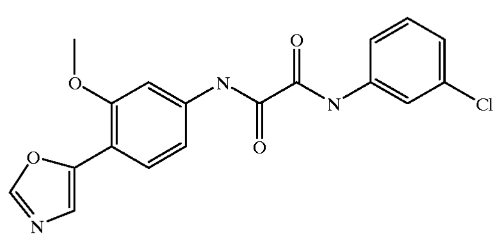 | 371.8 |
| 138. | 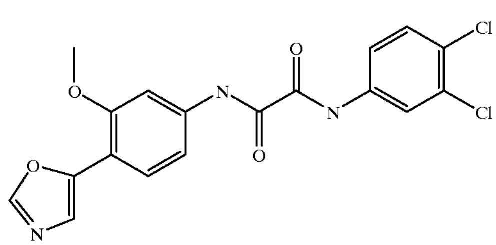 | 406.2 |

TABLE 3-continued

| Example | Structure | MS (ES) |
|---|---|---|
| 139. | 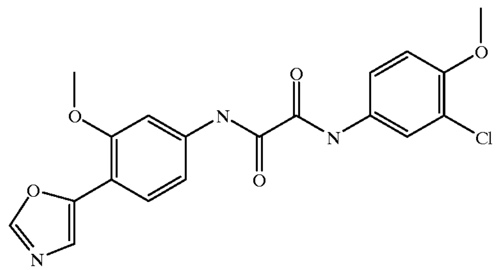 | 402.2 |
| 140. | 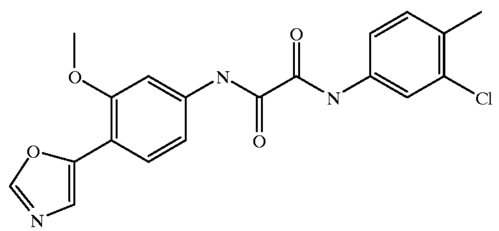 | 386.2 |
| 141. | 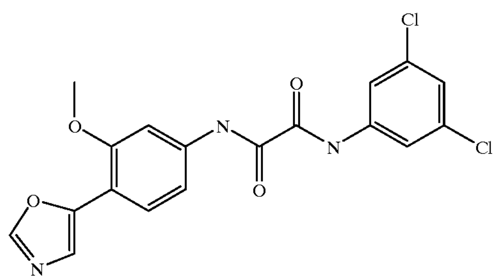 | 406.2 |
| 142. | 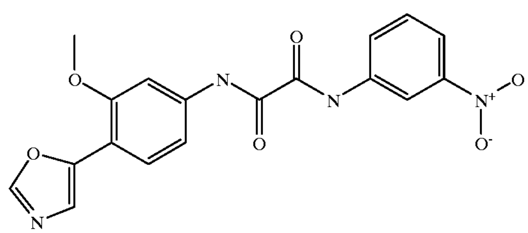 | 383.2 |
| 143. | 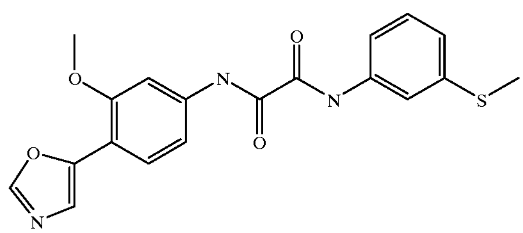 | 384 |
| 144. | 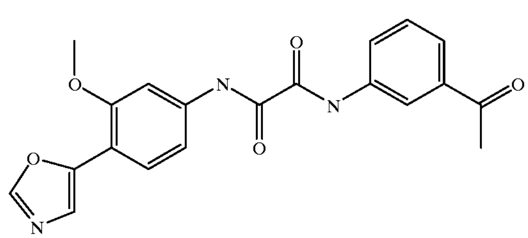 | 380.2 |

TABLE 3-continued

| Example | Structure | MS (ES) |
|---------|-----------|---------|
| 145. | 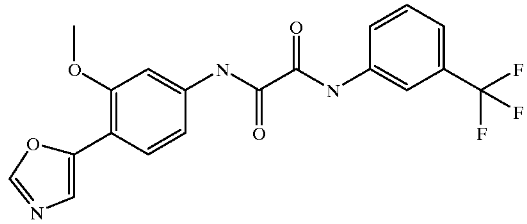 | 406.2 |
| 146. | 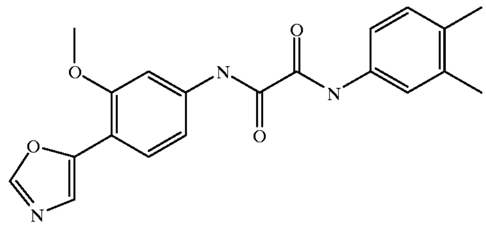 | 366.2 |
| 147. | 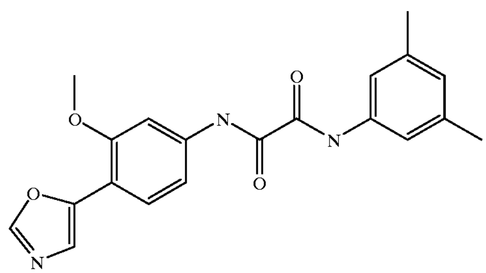 | 366.2 |
| 148. | 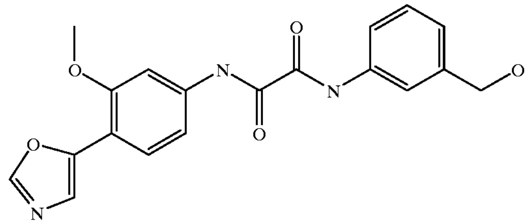 | 368.2 |
| 149. | 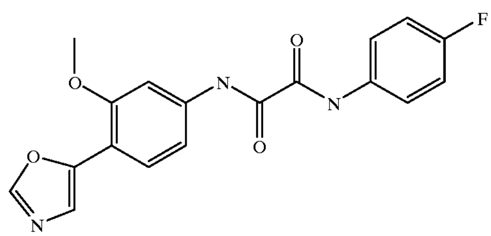 | 356 |
| 150. | 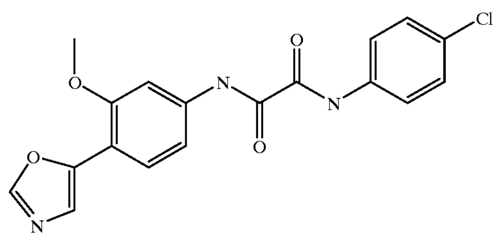 | 371.8 |

TABLE 3-continued

| Example | Structure | MS (ES) |
|---|---|---|
| 151. | 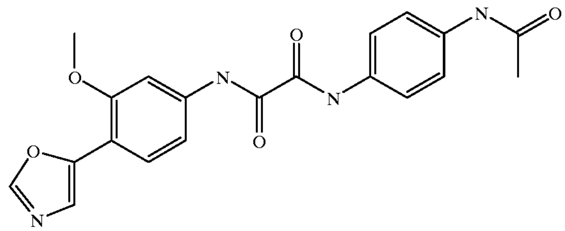 | 395 |
| 152. | 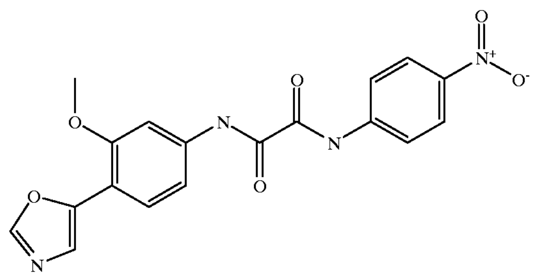 | 383.2 |
| 153. | 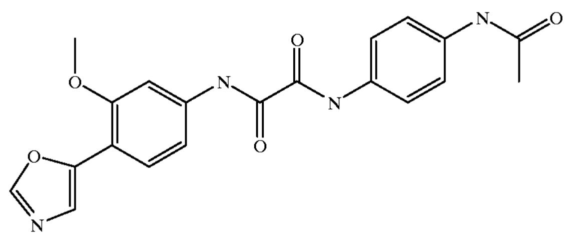 | 409.4 |
| 154. | 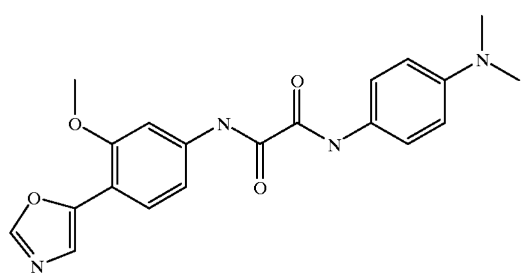 | 380.8 |
| 155. | 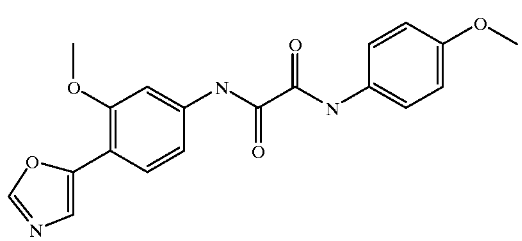 | 368.2 |
| 156. | 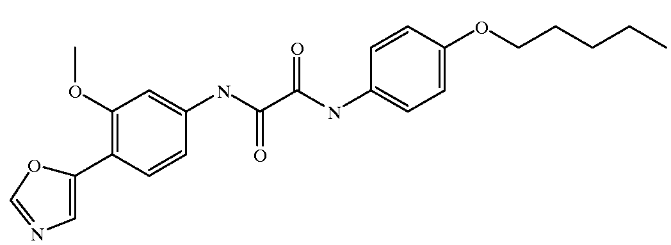 | 424.2 |

TABLE 3-continued

| Example | Structure | MS (ES) |
|---|---|---|
| 157. | 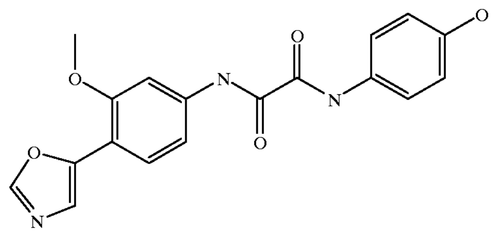 | 354.2 |
| 158. | 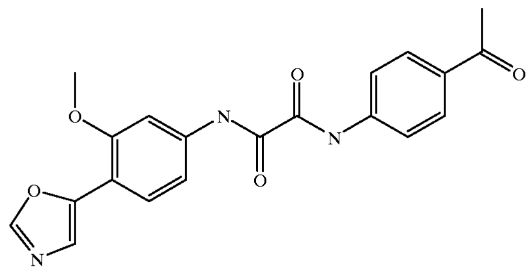 | 380.2 |
| 159. | 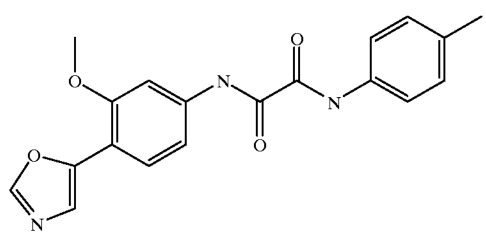 | 352.4 |
| 160. | 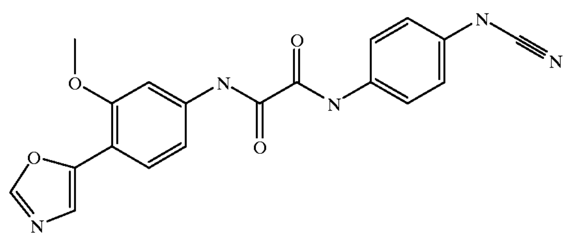 | 377.4 |
| 161. | 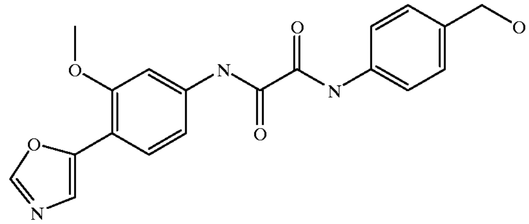 | 368.2 |
| 162. | 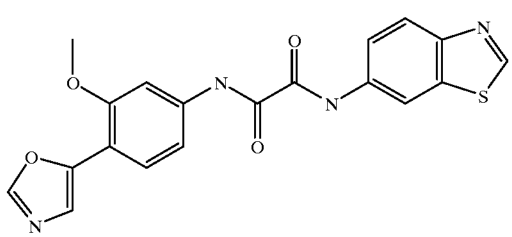 | 395 |

TABLE 3-continued

| Example | Structure | MS (ES) |
|---|---|---|
| 163. | 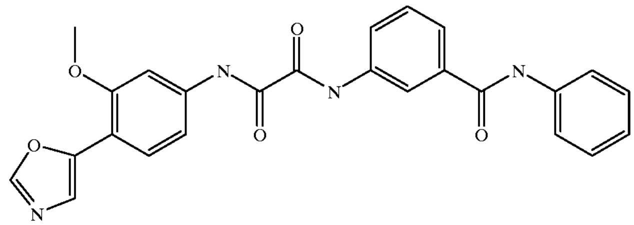 | 457.4 |
| 164. | 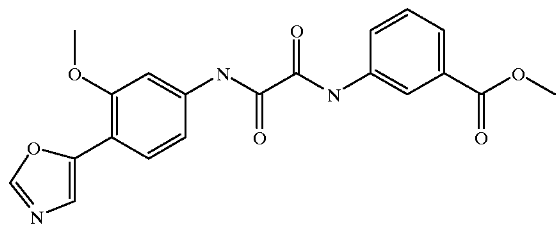 | 396 |
| 165. | 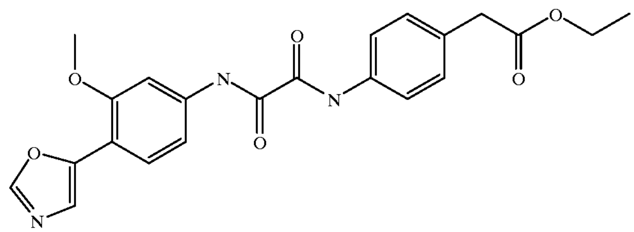 | 424 |
| 166. | 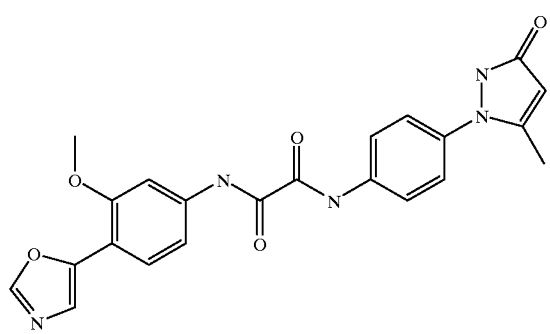 | 434.2 |
| 167. | 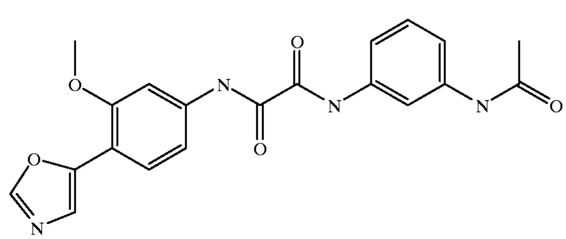 | 395 |
| 168. | 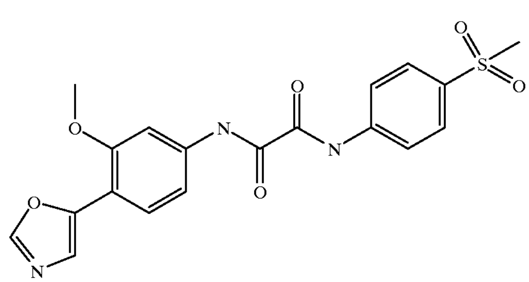 | 416.4 |

TABLE 3-continued

| Example | Structure | MS (ES) |
|---------|-----------|---------|
| 169. | 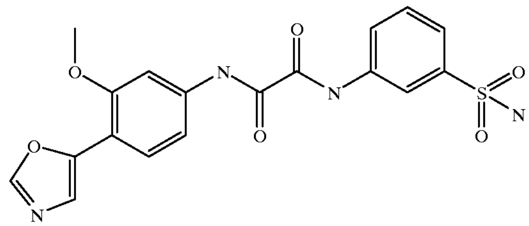 | 417.4 |
| 170. | 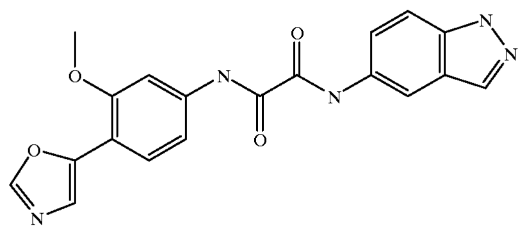 | 378.4 |
| 171. | 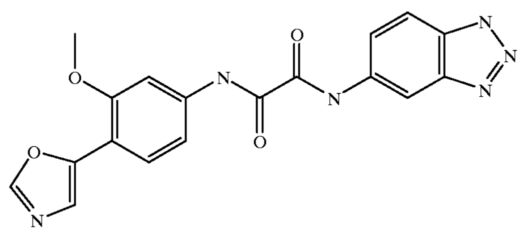 | 379.2 |
| 172. | 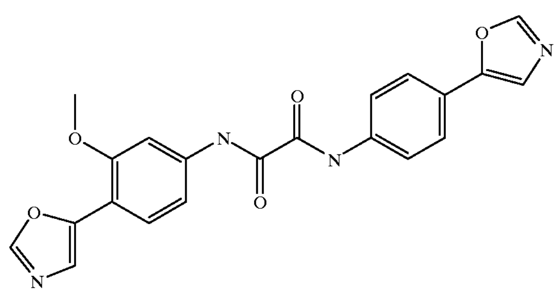 | 405.2 |
| 173. | 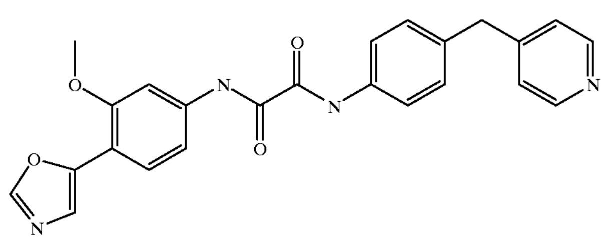 | 428.8 |
| 174. | 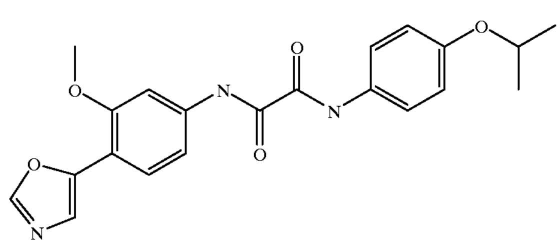 | 396 |

TABLE 3-continued
| Example | Structure | MS (ES) |
|---|---|---|
| 175. | 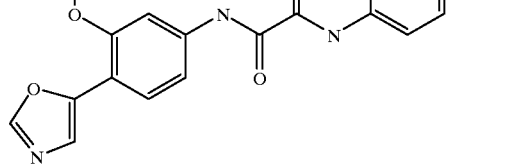 | 406.2 |
| 176. | 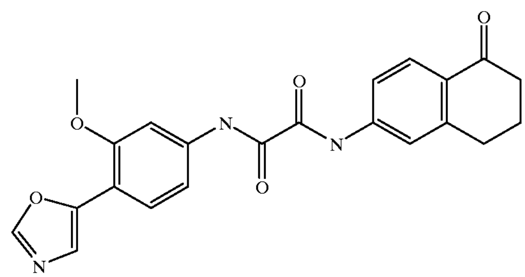 | 406.2 |
| 177. | 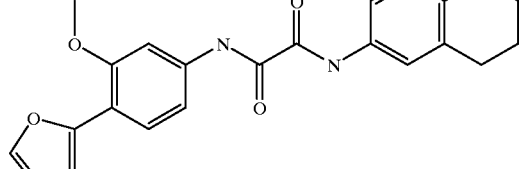 | 394.2 |
| 178. | 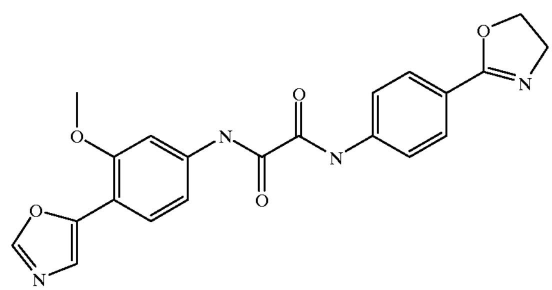 | 407 |
| 179. | 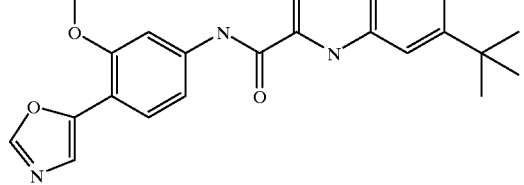 | 507.2 |

TABLE 3-continued

| Example | Structure | MS (ES) |
|---|---|---|
| 180. | 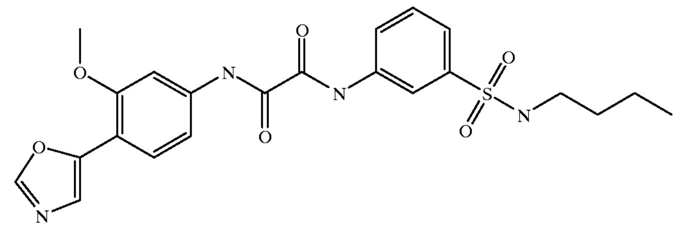 | 473.2 |
| 181. | 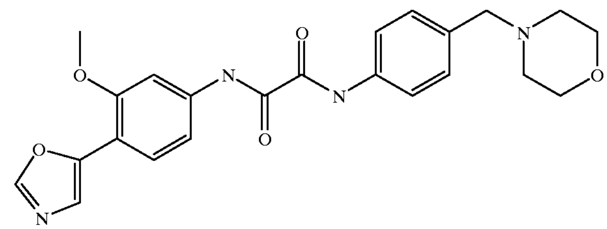 | 451.2 |
| 182. | 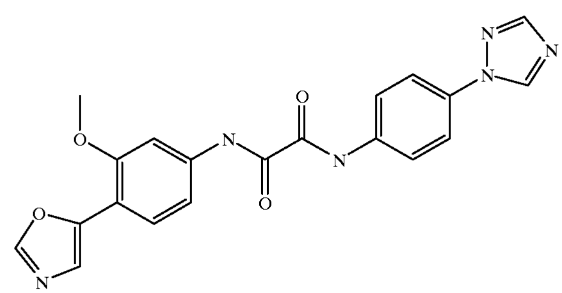 | 405.2 |
| 183. | 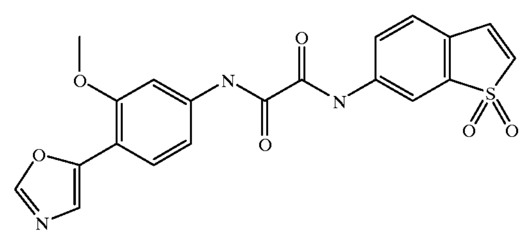 | 426 |
| 184. | 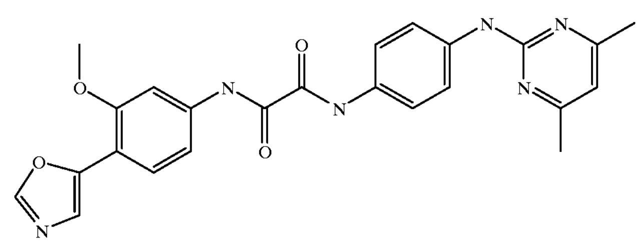 | 459.2 |
| 185. | 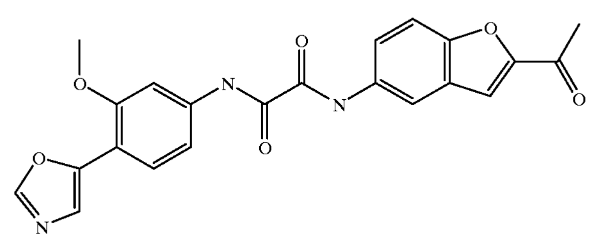 | 420.2 |

TABLE 3-continued

| Example | Structure | MS (ES) |
|---|---|---|
| 186. | 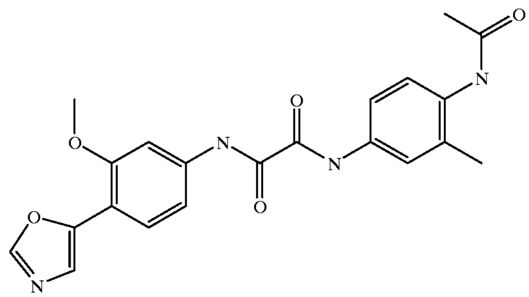 | 409.4 |
| 187. | 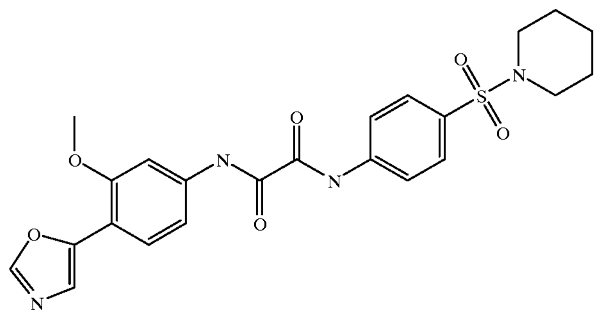 | 485.4 |
| 188. | 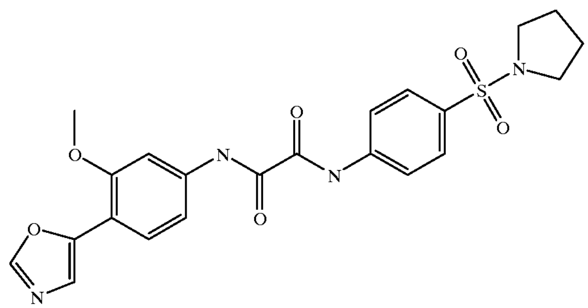 | 471.6 |
| 189. | 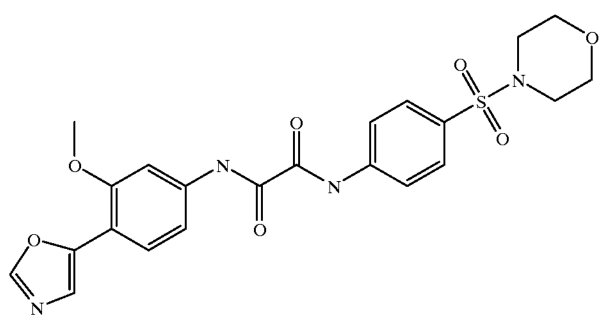 | 487.2 |
| 190. | 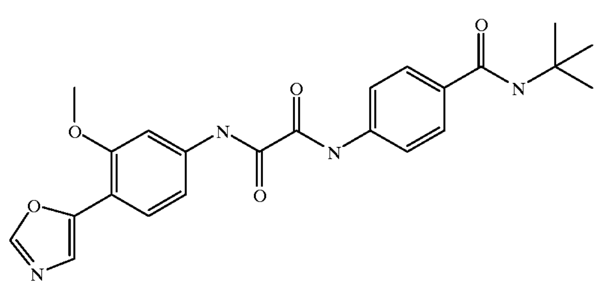 | 437.2 |

TABLE 3-continued

| Example | Structure | MS (ES) |
|---|---|---|
| 191. | 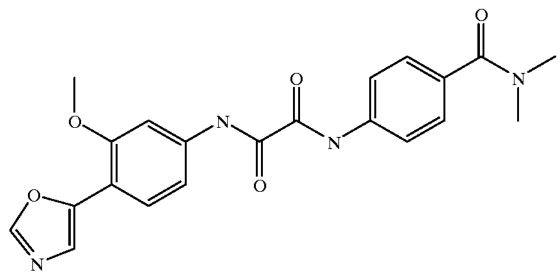 | 409.4 |
| 192. | 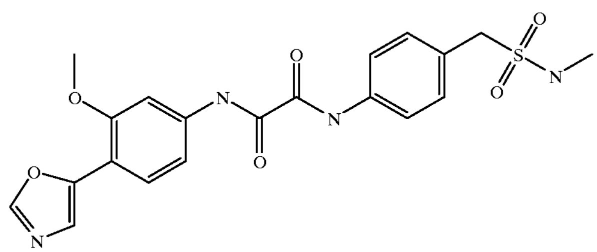 | 445.2 |
| 193. | 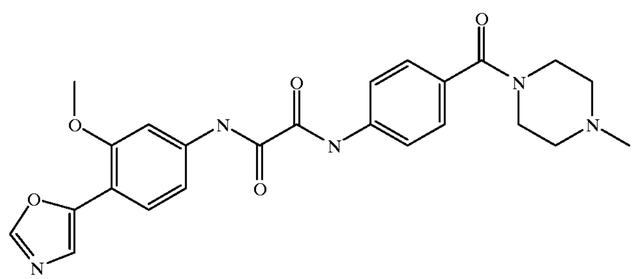 | 464 |

EXAMPLES 194–214

In a manner analogous to that described in Example 4, starting with N-[3-(aminomethyl)phenyl]-N'-[3-methoxy-4-(5-oxazolyl)phenyl]oxalamide trifluoroacetate (prepared as descibed in Example 3) and the appropriate carboxylic acid derivative the compounds shown in Table 5 also were prepared:

TABLE 5

| Example | Structure | MS (ES) |
|---|---|---|
| 194. | 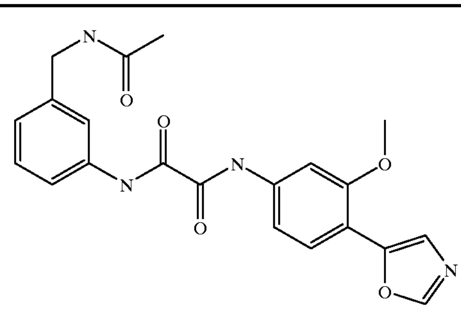 | 409.1 |

TABLE 5-continued

| Example | Structure | MS (ES) |
|---|---|---|
| 195. | 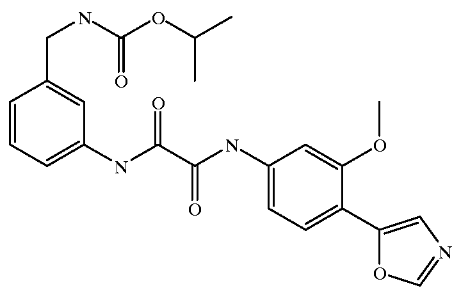 | 453.0 |
| 196. | 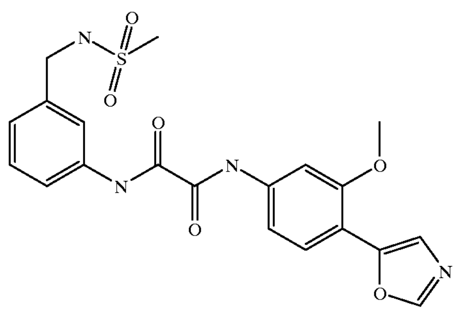 | 445.0 |
| 197. | 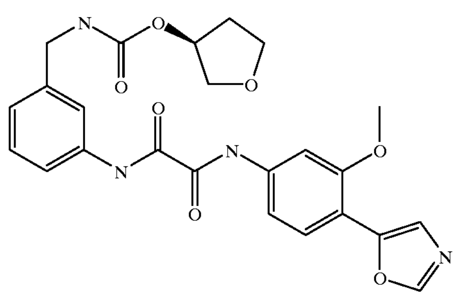 | 481.0 |
| 198. | 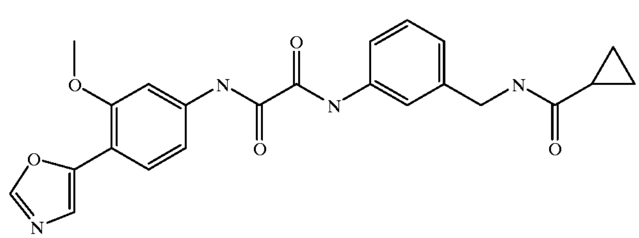 | 435.1 |
| 199. | 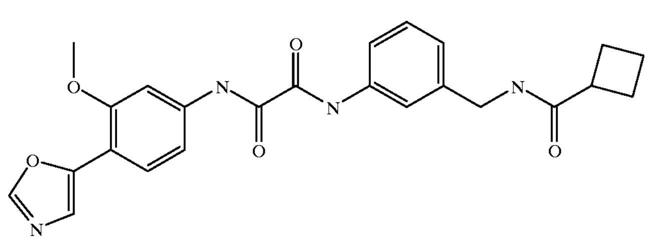 | 449.1 |

TABLE 5-continued

| Example | Structure | MS (ES) |
|---|---|---|
| 200. | 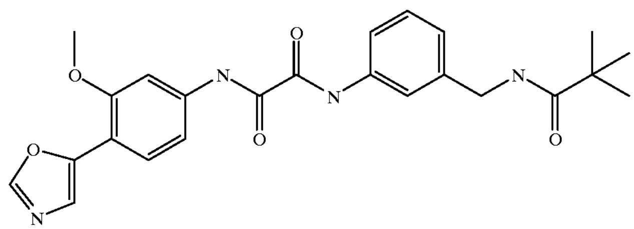 | 451.2 |
| 201. | 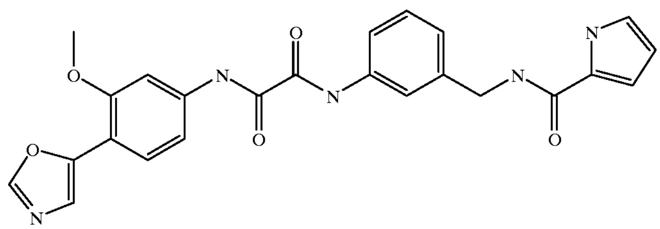 | 460.0 |
| 202. | 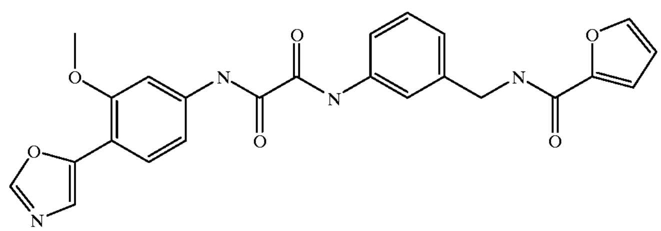 | 461.1 |
| 203. | 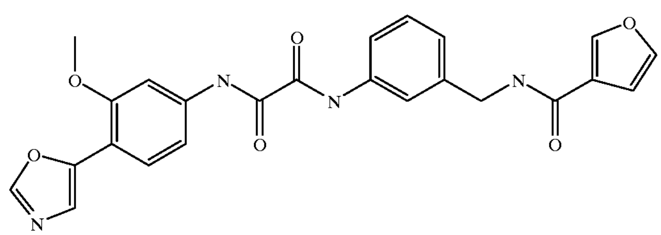 | 461.0 |
| 204. | 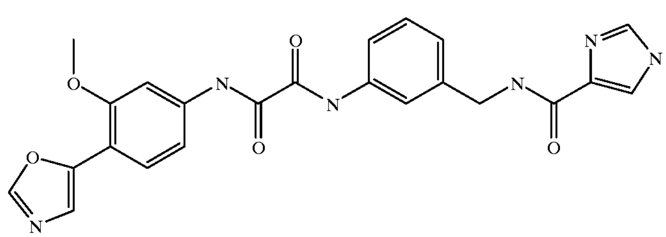 | 461.0 |
| 205. | 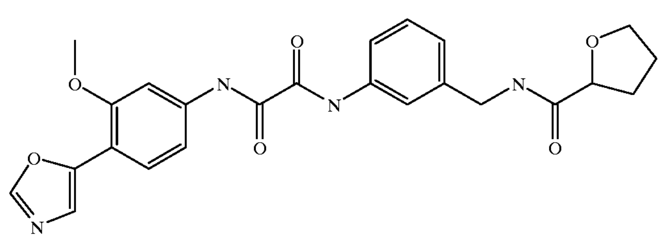 | 465.1 |

TABLE 5-continued

| Example | Structure | MS (ES) |
|---|---|---|
| 206. | 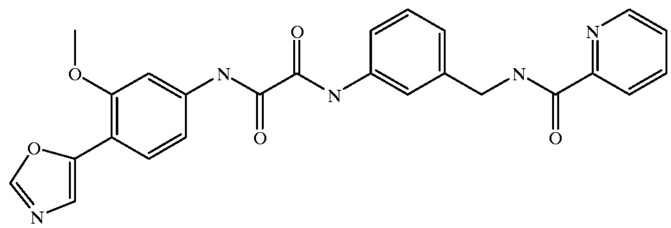 | 472.1 |
| 207. | 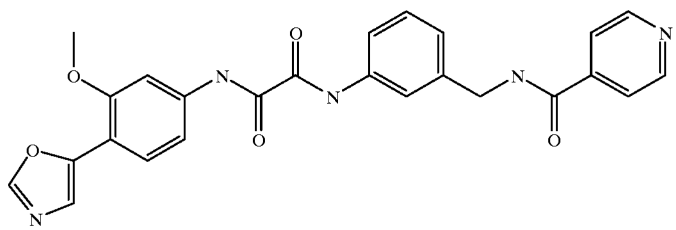 | 472.0 |
| 208. | 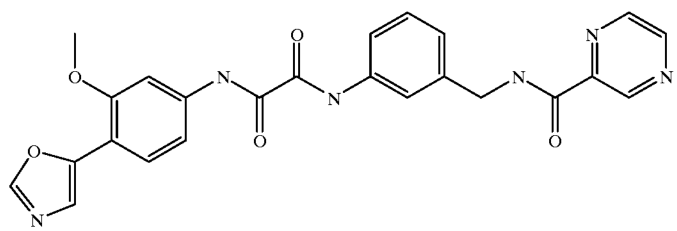 | 473.0 |
| 209. | 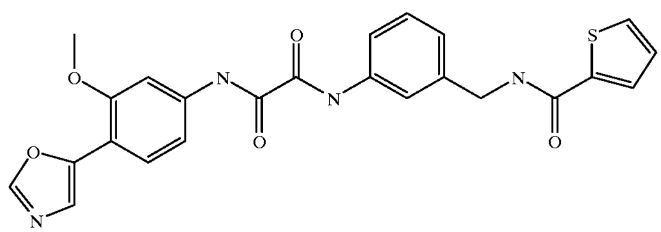 | 477.0 |
| 210. | 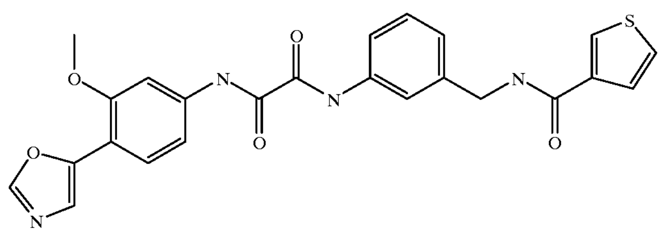 | 477.0 |
| 211. | 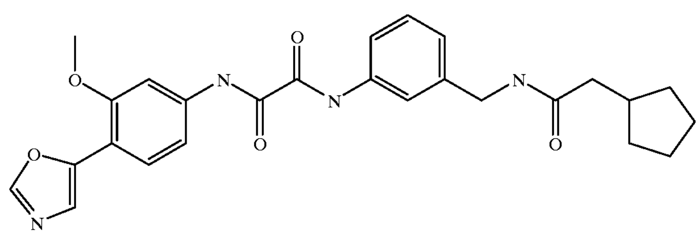 | 477.2 |

TABLE 5-continued

| Example | Structure | MS (ES) |
|---------|-----------|---------|
| 212. | 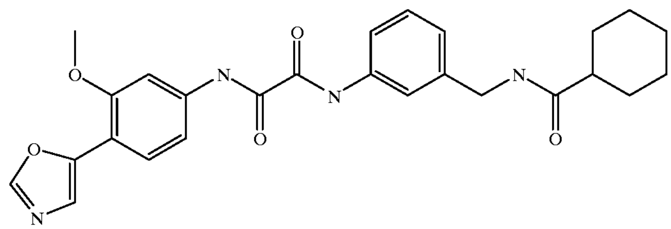 | 477.2 |
| 213. | 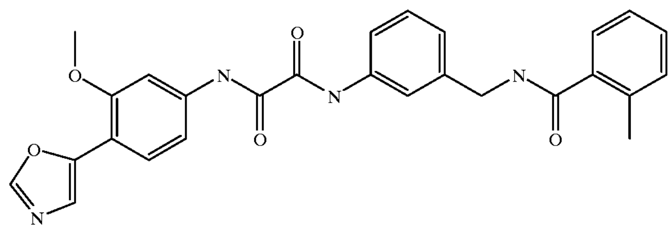 | 485.1 |
| 214. | 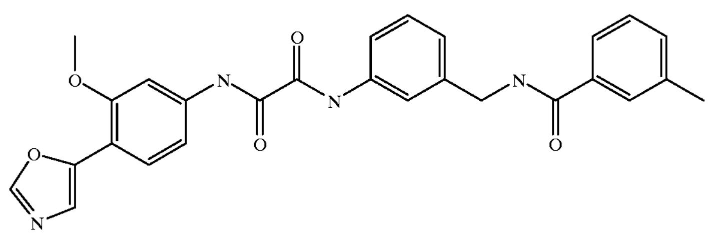 | 485.2 |

EXAMPLES 215–301

In a manner analogous to that described in Example 10, starting with N-[2-amino-1,1-dimethylethyl)-N'-(3-methoxy-4-oxazol-5-ylphenyl)oxalamide (prepared as described in Example 9) and the appropriate carboxylic acid the compounds shown in table 4 were also prepared:

TABLE 4

| Example | Structure | MS (ES) |
|---------|-----------|---------|
| 215. | 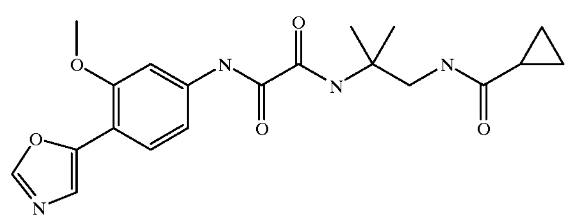 | 401.0 |
| 216. | 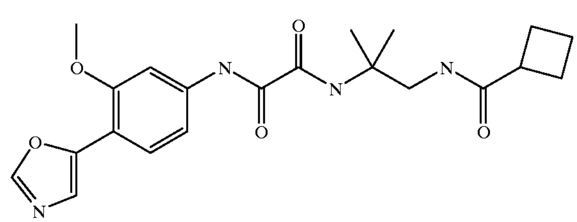 | 415.0 |

TABLE 4-continued
| Example | Structure | MS (ES) |
|---------|-----------|---------|
| 217. | 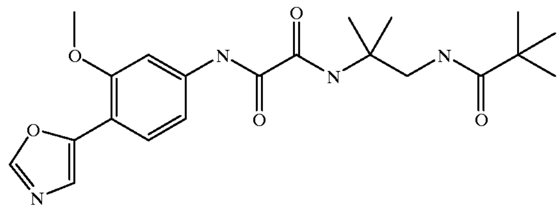 | 417.0 |
| 218. | 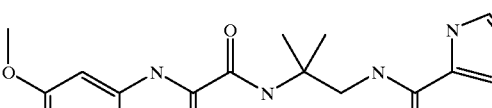 | 426.0 |
| 219. | 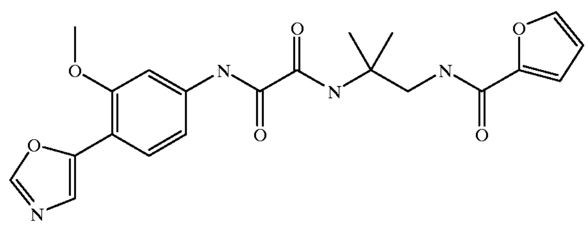 | 427.0 |
| 220. | 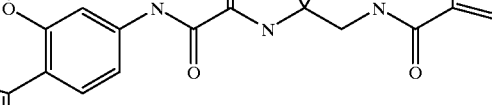 | 427.0 |
| 221. | 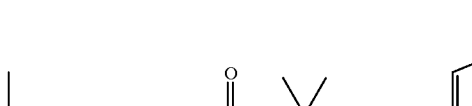 | 431.0 |
| 222. | 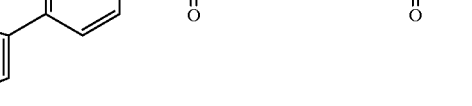 | 438.0 |

TABLE 4-continued

| Example | Structure | MS (ES) |
|---|---|---|
| 223. | 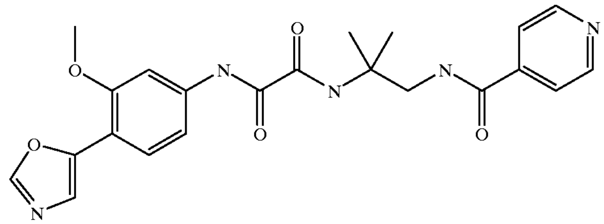 | 438.0 |
| 224. | 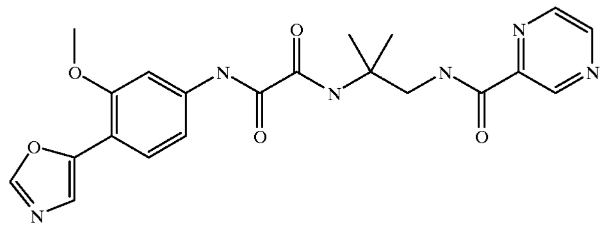 | 439.0 |
| 225. | 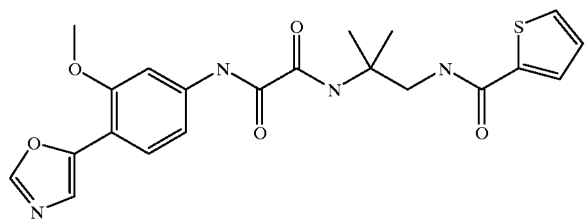 | 443.0 |
| 226. | 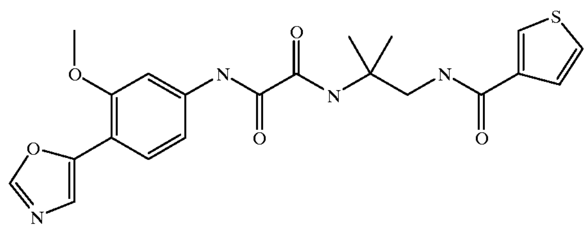 | 443.0 |
| 227. | 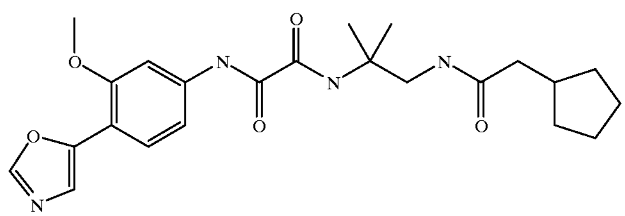 | 443.1 |
| 228. | 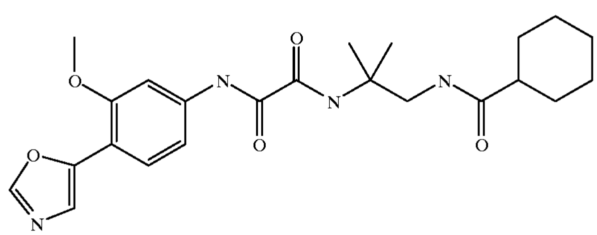 | 443.1 |

TABLE 4-continued

| Example | Structure | MS (ES) |
| --- | --- | --- |
| 229. | 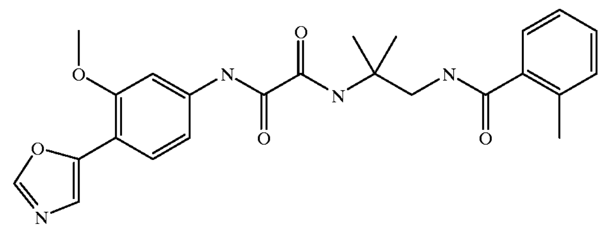 | 451.0 |
| 230. | 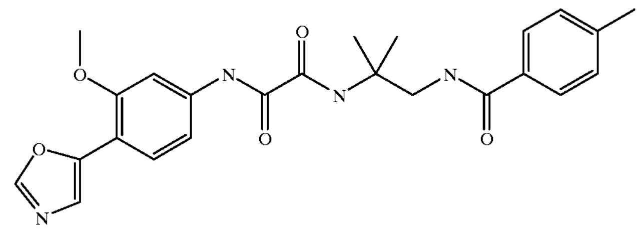 | 451.0 |
| 231. | 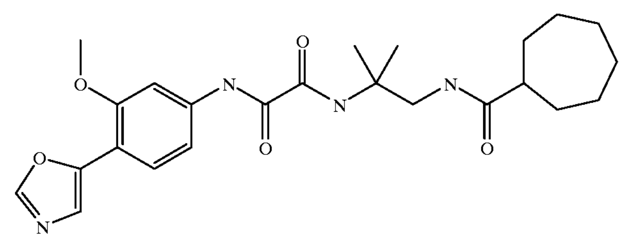 | 457.1 |
| 232. | 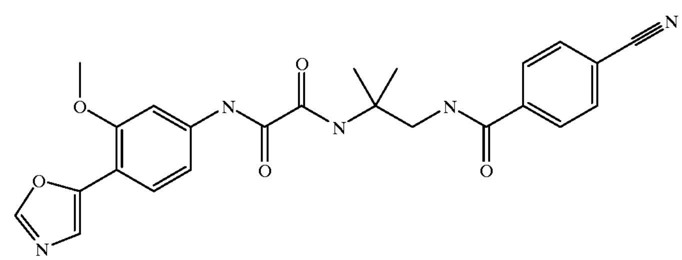 | 462.0 |
| 233. | 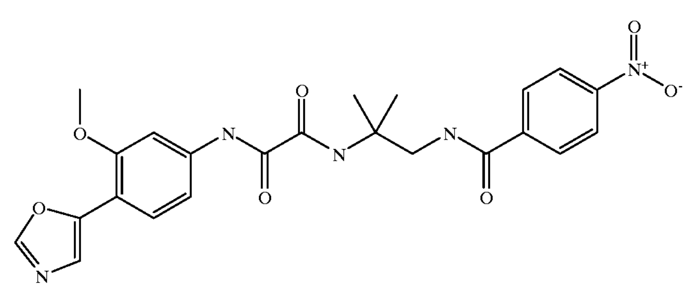 | 482.0 |
| 234. | 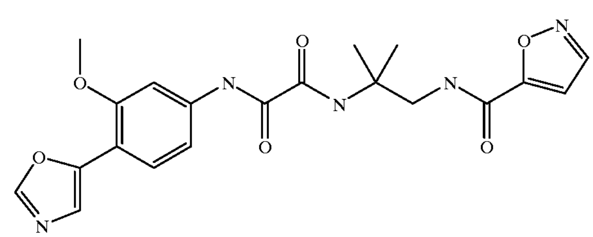 | 428.0 |

TABLE 4-continued

| Example | Structure | MS (ES) |
|---------|-----------|---------|
| 235. | 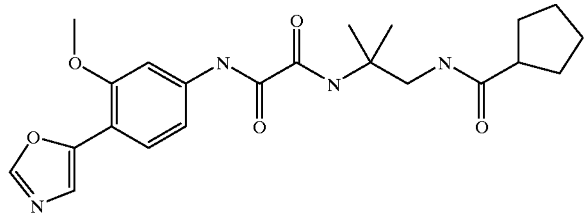 | 429.1 |
| 236. | 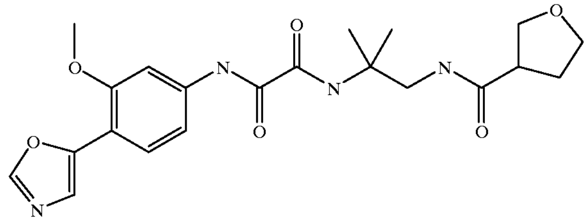 | 431.0 |
| 237. | 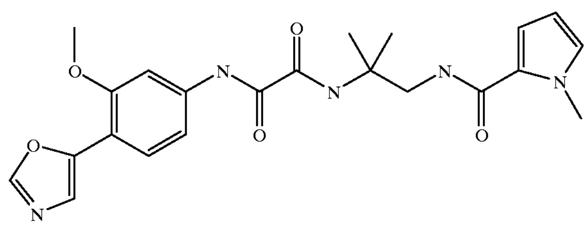 | 440.0 |
| 238. | 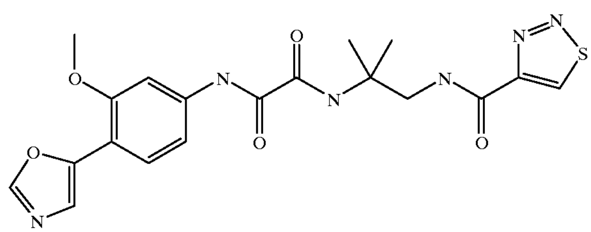 | 445.0 |
| 239. | 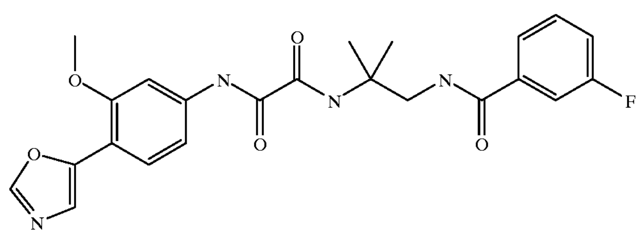 | 455.0 |
| 240. | 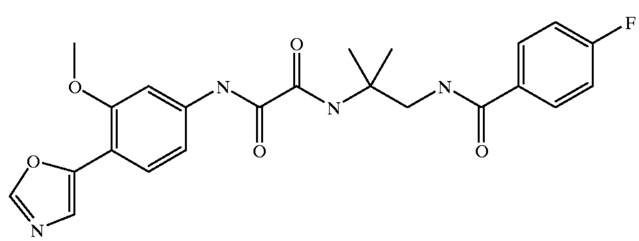 | 455.0 |

TABLE 4-continued

| Example | Structure | MS (ES) |
|---|---|---|
| 241. | 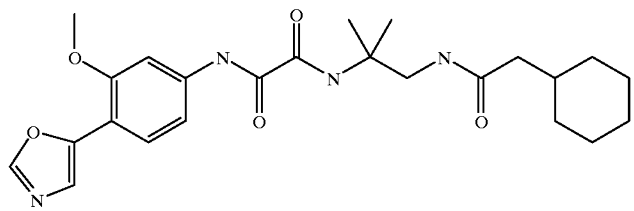 | 457.1 |
| 242. | 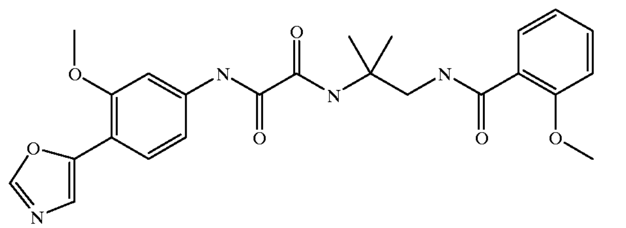 | 467.1 |
| 243. | 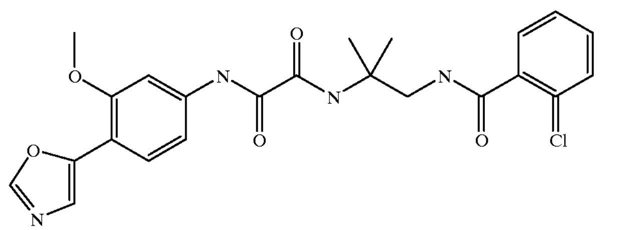 | 471.0 |
| 244. | 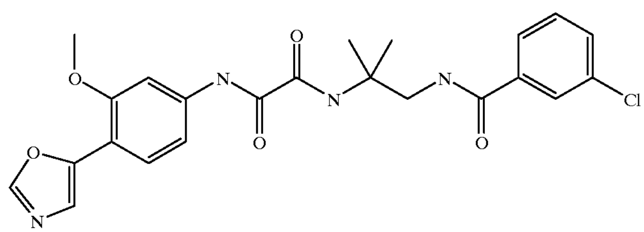 | 471.0 |
| 245. | 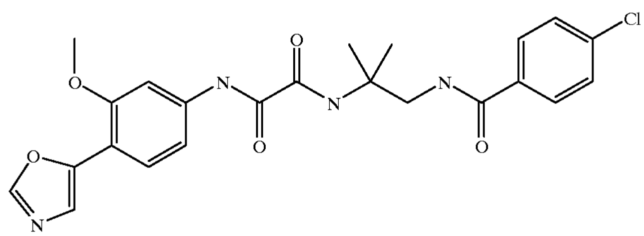 | 471.0 |
| 246. | 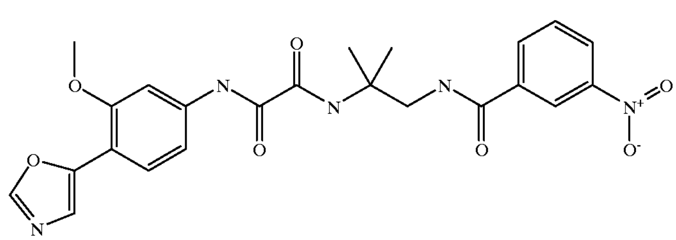 | 482.0 |

TABLE 4-continued

| Example | Structure | MS (ES) |
|---|---|---|
| 247. | 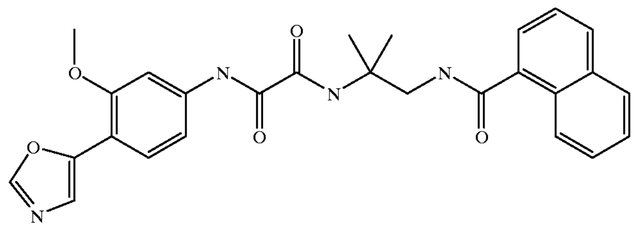 | 487.1 |
| 248. | 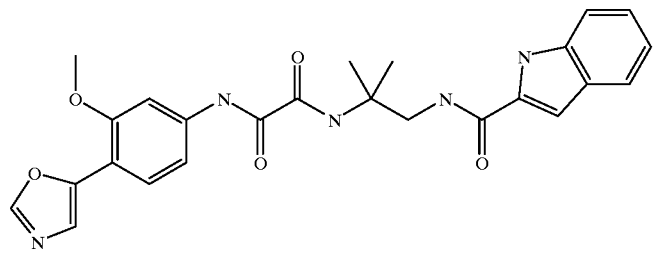 | 476.1 |
| 249. | 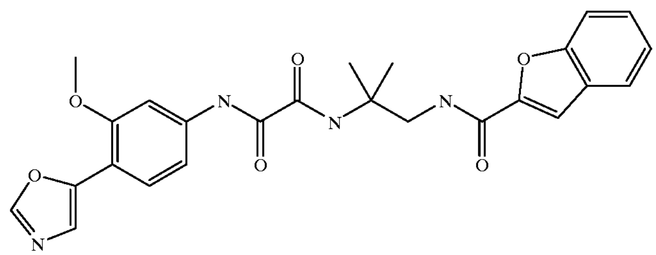 | 477.1 |
| 250. | 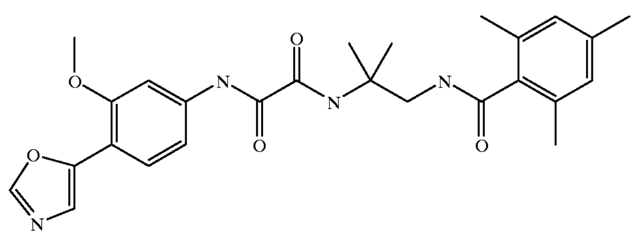 | 479.1 |
| 251. | 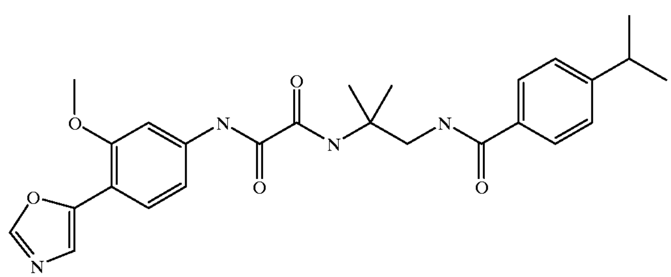 | 479.1 |
| 252. | 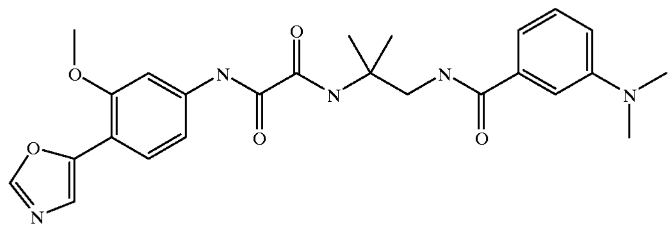 | 480.1 |

TABLE 4-continued

| Example | Structure | MS (ES) |
|---|---|---|
| 253. | 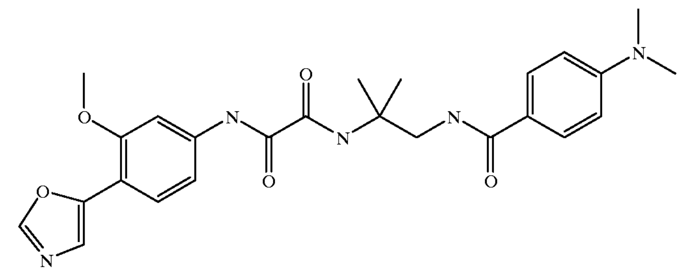 | 480.1 |
| 254. | 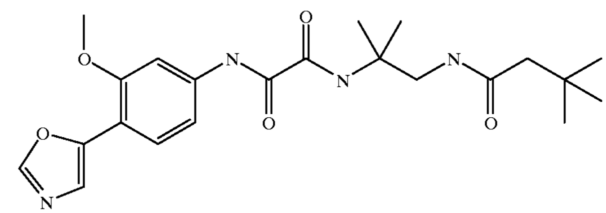 | 431.1 |
| 255. | 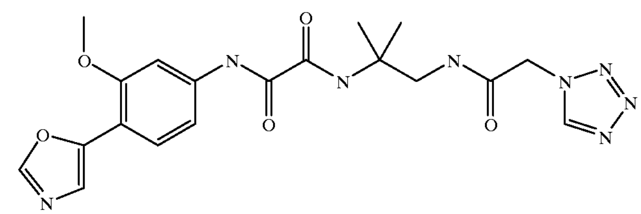 | 443.0 |
| 256. | 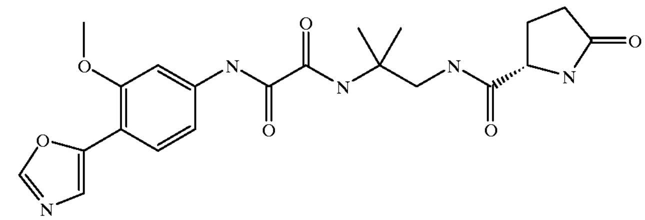 | 444.0 |
| 257. | 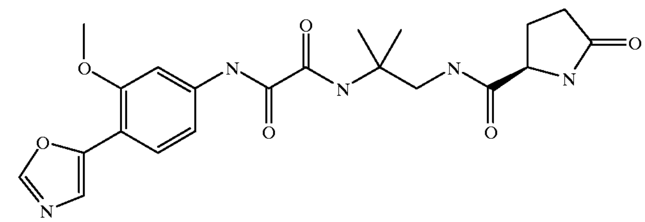 | 444.0 |
| 258. | 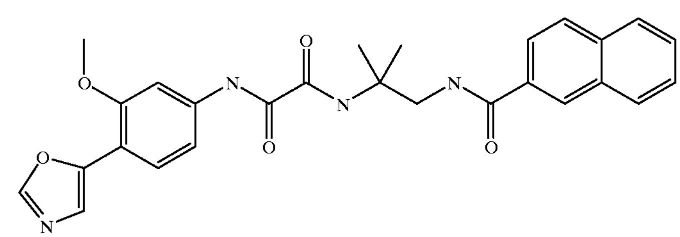 | 487.1 |

TABLE 4-continued

| Example | Structure | MS (ES) |
|---------|-----------|---------|
| 259. | 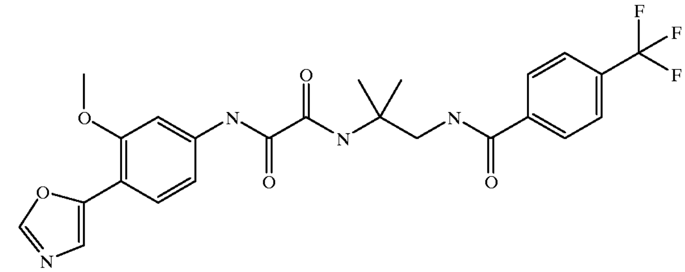 | 505.1 |
| 260. | 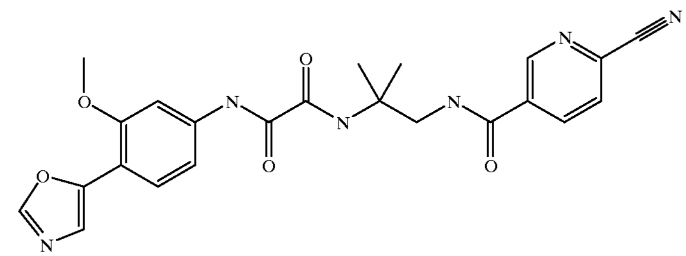 | 463.0 |
| 261. | 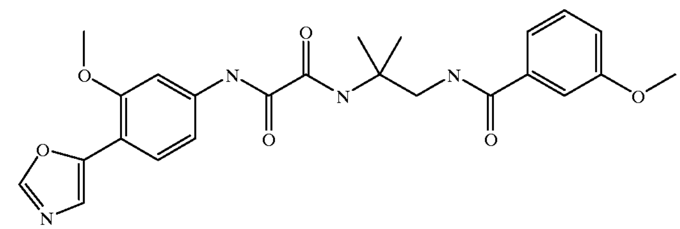 | 467.1 |
| 262. | 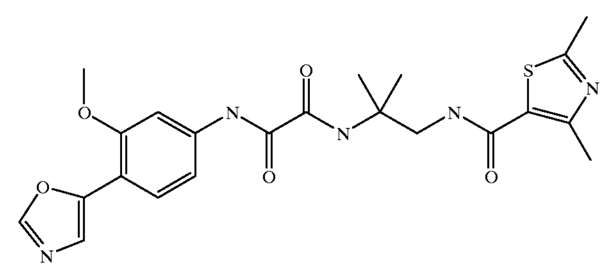 | 472.0 |
| 263. | 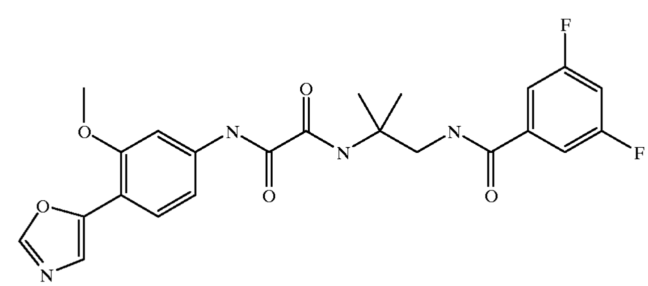 | 473.0 |
| 264. | 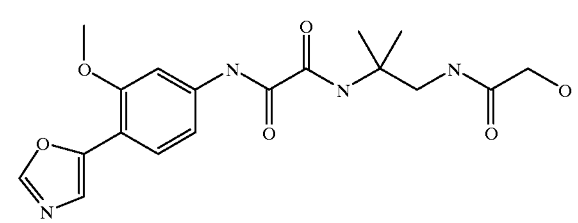 | 391.0 |

TABLE 4-continued

| Example | Structure | MS (ES) |
|---|---|---|
| 265. | 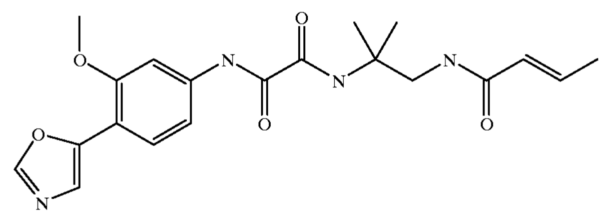 | 401.0 |
| 266. | 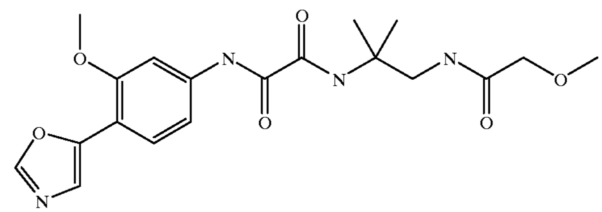 | 405.0 |
| 267. | 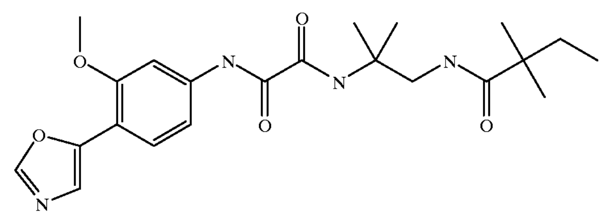 | 431.1 |
| 268. | 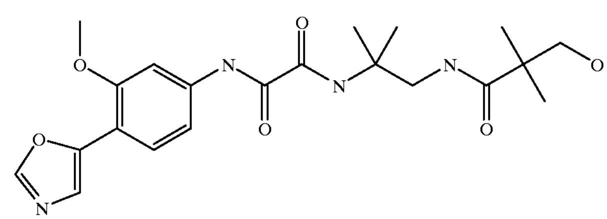 | 433.0 |
| 269. | 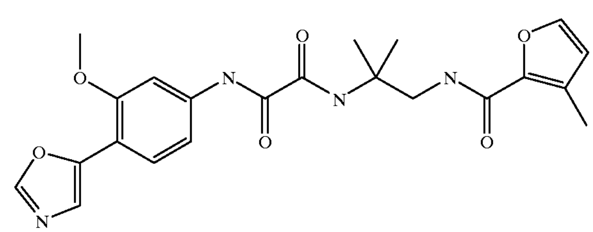 | 441.0 |
| 270. | 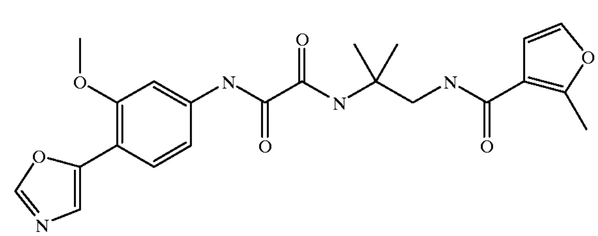 | 441.0 |

TABLE 4-continued
| Example | Structure | MS (ES) |
|---|---|---|
| 271. | 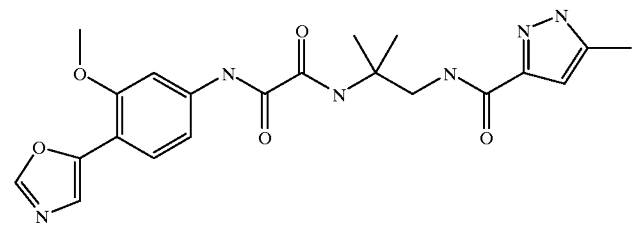 | 441.0 |
| 272. | 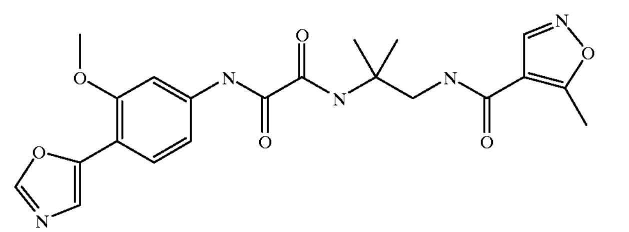 | 442.0 |
| 273. | 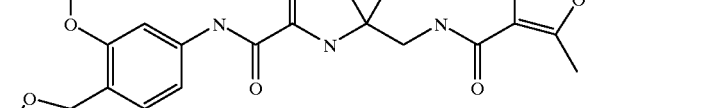 | 442.0 |
| 274. | 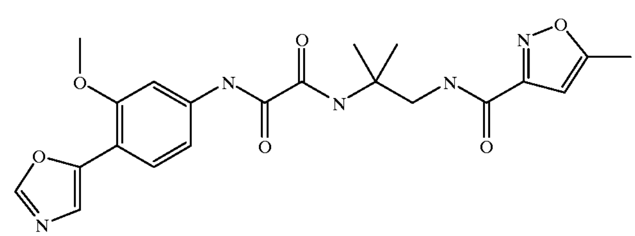 | 442.0 |
| 275. | 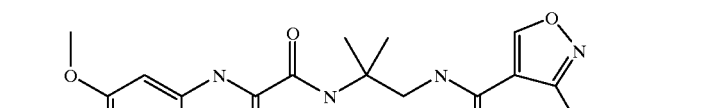 | 453.0 |
| 276. | 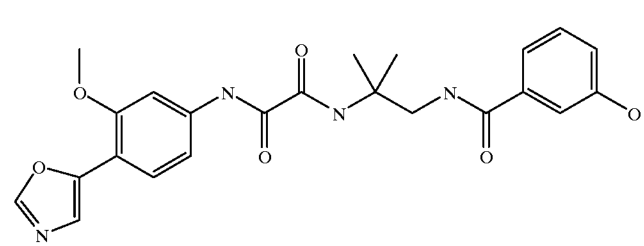 | 453.0 |

TABLE 4-continued

| Example | Structure | MS (ES) |
|---|---|---|
| 277. | 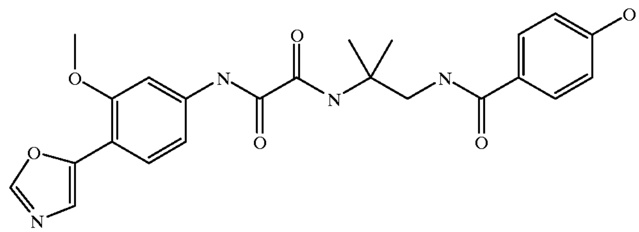 | 453.0 |
| 278. | 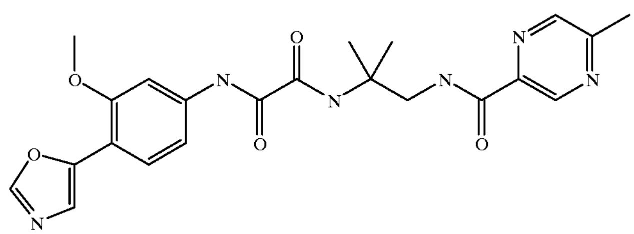 | 453.0 |
| 279. | 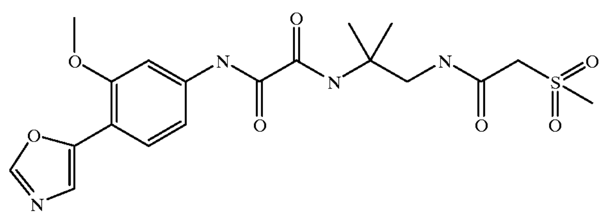 | 453.0 |
| 280. | 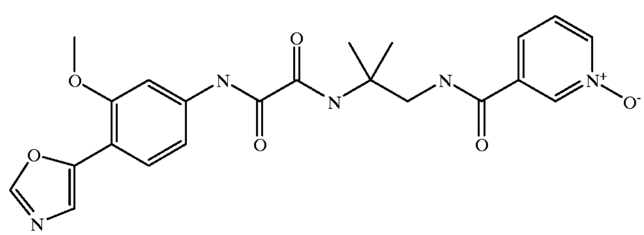 | 454.0 |
| 281. | 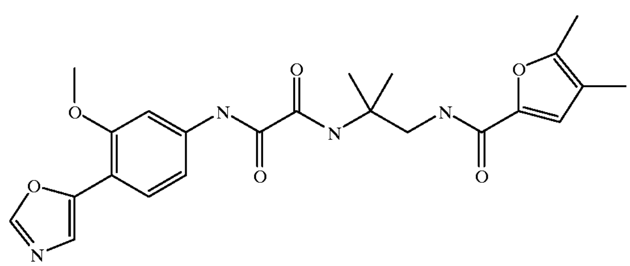 | 455.0 |
| 282. | 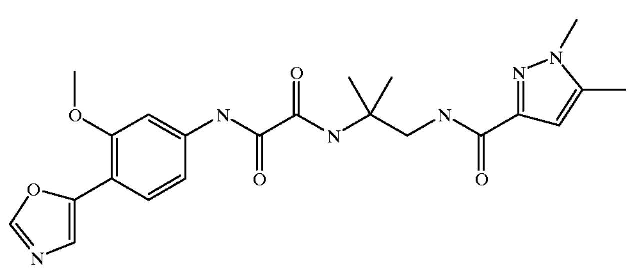 | 455.0 |

TABLE 4-continued

| Example | Structure | MS (ES) |
|---|---|---|
| 283. | 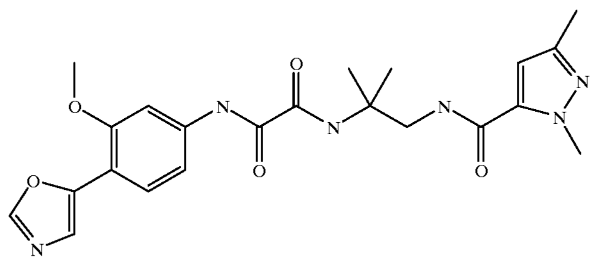 | 455.0 |
| 284. | 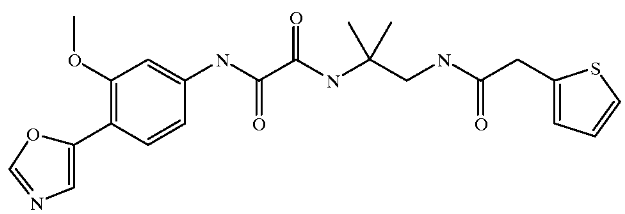 | 457.0 |
| 285. | 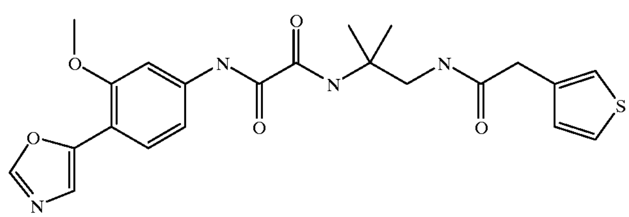 | 457.0 |
| 286. | 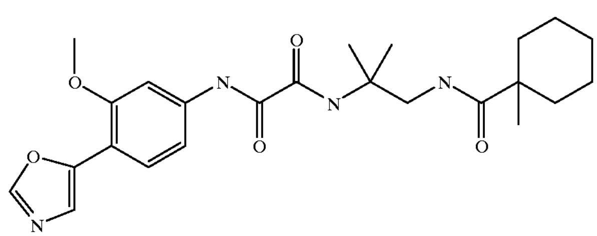 | 457.1 |
| 287. | 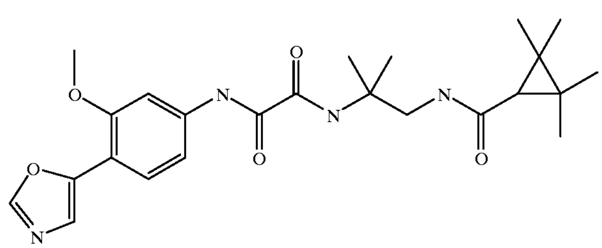 | 457.1 |
| 288. | 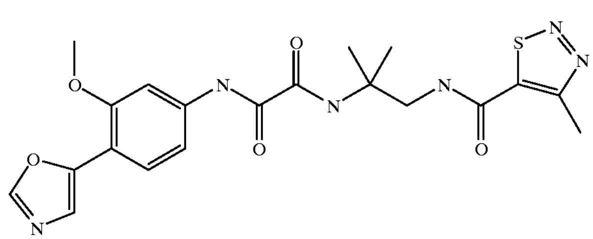 | 459.0 |

TABLE 4-continued

| Example | Structure | MS (ES) |
|---|---|---|
| 289. | 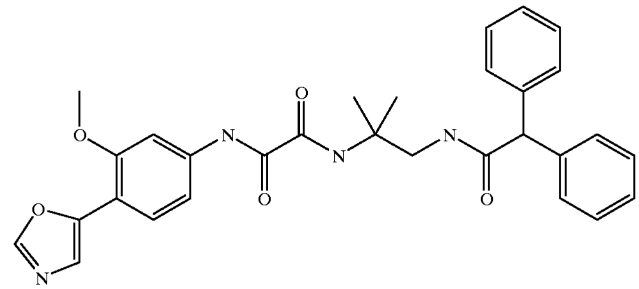 | 527.2 |
| 290. | 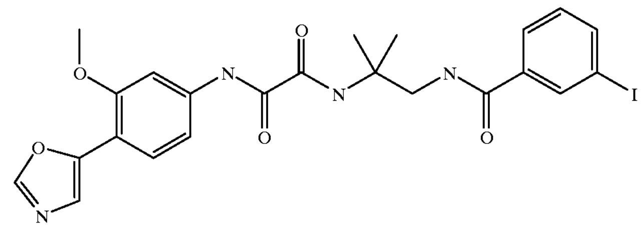 | 563.0 |
| 291. | 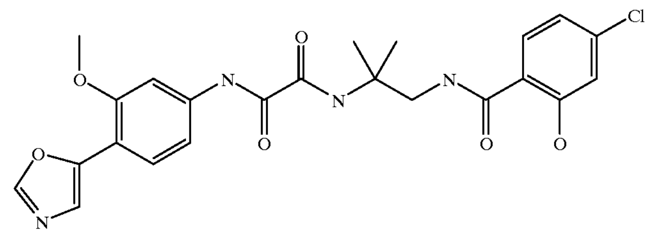 | 487.0 |
| 292. | 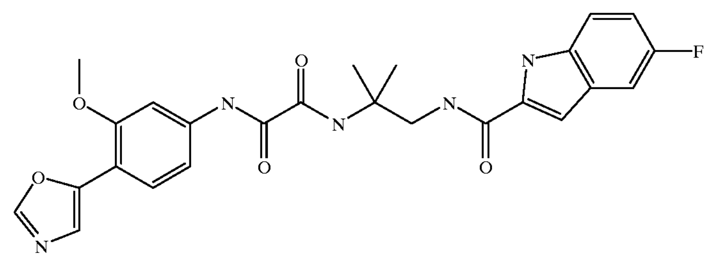 | 494.1 |
| 293. | 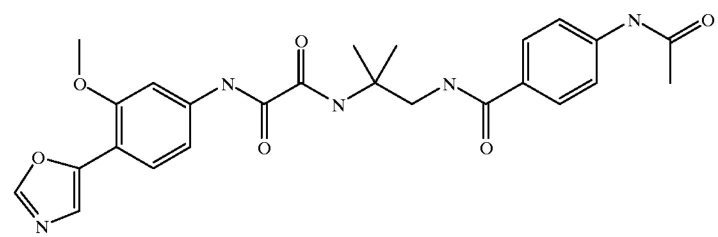 | 494.1 |
| 294. | 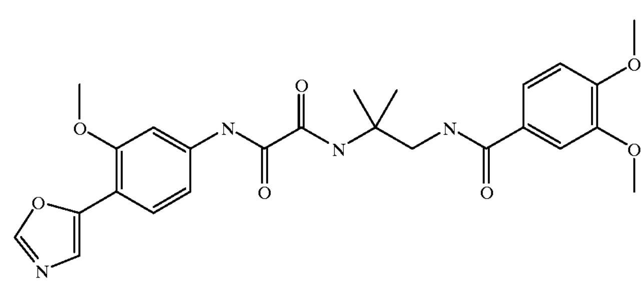 | 497.1 |

TABLE 4-continued
| Example | Structure | MS (ES) |
|---|---|---|
| 295. | 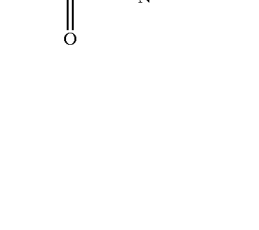 | 501.0 |
| 296. | 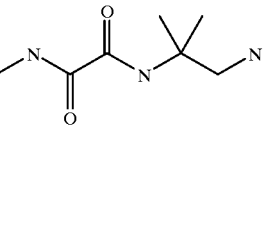 | 502.1 |
| 297. | 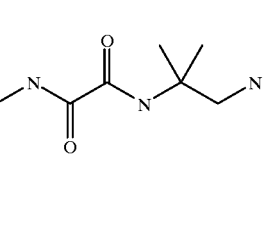 | 505.0 |
| 298. | 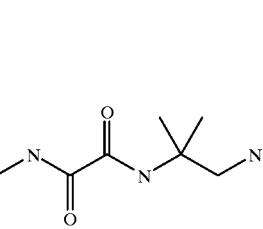 | 505.0 |
| 299. | 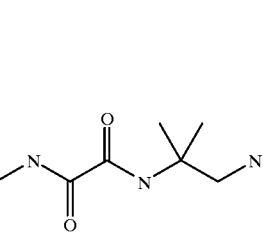 | 507.1 |
| 300. | 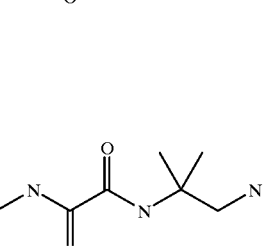 | 462.0 |

TABLE 4-continued

| Example | Structure | MS (ES) |
|---------|-----------|---------|
| 301. | 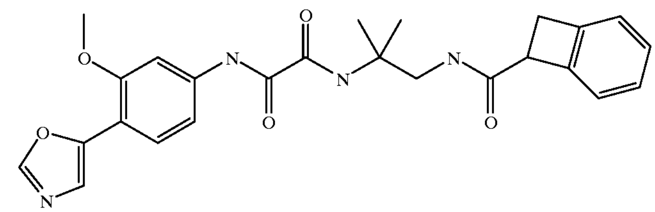 | 463.1 |

EXAMPLES 302–315; 438–458 AND 653–663

Typical methods used for the preparation of compounds of table 1c are described below:

EXAMPLE 440

N-[3-Methoxy-4-(5-oxazolyl)phenyl]-N'-[1,1-dimethyl-2-(1-oxido -4-pyridyl)ethyl]oxalamide 30 mg (0.1 mmol) of 60% 3-chloroperoxybenzoic acid were added to a stirred solution of 20 mg (0.051 mmol) of N-[3-methoxy-4-(5-oxazolyl)phenyl]-N'-[1,1-dimethyl-2-(4-pyridyl)ethyl]oxalamide in 1 ml of dichloromethane. The mixture was stirred for 1 hour then diluted with ethyl acetate, washed with sodium bisulphite solution, sodium bicarbonate solution and brine. The organic solution was dried over magnesium sulphate, evaporated to dryness and the residue triturated with diethyl ether to give 13 mg of N-[3-methoxy-4-(5-oxazolyl)phenyl]-N'-[1,1-dimethyl-2-(1-oxido-4-pyridyl)ethyl]oxalamide as an off-white solid. MS: m/e 411 [M+]+.

The starting material was prepared as follows:

i) A solution of 17.4 g (0.115 mol) of alpha, alpha-dimethyl-4-pyridineethanol in 115 ml of acetic acid was added dropwise to a mixture of 115 ml of acetic acid, 58 ml of concentrated sulphuric acid and 6.8 ml (0.126 mmol) of acetonitrile with cooling in an ice/salt bath. The resulting mixture was stirred for 2 hours at room temperature and the pH raised to 10 by the addition of 6M sodium hydroxide solution with ice cooling. The slurry was filtered, washed with ethyl acetate and the aqueous filtrate extracted twice with ethyl acetate. The combined organic extracts were dried over magnesium sulphate, evaporated to dryness and the residue chromatographed on silica gel using ethyl acetate/methanol (1:19), (1:9) and (3:17) for the gradient elution. There was obtained 1.87 g of N-[1,1-dimethyl-2-(4-pyridyl)ethyl]acetamide as an orange oil. $^1$H NMR (400 MHz CDCl$_3$) δ: 1.29 (6H,s), 1.91 (3H,s), 3.11 (2H,s), 5.10 (1H,br.s.), 7.07 (2H,d), 8.50(2H,d).

ii) A solution of 1.8 g (9.3 mmol) of N-[1,1-dimethyl-2-(4-pyridyl)ethyl]acetamide, 2.66 g (9.3 mmol) of titanium (IV) isopropoxide and 2.56 g (14 mmol) of diphenylsilane in 10 ml of tetrahydrofuran was stirred at room temperature for 20 hours. The resulting mixture was chromatographed on silica gel using dichloromethane/methanol/acetic acid/water (60:18:2:3) for the elution. The product was dissolved in 20 ml of concentrated hydrochloric acid and 50 ml of methanol and evaporated to dryness. The residue was evaporated with toluene five times to give 620 mg of alpha, alpha-dimethyl-4-pyridineethylamine hydrochloride (1:1), as a pale brown solid. $^1$H NMR (400 MHz DMSO) δ: 1.31 (6H,s), 3.26 (2H,s), 8.02 (2H,d), 8.4–8.6 (3H,br.s), 8.88 (2H,d).

iii) A mixture of 100 mg (0.45 mmol) of alpha, alpha-dimethyl-4-pyridineethylamine hydrochloride (1:1), 120 mg (0.45 mmol) of N-[3-methoxy-4-(5-oxazolyl)phenyl] oxalamic acid, 105 mg (0.68 mmol) of 1-hydroxybenzotriazole hydrate, 105 mg (0.54 mmol) of 1-(3-dimethylaminopropyl)-3-ethylcarbodiimide hydrochloride and 127 mg (1.1 mmol) of N-ethylmorpholine in 4 ml of dichloromethane was stirred for 20 hours at room temperature then diluted with ethyl acetate and washed with water and brine. The organic solution was dried over magnesium sulphate, evaporated to dryness and the residue chromatographed on silica gel using ethyl acetate/methanol (19:1) for the elution. After trituration with diethyl ether there was obtained 32 mg of N-[3-methoxy-4-(5-oxazolyl)phenyl]-N'-[1,1-dimethyl-2-(4-pyridyl) ethyl]oxalamide as a white solid. MS: m/e 395 [M+H]+.

EXAMPLE 455

2-[2-[[[3-Methoxy-4-(5-oxazolyl)anilino]oxalyl]amino]-2-methylpropyl]-5-benzofurancarboxylic acid A solution of 68 mg (0.12 mmol) of benzyl 2-[2-[[[3-methoxy-4-(5-oxazolyl)anilino]oxalyl]amino]-2-methylpropyl]-5-benzofurancarboxylate in 10 ml of tetrahydrofuran was hydrogenated with 20 mg of 10% palladium on carbon for 4 hours. The resulting suspension was filtered, evaporated to dryness and the residue triturated with diethyl ether to give 41 mg of 2-[2-[[[3-methoxy-4-(5-oxazolyl)anilino]oxalyl]amino]-2-methylpropyl]-5-benzofurancarboxylic acid as a white solid. MS: m/e 477.9 [M+]+.

The starting material was prepared as follows:

i) A solution of 1.976 g (22.46 mmol) of isobutyric acid in 8 ml of anhydrous tetrahydrofuran was added to a stirred suspension of 1.078 g (26.95 mmol) of 60% sodium hydride and 2.268 g (22.46 mmol) of diisopropylamine in in 40 ml of anhydrous tetrahydrofuran under a nitrogen atmosphere and the mixture heated to reflux for 15 minutes. After cooling to 0° C. a solution of 14.04 ml (22.46 mmol) of 1.6M butyllithium in hexanes was added maintaining the temperature at 0–5° C. After 5 minutes at 0° C. the mixture was warmed to 30–35° C. for 20 minutes, cooled to 0° C. and a solution of 5.3 g (22.46 mmol) of 2-(bromomethyl)-5-benzofurancarbonitrile in 15 ml of anhydrous tetrahydrofuran was added maintaining the temperature at 0° C. The suspension was stirred for 5 minutes at 0° C. then warmed to 30–35° C. for 20 minutes before being cooled to 15° C. and quenched by the careful addition of 50 ml of water and diluted with 50 ml of diethyl ether. The aqueous phase was separated, acidified with concentrated hydrochloric acid and extracted with diethyl ether. The organic phase was dried over magnesium sulphate, evaporated to dryness and the residue chromatographed on silica gel using ethyl acetate/petrol (1:2) for the elution. There was obtained 670 mg of 5-cyano-alpha, alpha-dimethyl-2-benzofuranpropionic acid as a white solid. $^1$H NMR (400 MHz CDCl$_3$) δ: 1.23 (6H,s), 3.01 (2H,s), 6.46 (1H,s), 7.38 (1H,d), 7.42 (1H,d), 7.75 (1H,s).

ii) A mixture of 652 mg (2.68 mmol) of 5-cyano-alpha, alpha-dimethyl-2-benzofuranpropionic acid, 732 mg (2.68 mmol) of diphenylphosphoryl azide and 269 mg (2.66 mmol) of triethylamine in 8 ml of tert-butanol was refluxed for 8 hours then evaporated to dryness and the residue dissolved in ethyl acetate and washed with saturated sodium bicarbonate solution. The organic phase was dried over magnesium sulphate, evaporated to dryness and chromatographed on silica gel using ethyl acetate/petrol (2:3) for the elution to give 225 mg of white solid which was suspended in 10 ml of 2M sodium hydroxide solution and stirred and refluxed for 20 hours. The resulting suspension was cooled, evaporated to dryness and 5 ml of ethylene glycol and 400 mg of potassium hydroxide were added. After heating at 190° C. for 20 minutes 2 ml of water were added and after a further 20 minutes another 15 ml of water were added and heating continued for 20 minutes until a thick paste remained which was cooled and dissolved in 20 ml of water. Concentrated hydrochloric acid was added to bring the pH to 2 then 25 ml of dioxan, 3 g (21.74 mmol) of potassium carbonate and 1.5 g (6.88 mmol) of di-tert-butyl dicarbonate were added and the mixture stirred for 24 hours. The solvent was removed by evaporation and the residue dissolved in diethyl ether and water. The aqueous phase was separated, acidified with 2M hydrochloric acid and extracted with diethyl ether. The organic phase was dried over magnesium sulphate and evaporated to dryness to give 106 mg of 2-[2-(tert-butoxyformamido)-2-methylpropyl]-5-benzofurancarboxylic acid as a colourless gum.

iii) A mixture of 105 mg (0.32 mmol) of 2-[2-(tert-butoxyformamido)-2-methylpropyl]-5-benzofurancarboxylic acid, 80 mg (0.53 mmol) of benzyl bromide, and 200 mg (1.45 mmol) of potassium carbonate in 4 ml of dimethylformamide was stirred at room temperature for 1 hour then diluted with diethyl ether and water. The organic phase was washed twice with water, dried over magnesium sulphate, evaporated to dryness and the residue chromatographed on silica gel using ethyl acetate/petrol (1:5) for the elution. There was obtained 104 mg of benzyl 2-[2-(tert-butoxyformamido)-2-methylpropyl]-5-benzofurancarboxylate as a colourless gum. $^{1}$H NMR (400 MHz CDCl$_3$) δ: 1.39 (6H,s), 1.50 (9H,s), 3.23 (2H,s), 4.49 (1H,s), 5.41 (2H,s), 6.52 (1H,s), 7.34–7.52 (6H,m),8.02 (1H,d), 8.30 (1H,s).

iv) 103 mg (0.24 mmol) of benzyl 2-[2-(tert-butoxyformamido)-2-methylpropyl]-5-benzofurancarboxylate were dissolved in 5 ml of trifluoroacetic acid/dichloromethane (1:1) for 10 minutes then evaporated to dryness and the residue dissolved in 1 ml of dimethylformamide and added to a stirred solution of 66 mg (0.25 mmol) of N-[3-methoxy-4-(5-oxazolyl)phenyl] oxalamic acid, 115 mg (1 mmol) of N-ethylmorpholine, 45 mg (0.29 mmol) of 1-hydroxybenzotriazole hydrate and 70 mg (0.37 mmol) of 1-(3-dimethylaminopropyl)-3-ethylcarbodiimide hydrochloride in 2 ml of dimethylformamide and the resulting mixture stirred at room temperature for 18 hours. After dilution with ethyl acetate the organic solution was washed with 2M hydrochloric acid, saturated sodium bicarbonate solution and water, dried over magnesium sulphate, evaporated to dryness and the residue chromatographed on silica gel using ethyl acetate/petrol (45:55) for the elution. After trituration with diethyl ether there was obtained 81 mg of benzyl 2-[2-[[[3-methoxy-4-(5-oxazolyl)anilino]oxalyl]amino]-2-methylpropyl]-5-benzofurancarboxylate as a white solid. MS m/e 568 [+H]$^+$.

EXAMPLE 443

2-[3-[2-[[[3-Methoxy-4-(5-oxazolyl)anilino]oxalyl)]amino]-2-methylpropyl]phenoxy]acetic acid A solution of 45 mg (0.081 mmol) of benzyl 2-[3-[[[3-methoxy-4-(5-oxazolyl)anilino]oxalyl]amino]-2-methylpropyl]phenoxy]acetate in 5 ml of ethanol/tetrahydrofuran (1:1) was hydrogenated with 4 mg of 10% palladium on carbon catalyst for 5 hours. The resulting suspension was filtered, evaporated to dryness and triturated with diethyl ether to give 29 mg of 2-[3-[2-[[[3-methoxy-4-(5-oxazolyl)amino]-2-methylpropyl]phenoxy]acetic acid as a white solid. MS: m/e 468 [M+]$^+$.

The starting material was prepared as follows:

i) 8 mg (0.2 mmol) of 60% sodium hydride were added to a stirred solution of 85 mg (0.2 mmol) of N-[2-(3-hydroxyphenyl)-1,1-dimethylethyl]-N'-[3-methoxy-4-(5-oxazolyl)phenyl]oxalamide in 1 ml of dimethylformamide. After 10 minutes 55 mg (0.24 mmol) of benzyl bromoacetate were added and the mixture stirred at room temperature for 4 hours. The resulting solution was diluted with ethyl acetate, washed twice with water, dried over magnesium sulphate and evaporated to dryness. The residue was chromatographed on silica gel using ethyl acetate/petrol (2:1) for the elution. There was obtained 51 mg of benzyl 2-[3-[2-[[[3-methoxy-4-(5-oxazolyl) anilino]oxalyl]amino]-2-methylpropyl]phenoxy]acetate as a white solid. MS: m/e 558 [M+H]$^+$.

In a manner analogous to that described in Example 1, starting with N-[3-methoxy-4-(5-oxazoyl)phenyl oxalamic acid, prepared as described in Example 1, parts (i) and (ii), and the appropriate amine, additional compounds shown in table 1c were also prepared.

TABLE 1c

| Name | Structure | MS (ES) (M + H)$^+$ | Ex No |
|---|---|---|---|
| N-[3-Methoxy-4-(5-oxazolyl)phenyl]N'-[1,1-dimethyl-2-(4-methylphenyl)ethyl]oxalamide | 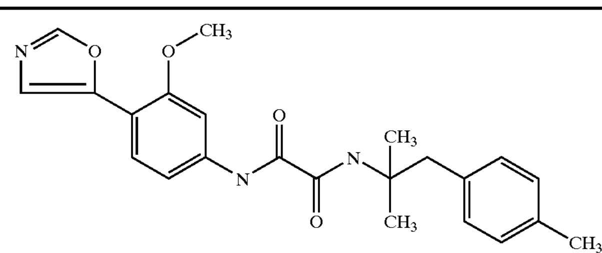 | 408 | 302 |

TABLE 1c-continued

| Name | Structure | MS (ES) (M + H)+ | Ex No |
|---|---|---|---|
| N-[1,1-Dimethyl-2-(2-methylphenyl)ethyl]-N'-[3-methoxy-4-(5-oxazolyl)phenyl]oxalamide | 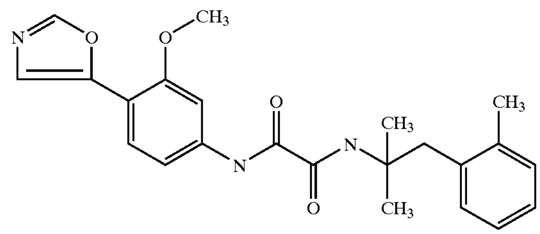 | 408 | 303 |
| N-[3-Methoxy-4-(5-oxazoly)phenyl]-N'-[1,1-dimethyl-2-(3-pyridyl)ethyl]oxalamide | 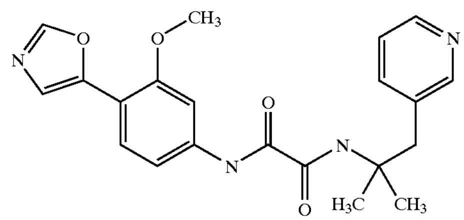 | 395 | 304 |
| N-[3-Methoxy-4-(5-oxazolyl)phenyl]-N'-[1,1-dimethyl-2-(3-methylphenyl)ethyl]oxalamide | 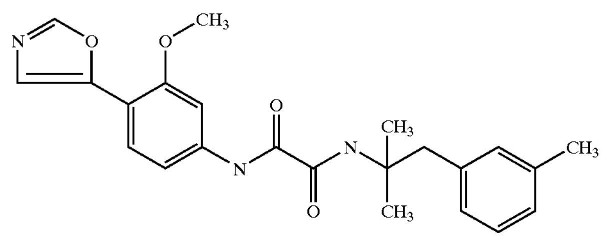 | 408 | 305 |
| N-[3-Methoxy-4-(5-oxazolyl)phenyl]-N'-[1,1-dimethyl-2-(2-thienyl)ethyl]oxalamide | 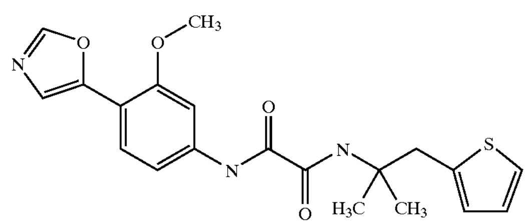 | 400 | 306 |
| N-[2-(4-Benzyloxy-phenyl)-1,1-dimethyl-ethyl]-N'-(3-methoxy-4-oxazol-5-yl-phenyl)-oxalamide | 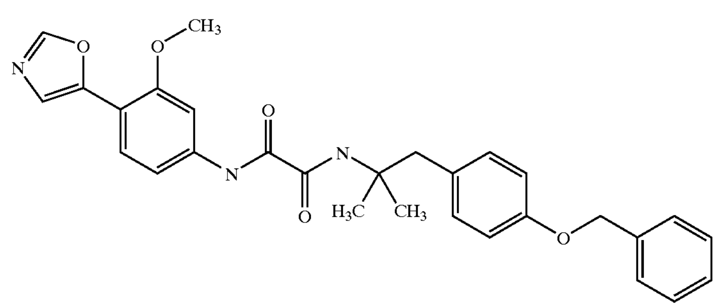 | 500 | 307 |
| N-[2-(4-Hydroxy-phenyl)-1,1-dimethyl-ethyl]-N'-(3-methoxy-4-oxazol-5-yl-phenyl)-oxalamide | 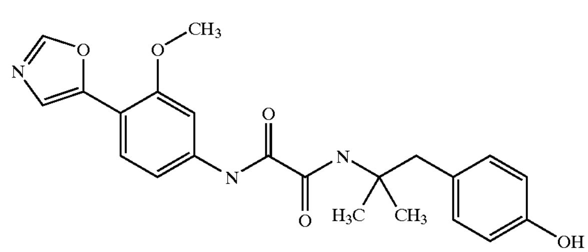 | 410 | 307 |

TABLE 1c-continued

| Name | Structure | MS (ES) (M + H)+ | Ex No |
|---|---|---|---|
| N-(3-Methoxy-4-oxazol-5-yl-phenyl)-N'-[2-(4-methoxy-phenyl)-1,1-dimethyl-ethyl]-oxalamide | 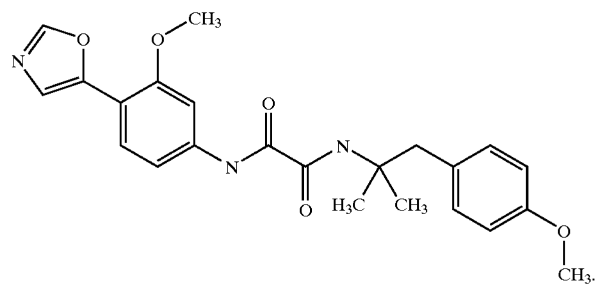 | 424 | 309 |
| N-[2-(2-Hydroxy-phenyl)-1,1-dimethyl-ethyl]-N'-(3-methoxy-4-oxazol-5-yl-phenyl)-oxalamide | 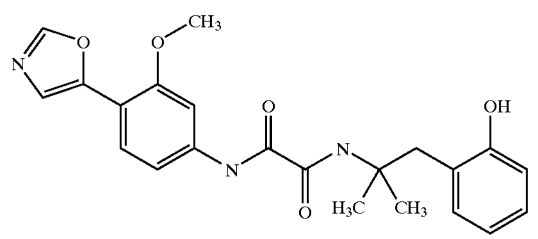 | 410 | 310 |
| N-(1,1-Dimethyl-2-phenyl-propyl)-N'-(3-methoxy-4-oxazol-5-yl-phenyl)-oxalamide | 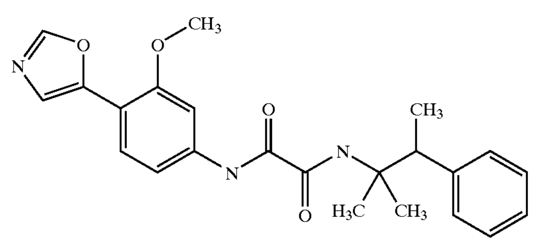 | 408 | 311 |
| N-[2-(3-Hydroxy-phenyl)-1,1-dimethyl-ethyl]-N'-(3-methoxy-4-oxazol-5-yl-phenyl)-oxalamide | 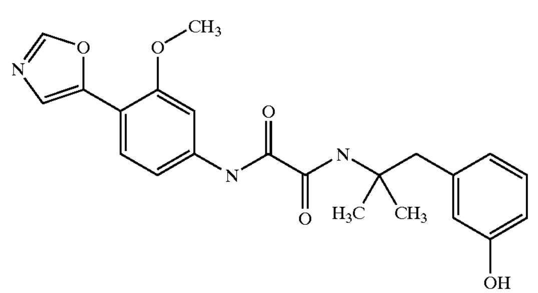 | 410 | 312 |
| N-(3-Methoxy-4-oxazol-5-yl-phenyl)-N'-[2-(3-methoxy-phenyl)-1,1-dimethyl-ethyl]-oxalamide | 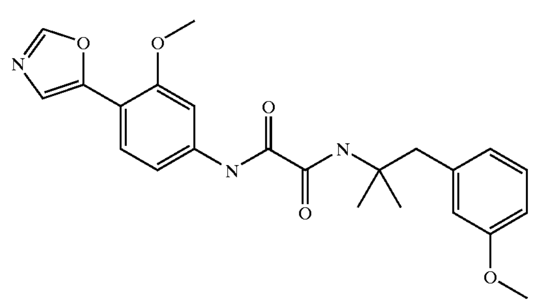 | 424 | 313 |

TABLE 1c-continued

| Name | Structure | MS (ES) (M + H)+ | Ex No |
|---|---|---|---|
| N-[2-[4-(Cyanomethoxy)phenyl]-1,1-dimethylethyl]-N'-[3-methoxy-4-(5-oxazolyl)phenyl]oxalamide | 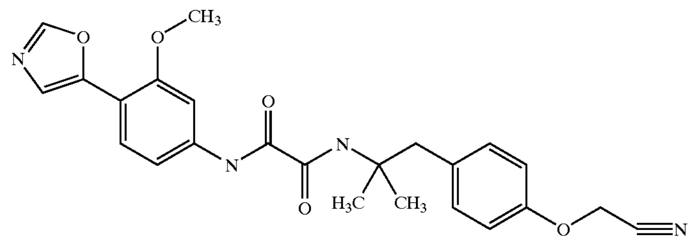 | 449 | 314 |
| 2-[-[-[[[3-Methoxy-4-(5-oxazolyl)anilino]amino]-2-methylpropyl]phenoxy]acetic acid | 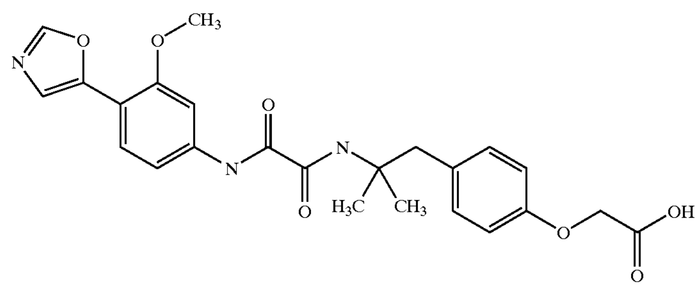 | 468 | 315 |
| 2-[2-[2-[[[3-Methoxy-4-(5-oxazolyl)anilino]oxalyl]amino]-2-methylpropyl]phenoxy]acetic acid | 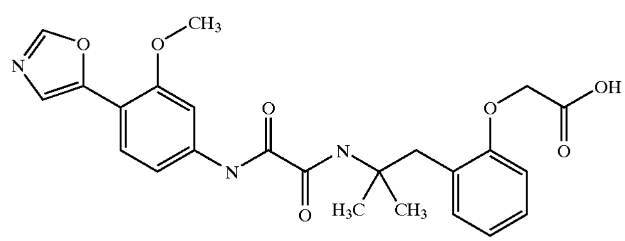 | 468 | 438 |
| N-[3-[2-[[[3-Methoxy-4-(5-oxazolyl)anilino]oxalyl]amino]-2-methylpropyl]phenoxy]acetic acid | 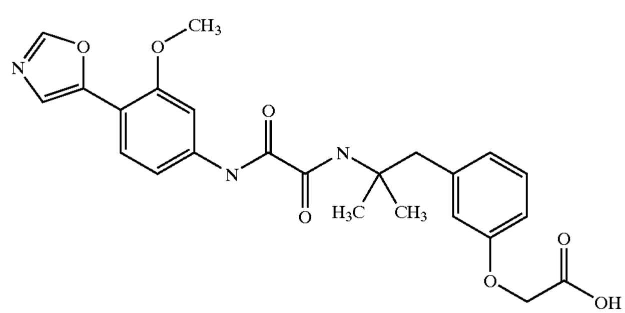 | 468 | 439 |
| N-[3-Methoxy-4-(5-oxazolyl)phenyl]-N'-[1,1-dimethyl-2-(1-oxido-4-pyridyl)ethyl]oxalamide | 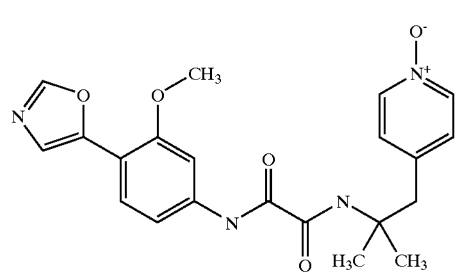 | 411 | 440 |

TABLE 1c-continued

| Name | Structure | MS (ES) (M + H)+ | Ex No |
|---|---|---|---|
| N-[3-Methoxy-4-(5-oxazolyl)phenyl]-N'-[1,1-dimethyl-2-(1-oxido-3-pyridyl)ethyl]oxalamide | 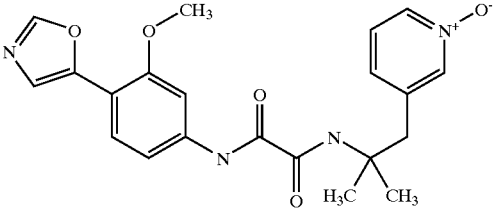 | 411 | 441 |
| N-[3-Mtethoxy-4-(5-oxazolyl)phenyl]-N'-[1,1-dimethyl-2-(1-oxido-2-pyridyl)ehtyl]oxalamide | 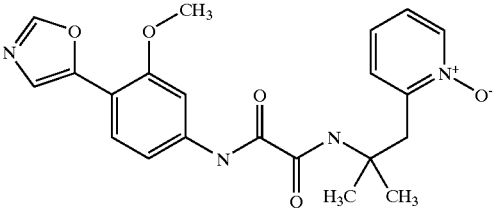 | 411 | 442 |
| 2-[3-[2-[[[3-Methoxy-4-(5-oxazolyl)anilino]oxalyl)]amino]-2-methylpropyl]phenoxy]acetic acid | 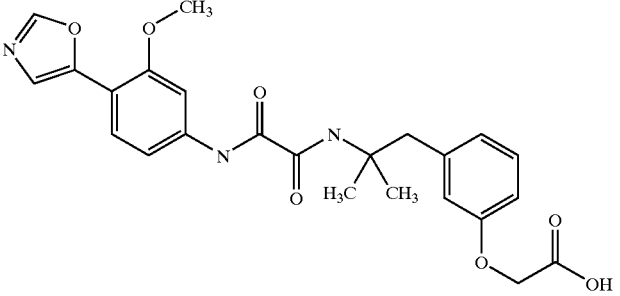 | 468 | 443 |
| N-[2-(2-Benzofuranyl)-1,1-dimethylethyl]-N'-[3-methoxy-4-(5-oxazolyl)phenyl]oxalamide | 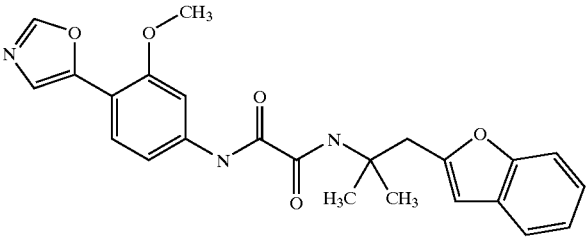 | 434 | 444 |
| N-[3-Methoxy-4-(5-oxazolyl)phenyl]-N'-[1,1-dimethyl-2-(3-methyl-2-benzofuranyl)ethyl]oxalamide | 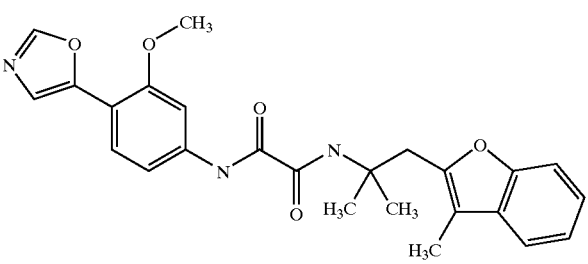 | 448 | 445 |

TABLE 1c-continued

| Name | Structure | MS (ES) (M + H)+ | Ex No |
|---|---|---|---|
| N-[2-(7-Methoxy-2-benzofuranyl)-1,1-dimethylethyl]-N'-[3-methoxy-4-(5-oxazolyl)phenyl]oxalamide | 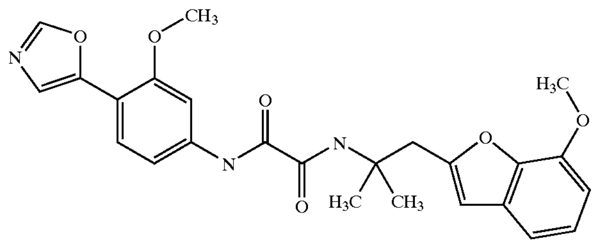 | 464 | 446 |
| N-[2-(5-Methoxy-2-benzofuranyl)-1,1-dimethylethyl]-N'-[3-methoxy-4-(5-oxazolyl)phenyl]oxalamide | 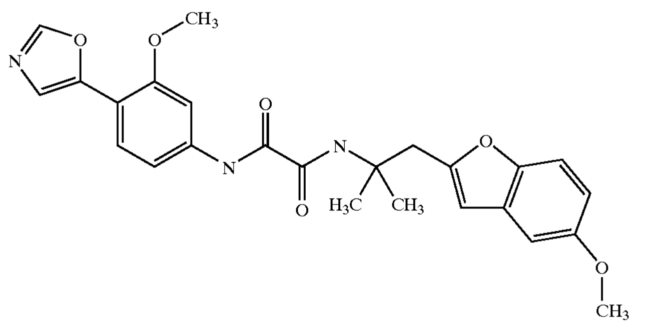 | 464 | 447 |
| N-[2-(6-Methoxy-2-benzofuranyl)-1,1-dimethylethyl]-N'-[3-methoxy-4-(5-oxazolyl)phenyl]oxalamide | 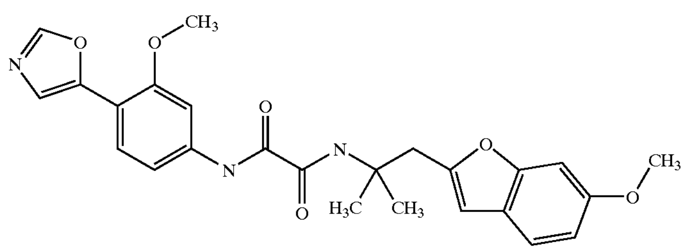 | 464 | 448 |
| Benzyl 4-[2-[[[3-methoxy-4-(5-oxazolyl)anilino]oxalyl]amino]-2-methylpropyl]benzoate | 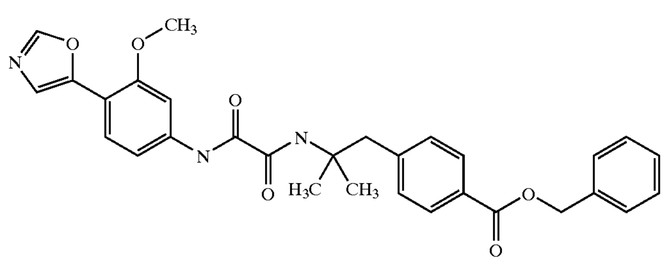 | 528 | 449 |
| 4-[2-[[[3-Methoxy-4-(5-oxazolyl)anilino]oxalyl]amino]-2-methylpropyl]benzoic acid | 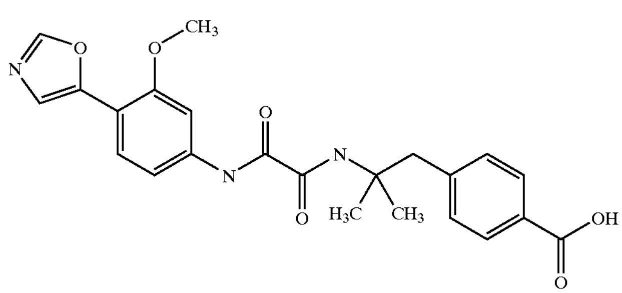 | 438 | 450 |

TABLE 1c-continued

| Name | Structure | MS (ES) (M + H)+ | Ex No |
|---|---|---|---|
| Benzyl 3-[2-[[[3-methoxy-4-(5-oxazolyl)anilino]oxalyl]amino]-2-methylpropyl]benzoate | 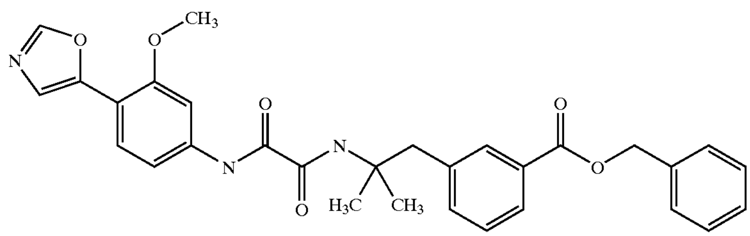 | 528 | 451 |
| 3-[2-[[[3-Methoxy-4-(5-oxazolyl)anilino]oxalyl]amino]-2-methylpropyl]benzoic amino | 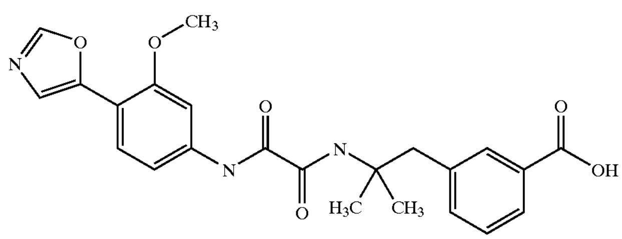 | 438 | 452 |
| N-[2-(3-Benzofuranyl)-1,1-dimethylethyl]-N'-[3-methoxy-4-(5-oxazolyl)phenyl]oxalamide | 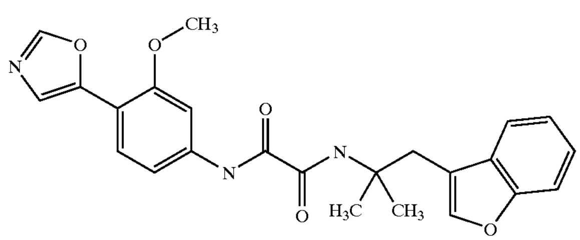 | 434 | 453 |
| Benzyl 2-[2-[[[3-methoxy-4-(5-oxazolyl)anilino]oxalyl]amino]-2-methylpropyl]-5-benzofurancarboxylate | 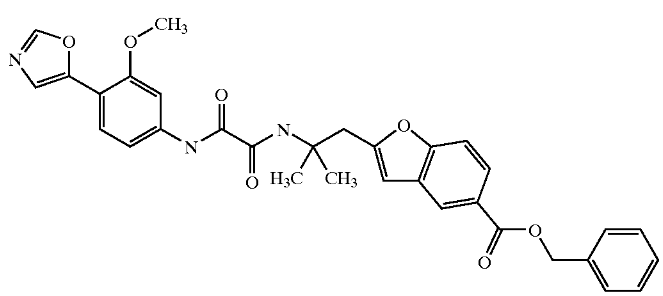 | 568 | 454 |
| 2-[2-[[[3-Methoxy-4-(5-oxazolyl)anilino]oxalyl]amino]-2-methylpropyl]-5-benzofurancarboxylic acid | 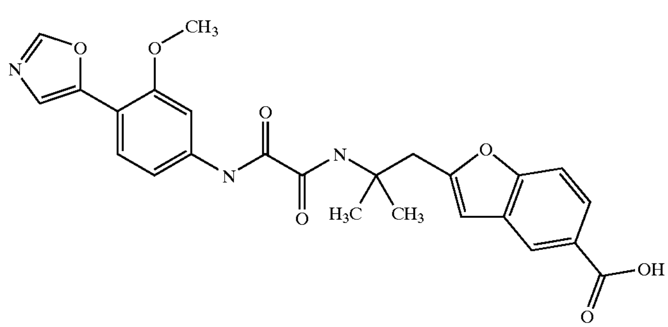 | 477.9 | 455 |

TABLE 1c-continued

| Name | Structure | MS (ES) (M + H)+ | Ex No |
|---|---|---|---|
| N-[3-Methoxy-4-(5-oxazolylphenyl]-N'-[1-[(4-pyridyl)methyl]-1-cyclopentyl]oxalamide | 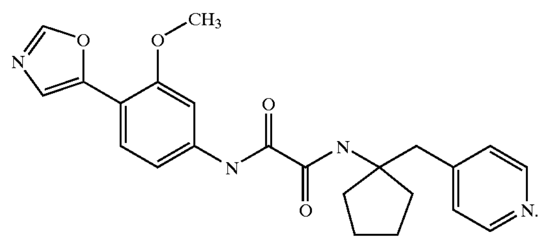 | 421 | 456 |
| N-[3-Methoxy-4-(5-oxazolyl)phenyl]-N'-[1-[(1-oxido-4-pyridyl)methyl]-1-cyclopentyl]oxalamide | 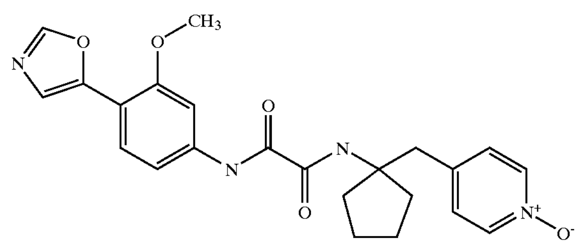 | 437 | 457 |
| N-[2-(4-Methoxy-2-benzofuranyl)-1,1 dimethylethyl]-N'-[3-methoxy-4-(5-oxazolyl)phenyl]oxalamide | 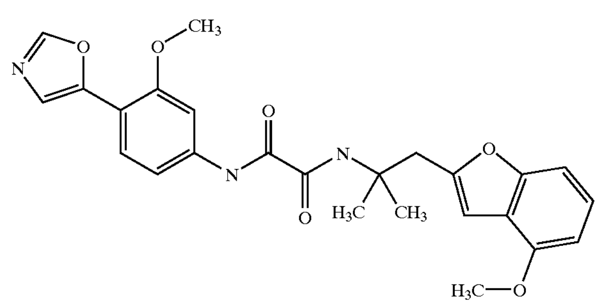 | 464 | 458 |
| N'-[3-Methoxy-4-(5-oxazolyl)phenyl]-N'-[2-(2,6-dimethyl-4-pyridyl)-1,1-dimethylethyl]oxalamide | 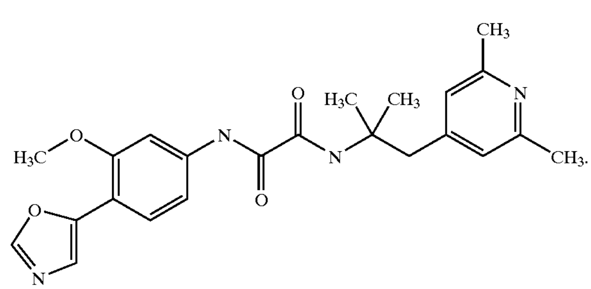 | 423.22 | 653 |
| N-[3-Methoxy-4-(5-oxazolyl)phenyl]-N'-[1,1-dimethyl-2-(2,6-dimethyl-1-oxido-4-pyridyl)ethyl]oxalamide | 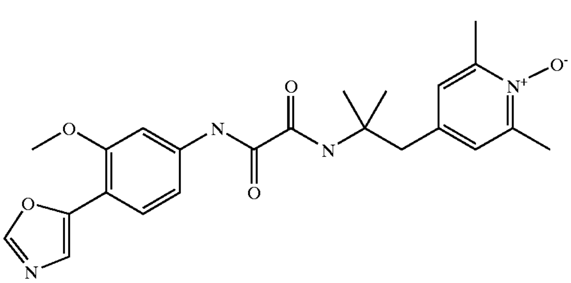 | 439.3 | 654 |

TABLE 1c-continued

| Name | Structure | MS (ES) (M + H)+ | Ex No |
|---|---|---|---|
| N-[3-Methoxy-4-(5-oxazolyl) phenyl]-N'-[1-[(4-pyridyl)methyl] 1-cyclopropyl]oxalamide | 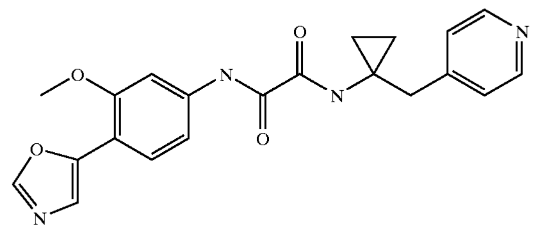 | 393 | 655 |
| N-[3-Methoxy-4-(5-oxazolyl) phenyl]-N'-[1-[(1-oxido-4-pyridyl)methyl]-1-cyclopropyl]oxalamide | 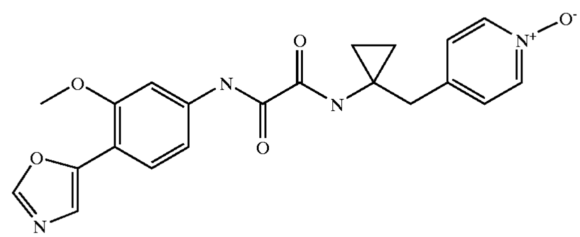 | 409 | 656 |
| N-[3-Methoxy-4-(5-oxazolyl) phenyl]-N'-[1-[(4-pyridyl)methyl]-1-cyclobutyl]oxalamide | 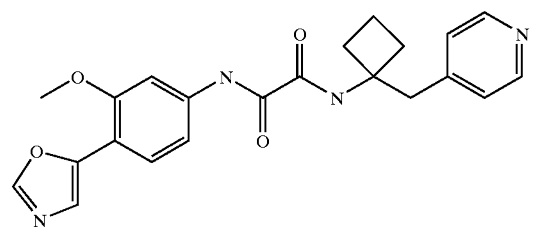 | 407 | 657 |
| N-[3-Methoxy-4-(5-oxazolyl) phenyl]-N'-[1-[(1-oxido-4-pyridyl)methyl]-1-cyclobutyl] oxalamide | 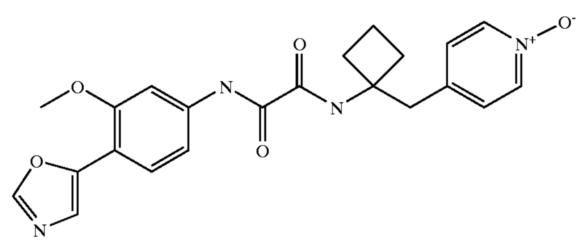 | 421 | 658 |
| N-[3-Methoxy-4-(5-oxazolyl) phenyl]-N'-[1-[(4-pyridyl)methyl]-1-cyclohexyl]oxalamide | 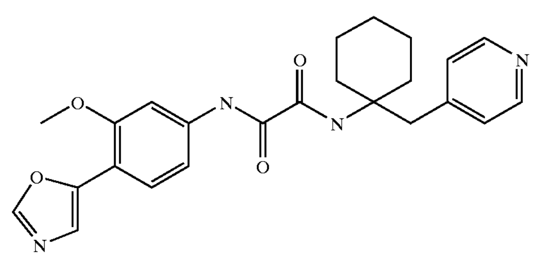 | 435 | 659 |
| N-[3-Methoxy-4-(5-oxazolyl) phenyl]-N'-[1-[(1-oxido-4-pyridyl)methyl]-1-cyclohexyl]oxalamide | 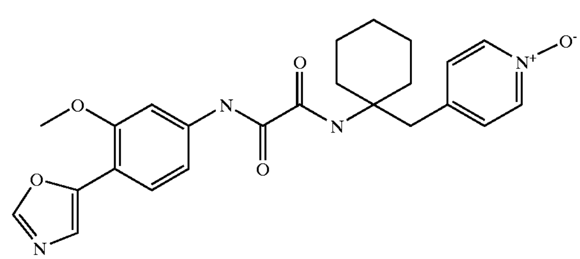 | 451 | 660 |

TABLE 1c-continued

| Name | Structure | MS (ES) (M + H)+ | Ex No |
|---|---|---|---|
| N-[3-Methoxy-4-(5-oxazolyl)phenyl]-N'-[1,1-dimethyl-2-(2-methyl-4-pyridyl)ethyl]oxalamide | 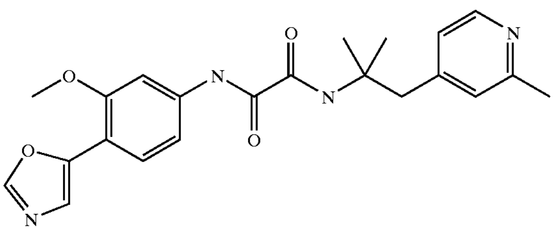 | 409 | 661 |
| N-[3-Methoxy-4-(5-oxazolyl)phenyl]-N'-[1,1-dimethyl-2-(2-methyl-1-oxido-4-pyridyl)ethyl]oxalamide | 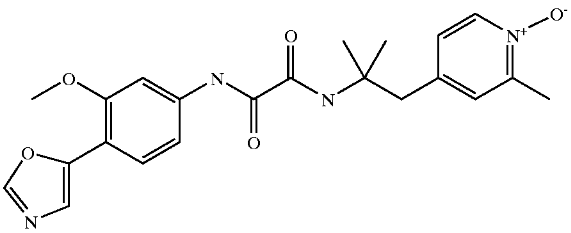 | 425 | 662 |
| 2-[2-[[[3-Methoxy-4-(5-oxazolyl)anilino]oxalyl]amino]-2-methylpropyl]-5-benzothiophenecarboxylic acid | | 494 | 663 |

EXAMPLES 316–330

In a manner analogous to that described in Example 11 starting with N-[2-(4-aminophenyl)-1,1-dimethylethyl]-N'-[3-methoxy-4-(5-oxazolyl)phenyl]oxalamide, prepared as described in example 21, and the appropriate aldehyde compounds shown in table 1d were also prepared.

TABLE 1d

| Name | Structure | MS (ES) (M + H)+ | Ex No |
|---|---|---|---|
| N-[3-Methoxy-4-(5-oxazolyl)phenyl]-N'-[1,1-dimethyl-2-[4-[(2-pyridinyl)methylamino]phenyl]ethyl]oxalamide | 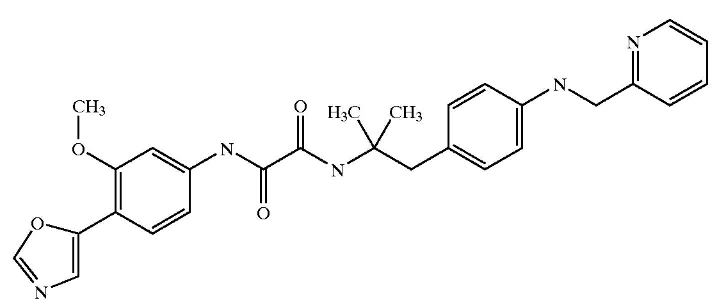 | 500.1 | 316 |

TABLE 1d-continued

| Name | Structure | MS (ES) (M + H)+ | Ex No |
|---|---|---|---|
| N-[3-Methoxy-4-(5-oxazolyl) phenyl]-N'-[1,1-dimethyl-2-[4-[(3-pyridyl) methylaminol]phenyl] ethyl]oxalamide | 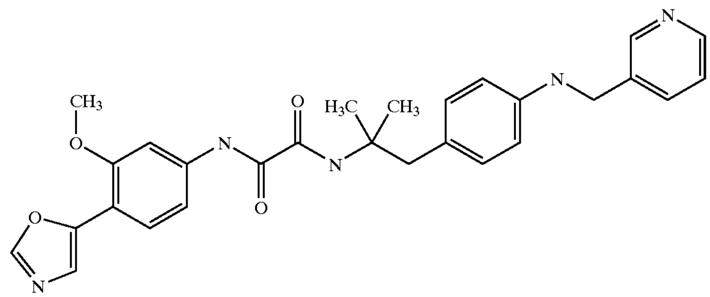 | 500.1 | 317 |
| N-[2-[4-(2-Furfurylamino) phenyl]-1,1-dimethylethyl] -N'-[3-methoxy-4-(5-oxazolyl) phenyl]oxalamide | 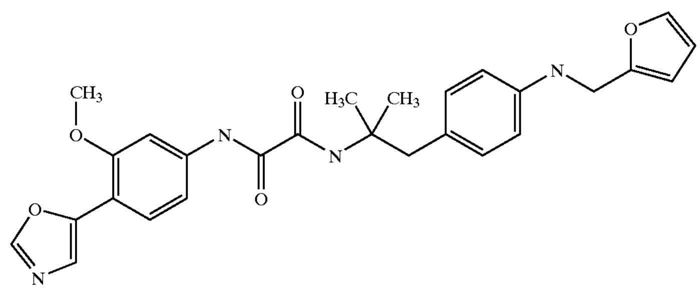 | 489.1 | 318 |
| N-[3-Methoxy-4-(5-oxazolyl) phenyl]-N'-[1,1-Dimethyl-2-[4-(2-thenylamino)phenyl] ethyl]oxalamide | 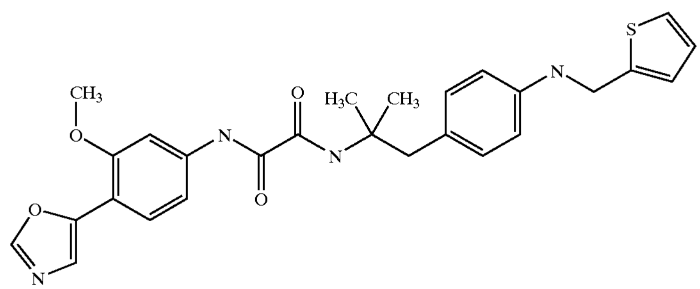 | 505.1 | 319 |
| N-[3-Methoxy-4-(5-oxazolyl) phenyl]-N'-[1,1-dimethyl-2-[4-(2,2-dimethylpropylamino) phenyl]ethyl]oxalamide | 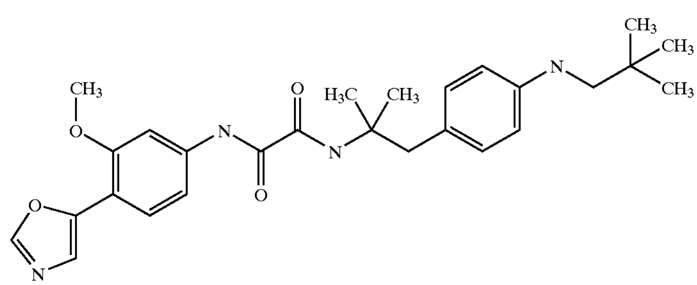 | 479.2 | 320 |
| N-[2-[4-[(1H-Imidazol-2-yl) methylamino]phenyl]-1,1-dimethylethyl]-N'-[3-methoxy-4-(5-oxazolyl) phenyl]oxalamide | 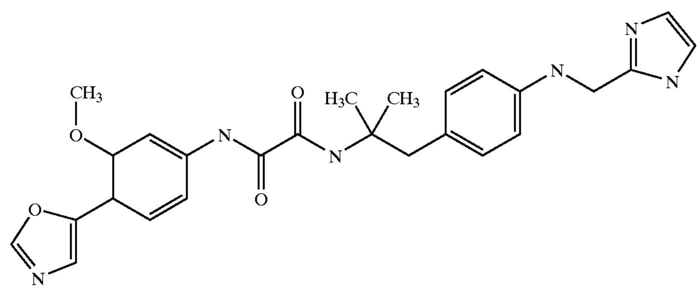 | 489.1 | 321 |

TABLE 1d-continued

| Name | Structure | MS (ES) (M + H)+ | Ex No |
|---|---|---|---|
| N-[3-Methoxy-4-(5-oxazolyl) phenyl]-N'-[1,1-dimethyl-2-[4-[(4-pyridyl) methylamino]phenyl]ethyl] oxalamide | 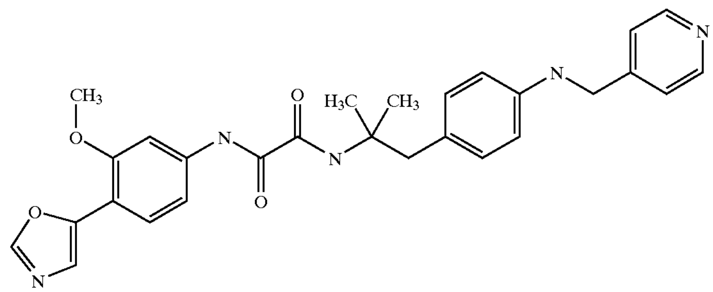 | 500.1 | 322 |
| N-[3-Methoxy-4-(5-oxazolyl) phenyl]-N'-[1,1-dimethyl-2-[4-[(2-thiazolyl) methylamino]phenyl]ethyl] oxalamide | 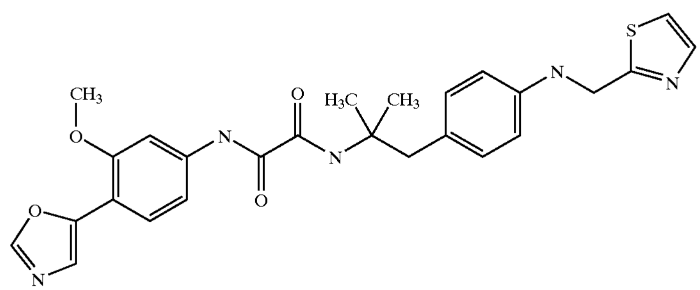 | 506.1 | 323 |
| N-[2-[4-(3-Furfurylamino) phenyl]-1,1-dimethylethyl]-N'-[3-methoxy-4-(5-oxazolyl) phenyl]oxalamide | 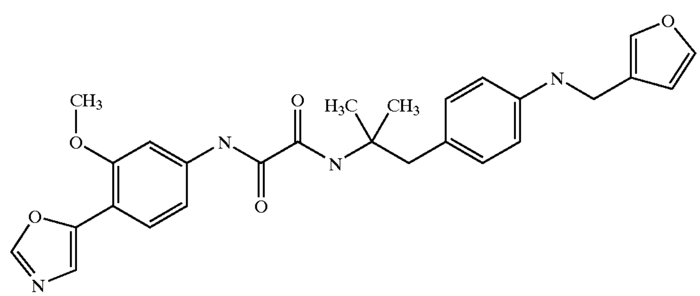 | 489.1 | 324 |
| N-[2-[4-[5-(Hydroxymethyl)-2-furfurylamino]phenyl]-1,1-dimethylethyl]-N'-[3-methoxy-4-(5-oxazolyl)phenyl]oxalamide | 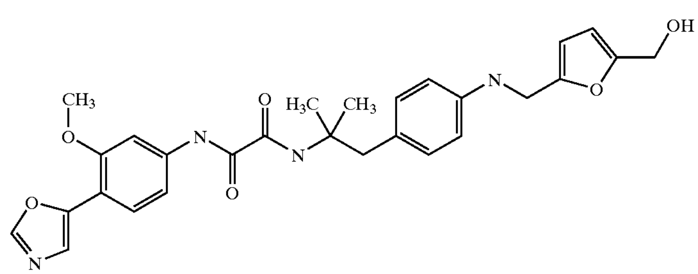 | 519.1 | 325 |
| N-[2-(4-Benzylaminophenyl)-1,1-dimethylethyl]-N'-[3-methoxy-4-(5-oxazolyl)phenyl]oxalamide | 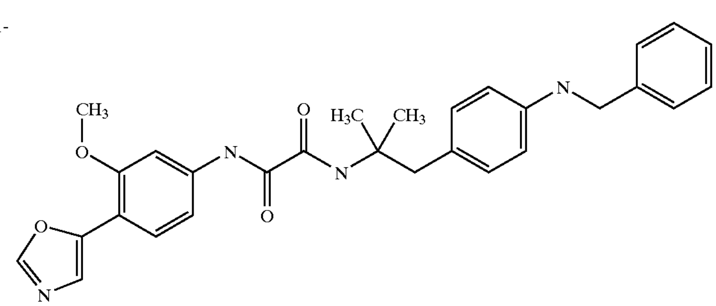 | 499.1 | 326 |

TABLE 1d-continued

| Name | Structure | MS (ES) (M + H)+ | Ex No |
|---|---|---|---|
| N-[2-[4-(2-Hydroxybenzyl-amino)phenyl]-1,1-dimethylethyl]-N'-[3-methoxy-4-(5-oxazolyl)phenyl]oxalamide | 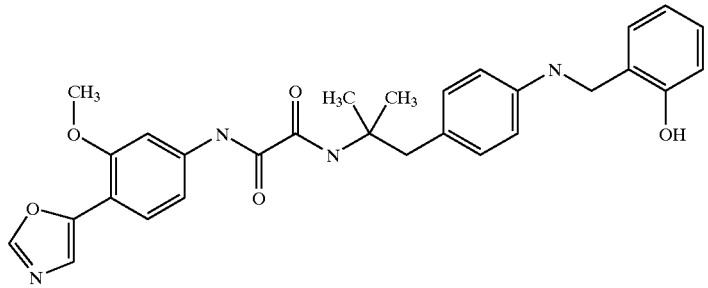 | 515.1 | 327 |
| N-[2-[4-(3-Cyanobenzyl-amino)phenyl]-1,1-dimethylethyl]-N'-[3-methoxy-4-(5-oxazolyl)phenyl]oxalamide | 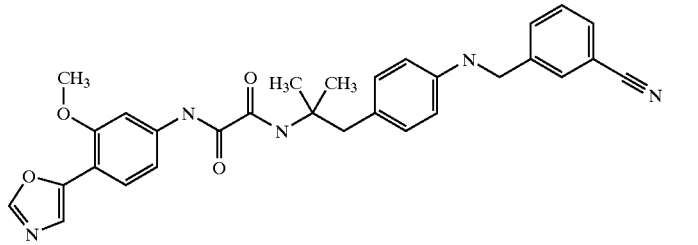 | 524.1 | 328 |
| N-[3-Methoxy-4-(5-oxazolyl)phenyl]-N'-[1,1-dimethyl-2-[4-[4-(3-pyridyl)benzylamino]phenyl]ethyl]oxalamide | 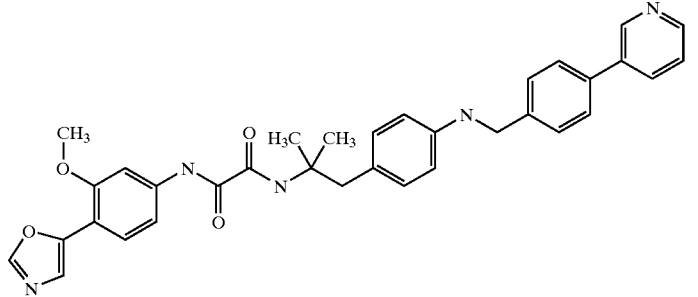 | 576.2 | 329 |
| N-[2-[4-(2-Fluorobenzyl-amino)phenyl]-1,1-dimethyl-ethyl]-N'-[3-methoxy-4-(5-oxazolyl)phenyl]oxalamide | 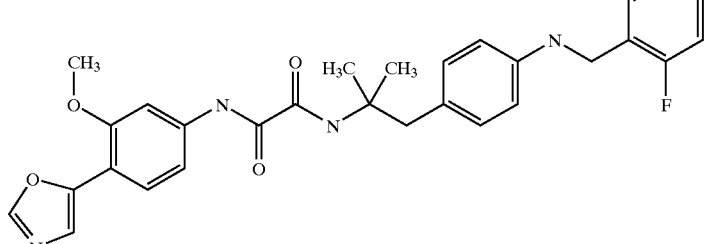 | 517.1 | 330 |

EXAMPLES 331–395 AND 596–597

In a manner analogous to that described in Example 22 starting from N-[2-(4-aminophenyl)-1,1-dimethylethyl]-N'-[3-methoxy-4-(5-oxazolyl)phenyl]oxalamide, prepared as described in example 21, and the appropriate carboxylic acid compounds shown in table 1e were also prepared.

TABLE 1e

| Name | Structure | MS (ES) (M + H)+ | Ex No |
|---|---|---|---|
| N-[2-[4-(Cyclopropylcarboxamido) phenyl]-1,1-dimethylethyl]-N'-[3-methoxy-4-(5-oxazolyl)phenyl] oxalamide | 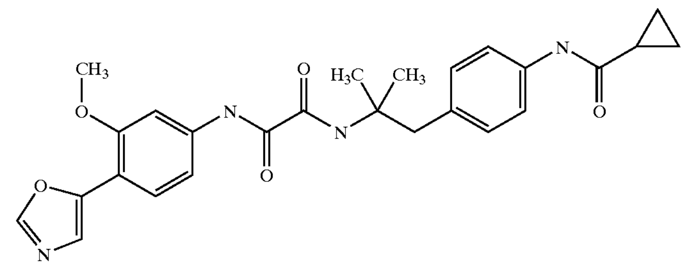 | 477.1 | 331 |
| N-[2-[4-(Cyclobutylcarboxamido) phenyl]-1,1-dimethylethyl]-N'-[3-methoxy-4-(5-oxazolyl)phenyl oxalamide | 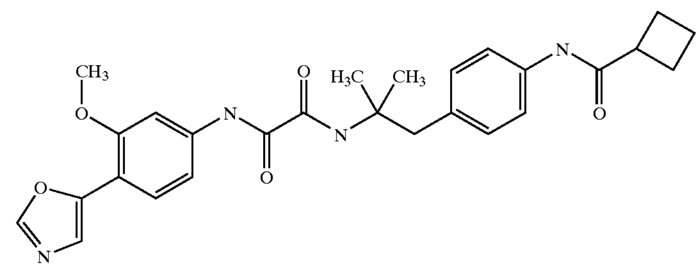 | 491.1 | 332 |
| N-{3-Methoxy-4-(5-oxazolyl)phenyl]-N'-[1,1-dimethyl-2-(4-pivalamidophenyl)-1,1-dimethylethyl] oxalamide | 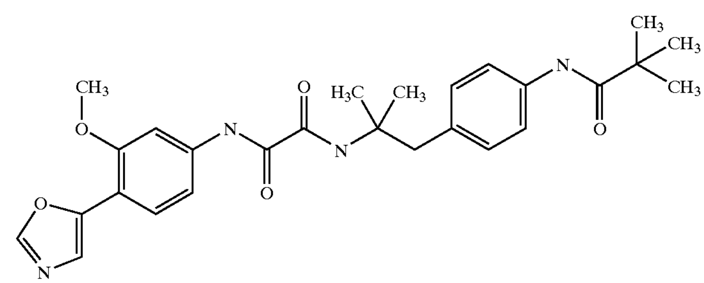 | 493.1 | 333 |
| N-[3-Methoxy-4-(5-oxazolyl)phenyl]-N'-[1,1-dimethyl-2-[4-[(1H-pyrrol-2-yl)carboxamido]phenyl]ethyl] oxalamide | 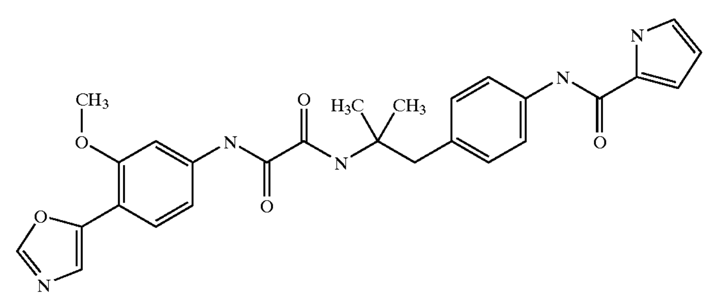 | 502.1 | 334 |
| N-[2-[4-[(2-Furyl)carboxamido]phenyl]-1,1-dimethylethyl]-N'-[3-methoxy-4-(5-oxazolyl)phenyl]oxalamide | 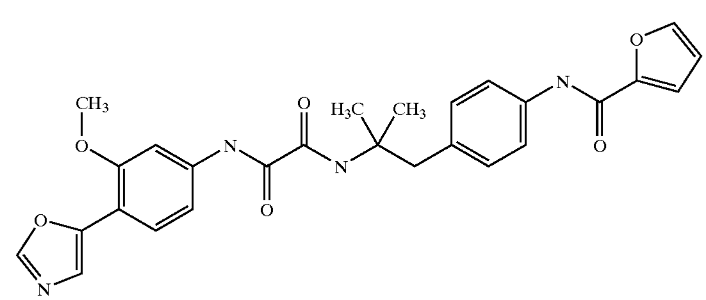 | 503.1 | 335 |

TABLE 1e-continued

| Name | Structure | MS (ES) (M + H)+ | Ex No |
|---|---|---|---|
| N-[2-[4-[(3-Furyl)carboxamido]phenyl]-1,1-dimethylethyl]-N'-[3-methoxy-4-(5-oxazolyl)phenyl]oxalamide | 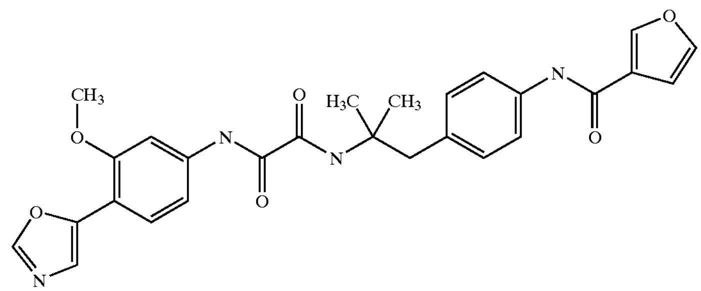 | 503.1 | 336 |
| N-[2-[4-[(1H-Imidazol-4-yl)carboxamido]phenyl]-1,1-dimethylethyl]-N'-[3-methoxy-4-(5-oxazolyl)phenyl]oxalamide | 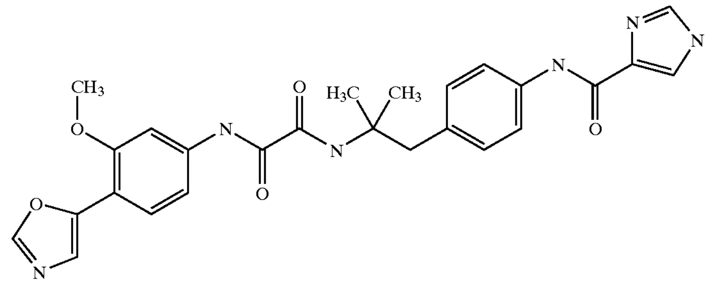 | 503.1 | 337 |
| N-[2-[4-[(Tetrahydro-2(RS)-furyl)carboxamido]phenyl]-1,1-dimethylethyl]-N'-[3-methoxy-4-(5-oxazolyl)phenyl]oxalamide | 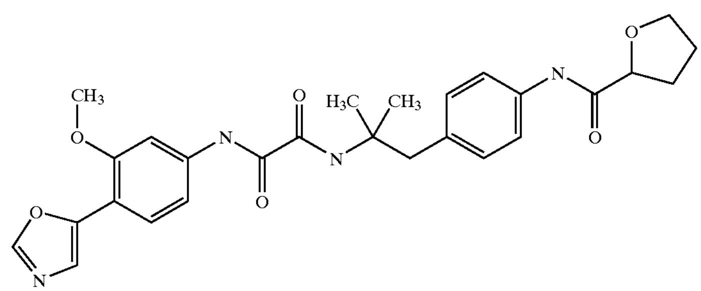 | 507.2 | 338 |
| N-[3-Methoxy-4-(5-oxazolyl)phenyl]-N'-[1,1-dimethyl-2-[4-[(2-pyridyl)carboxamido]phenyl]ethyl]oxalamide | 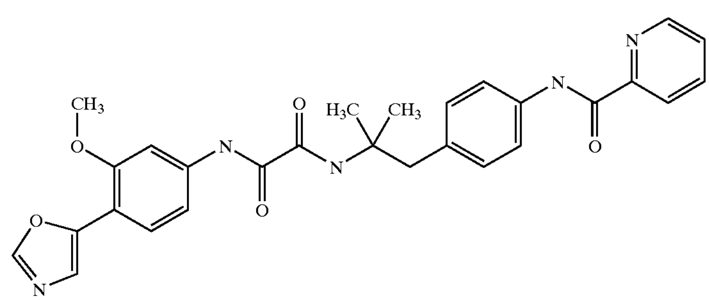 | 514.1 | 339 |
| N-[3-Methoxy-4-(5-oxazolyl)phenyl]-N'-[1,1-dimethyl-2-[4-[(4-pyridyl)carboxamido]phenyl]ethyl]oxalamide | 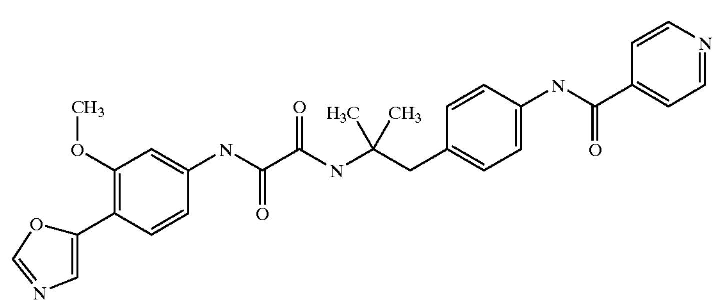 | 514.1 | 340 |

TABLE 1e-continued

| Name | Structure | MS (ES) (M + H)+ | Ex No |
|---|---|---|---|
| N-[3-Methoxy-4-(5-oxazolyl)phenyl]-N'-[1,1-dimethyl-2-[4-[(2-thienyl)carboxamido]phenyl]ethyl]oxalamide | 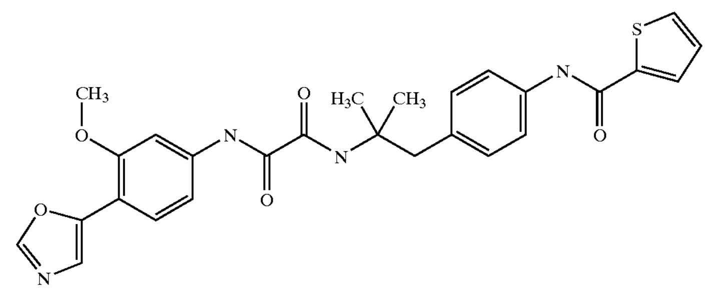 | 519.1 | 341 |
| N-[3-Methoxy-4-(5-oxazolyl)phenyl]-N'-[1,1-dimethyl-2-[4-[(3-thienyl)carboxamido]phenyl]ethyl]oxalamide | | 519.1 | 342 |
| N-[2-[4-(2-Cyclopentylacetamido)phenyl]-1,1-dimethylethyl]-N'-[3-methoxy-4-(5-oxazolyl)phenyl]oxalamide | 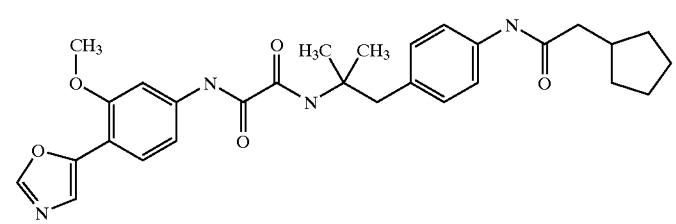 | 519.2 | 343 |
| N-[3-Methoxy-4-(5-oxazolyl)phenyl]-N'-[1,1-dimethyl-2-[4-(2-methylbenzamido)phenyl]ethyl]oxalamide | 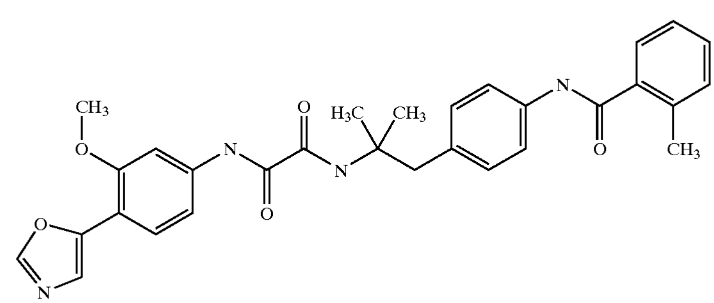 | 527.2 | 344 |
| N-[3-Methoxy-4-(5-oxazolyl)phenyl]-N'-[1,1-dimethyl-2-[4-(4-methylbenzamido)phenyl]ethyl]oxalamide | 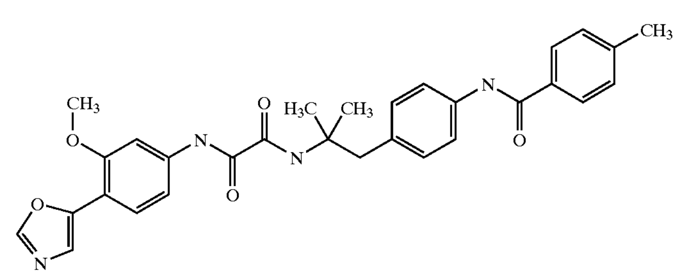 | 527.2 | 345 |

TABLE 1e-continued

| Name | Structure | MS (ES) (M + H)+ | Ex No |
|---|---|---|---|
| N-[2-[4-(Cycloheptylcarboxamido) phenyl]-1,1-dimethylethyl]-N'-[3-methoxy-4-(5-oxazolyl) phenyl]oxalamide | 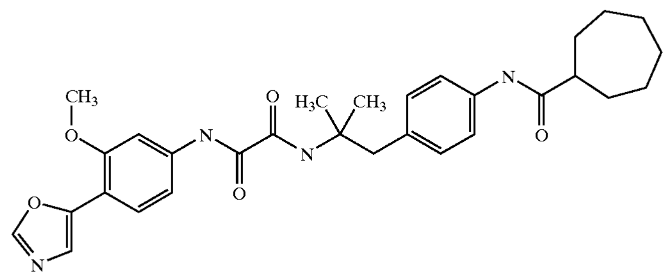 | 533.2 | 346 |
| N-[2-[4-[(5-Isoxazolyl) carboxamido]phenyl]-1,1-dimethylethyl]-N'-[3-methoxy-4-(5-oxazolyl)phenyl]oxalamide | 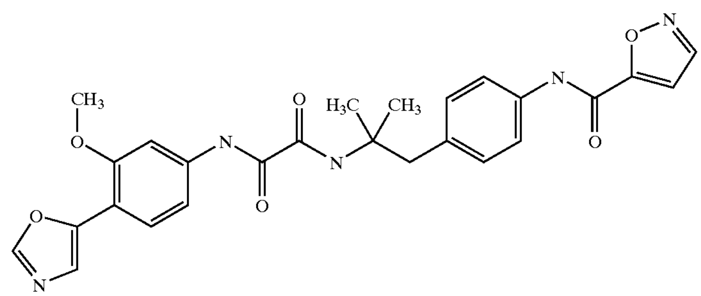 | 504.1 | 347 |
| N-[2-[4-(Cyclopentyl-carboxamido)phenyl]-1,1-dimethylethyl]-N'-[3-methoxy-4-(5-oxazolyl)phenyl]oxalamide | 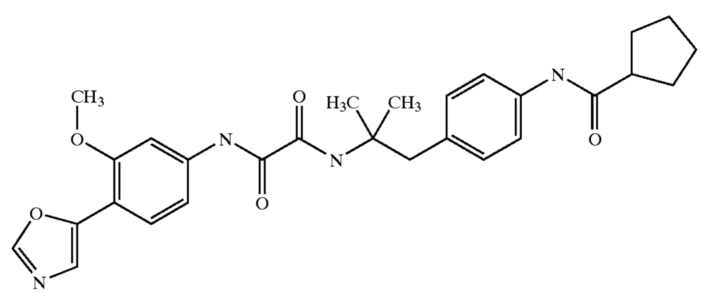 | 505.2 | 348 |
| N-[2-{4-[(Tetrahydro-3(RS)-furyl) carboxamido]phenyl}-1,1-dimethylethyl]-N'-[3-methoxy-4-(5-oxazolyl)phenyl]oxalamide | | 507.1 | 349 |
| N-[3-Methoxy-4-(5-oxazolyl)phenyl]-N'-1[1,1-dimethyl-2-[4-[(1-methyl-1H-pyrrol-2-yl)carboxamido]phenyl]ethyl]oxalamide | 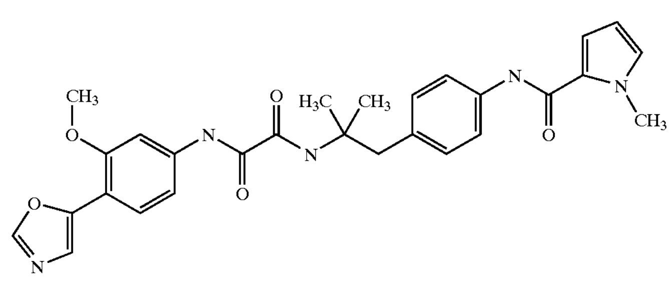 | 516.1 | 350 |

TABLE 1e-continued

| Name | Structure | MS (ES) (M + H)+ | Ex No |
|---|---|---|---|
| N-[3-Methoxy-4-(5-oxazolyl)phenyl]-N'-(1,1-dimethyl-2-[4-[(1,2,3-thiadiazol-4-yl)carboxamido]phenyl]ethyl]oxalamide | 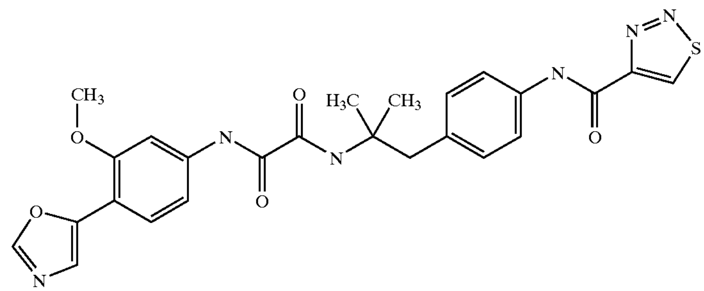 | 521.1 | 351 |
| N-[2-[4-(3-Fluorobenzamido)phenyl]-1,1-dimethylethyl]-N'-[3-methoxy-4-(5-oxazolyl)phenyl]oxalamide | 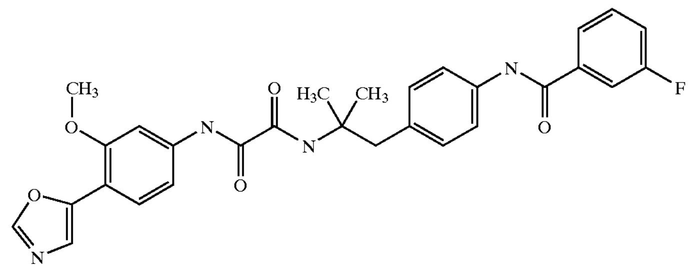 | 531.1 | 352 |
| N-[2-[4-(4-Fluorobenzamido)phenyl]-1,1-dimethylethyl]-N'-[3-methoxy-4-(5-oxazolyl)phenyl]oxalamide | 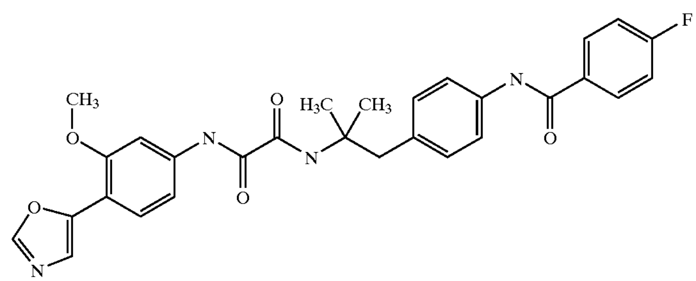 | 531.1 | 353 |
| N-[2-[4-(2-Methoxybenzamido)phenyl]-1,1-dimethylethyl]-N'-[3-methoxy-4-(5-oxazolyl)phenyl]oxalamide | 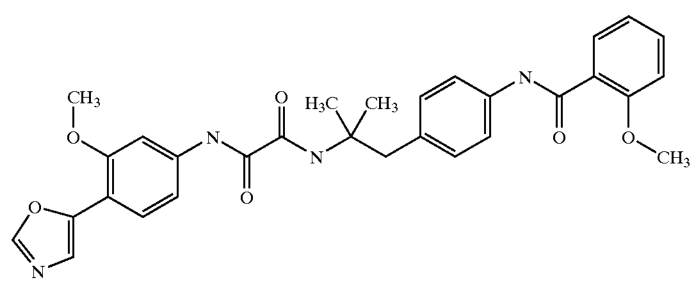 | 543.2 | 354 |
| N-[2-[4-(2-Chlorobenzamido)phenyl]-1,1-dimethylethyl]-N'-[3-methoxy-4-(5-oxazolyl)phenyl]oxalamide | 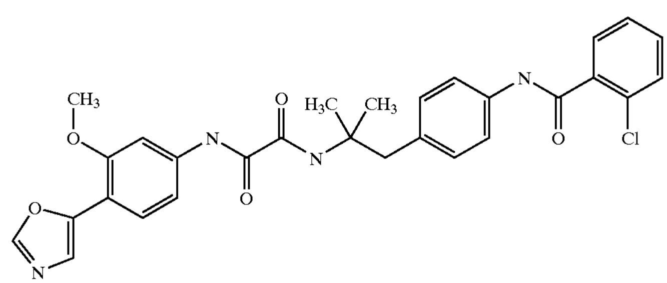 | 547.1 | 355 |

TABLE 1e-continued

| Name | Structure | MS (ES) (M + H)+ | Ex No |
|---|---|---|---|
| N-[2-[4-(3-Chlorobenzamido)phenyl]-1,1-dimethylethyl]-N'-[3-methoxy-4-(5-oxazolyl)phenyl]oxalamide | 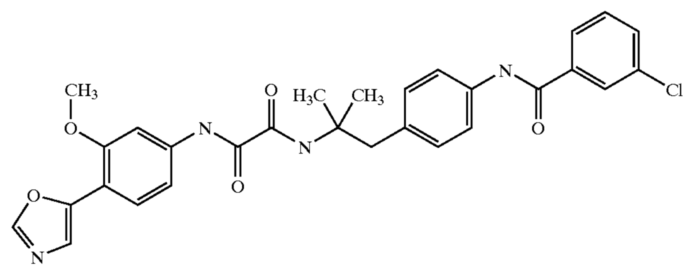 | 547.1 | 356 |
| N-[2-[4-(4-Chlorobenzamido)phenyl]-1,1-dimethylethyl]-N'-[3-methoxy-4-(5-oxazolyl)phenyl]oxalamide | 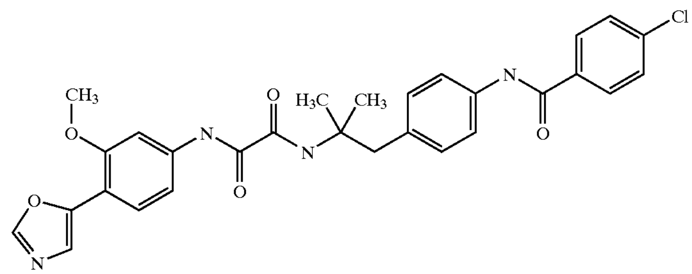 | 547.1 | 357 |
| N-[2-[4-[(1H-Indol-2-yl)carboxamido]phenyl]-1,1-dimethylethyl]-N'-[3-methoxy-4-(5-oxazolyl)phenyl]oxalamide | 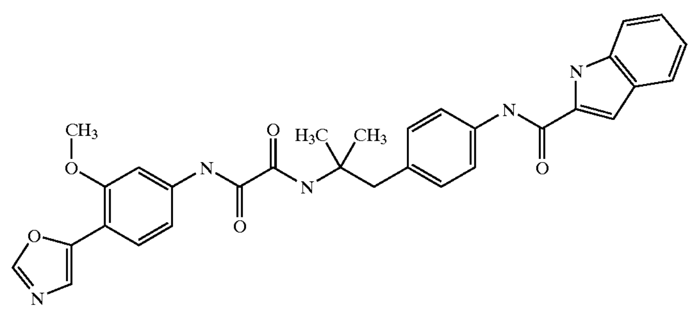 | 552.1 | 358 |
| N-[3-Methoxy-4-(5-oxazolyl)phenyl]-N'-[1,1-dimethyl-2-[4-[4-(dimethylamino)benzamido]phenyl]ethyl]oxalamide | 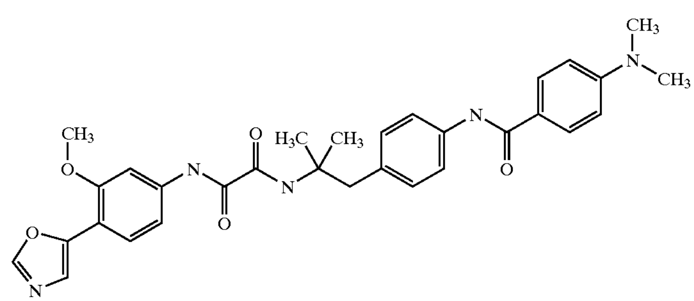 | 556.1 | 359 |
| N-[3-Methoxy-4-(5-oxazolyl)phenyl]-N'-[1,1-dimethyl-2-[4-(3,3-dimethylbutyramido)]phenyl]ethyl]oxalamide | 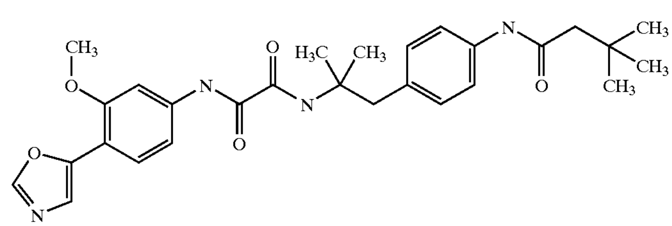 | 507.1 | 360 |

TABLE 1e-continued

| Name | Structure | MS (ES) (M + H)+ | Ex No |
|---|---|---|---|
| N-[3-Methoxy-4-(5-oxazolyl)phenyl]-N'-[1,1-dimethyl-2-[4-[2-(1-tetrazolyl)acetamido]phenyl]ethyl]oxalamide | 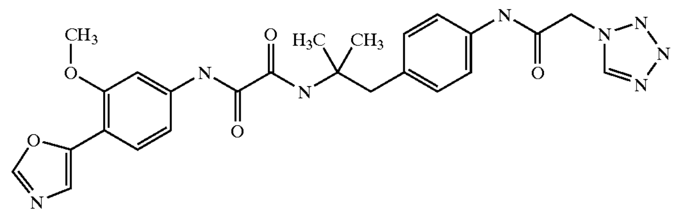 | 519.1 | 361 |
| N-[3-Methoxy-4-(5-oxazolyl)phenyl]-N'-[1,1-dimethyl-2-[4-[(5-oxo-2(S)-pyrrolidinyl) carboxamido]phenyl]ethyl]oxalamide | 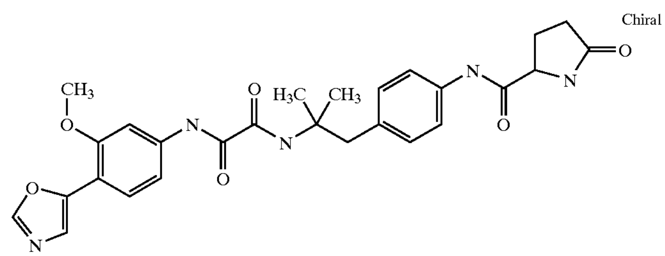 | 520.1 | 362 |
| N-[3-Methoxy-4-(5-oxazolyl)phenyl]-N'-(1,1-dimethyl-2-{4-[(5-oxo-2(R)-pyrrolidinyl)carboxamido]phenyl]ethyl]oxalamide | 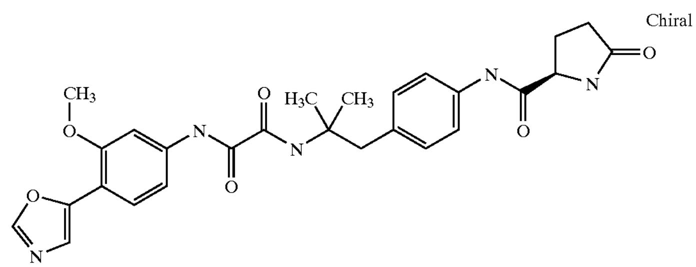 | 520.1 | 363 |
| N-[3-Methoxy-4-(5-oxazolyl)phenyl]-N'-[1,1-dimethyl-2-[4-[(2-naphthyl)carboxamido]phenyl]ethyl]oxalamide | 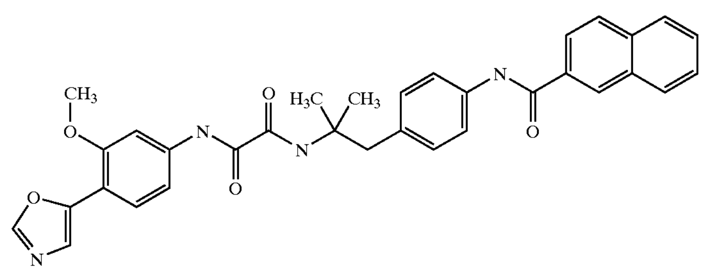 | 563.1 | 364 |
| N-[2-{4-[(6-Cyano-3-pyridyl)carboxamido]phenyl}-1,1-dimethylethyl]-N-[3-methoxy-4-(5-oxazolyl)phenyl]oxalamide | 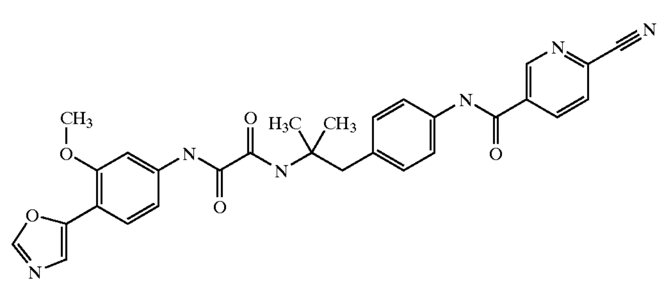 | 580.1 (M+ H+ ACN) | 365 |

TABLE 1e-continued

| Name | Structure | MS (ES) (M + H)+ | Ex No |
|---|---|---|---|
| N-[2-[4-(3-Methoxybenzamido) phenyl]-1,1-dimethylethyl]-N'-[3-methoxy-4-(5-oxazolyl)phenyl] oxalamide | 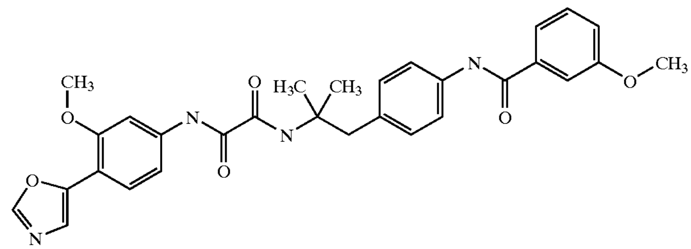 | 543.1 | 366 |
| N-[2-[4-(3,5-Difluorobenzamido) phenyl]-1,1-dimethylethyl]-N'-[3-methoxy-4-(5-oxazolyl)phenyl] oxalamide | 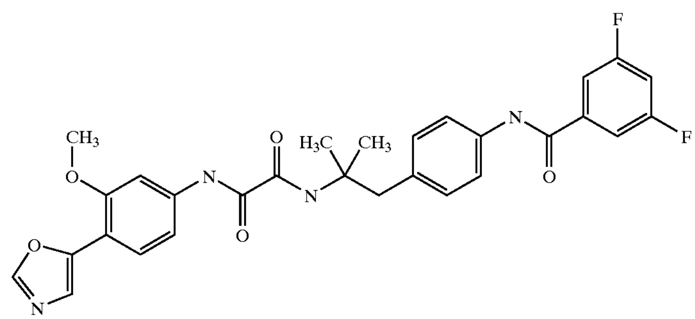 | 549.1 | 367 |
| N-[2-[4-[(1H-Indol-5-yl) carboxamido]phenyl]-1,1-dimethylethyl]-N-[3-methoxy-4-(5-oxazolyl)phenyl]oxalamide | 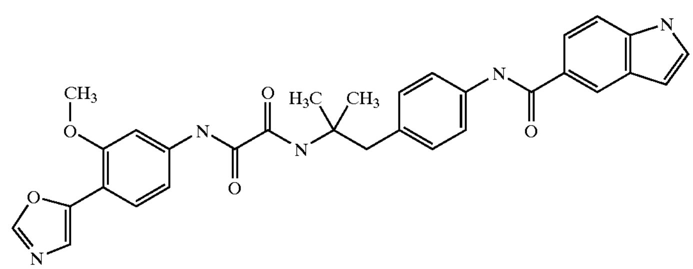 | 552.1 | 368 |
| (E)-N-[2-[4-(2-Butenamido)phenyl]-1,1-dimethylethyl]-N'-[3-methoxy-4-(5-oxazolyl)phenyl]oxalamide | 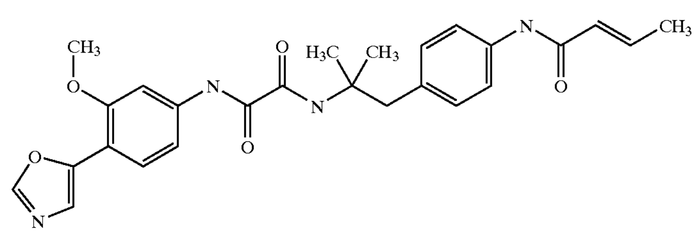 | 477.1 | 369 |
| N-[2-[4-(2-Methoxyacetamido) phenyl]-1,1-dimethylethyl]-N'-[3-methoxy-4-(5-oxazolyl)phenyl] oxalamide | 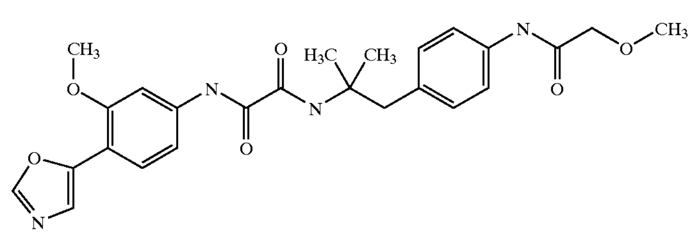 | 481.2 | 370 |

TABLE 1e-continued

| Name | Structure | MS (ES) (M + H)+ | Ex No |
|---|---|---|---|
| N-[3-methoxy-4-(5-oxazolyl)phenyl]-N'-[1,1-dimethyl-2-[4-[(2-methyl-3-furyl)carboxamido]phenyl]ethyl] oxalamide | 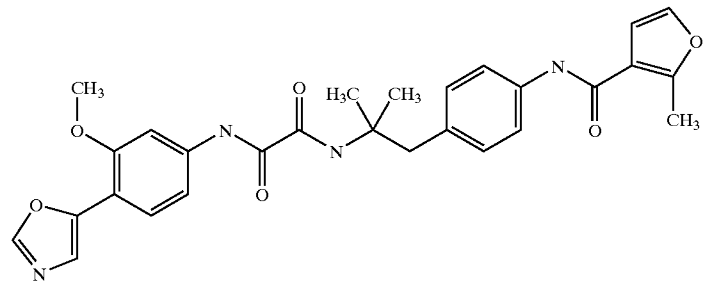 | 517.1 | 371 |
| N-[3-Methoxy-4-(5-oxazolyl)phenyl]-N'-[1,1-dimethyl-2-[4-[(5-methyl-4-isoxazolyl)carboxamido]phenyl]ethyl] oxalamide | 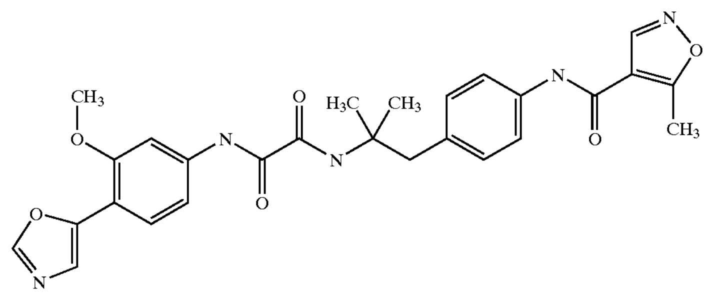 | 518.1 | 372 |
| N-[3-Methoxy-4-(5-oxazolyl)phenyl]-N-[1,1-dimethyl-2-[4-[(3-methyl-4-isoxazolyl)carboxamidol]phenyl]ethyl] oxalamide | 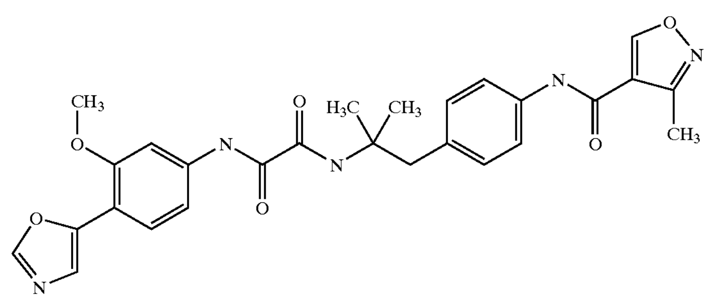 | 518.1 | 373 |
| N-[3-Methoxy-4-(5-oxazolyl)phenyl]-N'-[1,1-dimethyl-2-[4-[(5-methyl-3-isoxazolyl)carboxamido]phenyl]ethyl] oxalamide | 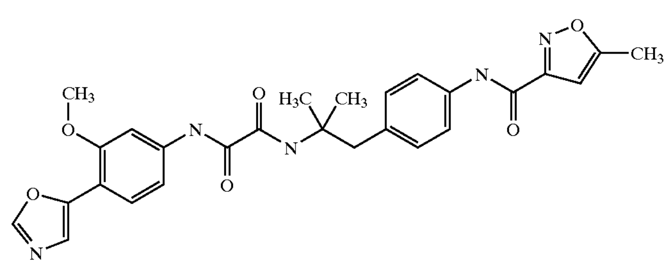 | 518.1 | 374 |
| N-[3-Methoxy-4-(5-oxazolyl)phenyl]-N-[1,1-dimethyl-2-[4-[(1-oxido-3-pyridyl) carboxamido]phenyl]ethyl] oxalamide | 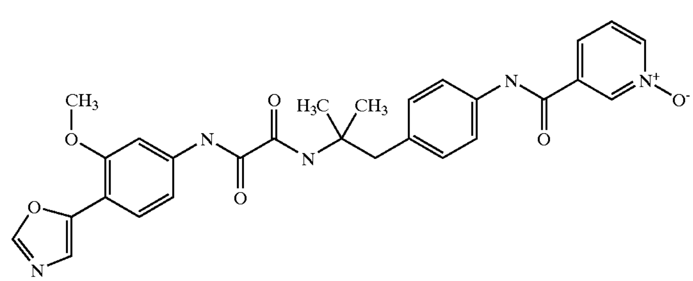 | 530.1 | 375 |

TABLE 1e-continued

| Name | Structure | MS (ES) (M + H)+ | Ex No |
|---|---|---|---|
| N-[3-Methoxy-4-(5-oxazolyl)phenyl]-N'-[1,1-dimethyl-2-[4-[(1-oxido-4-pyridyl)carboxamido]phenyl]ethyl]oxalamide | | 530.1 | 376 |
| N-[3-Methoxy-4-(5-oxazolyl)phenyl]-N'-[1,1-dimethyl-2-[4-[(4,5-dimethyl-2-furyl)carboxamido]phenyl]ethyl]oxalamide | 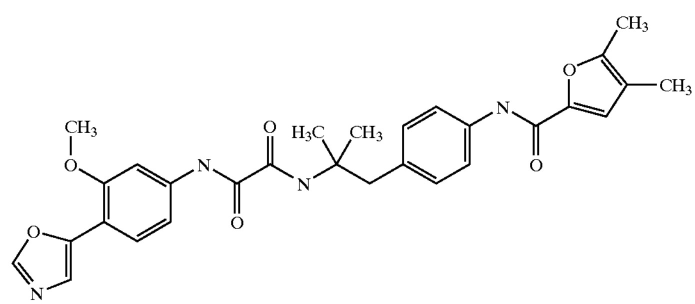 | 531.1 | 377 |
| N-[3-Methoxy-4-(5-oxazolyl)phenyl]-N'-[1,1-dimethyl-2-[4-[(2,5-dimethyl-2H-pyrazol-3-yl)carboxamido]phenyl]-1,1-dimethylethyl]oxalamide | 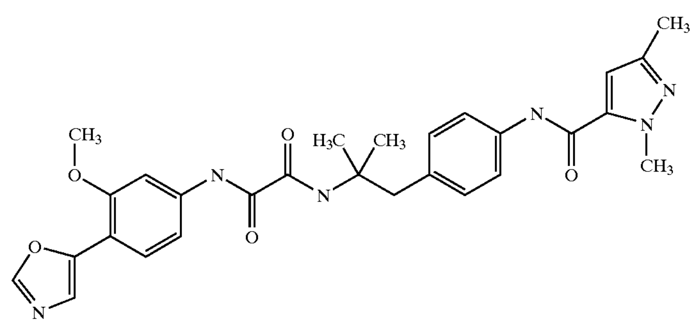 | 531.1 | 378 |
| N-[3-Methoxy-4-(5-oxazolyl)phenyl]-N'-[1,1-dimethyl-2-[4-[(3-methyl-2-thienyl)carboxamido]phenyl]ethyl]oxalamide | | 533.1 | 379 |
| N-[3-Methoxy-4-(5-oxazolyl)phenyl]-N'-[1,1-dimethyl-2-[4-[2-(3-thienyl)acetamido]phenyl]ethyl]oxalamide | 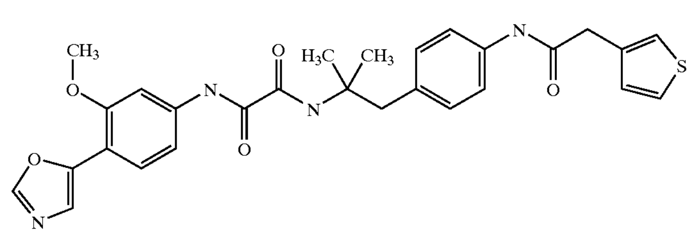 | 533.1 | 380 |

TABLE 1e-continued

| Name | Structure | MS (ES) (M + H)+ | Ex No |
|------|-----------|------------------|-------|
| N-[3-Methoxy-4-(5-oxazolyl)phenyl]-N'-[1,1-dimethyl-2-[4-[(4-methyl-2-thienyl)carboxamido]phenyl]ethyl]oxalamide | 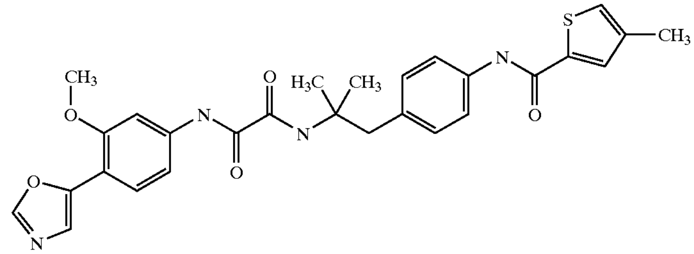 | 533.1 | 381 |
| N-[3-Methoxy-4-(5-oxazolyl)phenyl]-N'-[1,1-dimethyl-2-[4-[(4-methyl-1,2,3-thiadiazol-5-yl)carboxamido]phenyl]ethyl]oxalamide | 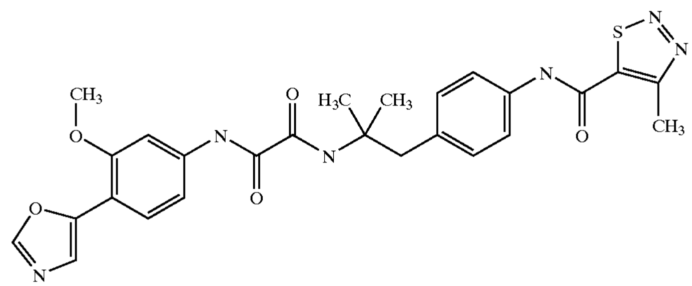 | 535 | 382 |
| N-[2-[4-(4-Acetamidobenzamido)phenyl]-1,1-dimethylethyl]-N'-[3-methoxy-4-(5-oxazolyl)phenyl]oxalamide | 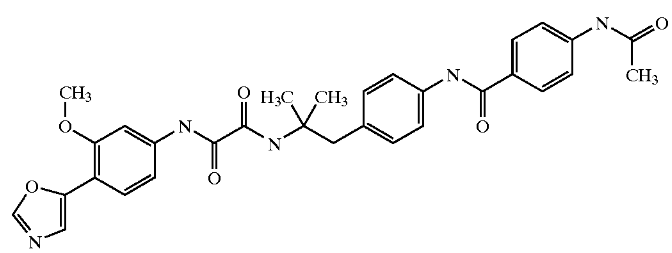 | 570.1 | 383 |
| N-[2-[4-(3,4-Dimethoxybenzamido)phenyl]-1,1-dimethylethyl]-N'-[3-methoxy-4-(5-oxazolyl)phenyl]oxalamide | 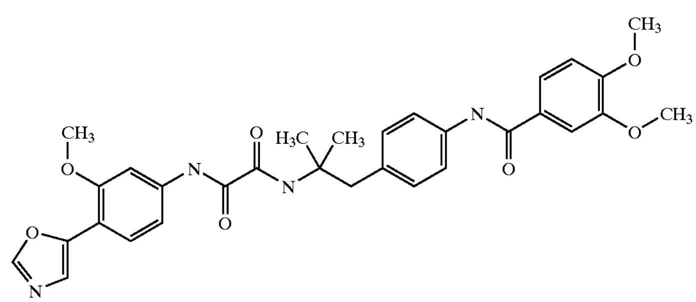 | 573.1 | 384 |
| N-[2-[4-(4-Chloro-2-methoxybenzamido)phenyl]-1,1-dimethylethyl]-N'-[3-methoxy-4-(5-oxazolyl)phenyl]oxalamide | 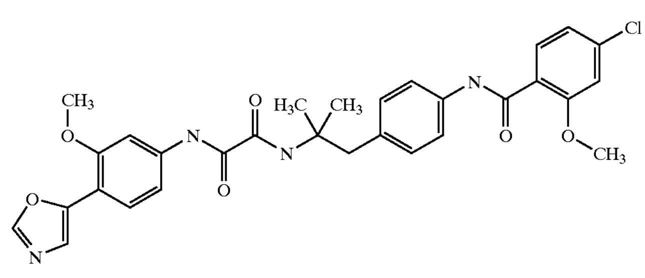 | 578.2 | 385 |

TABLE 1e-continued

| Name | Structure | MS (ES) (M + H)+ | Ex No |
|---|---|---|---|
| N-[2-[4-(2,6-Dichlorobenzamido)phenyl]-1,1-dimethylethyl]-N'-[3-methoxy-4-(5-oxazolyl)phenyl]oxalamide | 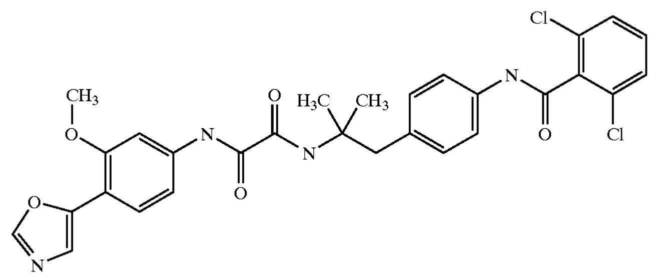 | 581 | 386 |
| N-[2-[4-[(Bicyclo[4.2.0]octa-1(6),2,4-triene-7(RS)-yl)carboxamido]phenyl]-1,1-dimethylethyl]-N'-[3-methoxy-4-(5-oxazolyl)phenyl]oxalamide | | 539.1 | 387 |
| N-[3-Methoxy-4-(5-oxazolyl)phenyl]-N'-[1,1-dimethyl-2-[4-(2-oxo-2-phenylacetamido)phenyl]ethyl]oxalamide | 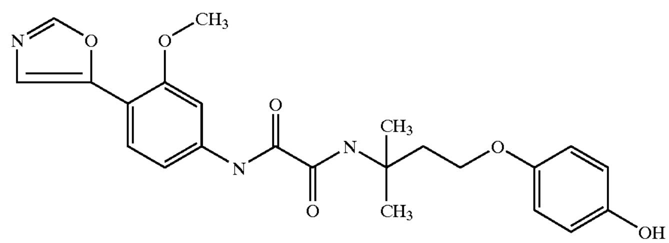 | 541.1 | 388 |
| N-[2-{4-[2-(2-Fluorophenyl)acetamido]phenyl}-1,1-dimethylethyl]-N'-[3-methoxy-4-(5-oxazolyl)phenyl]oxalamide | 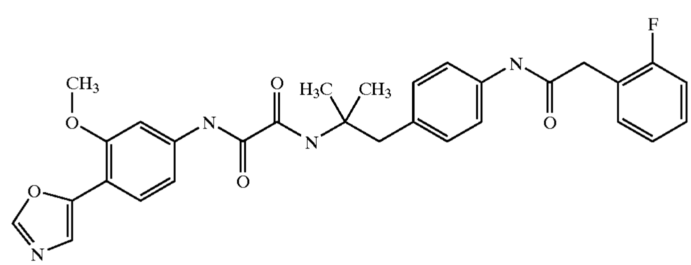 | 545 | 389 |
| N-[2-{4-[2-(4-Fluorophenyl)acetamido]phenyl}-1,1-dimethylethyl]-N'-[3-methoxy-4-(5-oxazolyl)phenyl]oxalamide | | 545 | 390 |
| N-[3-Methoxy-4-(5-oxazolyl)phenyl]-N'-[2-{4-[(4-methoxy-3-thienyl)carboxamido]phenyl}-1,1-dimethylethyl]oxalamide | | 549 | 391 |

TABLE 1e-continued

| Name | Structure | MS (ES) (M + H)+ | Ex No |
|---|---|---|---|
| N-[2-[4-(4-Acetylbenzamido) phenyl]-1,1-dimethylethyl]-N'-[3-methoxy-4-(5-oxazolyl)phenyl] oxalamide | 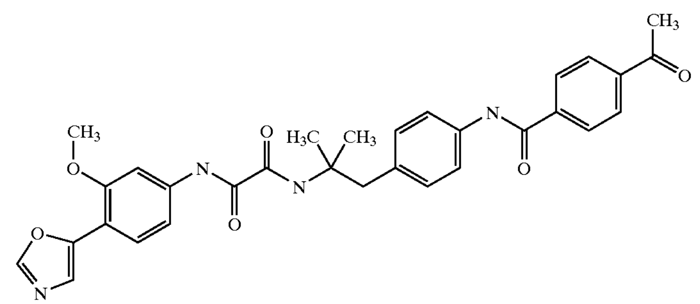 | 555.1 | 392 |
| N-[2-[4-[(1,3-Benzodioxol-5-yl) carboxamido]phenyl]-1,1-dimethylethyl]-N'-3-methoxy-4-(5-oxazolyl)phenyl]oxalamide | | 557.1 | 393 |
| N-[2-[4-[2-(2-Chlorophenyl) acetamido]phenyl]-1,1-dimethylethyl]-N'-[3-methoxy-4-(5-oxazolyl)phenyl]oxalamide | 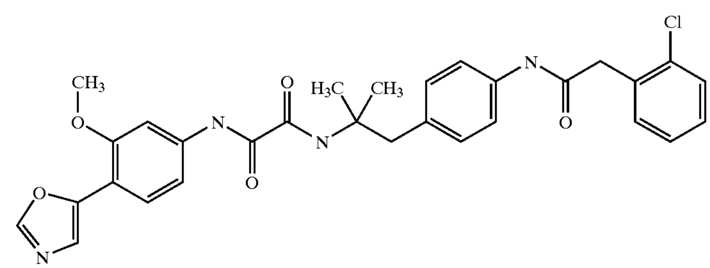 | 561.1 | 394 |
| N-[2-[4-[2-(4-Chlorophenyl) acetamido]phenyl]-1,1-dimethylethyl]-N'-[3-methoxy-4-(5-oxazolyl)phenyl]oxalamide | 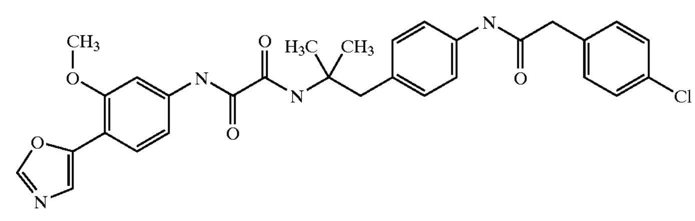 | 561.1 | 395 |
| tert-Butyl 4-[[4-[2-[[[3-methoxy-4-(5-oxazolyl)anilino]oxalyl]amino]-2-methylpropyl]phenyl]carbamoyl) benzoate | 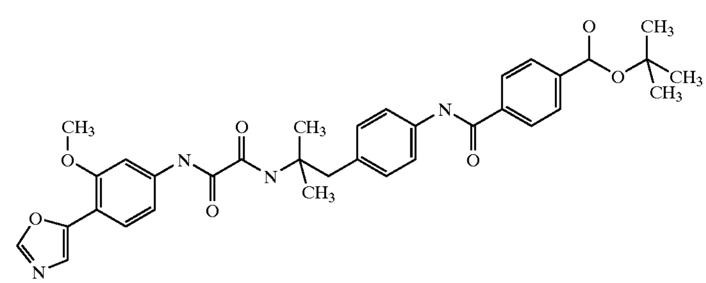 | 613 | 596 |

TABLE 1e-continued

| Name | Structure | MS (ES) (M + H)+ | Ex No |
|---|---|---|---|
| 4-[[4-[2-[[[3-Methoxy-4-(5-oxazolyl) anilino]oxalyl]amino]-2-methylpropyl]phenyl]carbamoyl] benzoic acid | 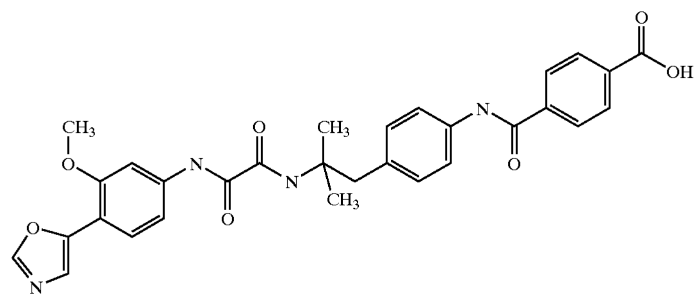 | 557 | 597 |

EXAMPLES 396–406; 433–437, 542–595 AND 635–650

Typical methods used for the preparation of the compounds of tables 1f$^1$, 1f$^2$ and 1f$^3$ are described below:

EXAMPLE 398
N-[3-Methoxy-4-(5-oxazolyl)phenyl]-N'-[1,1-dimethyl-3-(4-nitrophenoxy)propyl]oxalamide (i) A mixture of 0.5 g (3.94 mmol) of 2,4,4-trimethyl-5,6-dihydro-1,3(4H)oxazine and 0.5 g (3.6 mmol) of 4-nitrophenol were heated at 180 C under a nitrogen atmosphere for 6 hours. The resulting mixture was cooled and purified by chromatography on silica gel using ethyl acetate for the elution. There was obtained 524 mg of N-[1,1-dimethyl-3-(4-nitrophenoxy)propyl]acetamide.

(ii) 693 mg (2.61 mmol) of N-[1,1-dimeyhyl-3-(4-nitrophenoxy)propyl]acetamide, 815 mg (2.87 mmol) of titanium isopropoxide and 719 mg (3.91 mmol) of diphenylsilane were dissolved in 8 ml of tetrahydrofuran and left at room temperature for 18 hours. The resulting solution was dissolved in ethyl acetate and saturated sodium bicarbonate solution, filtered and the organic phase extracted twice with 2M hydrochloric acid. The combined acid extracts were basified with 2M sodium hydroxide solution, extracted with ethyl acetate and the organic extracts dried over magnesium sulphate, filtered and evaporated to dryness to give 266 mg of 1,1-dimethyl-3-(4-nitrophenoxy)propylamine. The 1,1-dimethyl-3-(4-nitrophenoxy)propylamine was then coupled to N-[3-methoxy-4-(5-oxazoyl)phenyl oxalamic acid by a procedure analogous to that described in example 1 to give N-[3-methoxy-4-(5-oxazolyl)phenyl]-N'-[1,1-dimethyl-3-(4-nitrophenoxy)propyl]oxalamide as a pale yellow solid. MS: m/e 469 [M+H]$^+$.

EXAMPLE 433
4-[3-[[[3-Methoxy-4-(5-oxazolyl)anilino]oxalyl]amino]-3-methylbutoxy]benzoic acid A solution of 650 mg (1.17 mmol) of benzyl 4-[3-[[[3-methoxy-4-(5-oxazolyl)anilino]oxalyl]amino]-3-methylbutoxy]benzoate in 20 ml of tetrahydrofuran was hydrogenated with 65 mg of 10% palladium on charcoal catalyst for 48 hours, a further 65 mg of catalyst being added after 24 hours and again after 44 hours. The resulting suspension was filtered, evaporated to dryness and the residue triturated with diethly ether to give 415 mg of 4-[3-[[[3-methoxy-4-(5-oxazolyl)anilino]oxalyl]amino]-3-methylbutoxy]benzoic acid as a white solid. MS: m/e 468 [M+H]$^+$.

The starting material was prepared as follows:

i) A mixture of 1.14 g (5 mmol) of benzyl 4-hydroxybenzoate and 800 mg (6.3 mmol) of 2,4,4-trimethyl-5,6-dihydro-1,3(4H)-oxazine was stirred and heated at 180° C. for 3 hours. A further 600 mg (4.72 mmol) of oxazine were added and heating was continued for 21 hours. The resulting mixture was cooled and chromatographed on silica gel using ethyl acetate/petrol (3:1) for the elution. There was obtained 1.52 g of benzyl 4-(3-acetamido-3-methylbutoxy)benzoate as a white solid. $^1$H NMR (400 MHz CDCl$_3$) δ: 1.43 (6H,s), 1.94 (3H,s), 2.26 (2H,t), 4.14 (2H,t), 5.36 (2H,s), 5.65 (1H,s), 6.91 (2H,d), 7.35–7.52 (5H,m), 8.05 (2H,d).

ii) A solution of 1.5 g (4.23 mmol) of benzyl 4-(3-acetamido-3-methylbutoxy)benzoate, 1.166 g (6.35 mmol) of diphenylsilane and 1.2 g (4.23 mmol) of titanium(IV) isopropoxide in 4 ml of tetrahydrofuran was stirred at room temperature for 6 hours. The resulting mixture was diluted with diethyl ether/2M sodium hydroxide solution, filtered and the organic phase extracted twice with 2M hydrochloric acid. The combined aqueous extracts were basified with 2M sodium hydroxide solution and extracted with ether. The organic extract was dried over magnesium sulphate and evaporated to dryness to give 1.16 g of benzyl 4-(3-amino-3-methylbutoxy)benzoate as a pale coloured gum. $^1$H NMR (400 MHz CDCl$_3$) δ: 1.22 (6H,s), 1.92 (2H,t), 4.08 (2H,t), 5.36 (2H,s), 6.90 (2H,d), 7.33–7.48 (5H,m), 8.05 (2H,d).

iii) A solution of 873 mg (3.33 mmol) of N-[3-methoxy-4-(5-oxazolyl)phenyl]oxalamic acid, 500 mg (3.27 mmol) of 1-hydroxybenzotriazole hydrate, 1.2 g (3.83 mmol) of benzyl 4-(3-amino-3-methylbutoxy)benzoate and 1 g (5.22 mmol) of 1-(3-dimethylaminopropyl)-3-ethylcarbodiimide hydrochloride in 10 ml of dimethylformamide was stirred at room temperature for 24 hours. The resulting mixture was diluted with ethyl acetate and washed with 2M hydrochloric acid, saturated sodium bicarbonate solution and water then dried over magnesium sulphate, evaporated to dryness and chromatographed on silica gel using ethyl acetate/petrol (2:1) for the elution. After trituration with diethyl ether there was obtained 765 mg of benzyl 4-[3-[[[3-methoxy-4-(5-oxazolyl)anilino]oxalyl]amino]-3-methylbutoxy] benzoate as a white solid. MS: m/e 558 [M+]$^+$.

EXAMPLE 434

2-[3-[[[3-Methoxy-4-(5-oxazolyl)anilino]oxalyl]amino]-3-methylbutoxy]benzoic acid In an analogous manner to that described in Example 433 but replacing benzyl 4-[3-[[[3-methoxy-4-(5-oxazolyl)anilino]oxalyl]amino]-3-methylbutoxy]benzoate with benzyl 2-[3-[[[3-methoxy-4-(5-oxazolyl)anilino]oxalyl]amino]-3-methylbutoxy]benzoate there was obtained 2-[3-[[[3-methoxy-4-(5-oxazolyl)anilino]oxalyl]amino-3-methylbutoxy]benzoic acid as a white solid. MS: m/e 468 [M+]$^+$.

The starting material was prepared as follows:

i) A solution of 917 mg (3.5 mmol) of N-[3-methoxy-4-(5-oxazolyl)phenyl]oxalamic acid, 650 mg (4.66 mmol) of 3-amino-3-methyl-1-butanol hydrochloride (1:1), 612 mg (4 mmol) of 1-hydroxybenzotriazole hydrate, 690 mg (6 mmol) of N-ethylmorpholine and 960 mg (5 mmol) of 1-(3-dimethylaminopropyl)-3-ethylcarbodiimide hydrochloride in 10 ml of dimethylformamide was stirred at room temperature for 20 hrs. The resulting mixture was diluted with ethyl acetate and washed with 2M hydrochloric acid, saturated sodium bicarbonate solution and water then dried over magnesium sulphate, evaporated to dryness and chromatographed on silica gel using ethyl acetate/petrol (3:1) for the elution. There was obtained 410 mg of N-(3-hydroxy-1,1-dimethylpropyl)-N'-[3-methoxy-4-(5-oxazolyl)phenyl]oxalamide as a pale yellow solid. MS: m/e 348 (M+H)$^+$.

ii) A solution of 48 mg (0.276 mmol) of diethyl azodicarboxylate in 2 ml of tetrahydrofuran was added to a mixture of 72 mg (0.275 mmol) of triphenylphosphine, 57 mg (0.25 mmol) of benzyl salicylate and 87 mg (0.25 mmol) of N-(3-hydroxy-1,1-dimethylpropyl)-N'-[3-methoxy-4-(5-oxazolyl)phenyl]oxalamide and left at room temperature for 1 hour. The resulting mixture was chromatographed twice on silica gel using first ethyl acetate/petrol (1:1) then methanol/dichloromethane (1:49) for the elutions. There was obtained 29 mg of benzyl 2-[3-[[[3-methoxy-4-(5-oxazolyl)anilino]oxalyl]amino]-3-methylbutoxy]benzoate as a colourless gum. MS: m/e 558 [M+H]$^+$.

EXAMPLE 435

3-[3-[[[3-Methoxy-4-(5-oxazolyl)anilino]oxalyl]amino]-3-methylbutoxy]benzoic acid In an analogous manner to that described in Example 433 but replacing benzyl 4-hydroxybenzoate with benzyl 3-hydroxybenzoate there was obtained 3-[3-methoxy-4-(5-oxazolyl)anilino]oxalyl]amino]-3-methylbutoxy]benzoic acid as a white solid. MS: m/e 468 [M+H]$^+$.

EXAMPLE 553

4-[2-[[[3-Methoxy-4-(5-oxazolyl)anilino]oxalyl]amino]-2-methylpropoxy]benzoic acid In an analogous manner to that described in Example 433 but replacing benzyl 4-[3-[[[3-methoxy-4-(5-oxazolyl)anilino]oxalyl]amino]-3-methylbutoxy]benzoate with benzyl 4-[2-[[[3-methoxy-4-(5-oxazolyl)anilino]oxalyl]amino]-2-methylpropoxy]benzoate there was obtained 4-[2-[[[3-methoxy-4-(5-oxazolyl)anilino]oxalyl]amino]-2-methylpropoxy]benzoic acid as a white solid. MS: m/e 454 [M+H]$^+$.

The starting material was prepared as follows:

(i) A solution of 0.280 g (4 mmol) of 2,2-dimethylaziridine (Cairns, J. Am. Chem. Soc. 1941, 63, 871) and 9 g (40 mmol) of benzyl 4-hydroxybenzoate in 30 ml of chloroform was heated under refluxed for 3 hr. The reaction mixture was allowed to cool and diluted with dichloromethane. The solution was washed with 2M sodium hydroxide solution, dried over anhydrous magnesium sulphate, and concentrated in vacuo. Column chromatography of the residue using (dichloromethane:methanol:acetic acid:water (240:12:3:2) afforded benzyl 4-(2-amino-2-methylpropoxy)benzoate (0.300 g, 1 mmol, 25%).

(ii) The benzyl 4-(2-amino-2-methylpropoxy)benzoate was coupled to N-[3-methoxy-4-(5-oxazolyl)phenyl]oxalamic acid in a manner analogous to that described for example 433, part (iii) to give benzyl 4-[2-[[[3-methoxy-4-(5-oxazolyl)anilino]oxalyl]amino]-2-methylpropoxy]benzoate as a white solid.

Example 561 was prepared in a manner analogous to that described for example 433, parts (i) and (ii) where the benzyl 4-hydroxybenzoate was replaced with 3-cyanophenol.

Examples 585, 388 and 589 were prepared from the compounds of examples 583, 587 and 586 respectively, by reacting the nitrile substituent with trimethylsilyl azide and dibutyl tin oxide according to the method of S. J. Wittenberger and B. G. J. Donner, J. Org. Chem., 1993, 58, 4139–4141.

For examples in table 1f[1] containing unprotected hydroxyl or amino groups suitable protecting groups were used, such as benzyl for hydroxyl and benzyloxycarbonyl for amino or similar groups, hereinbefore mentioned and well known in the art.

TABLE 1f[1]

| Name | Structure | MS (ES) (M + H)$^+$ | Ex No |
|---|---|---|---|
| N-[3-(4-Hydroxy-phenoxy)-1,1-dimethyl-propyl]-N'-(3-methoxy-4-oxazol-5-yl-phenyl)-oxalamide | 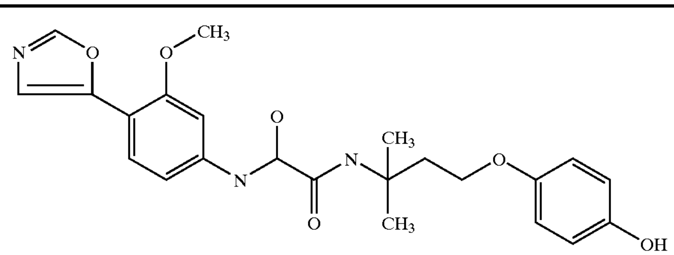 | 440 | 396 |

TABLE 1f¹-continued

| Name | Structure | MS (ES) (M + H)+ | Ex No |
|---|---|---|---|
| N-[3-Methoxy-4-(5-oxazolyl)phenyl]-N'-[3-(4-methoxyphenoxy)-1,1-dimethylpropyl]oxalamide | 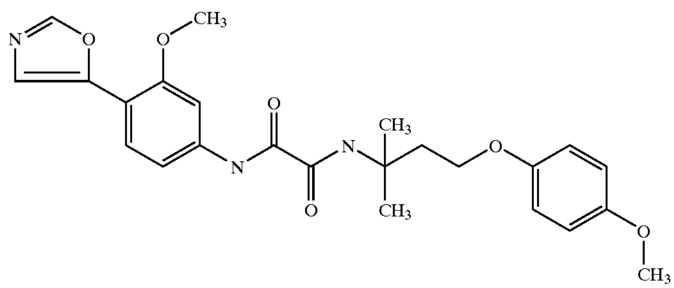 | 454 | 397 |
| N-[3-Methoxy-4-(5-oxazolyl)phenyl]-N'-[1,1-dimethyl-3-(4-nitrophenoxy)propyl]oxalamide | 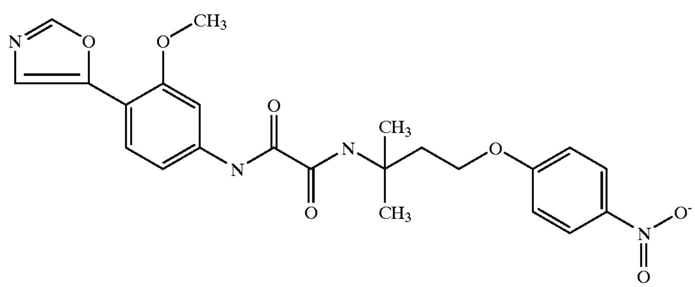 | 469 | 398 |
| N-[3-(2-Hydroxyphenoxy)-1,1-dimethylpropyl]-N'-[3-methoxy-4-(5-oxazolyl)phenyl]oxalamide | 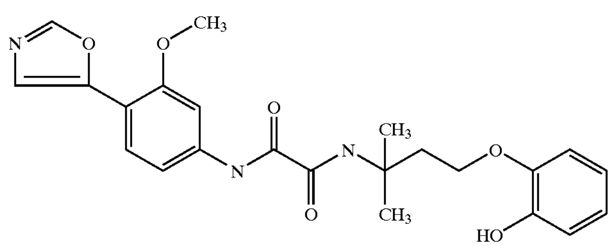 | 440 | 399 |
| N-[3-(4-Amino-phenoxy)-1,1-dimethyl-propyl]-N'-(3-methoxy-4-oxazol-5-yl-phenyl)-oxalamide | 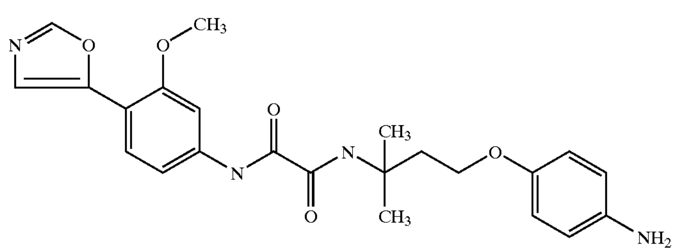 | 439 | 400 |
| N-[3-(4-Acetylamino-phenoxy)-1,1-dimethyl-propyl]-N'-(3-methoxy-4-oxazol-5-yl-phenyl)-oxalamide | 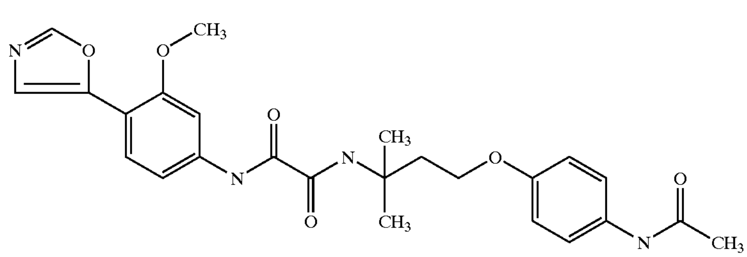 | 481 | 401 |

TABLE 1f¹-continued

| Name | Structure | MS (ES) (M + H)⁺ | Ex No |
|---|---|---|---|
| N-[3-Methoxy-4-(5-oxazolyl)phenyl]-N'-[1,1-dimethyl-3-(3-pyridyloxy)propyl]oxalamide | 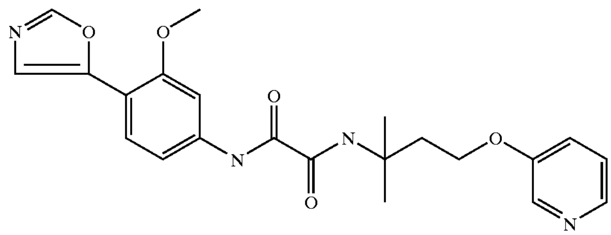 | 425 | 402 |
| N-[3-(3-Hydroxyphenoxy)-1,1-dimethylpropyl]-N'-[3-methoxy-4-(5-oxazolyl)phenyl]oxalamide | 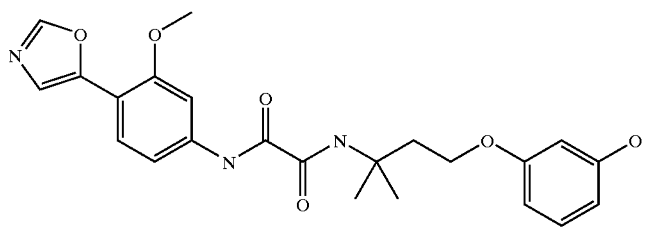 | 440 | 403 |
| N-[3-Methoxy-4-(5-oxazolyl)phenyl]-N'-[3-(3-methoxyphenoxy)-1,1-dimethylpropyl]oxalamide | 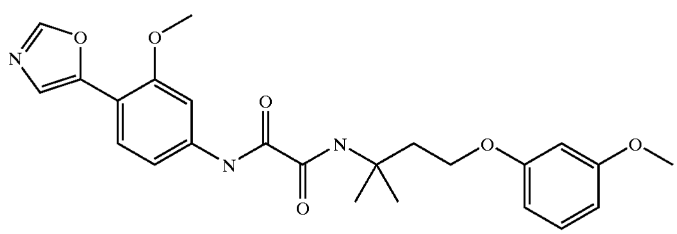 | 454 | 404 |
| N-[3-Methoxy-4-(5-oxazolyl)phenyl]-N'-[1,1-dimethyl-3-(3-nitrophenoxy)propyl]oxalamide | 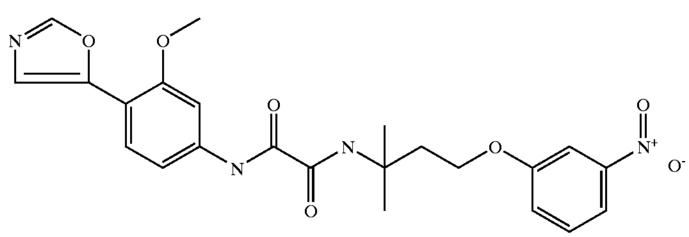 | 469 | 405 |
| N-[3-(3-Aminophenoxy)-1,1-dimethylpropyl]-N'-[3-methoxy-4-(5-oxazolyl)phenyl]oxalamide | 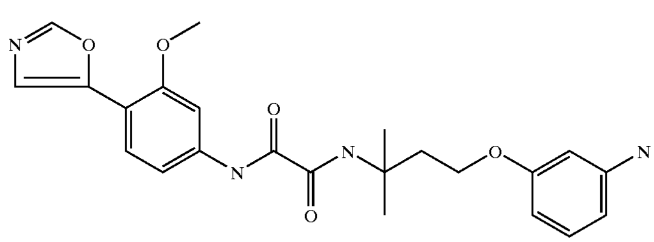 | 439 | 406 |
| 4-[3-[[[3-Methoxy-4-(5-oxazolyl)anilino]oxalyl]amino]-3-methylbutoxy]benzoic acid | 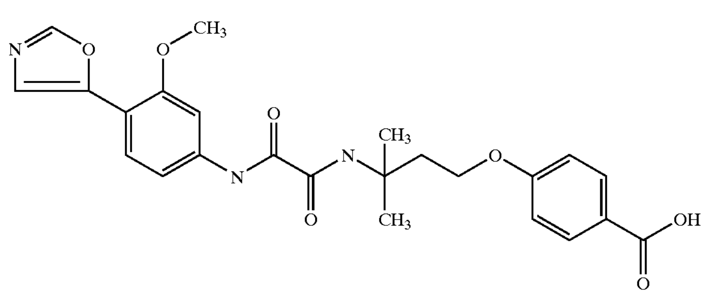 | 468 | 433 |

TABLE 1f¹-continued

| Name | Structure | MS (ES) (M + H)⁺ | Ex No |
|---|---|---|---|
| 2-[3-[[[3-Methoxy-4-(5-oxazolyl)anilino]oxalyl]amino]-3-methylbutoxy]benzoic acid | 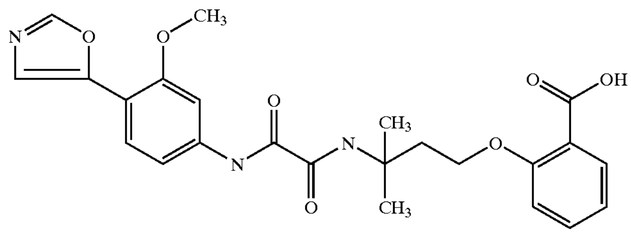 | 468 | 434 |
| 3-[3-[[[3-Methoxy-4-(5-oxazolyl)anilino]oxalyl]amino]-3-methylbutoxy]benzoic acid | 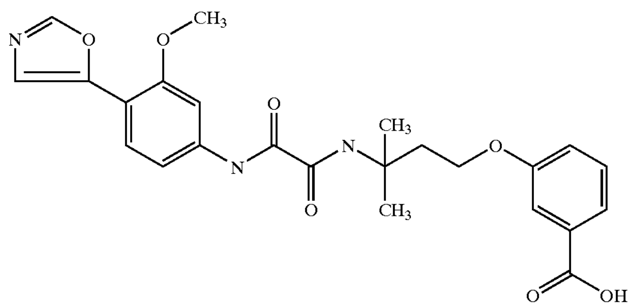 | 468 | 435 |
| 2-[4-[3-[[[3-Methoxy-4-(5-oxazolyl)anilino]oxalyl]amino]-3-methylbutoxy]phenoxy]acetic acid | 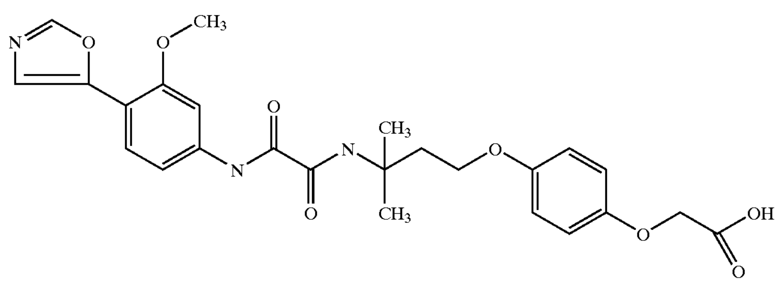 | 498 | 436 |
| 2-[2-[3-[[[3-Methoxy-4-(5-oxazolyl)anilino]oxalyl]amino]-3-methylbutoxy]phenoxy]acetic acid | 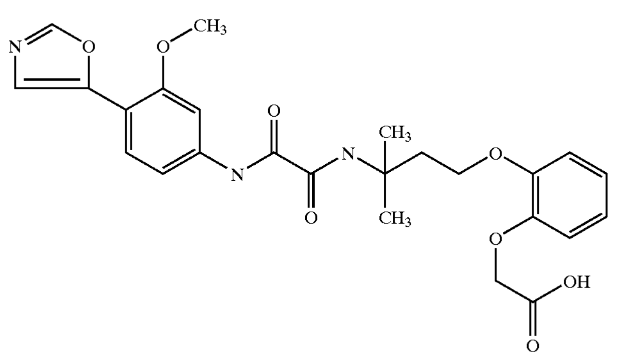 | 498 | 437 |
| N-[3-Methoxy-4-(5-oxazolyl)phenyl]-N'-(1,1-dimethyl-3-phenoxypropyl)oxalamide | 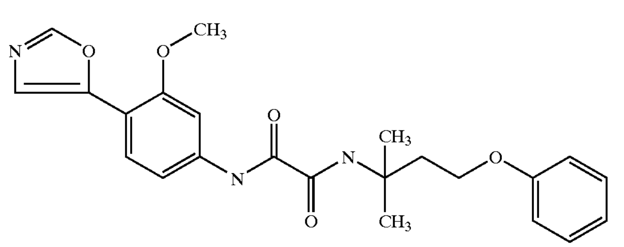 | 424 | 542 |

TABLE 1f¹-continued

| Name | Structure | MS (ES) (M + H)⁺ | Ex No |
|---|---|---|---|
| N-[3-Methoxy-4-(5-oxazolyl)phenyl]-N'-[1,1-dimethyl-3-(1-oxido-3-pyridyloxy)propyl]oxalamide | 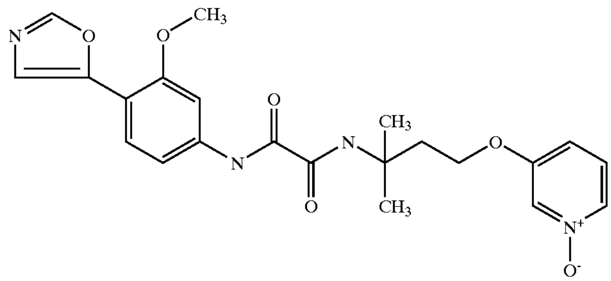 | 441 | 543 |
| N-[3-(3,4-Dihydroxyphenoxy)-1,1-dimethylpropyl]-N'-[3-methoxy-4-(5-oxazolyl)phenyl]oxalamide | 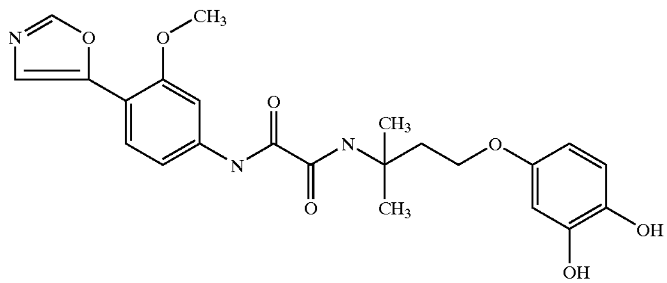 | 456 | 544 |
| N-[3-Methoxy-4-(5-oxazolyl)phenyl]-N'-[1,1-dimethyl-3-[4-(methylcarbamoyl)phenoxy]propyl]oxalamide | 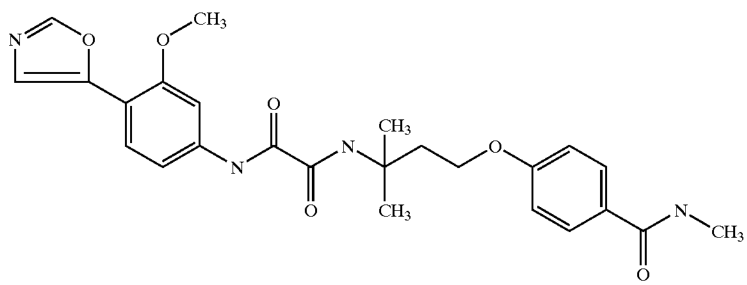 | 481 | 545 |
| N-[3-Methoxy-4-(5-oxazolyl)phenyl]-N'-[3-(3,4-dimethoxyphenoxy)-1,1-dimethylpropyl]oxalamide | 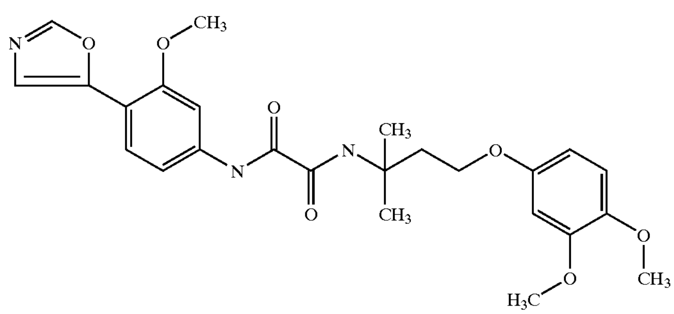 | 484 | 546 |
| N-[3-[4-[(2-Hydroxyethyl)carbamoyl]phenoxy]-1,1-dimethyl-propyl]-N'-[3-methoxy-4-(5-oxazolyl)phenyl]oxalamide | 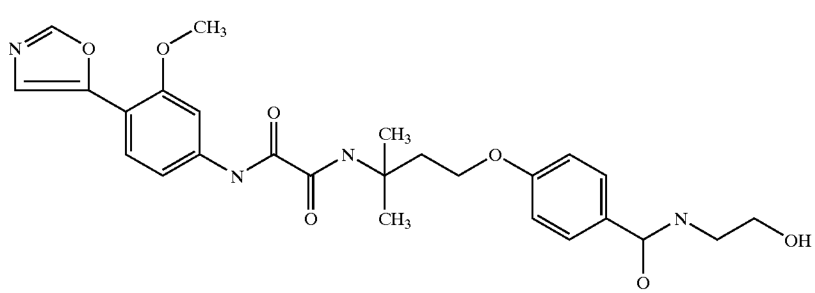 | 511 | 547 |

TABLE 1f[1]-continued

| Name | Structure | MS (ES) (M + H)+ | Ex No |
|---|---|---|---|
| N-[3-(3-Chlorophenoxy)-1,1-dimethylpropyl]-N'-[3-methoxy-4-(5-oxazolyl)phenyl]oxalamide | 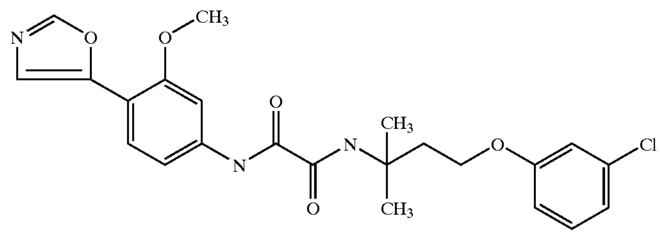 | 458 | 548 |
| N-[3-Methoxy-4-(5-oxazolyl)phenyl]-N'-[1,1-dimethyl-3-(3-pyridyloxy)propyl]oxalamide | 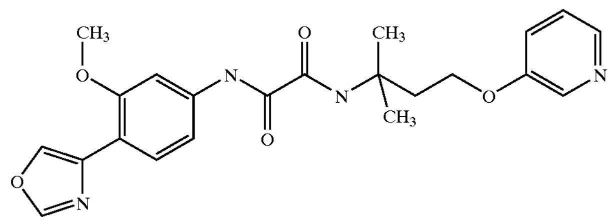 | 425 | 549 |
| N-[3-Methoxy-4-(5-oxazolyl)phenyl]-N'-[1,1-dimethyl-3-(2-pyridyloxy)propyl]oxalamide | 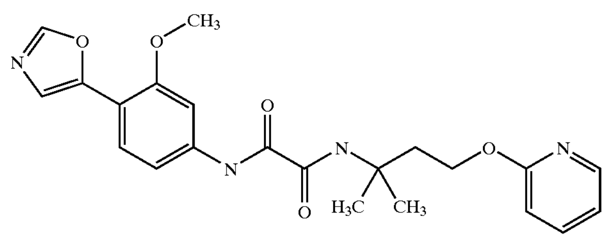 | 425 | 550 |
| 2-[4-[3-[[[3-Methoxy-4-(5-oxazolyl)anilino]oxalyl]amino]-3-methylbutoxy]phenyl]acetic acid | 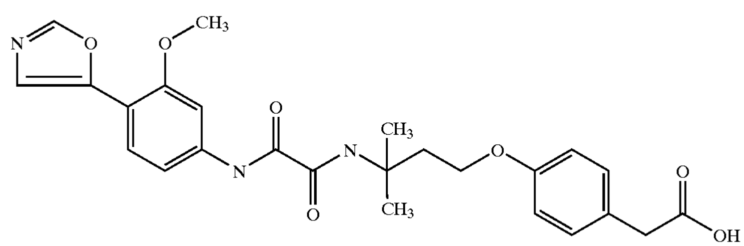 | 482 | 551 |
| 2-[3-[3-[[[3-Methoxy-4-(5-oxazolyl)anilino]oxalyl]amino]-3-methylbutoxy]phenyl]acetic acid | 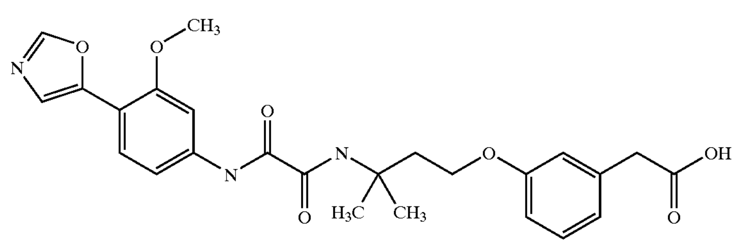 | 482 | 552 |
| 4-[2-[[[3-Methoxy-4-(5-oxazolyl)anilino]oxalyl]amino]-2-methylpropoxy]benzoic acid | 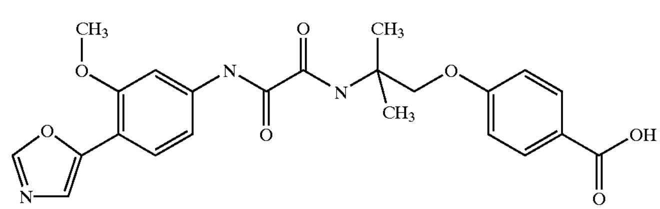 | 454 | 553 |

TABLE 1f¹-continued

| Name | Structure | MS (ES) (M + H)⁺ | Ex No |
|---|---|---|---|
| 4-[3-[[[3-Methoxy-4-(5-oxazolyl)anilino]oxalyl]amino]-3-methylbutoxy]-2-methylbenzoic acid | 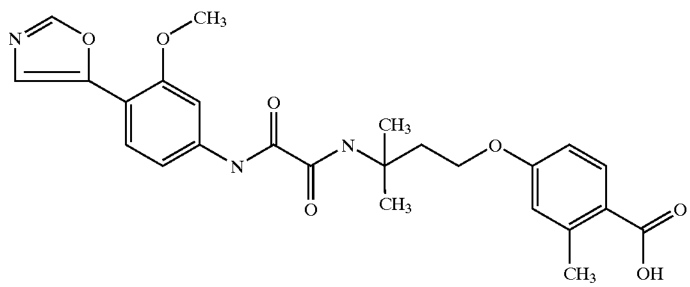 | 482 | 554 |
| 3-[3-[3-[[[3-Methoxy-4-(5-oxazolyl)anilino]oxalyl]amino]-3-methylbutoxy]phenyl]propionic acid | 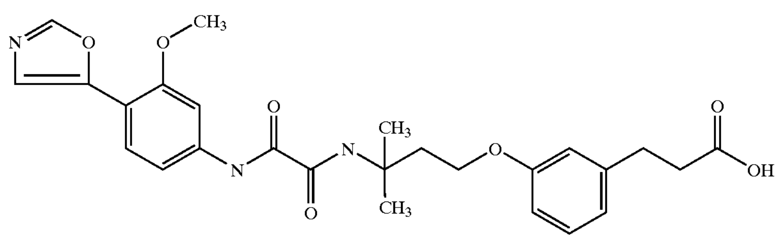 | 496 | 555 |
| 3-[4-[3-[[[3-Methoxy-4-(5oxazolyl)anilino]oxalyl]amino]-3-methylbutoxy]phenyl]propionic acid | 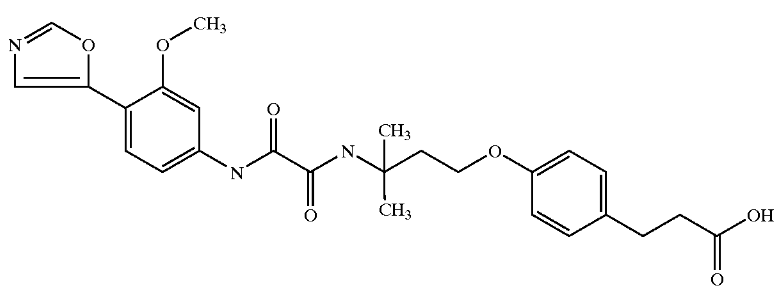 | 496 | 556 |
| 3-[2-[3-[[[3-Methoxy-4-(5-oxazolyl)anilino]oxalyl]amino]-3-methylbutoxy]phenyl]propionic acid | 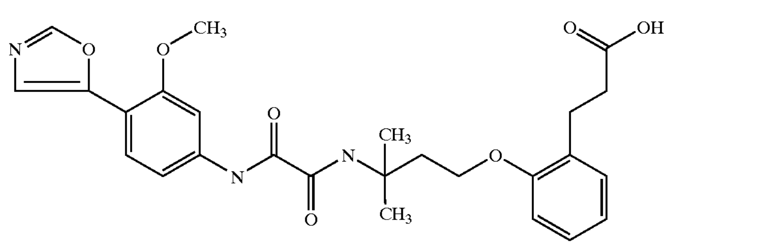 | 496 | 557 |
| 2-[3-[3-[[[3-Methoxy-4-(5-oxazolyl)anilino]oxalyl]amino]-3-methylbutoxy]phenoxy]acetic acid | 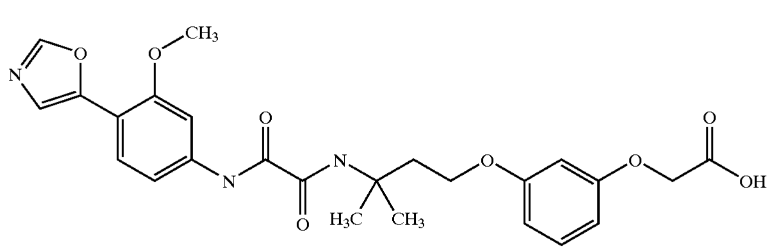 | 498 | 558 |

TABLE 1f¹-continued

| Name | Structure | MS (ES) (M + H)⁺ | Ex No |
|---|---|---|---|
| 4-[3-[[[3-Methoxy-4-(5-oxazolyl)anilino]oxalyl]amino]-3-methylbutoxy]-3-methylbenzoic acid | 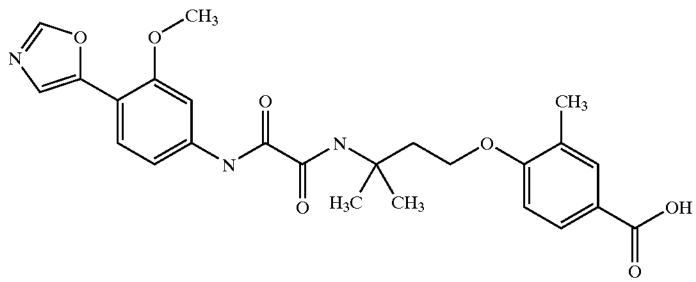 | 482 | 559 |
| N-[3-(4-Cyano-2-methoxyphenoxy)-1,1-dimethylpropyl]-N'-[3-methoxy-4-(5-oxazolyl)phenyl]oxalamide | | 479 | 560 |
| N-[3-(3-Cyanophenoxy)-1,1-dimethylpropyl]-N'-[3-methoxy-4-(5-oxazolyl)phenyl]oxalamide | 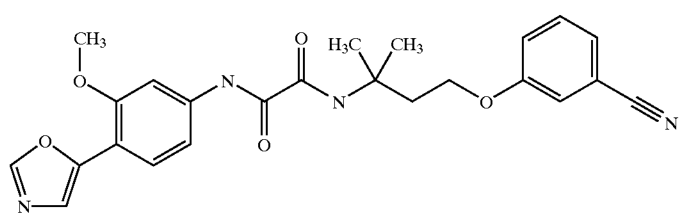 | 449.6 | 561 |
| N-[3-[4-(4-Acetyl-1-piperazinyl)phenoxy]-1,1-dimethylpropyl]-N'-[3-methoxy-4-(5-oxazolyl)phenyl]oxalamide | 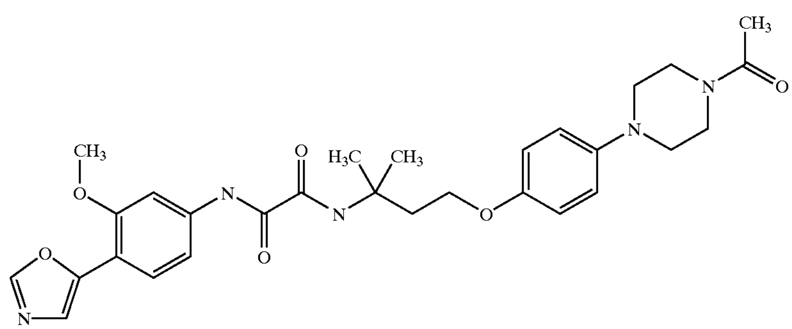 | 550.4 | 562 |
| N-[3-Methoxy-4-(5-oxazolyl)phenyl]-N'-[1,1-dimethyl-3-(2-morpholinophenoxy)propyl]oxalamide | 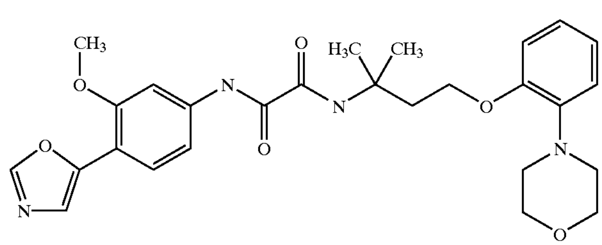 | 531.4 (M + Na)⁺ | 563 |

TABLE 1f¹-continued

| Name | Structure | MS (ES) (M + H)⁺ | Ex No |
|---|---|---|---|
| N-[3-Methoxy-4-(5-oxazolyl)phenyl]-N'-[1,1-dimethyl-3-[3-(dimethylamino)phenoxy]propyl]oxalamide | 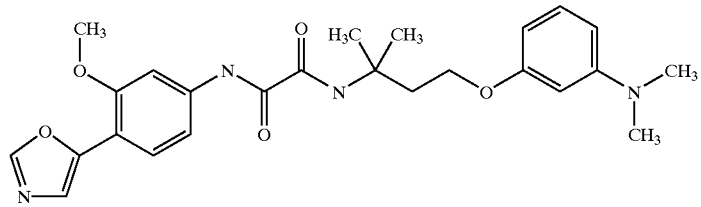 | 489.6 (M + Na)⁺ | 564 |
| N-[3-(1,3-Benzodioxol-5-yloxy)-1,1-dimethylpropyl]-N'-[3-methoxy-4-(5-oxazolyl)phenyl]oxalamide | 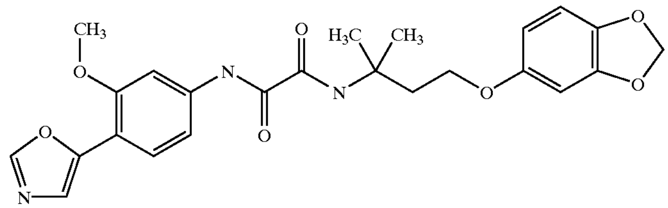 | 468.4 | 565 |
| N-[3-Methoxy-4-(5-oxazolyl)phenyl]-N'-[3-(3,4,5-trimethoxyphenoxy)-1,1-dimethylpropyl]oxalamide | 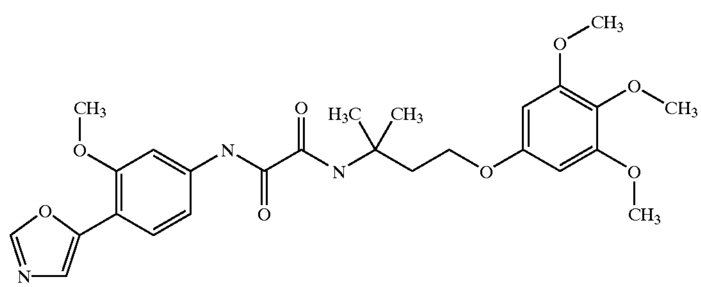 | 514.4 | 566 |
| N-[3-Methoxy-4-(5-oxazolyl)phenyl]-N'-[3-(3,5-dimethoxyphenoxy)-1,1-dimethylpropyl]oxalamide | 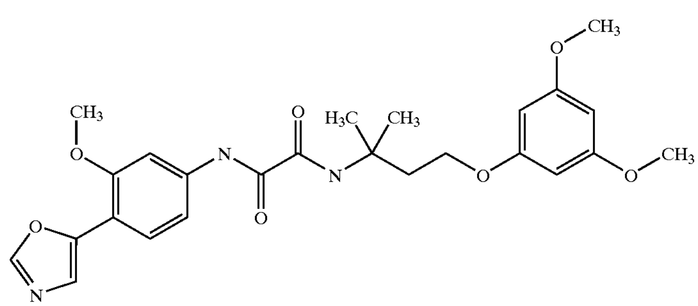 | 506 (M + Na)⁺ | 567 |
| N-[3-(5,6,7,8-Tetrahydro-5-oxo-2-naphthyloxy)-1,1-dimethylpropyl]-N'-[3-methoxy-4-(5-oxazolyl)phenyl]oxalamide | 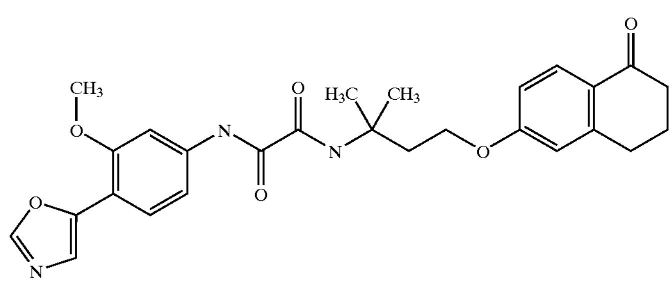 | 492.4 | 568 |

TABLE 1f¹-continued

| Name | Structure | MS (ES) (M + H)⁺ | Ex No |
|---|---|---|---|
| N-[3-(2-Acetamido-5-methylphenoxy)-1,1-dimethylpropyl]-N'-[3-methoxy-4-(5-oxazolyl)phenyl]oxalamide | 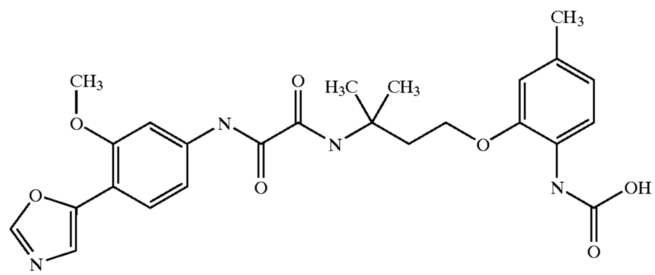 | 517.6 (M + Na)⁺ | 569 |
| N-[3-(3-Acetamidophenoxy)-1,1-dimethylpropyl]-N'-[3-methoxy-4-(5-oxazolyl)phenyl]oxalamide | 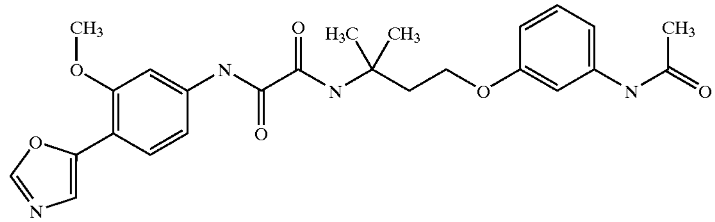 | 503.6 (M + Na)⁺ | 570 |
| N-[3-(1H-Indol-4-yloxy)-1,1-dimethylpropyl]-N'-[3-methoxy-4-(5-oxazolyl)phenyl]oxalamide | 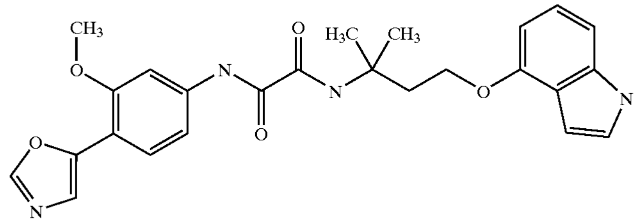 | 485.2 (M + Na)⁺ | 571 |
| N-[3-(2-Fluoro-6-methoxyphenoxy)-1,1-dimethylpropyl]-N'-[3-methoxy-4-(5-oxazolyl)phenyl]oxalamide | 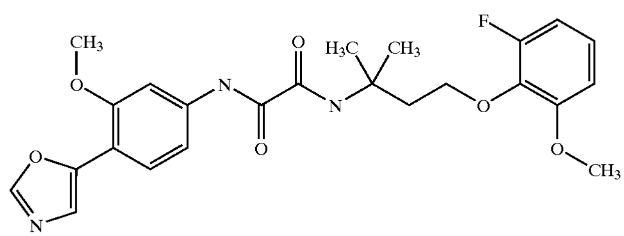 | 472.2 | 572 |
| N-[3-Methoxy-4-(5-oxazolyl)phenyl]-N'-[1,1-dimethyl-3-(2-oxo-2H-1-benzopyran-7-yloxy)propyl]oxalamide | 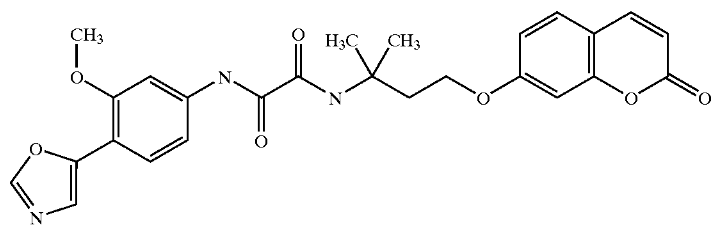 | 492.4 | 573 |
| N-[3-(4-Acetyl-3-methylphenoxy)-1,1-dimethylpropyl]-N'-[3-methoxy-4-(5-oxazolyl)phenyl]oxalamide | 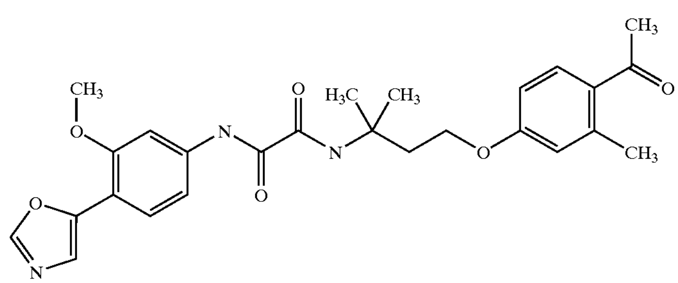 | 480.2 | 574 |

TABLE 1f¹-continued

| Name | Structure | MS (ES) (M + H)⁺ | Ex No |
|---|---|---|---|
| (E)-N-[3-Methoxy-4-(5-oxazolyl)phenyl]-N'-[1,1-dimethyl-3-[4-(3-oxo-1-butenyl)phenoxy]propyl]oxalamide | 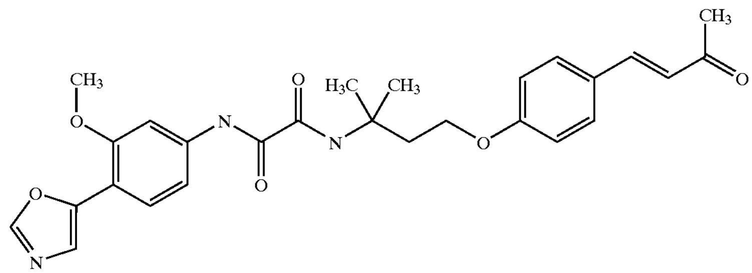 | 492.4 | 575 |
| N-[3-(3-Acetylphenoxy)-1,1-dimethylpropyl]-N'-[3-methoxy-4-(5-oxazolyl)phenyl]oxalamide | 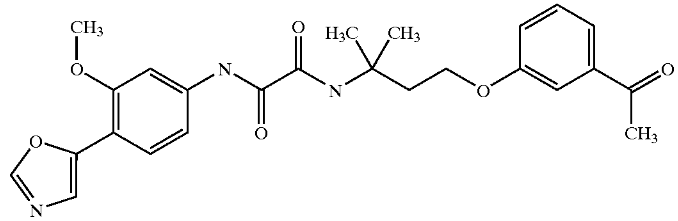 | 466.4 | 576 |
| N-[3-(4-Acetylphenoxy)-1,1-dimethylpropyl]-N'-[3-methoxy-4-(5-oxazolyl)phenyl]oxalamide | 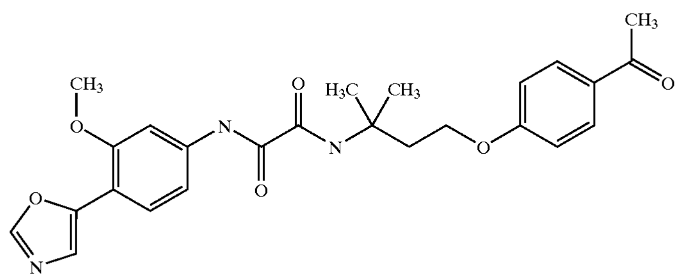 | 466.2 | 577 |
| N-[3-(4-Acetamido-2-chlorophenoxy)-1,1-dimethylpropyl]-N'-[3-methoxy-4-(5-oxazolyl)phenyl]oxalamide | 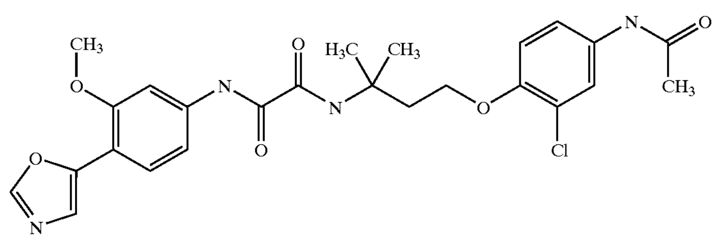 | 515.6 | 578 |
| N-[3-Methoxy-4-(5-oxazolyl)phenyl]-N'-[1,1-dimethyl-3-(4-pyridyloxy)propyl]oxalamide | 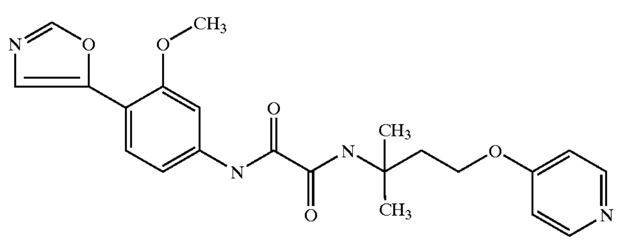 | 425 | 579 |
| N-[3-Methoxy-4-(5-oxazolyl)phenyl]-N'-[1,1-dimethyl-3-(1-oxido-4-pyridyloxy)propyl]oxalamide | 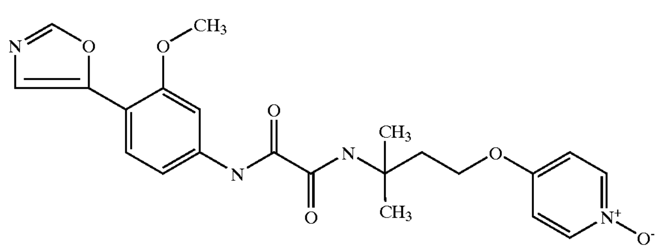 | 441 | 580 |

TABLE 1f¹-continued

| Name | Structure | MS (ES) (M + H)⁺ | Ex No |
|---|---|---|---|
| N-[3-Methoxy-4-(5-oxazolyl)phenyl]-N'-[1,1-dimethyl-3-(2,6-dimethyl-4-pyridyloxy)propyl]oxalamide | | 453 | 581 |
| N-[3-Methoxy-4-(5-oxazolyl)phenyl]-N'-[1,1-dimethyl-3-(2,6-dimethyl-1-oxido-4-pyridyloxy)propyl]oxalamide | | 469 | 582 |
| N-[2-(4-Cyanophenoxy)-1,1-dimethylethyl]-N'-[3-methoxy-4-(5-oxazolyl)phenyl]oxalamide | | 435 | 583 |
| N-[3-Methoxy-4-(5-oxazolyl)phenyl]-N'-[3-(2-methoxy-4-pyridyloxy)-1,1-dimethylpropyl]oxalamide | | 455 | 584 |
| N-[3-Methoxy-4-(5-oxazolyl)phenyl]-N'-[1,1-dimethyl-2-[4-(1H-tetrazol-5-yl)phenoxy]ethyl]oxalamide | | 478 | 585 |

TABLE 1f¹-continued

| Name | Structure | MS (ES) (M + H)⁺ | Ex No |
|---|---|---|---|
| N-[3-(4-Cyanophenoxy)-1,1-dimethylpropyl]-N'-[3-methoxy-4-(5-oxazolyl)phenyl]oxalamide | 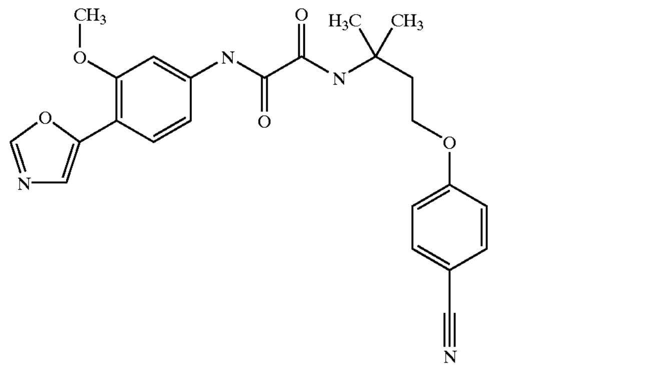 | 449 | 586 |
| N-[2-(3-Cyanophenoxy)-1,1-dimethylethyl]-N'-[3-methoxy-4-(5-oxazolyl)phenyl]oxalamide | 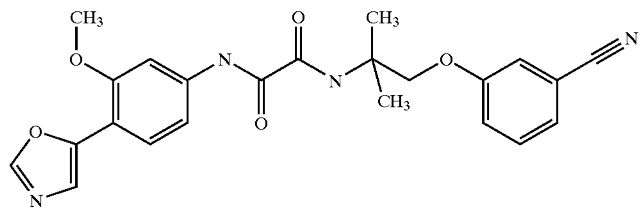 | 476 | 587 |
| N-[3-Methoxy-4-(5-oxazolyl)phenyl]-N'-[1,1-dimethyl-2-[3-(1H-tetrazol-5-yl)phenoxy]ethyl]oxalamide | 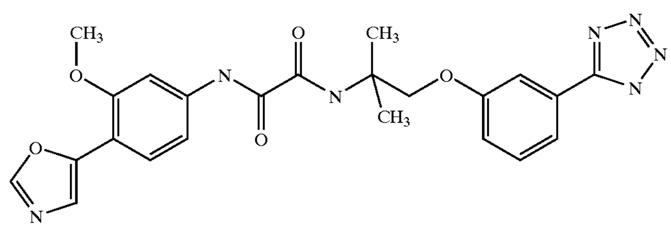 | 478 | 588 |
| N-[3-Methoxy-4-(5-oxazolyl)phenyl]-N'-[1,1-dimethyl-3-[4-(1H-tetrazol-5-yl)phenoxy]propyl]oxalamide | 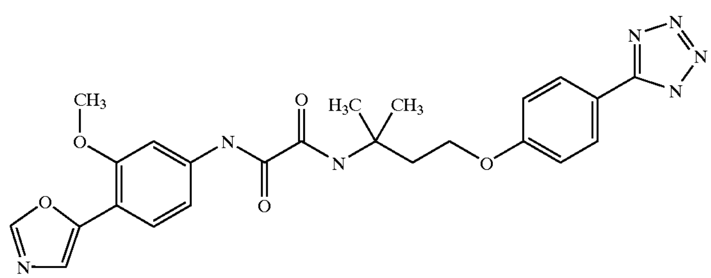 | 492 | 589 |
| Benzyl 4-[2-[1-[[[3-methoxy-4-(5-oxazolyl)anilino]oxalyl]amino]-1-cyclobutyl]ethoxy]benzoate | 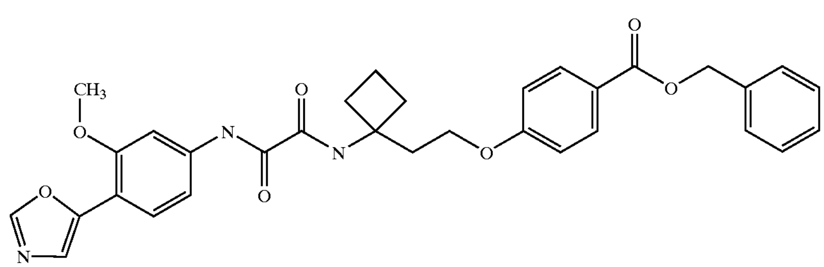 | 570.2 | 590 |

TABLE 1f¹-continued

| Name | Structure | MS (ES) (M + H)⁺ | Ex No |
|---|---|---|---|
| Benzyl 4-[2-[1-[[[3-methoxy-4-(5-oxazolyl)anilino]oxalyl]amino]-1-cyclopentyl]ethoxy]benzoate | 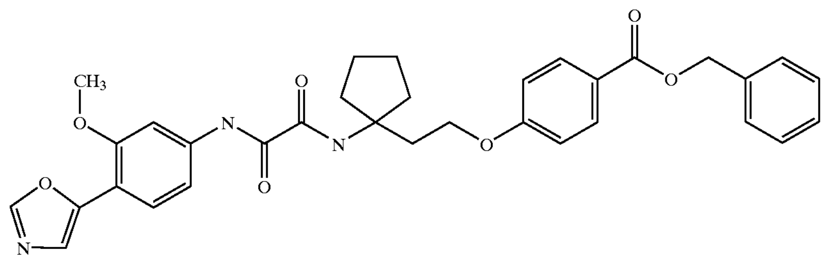 | 584.3 | 591 |
| Benzyl 4-[2-[1-[[[3-methoxy-4-(5-oxazolyl)anilino]oxalyl]amino]-1-cyclohexyl]ethoxy]benzoate | 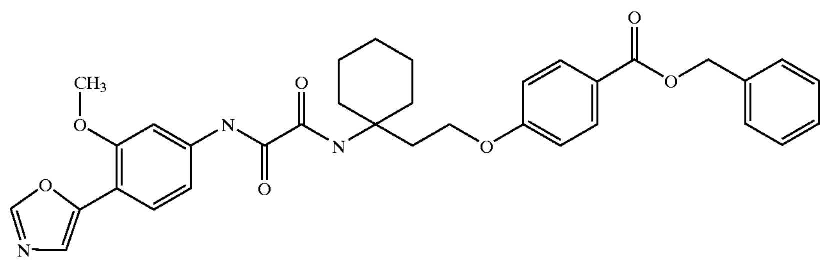 | 598.3 | 592 |
| 4-[2-[1-[[[3-Methoxy-4-(5-oxazolyl)anilino]oxalyl]amino]-1-cyclopentyl]ethoxy]benzoic acid | 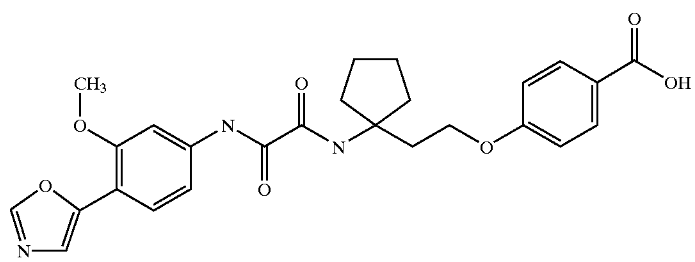 | 494.2 | 593 |
| 4-[2-[1-[[[3-Methoxy-4-(5-oxazolyl)anilino]oxalyl]amino]-1-cyclohexyl]ethoxy]benzoic acid | 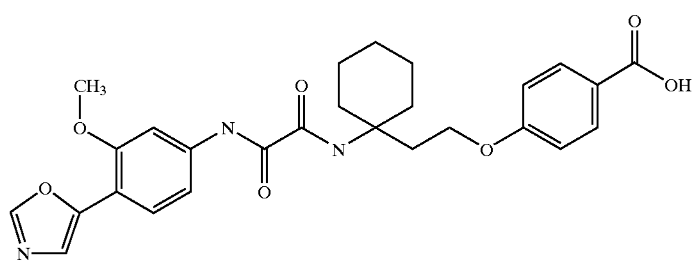 | 508.2 | 594 |
| 4-[2-[1-[[[3-Methoxy-4-(5-oxazolyl)anilino]oxalyl)amino]-1-cyclobutyl]ethoxy]benzoic acid | 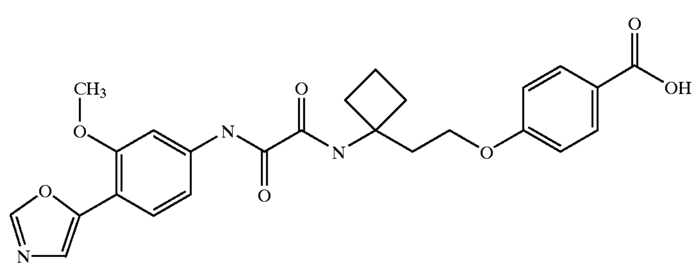 | 480.2 | 595 |

TABLE 1f¹-continued

| Name | Structure | MS (ES) (M + H)⁺ | Ex No |
|---|---|---|---|
| Benzyl 2-methoxy-4-[3-[[[3-methoxy-4-(5-oxazolyl)anilino]oxalyl]amino]-3-methylbutoxy]benzoate | 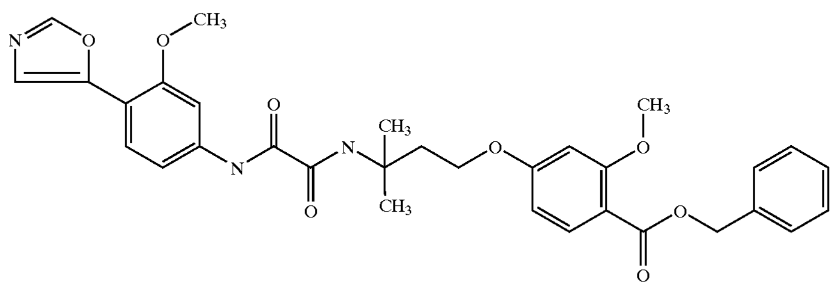 | 588 | 635 |
| 3-Chloro-4-[3-[[[3-methoxy-4-(5-oxazolyl)anilino]oxalyl]amino]-3-methylbutoxy]benzoic acid | 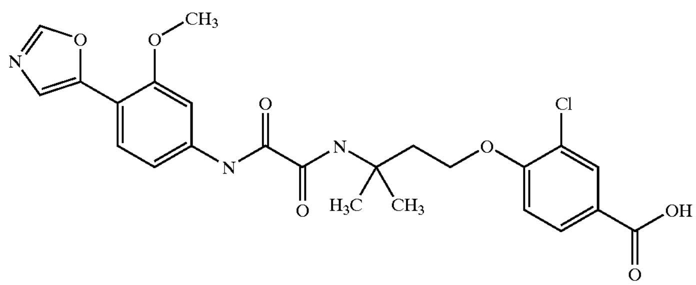 | 502 | 636 |
| 2-Methoxy-4-[3-[[[3-methoxy-4-(5-oxazolyl)anilino]oxalyl]amino]-3-methylbutoxy]benzoic acid | 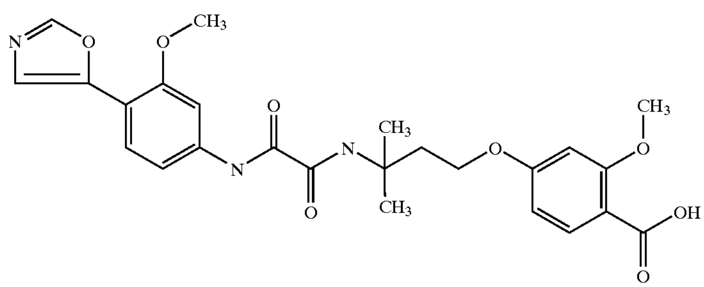 | 498 | 637 |
| 3-Methoxy-4-[3-[[[3-methoxy-4-(5-oxazolyl)anilino]oxalyl]amino]-3-methylbutoxy]benzoic acid | 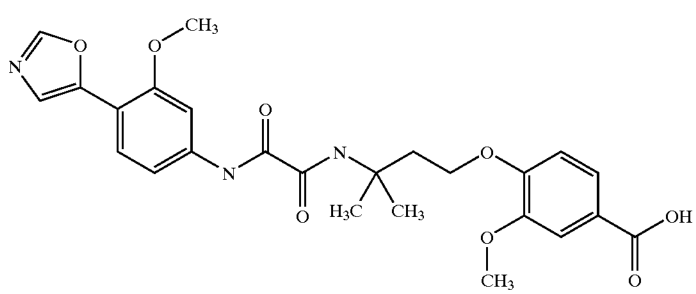 | 498 | 638 |
| 4-[2-[1-[[[3-Methoxy-4-(5-oxazolyl)anilino]oxalyl]amino]-1-cyclopropyl]ethoxy]benzoic acid | 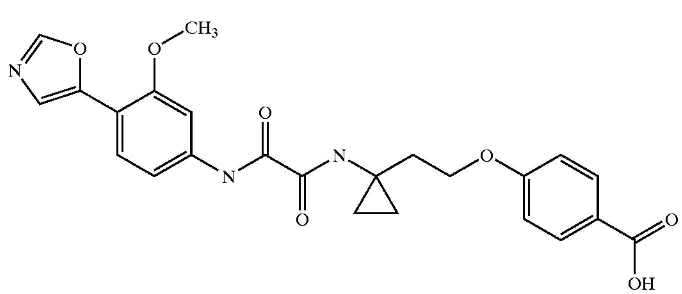 | 466 | 639 |

TABLE 1f[1]-continued

| Name | Structure | MS (ES) (M + H)+ | Ex No |
|---|---|---|---|
| 2-Chloro-4-[3-[[[3-methoxy-4-(5-oxazolyl)anilino]oxalyl]amino]-3-methylbutoxy]benzoic acid | 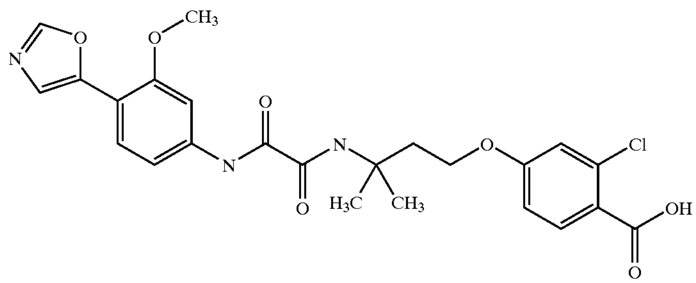 | 502 | 640 |
| 4-[3-[[[3-Methoxy-4-(5-oxazolyl)anilino]oxalyl]amino]-3-methylbutoxy]-2-quinolinecarboxylic acid | 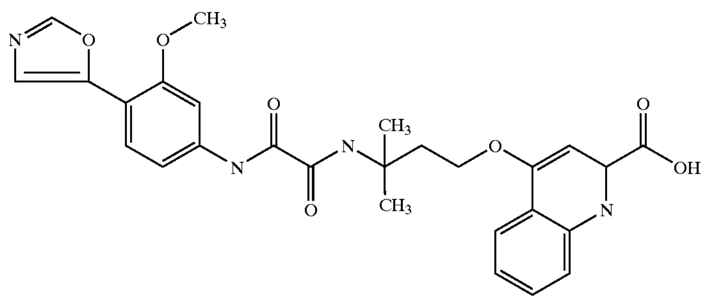 | 519 | 641 |
| (cis/trans)-4-[3-[[[3-Methoxy-4-(5-oxazolyl)anilino]oxalyl]amino]-3-methylbutoxy]-1-cyclohexanecarboxylic acid | 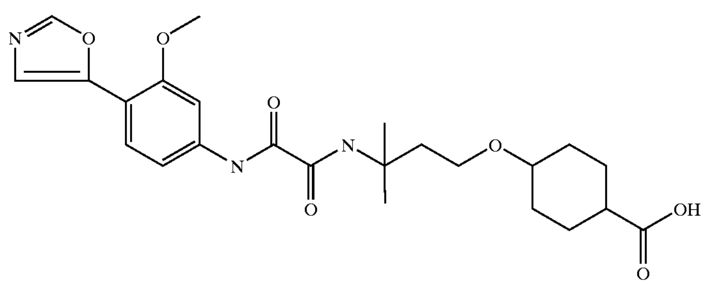 | 474 | 642 |
| (cis/trans)-4-[2-[[[3-Methoxy-4-(5-oxazolyl)anilino]oxalyl]amino]-2-methylpropoxy]-1-cyclohexanecarboxylic acid | 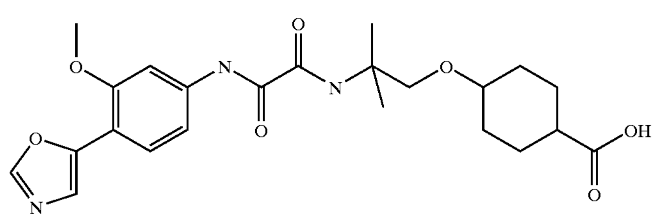 | 460 | 643 |
| 3-Fluoro-4-[3-[[[3-methoxy-4-(5-oxazolyl)anilino]oxalyl]amino]-3-methylbutoxy]benzoic acid | 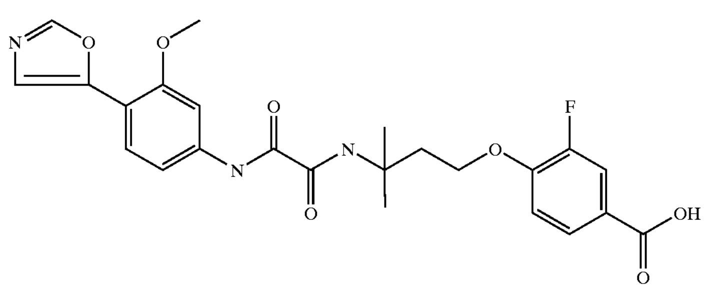 | 486 | 644 |

TABLE 1f¹-continued

| Name | Structure | MS (ES) (M + H)⁺ | Ex No |
|---|---|---|---|
| 3-Acetamido-4-[3-[[[3-methoxy-4-(5-oxazolyl)anilino]oxalyl]amino]-3-methylbutoxy]benzoic acid | 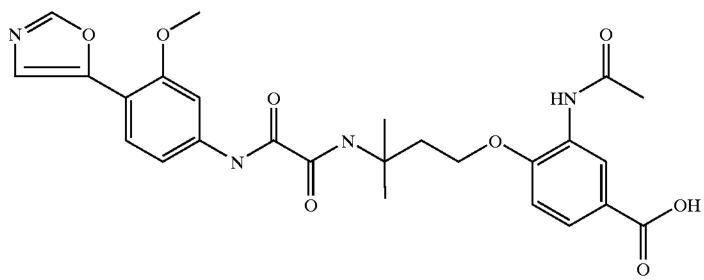 | 525 | 645 |
| 3-(Methanesulfonamido)-4-[3-[[[3-methoxy-4-(5-oxazolyl)anilino]oxalyl]amino]-3-methylbutoxy]benzoic acid | 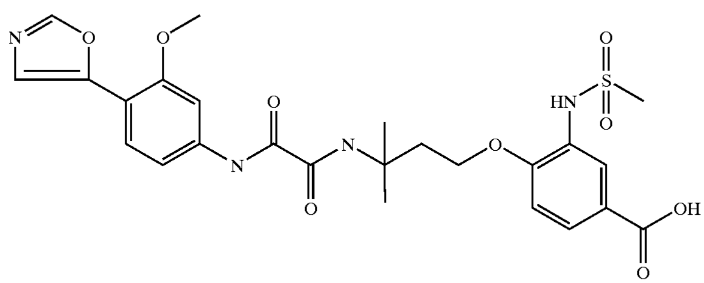 | 561 | 646 |
| 4-[3-[[[3-Methoxy-4-(5-oxazolyl)anilino]oxalyl]amino]-3-methylbutoxy]-3,5-dimethylbenzoic acid | 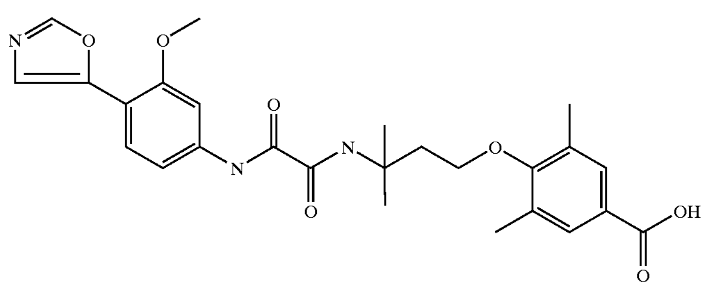 | 496 | 647 |
| 3-[3-[[[3-Methoxy-4-(5-oxazolyl)anilino]oxalyl]amino]-3-methylbutoxy]-2-pyridinecarboxylic acid | 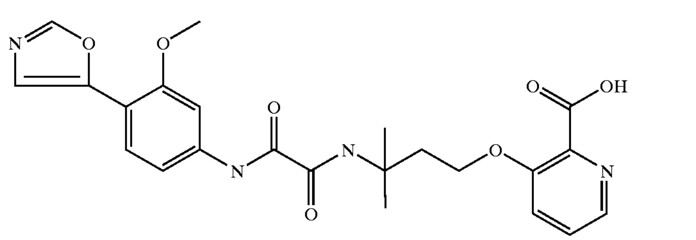 | 469 | 648 |
| 8-[3-[[[3-Methoxy-4-(5-oxazolyl)anilino]oxalyl]amino]-3-methylbutoxy]-2-quinolinecarboxylic acid | 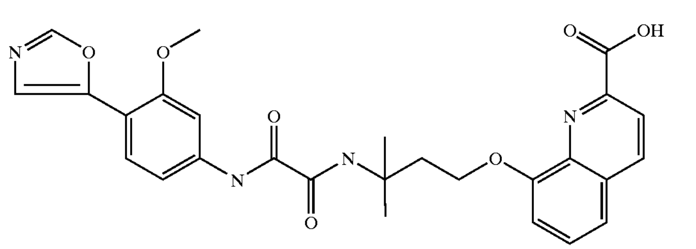 | 519 | 649 |

TABLE 1f¹-continued

| Name | Structure | MS (ES) (M + H)⁺ | Ex No |
|---|---|---|---|
| 5-[3-[[[3-Methoxy-4-(5-oxazolyl)anilino]oxalyl]amino]-3-methylbutoxy]-2-indolecarboxylic acid | 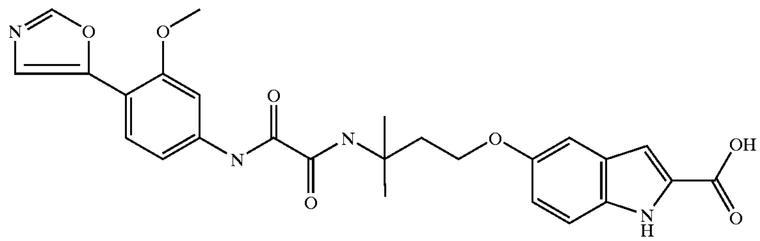 | 507 | 650 |

EXAMPLES 615–631 AND 664–670

Example 615

N-[3-Methoxy-4-(5-oxazolyl)phenyl]-N'-[1,1-dimethyl-2-(phenylthio)ethyl]oxalamide (i) A mixture of 2 g (17.7 mmol) of 2,4,4-trimethyl-2-oxazoline and 1.95 g (17.7 mmol) of thiophenol were heated at 120 C for 18 hours. After cooling the resulting solid was triturated with diethyl ether/petrol (1:2) and filtered off to give 2.55 g of N-[1,1-dimethyl-2-(phenylthio)ethyl]acetamide as a white solid.

(ii) A solution of 2.5 g (11.2 mmol) of N-[1,1-dimethyl-2-(phenylthio)ethyl]acetamide, 3.18 g (11.2 mmol) of titanium isopropoxide and 3.09 g (16.8 mmol) of diphenylsilane in 12 ml of tetrahydrofuran were stirred at room temperature for 18 hours. The resulting mixture was chromatographed on silica gel using 3%, 6% and 10% methanol in dichloromethane for the elution. There was obtained 2 g of 1,1-dimethyl-2-(phenylthio)ethylamine as a pale orange oil. The 1,1-dimethyl-2-(phenylthio)ethylamine was then coupled to N-[3-methoxy-4-(5-oxazoyl)phenyl oxalamic acid by a procedure analogous to that described in example 1 to afford N-[3-methoxy-4-(5-oxazolyl)phenyl]-N'-[1,1-dimethyl-2-(phenylthio)ethyl]oxalamide. MS: m/e 426 [M+H]⁺.

Example 616 was prepared by an analogous method to that described for example 615 but using 4-benzyloxythiophenol in place of the thiophenol and removing the protecting group using a mixture of hydrogen bromide in acetic acid.

The additional compounds in table 1f² were prepared in an analogous manner to that described for example 615 by reaction of the appropriate thiol with either 2,4,4-trimethyl-2-oxazoline or 2,4,4-trimethyl-5,6-dihydro-1,3(4H)oxazine and, where necessary, removal of any protecting groups by conventional methods.

TABLE 1f²

| Name | Structure | MS (ES) (M + H)⁺ | Ex No |
|---|---|---|---|
| N-[3-Methoxy-4-(5-oxazolyl)phenyl]-N'-[1,1-dimethyl-2-(phenylthio)ethyl]oxalamide | 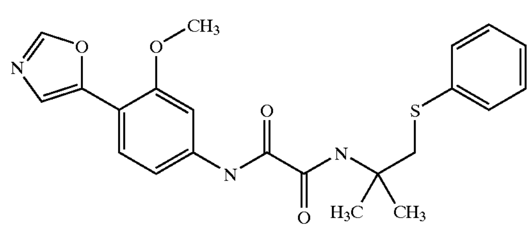 | 426 | 615 |
| N-[2-(4-Hydroxyphenylthio)-1,1-dimethylethyl]-N'-[3-methoxy-4-(5-oxazolyl)phenyl]oxalamide | 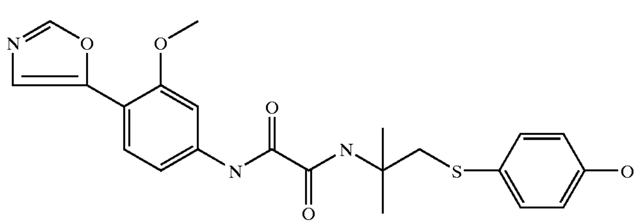 | 442 | 616 |

TABLE 1f²-continued

| Name | Structure | MS (ES) (M + H)⁺ | Ex No |
|---|---|---|---|
| N-[3-Methoxy-4-(5-oxazolyl)phenyl]-N'-[1,1-dimethyl-2-(phenylthio)ethyl]oxalamide | 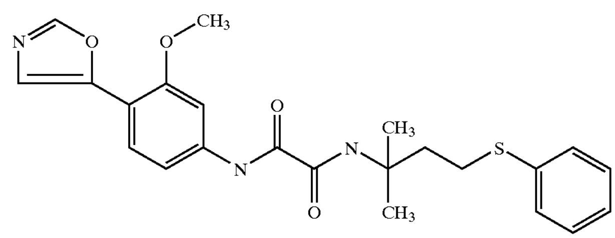 | 440 | 617 |
| N-[3-Methoxy-4-(5-oxazolyl)phenyl]-N'-[1,1-dimethyl-2-(2-pyridylthio)ethyl]oxalamide | 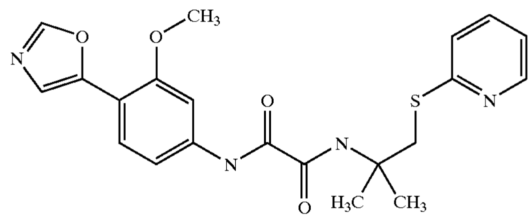 | 427 | 618 |
| N-[3-Methoxy-4-(5-oxazolyl)phenyl]-N'-[1,1-dimethyl-3-(2-pyridylthio)propyl]oxalamide | 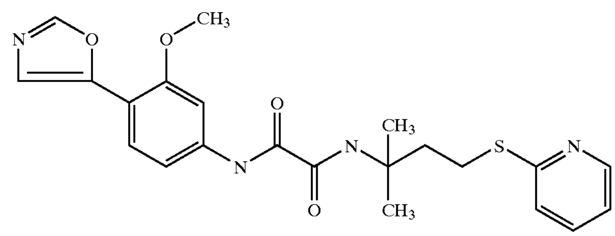 | 441 | 619 |
| N-[3-Methoxy-4-(5-oxazolyl)phenyl]-N'-[1,1-dimethyl-3-(2-thienylthio)propyl]oxalamide | 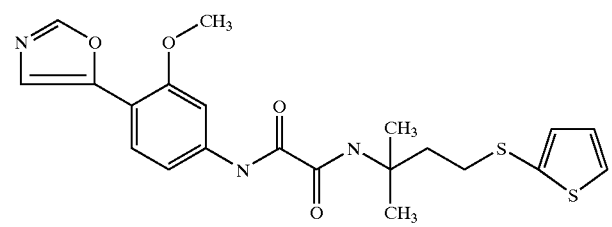 | 446 | 620 |
| N-[3-Methoxy-4-(5-oxazolyl)phenyl]-N'-[1,1-dimethyl-3-(2-pyrimidylthio)propyl]oxalamide | 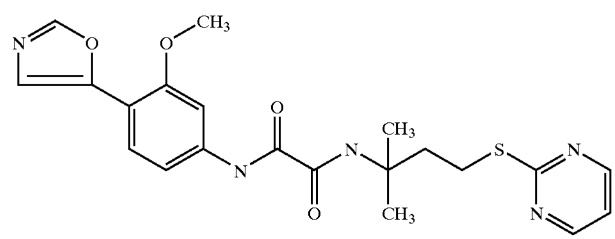 | 442 | 621 |
| N-[3-Methoxy-4-(5-oxazolyl)phenyl]-N'-[1,1-dimethyl-3-(4-pyridylthio)propyl]oxalamide | 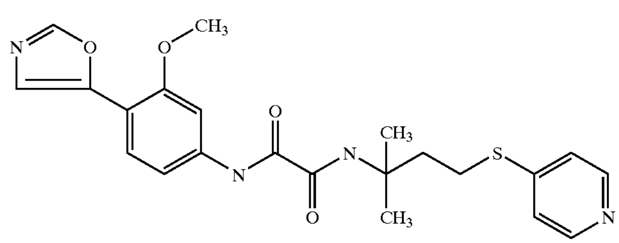 | 441 | 622 |

TABLE 1f²-continued

| Name | Structure | MS (ES) (M + H)⁺ | Ex No |
|---|---|---|---|
| N-[3-Methoxy-4-(5-oxazolyl)phenyl]-N'-[1,1-dimethyl-3-(2-thiazolylthio)propyl]oxalamide | 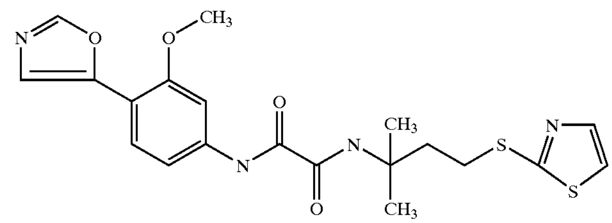 | 447 | 623 |
| N-[3-(4-Hydroxyphenylthio)-1,1-dimethylpropyl]-N'-[3-methoxy-4-(5-oxazolyl)phenyl]oxalamide | 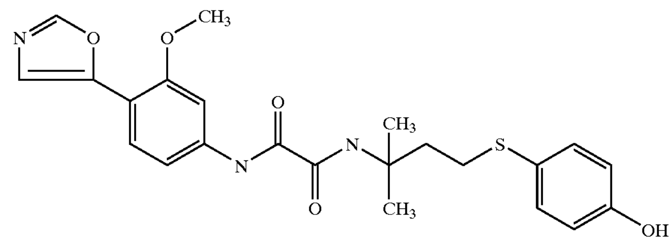 | 456 | 624 |
| N-[3-Methoxy-4-(5-oxazolyl)phenyl]-N'-[1,1-dimethyl-3-(5-methyl-1,3,4-thiadiazol-2-ylthio)propyl]oxalamide | 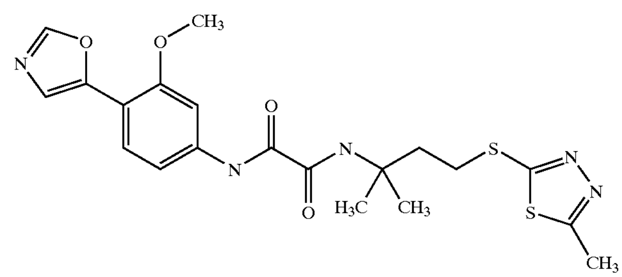 | 462 | 625 |
| N-[3-(2-Benzooxazolylthio)-1,1-dimethylpropyl]-N'-[3-methoxy-4-(5-oxazolyl)phenyl]oxalamide | 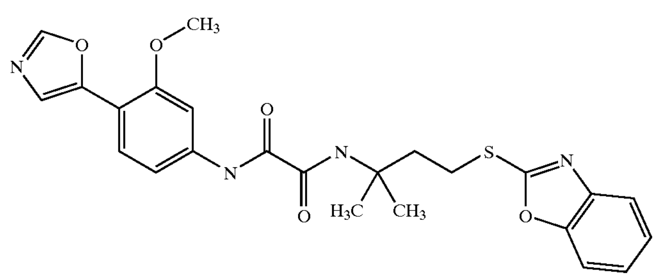 | 481 | 626 |
| N-[3-(2-Benzothiazolylthio)-1,1-dimethylpropyl]-N'-[3-methoxy-4-(5-oxazolyl)phenyl]oxalamide | 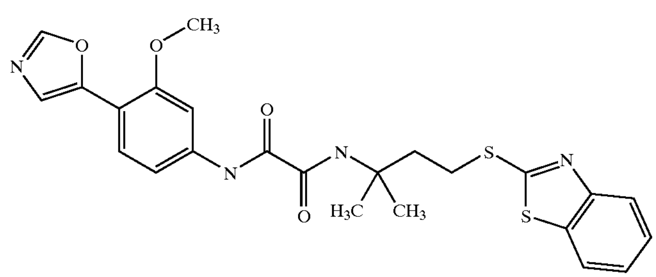 | 497 | 627 |
| Methyl 4-[2-[[[3-methoxy-4-(5-oxazolyl)anilino]oxalyl[amino]-2-methylpropylthio]benzoate | 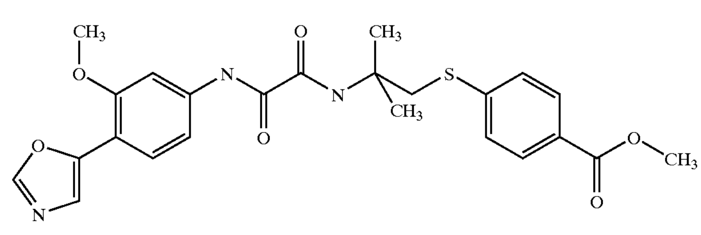 | 484 | 628 |

TABLE 1f²-continued

| Name | Structure | MS (ES) (M + H)⁺ | Ex No |
|---|---|---|---|
| tert-Butyl 6-[3-[[[3-methoxy-4-(5-oxazolyl)anilino]oxalyl]amino]-3-methylbutylthio]-3-pyridinecarboxylate | 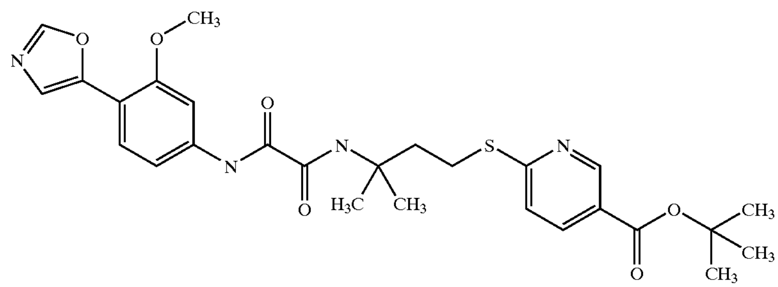 | 541 | 629 |
| 6-[3-[[[3-Methoxy-4-(5-oxazolyl)anilino]oxalyl]amino]-3-methylbutylthio]-3-pyridinecarboxylic acid trifluoroacetate (1:1) | 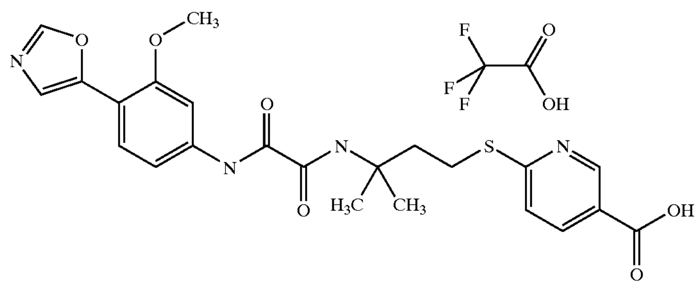 | 485 | 630 |
| 4-[3-[[[3-Methoxy-4-(5-oxazolyl)anilino]oxalyl]amino]-3-methylbutylthio]benzoic acid | 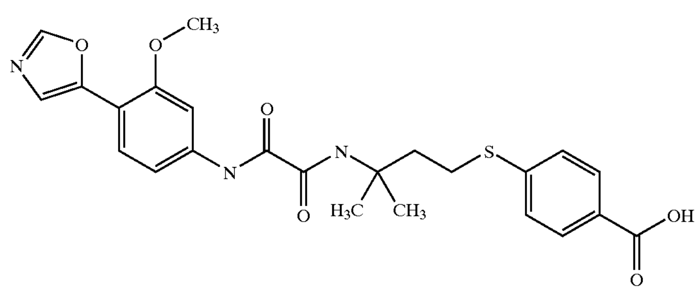 | 484 | 631 |
| N-[2-(4-Benzyloxyphenylthio)-1,1-dimethylethyl]-N'-[3-methoxy-4-(5-oxazolyl)phenyl]oxalamide | | 532 | 664 |
| N-[2-(4-Benzyloxyphenylthio)-1,1-dimethylethyl]-N'-[3-methoxy-4-(5-oxazolyl)phenyl]oxalamide | | 546 | 665 |

TABLE 1f²-continued

| Name | Structure | MS (ES) (M + H)⁺ | Ex No |
|---|---|---|---|
| 2-[3-[[[3-Methoxy-4-(5-oxazolyl)anilino]oxalyl]amino]-3-methylbutylthio]-5-benzoxazolecarboxylic acid | 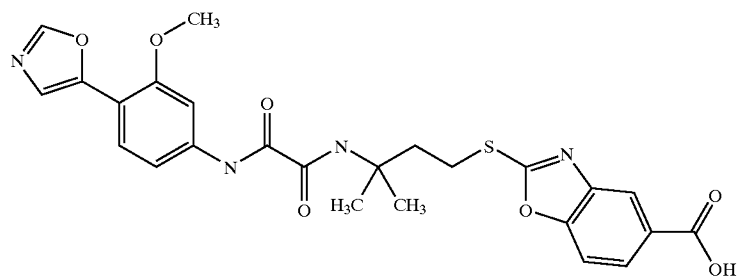 | 525 | 666 |
| N-[3-(1H-Imidazol-2-ylthio)-1,1-dimethylpropyl]-N'-[3-methoxy-4-(5-oxazolyl)phenyl] oxalamide | 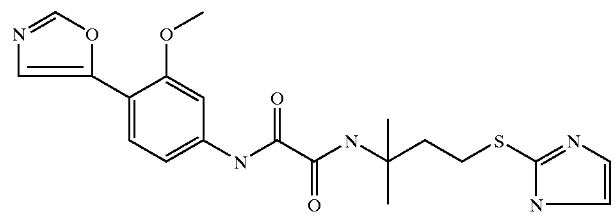 | 430 | 667 |
| 2-[3-[[[3-Methoxy-4-(5-oxazolyl)anilino]oxalyl]amino]-3-methylbutylthio]-3-pyridinecarboxylic acid trifluoroacetate (1:1) | 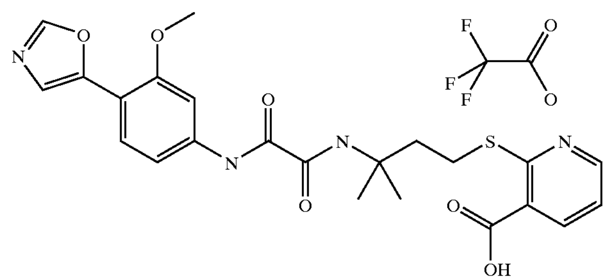 | 485 | 668 |
| 4-[2-[[[3-methoxy-4-(5-oxazolyl)anilino]oxalyl]amino]-2-methylpropylthio]benzoic acid | 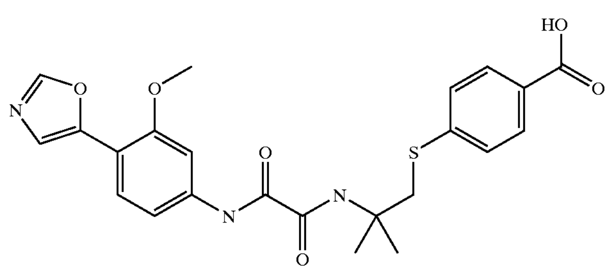 | 470 | 669 |
| 2-[3-[[[3-Methoxy-4-(5-oxazolyl)anilino]oxalyl]amino]-3-methylbutylthio]-6-benzoxazolecarboxylic acid | 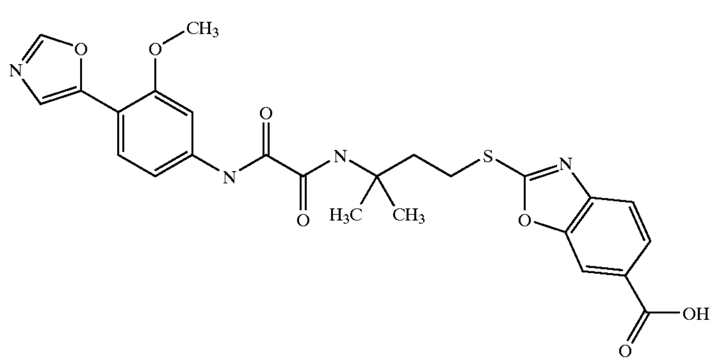 | 525 | 670 |

EXAMPLES 632–634

The compounds in table 1f³ were prepared in an analogous manner to that described for example 398 in table 1f¹ by replacing the 4-nitrophenol with the appropriate aniline and reaction with either 2,4,4-trimethyl-2-oxazoline or 2,4,4-trimethyl-5,6-dihydro-1,3(4H)oxazine and, where necessary, removal of any protecting groups by conventional methods.

and 0.5 g of palladium on activated charcoal in 50 ml of ethanol was stirred at room temperature under an atmosphere of hydrogen for 48 h. The reaction mixture was filtered and the filtrate concentrated in vacuo to afford 1.59 g (6.04 g mmol, 95%) of 2-[4-(4-methoxyphenyl)-piperazin-1-yl)-1,1-dimethylethylamine as a clear oil. The 2-[4-(4-methoxyphenyl)-piperazin-1-yl)-1,1-dimethylethylamine was then coupled to N-[3-methoxy-4-(5-oxazoyl)phenyl oxalamic acid by a procedure analo- TABLE 1f³

| Name | Structure | MS (ES) (M + H)⁺ | Ex No |
|------|-----------|------------------|-------|
| N-[3-Methoxy-4-(5-oxazolyl)phenyl]-N'-[1,1-dimethyl-2-(N-methylanilino) ethyl] oxalamide | 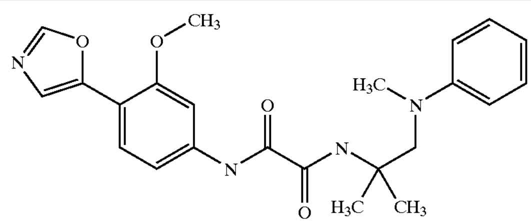 | 423 | 632 |
| N-(3-Anilino-1,1-dimethylpropyl)-N'-[3-methoxy-4-(5-oxazolyl)phenyl]oxalamide hydrochloride (1:1) | 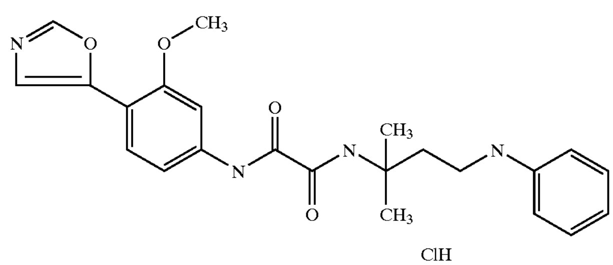 | 423 | 633 |
| 4-[3-[[[3-Methoxy-4-(5-oxazolyl)anilino]oxalyl]amino]-3-methylbutylamino]benzoic acid | 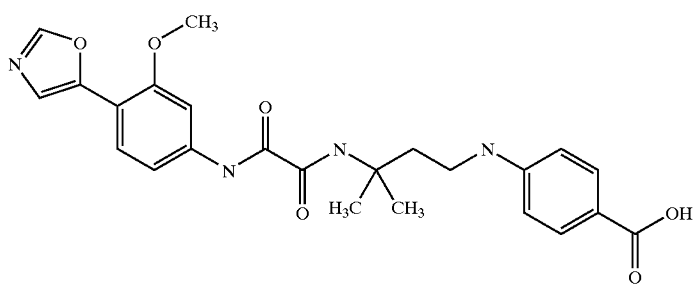 | 467 | 634 |

EXAMPLES 407–414; 459–541 AND 651–652

Typical methods used for the preparation of the compounds of table 1g are described below:

EXAMPLE 408

N-[3-Methoxy-4-(5-oxazolyl)phenyl]-N'-[2-[4-(4-methoxyphenyl)-1-piperazinyl]-1,1-dimethylethyl] oxalamide (i) A stirred solution of 3.23 g (16.8 mmol) of 1-(4-methoxyphenyl)piperazine, 2.00 g (16.8 mmol) of 2-methyl-2-nitropropan-1-ol and 5.34 g (50.4 mmol) of sodium carbonate in 40 ml of n-butanol was refluxed for 16 h. The reaction mixture was allowed to cool and diluted with 100 ml of dichloromethane. The solution was filtered and concentrated in vacuo. The residue was purified by flash chromatography on silica gel using petroleum ether/ethyl acetate (10:1) for the elution to afford 1.86 g (6.34 mmol, 38%) of 1-(4-methoxyphenyl)-4-(2-methyl-2nitropropyl)piperazine as a white solid.

(ii) A solution of 1.86 g (6.34 mmol) of 1-(4-methoxyphenyl)-4-(2-methyl-2-nitropropyl)piperazine gous to that described in example 1 to afford N-[3-methoxy-4-(5-oxazolyl)phenyl]-N'-[2-[4-(4-methoxyphenyl)-1-piperazinyl]1,1-dimethylethyl] oxalamide as a white solid. MS: m/e 508 [M+H]⁺.

Examples 407, 409, 410, 411, 412 and similar structures were prepared by an analogous procedure by replacing the 1-(4-methoxyphenyl)piperazine with the appropriately substituted piperazine.

Examples 413 and 414 were prepared by an analogous procedure by replacing the 1-(4-methoxyphenyl)piperazine with t-butyl-1-piperazinecarboxylate to give 4-(2-amino-2-methylpropyl)piperazine-1-carboxylic acid t-butyl ester which was then coupled to N-[3-methoxy-4-(5-oxazoyl) phenyl oxalamic acid. The resulting product could then be deprotected to give N-[3-Methoxy-4-(5-oxazolyl)phenyl]-N'-[1,1-dimethyl-2-(1-piperazinyl)ethyl]oxalamide that could be used for the preparation of examples 413, 414 and a variety of additional N-acyl and N-sulfonyl derivatives, such as those shown in table 1g, by using the appropriate acylating or sulfonylating reagent.

EXAMPLE 489

N-[2-[4-(Cyclohexylmethyl)-1-piperazinyl]-1,1-dimethylethyl]-N'-[3-methoxy-4-(5-oxazolyl)phenyl]oxalamide A stirred solution of 48 mg of N-[3-methoxy-4-(5-oxazolyl)phenyl]-N'-[1,1-dimethyl-2-(1-piperazinyl)ethyl]oxalamide (1.2 mmol) and 13 mg of cyclohexanecarboxaldehyde (1.2 mmol) in 1 ml of a 5% acetic acid/dichloromethane mixture was treated with a solution of 38 mg of sodium triacetoxyborohydride (1.8 mmol) in 1 ml of a 5% acetic acid/dichloromethane mixture. After stirring overnight at room temperature the reaction mixture was diluted with 10 ml of dichloromethane and washed with 8 ml of a sodium bicarbonate solution followed by 8 ml of water. The organic layer was then evaporated and purified using flash chromatography on a silica gel column eluting with 5% methanol/dichloromethane to give after evaporation of the fractions 14.3 mg (0.3 mmol, 25%) of N-[2-[4-(cyclohexylmethyl)-1-piperazinyl-1,1-dimethylethyl]-N'-[3-methoxy-4-(5-oxazolyl)phenyl]oxalamide in the form of a white solid. MS: m/e 498.2 [M+H]$^+$.

Additional N-alkylated compounds shown in table 1g were prepared by analogous methods.

TABLE 1g

| Name | Structure | MS (ES) (M + H)$^+$ | Ex No |
|---|---|---|---|
| N-[3-Methoxy-4-(5-oxazolyl)phenyl]-N'-[1,1-dimethyl-2-(4-phenyl-1-piperazinyl)ethyl]oxalamide | 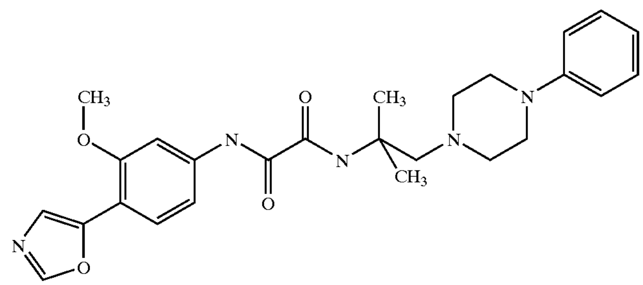 | 478 | 407 |
| N-[3-Methoxy-4-(5-oxazolyl)phenyl]-N'-[2-[4-(4-methoxyphenyl)-1-piperazinyl]-1,1-dimethylethyl]oxalamide | 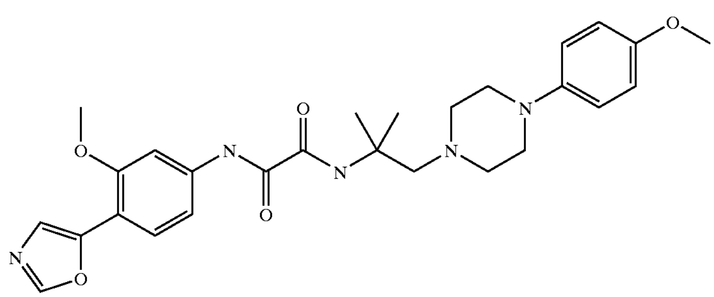 | 508 | 408 |
| N-[3-Methoxy-4-(5-oxazolyl)phenyl]-N'-[2-[4-(3-methoxyphenyl)-1-piperazinyl]-1,1-dimethylethyl]oxalamide | 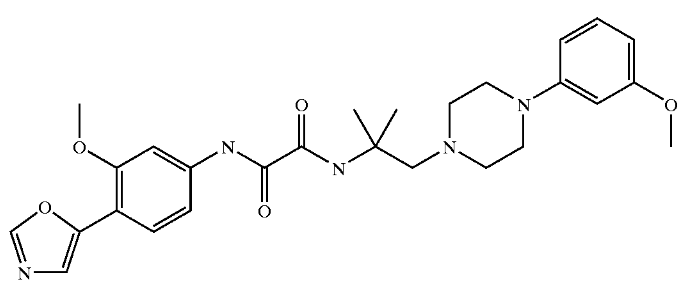 | 508 | 409 |
| N-[3-Methoxy-4-(5-oxazolyl)phenyl]-N'-[1,1-dimethyl-3-(4-phenyl-1-piperazinyl)propyl]oxalamide | 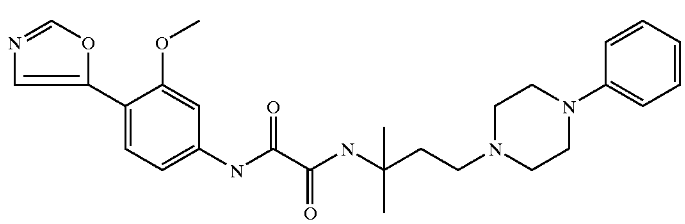 | 492 | 410 |

TABLE 1g-continued

| Name | Structure | MS (ES) (M + H)+ | Ex No |
|---|---|---|---|
| N-[3-Methoxy-4-(5-oxazolyl)phenyl]-N'-[2-[4-(2-methoxy-phenyl)-1-piperazinyl]-1,1-dimethylethyl]oxalamide | 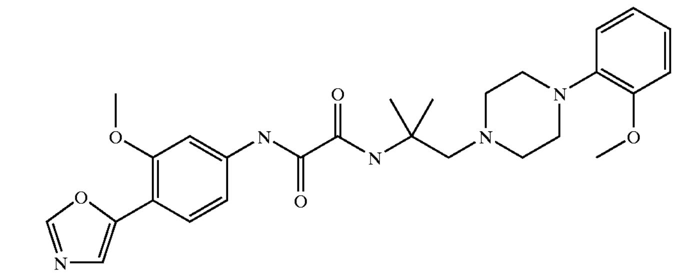 | 508 | 411 |
| N-[2-(4-Benzyl-1-piperazinyl)-1,1-dimethylethyl]-N'-[3-methoxy-4-(5-oxazolyl)phenyl]oxalamide | 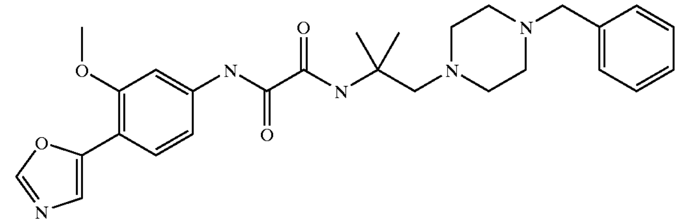 | 492 | 412 |
| N-[2-[4-(Benzenesulfonyl)-1-piperazinyl]-1,1-dimethylethyl]-N'-[3-methoxy-4-(5-oxazolyl)phenyl]oxalamide | 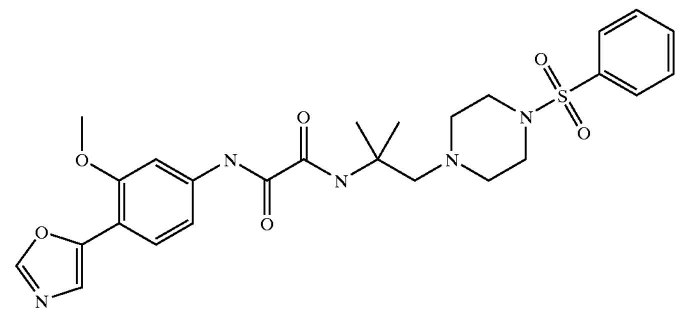 | 452 | 413 |
| N-[2-(4-Benzoyl-1-piperazinyl)-1,1-dimethylethyl]-N'-[3-methoxy-4-(5-oxazolyl)phenyl]oxalamide | 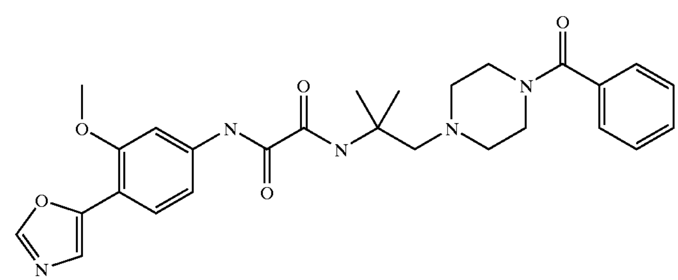 | 506 | 414 |
| N-[2-[4-[4-(Trifluoromethyl)phenyl]-1-piperazinyl]-1,1-dimethylethyl]-N'-[3-methoxy-4-(5-oxazolyl)phenyl]oxalamide | 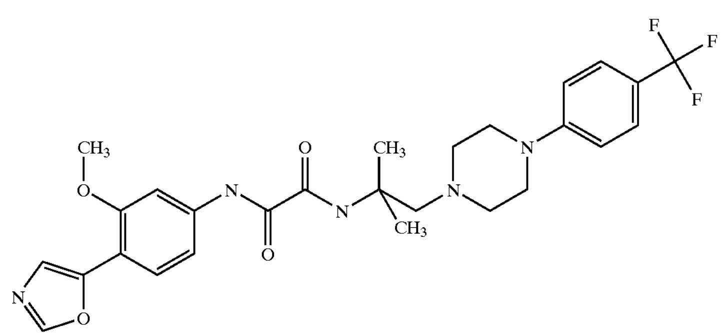 | 546 | 459 |

TABLE 1g-continued

| Name | Structure | MS (ES) (M + H)+ | Ex No |
|---|---|---|---|
| N-[3-Methoxy-4-(5-oxazolyl)phenyl]-N'-[1,1-dimethyl-2-[4-(2-methylphenyl)-1-piperazinyl]ethyl]oxalamide | 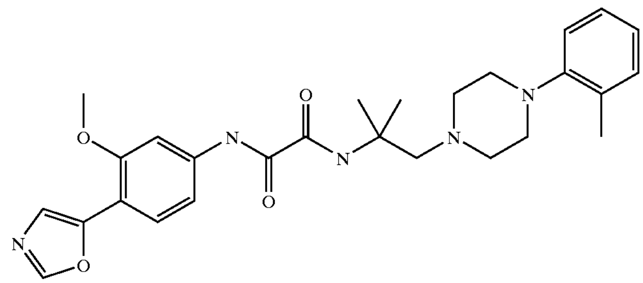 | 492 | 460 |
| N-[2-[4-(2-Fluorophenyl)-1-piperazinyl]-1,1-dimethylethyl]-N'-[3-methoxy-4-(5-oxazolyl)phenyl]oxalamide | 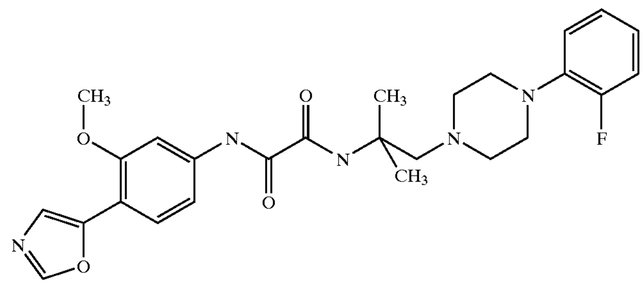 | 496 | 461 |
| N-[2-[4-(4-Fluorophenyl)-1-piperazinyl]-1,1-dimethylethyl]-N'-[3-methoxy-4-(5-oxazolyl)phenyl]oxalamide | 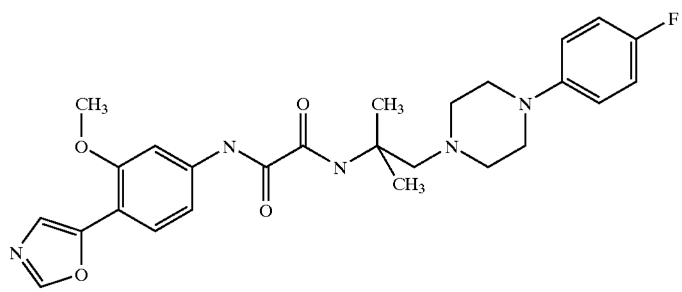 | 496 | 462 |
| N-[3-Methoxy-4-(5-oxazolyl)phenyl]-N'-[2-[4-(2-methoxyphenyl)-1-piperazinyl]-1,1-dimethylethyl]oxalamide | 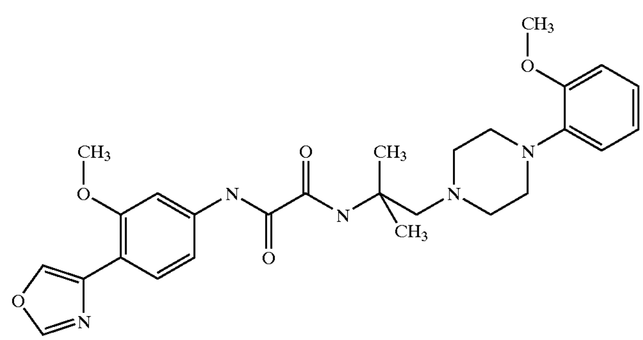 | 508 | 463 |
| N-[3-Methoxy-4-(5-oxazolyl)phenyl]-N'-[1,1-dimethyl-2-[4-(2-thiophenesulfonyl)-1-piperazinyl]ethyl]oxalamide | 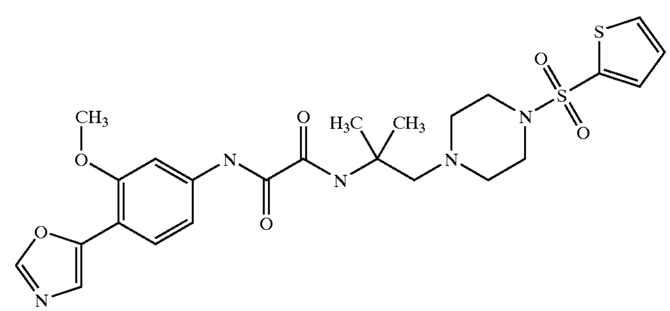 | 548 | 464 |

TABLE 1g-continued

| Name | Structure | MS (ES) (M + H)+ | Ex No |
|---|---|---|---|
| N-[3-Methoxy-4-(5-oxazolyl)phenyl]-N'-[1,1-dimethyl-2-[4-(2,4,6-trimethylbenzene-sulfonyl)-1-piperazinyl]ethyl]oxalamide | 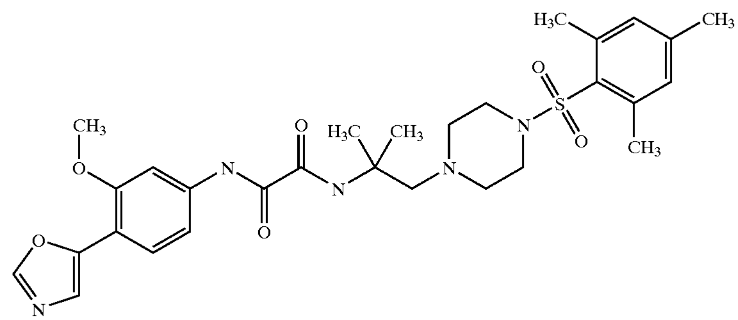 | 584.1 | 465 |
| N-[2-[4-(4-Fluorobenzene-sulfonyl)-1-piperazinyl]-1,1-dimethylethyl]-N'-[3-methoxy-4-(5-oxazolyl)phenyl]oxalamide | 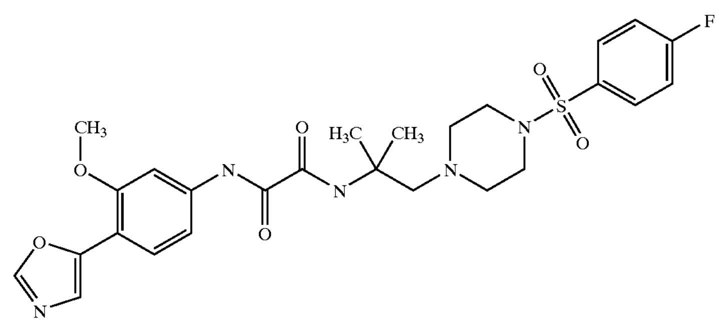 | 560.1 | 466 |
| N-[2-[4-(Trifluoromethane-sulfonyl)-1-piperazinyl]-1,1-dimethylethyl]-N'-[3-methoxy-4-(5-oxazolyl)phenyl)]oxalamide | 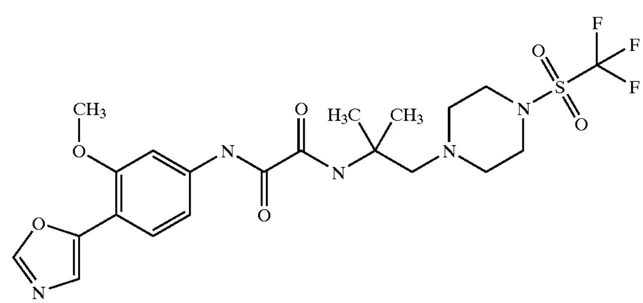 | 534 | 467 |
| N-[2-[4-(Isopropylsulfonyl)-1-piperazinyl]-1,1-dimethylethyl]-N'-[3-methoxy-4-(5-oxazolyl)phenyl)]oxalamide | 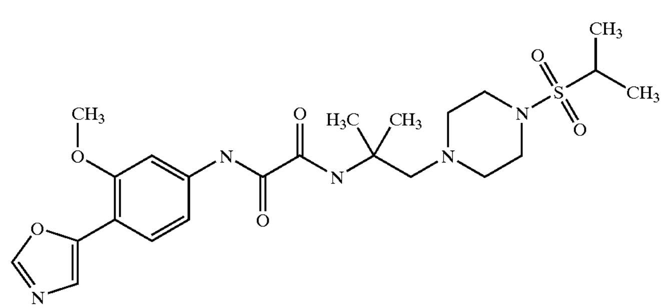 | 508.1 | 468 |

TABLE 1g-continued

| Name | Structure | MS (ES) (M + H)+ | Ex No |
|---|---|---|---|
| (E)-N-[3-Methoxy-4-(5-oxazolyl)phenyl]-N'-[1,1-dimethyl-2-[4-(styrylsulfonyl)-1-piperazinyl]ethyl]oxalamide | 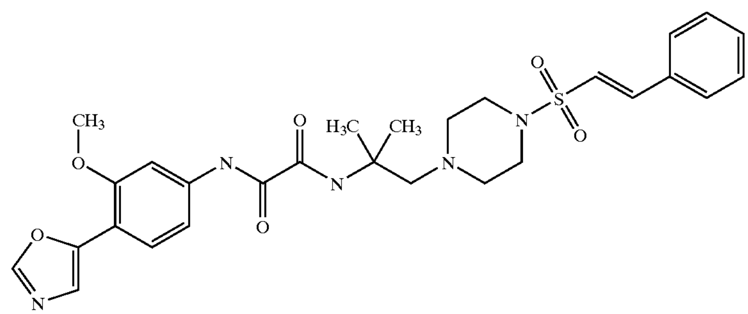 | 568.1 | 469 |
| N-[2-[4-(Ethanesulfonyl)-1-piperazinyl]-1,1-dimethylethyl]-N'-[3-methoxy-4-(5-oxazolyl)phenyl]oxalamide | 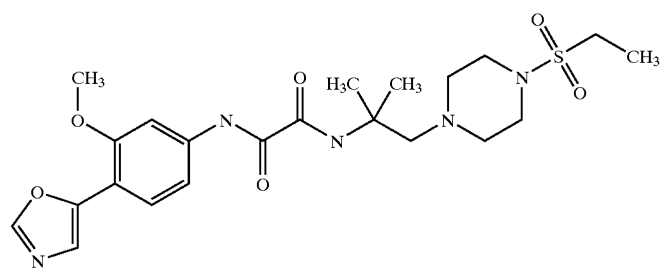 | 494.1 | 470 |
| N-[3-Methoxy-4-(5-oxazolyl)phenyl]-N'-[1,1-dimethyl-2-[4-(propanesulfonyl)-1-piperazinyl]ethyl]oxalamide | 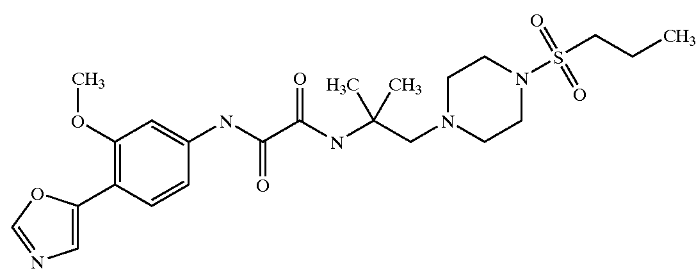 | 508.1 | 471 |
| N-[2-[4-(3-Chloropropane-sulfonyl)-1-piperazinyl]-1,1-dimethylethyl]-N'-[3-methoxy-4-(5-oxazolyl)phenyl]oxalamide | 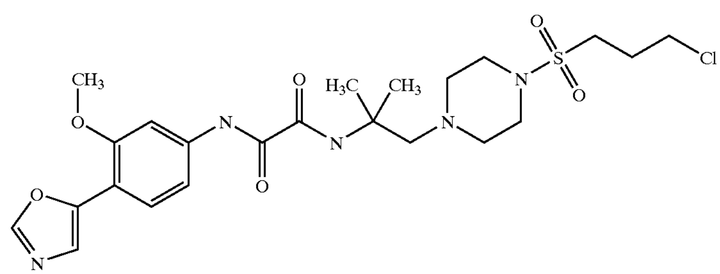 | 542.1 | 472 |
| N-[3-Methoxy-4-(5-oxazolyl)phenyl]-N'-[1,1-dimethyl-2-[4-(o-toluenesulfonyl)-1-piperazinyl]ethyl]oxalamide | 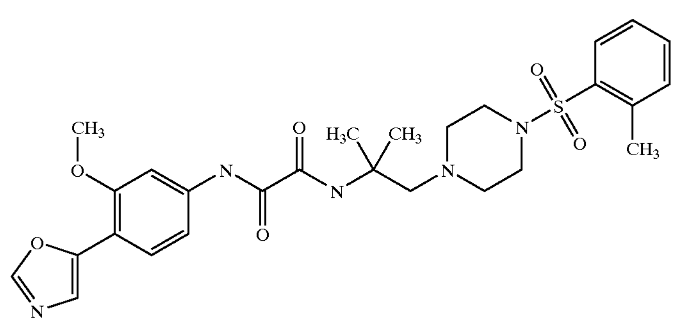 | 556.1 | 473 |

TABLE 1g-continued

| Name | Structure | MS (ES) (M + H)+ | Ex No |
|---|---|---|---|
| N-[2-[4-(2-Fluorobenzene-sulfonyl)-1-piperazinyl]-1,1-dimethylethyl]-N'-[3-methoxy-4-(5-oxazolyl)phenyl]oxalamide | 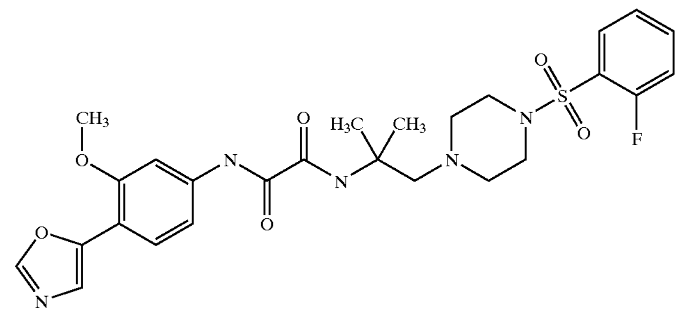 | 560.1 | 474 |
| N-[2-[4-(2-Cyanobenzenesulfonyl)-1-piperazinyl]-1,1-dimethylethyl]-N'-[3-methoxy-4-(5-oxazolyl)phenyl]oxalamide | 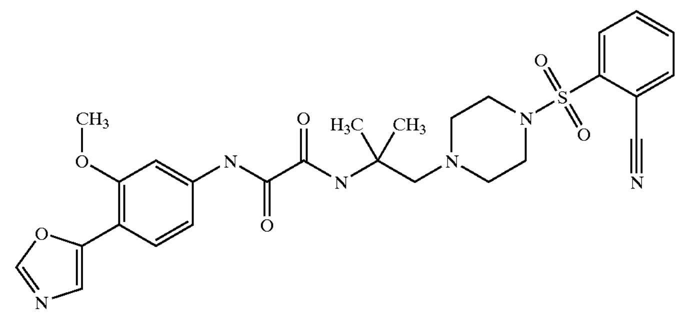 | 567.1 | 475 |
| N-[3-Methoxy-4-(5-oxazolyl)phenyl]-N'-[2-[4-(3,5-dimethyl-4-isoxazolylsulfonyl)-1-piperazinyl]-1,1-dimethyl-ethyl]oxalamide | 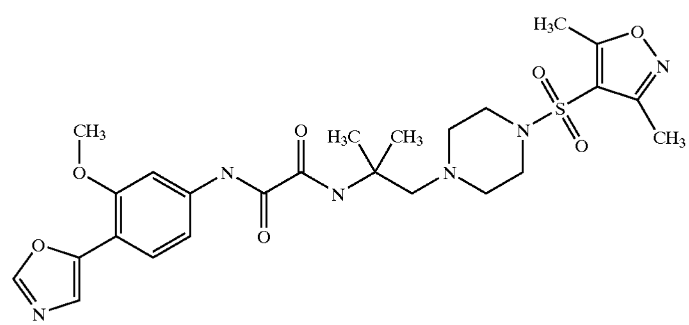 | 561.1 | 476 |
| N-[2-[4-(5-Fluoro-2-methylbenzenesulfonyl)-1-piperazinyl]-1,1-dimethylethyl]-N'-[3-methoxy-4-(5-oxazolyl)phenyl]oxalamide | 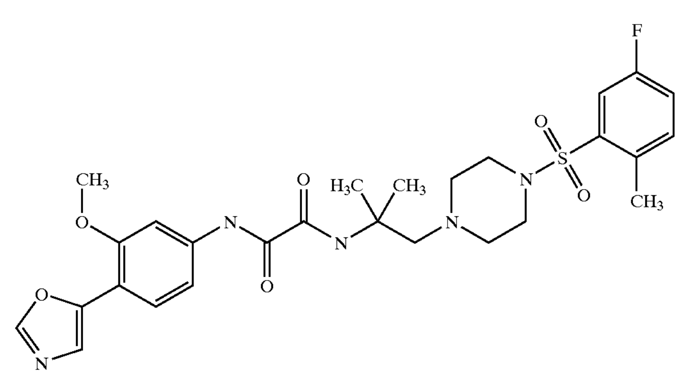 | 574.1 | 477 |

TABLE 1g-continued

| Name | Structure | MS (ES) (M + H)+ | Ex No |
|---|---|---|---|
| N-[2-[4-(2,5-Difluorobenzenesulfonyl)-1-piperazinyl]-1,1-dimethylethyl]-N'-[3-methoxy-4-(5-oxazolyl)phenyl]oxalamide | 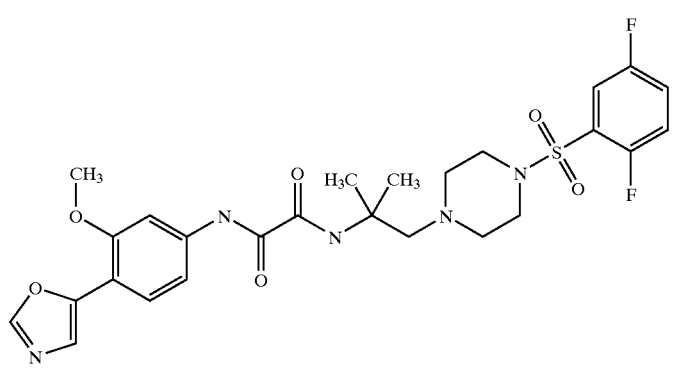 | 578.1 | 478 |
| N-[3-Methoxy-4-(5-oxazolyl)phenyl]-N'-[1,1-dimethyl-2-[4-(1-methyl-1H-imidazole-4-sulfonyl)-1-piperazinyl]ethyl]oxalamide | 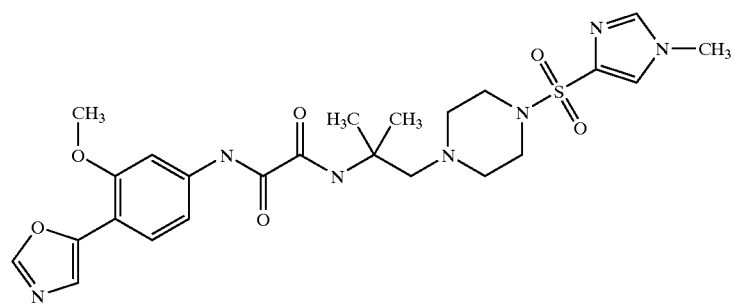 | 546.1 | 479 |
| N-[2-[4-(2,6-Difluorobenzensulfonyl)-1-piperazinyl]-1,1-dimethylethyl]-N'-[3-methoxy-4-(5-oxazolyl)phenyl]oxalamide | 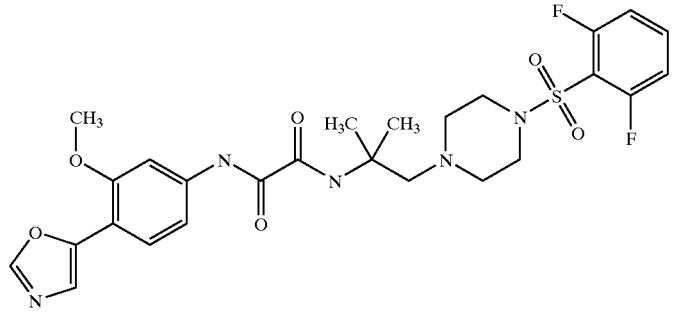 | 578.1 | 480 |
| N-[2-[4-(3,4-Difluorobenzensulfonyl)-1-piperazinyl]-1,1-dimethylethyl]-N'-[3-methoxy-4-(5-oxazolyl)phenyl]oxalamide | 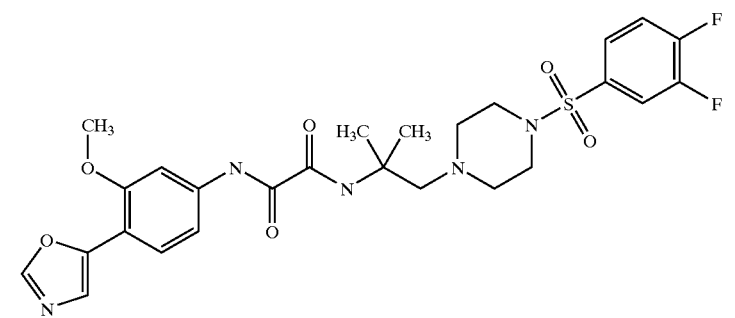 | 578.1 | 481 |

TABLE 1g-continued

| Name | Structure | MS (ES) (M + H)+ | Ex No |
|---|---|---|---|
| N-[2-[4-(Cyclohexylmethanesulfonyl)-1-piperazinyl]-1,1-dimethylethyl]-N'-[3-methoxy-4-(5-oxazolyl)phenyl]oxalamide | 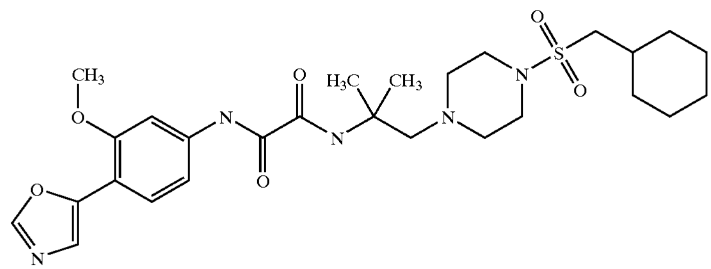 | 562.2 | 482 |
| N-[3-Methoxy-4-(5-oxazolyl)phenyl]-N'-[1,1-dimethyl-2-[4-(2-phenylethanesulfonyl)-1-piperazinyl]ethyl]oxalamide | 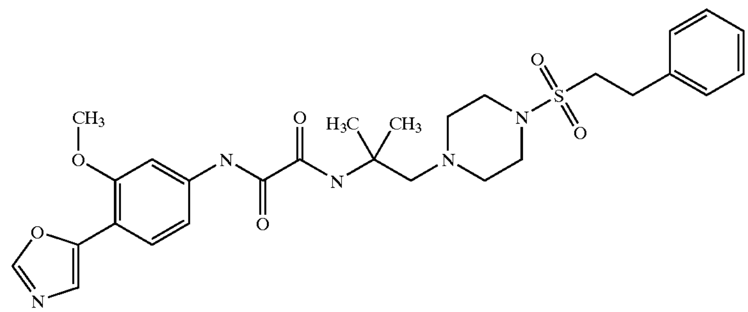 | 570.1 | 483 |
| N-[3-Methoxy-4-(5-oxazolyl)phenyl]-N'-[2-[4-(2,4-dimethoxyphenyl)-1-piperazinyl]-1,1-dimethylethyl]oxalamide | 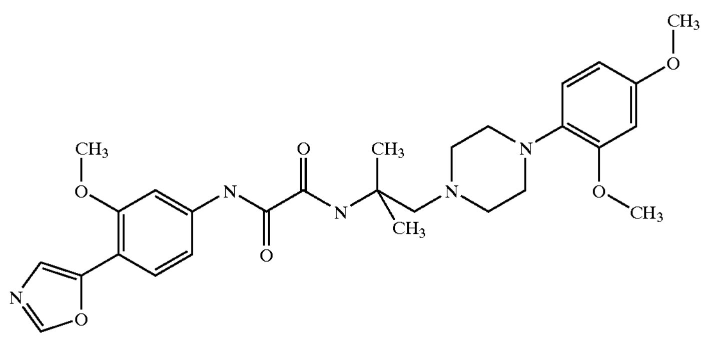 | 538 | 484 |
| N-[3-Methoxy-4-(5-oxazolyl)phenyl]-N'-[1,1-dimethyl-2-[4-(4-methylphenyl)-1-piperazinyl]ethyl]oxalamide | 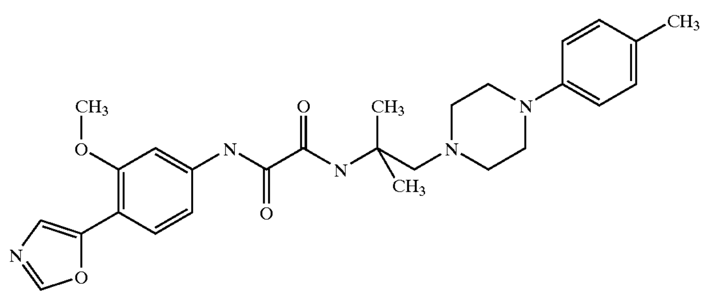 | 492 | 485 |
| N-[3-Methoxy-4-(5-oxazolyl)phenyl]-N'-[1,1-dimethyl-2-[4-(2,4-dimethylphenyl)-1-piperazinyl]ethyl]oxalamide | 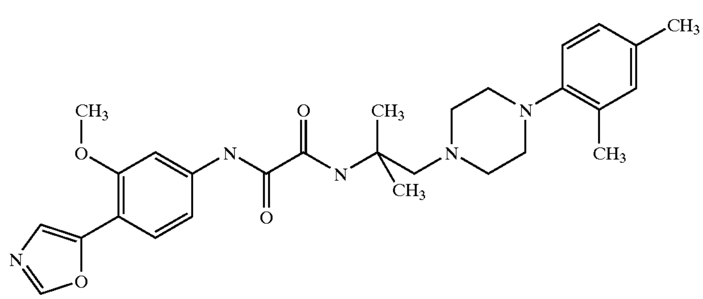 | 506 | 486 |

TABLE 1g-continued

| Name | Structure | MS (ES) (M + H)+ | Ex No |
|---|---|---|---|
| N-[3-Methoxy-4-(5-oxazolyl)phenyl]-N'-[2-[4-(3,4-dimethoxyphenyl)-1-piperazinyl]-1,1-dimethylethyl]oxalamide | 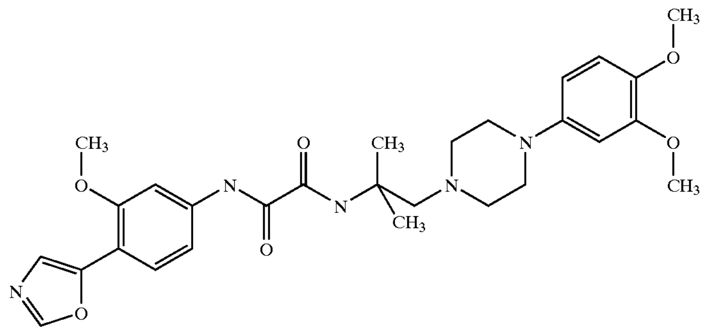 | 538 | 487 |
| N-[2-(4-Cyclohexyl-1-piperazinyl)-1,1-dimethylethyl]-N'-[3-methoxy-4-(5-oxazolyl)phenyl]oxalamide | 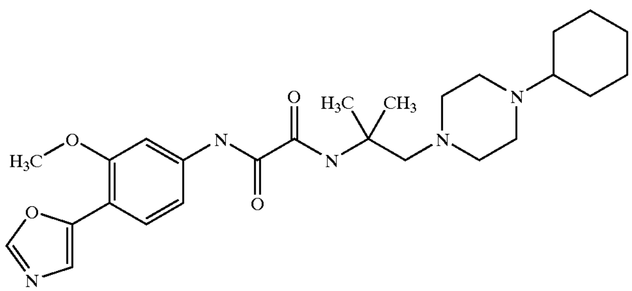 | 484.4 | 488 |
| N-[2-[4-(Cyclohexylmethyl)-1-piperazinyl]-1,1-dimethylethyl]-N'-[3-methoxy-4-(5-oxazolyl)phenyl]oxalamide | 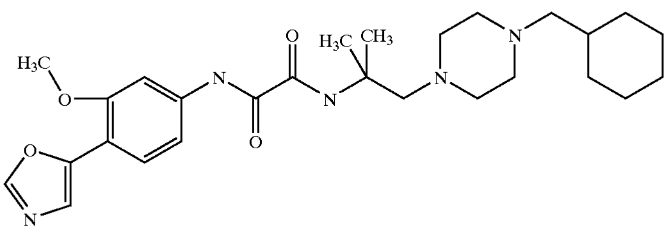 | 498.2 | 489 |
| N-[2-[4-(2-Methoxybenzyl)-1-piperazinyl]-1,1-dimethylethyl]-N'-[3-methoxy-4-(5-oxazolyl)phenyl]oxalamide | 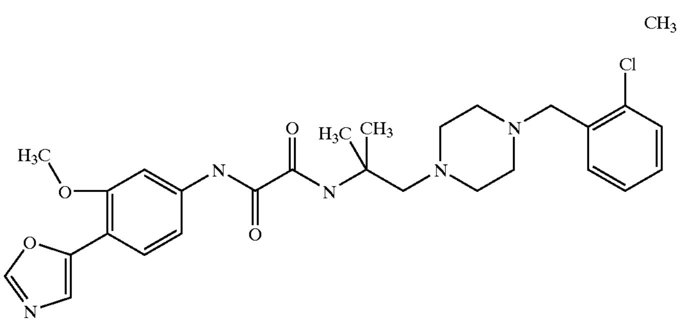 | 522.1 | 490 |
| N-[2-[4-(2-Hydroxybenzyl)-1-piperazinyl]-1,1-dimethylethyl]-N'-[3-methoxy-4-(5-oxazolyl)phenyl]oxalamide | 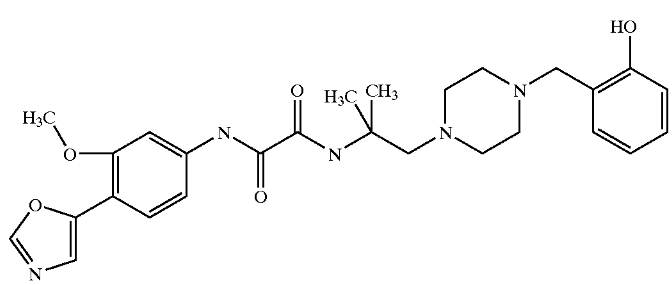 | 508.1 | 491 |

TABLE 1g-continued

| Name | Structure | MS (ES) (M + H)+ | Ex No |
|---|---|---|---|
| N-[3-Methoxy-4-(5-oxazolyl)phenyl]-N'-[1,1-dimethyl-2-[4-(2-methylbenzyl)-1-piperazinyl]ethyl]oxalamide | 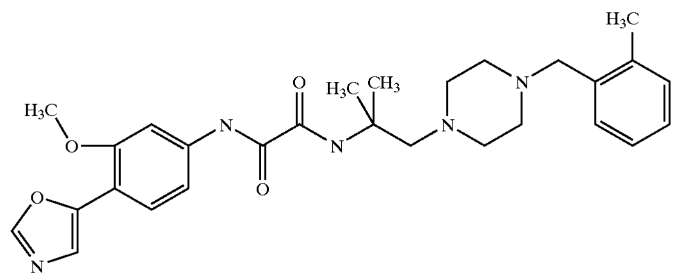 | 506.1 | 492 |
| N-[3-Methoxy-4-(5-oxazolyl)phenyl]-N'-[1,1-dimethyl-2-[4-(2-thenyl)-1-piperazinyl]ethyl]oxalamide | 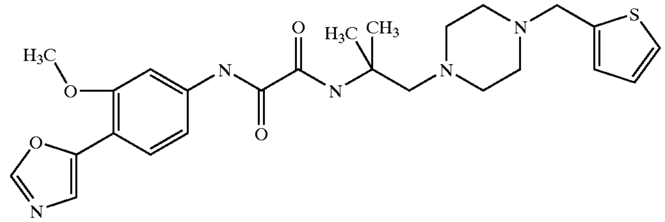 | 498.1 | 493 |
| N-[3-Methoxy-4-(5-oxazolyl)phenyl]-N'-[1,1-dimethyl-2-[4-(2(RS)-phenylpropyl)-1-piperazinyl]ethyl]oxalamide | 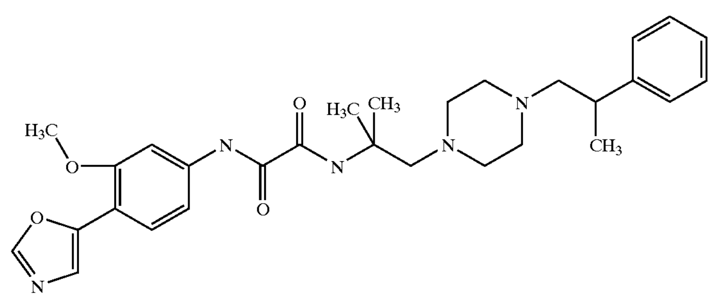 | 520.2 | 494 |
| N-[3-methoxy-4-(5-oxazolyl)phenyl]-N'-[1,1-dimethyl-2-(4-pivaloyl-1-piperazinyl)ethyl]oxalamide | 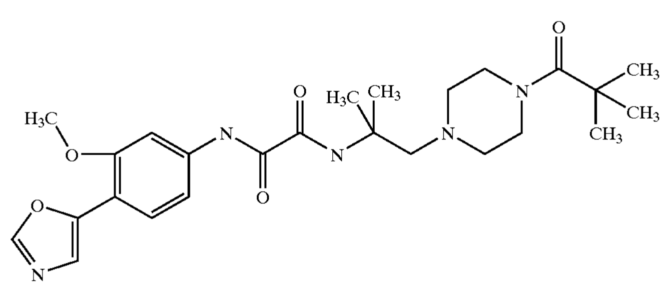 | 486.1 | 495 |
| N-[2-[4-(2-Furoyl)-1-piperazinyl]-1,1-dimethylethyl]-N'-[3-methoxy-4-(5-oxazolyl)phenyl]oxalamide | 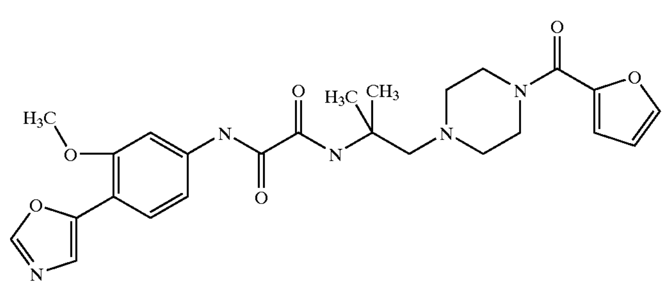 | 496.1 | 496 |

TABLE 1g-continued

| Name | Structure | MS (ES) (M + H)+ | Ex No |
|---|---|---|---|
| N-[3-Methoxy-4-(5-oxazolyl)phenyl]-N'-[1,1-dimethyl-2-4-(2-thenoyl)-1-piperazinyl]ethyl]oxalamide | 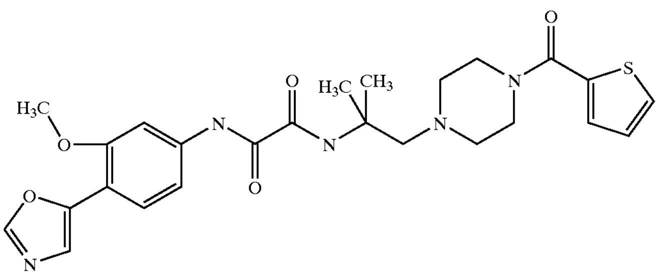 | 512.1 | 497 |
| N-[3-Methoxy-4-(5-oxazolyl)phenyl]-N'-[1,1-dimethyl-2-[4-(3-thenoyl)-1-piperazinyl]ethyl]oxalamide | 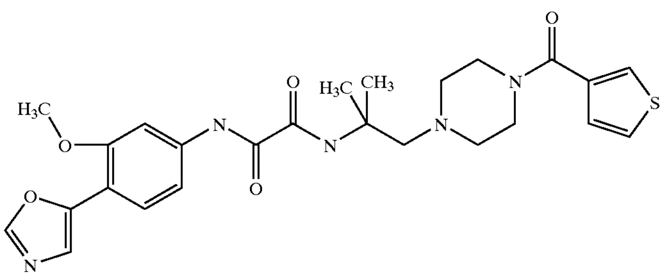 | 512 | 498 |
| N-[2-[4-(2-Cyclopentylacetyl)-1-piperazinyl]-1,1-dimethyl-ethyl]-N'-[3-methoxy-4-(5-oxazolyl)phenyl)]oxalamide | 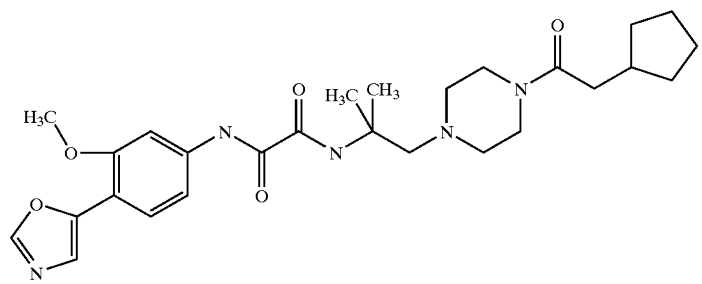 | 512.1 | 499 |
| N-[2-[4-(Cyclohexylcarbonyl)-1-piperazinyl]-1,1-dimethylethyl]-N'-[3-methoxy-4-(5-oxazolyl)phenyl]oxalamide | 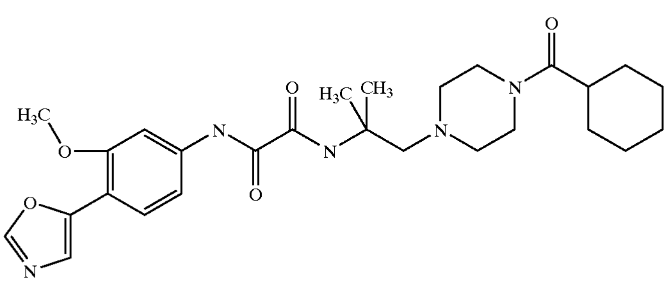 | 512.1 | 500 |
| N-[3-Methoxy-4-(5-oxazolyl)phenyl]-N'-[1,1-dimethyl-2-[4-(2-methylbenzoyl)-1-piperazinyl]ethyl]oxalamide | 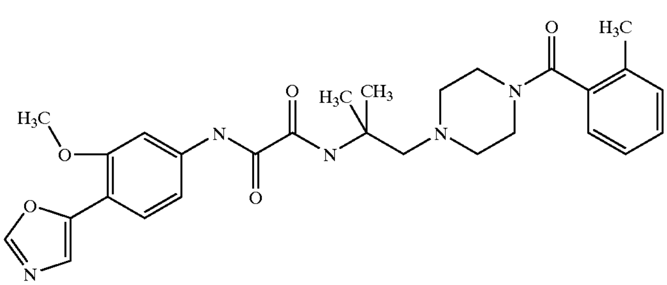 | 520.1 | 501 |

TABLE 1g-continued

| Name | Structure | MS (ES) (M + H)+ | Ex No |
|---|---|---|---|
| N-[3-Methoxy-4-(5-oxazolyl)phenyl]-N'-[1,1-dimethyl-2-[4-(4-methylbenzoyl)-1-piperazinyl]ethyl]oxalamide | 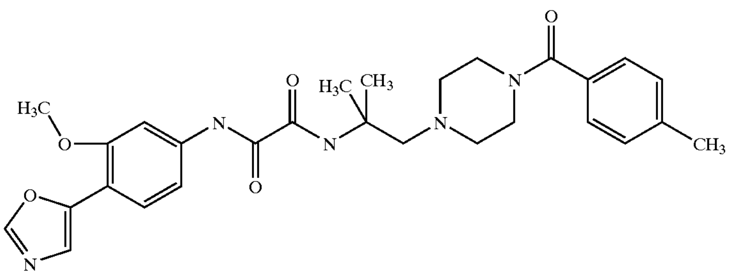 | 520.1 | 502 |
| N-[2-[4-(Cycloheptylcarbonyl)-1-piperazinyl]-1,1-dimethylethyl]-N'-[3-methoxy-4-(5-oxazolyl)phenyl]oxalamide | 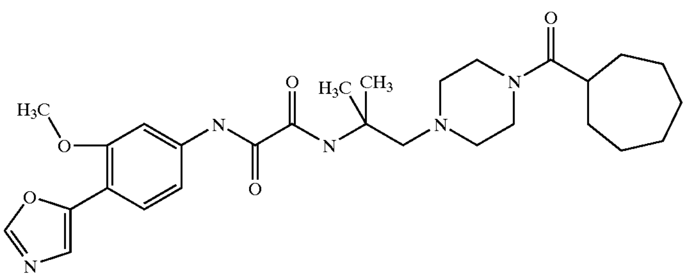 | 526.2 | 503 |
| N-[3-Methoxy-4-(5-oxazolyl)phenyl]-N'-]1,1-dimethyl-2-[4-[(1H-pyrazol-4-yl)carbonyl]-1-piperazinyl]ethyl]oxalamide | 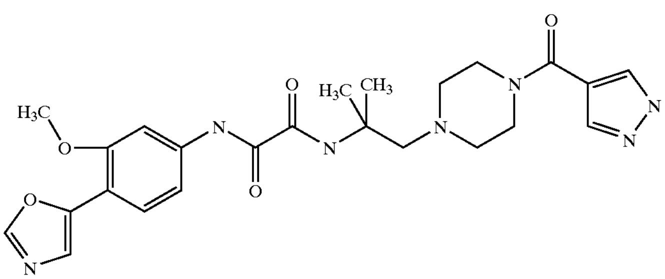 | 496.1 | 504 |
| N-[2-[4-(Cyclopentylcarbonyl)-1-piperazinyl]-1,1-dimethylethyl]-N'-[3-methoxy-4-(5-oxazolyl)phenyl]oxalamide | 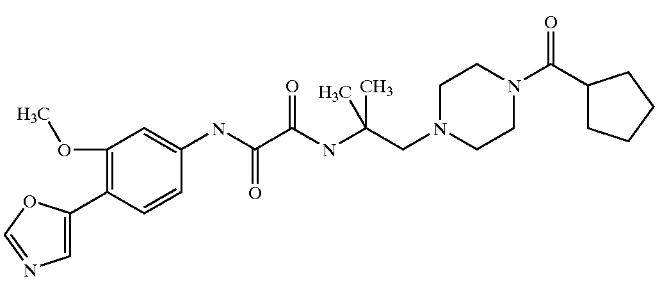 | 498.1 | 505 |
| N-[3-Methoxy-4-(5-oxazolyl)phenyl]-N'-[1,1-Dimethyl-2-[4-[(1-methyl-1H-pyrrol-2-yl)carbonyl]-1-piperazinyl]ethyl]oxalamide | 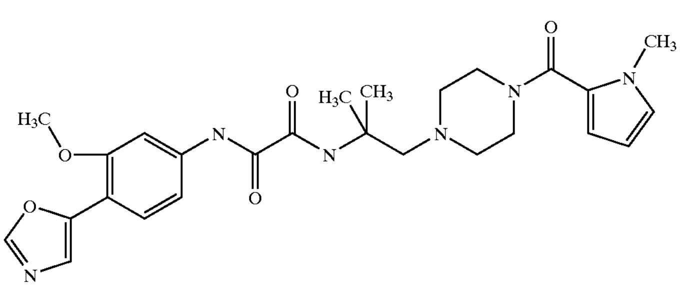 | 509.1 | 506 |

TABLE 1g-continued

| Name | Structure | MS (ES) (M + H)+ | Ex No |
|---|---|---|---|
| N-[3-Methoxy-4-(5-oxazolyl)phenyl]-N'-[1,1-dimethyl-2-[4-[(1,2,3-thiadiazol-4-yl)carbonyl]-1-piperazinyl]-ethyl]oxalamide | 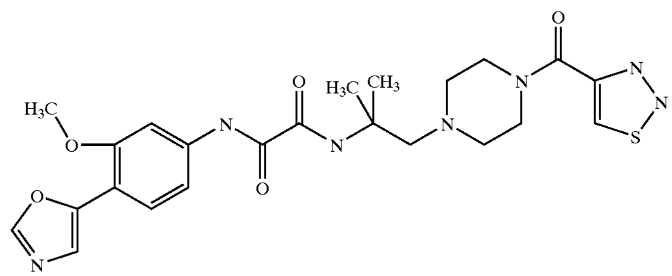 | 514.1 | 507 |
| N-[2-[4-(3-Fluorobenzoyl)-1-piperazinyl]-1,1-dimethylethyl]-N'-[3-methoxy-4-(5-oxazolyl)phenyl]oxalamide | 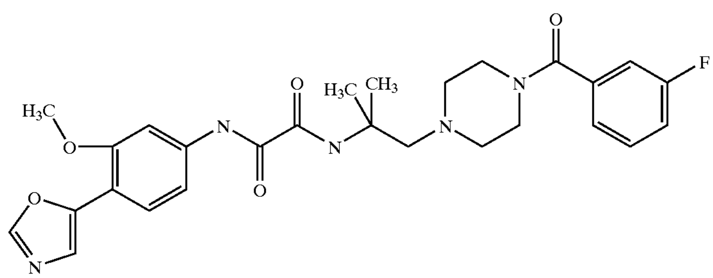 | 524.1 | 508 |
| N-[2-[4-(4-Fluorobenzoyl)-1-piperazinyl]-1,1-dimethylethyl]-N'-[3-methoxy-4-(5-oxazolyl)phenyl]oxalamide | 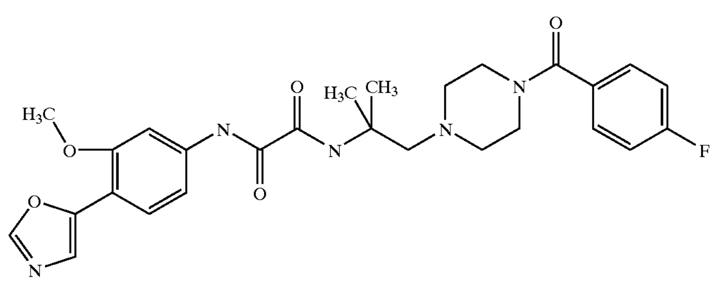 | 524.1 | 509 |
| N-[2-[4-(Cyclopropylcarbonyl)-1-piperazinyl]-1,1-dimethylethyl]-N'-[3-methoxy-4-(5-oxazolyl)phenyl]oxalamide | 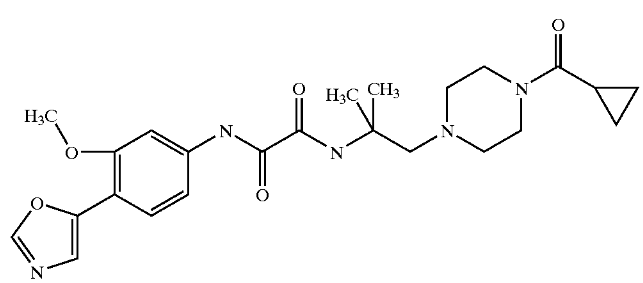 | 470.1 | 510 |
| N-[2-[4-(2-Cyclopropylcarbonyl)-1-piperazinyl]-1,1-dimethylethyl]-N'-[3-methoxy-4-(5-oxazolyl)phenyl]oxalamide | 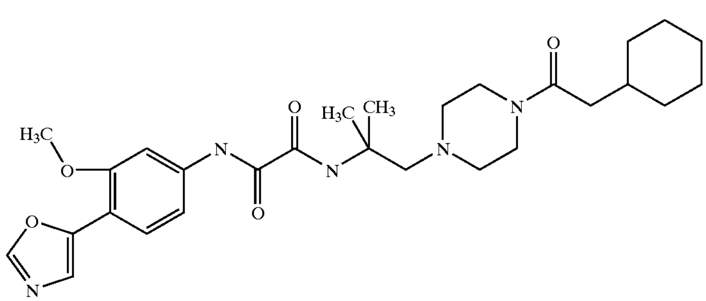 | 526.2 | 511 |

TABLE 1g-continued

| Name | Structure | MS (ES) (M + H)+ | Ex No |
|---|---|---|---|
| N-[3-Methoxy-4-(5-oxazolyl)phenyl]-N'-[2-[4-(3,3-dimethylbutyryl)-1-piperazinyl]-1,1-dimethylethyl]oxalamide | 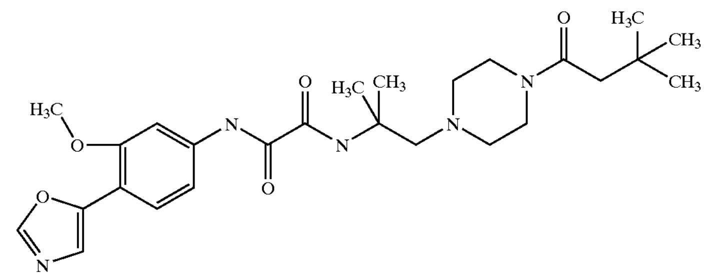 | 500.2 | 512 |
| N-[2-[4-(3-Hydroxy-2,2-dimethylpropionyl)-1-piperazinyl]-1,1-dimethylethyl]-N'-[3-methoxy-4-(5-oxazolyl)phenyl]oxalamide | 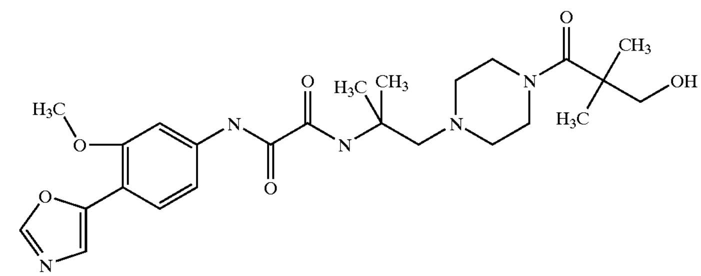 | 502.1 | 513 |
| N-[3-Methoxy-4-(5-oxazolyl)phenyl]-N'-[1,1-dimethyl-2-[4-(3-methyl-2-furoyl)-1-piperazinyl]ethyl]oxalamide | 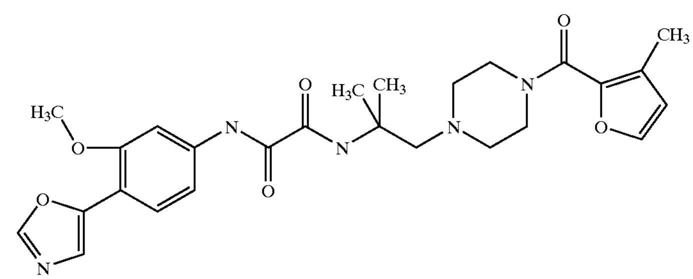 | 510.1 | 514 |
| N-[3-Methoxy-4-(5-oxazolyl)phenyl]-N'-[1,1-dimethyl-2-[4-(2-methyl-3-furoyl)-1-piperazinyl]ethyl]oxalamide | 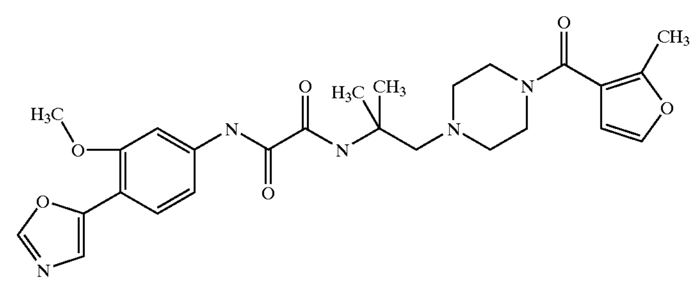 | 510.1 | 515 |
| N-[3-Methoxy-4-(5-oxazolyl)phenyl]-N'-[1,1-dimethyl-2-[4-[(5-methyl-1H-pyrazol-3-yl)carbonyl]-1-piperazinyl]ethyl]oxalamide | 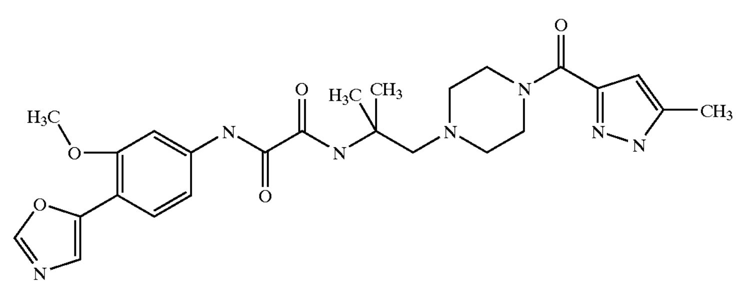 | 510.1 | 516 |

TABLE 1g-continued

| Name | Structure | MS (ES) (M + H)+ | Ex No |
|---|---|---|---|
| N-[3-Methoxy-4-(5-oxazolyl)phenyl]-N'-[1,1-dimethyl-2-[4-[(5-methyl-4-isoxazolyl)carbonyl]-1-piperazinyl]ethyl]oxalamide | 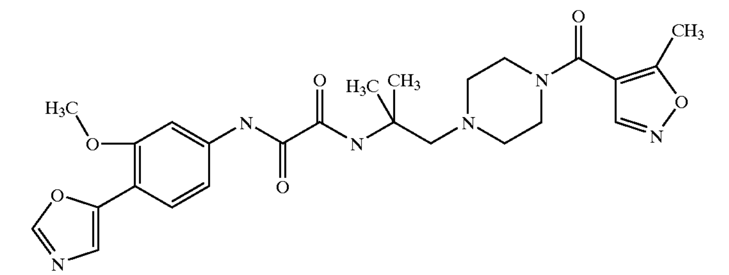 | 511.1 | 517 |
| N-[3-Methoxy-4-(5-oxazolyl)phenyl]-N'-[1,1-dimethyl-2-[4-[(5-methyl-3-isoxazolyl)carbonyl]-1-piperazinyl]ethyl]oxalamide | 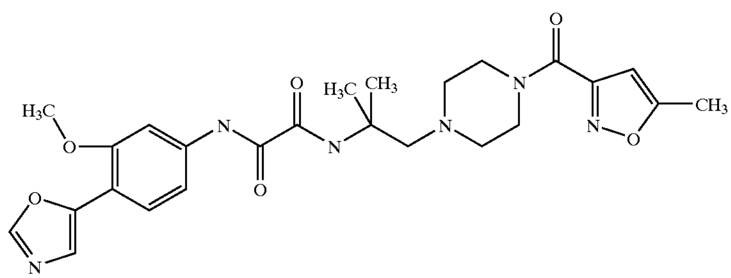 | 511.1 | 518 |
| N-[2-[4-(4-Aminobenzoyl)-1-piperazinyl]-1,1-dimethylethyl]-N'-[3-methoxy-4-(5-oxazolyl)phenyl]oxalamide | 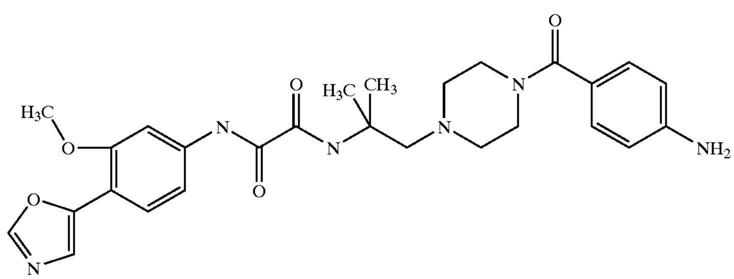 | 521.1 | 519 |
| N-[2-[4-(2-Hydroxybenzoyl)-1-piperazinyl]-1,1-dimethylethyl]-N'-[3-methoxy-4-(5-oxazolyl)phenyl]oxalamide | 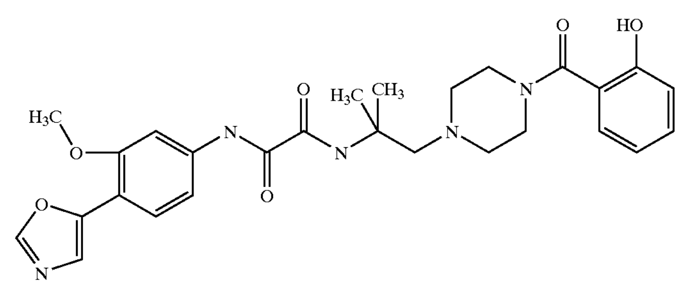 | 522.1 | 520 |
| N-[2-[4-(4-Hydroxybenzoyl)-1-piperazinyl]-1,1-dimethylethyl]-N'-[3-methoxy-4-(5-oxazolyl)phenyl]oxalamide | 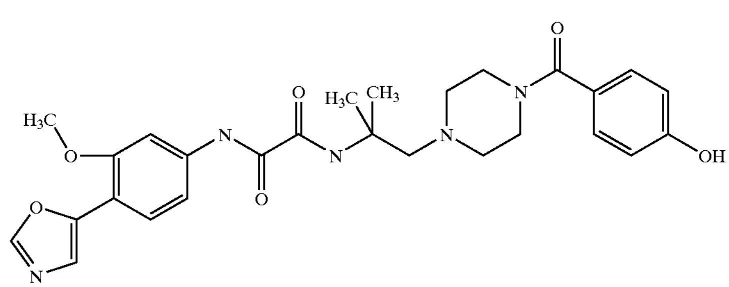 | 522.1 | 521 |

TABLE 1g-continued

| Name | Structure | MS (ES) (M + H)+ | Ex No |
|---|---|---|---|
| N-[3-Methoxy-4-(5-oxazolyl)phenyl]-N'-[1,1-dimethyl-2-[4-[(2,5-dimethyl-2H-pyrazol-3-yl)carbonyl]-1-piperazinyl]ethyl]oxalamide | 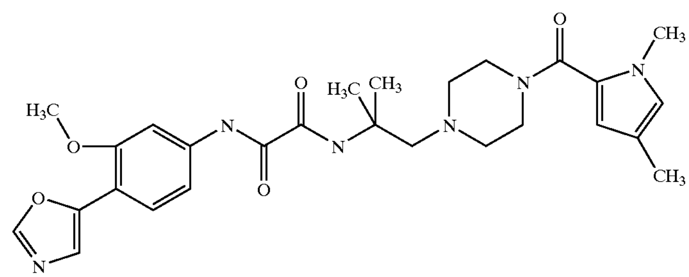 | 524.1 | 522 |
| N-[3-Methoxy-4-(5-oxazolyl)phenyl]-N'-[1,1-dimethyl-2-[4-(3-methyl-2-thenoyl)-1-piperazinyl]ethyl]oxalamide | 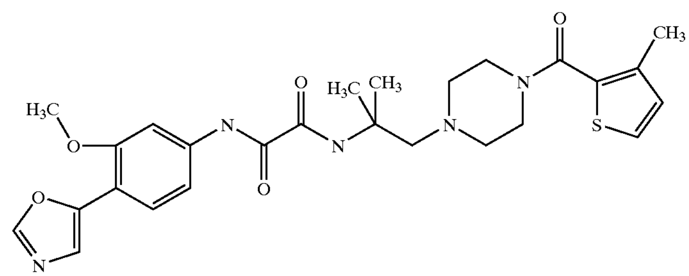 | 526.1 | 523 |
| N-[3-Methoxy-4-(5-oxazolyl)phenyl]-N'-[1,1-dimethyl-2-[4-(4-methyl-2-thenoyl)-1-piperazinyl]ethyl]oxalamide | 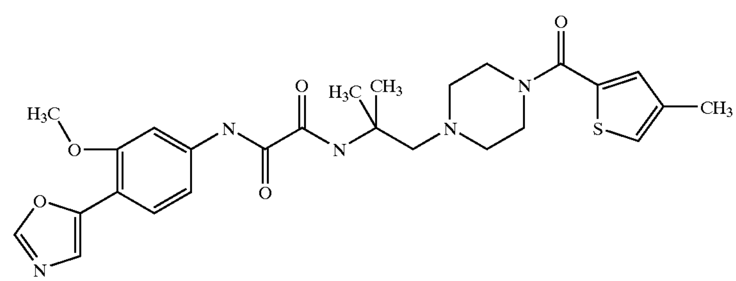 | 526.1 | 524 |
| N-[3-Methoxy-4-(5-oxazolyl)phenyl-N'-[1,1-dimethyl-2-[4-[(2,2,3,3-tetramethyl-1-cyclopropyl)carbonyl]-1-piperazinyl]ethyl]oxalamide | 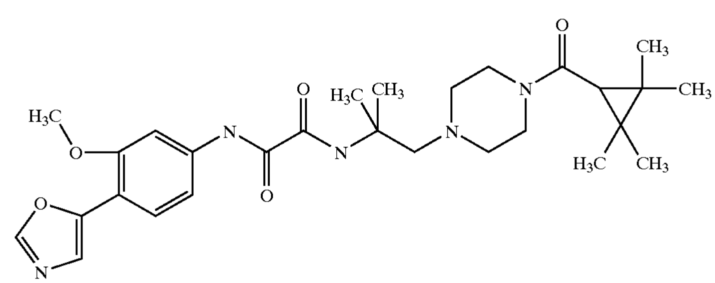 | 526.2 | 525 |
| N-[3-Methoxy-4-(5-oxazolyl)phenyl]-N'-[1,1-dimethyl-2-[4-[(4-methyl-1,2,3-thiadiazol-5-yl)carbonyl]-1-piperazinyl]ethyl]oxalamide | 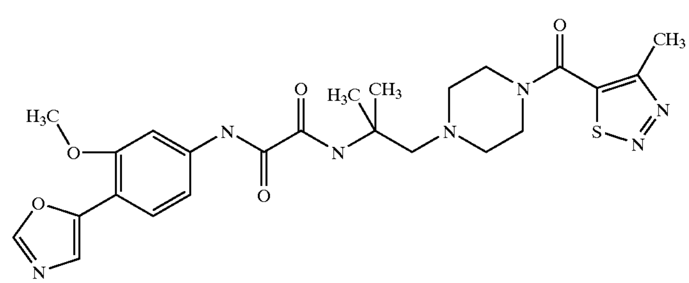 | 528.1 | 526 |

TABLE 1g-continued

| Name | Structure | MS (ES) (M + H)+ | Ex No |
|---|---|---|---|
| N-[2-[4-(3-Cyanobenzoyl)-1-piperazinyl]-1,1-dimethylethyl]-N'-[3-methoxy-4-(5-oxazolyl)phenyl]oxalamide | 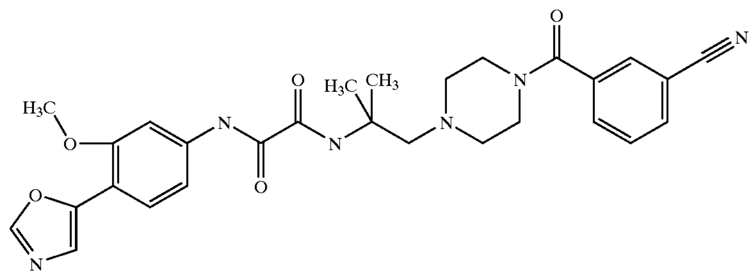 | 531.1 | 527 |
| N-[2-[4-[(Bicyclo[4.2.0]octa-1(6),2,4-trien-7-yl)carbonyl]-1-piperazinyl]-1,1-dimethylethyl]-N'-[3-methoxy-4-(5-oxazolyl)phenyl]oxalamide | 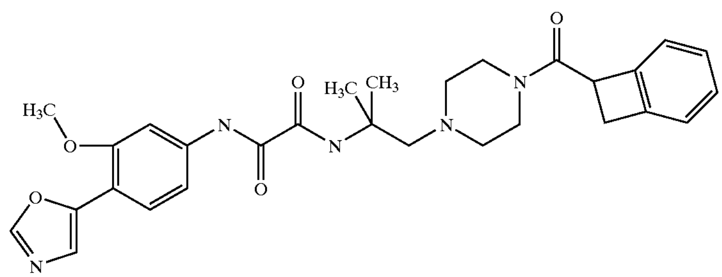 | 532.1 | 528 |
| N-[2-[4-(3-Hydroxybenzoyl)-1-piperazinyl]-1,1-dimethylethyl]-N'-[3-methoxy-4-(5-oxazolyl)phenyl]oxalamide | 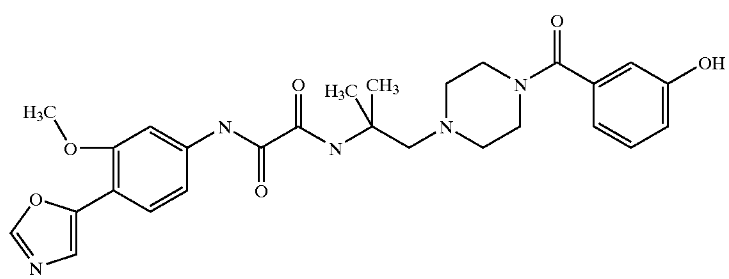 | 522.1 | 529 |
| N-[2-[4-(2-Ethylbutyl)-1-piperazinyl]-1,1-dimethylethyl]-N'-[3-methoxy-4-(5-oxazolyl)phenyl]oxalamide | 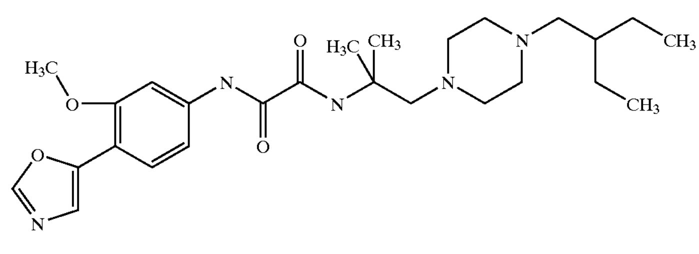 | 486.1 | 530 |
| N-[3-Methoxy-4-(5-oxazolyl)phenyl]-N'-[1,1-dimethyl-2-[4-(2-phenylethyl)-1-piperazinyl]ethyl]oxalamide | 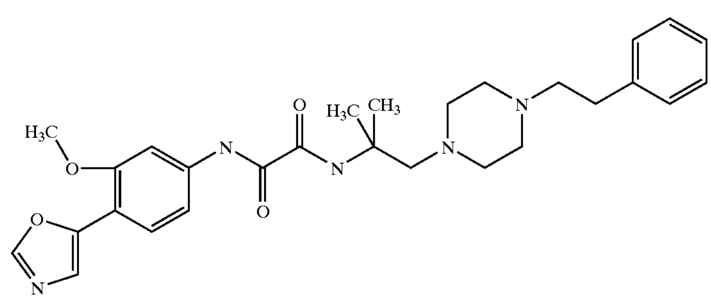 | 506.2 | 531 |

TABLE 1g-continued

| Name | Structure | MS (ES) (M + H)+ | Ex No |
|---|---|---|---|
| N-[3-Methoxy-4-(5-oxazolyl)phenyl]-N'-[1,1-dimethyl-2-[4-[3-(methylthio)propyl]-1-piperazinyl]ethyl]oxalamide | 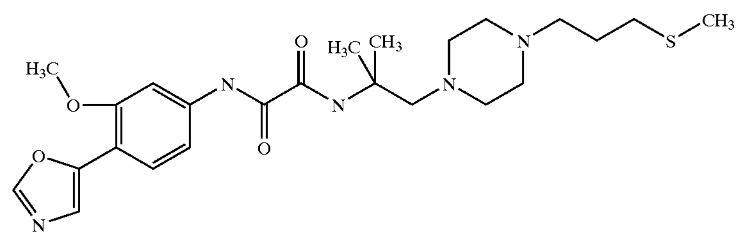 | 490.1 | 532 |
| N-[2-[4-(2,6-Difluorobenzyl)-1-piperazinyl]-1,1-dimethylethyl]-N'-[3-methoxy-4-(5-oxazolyl)phenyl]oxalamide | 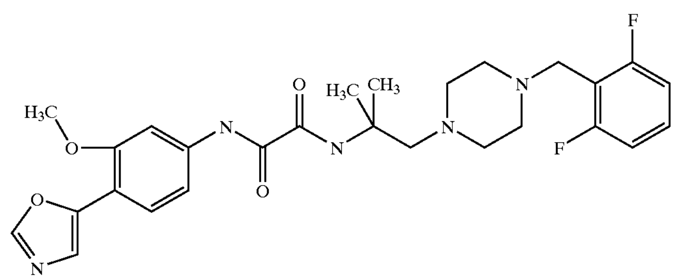 | 528.1 | 533 |
| N-[2-[4-(3-Furfuryl)-1-piperazinyl]-1,1-dimethylethyl]-N'-[3-methoxy-4-(5-oxazolyl)phenyl]oxalamide | 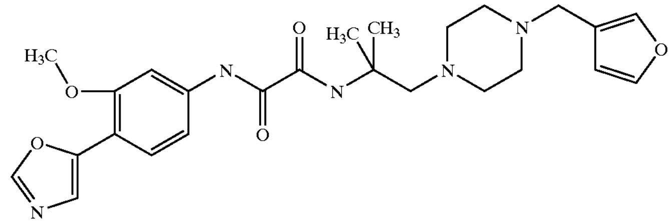 | 482.1 | 534 |
| N-[2-[4-[(2-Benzofuranyl)methyl]-1-piperazinyl]-1,1-dimethylethyl]-N'-[3-methoxy-4-(5-oxazolyl)phenyl)]oxalamide | 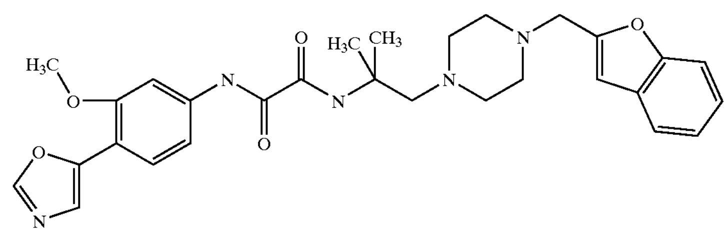 | 532.1 | 535 |
| N-[2-[4-(2-Cyanobenzyl)-1-piperazinyl]-1,1-dimethyl]-N'-[3-methoxy-4-(5-oxazolyl)phenyl]oxalamide | 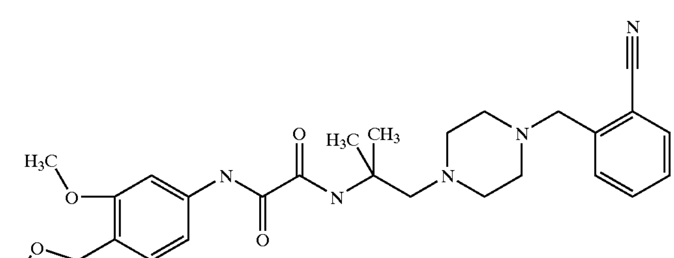 | 517.1 | 536 |

TABLE 1g-continued

| Name | Structure | MS (ES) (M + H)+ | Ex No |
|---|---|---|---|
| N-[3-Methoxy-4-(5-oxazolyl)phenyl]-N'-[2-[4-(3,3-dimethylbutyl)-1-piperazinyl]-1,1-dimethylethyl]oxalamide | 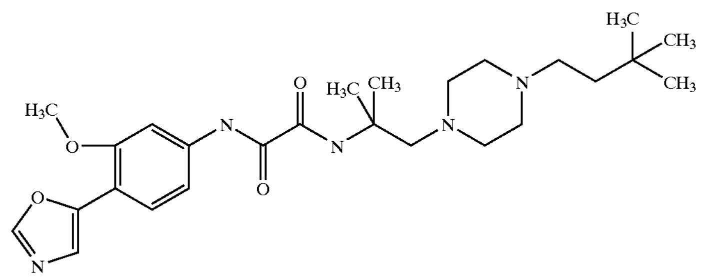 | 486.2 | 537 |
| N-[3-Methoxy-4-(5-oxazolyl)phenyl]-N'-[1,1-dimethyl-2-[4-[(2-quinolinyl)methyl]-1-piperazinyl]ethyl]oxalamide | 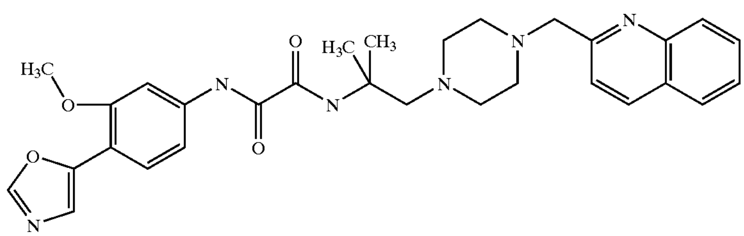 | 543.2 | 538 |
| tert-Butyl 4-[2-[[[3-methoxy-4-(5-oxazolyl)anilino]oxalyl]amino]-2-methylpropyl]-1-piperazineacetate | 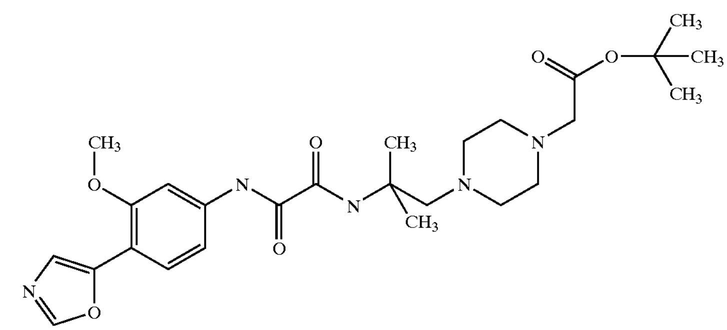 | 516 | 539 |
| 4-[2-[[[3-Methoxy-4-(5-oxazolyl)anilino]oxalyl]amino]-2-methylpropyl]-1-piperazineacetic acid trifluoroacetate (1:1) | 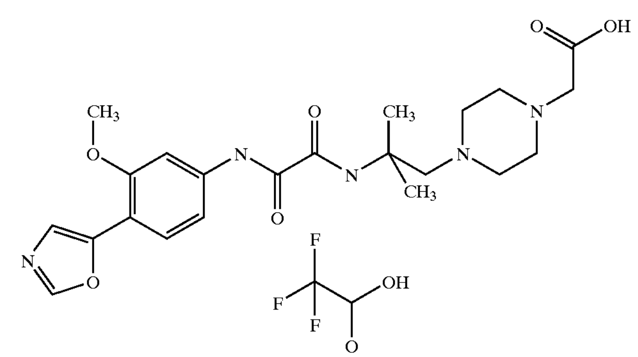 | 460 | 540 |
| N-[2-[4-(Cyclopropylmethyl)-1-piperazinyl]-1,1-dimethyl]-N'-[3-methoxy-4-(5-oxazolyl)phenyl]oxalamide | 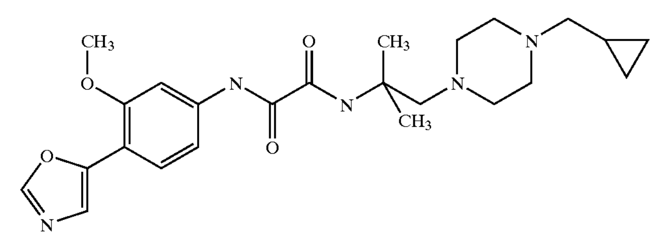 | 456 | 541 |

TABLE 1g-continued

| Name | Structure | MS (ES) (M + H)+ | Ex No |
|---|---|---|---|
| tert-Butyl 4-[4-[2-[[[3-methoxy-4-(5-oxazolyl)anilino]oxalyl]amino]-2-methylpropyl]-1-piperazinyl]benzoate | 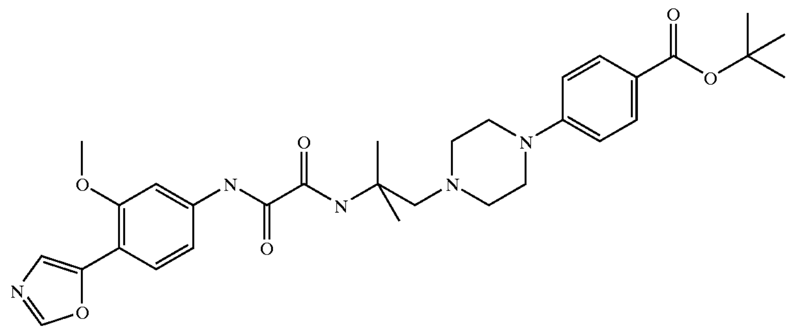 | 578 | 651 |
| 4-[4-[2-[[[3-Methoxy-4-(5-oxazolyl)anilino]oxalyl]amino]-2-methylpropyl]-1-piperazinyl]benzoic acid trifluoroacetate (1:1) | 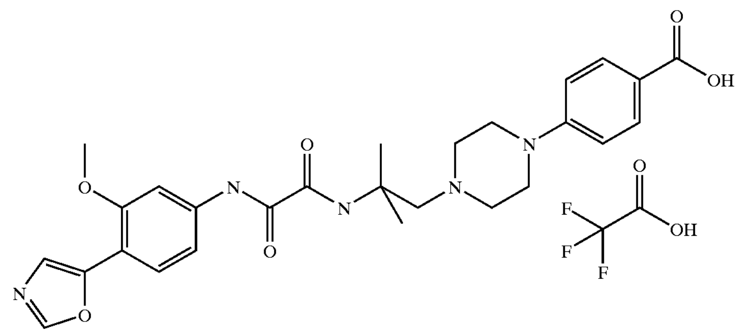 | 522 | 652 |

EXAMPLES 415–420

In a manner analogous to that described in Example 4 starting with N-[3-(aminomethylphenyl]-N'-[3-methoxy-4-(5-oxazolyl)phenyl]oxalamide and the appropriate carboxylic acid chloride compounds shown in table 1h were prepared.

TABLE 1h

| Name | Structure | ME(ES) (M + H)+ | Ex No |
|---|---|---|---|
| Phenyl[3-[[[4-(5-oxazolyl)anilino]oxalyl]amino]benzyl]carbamate | 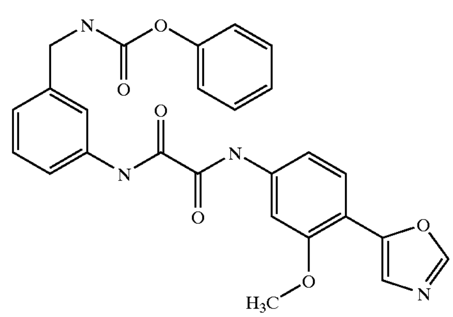 | 487 | 415 |
| N-[3-[(3-Fluorobenzamido)methyl]phenyl]-N'-[3-methoxy-4-(5-oxazolyl)phenyl]oxalamide | 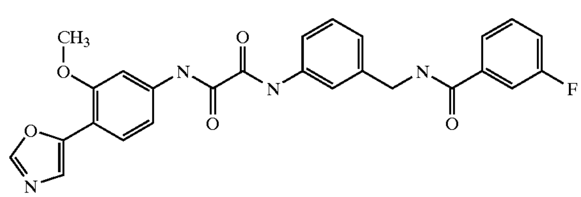 | 489 | 416 |

TABLE 1h-continued

| Name | Structure | ME(ES) (M + H)+ | Ex No |
|------|-----------|-----------------|-------|
| N-[3-[(3-Chlorobenzamido)methyl]phenyl]-N'-[3-methoxy-4-(5-oxazolyl)phenyl]oxalamide | 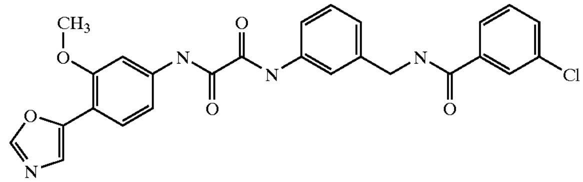 | 505 | 417 |
| N-[3-[(3-Methoxybenzamido)methyl]phenyl]-N'-[3-methoxy-4-(5-oxazolyl)phenyl]oxalamide | 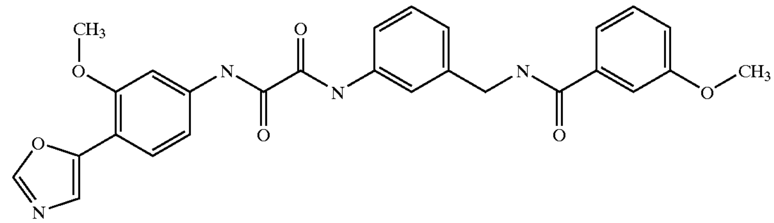 | 501.2 | 418 |
| N-[3-[(3,4-Dimethoxybenzamido)methyl]phenyl]-N'-[3-methoxy-4-(5-oxazolyl)phenyl]oxalamide | 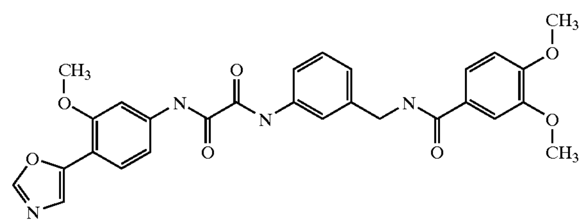 | 531.2 | 419 |
| N-[3-[(3-Cyanobenzamido)methyl]phenyl]-N'-[3-methoxy-4-(5-oxazolyl)phenyl]oxalamide | 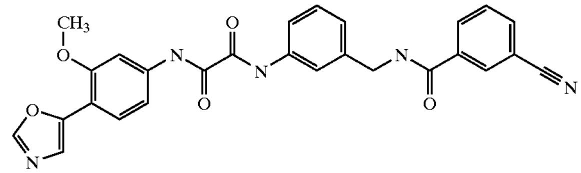 | 496.1 | 420 |

EXAMPLES 421–427 AND 598–614

Typical methods used for the preparation of the compounds of table 1b are described below:

Examples 421 and 423 were prepared by reaction of N-[3-methoxy-4-(5-oxazolyl)phenyl]-N'-[1,1-dimethyl-2-(4-piperidinyl)ethyl]oxalamide with the appropriate acylating reagent.

Example 424 was prepared in a manner analogous to that described in Example 1, starting with N-[3-methoxy-4-(5-oxazoyl)phenyl oxalamic acid, prepared as described in Example 1, parts (i) and (ii), and the appropriate amine.

EXAMPLE 422
N-[3-Methoxy-4-(5-oxazolyl)phenyl]-N'-[1,1-dimethyl-2-(phenylthio)ethyl]oxalamide (i) A mixture of 2 g (17.7 mmol) of 2,4,4-trimethyl-2-oxazoline and 1.95 g (17.7 mmol) of thiophenol were heated at 120 C for 18 hours. After cooling the resulting solid was triturated with diethyl ether/petrol (1:2) and filtered off to give 2.55 g of N-[1,1-dimethyl-2-(phenylthio)ethyl]acetamide as a white solid.

(ii) A solution of 2.5 g (11.2 mmol) of N-[1,1-dimethyl-2-(phenylthio)ethyl]acetamide, 3.18 g (11.2 mmol) of titanium isopropoxide and 3.09 g (16.8 mmol) of diphenylsilane in 12 ml of tetrahydrofuran were stirred at room temperature for 18 hours. The resulting mixture was chromatographed on silica gel using 3%, 6% and 10% methanol in dichloromethane for the elution. There was obtained 2 g of 1,1-dimethyl-2-(phenylthio)ethylamine as a pale orange oil. The 1,1-dimethyl-2-(phenylthio)ethylamine was then coupled to N-[3-methoxy-4-(5-oxazoyl)phenyl oxalamic acid by a procedure analogous to that described in example 1 to afford N-[3-methoxy-4-(5-oxazolyl)phenyl]-N'-[1,1-dimethyl-2-(phenylthio)ethyl]oxalamide. MS: m/e 426 [M+H]+.

Example 427 was prepared by an analogous method to that described for example 422 but using 4-benzyloxythiophenol in place of the thiophenol and removing the protecting group using a mixture of hydrogen bromide in acetic acid.

Example 607 was prepared starting from benzofuran-3-acetic ethyl ester by alkylation iodomethane using potassium tertiary butoxide as base followed by alkaline hydrolysis, Curtius reaction, hydrolysis in ethylene glycol and water at 180° C. The resulting amine was then coupled to N-[3-methoxy-4-(5-oxazoyl)phenyl oxalamic acid as described in Example 1.

Example 426 was prepared in a manner analogous to that described for example 408 in table 1 g using tetrahydroquinoline in place of 1-(4-methoxyphenyl)piperazine.

EXAMPLE 610

N-[2-[1-(Methanesulfonyl)-4-piperidinyl]-1,1-dimethylethyl]-N'-[3-methoxy-4-(5-oxazolyl)phenyl]oxalamide 14 mg (0.12 mmol) of methanesulphonyl chloride were added to a solution of 40 mg (0.1 mmol) of N-[3-methoxy-4-(5-oxazolyl)phenyl-N'-[1,1-dimethyl-2-(4-piperidinyl)ethyl]oxalamide in 1 ml of dichloromethane followed by 17 mg (0.15 mmol) of N-ethylmorpholine and the mixture stirred at room temperature for 4 hours. The resulting solution was diluted with ethyl acetate, washed with 2M hydrochloric acid and saturated sodium bicarbonate solution, dried over magnesium sulphate, evaporated to dryness and the residue triturated with diethyl ether. There was obtained 23 mg of N-[2-[1-(methanesulfonyl)-4-piperidinyl]-1,1-dimethylethyl]-N'-[3-methoxy-4-(5-oxazolyl)phenyl]oxalamide as an off-white solid. MS m/e 479 [M+H]$^+$.

The starting material was prepared as follows:

i) A solution of 4.65 g (31 mmol) of alpha, alpha-dimethyl-4-pyridineethylamine, 15.6 g (0.154 mol) of triethylamine and 13.5 g (61.9 mmol) of di-tert-butyl dicarbonate in 100 ml of methanol was stirred at room temperature for 2 days then evaporated to dryness. The residue was dissolved in ethyl acetate, washed with water, dried over magnesium sulphate, evaporated to dryness and chromatographed on silica gel using ethyl acetate/petrol (2:1) for the elution. There was obtained 2.12 g of tert-butyl[1,1-dimethyl-2-(4-pyridyl)ethyl]carbamate as a pale (orange solid. $^1$H NMR (400 MHz CDCl$_3$) δ: 1.29 (6H,s), 1.49 (9H,s), 3.04 (2H,s), 4.30 (1H, br.s), 7.10 (2H,d), 8.52 (2H,d).

ii) 2.1 g (8.4 mmol) of tert-butyl[1,1-dimethyl-2-(4-pyridyl)ethyl]carbamate, in 20 ml of methanol were hydrogenated with 400 mg of 10% palladium on carbon catalyst at 70° C. and 7 Bar for 6 days. The resulting suspension was filtered, evaporated to dryness and the residue triturated with diethyl ether/petrol (1:9) to give 1.2 g of tert-butyl [1,1-dimethyl-2-(4-piperidinyl)ethyl]carbamate as a white solid. $^1$H NMR (400 MHz DMSO) δ: 1.18 (6H,s), 1.28–1.41 (2H,m), 1.37 (9H,s), 1.52–1.69 (3H,m), 1.75–1.83 (2H,d), 2.74–2.84 (2H,t), 3.12–3.21 (2H,d), 6.40–6.48 (1H,br.s), 8.60–8.95 (1H,br.s).

iii) A solution of 1.2 g (4.68 mmol) of tert-butyl[1,1-dimethyl-2-(4-piperidinyl)ethyl]carbamate, 945 mg (9.36 mmol) of triethylamine and 2.33 g (9.36 mmol) of N-(benzyloxycarbonyloxy)succinimide in 20 ml of dichloromethane was stirred at room temperature for 18 hours then washed with 10% citric acid solution and saturated sodium bicarbonate solution. The organic phase was dried over magnesium sulphate, evaporated to dryness and the residue chromatographed on silica gel using ethyl acetate/petrol (1:2) for the elution. There was obtained 1.89 g of benzyl 4-[2-(tert-butoxyformamido)-2-methylpropyl]-1-piperidinecarboxylate. $^1$H NMR (400 MHz CDCl$_3$) δ: 1.15–1.32 (2H,m), 1.29 (6H,s), 1.42 (9H,s), 1.49–1.78 (5H,m), 2.75–2.90 (2H,m), 4.05–4.16 (2H,m), 4.41 (1H,br.s), 5.12 (2H,s), 7.27–7.42 (5H,m).

iv) A solution of 1.79 g (4.6 mmol) of benzyl 4-[2-(tert-butoxyformamido)-2-methylpropyl]-1-piperidinecarboxylate in 6 ml of trifluoroacetic acid/dichloromethane (1:1) was stirred at room temperature for 5 minutes then evaporated to dryness. The residue was dissolved in 20 ml of dichloromethane along with 1.2 g (4.58 mmol) of N-[3-methoxy-4-(5-oxazolyl)phenyl] oxalamic acid, 1.1 g (5.74 mmol) of 1-(3-dimethylaminopropyl)-3-ethylcarbodiimide hydrochloride, 1.32 g (11.5 mmol) of N-ethylmorpholine and 1.1 g (6.9 mmol) of 1-hydroxy-7-azabenzotriazole. After stirring overnight the solution was diluted with ethyl acetate, washed with 10% citric acid solution and saturated sodium bicarbonate solution, dried over magnesium sulphate evaporated to dryness and chromatographed on silica gel using ethyl acetate/petrol (1:1) for the elution. There was obtained 1.14 g of benzyl 4-{2-[[[3-methoxy-4-(5-oxazolyl)phenylamino]oxalyl]amino]-2-methylpropyl}-1-piperidinecarboxylate as a white foam. MS: m/e 535 [M+H]$^+$.

v) A solution of 1.1 g (2.05 mmol) of benzyl 4-{2-[[[3-methoxy-4-(5-oxazolyl)phenylamino]oxalyl]amino]-2-methylpropyl}-1-piperidinecarboxylate in 25 ml of methanol was hydrogenated with 100 mg of 10% palladium on carbon catalyst for 4 hours. The resulting suspension was filtered and evaporated to dryness to give 732 mg of N-[3-methoxy-4-(5-oxazolyl)phenyl]-N'-[1,1-dimethyl-2-(4-piperidinyl)ethyl]oxalamide as an off-white solid. MS: m/e 401 [M+]$^+$.

Example 616 was prepared starting from benzofuran-3-acetic ethyl ester by alkylation iodomethane using potassium tertiary butoxide as base followed by alkaline hydrolysis, Curtius reaction, hydrolysis in ethylene glycol and water at 180° C. The resulting amine was then coupled to N-[3-methoxy-4-(5-oxazoyl)phenyl oxalamic acid as described in Example 1

EXAMPLE 619

N-[2-[1-(Methanesulfonyl)-4-piperidinyl]-1,1-dimethylethyl]-N'-[3-methoxy-4-(5-oxazolyl)phenyl]oxalamide 14 mg (0.12 mmol) of methanesulphonyl chloride were added to a solution of 40 mg (0.1 mmol) of N-[3-methoxy-4-(5-oxazolyl)phenyl-N'-[1,1-dimethyl-2-(4-piperidinyl)ethyl]oxalamide in 1 ml of dichloromethane followed by 17 mg (0.15 mmol) of N-ethylmorpholine and the mixture stirred at room temperature for 4 hours. The resulting solution was diluted with ethyl acetate, washed with 2M hydrochloric acid and saturated sodium bicarbonate solution, dried over magnesium sulphate, evaporated to dryness and the residue triturated with diethyl ether. There was obtained 23 mg of N-[2-[1-(methanesulfonyl)-4-piperidinyl]-1,1-dimethylethyl]-N'-(3-methoxy-4-(5-oxazolyl)phenyl]oxalamide as an off-white solid. MS m/e 479 [M+]$^+$.

The starting material was prepared as follows:

i) A solution of 4.65 g (31 mmol) of alpha, alpha-dimethyl-4-pyridineethylamine, 15.6 g (0.154 mol) of triethylamine and 13.5 g (61.9 mmol) of di-tert-butyl dicarbonate in 100 ml of methanol was stirred at room temperature for 2 days then evaporated to dryness. The residue was dissolved in ethyl acetate, washed with water, dried over magnesium sulphate, evaporated to dryness and chromatographed on silica gel using ethyl acetate/petrol (2:1) for the elution. There was obtained 2.12 g of tert-butyl[1,1-dimethyl-2-(4-pyridyl)ethyl]carbamate as a pale orange solid. $^1$H NMR (400 MHz CDCl$_3$) δ: 1.29 (6H,s), 1.49 (9H,s), 3.04 (2H,s), 4.30 (1H, br.s), 7.10 (2H,d), 8.52 (2H,d).

ii) 2.1 g (8.4 mmol) of tert-butyl[1,1-dimethyl-2-(4-pyridyl)ethyl]carbamate, in 20 ml of methanol were hydrogenated with 400 mg of 10% palladium on carbon catalyst at 70° C. and 7 Bar for 6 days. The resulting suspension was filtered, evaporated to dryness and the residue triturated with diethyl ether/petrol (1:9) to give 1.2 g of tert-butyl [1,1-dimethyl-2-(4-piperidinyl)ethyl]carbamate as a white solid. $^1$H NMR (400 MHz DMSO) δ: 1.18 (6H,s), 1.28–1.41 (2H,m), 1.37 (9H,s), 1.52–1.69 (3H,m), 1.75–1.83 (2H,d), 2.74–2.84 (2H,t), 3.12–3.21 (2H,d), 6.40–6.48 (1H,br.s), 8.60–8.95 (1H,br.s).

iii) A solution of 1.2 g (4.68 mmol) of tert-butyl[1,1-dimethyl-2-(4-piperidinyl)ethyl]carbamate, 945 mg (9.36 mmol) of triethylamine and 2.33 g (9.36 mmol) of N-(benzyloxycarbonyloxy)succinimide in 20 ml of dichloromethane was stirred at room temperature for 18 hours then washed with 10% citric acid solution and saturated sodium bicarbonate solution. The organic phase was dried over magnesium sulphate, evaporated to dryness and the residue chromatographed on silica gel using ethyl acetate/petrol (1:2) for the elution. There was obtained 1.89 g of benzyl 4-[2-(tert-butoxyformamido)-2-methylpropyl]-1-piperidinecarboxylate. $^1$H NMR (400 MHz CDCl$_3$) δ: 1.15–1.32 (2H,m), 1.29 (6H,s), 1.42 (9H,s), 1.49–1.78 (5H,m), 2.75–2.90 (2H,m), 4.05–4.16 (2H,m), 4.41 (1H,br.s), 5.12 (2H,s), 7.27–7.42 (5H,m).

iv) A solution of 1.79 g (4.6 mmol) of benzyl 4-[2-(tert-butoxyformamido)-2-methylpropyl]-1-piperidinecarboxylate in 6 ml of trifluoroacetic acid/dichloromethane (1:1) was stirred at room temperature for 5 minutes then evaporated to dryness. The residue was dissolved in 20 ml of dichloromethane along with 1.2 g (4.58 mmol) of N-[3-methoxy-4-(5-oxazolyl)phenyl]oxalamic acid, 1.1 g (5.74 mmol) of 1-(3-dimethylaminopropyl)-3-ethylcarbodiimide hydrochloride, 1.32 g (11.5 mmol) of N-ethylmorpholine and 1.1 g (6.9 mmol) of 1-hydroxy-7-azabenzotriazole. After stirring overnight the solution was diluted with ethyl acetate, washed with 10% citric acid solution and saturated sodium bicarbonate solution, dried over magnesium sulphate evaporated to dryness and chromatographed on silica gel using ethyl acetate/petrol (1:1) for the elution. There was obtained 1.14 g of benzyl 4-{2-[[[3-methoxy-4-(5-oxazolyl)phenylamino]oxalyl]amino]-2-methylpropyl}-1-piperidinecarboxylate as a white foam. MS: m/e 535 [M+H]$^+$.

v) A solution of 1.1 g (2.05 mmol) of benzyl 4-{2-[[[3-methoxy-4-(5-oxazolyl)phenylamino]oxalyl]amino]-2-methylpropyl}-1-piperidinecarboxylate in 25 ml of methanol was hydrogenated with 100 mg of 10% palladium on carbon catalyst for 4 hours. The resulting suspension was filtered and evaporated to dryness to give 732 mg of N-[3-methoxy-4-(5-oxazolyl)phenyl]-N'-[1,1-dimethyl-2-(4-piperidinyl)ethyl]oxalamide as an off-white solid. MS: m/e 401 [M+H]$^+$.

The remaining examples in table 1b were prepared by methods analogous to those described above, as appropriate to the structure, or by methods previously described for related structures.

TABLE 1b

| Name | Structure | MS (ES) (M + H)$^+$ | Ex No |
|---|---|---|---|
| Benzyl 4-{2-[[[3-methoxy-4-(5-oxazolyl)phenyl-amino]oxalyl]amino]-2-methylpropyl}-1-piperidinecarboxylate | 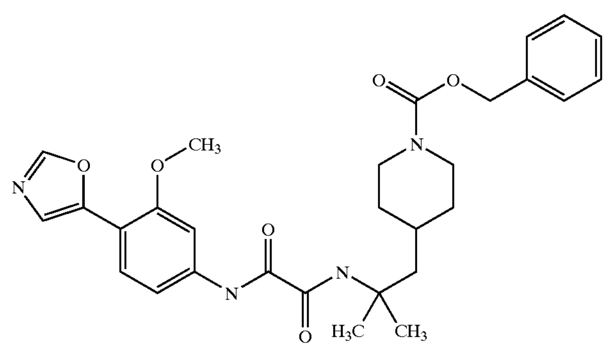 | 535 | 421 |
| N-[3-Methoxy-4-(5-oxazolyl)phenyl]-N'-[1,1-dimethyl-2-(phenylthio)ethyl]oxalamide | 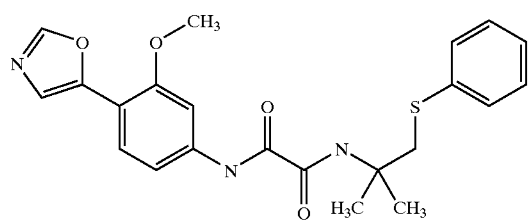 | 426 | 422 |
| N-[2-(1-Acetyl-4-piperidinyl)-1,1-dimethylethyl]-N'-[3-methoxy-4-(5-oxazolyl)phenyl]oxalamide | 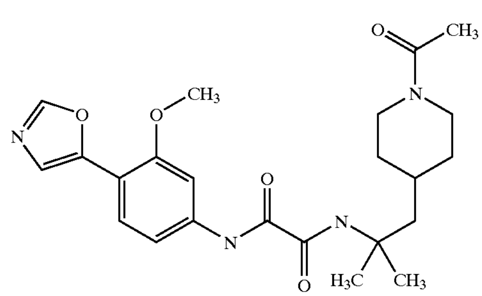 | 443 | 423 |

TABLE 1b-continued

| Name | Structure | MS (ES) (M + H)+ | Ex No |
|------|-----------|------------------|-------|
| N-(2-Cyclohexyl)-1,1-dimethylethyl)-N'-[3-methoxy-4-(5-oxazolyl)phenyl]oxalamide | 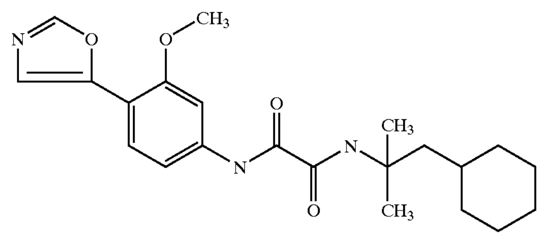 | 400 | 424 |
| N-[3-Methoxy-4-(5-oxazolyl)phenyl]-N'-[1,1-dimethyl-2-(N-methylanilino)ethyl]oxalamide | 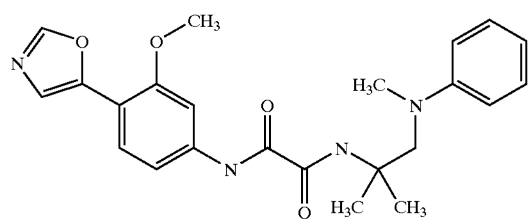 | 423 | 425 |
| N-[2-(1,2,3,4-Tetrahydro-1-quinolyl)-1,1-dimethylethyl]-N'-[3-methoxy-4-(5-oxazolyl)phenyl]oxalamide | 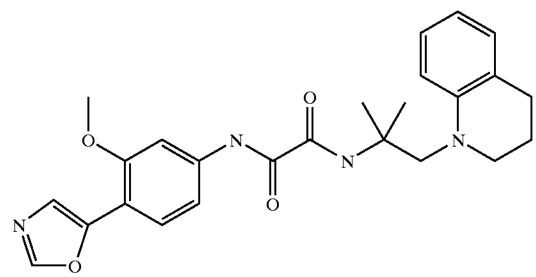 | 449 | 426 |
| N-[2-(4-Hydroxyphenylthio)-1,1-dimethylethyl]-N'-[3-methoxy-4-(5-oxazolyl)phenyl]oxalamide | 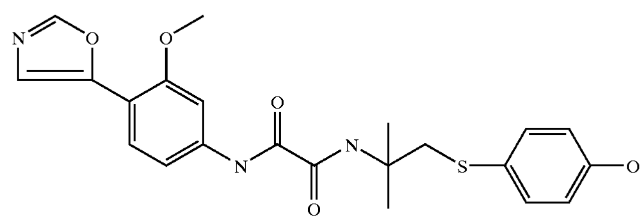 | 442 | 427 |
| N-[3-(4-Hydroxyphenyl)-1,1-dimethylpropyl]-N'-[3-methoxy-4-(5-oxazolyl)phenyl]oxalamide | 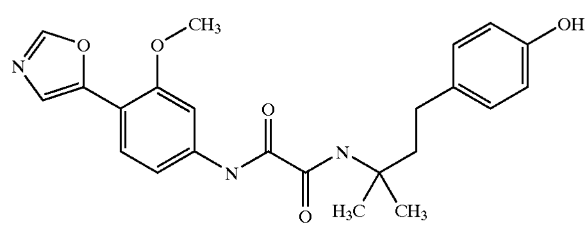 | 424 | 598 |
| N-[3-Methoxy-4-(5-oxazolyl)phenyl]-N'-[1,1-dimethyl-2-[(1-oxido-4-pyridyl)carboxamido]ethyl]oxalamide | 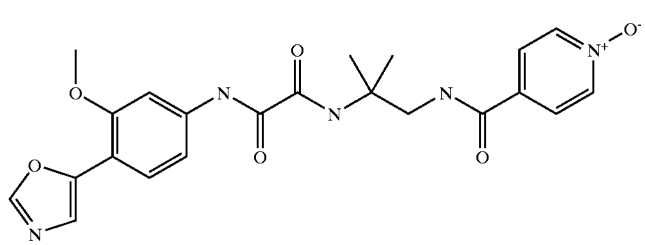 | 454 | 599 |

TABLE 1b-continued

| Name | Structure | MS (ES) (M + H)+ | Ex No |
|------|-----------|------------------|-------|
| N-[2-(4-Acetylbenzamido)-1,1-dimethylethyl]-N'-[3-methoxy-4-(5-oxazolyl)phenyl]oxalamide | 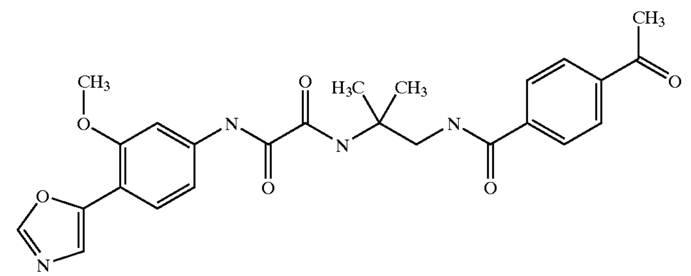 | 479.1 | 600 |
| N-[3-Methoxy-4-(5-oxazolyl)phenyl]-N'-[3-[(4-methylbenzamido)methyl]phenyl]oxalamide | 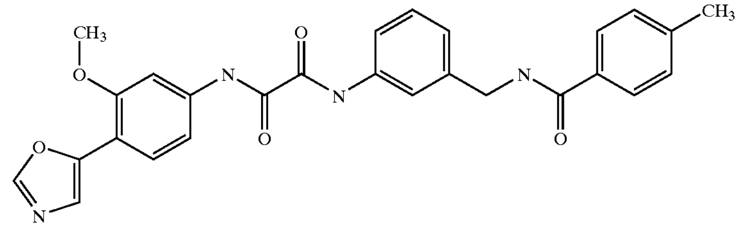 | 485.1 | 601 |
| N-[3-[(2-Methoxybenzamido)methyl]phenyl]-N'-[3-methoxy-4-(5-oxazolyl)phenyl]oxalamide | 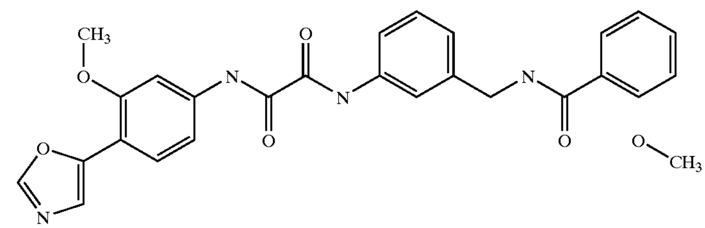 | 501.1 | 602 |
| N-[3-[(4-Chlorobenzmido)methyl]phenyl]-N'-[3-methoxy-4-(5-oxazolyl)phenyl]oxalamide | 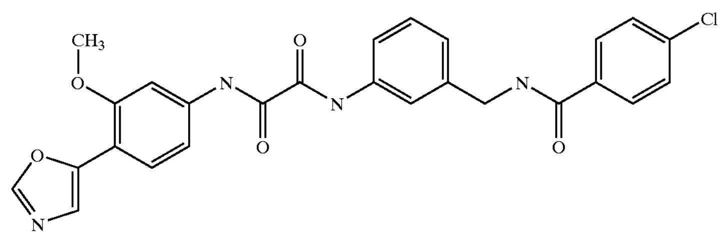 | 505.1 | 603 |
| N-[3-[[(1,3-Benzodioxol-5-yl)carboxamido]methyl]phenyl]-N'-[3-methoxy-4-(5-oxazolyl)phenyl]oxalamide | 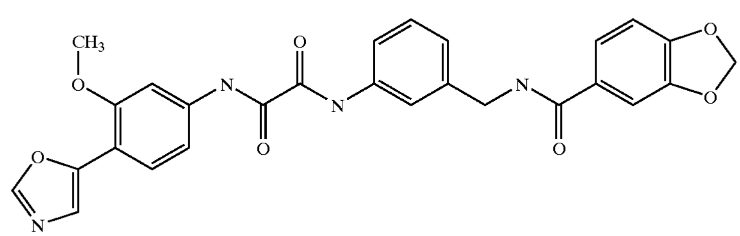 | 515.2 | 604 |
| N-[2-(2,3-Dihydro-1-indolyl)-1,1-dimethylethyl]-N'-[3-methoxy-4-(5-oxazolyl)phenyl]oxalamide | 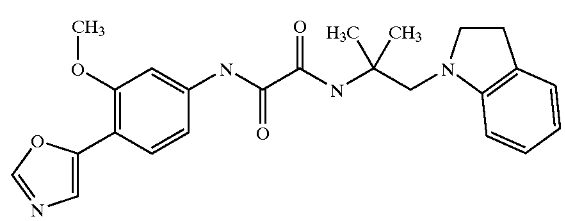 | 435 | 605 |

TABLE 1b-continued

| Name | Structure | MS (ES) (M + H)+ | Ex No |
|---|---|---|---|
| N-[2,(3,4-Dihydro-6-methyl-2H-quinol-1-yl)-1,1-dimethylethyl]-N'-[3-methoxy-4-(5-oxazolyl)phenyl]oxalamide | 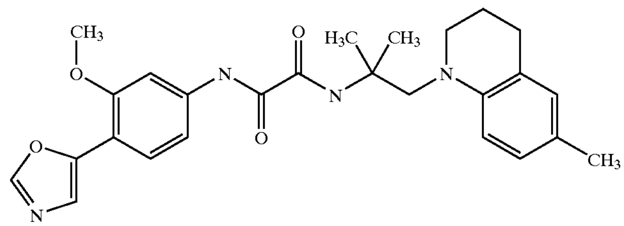 | 463 | 606 |
| N-[1-(3-Benzofuranyl)-1-methylethyl]-N'-[3-methoxy-4-(5-oxazolyl)phenyl]oxalamide | 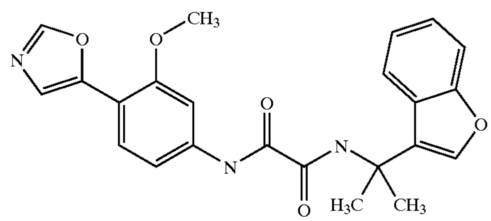 | 420 | 607 |
| N-[3-Methoxy-4-(5-oxazolyl)pheny]-N'-[1,1-dimethyl-3-(4-phenoxy-piperidino)propyl]oxalamide | 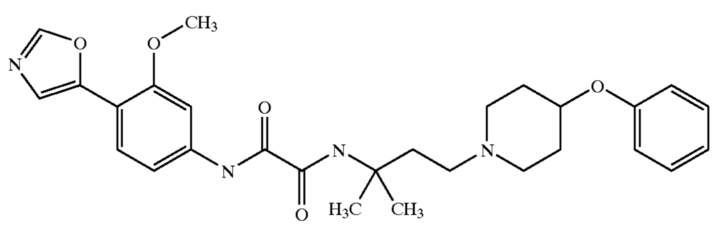 | 507 | 608 |
| N-[2-(1-Butyryl-4-piperidinyl)-1,1-dimethylethyl]-N'-[3-methoxy-4-(5-oxazolyl)phenyl]oxalamide | 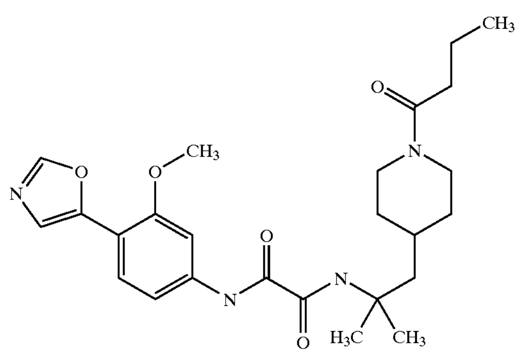 | 471 | 609 |
| N-[2-[1-(Methanesulfonyl)-4-piperidinyl]-1,1-dimethylethyl]-N'-[3-methoxy-4-(5-oxazolyl)phenyl]oxalamide | 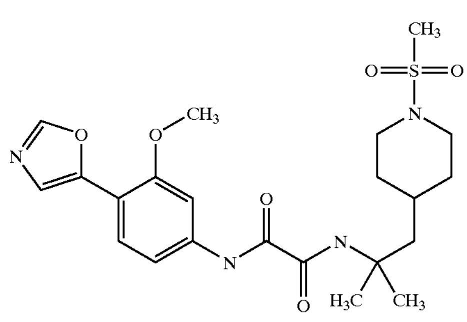 | 479 | 610 |

TABLE 1b-continued

| Name | Structure | MS (ES) (M + H)+ | Ex No |
|---|---|---|---|
| N-[2-[1-(Benzenesulfonyl)-4-piperidinyl]-1,1-dimethylethyl]-N'-[3-methoxy-4-(5-oxazolyl)phenyl]oxalamide | 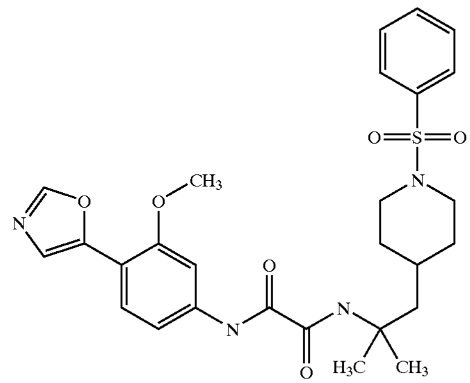 | 541 | 611 |
| N-[2-(1-Isobutyryl-4-piperidinyl)-1,1-dimethylethyl]-N'-[3-methoxy-4-(5-oxazolyl)phenyl]oxalamide | 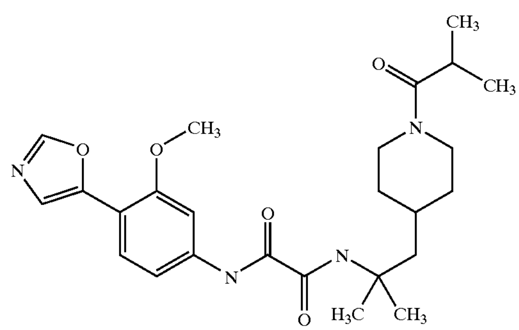 | 471 | 612 |
| tert-Butyl 4-[3-[[[3-methoxy-4-(5-oxazolyl)anilino] oxalyl] amino]-3-methylbutyl]-1-piperidinecarboxylate | 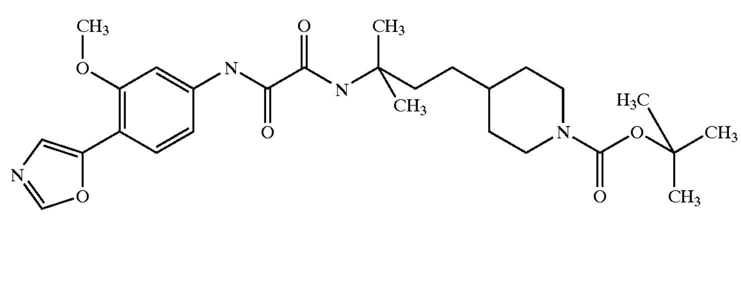 | 515 | 613 |
| N-[3-Methoxy-4-(5-oxazolyl)phenyl]-N'-[1,1-dimethyl-3-(4-piperidinyl)propyl]oxalamide | 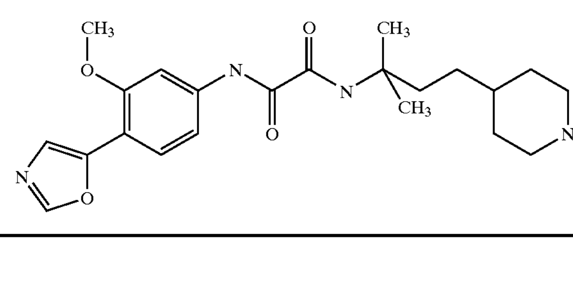 | 415 | 614 |

EXAMPLES 428–432

Examples 428, 431 and 432 of table 1i were prepared in a manner analogues to that described for example 408 in table 1g but using N-[3-methoxy-4-(4-oxazoyl)phenyl oxalamic acid or N-[3-methoxy-4-(2-methyl-4-oxazoyl)phenyl oxalamic acid in place of N-[3-methoxy-4-(5-oxazoyl) phenyl oxalamic acid for the coupling step.

Examples 429 and 430 of table 1i were prepared by analogues procedures to those described for the preparation of the compounds of table 1f.

TABLE 1i

| Name | Structure | MS(ES) (M + H)+ | Ex No |
|------|-----------|-----------------|-------|
| N-[3-Methoxy-4-(4-oxazolyl)phenyl]-N'-[1,1-dimethyl-2-(4-phenyl-1-piperazinyl)ethyl]oxalamide | 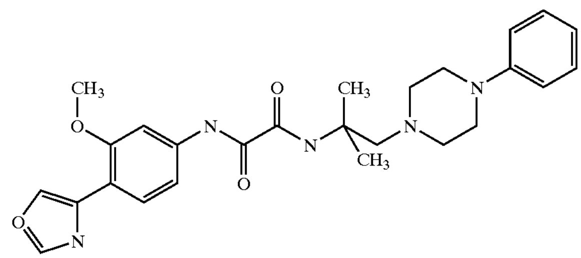 | 478 | 428 |
| N-[2-(4-Benzyloxyphenyl)-1,1-dimethylethyl]-N'-[3-methoxy-4-(4-oxazolyl)phenyl]oxalamide | 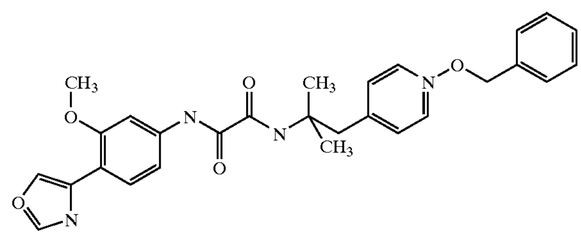 | 500 | 429 |
| N-[2-(4-Hydroxyphenyl)-1,1-dimethylethyl]-N'-[3-methoxy-4-(4-oxazolyl)phenyl]oxalamide | 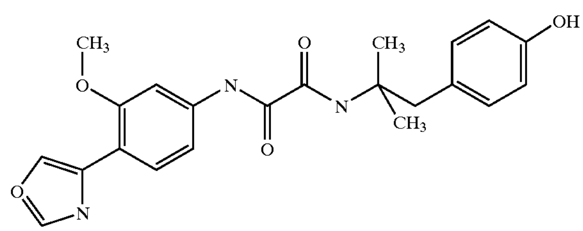 | 410 | 430 |
| N-[3-Methoxy-4-(4-oxazolyl)phenyl]-N'-[2-[4-(4-methoxyphenyl)-1-piperazinyl]-1,1-dimethylethyl]oxalamide | 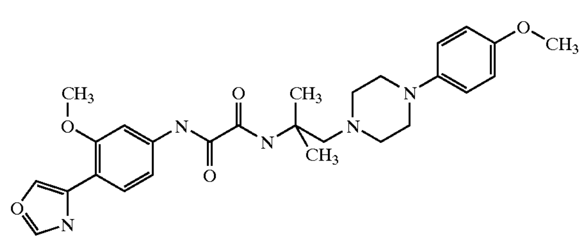 | 508 | 431 |
| N-[3-Methoxy-4-(2-methyl-4-oxazolyl)-phenyl]-N'-[2-[4-(4-methoxyphenyl)-1-piperazinyl]-1,1-dimethylethyl]oxalamide | 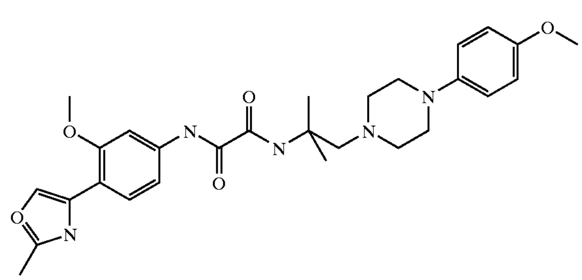 | 522.4 | 432 |

The features disclosed in the foregoing description, or the following claims, or the accompanying drawings, expressed in their specific forms or in terms of a means for performing the disclosed function, or a method or process for attaining the disclosed result, as appropriate, may, separately, or in any combination of such features, be utilised for realising the invention in diverse forms thereof.

What is claimed is:

1. The compound of the formula

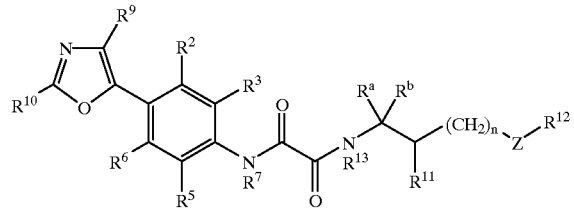

XVIII wherein
- $R^2$ is hydrogen, unsubstituted lower alkyl, lower alkoxy, halo, hydroxy or cyano;
- $R^3$ is hydrogen, unsubstituted lower alkyl, lower alkoxy, halo, or cyano;
- $R^5$ is hydrogen, unsubstituted lower alkyl, lower alkoxy, halo, or cyano;
- $R^6$ is hydrogen, unsubstituted lower alkyl, lower alkoxy, halo, or cyano;
- $R^7$ is hydrogen, or unsubstituted lower alkyl;
- $R^9$ is hydrogen, lower alkyl, or aryl-lower alkyl; and
- $R^{10}$ is hydrogen
- $R^{11}$ is H or lower alkyl, $R^{13}$ is H or unsubstituted lower alkyl,
- n=0 or 1,
- $R^a$, $R^b$ are lower alkyl or $R^a$ and $R^b$ taken together with the carbon atom to which they are attached form a 3 to 7 member carbocycle, and
- $R^{12}$ is heterocyclyl, aryl or lower cycloalkyl and Z is O, S or $NR^{28}$, wherein $R^{28}$ is H or lower alkyl.

2. The compound of claim 1 of the formula

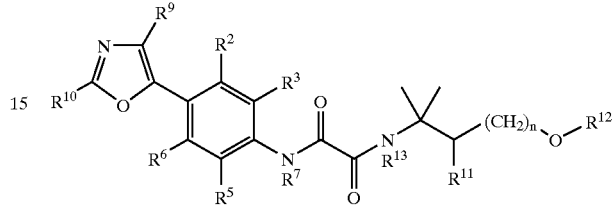

XIVa wherein
- $R^{11}$ is H or lower alkyl, $R^{13}$ is H or unsubstituted lower alkyl,
- n=0 or 1 and
- $R^{12}$ is heterocyclyl, aryl or lower cycloalkyl.

3. The compound of claim 2 wherein
$R^2$ is methoxy and $R^3$, $R^5$, $R^6$, $R^9$, $R^{10}$, $R^{11}$ and $R^{13}$ are hydrogen.

4. The compound of claim 3 wherein $R^{12}$ is aryl, a 3 to 7 membered cycloalkyl ring, or a 5 or 6-membered monocyclic or 9 or 10-membered bicyclic saturated or unsaturated heterocyclic ring with 1 to 4 heteroatoms selected from nitrogen, oxygen, and sulfur.

5. The compound of claim 4 selected from the group consisting of:

| Name | Structure |
|---|---|
| N-[3-(4-Hydroxy-phenoxy)-1,1-dimethyl-propyl]-N'-(3-methoxy-4-oxazol-5-yl-phenyl)-oxalamide | 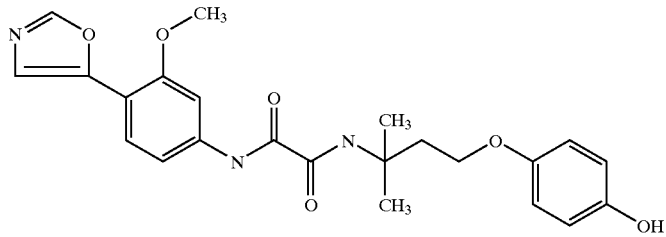 |
| N-[3-Methoxy-4-(5-oxazolyl)phenyl]-N'-[3-(4-methoxyphenoxy)-1,1-dimethylpropyl]oxalamide | 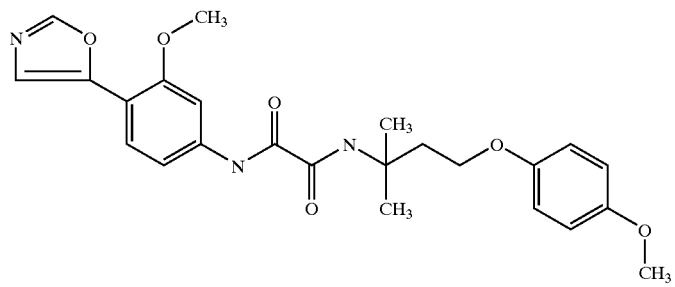 |

-continued

| Name | Structure |
|---|---|
| N-[3-Methoxy-4-(5-oxazolyl)phenyl]-N'-[1,1-dimethyl-3-(4-nitrophenoxy)propyl]oxalamide | 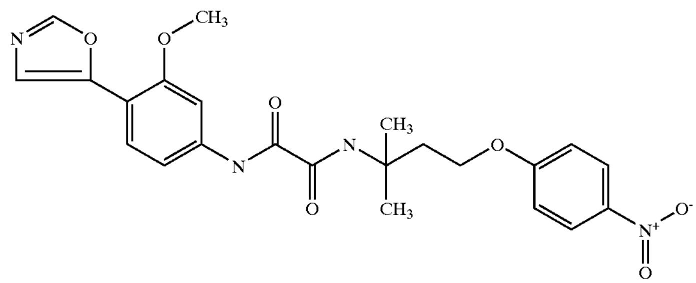 |
| N-[3-(2-Hydroxyphenoxy)-1,1-dimethylpropyl]-N'-[3-methoxy-4-(5-oxazolyl)phenyl]oxalamide | 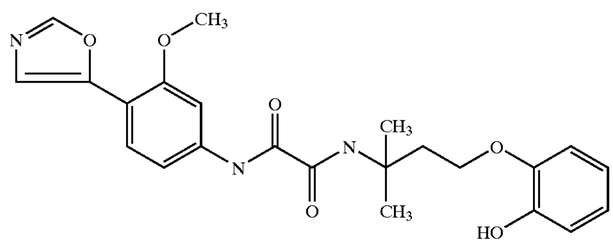 |
| N-[3-(4-Amino-phenoxy)-1,1-dimethyl-propyl]-N'-(3-methoxy-4-oxazol-5-yl-phenyl)-oxalamide | 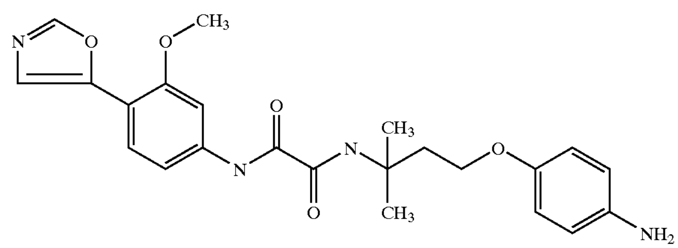 |
| N-[3-(-Acetylamino-phenoxy)-1,1-dimethyl-propyl]-N'-(3-methoxy-4-oxazol-5-yl-phenyl)-oxalamide | 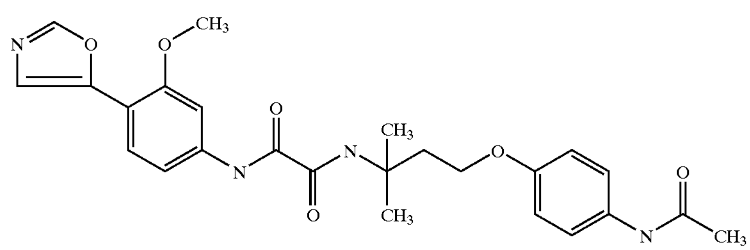 |
| N-[3-Methoxy-4-(5-oxazolyl)phenyl]-N'-[1,1-dimethyl-3-(3-pyridyloxy)propyl]oxalamide | 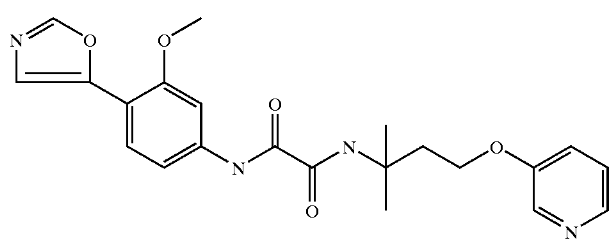 |
| N-[3-(3-Hydroxyphenoxy)-1,1-dimethylpropyl]-N'-[3-methoxy-4-(5-oxazolyl)phenyl]oxalamide | 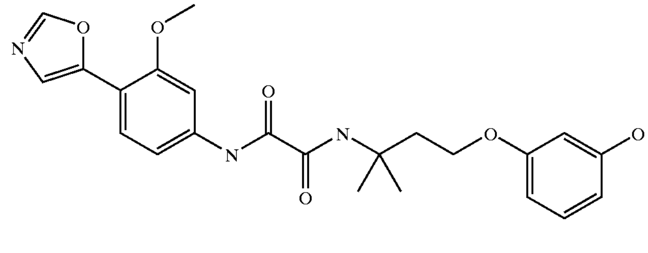 |

-continued

| Name | Structure |
|---|---|
| N-[3-Methoxy-4-(5-oxazolyl)phenyl]-N'-[3-(3-methoxyphenoxy)-1,1-dimethylpropyl]oxalamide | 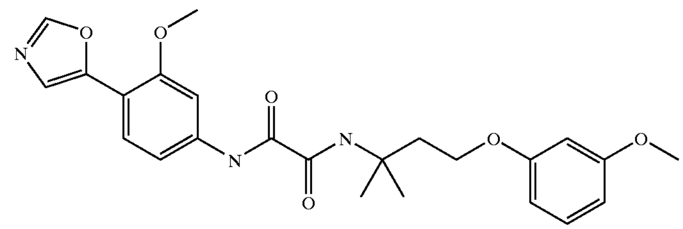 |
| N-[3-Methoxy-4-(5-oxazolyl)phenyl]-N'-[1,1-dimethyl-3-(3-nitrophenoxy)propyl]oxalamide | 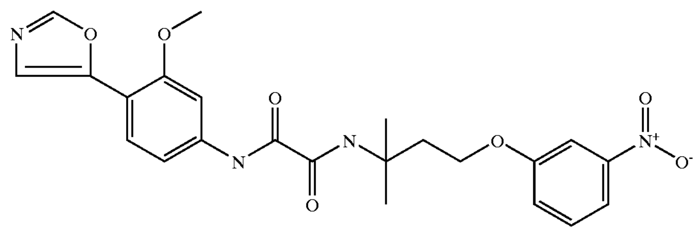 |
| N-[3-(3-Aminophenoxy)-1,1-dimethylpropyl)-N'-[3-methoxy-4-(5-oxazolyl)phenyl]oxalamide | 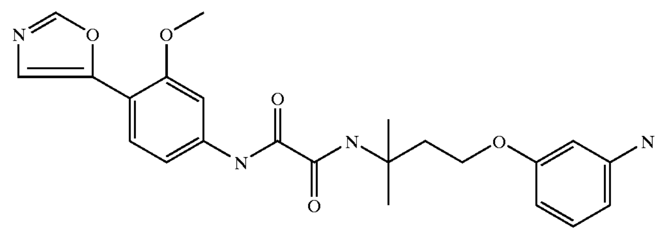 |
| 4-[3-[[[3-Methoxy-4-(5-oxazolyl)anilio]oxalyl]amino]-3-methylbutoxy]benzoic acid | 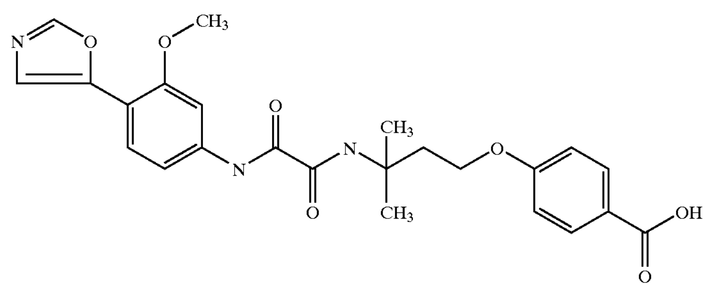 |
| 2-[3-[[[3-Methoxy-4-(5-oxazolyl)anilino]oxalyl]amino]-3-methylbutoxy]benzoic acid | 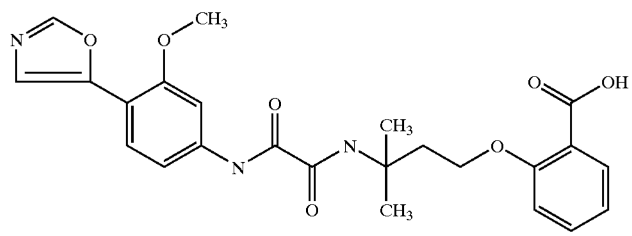 |
| 3-[3-[[[3-Methoxy-4-(5-oxazolyl)anilino]oxalyl]amino]-3-methylbutoxy]benzoic acid | 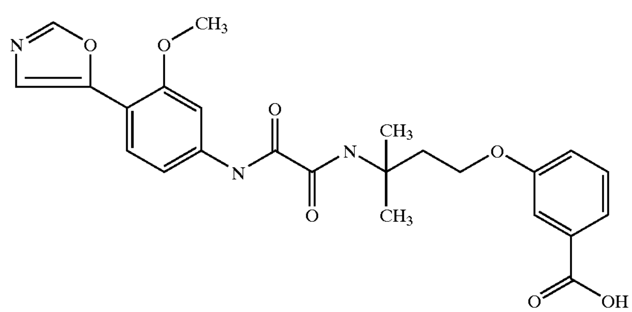 |

-continued

| Name | Structure |
|---|---|
| 2-[4-[3-[[[3-Methoxy-4-(5-oxazolyl)anilino]oxalyl]amino]-3-methylbutoxy]phenoxy]acetic acid | 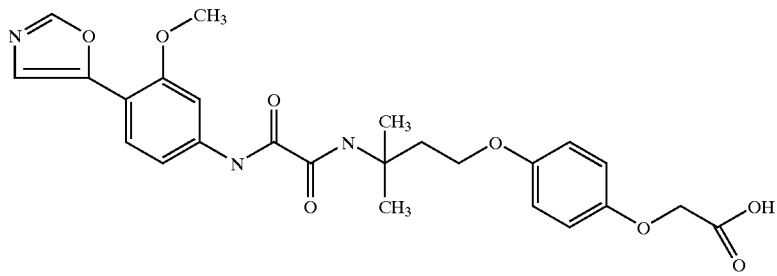 |
| 2-[2-[3-[[[3-Methoxy-4-(5-oxazolyl)anilino]oxalyl]amino]-3-methylbutoxy]phenoxy]acetic acid | 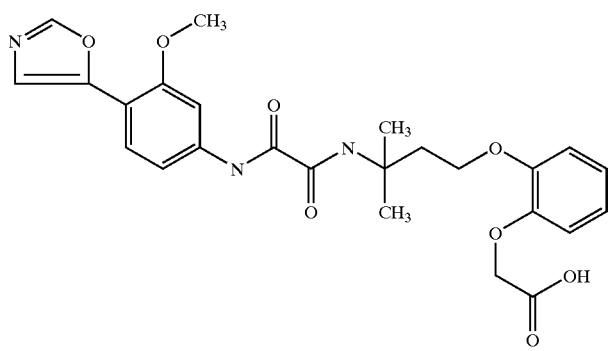 |
| N-[3-Methoxy-4-(5-oxazolyl)phenyl]-N'-(1,1-dimethyl-3-phenoxypropyl)oxalamide | 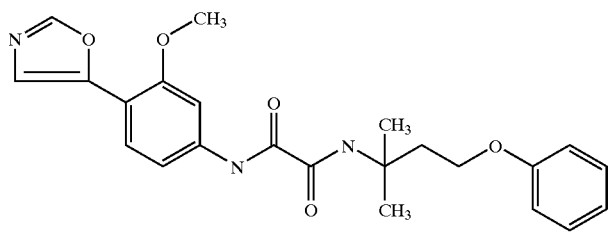 |
| N-[3-Methoxy-4-(5-oxazolyl)phenyl]-N'-[1,1-dimethyl-3-(1-oxido-3-pyridyloxy)propyl]oxalamide | 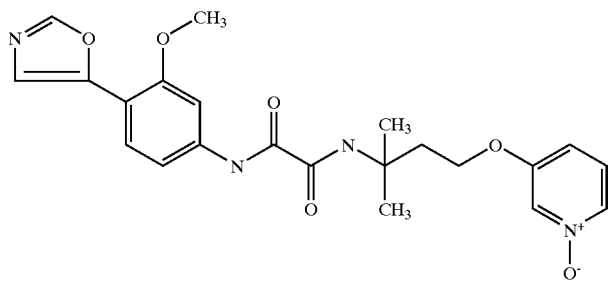 |
| N-[3-(3,4-Dihydroxyphenoxy)-1,1-dimethylpropyl]-N'-[3-methoxy-4-(5-oxazolyl)phenyl]oxalamide | 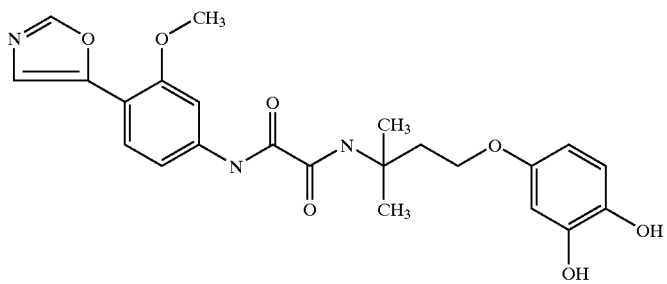 |

-continued

| Name | Structure |
|---|---|
| N-[3-Methoxy-4-(5-oxazolyl)phenyl]-N'-[1,1-dimethyl-3-[4-(methylcarbamoyl)phenoxy]propyl]oxalamide | 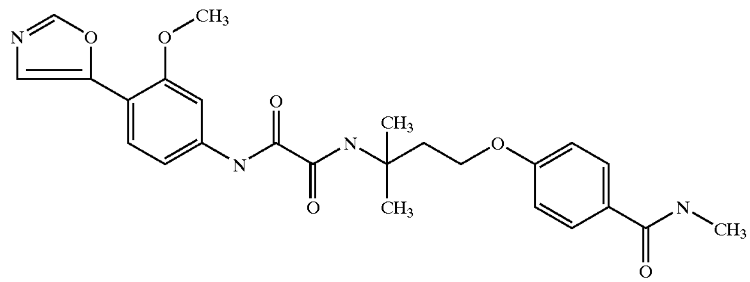 |
| N-[3-Methoxy-4-(5-oxazolyl)phenyl]-N'-[3-(3,4-dimethoxyphenoxy)-1,1-dimethylpropyl]oxalamide | 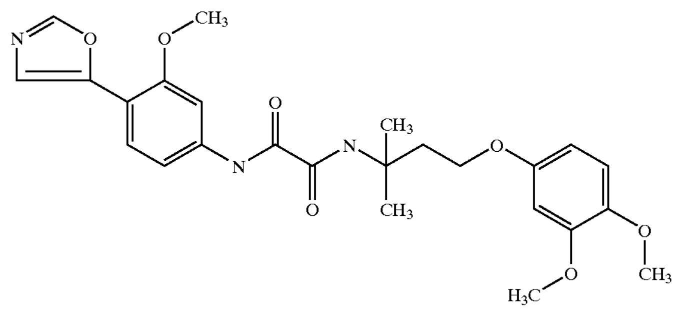 |
| N-[3-[4-[(2-Hydroxyethyl)carbamoyl]phenoxy]-1,1-dimethylpropyl]-N'-[3-methoxy-4-(5-oxazolyl)phenyl]oxalamide | |
| N-[3-(3-Chlorophenoxy)-1,1-dimethylpropyl]-N'-[3-methoxy-4-(5-oxazolyl)phenyl]oxalamide | 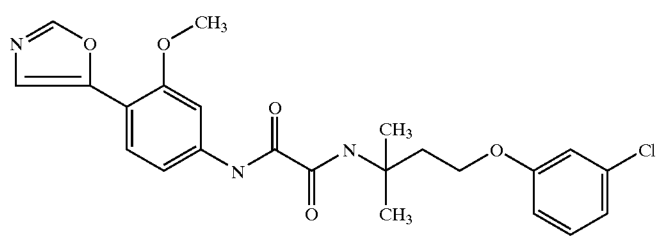 |
| N-[3-Methoxy-4-(5-oxazolyl)phenyl]-N'-[1,1-dimethyl-3-(3-pyridyloxy)propyl]oxalamide | 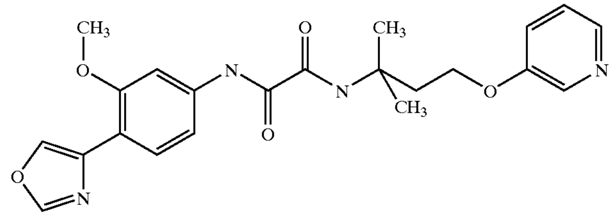 |
| N-[3-Methoxy-4-(5-oxazolyl)phenyl]-N'-[1,1-dimethyl-3-(2-pyridyloxy)propyl]oxalamide | 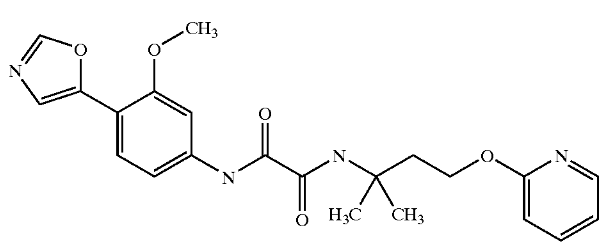 |

-continued

| Name | Structure |
|---|---|
| 2-[4-[3-[[[3-Methoxy-4-(5-oxazolyl)anilino]oxalyl]amino]-3-methylbutoxy]phenyl]acetic acid | 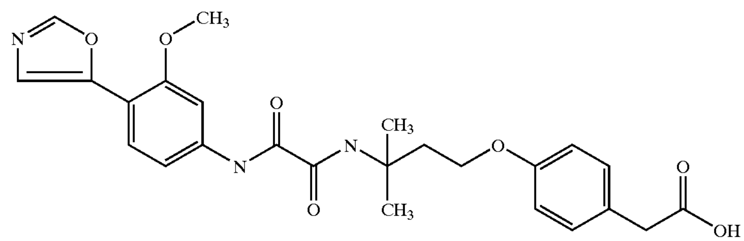 |
| 2-[3-[3-[[[3-Methoxy-4-(5-oxazolyl)anilino]oxalyl]amino]-3-methylbutoxy]phenyl]acetic acid | 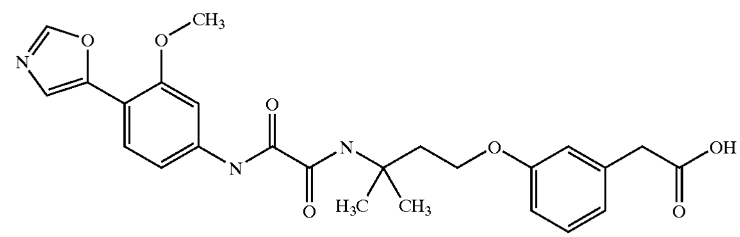 |
| 4-[2-[[[3-Methoxy-4-(5-oxazolyl)anilino]oxalyl]amino]-2-methylpropoxy]benzoic acid | 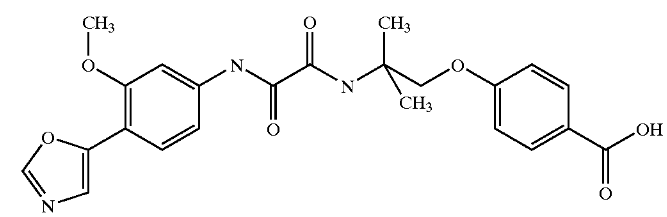 |
| 4-[3-[[[3-Methoxy-4-(5-oxazolyl)anilino]oxalyl]amino]-3-methylbutoxy]-2-methylbenzoic acid | 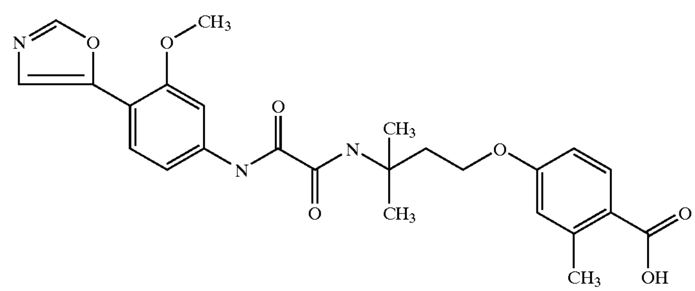 |
| 3-[3-[3-[[[3-Methoxy-4-(5-oxazolyl)anilino]oxalyl]amino]-3-methylbutoxy]phenyl]propionic acid | 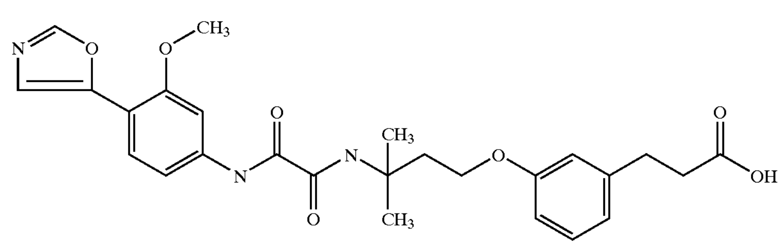 |
| 3-[4-[3-[[[3-Methoxy-4-(5oxazolyl)anilino]oxalyl]amino]-3-methylbutoxy]phenyl]propionic acid | 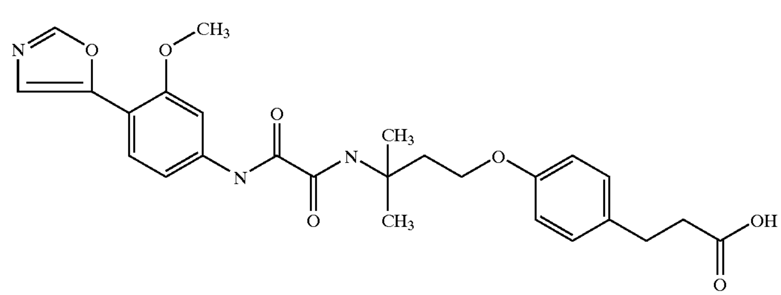 |

| Name | Structure |
|---|---|
| 3-[2-[3-[[[3-Methoxy-4-(5-oxazolyl)anilino]oxalyl]amino]-3-methylbutoxy]phenyl]propionic acid | 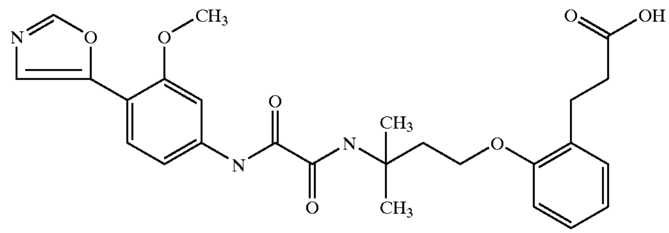 |
| 2-[3-[3-[[[3-Methoxy-4-(5-oxazolyl)anilino]oxalyl]amino]-3-3-methylbutoxy]phenoxy]acetic acid | 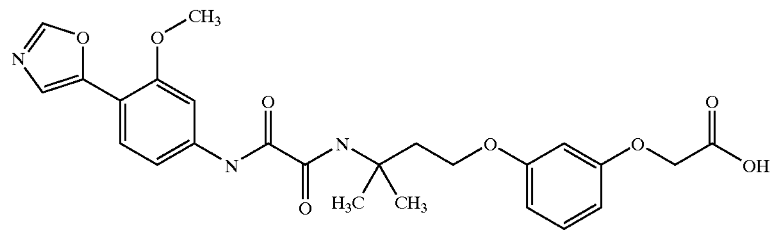 |
| 4-[3-[[[3-Methoxy-4-(5-oxazolyl)anilino]oxalyl-amino]-3-methylbutoxy]-3-methylbenzoic acid | 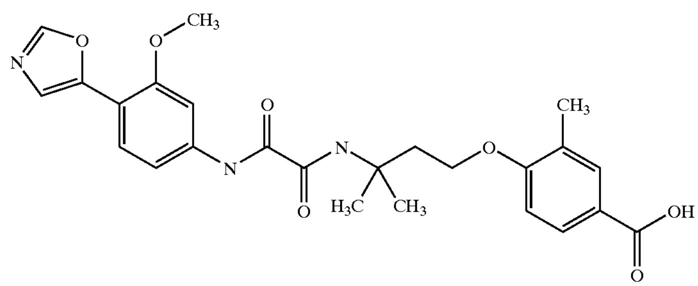 |
| N-[3-(4-Cyano-2-methoxyphenoxy)-1,1-dimethylpropyl]-N'-[3-methoxy-4-(5-oxazolyl)phenyl]oxalamide | 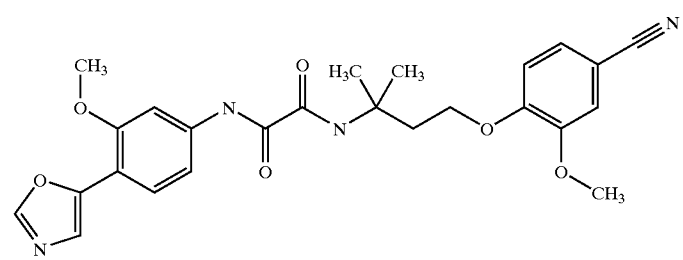 |
| N-[3-(3-Cyanophenoxy-1,1-dimethylpropyl]-N'-[3-methoxy-4-(5-oxazolyl)phenyl]oxalamide | 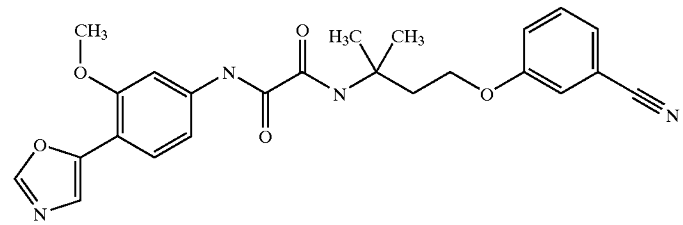 |

| Name | Structure |
|---|---|
| N-[3-[4-(4-Acetyl-1-piperazinyl)phenoxy]-1,1-dimethylpropyl]-N'-[3-methoxy-4-(5-oxazolyl)phenyl]oxalamide | 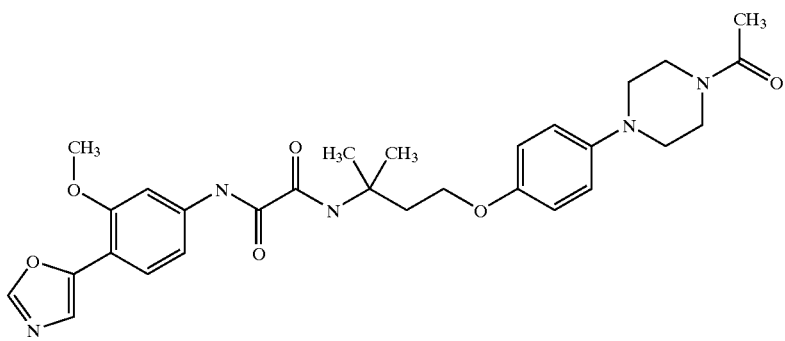 |
| N-[3-Methoxy-4-(5-oxazolyl)phenyl]-N'-[1,1-dimethyl-3-(2-morpholinophenoxy)propyl]oxalamide | 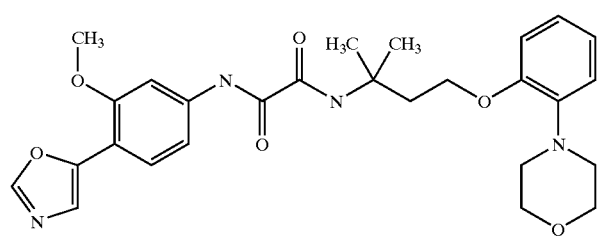 |
| N-[3-Methoxy-4-(5-oxazolyl)phenyl]-N'-[1,1-dimethyl-3-[3-(dimethylamino)phenoxy]propyl]oxalamide | 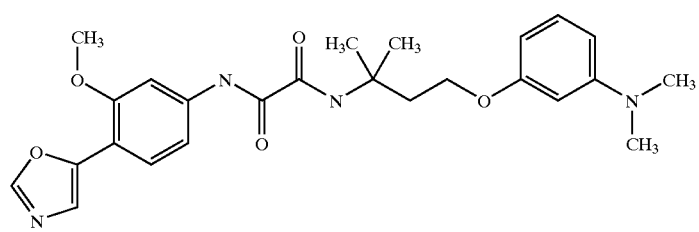 |
| N-[3-(1,3-Benzodioxol-5-yloxy)-1,1-dimethylpropyl]-N'-[3-methoxy-4-(5-oxazolyl)phenyl]oxalamide | 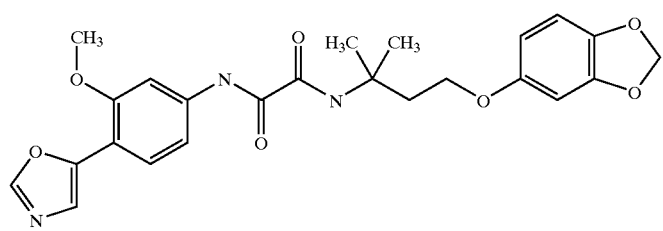 |
| N-[3-Methoxy-4-(5-oxazolyl)phenyl]-N'-[3-(3,4,5-trimethoxyphenoxy)-1,1-dimethylpropyl]oxalamide | 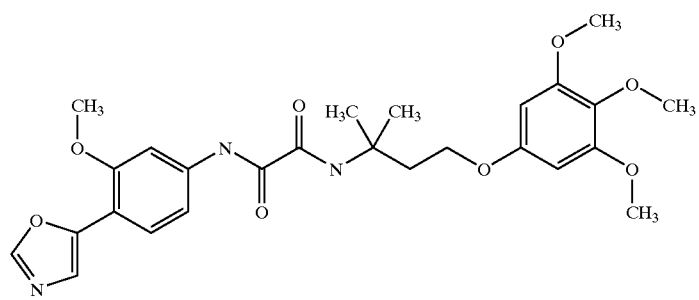 |

-continued

| Name | Structure |
|---|---|
| N-[3-Methoxy-4-(5-oxazolyl)phenyl]-N'-[3-(3,5-dimethoxyphenoxy)-1,1-dimethylpropyl]oxalamide | 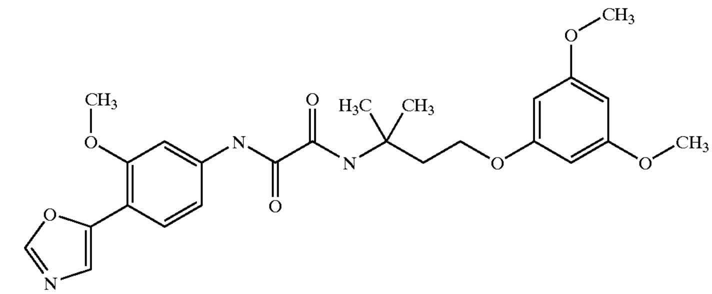 |
| N-[3-(5,6,7,8-Tetrahydro-5-oxo-2-naphthyloxy)-1,1-dimethylpropyl]-N'-(3-methoxy-4-(5-oxazolyl)phenyl]oxalamide | 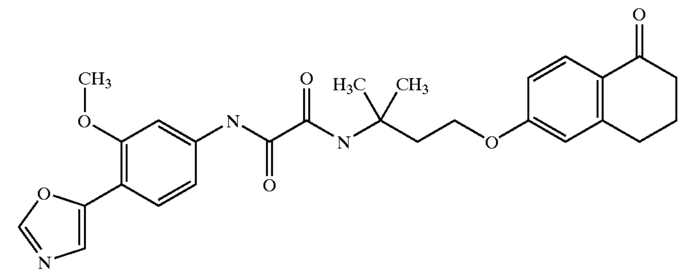 |
| N-[3-(2-Acetamido-5-methylphenoxy)-1,1-dimethylpropyl]-N'-[3-methoxy-4-(5-oxazolyl)phenyl]oxalamide | 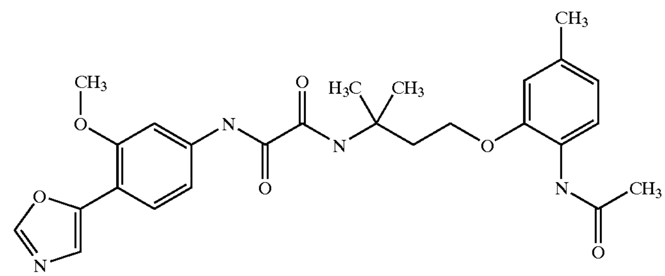 |
| N-[3-(3-Acetamidophenoxy)-1,1-dimethylpropyl]-N'-[3-methoxy-4-(5-oxazolyl)phenyl]oxalamide | 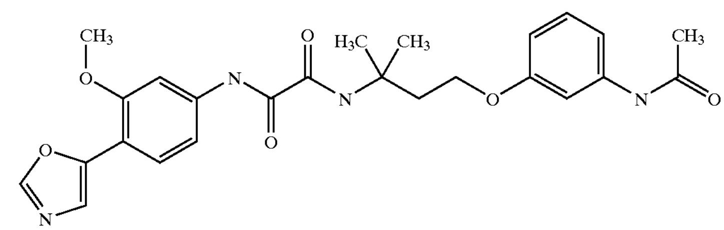 |
| N-[3-(1H-Indol-4-yloxy)-1,1-dimethylpropyl]-N'-[3-methoxy-4-(5-oxazolyl)phenyl]oxalamide | 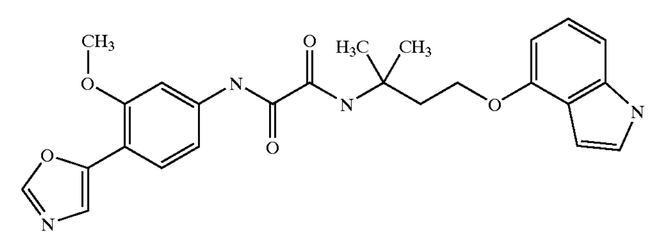 |
| N-[3-(2-Fluoro-6-methoxyphenoxy)-1,1-dimethylpropyl]-N'-[3-methoxy-4-(5-oxazolyl)phenyl]oxalamide | 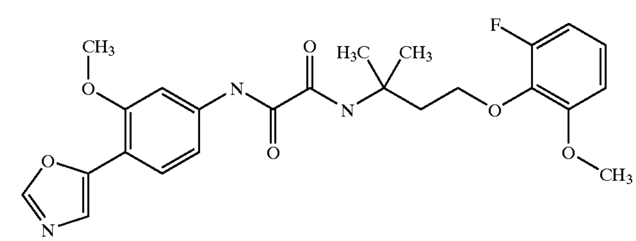 |

-continued

| Name | Structure |
|---|---|
| N-[3-Methoxy-4-(5-oxazolyl)phenyl]-N'-[1,1-dimethyl-3-2-oxo-2H-1-benzopyran-7-yloxy)propyl]oxalamide | 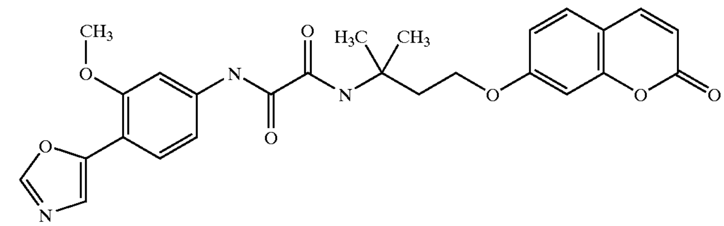 |
| N-[3-(4-Acetyl-3-methylphenoxy)-1,1-dimethylpropyl]-N'-[3-methoxy-4-(5-oxazolyl)phenyl]oxalamide | 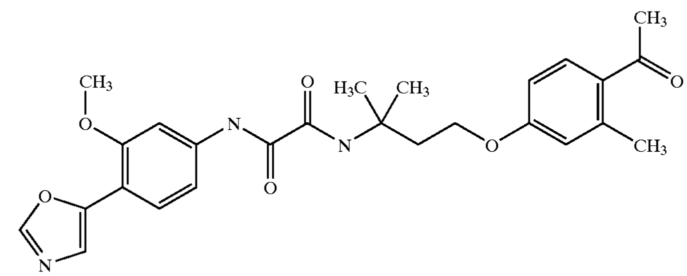 |
| (E)-N-[3-Methoxy-4-(5-oxazolyl)phenyl]-N'-[1,1-dimethyl-3-[4-(3-oxo-1-butenyl)phenoxy]propyl]oxalamide | 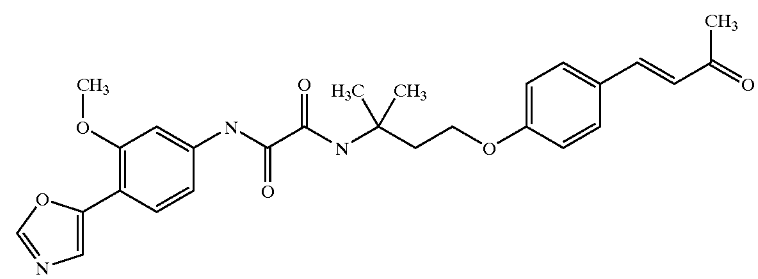 |
| N-[3-(3-Acetylphenoxy)-1,1-dimethylpropyl]-N'-[3-methoxy-4-(5-oxazolyl)phenyl]oxalamide | 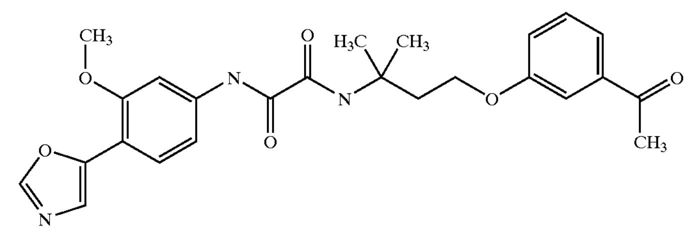 |
| N-[3-(4-Acetylphenoxy)-1,1-dimethylpropyl]-N'-[3-methoxy-4-(5-oxazolyl)phenyl]oxalamide | 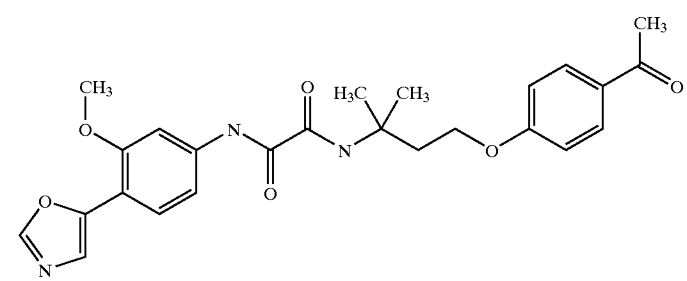 |
| N-[3-(4-Acetamido-2-chlorophenoxy)-1,1-dimethylpropyl]-N'-[3-methoxy-4-(5-oxazolyl)phenyl]oxalamide | 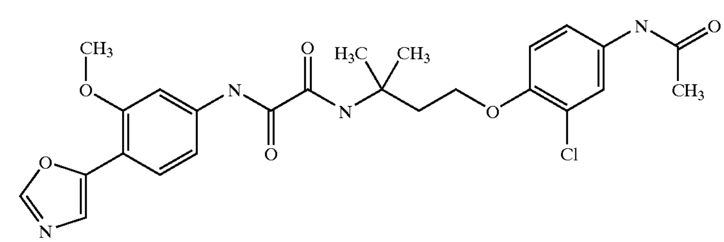 |

-continued

| Name | Structure |
|---|---|
| N-[3-Methoxy-4-(5-oxazolyl)phenyl]-N'-[1,1-dimethyl-3-(4-pyridyloxy)propyl]oxalamide | 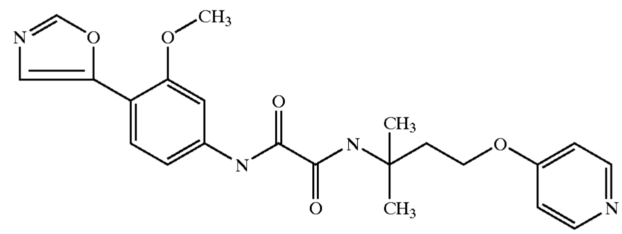 |
| N-[3-Methoxy-4-(5-oxazolyl)phenyl]-N'-[1,1-dimethyl-3-(1-oxido-4-pyridyloxy)propyl]oxalamide | 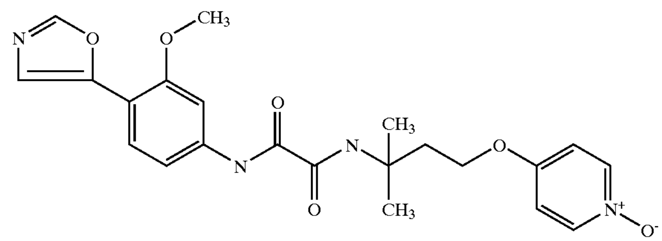 |
| N-[3-Methoxy-4-(5-oxazolyl)phenyl]-N'-[1,1-dimethyl-3-(2,6-dimethyl-4-pyridyloxy)propyl]oxalamide | 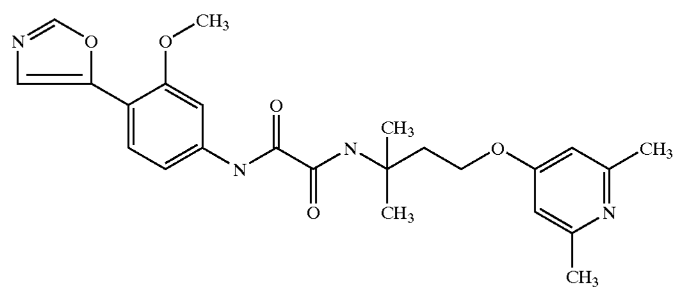 |
| N-[3-Methoxy-4-(5-oxazolyl)phenyl]-N'-[1,1-dimethyl-3-(2,6-dimethyl-1-oxido-4-pyridyloxy)propyl]oxalamide | 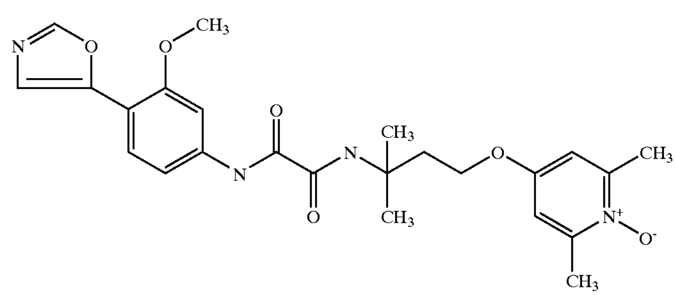 |
| N-[2-(4-Cyanophenoxy)-1,1-dimethylethyl]-N'-(3-methoxy-4-(5-oxazolyl)phenyl]oxalamide | |
| N-[3-Methoxy-4-(5-oxazolyl)phenyl]-N'-[3-(2-methoxy-4-pyridyloxy)-1,1-dimethylpropyl]oxalamide | 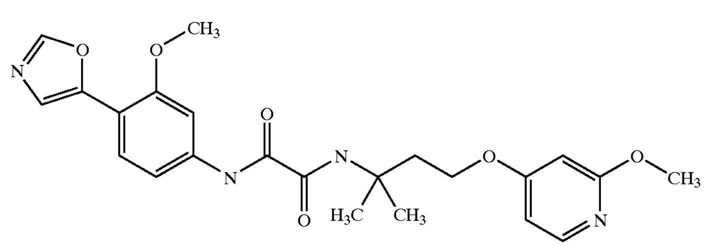 |

-continued

| Name | Structure |
|---|---|
| N-[3-Methoxy-4-(5-oxazolyl)phenyl]-N'-[1,1-dimethyl-2-[4-(1H-tetrazol-5-yl)phenoxy]ethyl]oxalamide | 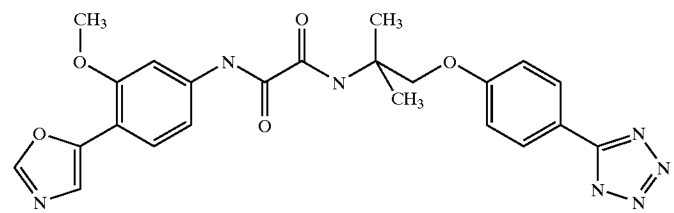 |
| N-[3-(4-Cyanophenoxy)-1,1-dimethylpropyl]-N'-[3-methoxy-4-(5-oxazolyl)phenyl]oxalamide | 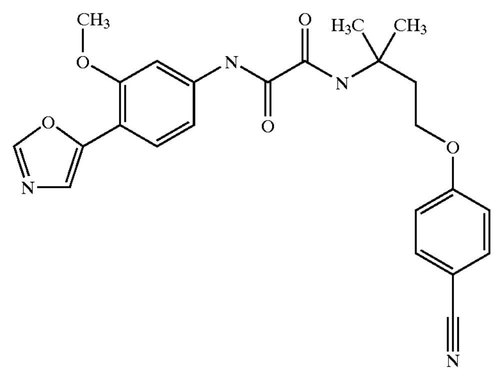 |
| N-[2-(3-Cyanophenoxy)-1,1-dimethylethyl)-N'-[3-methoxy-4-(5-oxazolyl)phenyl]oxalamide | 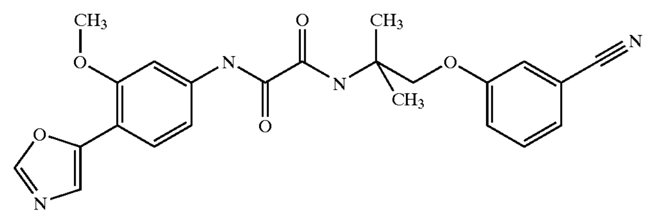 |
| N-[3-Methoxy-4-(5-oxazolyl)phenyl]-N'-[1,1-dimethyl-2-[3-(1H-tetrazol-5-yl)phenoxy]ethyl]oxalamide | 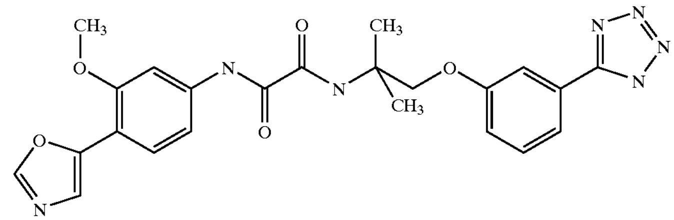 |
| N-[3-Methoxy-4-(5-oxazolyl)phenyl]-N'-[1,1-dimethyl-3-[4-(1H-tetrazol-5-yl)phenoxy]propyl]oxalamide | 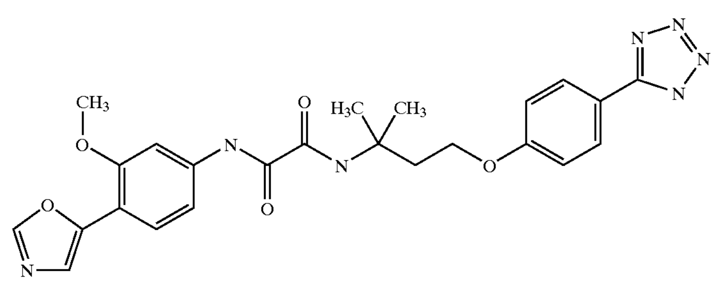 |

| Name | Structure |
|------|-----------|
| Benzyl 2-methoxy-4-[3-[[[3-methoxy-4-(5-oxazolyl)anilino]oxalyl]amino]-3-methylbutoxy]benzoate | 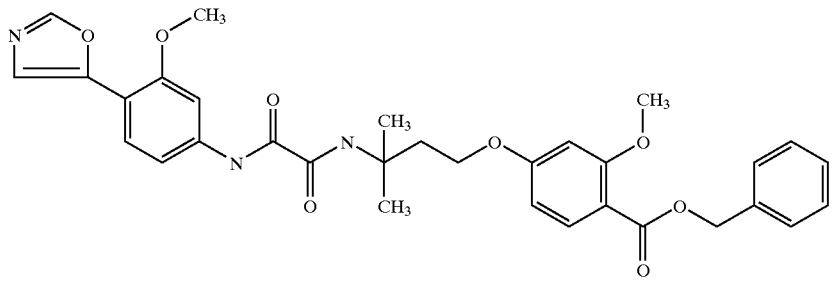 |
| 3-Chloro-4-[3-[[[3-methoxy-4-(5-oxazolyl)anilino]oxalyl]amino]-3-methylbutoxy]benzoic acid | 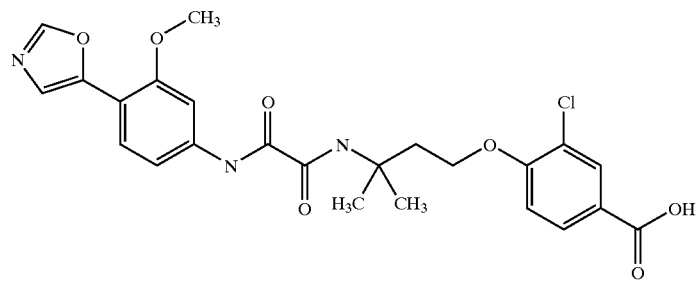 |
| 2-Methoxy-4-[3-[[[3-methoxy-4-(5-oxazolyl)anilino]oxalyl]amino]-3-methylbutoxy]benzoic acid | 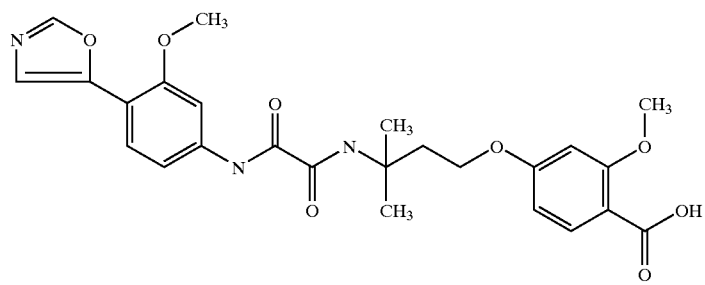 |
| 3-Methoxy-4-[3-[[[3-methoxy-4-(5-oxazolyl)anilino]oxalyl]amino]-3-methylbutoxy]benzoic acid | 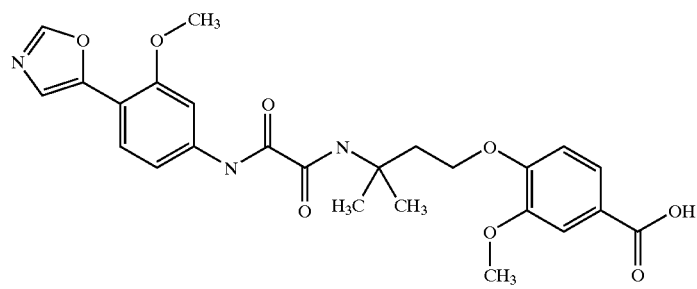 |
| 2-Chloro-4-[3-[[[3-methoxy-4-(5-oxazolyl)anilino]oxalyl)amino]-3-methylbutoxy-benzoic acid | 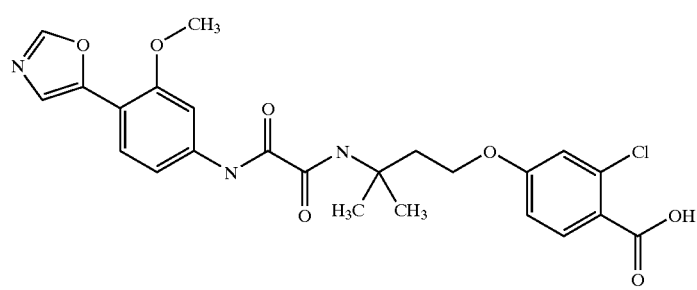 |

| Name | Structure |
|---|---|
| 4-[3-[[[3-Methoxy-4-(5-oxazolyl)anilino]oxalyl]amino]-3-methylbutoxy]-2-quinolinecarboxylic acid | 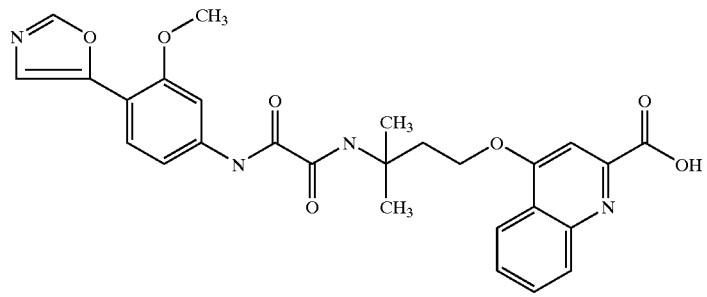 |
| (cis/trans)-4-[3-[[[3-Methoxy-4-(5-oxazolyl)anilino]oxalyl]amino]-3-methylbutoxy]-1-cyclohexanecarboxylic acid | 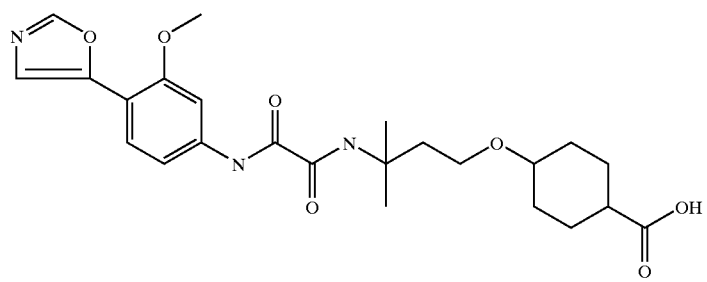 |
| (cis/trans)-4-[2-[[[3-Methoxy-4-(5-oxazolyl)anilino]oxalyl]amino]-2-methylpropoxy]-1-cyclohexanecarboxylic acid | 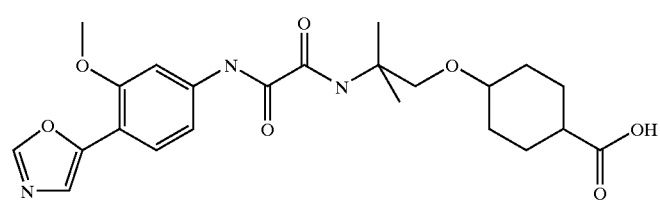 |
| 3-Fluoro-4-[3-[[[3-methoxy-4-(5-oxazolyl)anilino]oxalyl]amino]-3-methylbutoxy)benzoic acid | 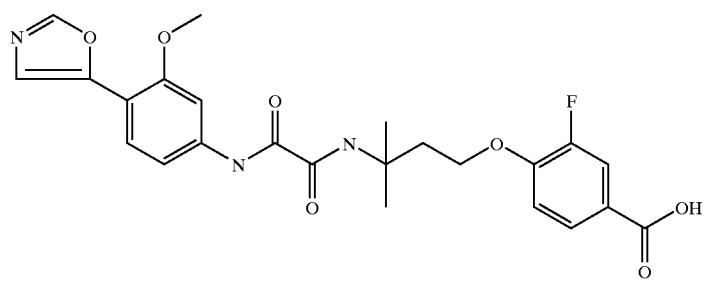 |
| 3-Acetamido-4-[3-[[[3-methoxy-4-(5-oxazolyl)anilino)oxalyl]amino]-3-methylbutoxy]benzoic acid | 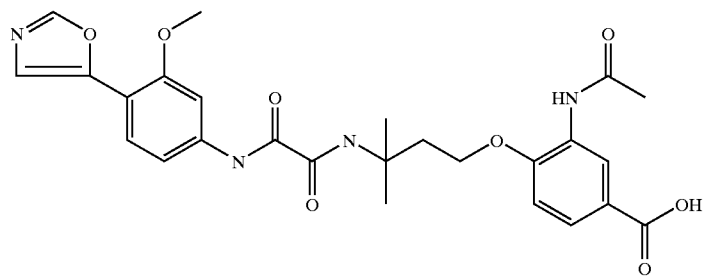 |

-continued

| Name | Structure |
|---|---|
| 3-(Methanesulfonamido)-4-[3-[[[3-methoxy-4-(5-oxazolyl)anilino]oxalyl]amino]-3-methylbutoxy]benzoic acid | 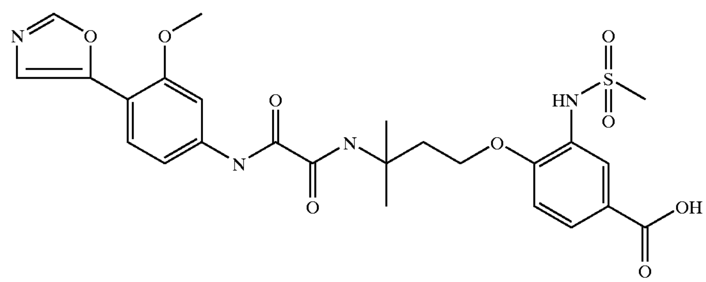 |
| 4-[3-[[[3-Methoxy-4-(5-oxazolyl)anilino]oxalyl]amino]-3-methylbutoxy]-3,5-dimethylbenzoic acid | 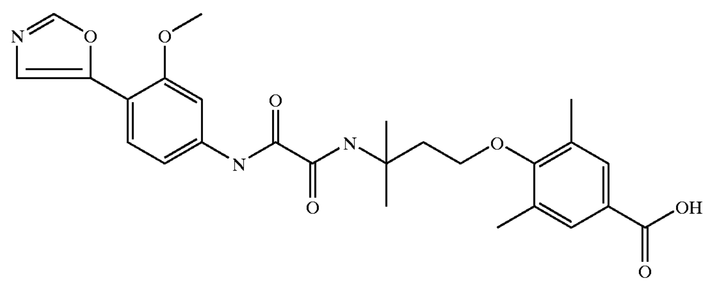 |
| 3-[3-[[[3-Methoxy-4-(5-oxazolyl)anilino]oxalyl]amino]-3-methylbutoxy]-2-pyridinecarboxylic acid | 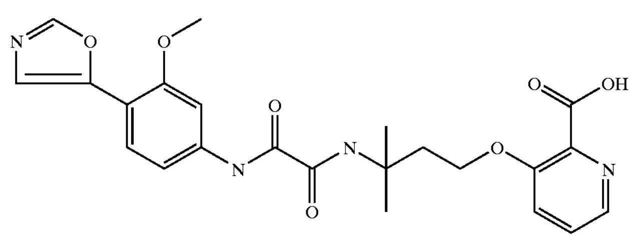 |
| 8-[3-[[[3-Methoxy-4-(5-oxazolyl)anilino]oxalyl]amino)-3-methylbutoxy]-2-quinolinecarboxylic acid | and |
| 5-[3-[[[3-Methoxy-4-(5-oxazolyl)anilino)oxalyl]amino]-3-methylbutoxy]-2-indolecarboxylic acid | . |

6. The compound of claim 1 of the formula:

XIVb

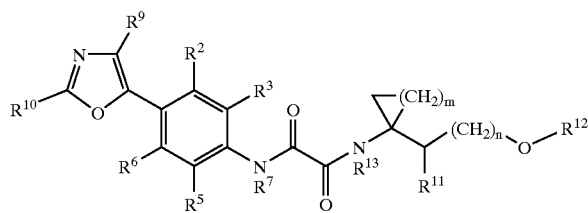

wherein $R^{11}$ is H or lower alkyl, $R^{13}$ is H or unsubstituted lower alkyl, n=0 or 1, m=1 to 5 and, $R^{12}$ is heterocyclyl, aryl or lower cycloalkyl.

7. The compound of 6 wherein $R^2$ is methoxy and $R^3$, $R^5$, $R^6$, $R^9$, $R^{10}$, $R^{11}$ and $R^{13}$ are hydrogen.

8. The compound of claim 7 wherein $R^{12}$ is aryl, a 3 to 7 membered cycloalkyl ring, or a 5 or 6-membered monocyclic or 9 or 10-membered bicyclic saturated or unsaturated ring with 1 to 4 heteroatoms selected from nitrogen, oxygen, and sulfur.

9. The compound of claim 8 selected from the group consisting of:

4-[2-[1-[[[3-Methoxy-4-(5-oxazolyl)anilino]oxalyl]amino]-1-cyclopropyl]ethoxy]benzoic acid

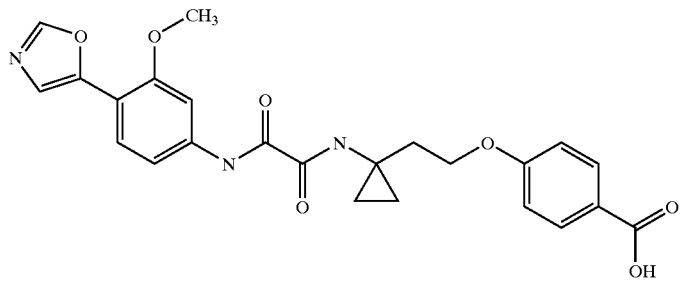

Benzyl 4-[2-[1-[[[3-methoxy-4-(5-oxazolyl)anilino]oxalyl]amino]-1-cyclobutyl]ethoxy]benzoate

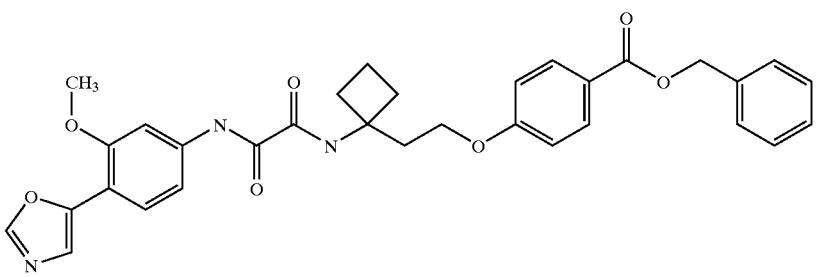

Benzyl 4-[2-[1-[[[3-methoxy-4-(5-oxazolyl)anilino]oxalyl]amino]-1-cyclopentyl]ethoxy]benzoate

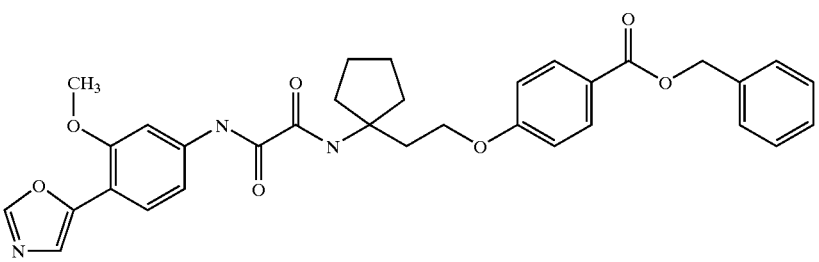

Benzyl 4-[2-[1-[[[3-methoxy-4-(5-oxazolyl)anilino]oxalyl]amino]-1-cyclohexyl]ethoxy]benzoate

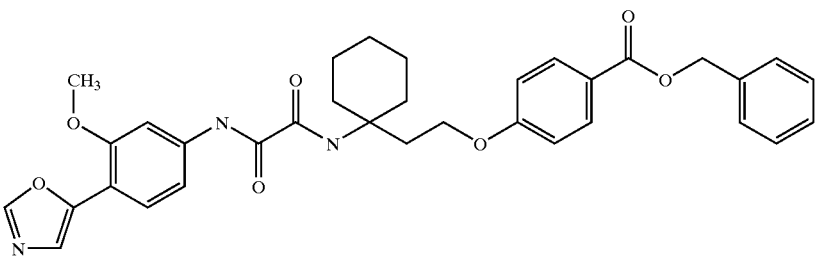

| Name | Structure |
|---|---|
| 4-[2-[1-[[[3-Methoxy-4-(5-oxazolyl)anilino]oxalyl]amino]-1-cyclopentyl]ethoxy]benzoic acid | 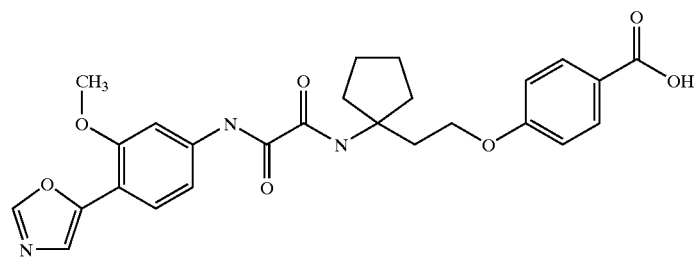 |
| 4-[2-[1-[[[3-Methoxy-4-(5-oxazolyl)anilino]oxalyl]amino]-1-cyclohexyl]ethoxy]benzoic acid | 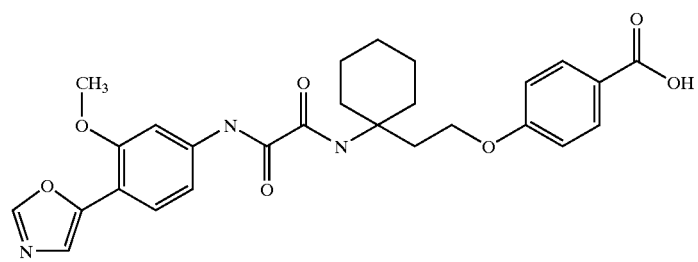 |
| and 4-[2-[1-[[[3-Methoxy-4-(5-oxazolyl)anilino]oxalyl]amino]-1-cyclobutyl]ethoxy]benzoic acid | 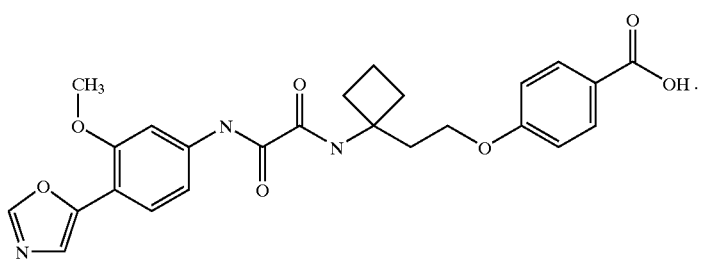 |

10. The compound of claim 1 of the formula

XIX

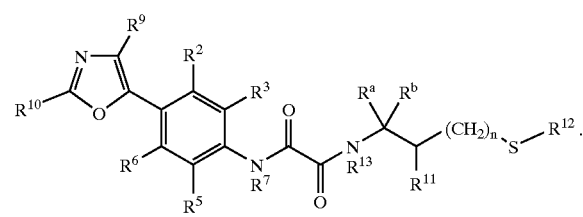

11. The compound of claim 10 wherein $R^2$ is methoxy and $R^3$, $R^5$, $R^6$, $R^9$, $R^{10}$, $R^{11}$ and $R^{13}$ are hydrogen.

12. The compound of claim 11 wherein $R^{12}$ is aryl, a 3 to 7 membered cycloalkyl ring, or a 5 or 6-membered monocyclic or 9 or 10-membered bicyclic saturated or unsaturated heterocyclic ring with 1 to 4 heteroatoms selected from nitrogen, oxygen, and sulfur.

13. The compound of claim 12 selected from the group consisting of:

| Name | Structure |
|---|---|
| N-[3-Methoxy-4-(5-oxazolyl)phenyl]-N'-[1,1-dimethyl-2-(phenylthio)ethyl]oxalamide | 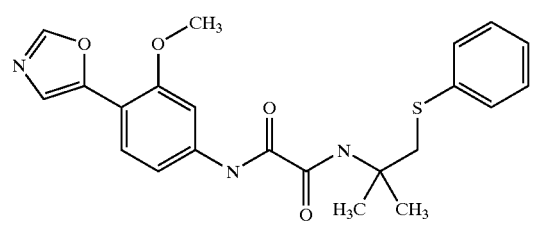 |

-continued

| Name | Structure |
|---|---|
| N-[2-(4-Hydroxyphenylthio)-1,1-dimethylethyl]-N'-[3-methoxy-4-(5-oxazolyl)phenyl]oxalamide | 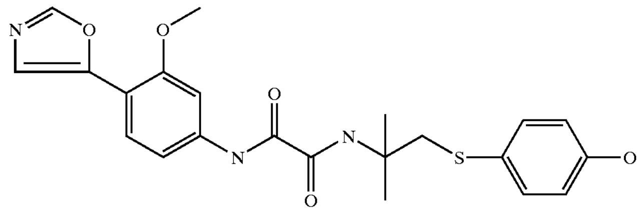 |
| N-[3-Methoxy-4-(5-oxazolyl)phenyl]-N'-[1,1-dimethyl-2-(phenylthio)ethyl]oxalamide | 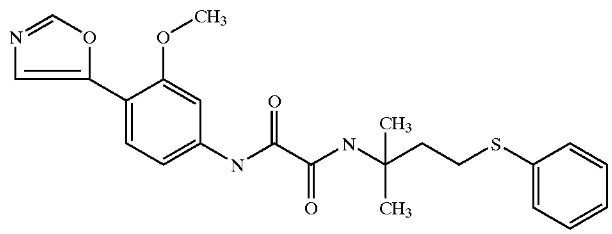 |
| N-[3-Methoxy-4-(5-oxazolyl)phenyl]-N'-[1,1-dimethyl-2-(2-pyridylthio)ethyl]oxalamide | 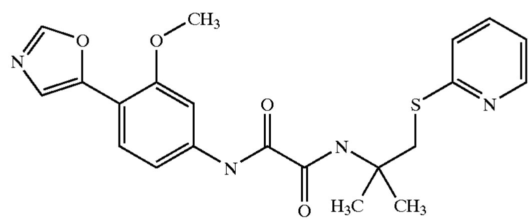 |
| N-[3-Methoxy-4-(5-oxazolyl)phenyl]-N'-[1,1-dimethyl-3-(2-pyridylthio)propyl]oxalamide | 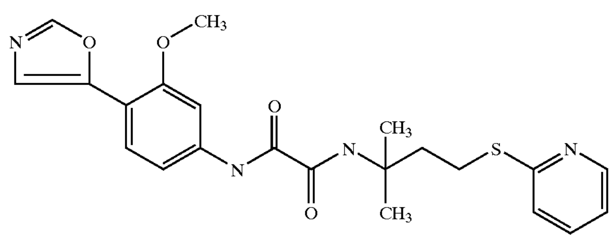 |
| N-[3-Methoxy-4-(5-oxazolyl)phenyl]-N'-[1,1-dimethyl-3-(2-thienylthio)propyl]oxalamide | 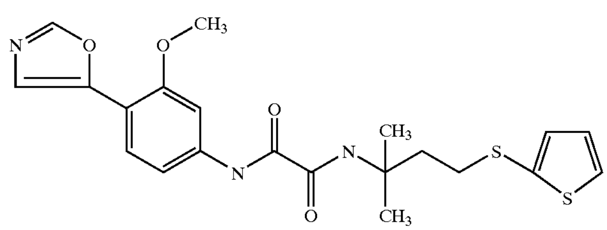 |
| N-[3-Methoxy-4-(5-oxazolyl)phenyl]-N'-[1,1-dimethyl-3-(2-pyrimidylthio)propyl]oxalamide | 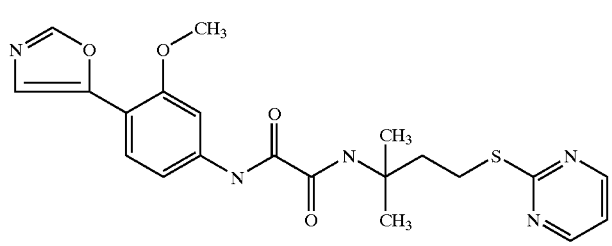 |

-continued

| Name | Structure |
|---|---|
| N-[3-Methoxy-4-(5-oxazolyl)phenyl]-N'-[1,1-dimethyl-3-(4-pyridylthio)propyl]oxalamide | 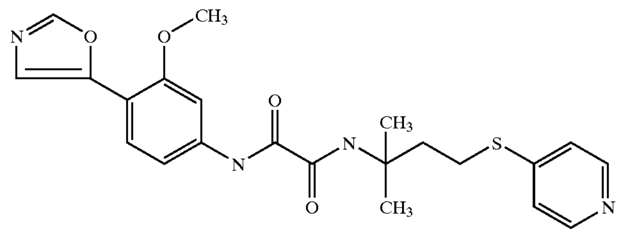 |
| N-[3-Methoxy-4-(5-oxazolyl)phenyl]-N'-[1,1-dimethyl-3-(2-thiazolylthio)propyl]oxalamide | 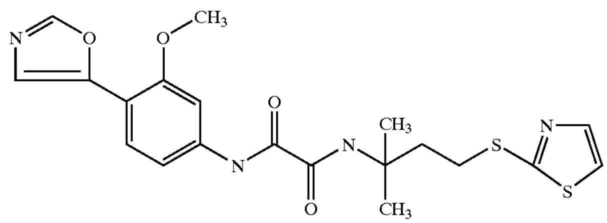 |
| N-[3-(4-Hydroxyphenylthio)-1,1-dimethylpropyl]-N'-[3-methoxy-4-(5-oxazolyl)phenyl]oxalamide | 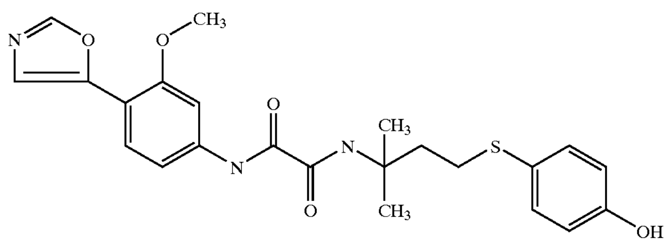 |
| N-[3-Methoxy-4-(5-oxazolyl)phenyl]-N'-[1,1-dimethyl-3-(5-methyl-1,3,4-thiadiazol-2-ylthio)propyl]oxalamide | 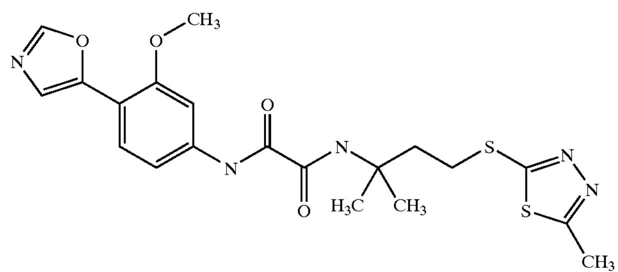 |
| N-[3-(2-Benzooxazolylthio)-1,1-dimethylpropyl]-N'-[3-methoxy-4-(5-oxazolyl)phenyl]oxalamide | 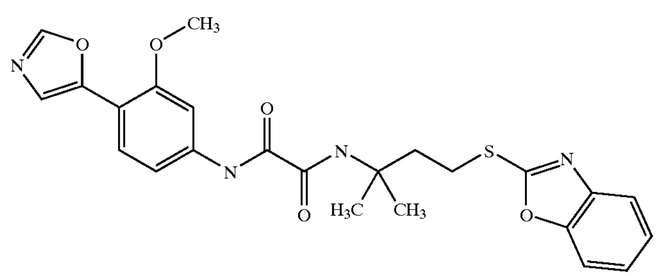 |
| N-[3-(2-Benzothiazolylthio)-1,1-dimethylpropyl]-N'-[3-methoxy-4-(5-oxazolyl)phenyl]oxalamide | 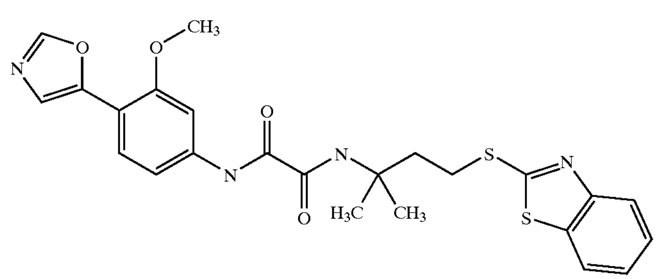 |

-continued

| Name | Structure |
|---|---|
| Methyl 4-[2-[[[3-methoxy-4-(5-oxazolyl)anilino]oxalyl]amino]-2-methylpropylthio]benzoate | 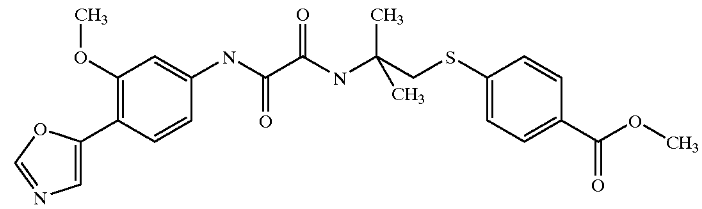 |
| tert-Butyl 6-[3-[[[3-methoxy-4-(5-oxazolyl)anilino]oxalyl]amino]-3-methylbutylthio]-3-pyridinecarboxylate | 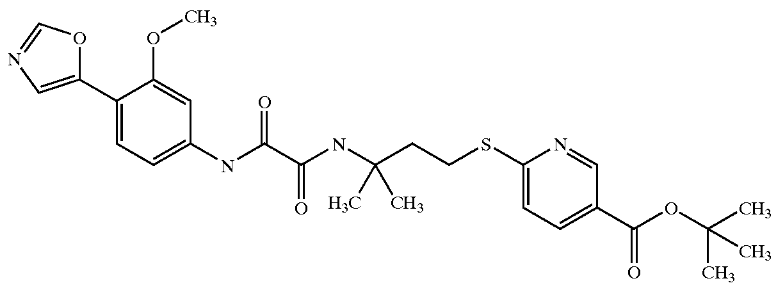 |
| 6-[3-[[[3-Methoxy-4-(5-oxazolyl)anilino]oxalyl]amino]-3-methylbutylthio]-3-pyridinecarboxylic acid trifluoroacetate (1:1) | 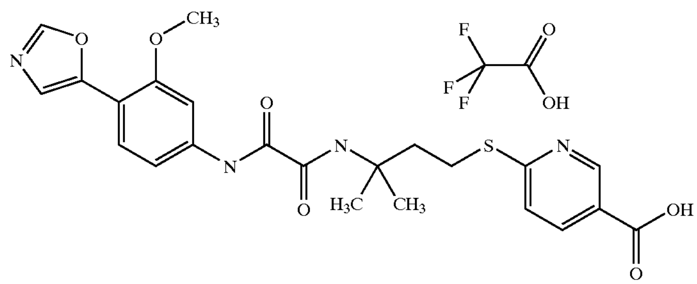 |
| 4-[3-[[[3-Methoxy-4-(5-oxazolyl)anilino]oxalyl]amino]-3-methylbutylthio]benzoic acid | 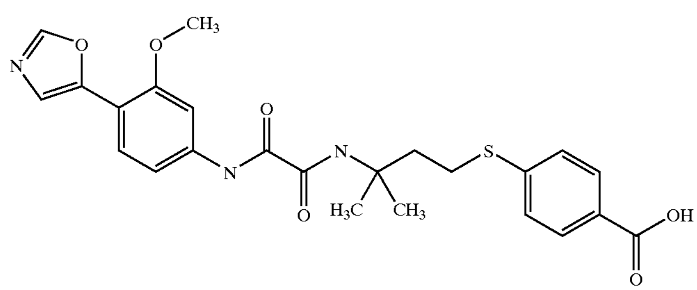 |
| N-[2-(4-Benzyloxyphenylthio)-1,1-dimethylethyl]-N'-[3-methoxy-4-(5-oxazolyl)phenyl]oxalamide | 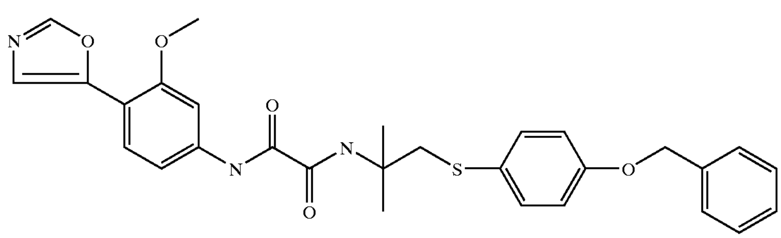 |

-continued

| Name | Structure |
|---|---|
| N-[2-(4-Benzyloxyphenylthio)-1,1-dimethylpropyl]-N'-[3-methoxy-4-(5-oxazolyl)phenyl]oxalamide | 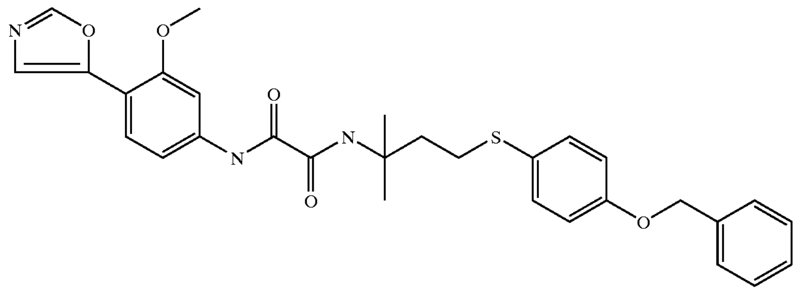 |
| 2-[3-[[[3-Methoxy-4-(5-oxazolyl)anilino]oxalyl]amino]-3-methylbutylthio]-5-benzoxazolecarboxylic acid | 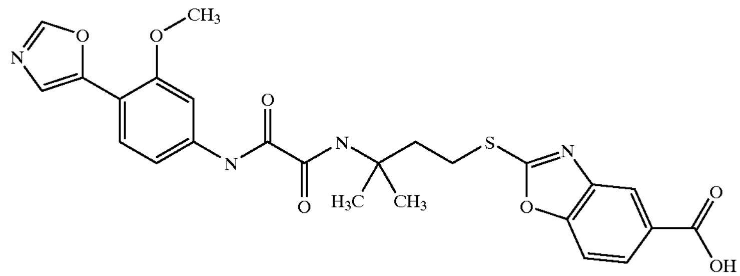 |
| N-[3-(1H-Imidazol-2-ylthio)-1,1-dimethylpropyl]-N'-[3-methoxy-4-(5-oxazolyl)phenyl]oxalamide | 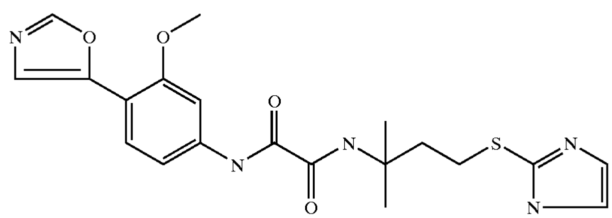 |
| 2-[3-[[[3-Methoxy-4-(5-oxazolyl)anilino]oxalyl]amino]-3-methylbutylthio]-3-pyridinecarboxylic acid trifluoroacetate (1:1) | 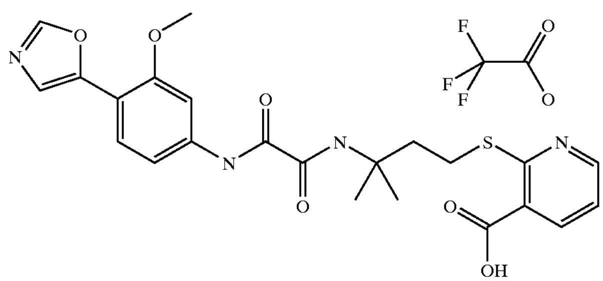 |
| 4-[2-[[[3-methoxy-4-(5-oxazolyl)anilino]oxalyl]amino]-2-methylpropylthio]benzoic acid | 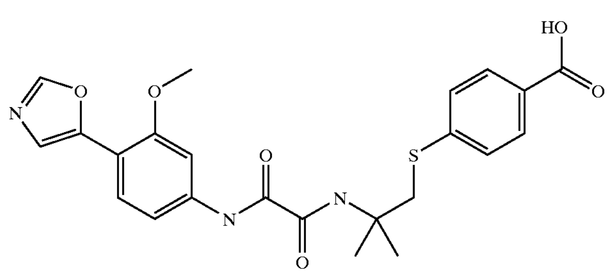 |

| Name | Structure |
|---|---|
| and 2-[3-[[[3-Methoxy-4-(5-oxazolyl)anilino]oxalyl]amino]-3-methylbutylthio]-6-benzoxazolecarboxylic acid | |

14. The compound of claim 1 of the formula

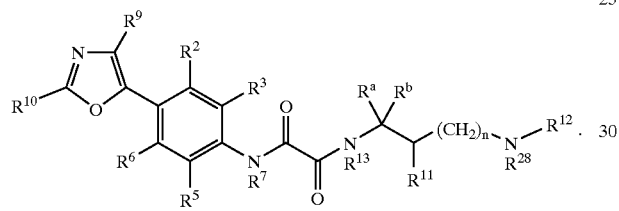 XX

15. Compound of claim 14, wherein $R^2$ is methoxy and $R^3$, $R^5$, $R^6$, $R^9$, $R^{10}$, $R^{11}$ and $R^{13}$ are hydrogen and $R^{28}$ is hydrogen or methyl.

16. The compound of claim 15 wherein $R^{12}$ is aryl.

17. The compound of claim 16 selected from the group consisting of:

| Name | Structure |
|---|---|
| N-[3-Methoxy-4-(5-oxazolyl)phenyl)-N'-[1,1-dimethyl-2-(N methylanilino) ethyl] oxalamide | 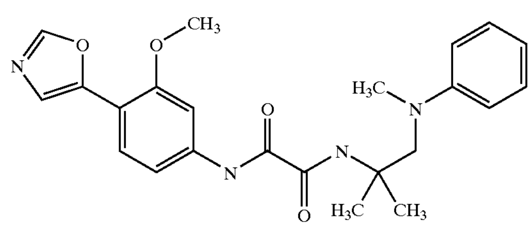 |
| N-(3-Anilino-1,1-dimethylpropyl)-N'-[3-methoxy-4-(5-oxazolyl)phenyl]oxalamide hydrochloride (1:1) | 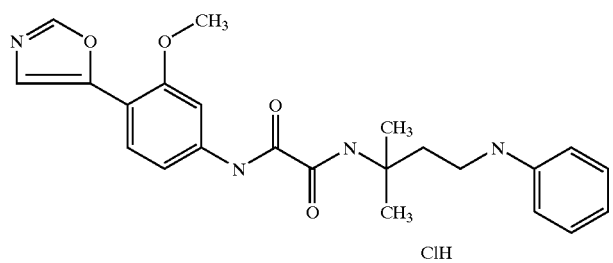 |

-continued
| Name | Structure |
|------|-----------|
| 4-[3-[[[3-Methoxy-4-(5-oxazolyl)anilino]oxalyl]amino]-3-methylbutylamino]benzoic acid | 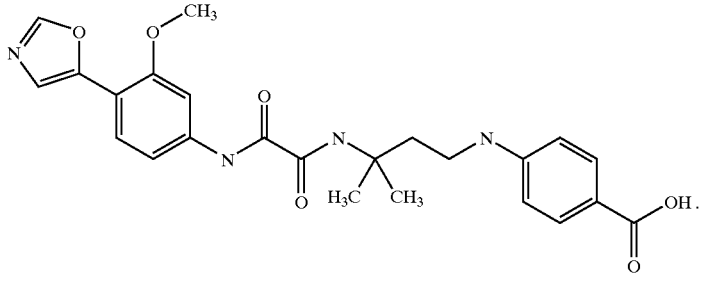 |
* * * * *